United States Patent
Strohbach et al.

(10) Patent No.: US 11,559,538 B2
(45) Date of Patent: Jan. 24, 2023

(54) SUBSTITUTED 1,2-OXABOROLAN-2-OLS AS PDE4 INHIBITORS

(71) Applicant: Pfizer Inc., New York, NY (US)

(72) Inventors: Joseph Walter Strohbach, Wentzville, MO (US); Tsutomu Akama, Tokyo (JP); David Clive Blakemore, East Lyme, CT (US); Robert Toms Jacobs, Wake Forest, NC (US); Peter Jones, Sharon, MA (US); David Christopher Limburg, Salem, CT (US); Martins Sunday Oderinde, Ewing, NJ (US); Matthew Alexander Perry, Uncasville, CT (US); Jacob John Plattner, Bend, OR (US); Rubben Federico Torella, Cambridge, MA (US); Yasheen Zhou, Moraga, CA (US); Thean Yeow Yeoh, Salem, CT (US)

(73) Assignee: Pfizer Inc., New York, NY (US)

( * ) Notice: Subject to any disclaimer, the term of this patent is extended or adjusted under 35 U.S.C. 154(b) by 266 days.

(21) Appl. No.: 17/082,102

(22) Filed: Oct. 28, 2020

(65) Prior Publication Data
US 2021/0069219 A1 Mar. 11, 2021

Related U.S. Application Data

(62) Division of application No. 16/593,171, filed on Oct. 4, 2019, now Pat. No. 10,946,031.

(60) Provisional application No. 62/889,599, filed on Aug. 21, 2019, provisional application No. 62/741,868, filed on Oct. 5, 2018.

(51) Int. Cl.
| C07F 5/02 | (2006.01) |
| A61K 31/69 | (2006.01) |
| A61K 31/519 | (2006.01) |

(52) U.S. Cl.
CPC ............ *A61K 31/69* (2013.01); *A61K 31/519* (2013.01); *C07F 5/025* (2013.01); *C07B 2200/13* (2013.01)

(58) Field of Classification Search
CPC ...................................................... C07F 5/02
USPC .......................................................... 568/2
See application file for complete search history.

(56) References Cited

FOREIGN PATENT DOCUMENTS

| WO | 1995/033754 | 12/1995 |
| WO | 2006/089067 | 8/2006 |
| WO | 2009/111676 | 9/2009 |
| WO | 2012/067663 | 5/2012 |
| WO | 2013/050591 | 4/2013 |
| WO | 2013/057740 | 4/2013 |
| WO | 2014/120715 | 8/2014 |
| WO | 2014/147009 | 9/2014 |
| WO | 2014/197634 | 12/2014 |

OTHER PUBLICATIONS

Fang et al., "The First Preparation of 4-Substituted 1,2-Oxaborol-2(5H)-ols and their Palladium-Catalyzed Cross-Coupling with Aryl Halides to Prepare Stereodefined 2,3-Disubstituted Allyl Alcohols", Synthesis, vol. 7, pp. 1148-1154 (2006).
Maynard et al., "Discovery of a Potent Boronic Acid Derived Inhibitor of the HCV RNA-Dependent RNA Polymerase", J. Med Chem., vol. 57, pp. 1902-1913 (2014).
Roscales et al., "Transition-Metal-Free Direct anti-Carboboration of Alkynes with Boronic Acids to Produce Alkenylheteroarenes", Organic Letters, vol. 17, pp. 1605-1608 (2015).
Yan et al., Chinese J. Org. Chem., vol. 32, pp. 597-600 (2012) (Abstract in English).
Yu et al., "A New Synthetic Method of (Z)-4-Aryl-but-2-en-1-ols via Suzuki-Miyaura Cross-Coupling Reaction of 4-Substituted 1,2-Oxaborol-2(5H)-ols with Benzyl Bromides", Chin. J. Chem. vol. 30(12), pp. 2798-2804 (2012).
Cui et al., "One-Pot Synthesis of Functionalized 2,5-Dihydrofurans via an Amine-Promoted Petasis Borono-Mannich Reaction", Org. Letters, vol. 15(23), pp. 5944-5947 (2013).
Yu et al., "Suzuki-Miyaura cross-coupling reaction of 1,2-oxaborol-2(5H)-ols with carboxylic anhydrides: a new method to furans", Tetrahedron Letters, vol. 55(30), pp. 4071-4074 (2014).
Fenneteau, et al., "Liebeskind-Srogl cross-coupling on γ-carboxyl-γ-butyrolactone derivatives: application to the side chain of amphidinolides C and F", Tetrahedron Letters, vol. 56(24), pp. 3758-3761 (2015).
Butcher et al., "Regioselective Copper-Catalyzed Boracarboxylation of Vinyl Arenes", Organic Letters, vol. 18(24), pp. 6428-6431, Dec. 16, 2016.

*Primary Examiner* — Douglas M Willis
(74) *Attorney, Agent, or Firm* — Young-In Julia Oh

(57) ABSTRACT

The present invention relates to boron containing compounds of Formula (IA):

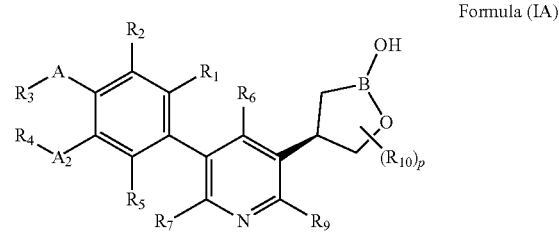

that inhibit phosphodiesterase 4 (PDE4). The invention also encompasses pharmaceutical compositions containing these compounds and methods for treating diseases, conditions, or disorders ameliorated by inhibition of PDE4.

4 Claims, 12 Drawing Sheets

SUBSTITUTED 1,2-OXABOROLAN-2-OLS AS PDE4 INHIBITORS

This application is a divisional of U.S. patent application Ser. No. 16/593,171 filed Oct. 4, 2019, which claims priority to U.S. Provisional Patent Application No. 62/889,599 filed on Aug. 21, 2019 and U.S. Provisional Patent Application No. 62/741,868 filed on Oct. 5, 2018. All applications to which priority is claimed are hereby incorporated by reference in their entirety for all purposes.

FIELD OF THE INVENTION

The present invention relates to pharmaceutically active boron containing compounds that inhibit phosphodiesterase 4 (PDE4), pharmaceutical compositions containing these compounds, and the use of these compounds for treating or preventing diseases, conditions, or disorders ameliorated by inhibition of PDE4.

BACKGROUND

Inflammation is a major component of numerous diseases and individuals with such diseases often exhibit high levels of inflammatory regulators that include, but are not limited to, the following cytokines IL-1α, IL-1β, IL-2, IL-3, IL-4, IL-5, IL-6, IL-7, IL-9, IL-12, IL-13, IL-17, IL-18, IL-23, IL-31, IL-33, TNF-α, IFN-α, IFN-β, and IFN-γ. A non-limiting list of disease states that are directly associated with inflammatory cytokines include: atopic dermatitis wherein inflammatory cytokines induce inflammation; psoriasis wherein inflammatory cytokines induce dermatitis; arthritis wherein inflammatory cytokines can lead to lesions in the synovial membrane and destruction of joint cartilage and bone; fibrosis wherein inflammatory cytokines can attack traumatized tissue; lupus wherein inflammatory cytokines can exacerbate the immune complex deposition and damage; allergy wherein inflammatory cytokines can induce inflammation, production of IgE, and congestion; fibromyalgia wherein inflammatory cytokines are elevated in patients; and surgical complications wherein inflammatory cytokines can avert healing.

Other diseases associated with chronic inflammation include: cancer; heart attack wherein chronic inflammation contributes to coronary atherosclerosis; Alzheimer's disease wherein chronic inflammation negatively effects brain cells; congestive heart failure wherein chronic inflammation causes heart muscle wasting; stroke wherein chronic inflammation promotes thromboembolic events; and aortic valve stenosis wherein chronic inflammation damages heart valves. Arteriosclerosis, osteoporosis, Parkinson's disease, bacterial infection, viral infection, inflammatory bowel disease including Crohn's disease and ulcerative colitis, as well as multiple sclerosis (a typical autoimmune inflammatory-related disease) are also related to inflammation. Current methods available for the treatment of such inflammatory diseases can be unsatisfactory due to a lack of sufficient efficacy and/or drug related side effects associated therein. Therefore a need exists for new therapeutic methods that modulate inflammatory process involved in the diseases, conditions, and disorders, disclosed herein.

In particular, Atopic Dermatitis (AD) is an inflammatory skin disease that, typically, manifests during early childhood but can appear in adolescence or adulthood and follows either a chronic or a relapsing/remitting disease progression. AD patients display pruritic skin and show susceptibility to cutaneous secondary bacterial, viral and fungal infections. Patients with AD can also demonstrate a compromised barrier function that leads to activation of keratinocytes and other immune cells. A number of inflammatory cytokines are involved in the symptoms characteristic of AD including, but not limited to, IL-1 IL-2, IL-3, IL-4, IL-5, IL-6, IL-12, IL-13, IL-17, IL-18, IL-22, IL-23, IL-31, IL-33, IL-36, and TNF-α. Inflammatory cytokines facilitate the production of various chemoattractants or chemokines which support the recruitment of leukocytes to the disease site. Chemokines that contribute to inflammation in AD patients include, but not limited to, CCL1, CCL2, CCL3, CCL4, CCL5, CCL11, CCL13, CCL17, CCL18, CCL20, CCL22, CCL26 and CCL27.

There are limited therapeutic options for the treatment of AD. The topical use of anti-inflammatory steroids has been utilized in AD treatment particularly in the case of acute disease flares. The steroids suppress the activation and proliferation of inflammatory cells as well as keratinocytes and fibroblasts. However, steroids can cause adverse local side effects that include, but are not restricted to, skin atrophy, telangiectasia (abnormal dilation of capillary vessels), epidermal barrier disturbance, striae, rosacea, acne, hypertrichosis, hypopigmentation, delayed wound healing and alterations in skin elasticity. Emollients including petrolatum and over-the-counter moisturizers have been used to reduce the use of topical steroids. Topical application of mevalonic acid and nicotinamide has been used to improve the epidermal barrier permeability through the production of cholesterol and ceramide. Topical calcineurin inhibitors (TCI) such as tacrolimus and pimecrolimus have been used in the treatment of AD. Cyclosporine A (CyA) has been used as an immunosuppressant to inhibit calcineurin phosphatase thereby leading to reduction in levels of IL-2 and inhibition of T cell proliferation. Systemic treatment include humanized monoclonal antibodies such as Omalizumab, Efalizumab and Etanercept, Dupilumab that target serum IgE, LFA-1, TNF-α, and IL-4r respectively [Rahman, Inf. & All. 2011, 10, 486]. Additional eczema, skin and disease conditions include hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, and hidradenitis suppurativa [Eyerich and Eyerich, J. Eur. Ac. Derm. Ven., 32, 692 (2018)].

Psoriasis is an immune-mediated chronic skin disease that exists in several different forms including plaque psoriasis, pustular psoriasis, nail psoriasis, flexural psoriasis, guttate psoriasis, psoriatic arthritis, erythrodermic psoriasis, and inverse psoriasis. Plaque psoriasis (psoriasis vulgaris) is the most common form of psoriasis and typically appears as patches of raised red skin covered by a flaky white buildup. Pustular psoriasis appears as raised bumps that are filled with non-infectious pus (pustules). The skin under and surrounding pustules is red and tender. Pustular psoriasis can be localized, commonly to the hands and feet, or generalized with widespread patches occurring on any part of the body. Nail psoriasis produces a variety of changes in the appearance of finger and toe nails. These changes include discoloring under the nail plate, pitting of the nails, lines going across the nails, thickening of the skin under the nail, and the loosening (onycholysis) and crumbling of the nail. Flexural psoriasis (inverse psoriasis) appears as smooth inflamed patches of skin. It occurs in skin folds, particularly around the genitals (between the thigh and groin), the armpits, under an overweight stomach (pannus), and under the breasts (inframammary fold). It is aggravated by friction and sweat, and is vulnerable to fungal infections. Guttate psoriasis is characterized by numerous small oval spots. These spots of psoriasis appear over large areas of the body, such as the trunk, limbs, and scalp. Psoriatic arthritis involves joint and connective tissue inflammation. Psoriatic arthritis can affect any joint but is most common in the joints of the fingers and toes. Psoriatic arthritis can result in swelling of the fingers and toes known as dactylitis. Psoriatic arthritis can also affect the hips, knees and spine (spondylitis). Erythrodermic psoriasis involves the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. Current therapies available for treatment of psoriasis include topical treatment, phototherapy, and systemic applications. The treatments are either cosmetically undesirable, inconvenient for long-term use, or have limited effectiveness.

Inflammatory Bowel Disease (IBD) describes a group of intestinal disorders that involve inflammation of the digestive tract including ulcerative colitis and Crohn's disease. Ulcerative Colitis (UC) causes periodic and chronic inflammation and ulcers in the lining of the large intestine (colon). Crohn's disease (CD) is characterized by inflammation of the lining of the gastrointestinal tract and can penetrate into related tissues. Patients with IBD can exhibit diarrhea, abdominal pain, fatigue, and weight loss, and these conditions can be severe and debilitating. As the symptoms vary depending on the level and duration of inflammation, an agent that modulates said inflammation would be useful in treating IBD.

Phosphodiesterases (PDEs) represent a family of enzymes that catalyze the hydrolysis of various cyclic nucleoside monophosphates including cyclic adenosine monophosphate (cAMP) and cyclic guanosine monophosphate (cGMP). PDEs regulate the level of cyclic nucleotides within cells and maintain cyclic nucleotide homeostasis by hydrolyzing such cyclic mononucleotides resulting in termination of their messenger role. PDE enzymes can be grouped into families according to their specificity toward hydrolysis of cAMP and/or cGMP, their sensitivity to regulation by calcium and calmodulin, and their selective inhibition by various compounds.

The PDE4 enzyme sub-family consists of four genes which produce 4 isoforms of the PDE4 enzyme designated PDE4A, PDE4B, PDE4C, and PDE4D [Wang et al., Biochem. Biophys. Res. Comm., 234, 320 (1997)]. In addition, various splice variants of each PDE4 isoform have been identified. PDE4 isoenzymes specifically inactivate cAMP by catalyzing its hydrolysis to adenosine 5'-monophosphate (AMP). Regulation of cAMP activity is important in many biological processes including inflammation.

The compounds of the present invention inhibit phosphodiesterases, including PDE4, and modulate inflammatory cytokine levels and are, therefore, useful in treating inflammatory disorders such as atopic dermatitis, eczema, psoriasis, arthritis, asthma, fibrosis, lupus, allergy, fibromyalgia, wound healing, ulcerative colitis, Crohn's disease, inflammatory bowel disease, and inflammation resulting from surgical complications.

SUMMARY OF THE INVENTION

The present invention provides compounds of Formula (I) that inhibit PDE4 and are useful for treating or preventing disorders ameliorated by inhibition of PDE4 in humans, X—Y—Z            Formula (I)

or a pharmaceutically acceptable salt thereof, wherein

X is phenyl, pyridine, pyrimidine, pyrazine, pyridazine, or triazine, wherein each is optionally substituted with 1, 2, 3, 4, or 5 substituents that are independently deuterium, $(C_2-C_6)$alkenyl, $(C_2-C_6)$alkenyloxy, $(C_2-C_6)$alkenylthio, $(C_1-C_6)$alkoxy, $(C_1-C_6)$alkoxy-$d_{1-13}$, $(C_1-C_6)$alkoxy$(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkyl-$d_{1-13}$, $(C_1-C_6)$alkylcarbonyl, $(C_1-C_6)$alkylthio, $(C_2-C_6)$alkynyl, $(C_2-C_6)$alkynyloxy, $(C_2-C_6)$alkynylthio, aryl, aryl$(C_1-C_6)$alkoxy, aryl$(C_1-C_6)$alkyl, aryl$(C_1-C_6)$alkylthio, aryloxy, arylthio, carboxy, carboxy$(C_1-C_6)$alkoxy, carboxy$(C_1-C_6)$alkyl, cyano, $(C_3-C_8)$cycloalkyl, $(C_3-C_8)$cycloalkyl$(C_1-C_6)$alkoxy, $(C_3-C_8)$cycloalkyl$(C_1-C_6)$alkyl, $C_3-C_8)$cycloalkyl$(C_1-C_6)$alkylthio, $(C_3-C_8)$cycloalkyloxy, $(C_3-C_8)$cycloalkylthio, halogen, halo$(C_1-C_6)$alkoxy, halo$(C_1-C_6)$alkyl, halo$(C_1-C_6)$alkylthio, (5-6 membered)heteroaryl, (5-6 membered)heteroaryl$(C_1-C_6)$alkoxy, (5-6 membered)heteroaryl$(C_1-C_6)$alkyl, (5-6 membered)heteroaryl$(C_1-C_6)$alkylthio, (5-6 membered)heteroaryloxy, (5-6 membered)heteroarylthio, (4-7 membered)heterocycle containing at least one heteroatom independently selected from the group consisting of O, N, and S, (4-7 membered)heterocycle$(C_1-C_6)$alkoxy, (4-7 membered)heterocycle$(C_1-C_6)$alkyl, (4-7 membered)heterocycle$(C_1-C_6)$alkylthio, (4-7 membered)heterocycleoxy, (4-7 membered)heterocyclethio, hydroxy, hydroxy$(C_1-C_6)$alkoxy, hydroxy$(C_1-C_6)$alkyl, mercapto, nitro, thio$(C_1-C_6)$alkyl, —$NR_AR_B$, $NR_AR_B$ $(C_1-C_6)$alkoxy, $NR_AR_B$ $(C_1-C_6)$alkyl, or $(NR_AR_B)$carbonyl; $R_A$ and $R_B$ are independently hydrogen, $(C_1-C_6)$alkyl, or $(C_1-C_6)$alkylcarbonyl; Y is phenyl, pyridine, pyrimidine, pyrazine, pyridazine, triazine, furan, thiophene, pyrrole, oxazole, thiazole, imidazole, isoxazole, isothiazole, pyrazole, oxadiazole, thiadiazole, or triazole, wherein each is optionally substituted with 1, 2, or 3 substituents that are independently deuterium, $(C_1-C_6)$alkoxy, $(C_1-C_6)$alkoxy-$d_{1-13}$, $(C_1-C_6)$alkoxy$(C_1-C_6)$alkoxy, $(C_1-C_6)$alkoxy$(C_1-C_6)$alkyl, $(C_1-C_6)$alkoxycarbonyl, $(C_1-C_6)$alkoxycarbonyl$(C_1-C_6)$alkyl, $(C_1-C_3)$alkyl, $(C_1-C_3)$alkyl-$d_{1-7}$, $(C_1-C_6)$alkyl, $(C_1-C_6)$alkyl-$d_{1-13}$, $(C_1-C_6)$alkylcarbonyl, $(C_1-C_6)$alkylthio, carboxy, carboxy$(C_1-C_6)$alkoxy, carboxy$(C_1-C_6)$alkyl, cyano, halogen, halo$(C_1-C_6)$alkoxy, halo$(C_1-C_6)$alkyl, hydroxy, hydroxy$(C_1-C_6)$alkoxy, hydroxy$(C_1-C_6)$alkyl, mercapto, nitro, —$NR_CR_D$, $NR_CR_D(C_1-C_6)$alkoxy, $NR_CR_D(C_1-C_6)$alkyl, or $(NR_CR_D)$carbonyl; $R_C$ and $R_D$ are independently hydrogen, $(C_1-C_6)$alkyl, or $(C_1-C_6)$alkylcarbonyl; Z is

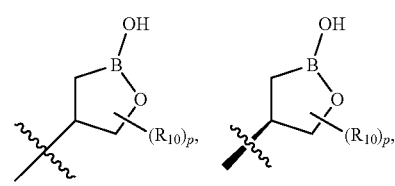

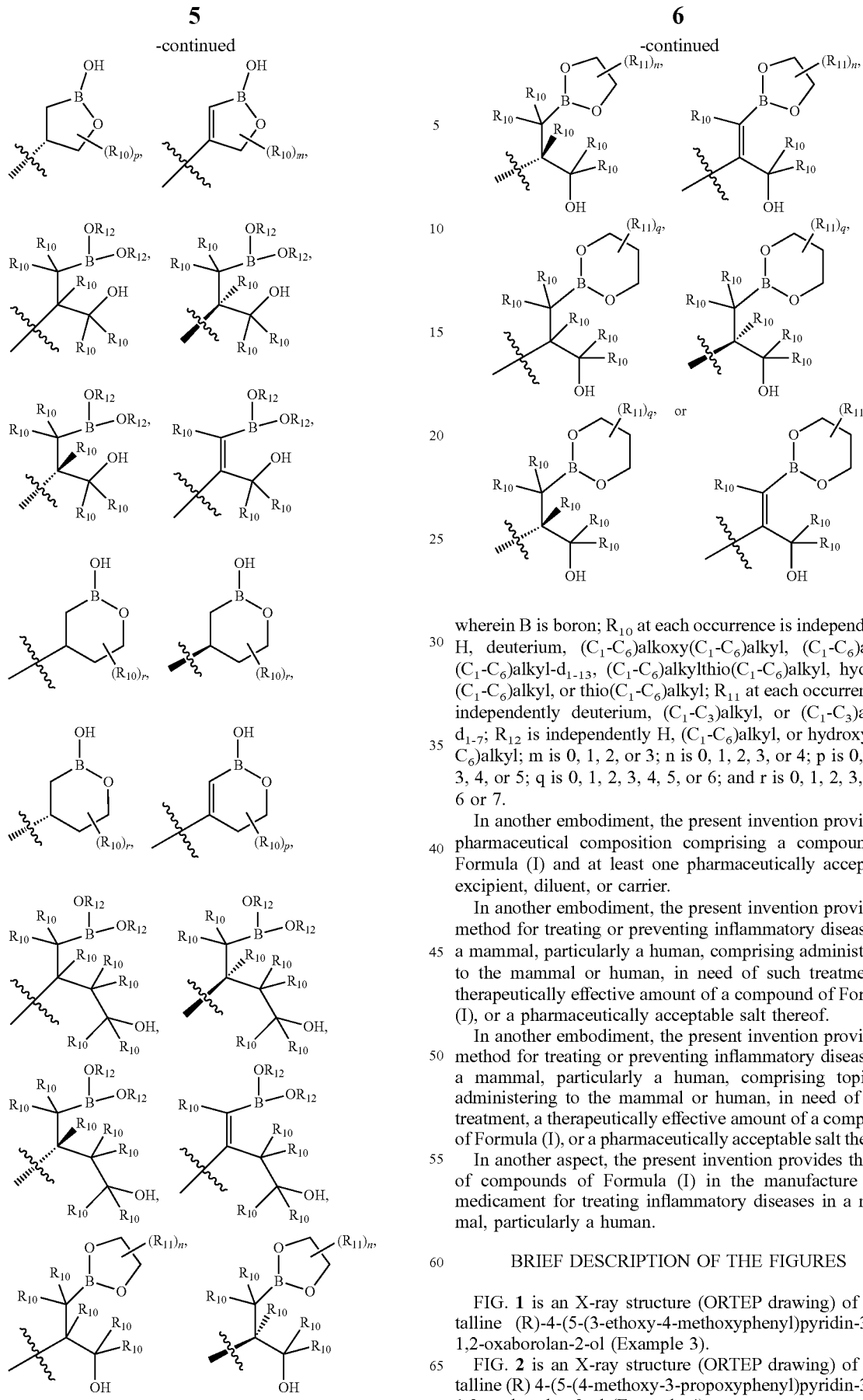

wherein B is boron; $R_{10}$ at each occurrence is independently H, deuterium, $(C_1-C_6)$alkoxy$(C_1-C_6)$alkyl, $(C_1-C_6)$alkyl, $(C_1-C_6)$alkyl-$d_{1-13}$, $(C_1-C_6)$alkylthio$(C_1-C_6)$alkyl, hydroxy$(C_1-C_6)$alkyl, or thio$(C_1-C_6)$alkyl; $R_{11}$ at each occurrence is independently deuterium, $(C_1-C_3)$alkyl, or $(C_1-C_3)$alkyl-$d_{1-7}$; $R_{12}$ is independently H, $(C_1-C_6)$alkyl, or hydroxy$(C_1-C_6)$alkyl; m is 0, 1, 2, or 3; n is 0, 1, 2, 3, or 4; p is 0, 1, 2, 3, 4, or 5; q is 0, 1, 2, 3, 4, 5, or 6; and r is 0, 1, 2, 3, 4, 5, 6 or 7.

In another embodiment, the present invention provides a pharmaceutical composition comprising a compound of Formula (I) and at least one pharmaceutically acceptable excipient, diluent, or carrier.

In another embodiment, the present invention provides a method for treating or preventing inflammatory diseases in a mammal, particularly a human, comprising administering to the mammal or human, in need of such treatment, a therapeutically effective amount of a compound of Formula (I), or a pharmaceutically acceptable salt thereof.

In another embodiment, the present invention provides a method for treating or preventing inflammatory diseases in a mammal, particularly a human, comprising topically administering to the mammal or human, in need of such treatment, a therapeutically effective amount of a compound of Formula (I), or a pharmaceutically acceptable salt thereof.

In another aspect, the present invention provides the use of compounds of Formula (I) in the manufacture of a medicament for treating inflammatory diseases in a mammal, particularly a human.

DETAILED DESCRIPTION OF THE INVENTION

Figure 1:
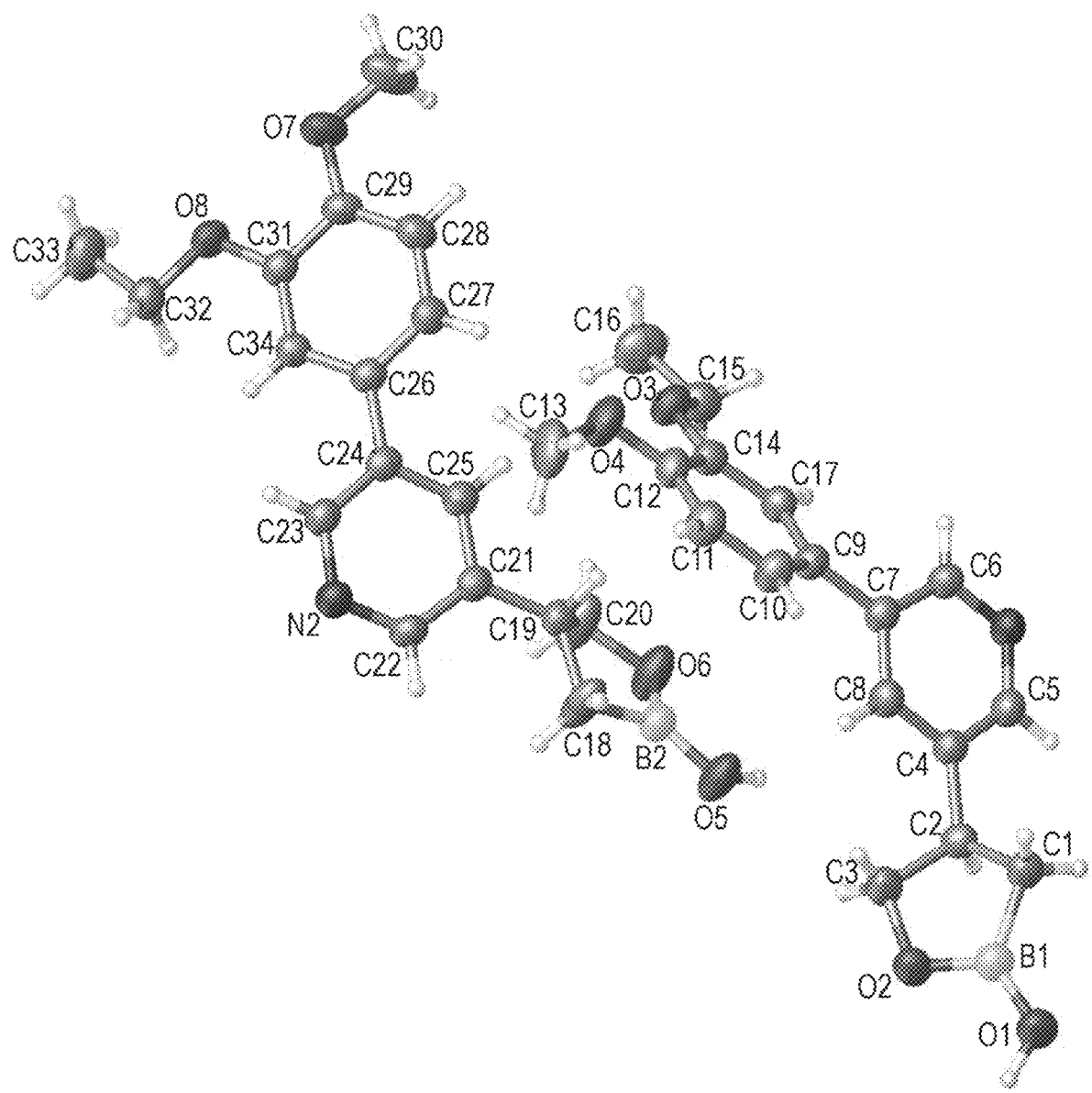
FIG. 1 is an X-ray structure (ORTEP drawing) of crystalline (R)-4-(5-(3-ethoxy-4-methoxyphenyl)pyridin-3-yl)-1,2-oxaborolan-2-ol (Example 3).

In another embodiment, the present invention provides compounds of Formula (I)

$$X-Y-Z \qquad \text{Formula (I)}$$

or a pharmaceutically acceptable salt thereof, wherein X is phenyl, pyridine, or pyrimidine, wherein each is optionally substituted with 1, 2, 3, 4, or 5 substituents that are independently deuterium, $(C_2-C_6)$alkenyl, $(C_2-C_6)$alkenyloxy, $(C_2-C_6)$alkenylthio, $(C_1-C_6)$alkoxy, $(C_1-C_6)$alkoxy-$d_{1-13}$, $(C_1-C_6)$alkoxy$(C_1-C_6)$alkoxy, $(C_1-C_6)$alkoxy$(C_1-C_6)$alkyl, $(C_1-C_6)$alkoxycarbonyl, $(C_1-C_6)$alkyl, $(C_1-C_6)$alkyl-$d_{1-13}$, $(C_1-C_6)$alkylcarbonyl, $(C_1-C_6)$alkylthio, $(C_2-C_6)$alkynyl, $(C_2-C_6)$alkynyloxy, $(C_2-C_6)$alkynylthio, aryl, aryl$(C_1-C_6)$alkoxy, aryl$(C_1-C_6)$alkyl, aryl$(C_1-C_6)$alkylthio, aryloxy, arylthio, carboxy, carboxy$(C_1-C_6)$alkoxy, carboxy$(C_1-C_6)$alkyl, cyano, $(C_3-C_8)$cycloalkyl, $(C_3-C_8)$cycloalkyl$(C_1-C_6)$alkoxy, $(C_3-C_8)$cycloalkyl$(C_1-C_6)$alkyl, $C_3-C_8)$cycloalkyl$(C_1-C_6)$alkylthio, $(C_3-C_8)$cycloalkyloxy, $(C_3-C_8)$cycloalkylthio, halogen, halo$(C_1-C_6)$alkoxy, halo$(C_1-C_6)$alkyl, halo$(C_1-C_6)$alkylthio, (5-6 membered)heteroaryl, (5-6 membered)heteroaryl$(C_1-C_6)$alkoxy, (5-6 membered)heteroaryl$(C_1-C_6)$alkyl, (5-6 membered)heteroaryl$(C_1-C_6)$alkylthio, (5-6 membered)heteroaryloxy, (5-6 membered)heteroarylthio, (4-7 membered)heterocycle containing at least one heteroatom independently selected from the group consisting of O, N, and S, (4-7 membered)heterocycle$(C_1-C_6)$alkoxy, (4-7 membered)heterocycle$(C_1-C_6)$alkyl, (4-7 membered)heterocycle$(C_1-C_6)$alkylthio, (4-7 membered)heterocycleoxy, (4-7 membered)heterocyclethio, hydroxy, hydroxy$(C_1-C_6)$alkoxy, hydroxy$(C_1-C_6)$alkyl, mercapto, nitro, thio$(C_1-C_6)$alkyl, —$NR_AR_B$, $NR_AR_B$ $(C_1-C_6)$alkoxy, $NR_AR_B$ $(C_1-C_6)$alkyl, or $(NR_AR_B)$carbonyl; $R_A$ and $R_B$ are independently hydrogen, $(C_1-C_6)$alkyl, or $(C_1-C_6)$alkylcarbonyl; Y is phenyl, pyridine, pyrimidine, pyrazine, pyridazine, thiazole, pyrazole, or thiadiazole, wherein each is optionally substituted with 1, 2, or 3 substituents that are independently deuterium, $(C_1-C_6)$alkoxy, $(C_1-C_6)$alkoxy-$d_{1-13}$, $(C_1-C_6)$alkoxy$(C_1-C_6)$alkoxy, $(C_1-C_6)$alkoxy$(C_1-C_6)$alkyl, $(C_1-C_6)$alkoxycarbonyl, $(C_1-C_6)$alkoxycarbonyl$(C_1-C_6)$alkyl, $(C_1-C_3)$alkyl, $(C_1-C_3)$alkyl-$d_{1-7}$, $(C_1-C_6)$alkyl, $(C_1-C_6)$alkyl-$d_{1-13}$, $(C_1-C_6)$alkylcarbonyl, $(C_1-C_6)$alkylthio, carboxy, carboxy$(C_1-C_6)$alkoxy, carboxy$(C_1-C_6)$alkyl, cyano, halogen, halo$(C_1-C_6)$alkoxy, halo$(C_1-C_6)$alkyl, hydroxy, hydroxy$(C_1-C_6)$alkoxy, hydroxy$(C_1-C_6)$alkyl, mercapto, nitro, —$NR_CR_D$, $NR_CR_D(C_1-C_6)$alkoxy, $NR_CR_D$ $(C_1-C_6)$alkyl, or $(NR_CR_D)$carbonyl; $R_C$ and $R_D$ are independently hydrogen, $(C_1-C_6)$alkyl, or $(C_1-C_6)$alkylcarbonyl; Z is as defined in the Summary section herein; $R_{10}$ at each occurrence is H, deuterium, $(C_1-C_6)$alkyl, $(C_1-C_6)$alkyl-$d_{1-13}$, or hydroxy$(C_1-C_6)$alkyl; $R_{11}$ at each occurrence is deuterium, methyl, or methyl-$d_3$; $R_{12}$ is independently H, $(C_1-C_6)$alkyl, or hydroxy$(C_1-C_6)$alkyl; m is 0, 1, 2, or 3; n is 0 or 1; p is 0, 1, 2, 3, 4, or 5; q is 0, 1, 2, or 3; and r is 0, 1, 2, 3, 4, 5, 6 or 7

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered)heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

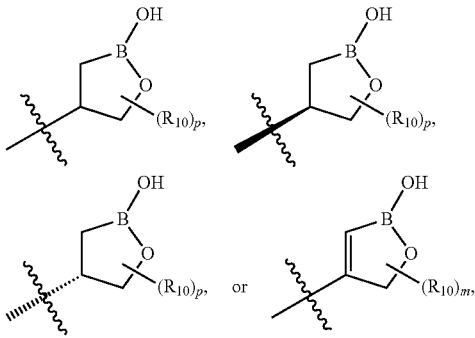

$R_{10}$ at each occurrence is H, methyl or hydroxymethyl; m is 1; and p is 1.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (3-7 membered)heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

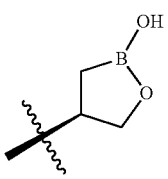

wherein B is boron.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

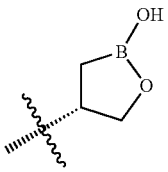

wherein B is boron.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

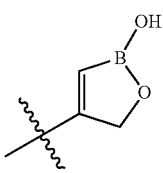

wherein B is boron.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

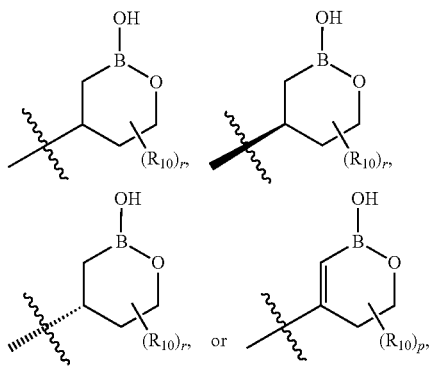

wherein B is boron; $R_{10}$ at each occurrence is H, methyl or hydroxymethyl; p is 1; and r is 1.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

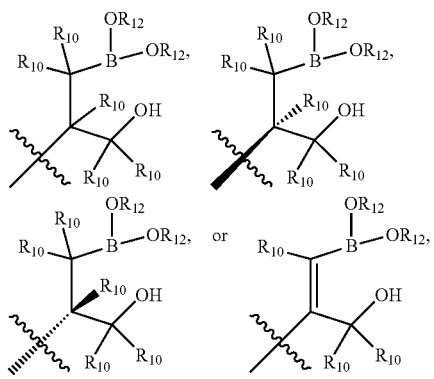

wherein B is boron; $R_{10}$ at each occurrence is H, methyl or hydroxymethyl; $R_{12}$ is at each occurrence independently H, $(C_1-C_6)$alkyl, or hydroxy$(C_1-C_6)$alkyl.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

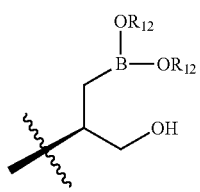

wherein B is boron; $R_{12}$ is at each occurrence independently H, $(C_1-C_6)$alkyl, or hydroxy$(C_1-C_6)$alkyl.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

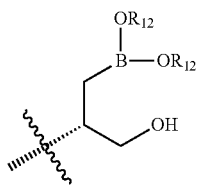

wherein B is boron; $R_{12}$ is at each occurrence independently H, $(C_1-C_6)$alkyl, or hydroxy$(C_1-C_6)$alkyl.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

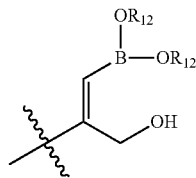

wherein B is boron; and $R_{12}$ is at each occurrence independently H, $(C_1-C_6)$alkyl, or hydroxy$(C_1-C_6)$alkyl.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

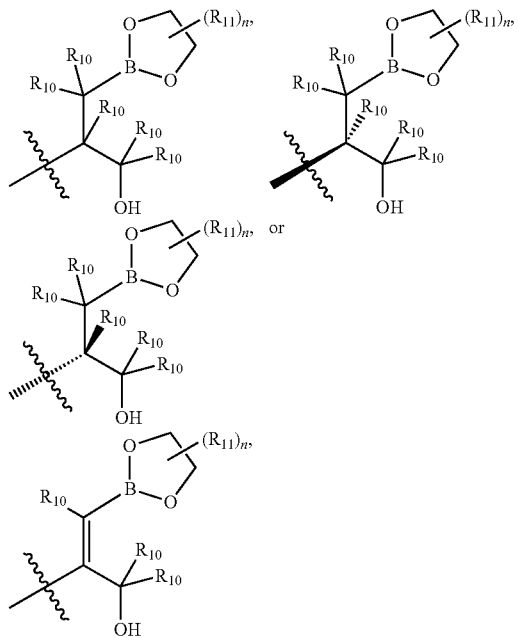

wherein B is boron; $R_{10}$ at each occurrence is H, methyl or hydroxymethyl; $R_{11}$ at each occurrence is independently $(C_1-C_3)$alkyl; and n is 0, 1, 2, 3, or 4.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

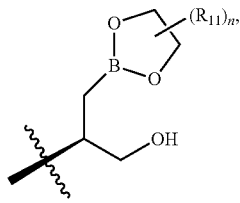

wherein B is boron; $R_{11}$ is methyl; and n is 0 or 1.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

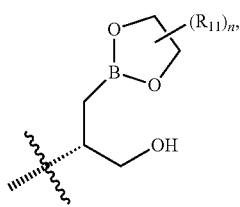

wherein B is boron; $R_{11}$ is methyl; and n is 0 or 1.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

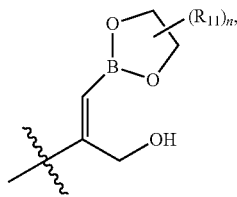

wherein B is boron; $R_{11}$ is methyl; and n is 0 or 1.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$ alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered) heterocycleoxy, or hydroxy$(C_1-C_6)$alkoxy; Y is phenyl, pyridine, pyrimidine, pyrazine, pyridazine, thiazole, pyrazole, or thiadiazole, wherein each is optionally substituted with 1 substituent that is $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

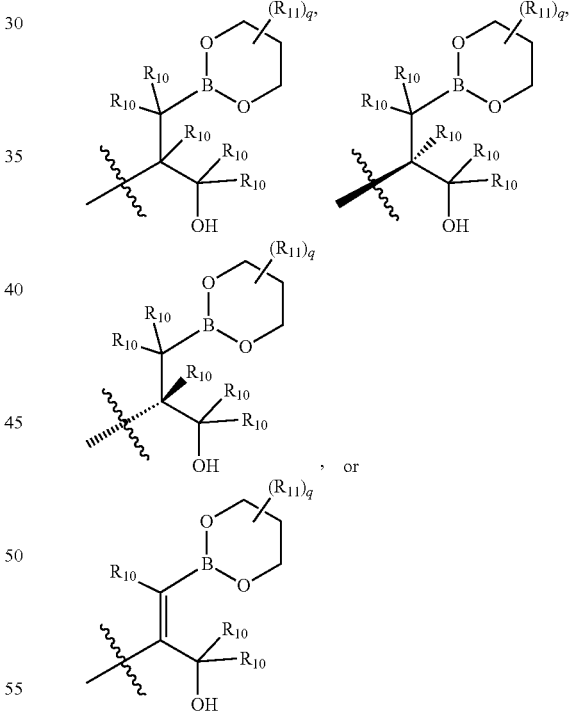

wherein B is boron; $R_{10}$ at each occurrence is H, methyl or hydroxymethyl; $R_{11}$ at each occurrence is independently $(C_1-C_3)$alkyl; and q is 0, 1, 2, 3, 4, 5, or 6.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently $(C_1-C_6)$alkoxy, $(C_1-C_6)$ alkyl, $(C_1-C_6)$alkylthio, cyano, $(C_3-C_8)$cycloalkyloxy, halogen, halo$(C_1-C_6)$alkoxy, halo$(C_1-C_6)$alkyl, (4-7 membered)

heterocycleoxy, or hydroxy(C₁-C₆)alkoxy; Y is phenyl, pyridine, pyrimidine, pyrazine, pyridazine, thiazole, pyrazole, or thiadiazole, wherein each is optionally substituted with 1 substituent that is (C₁-C₆)alkoxy, (C₁-C₆)alkoxy(C₁-C₆)alkyl, (C₁-C₆)alkoxycarbonyl(C₁-C₆)alkyl, (C₁-C₃)alkyl, (C₁-C₆)alkyl, carboxy(C₁-C₆)alkyl, halogen, halo(C₁-C₆)alkyl, hydroxy(C₁-C₆)alkoxy, or hydroxy(C₁-C₆)alkyl; Z is

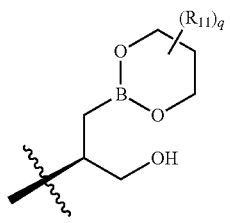

wherein B is boron; R₁₁ at each occurrence is methyl; and q is 0, 1, 2, or 3.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently (C₁-C₆)alkoxy, (C₁-C₆)alkyl, (C₁-C₆)alkylthio, cyano, (C₃-C₈)cycloalkyloxy, halogen, halo(C₁-C₆)alkoxy, halo(C₁-C₆)alkyl, (4-7 membered) heterocycleoxy, or hydroxy(C₁-C₆)alkoxy; Y is phenyl, pyridine, pyrimidine, pyrazine, pyridazine, thiazole, pyrazole, or thiadiazole, wherein each is optionally substituted with 1 substituent that is (C₁-C₆)alkoxy, (C₁-C₆)alkoxy(C₁-C₆)alkyl, (C₁-C₆)alkoxycarbonyl(C₁-C₆)alkyl, (C₁-C₃)alkyl, (C₁-C₆)alkyl, carboxy(C₁-C₆)alkyl, halogen, halo(C₁-C₆)alkyl, hydroxy(C₁-C₆)alkoxy, or hydroxy(C₁-C₆)alkyl; Z is

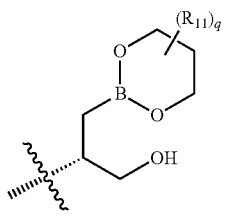

wherein B is boron; R₁₁ at each occurrence is methyl; and q is 0, 1, 2, or 3.

In another embodiment, the present invention provides compounds of Formula (I), or a pharmaceutically acceptable salt thereof, wherein X is phenyl, pyridine, or pyrimidine, wherein each is optionally substituted with 1, 2, or 3 substituents that are independently (C₁-C₆)alkoxy, (C₁-C₆)alkyl, (C₁-C₆)alkylthio, cyano, (C₃-C₈)cycloalkyloxy, halogen, halo(C₁-C₆)alkoxy, halo(C₁-C₆)alkyl, (4-7 membered) heterocycleoxy, or hydroxy(C₁-C₆)alkoxy; Y is phenyl, pyridine, pyrimidine, pyrazine, pyridazine, thiazole, pyrazole, or thiadiazole, wherein each is optionally substituted with 1 substituent that is (C₁-C₆)alkoxy, (C₁-C₆)alkoxy(C₁-C₆)alkyl, (C₁-C₆)alkoxycarbonyl(C₁-C₆)alkyl, (C₁-C₃)alkyl, (C₁-C₆)alkyl, carboxy(C₁-C₆)alkyl, halogen, halo(C₁-C₆)alkyl, hydroxy(C₁-C₆)alkoxy, or hydroxy(C₁-C₆)alkyl; Z is

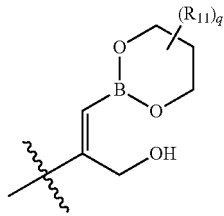

wherein B is boron; R₁₁ at each occurrence is methyl; and q is 0, 1, 2, or 3.

In another embodiment, the present invention provides compounds of Formula (I), or a pharmaceutically acceptable salt thereof, wherein X is

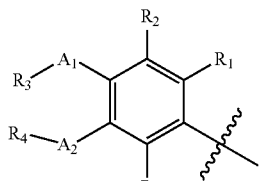

,

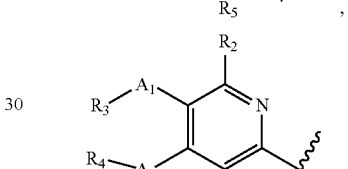

,

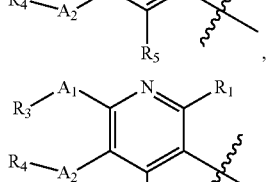

,

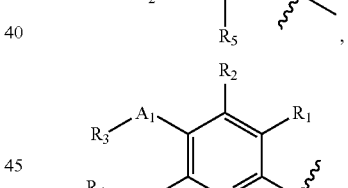

,

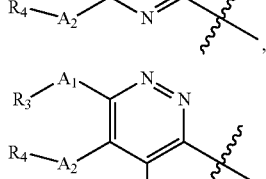

,

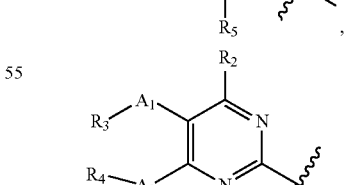

,

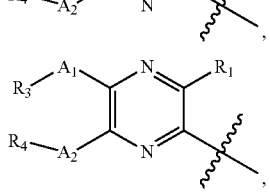

,

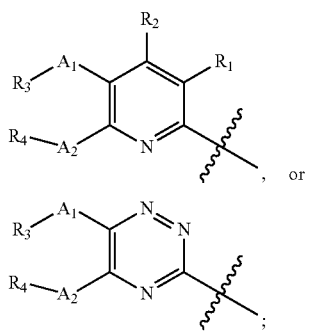
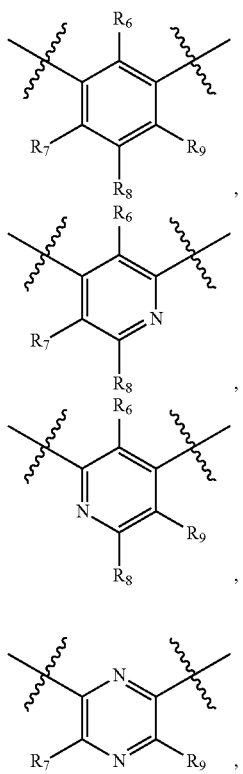
$A_1$ and $A_2$ are independently O or S; $R_1$, $R_2$, and $R_5$ are independently H, deuterium, cyano, halogen, or halo($C_1$-$C_6$)alkyl; $R_3$ and $R_4$ are independently H, ($C_1$-$C_6$)alkyl, ($C_1$-$C_6$)alkyl-$d_{1-13}$, ($C_3$-$C_8$)cycloalkyl, halo($C_1$-$C_6$)alkyl, or hydroxy($C_1$-$C_6$)alkyl; Y is
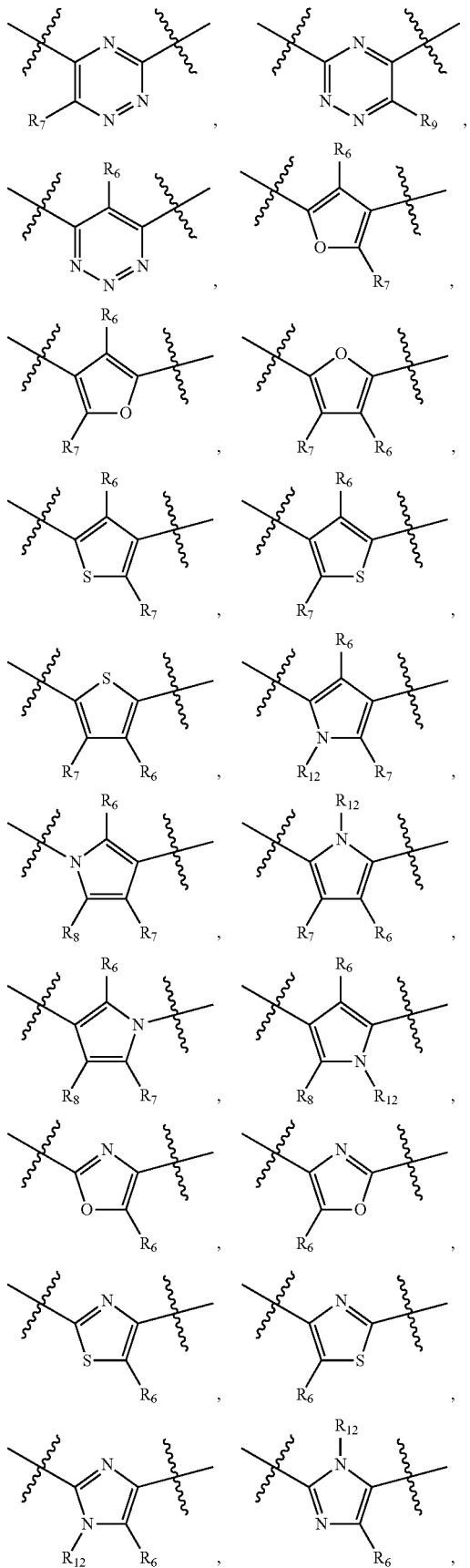

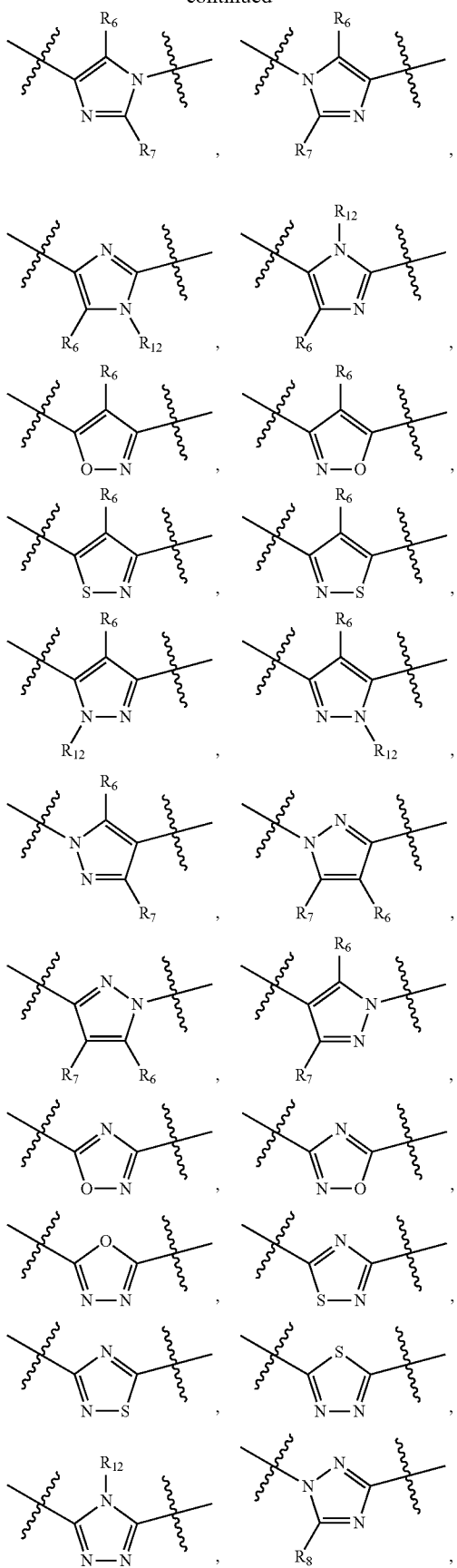

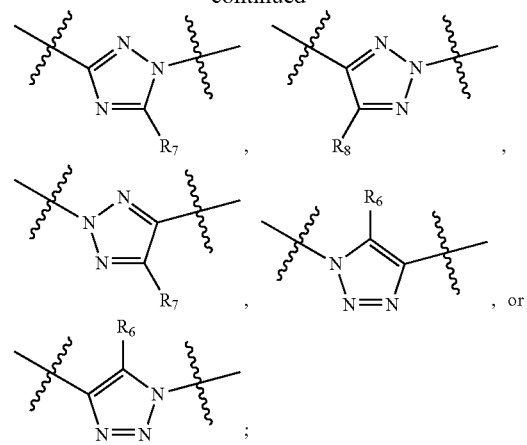

$R_6$, $R_7$, $R_8$, and $R_9$ are independently H, deuterium, $(C_1-C_6)$alkoxy, $(C_1-C_6)$alkoxy-$d_{1-13}$, $(C_1-C_6)$alkoxy$(C_1-C_6)$alkoxy, $(C_1-C_6)$alkoxy$(C_1-C_6)$alkyl, $(C_1-C_6)$alkoxycarbonyl, $(C_1-C_6)$alkoxycarbonyl$(C_1-C_6)$alkyl, $(C_1-C_3)$alkyl, $(C_1-C_3)$alkyl-$d_{1-7}$, $(C_1-C_6)$alkyl, $(C_1-C_6)$alkyl-$d_{1-13}$, $(C_1-C_6)$alkylcarbonyl, $(C_1-C_6)$alkylthio, carboxy, carboxy$(C_1-C_6)$alkoxy, carboxy$(C_1-C_6)$alkyl, cyano, halogen, halo$(C_1-C_6)$alkoxy, halo$(C_1-C_6)$alkyl, hydroxy, hydroxy$(C_1-C_6)$alkoxy, hydroxy$(C_1-C_6)$alkyl, mercapto, nitro, —$NR_CR_D$, $NR_CR_D(C_1-C_6)$alkoxy, $NR_CR_D(C_1-C_6)$alkyl, or $(NR_CR_D)$carbonyl; $R_C$ and $R_D$ are independently hydrogen, $(C_1-C_6)$alkyl, or $(C_1-C_6)$alkylcarbonyl; Z is as defined in the Summary section herein; $R_{10}$ at each occurrence is independently H, deuterium, $(C_1-C_6)$alkoxy$(C_1-C_6)$alkyl, $(C_1-C_6)$alkyl, $(C_1-C_6)$alkyl-$d_{1-13}$, $(C_1-C_6)$alkylthio$(C_1-C_6)$alkyl, hydroxy$(C_1-C_6)$alkyl, or thio$(C_1-C_6)$alkyl; $R_{11}$ at each occurrence is independently $(C_1-C_3)$alkyl or $(C_1-C_3)$alkyl-$d_{1-7}$; $R_{12}$ is independently H, $(C_1-C_6)$alkyl, or hydroxy$(C_1-C_6)$alkyl; m is 0, 1, 2, or 3; n is 0, 1, 2, 3, or 4; p is 0, 1, 2, 3, 4, or 5; q is 0, 1, 2, 3, 4, 5, or 6; and r is 0, 1, 2, 3, 4, 5, 6 or 7.

In another embodiment, the present invention provides compounds of Formula (I), or a pharmaceutically acceptable salt thereof, wherein X is

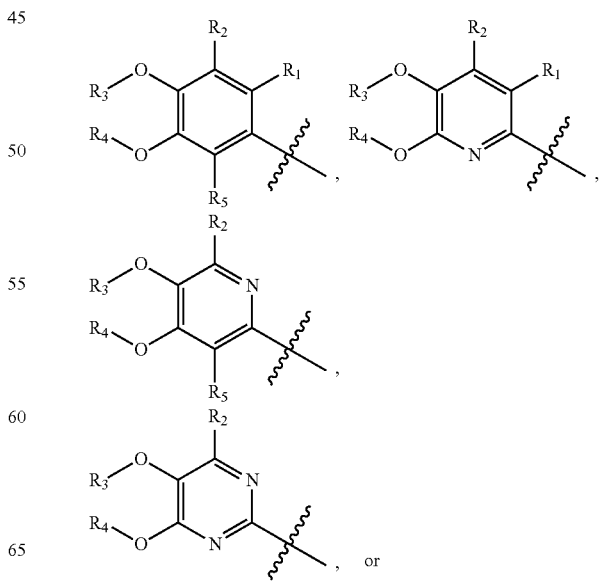

-continued

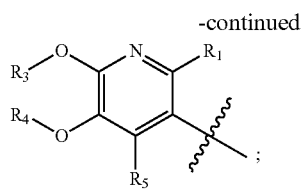

$R_1$, $R_2$, and $R_5$ are independently H, cyano, halogen, or halo($C_1$-$C_6$)alkyl; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; Y is

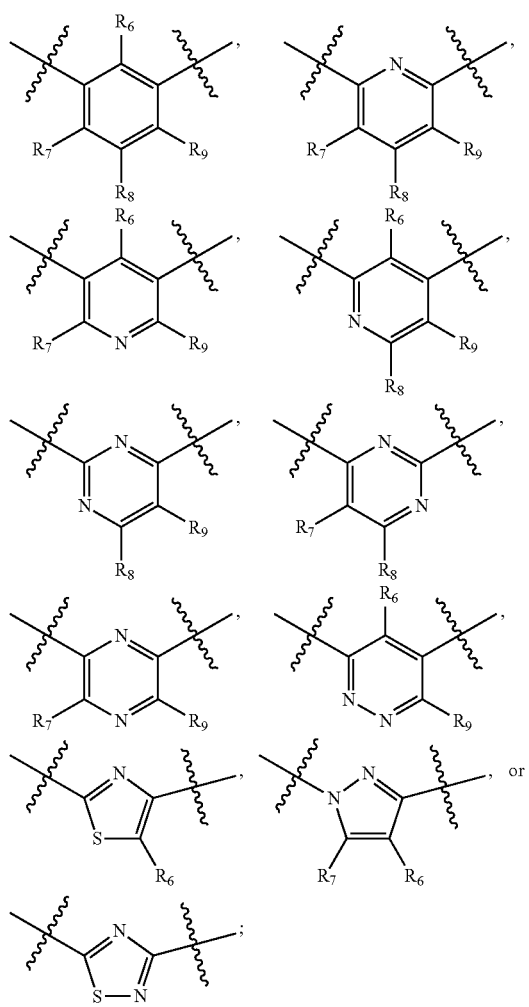

$R_6$, $R_7$, $R_8$, and $R_9$ are independently H, ($C_1$-$C_6$)alkoxy, ($C_1$-$C_6$)alkoxy($C_1$-$C_6$)alkyl, ($C_1$-$C_6$)alkoxycarbonyl($C_1$-$C_6$)alkyl, ($C_1$-$C_3$)alkyl, ($C_1$-$C_6$)alkyl, carboxy($C_1$-$C_6$)alkyl, halogen, halo($C_1$-$C_6$)alkyl, hydroxy($C_1$-$C_6$)alkoxy, or hydroxy($C_1$-$C_6$)alkyl; Z is as defined in the Summary section herein; $R_{10}$ at each occurrence is independently H, ($C_1$-$C_6$)alkoxy($C_1$-$C_6$)alkyl, ($C_1$-$C_6$)alkyl, ($C_1$-$C_6$)alkylthio($C_1$-$C_6$)alkyl, hydroxy($C_1$-$C_6$)alkyl, or thio($C_1$-$C_6$)alkyl; $R_{11}$ at each occurrence is independently ($C_1$-$C_3$)alkyl; $R_{12}$ is independently H, ($C_1$-$C_6$)alkyl, or hydroxy($C_1$-$C_6$)alkyl; m is 0, 1, 2, or 3; n is 0, 1, 2, 3, or 4; p is 0, 1, 2, 3, 4, or 5; q is 0, 1, 2, 3, 4, 5, or 6; and r is 0, 1, 2, 3, 4, 5, 6 or 7.

In another embodiment, the present invention provides compounds of Formula (I), or a pharmaceutically acceptable salt thereof, wherein X is

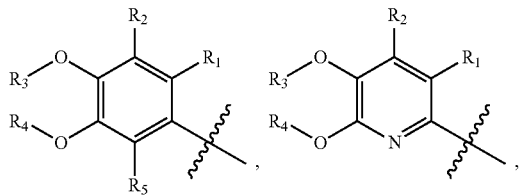

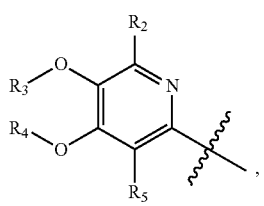

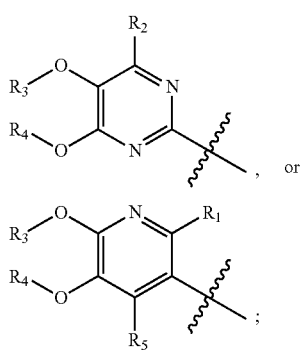, or

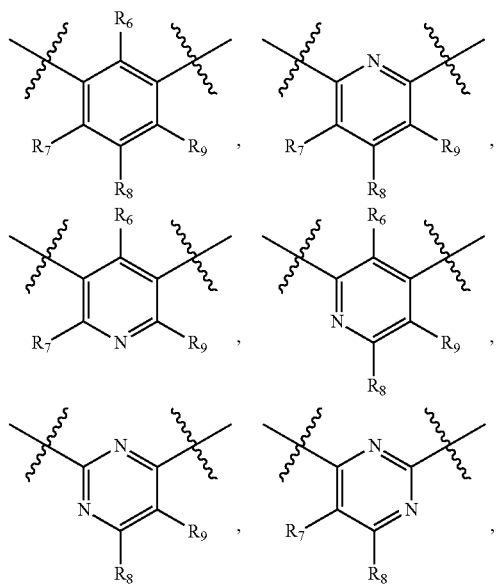

$R_1$, $R_2$, and $R_5$ are independently H, cyano, halogen, or halo($C_1$-$C_6$)alkyl; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; Y is

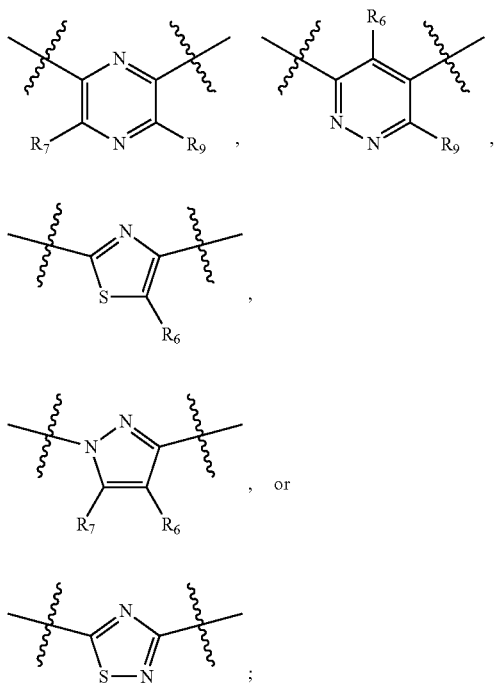

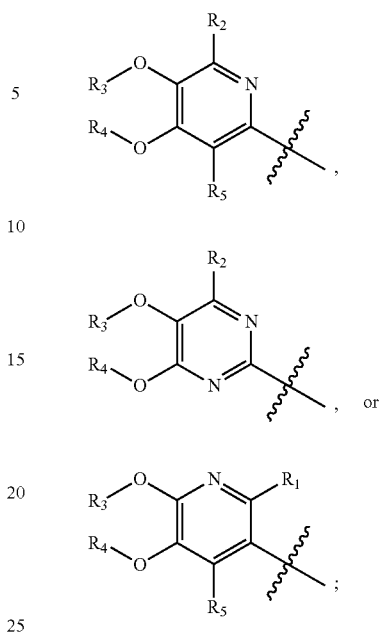

$R_6$, $R_7$, $R_8$, and $R_9$ are independently H, $(C_1-C_6)$alkoxy, $(C_1-C_6)$alkoxy$(C_1-C_6)$alkyl, $(C_1-C_6)$alkoxycarbonyl$(C_1-C_6)$alkyl, $(C_1-C_3)$alkyl, $(C_1-C_6)$alkyl, carboxy$(C_1-C_6)$alkyl, halogen, halo$(C_1-C_6)$alkyl, hydroxy$(C_1-C_6)$alkoxy, or hydroxy$(C_1-C_6)$alkyl; Z is

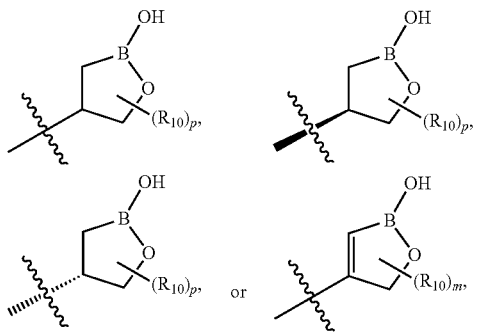

wherein B is boron; $R_{10}$ at each occurrence is independently H, $(C_1-C_6)$alkyl, or hydroxy$(C_1-C_6)$alkyl; m is 0, 1, 2, or 3; and p is 0, 1, 2, 3, 4, or 5.

In another embodiment, the present invention provides compounds of Formula (I), or a pharmaceutically acceptable salt thereof, wherein X is

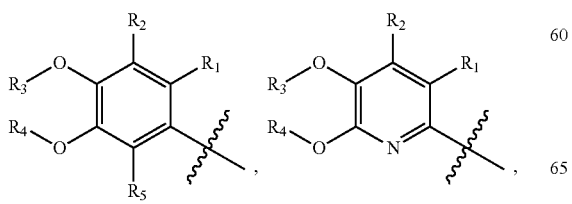

$R_1$, $R_2$, and $R_5$ are independently H, cyano, halogen, or halo$(C_1-C_6)$alkyl; $R_3$ and $R_4$ are independently $(C_1-C_6)$alkyl, $(C_3-C_8)$cycloalkyl, halo$(C_1-C_6)$alkyl, or hydroxy$(C_1-C_6)$alkyl; Y is

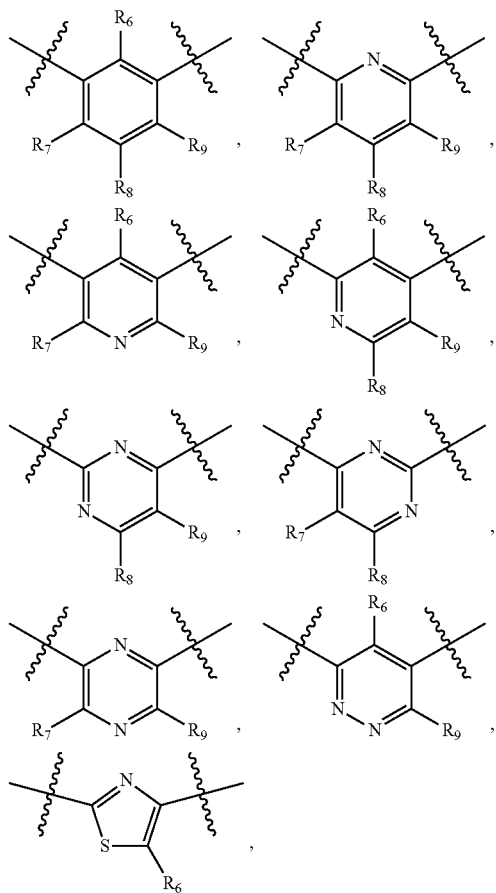

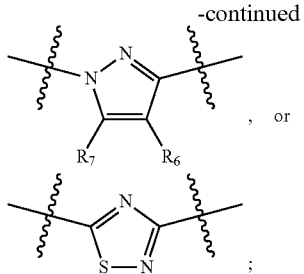

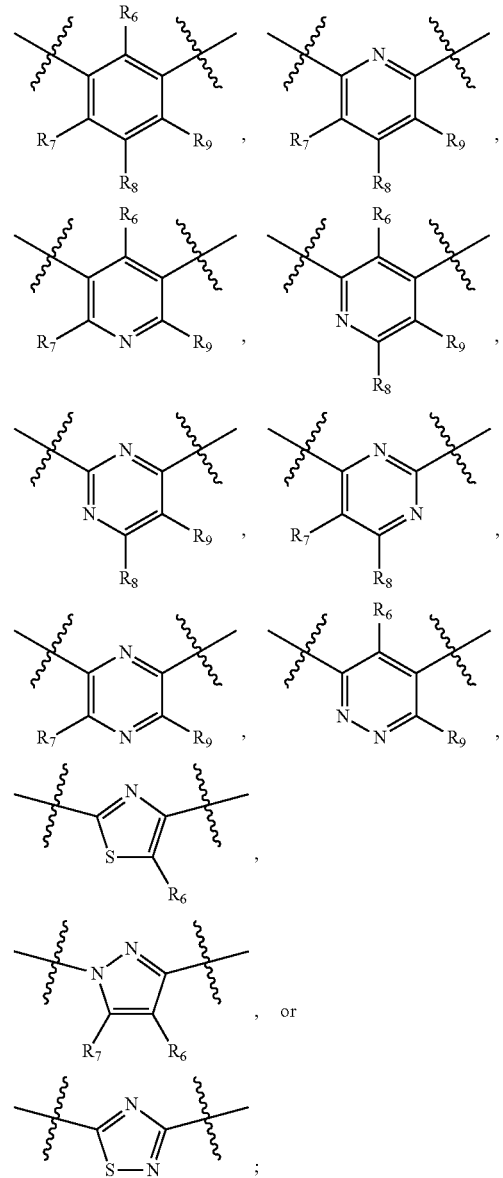

$R_6$, $R_7$, $R_8$, and $R_9$ are independently H, $(C_1$-$C_6)$alkoxy, $(C_1$-$C_6)$alkoxy$(C_1$-$C_6)$alkyl, $(C_1$-$C_6)$alkoxycarbonyl$(C_1$-$C_6)$alkyl, $(C_1$-$C_3)$alkyl, $(C_1$-$C_6)$alkyl, carboxy$(C_1$-$C_6)$alkyl, halogen, halo$(C_1$-$C_6)$alkyl, hydroxy$(C_1$-$C_6)$alkoxy, or hydroxy$(C_1$-$C_6)$alkyl; and Z is

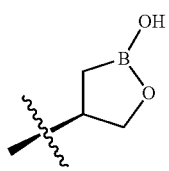

wherein B is boron.

In another embodiment, the present invention provides compounds of Formula (I), or a pharmaceutically acceptable salt thereof, wherein X is

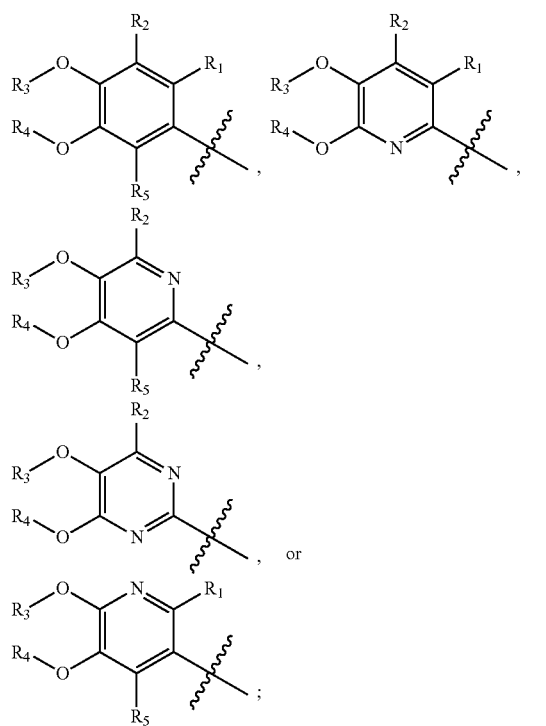

$R_1$, $R_2$, and $R_5$ are independently H, cyano, halogen, or halo$(C_1$-$C_6)$alkyl; $R_3$ and $R_4$ are independently $(C_1$-$C_6)$alkyl, $(C_3$-$C_8)$cycloalkyl, halo$(C_1$-$C_6)$alkyl, or hydroxy$(C_1$-$C_6)$alkyl; Y is $R_6$, $R_7$, $R_8$, and $R_9$ are independently H, $(C_1$-$C_6)$alkoxy, $(C_1$-$C_6)$alkoxy$(C_1$-$C_6)$alkyl, $(C_1$-$C_6)$alkoxycarbonyl$(C_1$-$C_6)$alkyl, $(C_1$-$C_3)$alkyl, $(C_1$-$C_6)$alkyl, carboxy$(C_1$-$C_6)$alkyl, halogen, halo$(C_1$-$C_6)$alkyl, hydroxy$(C_1$-$C_6)$alkoxy, or hydroxy$(C_1$-$C_6)$alkyl; and Z is

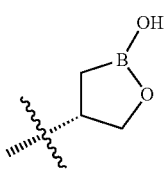

wherein B is boron.

In another embodiment, the present invention provides compounds of Formula (I), or a pharmaceutically acceptable salt thereof, wherein X is

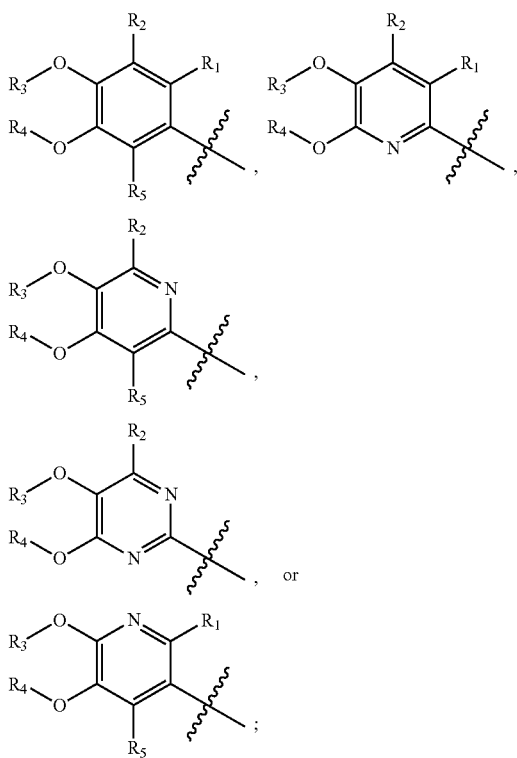

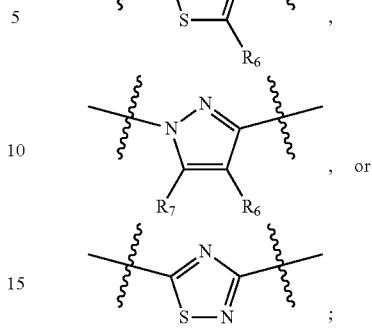

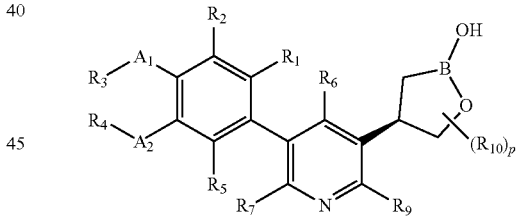

$R_1$, $R_2$, and $R_5$ are independently H, cyano, halogen, or halo($C_1$-$C_6$)alkyl; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; Y is

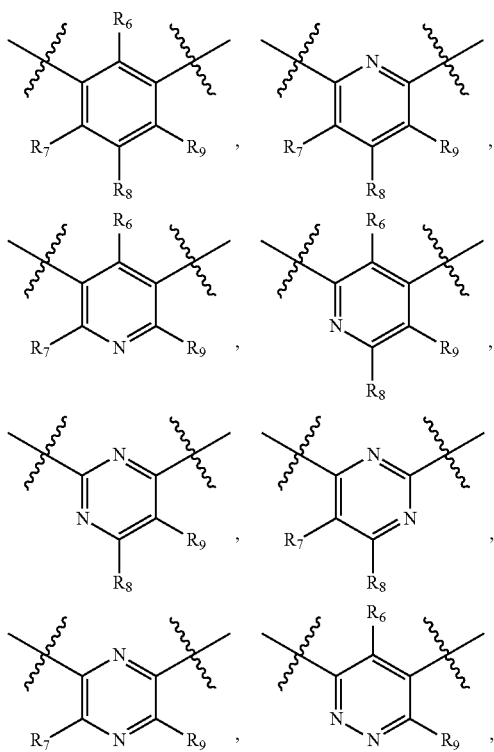

$R_6$, $R_7$, $R_8$, and $R_9$ are independently H, ($C_1$-$C_6$)alkoxy, ($C_1$-$C_6$)alkoxy($C_1$-$C_6$)alkyl, ($C_1$-$C_6$)alkoxycarbonyl($C_1$-$C_6$)alkyl, ($C_1$-$C_3$)alkyl, ($C_1$-$C_6$)alkyl, carboxy($C_1$-$C_6$)alkyl, halogen, halo($C_1$-$C_6$)alkyl, hydroxy($C_1$-$C_6$)alkoxy, or hydroxy($C_1$-$C_6$)alkyl; and Z is

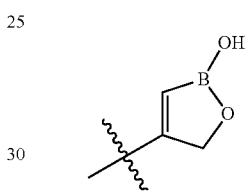

wherein B is boron.

In another embodiment, the present invention provides compounds of Formula (IA)

Formula (IA)

or a pharmaceutically acceptable salt thereof, wherein B is boron; $A_1$ and $A_2$ are independently O or S; $R_1$, $R_2$, and $R_5$ are independently H, deuterium, ($C_2$-$C_6$)alkenyl, ($C_2$-$C_6$)alkenyloxy, ($C_2$-$C_6$)alkenylthio, ($C_1$-$C_6$)alkoxy, ($C_1$-$C_6$)alkoxy-$d_{1-13}$, ($C_1$-$C_6$)alkoxy($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkyl, ($C_1$-$C_6$)alkyl-$d_{1-13}$, ($C_1$-$C_6$)alkylcarbonyl, ($C_1$-$C_6$)alkylthio, ($C_2$-$C_6$)alkynyl, ($C_2$-$C_6$)alkynyloxy, ($C_2$-$C_6$)alkynylthio, aryl, aryl($C_1$-$C_6$)alkoxy, aryl($C_1$-$C_6$)alkyl, aryl($C_1$-$C_6$)alkylthio, aryloxy, arylthio, carboxy, carboxy($C_1$-$C_6$)alkoxy, carboxy($C_1$-$C_6$)alkyl, cyano, ($C_3$-$C_8$)cycloalkyl, ($C_3$-$C_8$)cycloalkyl($C_1$-$C_6$)alkoxy, ($C_3$-$C_8$)cycloalkyl($C_1$-$C_6$)alkyl, $C_3$-$C_8$)cycloalkyl($C_1$-$C_6$)alkylthio, ($C_3$-$C_8$)cycloalkyloxy, ($C_3$-$C_8$)cycloalkylthio, halogen, halo($C_1$-$C_6$)alkoxy, halo($C_1$-$C_6$)alkyl, halo($C_1$-$C_6$)alkylthio, (5-6 membered)heteroaryl, (5-6 membered)heteroaryl($C_1$-$C_6$)alkoxy, (5-6 membered)heteroaryl($C_1$-$C_6$)alkyl, (5-6 membered)heteroaryl($C_1$-$C_6$)alkylthio, (5-6 membered)heteroaryloxy, (5-6 membered)heteroarylthio, (4-7 membered)heterocycle containing at least one heteroatom independently selected from the group consisting of O, N, and S, (4-7 membered)heterocycle($C_1$-$C_6$)alkoxy, (4-7 membered)heterocycle($C_1$-$C_6$)alkyl, (4-7 membered)heterocycle($C_1$-$C_6$)alkylthio, (4-7 membered) heterocycleoxy, (4-7 membered)heterocyclethio, hydroxy, hydroxy($C_1$-$C_6$)alkoxy, hydroxy($C_1$-$C_6$)alkyl, mercapto, nitro, thio($C_1$-$C_6$)alkyl, —$NR_AR_B$, $NR_AR_B$ ($C_1$-$C_6$)alkoxy, $NR_AR_B$ ($C_1$-$C_6$)alkyl, or ($NR_AR_B$)carbonyl; $R_A$ and $R_B$ are independently hydrogen, ($C_1$-$C_6$)alkyl, or ($C_1$-$C_6$)alkylcarbonyl; $R_3$ and $R_4$ are independently H, deuterium, ($C_1$-$C_3$)alkyl, ($C_1$-$C_3$)alkyl-$d_{1-7}$, ($C_1$-$C_6$)alkyl, ($C_1$-$C_6$)alkyl-$d_{1-13}$, ($C_3$-$C_8$)cycloalkyl, halo($C_1$-$C_6$)alkyl, or hydroxy($C_1$-$C_6$)alkyl; $R_6$, $R_7$, and $R_9$ are independently, H, deuterium, ($C_1$-$C_6$)alkoxy, ($C_1$-$C_6$)alkoxy-$d_{1-13}$, ($C_1$-$C_6$)alkoxy($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_3$)alkyl, ($C_1$-$C_3$)alkyl-$d_{1-7}$, ($C_1$-$C_6$)alkyl, ($C_1$-$C_6$)alkyl-$d_{1-13}$, ($C_1$-$C_6$)alkylcarbonyl, ($C_1$-$C_6$)alkylthio, carboxy, carboxy($C_1$-$C_6$)alkoxy, carboxy($C_1$-$C_6$)alkyl, cyano, halogen, halo($C_1$-$C_6$)alkoxy, halo($C_1$-$C_6$)alkyl, hydroxy, hydroxy($C_1$-$C_6$)alkoxy, hydroxy($C_1$-$C_6$)alkyl, mercapto, nitro, —$NR_CR_D$, $NR_CR_D$($C_1$-$C_6$)alkoxy, $NR_CR_D$($C_1$-$C_6$)alkyl, or ($NR_CR_D$)carbonyl; RC and $R_D$ are independently hydrogen, ($C_1$-$C_6$)alkyl, or ($C_1$-$C_6$)alkylcarbonyl; $R_{10}$ at each occurrence is independently deuterium, ($C_1$-$C_6$)alkoxy($C_1$-$C_6$)alkyl, ($C_1$-$C_3$)alkyl, ($C_1$-$C_3$)alkyl-$d_{1-7}$, ($C_1$-$C_6$)alkyl, ($C_1$-$C_6$)alkyl-$d_{1-13}$, ($C_1$-$C_6$)alkylthio($C_1$-$C_6$)alkyl, hydroxy($C_1$-$C_6$)alkyl, or thio($C_1$-$C_6$)alkyl; and p is 0, 1, 2, 3, 4, or 5.

In another embodiment, the present invention provides compounds of Formula (IA), or a pharmaceutically acceptable salt thereof, wherein B is boron; $A_1$ and $A_2$ are O; $R_1$, $R_2$, and $R_5$ are independently H, cyano, halogen, or halo ($C_1$-$C_6$)alkyl; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently, H, ($C_1$-$C_6$)alkoxy, ($C_1$-$C_6$)alkoxy($C_1$-$C_6$)alkyl, ($C_1$-$C_6$)alkoxycarbonyl($C_1$-$C_6$)alkyl, ($C_1$-$C_6$)alkyl, carboxy($C_1$-$C_6$)alkyl, halogen, halo($C_1$-$C_6$)alkyl, hydroxy($C_1$-$C_6$)alkoxy, or hydroxy($C_1$-$C_6$)alkyl; $R_{10}$ is ($C_1$-$C_3$)alkyl, ($C_1$-$C_6$)alkyl or hydroxy($C_1$-$C_6$)alkyl; and p is 0 or 1.

In another embodiment, the present invention provides compounds of Formula (IA), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently H or ($C_1$-$C_3$)alkyl; $R_{10}$ is methyl; and p is 0, 1, or 2.

In another embodiment, the present invention provides compounds of Formula (IA), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently H or ($C_1$-$C_3$)alkyl; and p is 0.

In another embodiment, the present invention provides compounds of Formula (IA), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_3$)alkyl; $R_6$, $R_7$, and $R_9$ are independently H or ($C_1$-$C_3$)alkyl; and p is 0.

In another embodiment, the present invention provides compounds of Formula (IA), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_3$)alkyl; $R_6$, $R_7$, and $R_9$ are H; and p is 0.

In another embodiment, the present invention provides compounds of Formula (IB)

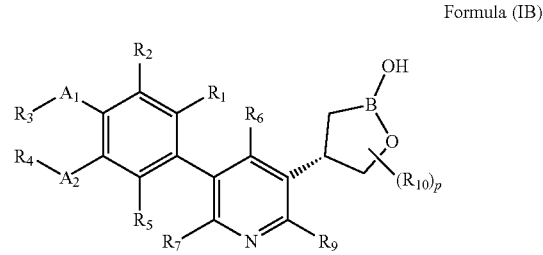

Formula (IB)

or a pharmaceutically acceptable salt thereof, wherein B is boron; $A_1$ and $A_2$ are independently O or S; $R_1$, $R_2$, and $R_5$ are independently H, deuterium, ($C_2$-$C_6$)alkenyl, ($C_2$-$C_6$)alkenyloxy, ($C_2$-$C_6$)alkenylthio, ($C_1$-$C_6$)alkoxy, ($C_1$-$C_6$)alkoxy-$d_{1-13}$, ($C_1$-$C_6$)alkoxy($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkyl, ($C_1$-$C_6$)alkyl-$d_{1-13}$, ($C_1$-$C_6$)alkylcarbonyl, ($C_1$-$C_6$)alkylthio, ($C_2$-$C_6$)alkynyl, ($C_2$-$C_6$)alkynyloxy, ($C_2$-$C_6$)alkynylthio, aryl, aryl($C_1$-$C_6$)alkoxy, aryl($C_1$-$C_6$)alkyl, aryl($C_1$-$C_6$)alkylthio, aryloxy, arylthio, carboxy, carboxy($C_1$-$C_6$)alkoxy, carboxy($C_1$-$C_6$)alkyl, cyano, ($C_3$-$C_8$)cycloalkyl, ($C_3$—C)cycloalkyl($C_1$-$C_6$)alkoxy, ($C_3$-$C_8$)cycloalkyl($C_1$-$C_6$)alkyl, $C_3$-$C_8$)cycloalkyl($C_1$-$C_6$)alkylthio, ($C_3$-$C_8$)cycloalkyloxy, ($C_3$-$C_8$)cycloalkylthio, halogen, halo($C_1$-$C_6$)alkoxy, halo($C_1$-$C_6$)alkyl, halo($C_1$-$C_6$)alkylthio, (5-6 membered)heteroaryl, (5-6 membered)heteroaryl($C_1$-$C_6$)alkoxy, (5-6 membered)heteroaryl($C_1$-$C_6$)alkyl, (5-6 membered)heteroaryl($C_1$-$C_6$)alkylthio, (5-6 membered)heteroaryloxy, (5-6 membered)heteroarylthio, (4-7 membered)heterocycle containing at least one heteroatom independently selected from the group consisting of O, N, and S, (4-7 membered)heterocycle($C_1$-$C_6$)alkoxy, (4-7 membered)heterocycle($C_1$-$C_6$)alkyl, (4-7 membered)heterocycle($C_1$-$C_6$)alkylthio, (4-7 membered) heterocycleoxy, (4-7 membered)heterocyclethio, hydroxy, hydroxy($C_1$-$C_6$)alkoxy, hydroxy($C_1$-$C_6$)alkyl, mercapto, nitro, thio($C_1$-$C_6$)alkyl, —$NR_AR_B$, $NR_AR_B$ ($C_1$-$C_6$)alkoxy, $NR_AR_B$ ($C_1$-$C_6$)alkyl, or ($NR_AR_B$)carbonyl; $R_A$ and $R_B$ are independently hydrogen, ($C_1$-$C_6$)alkyl, or ($C_1$-$C_6$)alkylcarbonyl; $R_3$ and $R_4$ are independently H, deuterium, ($C_1$-$C_3$)alkyl, ($C_1$-$C_3$)alkyl-$d_{1-7}$, ($C_1$-$C_6$)alkyl, ($C_1$-$C_6$)alkyl-$d_{1-13}$, ($C_3$-$C_8$)cycloalkyl, halo($C_1$-$C_6$)alkyl, or hydroxy($C_1$-$C_6$)alkyl; $R_6$, $R_7$, and $R_9$ are independently, H, deuterium, ($C_1$-$C_6$)alkoxy, ($C_1$-$C_6$)alkoxy-$d_{1-13}$, ($C_1$-$C_6$)alkoxy($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_3$)alkyl, ($C_1$-$C_6$)alkyl, ($C_1$-$C_6$)alkylcarbonyl, ($C_1$-$C_6$)alkylthio, carboxy, carboxy($C_1$-$C_6$)alkoxy, carboxy($C_1$-$C_6$)alkyl, cyano, halogen, halo($C_1$-$C_6$)alkoxy, halo($C_1$-$C_6$)alkyl, hydroxy, hydroxy($C_1$-$C_6$)alkoxy, hydroxy($C_1$-$C_6$)alkyl, mercapto, nitro, —$NR_CR_D$, $NR_CR_D$($C_1$-$C_6$)alkoxy, $NR_CR_D$ ($C_1$-$C_6$)alkyl, or ($NR_CR_D$)carbonyl; $R_C$ and $R_D$ are independently hydrogen, ($C_1$-$C_6$)alkyl, or ($C_1$-$C_6$)alkylcarbonyl; $R_{10}$ at each occurrence is independently deuterium, ($C_1$-$C_6$)alkoxy($C_1$-$C_6$)alkyl, ($C_1$-$C_3$)alkyl, ($C_1$-$C_3$)alkyl-$d_{1-7}$, ($C_1$-$C_6$)alkyl, ($C_1$-$C_6$)alkyl-$d_{1-13}$, ($C_1$-$C_6$)alkylthio($C_1$-$C_6$)alkyl, hydroxy($C_1$-$C_6$)alkyl, or thio($C_1$-$C_6$)alkyl; and p is 0, 1, 2, 3, 4, or 5.

In another embodiment, the present invention provides compounds of Formula (IB), or a pharmaceutically acceptable salt thereof, wherein B is boron; $A_1$ and $A_2$ are O; $R_1$, $R_2$, and $R_5$ are independently H, cyano, halogen, or halo ($C_1$-$C_6$)alkyl; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently, H, ($C_1$-$C_6$)alkoxy, ($C_1$-$C_6$)alkoxy($C_1$-$C_6$)alkyl, ($C_1$-$C_6$)alkoxycarbonyl($C_1$-$C_6$)alkyl, ($C_1$-$C_6$)alkyl, carboxy($C_1$-$C_6$)alkyl, halogen, halo($C_1$-$C_6$)alkyl, hydroxy($C_1$-$C_6$)alkoxy, or hydroxy($C_1$-$C_6$)alkyl; $R_{10}$ is ($C_1$-$C_3$)alkyl, ($C_1$-$C_6$)alkyl or hydroxy($C_1$-$C_6$)alkyl; and p is 0 or 1.

In another embodiment, the present invention provides compounds of Formula (IB), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently H or ($C_1$-$C_3$)alkyl; $R_{10}$ is methyl; and p is 0, 1, or 2.

In another embodiment, the present invention provides compounds of Formula (IB), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently H or ($C_1$-$C_3$)alkyl; and p is 0.

In another embodiment, the present invention provides compounds of Formula (IB), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_3$)alkyl; $R_6$, $R_7$, and $R_9$ are independently H or ($C_1$-$C_3$)alkyl; and p is 0.

In another embodiment, the present invention provides compounds of Formula (IB), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_3$)alkyl; $R_6$, $R_7$, and $R_9$ are H; and p is 0.

In another embodiment, the present invention provides compounds of Formula (IC)

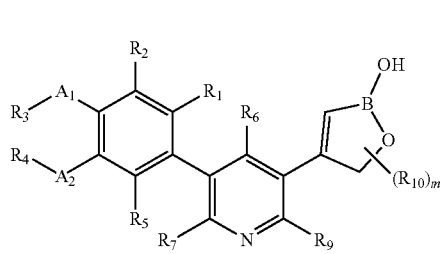

Formula (IC)

or a pharmaceutically acceptable salt thereof, wherein B is boron; $A_1$ and $A_2$ are independently O or S; $R_1$, $R_2$, and $R_5$ are independently H, deuterium, ($C_2$-$C_6$)alkenyl, ($C_2$-$C_6$)alkenyloxy, ($C_2$-$C_6$)alkenylthio, ($C_1$-$C_6$)alkoxy, ($C_1$-$C_6$)alkoxy-$d_{1-13}$, ($C_1$-$C_6$)alkoxy($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkyl, ($C_1$-$C_6$)alkyl-$d_{1-13}$, ($C_1$-$C_6$)alkylcarbonyl, ($C_1$-$C_6$)alkylthio, ($C_2$-$C_6$)alkynyl, ($C_2$-$C_6$)alkynyloxy, ($C_2$-$C_6$)alkynylthio, aryl, aryl($C_1$-$C_6$)alkoxy, aryl($C_1$-$C_6$)alkyl, aryl($C_1$-$C_6$)alkylthio, aryloxy, arylthio, carboxy, carboxy($C_1$-$C_6$)alkoxy, carboxy ($C_1$-$C_6$)alkyl, cyano, ($C_3$-$C_8$)cycloalkyl, ($C_3$-$C_8$)cycloalkyl ($C_1$-$C_6$)alkoxy, ($C_3$-$C_8$)cycloalkyl($C_1$-$C_6$)alkyl, $C_3$-$C_8$)cycloalkyl($C_1$-$C_6$)alkylthio, ($C_3$-$C_8$)cycloalkyloxy, ($C_3$-$C_8$) cycloalkylthio, halogen, halo($C_1$-$C_6$)alkoxy, halo($C_1$-$C_6$) alkyl, halo($C_1$-$C_6$)alkylthio, (5-6 membered)heteroaryl, (5-6 membered)heteroaryl($C_1$-$C_6$)alkoxy, (5-6 membered)heteroaryl($C_1$-$C_6$)alkyl, (5-6 membered)heteroaryl($C_1$-$C_6$)alkylthio, (5-6 membered)heteroaryloxy, (5-6 membered)heteroarylthio, (4-7 membered)heterocycle containing at least one heteroatom independently selected from the group consisting of O, N, and S, (4-7 membered)heterocycle($C_1$-$C_6$) alkoxy, (4-7 membered)heterocycle($C_1$-$C_6$)alkyl, (4-7 membered)heterocycle($C_1$-$C_6$)alkylthio, (4-7 membered) heterocycleoxy, (4-7 membered)heterocyclethio, hydroxy, hydroxy($C_1$-$C_6$)alkoxy, hydroxy($C_1$-$C_6$)alkyl, mercapto, nitro, thio($C_1$-$C_6$)alkyl, —$NR_AR_B$, $NR_AR_B$ ($C_1$-$C_6$)alkoxy, $NR_AR_B$ ($C_1$-$C_6$)alkyl, or ($NR_AR_B$)carbonyl; $R_A$ and $R_B$ are independently hydrogen, ($C_1$-$C_6$)alkyl, or ($C_1$-$C_6$)alkylcarbonyl; $R_3$ and $R_4$ are independently H, deuterium, ($C_1$-$C_3$) alkyl, ($C_1$-$C_3$)alkyl-$d_{1-7}$, ($C_1$-$C_6$)alkyl, ($C_1$-$C_6$)alkyl-$d_{1-13}$, ($C_3$-$C_8$)cycloalkyl, halo($C_1$-$C_6$)alkyl, or hydroxy($C_1$-$C_6$)alkyl; $R_6$, $R_7$, and $R_9$ are independently, H, deuterium, ($C_1$-$C_6$)alkoxy, ($C_1$-$C_6$)alkoxy-$d_{1-13}$, ($C_1$-$C_6$)alkoxy($C_1$-$C_6$) alkoxy, ($C_1$-$C_6$)alkoxy($C_1$-$C_6$)alkyl, ($C_1$-$C_6$) alkoxycarbonyl, ($C_1$-$C_6$)alkoxycarbonyl($C_1$-$C_6$)alkyl, ($C_1$-$C_3$)alkyl, ($C_1$-$C_3$)alkyl-$d_{1-7}$, ($C_1$-$C_6$)alkyl, ($C_1$-$C_6$)alkyl-$d_{1-13}$, ($C_1$-$C_6$)alkylcarbonyl, ($C_1$-$C_6$)alkylthio, carboxy, carboxy($C_1$-$C_6$)alkoxy, carboxy($C_1$-$C_6$)alkyl, cyano, halogen, halo($C_1$-$C_6$)alkoxy, halo($C_1$-$C_6$)alkyl, hydroxy, hydroxy($C_1$-$C_6$)alkoxy, hydroxy($C_1$-$C_6$)alkyl, mercapto, nitro, —$NR_C$ $R_D$, $NR_CR_D$($C_1$-$C_6$)alkoxy, $NR_CR_D$($C_1$-$C_6$)alkyl, or ($NR_C$ $R_D$)carbonyl; $R_C$ and $R_D$ are independently hydrogen, ($C_1$-$C_6$)alkyl, or ($C_1$-$C_6$)alkylcarbonyl; $R_{10}$ at each occurrence is independently deuterium, ($C_1$-$C_6$)alkoxy($C_1$-$C_6$)alkyl, ($C_1$-$C_3$)alkyl, ($C_1$-$C_3$)alkyl-$d_{1-7}$, ($C_1$-$C_6$)alkyl, ($C_1$-$C_6$)alkyl-$d_{1-13}$, ($C_1$-$C_6$)alkylthio($C_1$-$C_6$)alkyl, hydroxy($C_1$-$C_6$)alkyl, or thio($C_1$-$C_6$)alkyl; and p is 0, 1, 2, 3, 4, or 5.

In another embodiment, the present invention provides compounds of Formula (IC), or a pharmaceutically acceptable salt thereof, wherein B is boron; $A_1$ and $A_2$ are O; $R_1$, $R_2$, and $R_5$ are independently H, cyano, halogen, or halo ($C_1$-$C_6$)alkyl; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently, H, ($C_1$-$C_6$)alkoxy, ($C_1$-$C_6$)alkoxy($C_1$-$C_6$)alkyl, ($C_1$-$C_6$)alkoxycarbonyl($C_1$-$C_6$) alkyl, ($C_1$-$C_6$)alkyl, carboxy($C_1$-$C_6$)alkyl, halogen, halo($C_1$-$C_6$)alkyl, hydroxy($C_1$-$C_6$)alkoxy, or hydroxy($C_1$-$C_6$)alkyl; $R_{10}$ is ($C_1$-$C_3$)alkyl, ($C_1$-$C_6$)alkyl or hydroxy($C_1$-$C_6$)alkyl; and p is 0 or 1.

In another embodiment, the present invention provides compounds of Formula (IC), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently H or ($C_1$-$C_3$)alkyl; $R_{10}$ is methyl; and p is 0, 1, or 2.

In another embodiment, the present invention provides compounds of Formula (IC), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_6$)alkyl, ($C_3$-$C_8$)cycloalkyl, halo($C_1$-$C_6$)alkyl, or hydroxy($C_1$-$C_6$)alkyl; $R_6$, $R_7$, and $R_9$ are independently H or ($C_1$-$C_3$)alkyl; and p is 0.

In another embodiment, the present invention provides compounds of Formula (IC), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_3$)alkyl; $R_6$, $R_7$, and $R_9$ are independently H or ($C_1$-$C_3$)alkyl; and p is 0.

In another embodiment, the present invention provides compounds of Formula (IC), or a pharmaceutically acceptable salt thereof, wherein B is boron; $A_1$ and $A_2$ are O; $R_1$, $R_2$, and $R_5$ are H; $R_3$ and $R_4$ are independently ($C_1$-$C_3$)alkyl; $R_6$, $R_7$, and $R_9$ are H; and p is 0.

In another embodiment, the present invention provides the following compounds: (R) 4-(5-(3,4-dimethoxyphenyl) pyridin-3-yl)-1,2-oxaborolan-2-ol; (S) 4-(5-(3,4-dimethoxyphenyl)pyridin-3-yl)-1,2-oxaborolan-2-ol; (R) 4-(5-(3-ethoxy-4-methoxyphenyl)pyridin-3-yl)-1,2-oxaborolan-2-ol; (S) 4-(5-(3-ethoxy-4-methoxyphenyl)pyridin-3-yl)-1,2-oxaborolan-2-ol; (R) 4-(5-(3-isopropoxy-4-methoxyphenyl) pyridin-3-yl)-1,2-oxaborolan-2-ol; (S) 4-(5-(3-isopropoxy-4-methoxyphenyl)pyridin-3-yl)-1,2-oxaborolan-2-ol; (R) 4-(5-(3-cyclopropoxy-4-methoxyphenyl)pyridin-3-yl)-1,2-oxaborolan-2-ol; (S) 4-(5-(3-cyclopropoxy-4-methoxyphenyl)pyridin-3-yl)-1,2-oxaborolan-2-ol; (R) 4-(5-(3-(2-hydroxyethoxy)-4-methoxyphenyl)pyridin-3-yl)-1,2-oxaborolan-2-ol; (S) 4-(5-(3-(2-hydroxyethoxy)-4-methoxyphenyl)pyridin-3-yl)-1,2-oxaborolan-2-ol; (R) 4-(5-(3-(3-hydroxypropoxy)-4-methoxyphenyl)pyridin-3-yl)-1,2-oxaborolan-2-ol; (S) 4-(5-(3-(3-hydroxypropoxy)-4-methoxyphenyl)pyridin-3-yl)-1,2-oxaborolan-2-ol; (R) 4-(5-(2-(difluoromethyl)-3-ethoxy-4-methoxyphenyl)pyridin-3-yl)-1,2-oxaborolan-2-ol; (S) 4-(5-(2-(difluoromethyl)-3-ethoxy-4-methoxyphenyl)pyridin-3-yl)-1,2-oxaborolan-2-ol; (R) 4-(5-(3-ethoxy-5-fluoro-4-methoxyphenyl) pyridin-3-yl)-1,2-oxaborolan-2-ol; (S) 4-(5-(3-ethoxy-5-fluoro-4-methoxyphenyl)pyridin-3-yl)-1,2-oxaborolan-2-ol; (R) 4-(5-(3-chloro-5-ethoxy-4-methoxyphenyl)pyridin-3-yl)-1,2-oxaborolan-2-ol; (S) 4-(5-(3-chloro-5-ethoxy-4-methoxyphenyl)pyridin-3-yl)-1,2-oxaborolan-2-ol; (R) 4-(5-(5-ethoxy-2-fluoro-4-methoxyphenyl)pyridin-3-yl)-1,2-oxaborolan-2-ol; (S) 4-(5-(5-ethoxy-2-fluoro-4-methoxyphenyl)pyridin-3-yl)-1,2-oxaborolan-2-ol; (R) 4-(5-(2-chloro-5-ethoxy-4-methoxyphenyl)pyridin-3-yl)-1,2-oxaborolan-2-ol; (S) 4-(5-(2-chloro-5-ethoxy-4-methoxyphenyl)pyridin-3-yl)-1,2-oxaborolan-2-ol; (R) 4-(3-fluoro-5-methoxy-6-propoxy-[2,3'-bipyridin]-5'-yl)-1,2-oxaborolan-2-ol; (S) 4-(3-fluoro-5-methoxy-6-propoxy-[2,3'-bipyridin]-5'-yl)-1,2-oxaborolan-2-ol; (R) 4-(5-(4-(difluoromethoxy)-3-propoxyphenyl)pyridin-3-yl)-1,2-oxaborolan-2-ol; (S) 4-(5-(4-(difluoromethoxy)-3-propoxyphenyl)pyridin-3-yl)-1,2-oxaborolan-2-ol; (R) 4-(6'-methoxy-5'-propoxy-[3,3'-bipyridin]-5-yl)-1,2-oxaborolan-2-ol; (S) 4-(6'-methoxy-5'-propoxy-[3,3'-bipyridin]-5-yl)-1,2-oxaborolan-2-ol; (R) 4-(5-(3-ethoxy-4-methoxyphenyl)-6-methylpyridin-3-yl)-1,2-oxaborolan-2-ol; (S) 4-(5-(3-ethoxy-4-methoxyphenyl)-6-methylpyridin-3-yl)-1,2-oxaborolan-2-ol; (R) 4-(5-(3-ethoxy-4-methoxyphenyl)-4-methylpyridin-3-yl)-1,2-oxaborolan-2-ol; (S) 4-(5-(3-ethoxy-4-methoxyphenyl)-4-methylpyridin-3-yl)-1,2-oxaborolan-2-ol; (R) 4-(2-(4-methoxy-3-propoxyphenyl)-6-methylpyrimidin-4-yl)-1,2-oxaborolan-2-ol; (S) 4-(2-(4-methoxy-3-propoxyphenyl)-6-methylpyrimidin-4-yl)-1,2-oxaborolan-2-ol; (R) 4-(2-(4-methoxy-3-propoxyphenyl)-6-(trifluoromethyl)pyrimidin-4-yl)-1,2-oxaborolan-2-ol; (S) 4-(2-(4-methoxy-3-propoxyphenyl)-6-(trifluoromethyl)pyrimidin-4-yl)-1,2-oxaborolan-2-ol; (R) 4-(6-(3-ethoxy-4-methoxyphenyl) pyrazin-2-yl)-1,2-oxaborolan-2-ol; (S) 4-(6-(3-ethoxy-4-methoxyphenyl)pyrazin-2-yl)-1,2-oxaborolan-2-ol; 4-(5-(4-methoxy-3-propoxyphenyl)pyridin-3-yl)-1,2-oxaborol-2 (5H)-ol; (R) 4-(6-(4-methoxy-3-propoxyphenyl)pyridin-2-yl)-1,2-oxaborinan-2-ol; (S) 4-(6-(4-methoxy-3-propoxyphenyl)pyridin-2-yl)-1,2-oxaborinan-2-ol; (R) 4-(6-(4-methoxy-3-propoxyphenyl)pyridin-2-yl)-3-methyl-1,2-oxaborolan-2-ol; (S) 4-(6-(4-methoxy-3-propoxyphenyl) pyridin-2-yl)-3-methyl-1,2-oxaborolan-2-ol; 4-(6-(4-methoxy-3-propoxyphenyl)pyridin-2-yl)-3-methyl-1,2-oxaborol-2(5H)-ol; (R) 4-(6-(4-methoxy-3-propoxyphenyl) pyridin-2-yl)-4-methyl-1,2-oxaborolan-2-ol; (S) 4-(6-(4-methoxy-3-propoxyphenyl)pyridin-2-yl)-4-methyl-1,2-oxaborolan-2-ol; (R) 4-(6-(4-methoxy-3-propoxyphenyl) pyridazin-4-yl)-5-methyl-1,2-oxaborolan-2-ol; (S) 4-(6-(4-methoxy-3-propoxyphenyl)pyridazin-4-yl)-5-methyl-1,2-oxaborolan-2-ol; (R) 4-(hydroxymethyl)-4-(5-(4-methoxy-3-propoxyphenyl)pyridin-3-yl)-1,2-oxaborolan-2-ol; (S) 4-(hydroxymethyl)-4-(5-(4-methoxy-3-propoxyphenyl) pyridin-3-yl)-1,2-oxaborolan-2-ol; (R) 4-(5-(3-(2-fluoroethoxy)-4-methoxyphenyl)pyridin-3-yl)-1,2-oxaborolan-2-ol; (S) 4-(5-(3-(2-fluoroethoxy)-4-methoxyphenyl)pyridin-3-yl)-1,2-oxaborolan-2-ol; (R) 4-(3'-(3-fluoropropoxy)-4'-methoxy-[1,1'-biphenyl]-3-yl)-1,2-oxaborolan-2-ol; (S) 4-(3'-(3-fluoropropoxy)-4'-methoxy-[1,1'-biphenyl]-3-yl)-1,2-oxaborolan-2-ol; (R) 3'-(2-hydroxy-1,2-oxaborolan-4-yl)-4-methoxy-3-propoxy-[1,1'-biphenyl]-2-carbonitrile; (S) 3'-(2-hydroxy-1,2-oxaborolan-4-yl)-4-methoxy-3-propoxy-[1,1'-biphenyl]-2-carbonitrile; (R) 3'-(2-hydroxy-2,5-dihydro-1,2-oxaborol-4-yl)-4-methoxy-3-propoxy-[1,1'-biphenyl]-2-carbonitrile; (S) 3'-(2-hydroxy-2,5-dihydro-1,2-oxaborol-4-yl)-4-methoxy-3-propoxy-[1,1'-biphenyl]-2-carbonitrile; (R) 4-(5-(2-fluoro-4-methoxy-5-propoxyphenyl)pyridin-3-yl)-1,2-oxaborolan-2-ol; (S) 4-(5-(2-fluoro-4-methoxy-5-propoxyphenyl)pyridin-3-yl)-1,2-oxaborolan-2-ol; (R) 4-(6-(hydroxymethyl)-2-(4-methoxy-3-propoxyphenyl) pyrimidin-4-yl)-1,2-oxaborolan-2-ol; (S) 4-(6-(hydroxymethyl)-2-(4-methoxy-3-propoxyphenyl) pyrimidin-4-yl)-1,2-oxaborolan-2-ol; (R) 4-(2-(3-ethoxy-4-methoxyphenyl)thiazol-4-yl)-1,2-oxaborolan-2-ol; (S) 4-(2-(3-ethoxy-4-methoxyphenyl)thiazol-4-yl)-1,2-oxaborolan-2-ol; (2R)-2-(5-(4-methoxy-3-propoxyphenyl)pyridin-3-yl)-3-(4,4,6-trimethyl-1,3,2-dioxaborinan-2-yl)propan-1-ol; (2S)-2-(5-(4-methoxy-3-propoxyphenyl)pyridin-3-yl)-3-(4,4,6-trimethyl-1,3,2-dioxaborinan-2-yl)propan-1-ol; (R) 4-(5-methoxy-6-propoxy-[2,3'-bipyridin]-5'-yl)-1,2-oxaborolan-2-ol: (S) 4-(5-methoxy-6-propoxy-[2,3'-bipyridin]-5'-yl)-1,2-oxaborolan-2-ol; (R) 4-(3'-(2-fluoroethoxy)-4'-methoxy-[1,1'-biphenyl]-3-yl)-1,2-oxaborolan-2-ol; (S) 4-(3'-(2-fluoroethoxy)-4'-methoxy-[1,1'-biphenyl]-3-yl)-1,2-oxaborolan-2-ol; (R) 4-(4-(hydroxymethyl)-6-(4-methoxy-3-propoxyphenyl)pyridin-2-yl)-1,2-oxaborolan-2-ol; (S) 4-(4-(hydroxymethyl)-6-(4-methoxy-3-propoxyphenyl)pyridin-2-yl)-1,2-oxaborolan-2-ol; (R) 4-(6-(3-(cyclopentyloxy)-4-methoxyphenyl)pyridin-2-yl)-1,2-oxaborolan-2-ol; (S) 4-(6-(3-(cyclopentyloxy)-4-methoxyphenyl)pyridin-2-yl)-1,2-oxaborolan-2-ol; (R) 4-(5-(4-methoxy-3-(thietan-3-yloxy)phenyl)pyridin-3-yl)-1,2-oxaborolan-2-ol; (S) 4-(5-(4-methoxy-3-(thietan-3-yloxy) phenyl)pyridin-3-yl)-1,2-oxaborolan-2-ol; (R) 4-(5-(5-ethoxy-4-methoxy-2-methylphenyl)pyridin-3-yl)-1,2-oxaborolan-2-ol; (S) 4-(5-(5-ethoxy-4-methoxy-2-methylphenyl)pyridin-3-yl)-1,2-oxaborolan-2-ol; (R) 4-(5-(3-ethoxy-4-methoxyphenyl)-1,2,4-thiadiazol-3-yl)-1,2-oxaborolan-2-ol; (S) 4-(5-(3-ethoxy-4-methoxyphenyl)-1,2,4-thiadiazol-3-yl)-1,2-oxaborolan-2-ol; (R) 4-(5-(3-ethoxy-2-fluoro-4-methoxyphenyl)pyridin-3-yl)-1,2-oxaborolan-2-ol; (S) 4-(5-(3-ethoxy-2-fluoro-4-methoxyphenyl)pyridin-3-yl)-1,2-oxaborolan-2-ol; (R) 4-(3'-isopropoxy-4'-methoxy-[1,1'-biphenyl]-3-yl)-1,2-oxaborolan-2-ol; (S) 4-(3'-isopropoxy-4'-methoxy-[1,1'-biphenyl]-3-yl)-1,2-oxaborolan-2-ol; (R) 4-(3'-ethoxy-4'-methoxy-[1,1'-biphenyl]-3-yl)-1,2-oxaborolan-2-ol; (S) 4-(3'-ethoxy-4'-methoxy-[1,1'-biphenyl]-3-yl)-1,2-oxaborolan-2-ol; (R) 4-(5-(4-methoxy-3-((tetrahydrothiophen-3-yl)oxy)phenyl) pyridin-3-yl)-1,2-oxaborolan-2-ol; (S) 4-(5-(4-methoxy-3-((tetrahydrothiophen-3-yl)oxy)phenyl)pyridin-3-yl)-1,2-oxaborolan-2-ol; (R) 4-(5-(2-fluoro-4-methoxy-3-propoxyphenyl)pyridin-3-yl)-1,2-oxaborolan-2-ol; (S) 4-(5-

(2-fluoro-4-methoxy-3-propoxyphenyl)pyridin-3-yl)-1,2-oxaborolan-2-ol; (R)-4-(6-((S)-1-hydroxyethyl)-2-(4-methoxy-3-propoxyphenyl)pyrimidin-4-yl)-1,2-oxaborolan-2-ol; (R)-4-(6-((R)-1-hydroxyethyl)-2-(4-methoxy-3-propoxyphenyl)pyrimidin-4-yl)-1,2-oxaborolan-2-ol; (S)-4-(6-((S)-1-hydroxyethyl)-2-(4-methoxy-3-propoxyphenyl)pyrimidin-4-yl)-1,2-oxaborolan-2-ol; (S)-4-(6-((R)-1-hydroxyethyl)-2-(4-methoxy-3-propoxyphenyl)pyrimidin-4-yl)-1,2-oxaborolan-2-ol (R) 4-(5-(4-methoxy-3-propoxyphenyl)-4-methylpyridin-3-yl)-1,2-oxaborolan-2-ol; (S) 4-(5-(4-methoxy-3-propoxyphenyl)-4-methylpyridin-3-yl)-1,2-oxaborolan-2-ol; (R) 6-(6-(2-hydroxy-1,2-oxaborolan-4-yl)pyridin-2-yl)-3-methoxy-2-propoxybenzonitrile; (S) 6-(6-(2-hydroxy-1,2-oxaborolan-4-yl)pyridin-2-yl)-3-methoxy-2-propoxybenzonitrile; (R) 4-(4'-methoxy-3'-propoxy-[1,1'-biphenyl]-3-yl)-1,2-oxaborolan-2-ol; (S) 4-(4'-methoxy-3'-propoxy-[1,1'-biphenyl]-3-yl)-1,2-oxaborolan-2-ol; (R) 4-(2-(5-ethoxy-2-fluoro-4-methoxyphenyl)thiazol-4-yl)-1,2-oxaborolan-2-ol; (S) 4-(2-(5-ethoxy-2-fluoro-4-methoxyphenyl)thiazol-4-yl)-1,2-oxaborolan-2-ol; (R) 4-(3-(4-(cyclopentyloxy)-5-methoxypyrimidin-2-yl)phenyl)-1,2-oxaborolan-2-ol; (S) 4-(3-(4-(cyclopentyloxy)-5-methoxypyrimidin-2-yl)phenyl)-1,2-oxaborolan-2-ol; (R) 4-(5-(3-ethoxy-4-methoxy-2-(trifluoromethyl)phenyl)pyridin-3-yl)-1,2-oxaborolan-2-ol; (S) 4-(5-(3-ethoxy-4-methoxy-2-(trifluoromethyl)phenyl)pyridin-3-yl)-1,2-oxaborolan-2-ol; (R) 4-(5-(3,4-diethoxyphenyl)pyridin-3-yl)-1,2-oxaborolan-2-ol; (S) 4-(5-(3,4-diethoxyphenyl)pyridin-3-yl)-1,2-oxaborolan-2-ol; (R) 4-(5-(3-(cyclopentyloxy)-4-(methylthio)phenyl)pyridin-3-yl)-1,2-oxaborolan-2-ol; (S) 4-(5-(3-(cyclopentyloxy)-4-(methylthio)phenyl)pyridin-3-yl)-1,2-oxaborolan-2-ol; (R) 4-(2-(4-methoxy-3-propoxyphenyl)-6-(methoxymethyl)pyrimidin-4-yl)-1,2-oxaborolan-2-ol; (S) 4-(2-(4-methoxy-3-propoxyphenyl)-6-(methoxymethyl)pyrimidin-4-yl)-1,2-oxaborolan-2-ol; (R) 4-(5-(4-ethoxy-3-propoxyphenyl)pyridin-3-yl)-1,2-oxaborolan-2-ol; (S) 4-(5-(4-ethoxy-3-propoxyphenyl)pyridin-3-yl)-1,2-oxaborolan-2-ol; (R) 4-(5-(2-fluoro-3,4-dimethoxyphenyl)pyridin-3-yl)-1,2-oxaborolan-2-ol; (S) 4-(5-(2-fluoro-3,4-dimethoxyphenyl)pyridin-3-yl)-1,2-oxaborolan-2-ol; (R) 4-(4'-methoxy-3'-(pentyloxy)-[1,1'-biphenyl]-3-yl)-1,2-oxaborolan-2-ol; (S) 4-(4'-methoxy-3'-(pentyloxy)-[1,1'-biphenyl]-3-yl)-1,2-oxaborolan-2-ol; (R) 4-(5-(4-(methylthio)-3-propoxyphenyl)pyridin-3-yl)-1,2-oxaborolan-2-ol; (S) 4-(5-(4-(methylthio)-3-propoxyphenyl)pyridin-3-yl)-1,2-oxaborolan-2-ol; (R) 4-(6-(4-methoxy-3-propoxyphenyl)pyrazin-2-yl)-1,2-oxaborolan-2-ol; (S) 4-(6-(4-methoxy-3-propoxyphenyl)pyrazin-2-yl)-1,2-oxaborolan-2-ol; (R) 4-(2'-fluoro-4'-methoxy-3'-propoxy-[1,1'-biphenyl]-3-yl)-1,2-oxaborolan-2-ol; (S) 4-(2'-fluoro-4'-methoxy-3'-propoxy-[1,1'-biphenyl]-3-yl)-1,2-oxaborolan-2-ol; (R) 3'-(2-hydroxy-1,2-oxaborolan-4-yl)-4,5-dimethoxy-[1,1'-biphenyl]-3-carbonitrile; (S) 3'-(2-hydroxy-1,2-oxaborolan-4-yl)-4,5-dimethoxy-[1,1'-biphenyl]-3-carbonitrile; (R) 3-ethoxy-5-(5-(2-hydroxy-1,2-oxaborolan-4-yl)pyridin-3-yl)-2-methoxybenzonitrile; (S) 3-ethoxy-5-(5-(2-hydroxy-1,2-oxaborolan-4-yl)pyridin-3-yl)-2-methoxybenzonitrile; 4-(3-(6-ethoxy-5-methoxypyridin-2-yl)phenyl)-1,2-oxaborol-2(5H)-ol; (R) 4-(3-(6-ethoxy-5-methoxypyridin-2-yl)phenyl)-1,2-oxaborolan-2-ol; (S) 4-(3-(6-ethoxy-5-methoxypyridin-2-yl)phenyl)-1,2-oxaborolan-2-ol; (R) 4-(3-(4,5-dimethoxypyrimidin-2-yl)phenyl)-1,2-oxaborolan-2-ol; (S) 4-(3-(4,5-dimethoxypyrimidin-2-yl)phenyl)-1,2-oxaborolan-2-ol; (R) 4-(6-(3-(cyclopentyloxy)-4-methoxyphenyl)pyrazin-2-yl)-1,2-oxaborolan-2-ol; (S) 4-(6-(3-(cyclopentyloxy)-4-methoxyphenyl)pyrazin-2-yl)-1,2-oxaborolan-2-ol; (R) 4-(6-(4-methoxy-3-propoxyphenyl)pyridin-2-yl)-1,2-oxaborolan-2-ol; (S) 4-(6-(4-methoxy-3-propoxyphenyl)pyridin-2-yl)-1,2-oxaborolan-2-ol; 4-(3'-(cyclopentyloxy)-4'-methoxy-[1,1'-biphenyl]-3-yl)-1,2-oxaborol-2(5H)-ol; (R) 4-(3'-(cyclopentyloxy)-4'-methoxy-[1,1'-biphenyl]-3-yl)-1,2-oxaborolan-2-ol; (S) 4-(3'-(cyclopentyloxy)-4'-methoxy-[1,1'-biphenyl]-3-yl)-1,2-oxaborolan-2-ol (R) 4-(6-(3-(cyclopentyloxy)-4-methoxyphenyl)-5-fluoropyridin-2-yl)-1,2-oxaborolan-2-ol; (S) 4-(6-(3-(cyclopentyloxy)-4-methoxyphenyl)-5-fluoropyridin-2-yl)-1,2-oxaborolan-2-ol; (R) 4-(2-(3-(cyclopentyloxy)-4-methoxyphenyl)-6-methoxypyrimidin-4-yl)-1,2-oxaborolan-2-ol; (S) 4-(2-(3-(cyclopentyloxy)-4-methoxyphenyl)-6-methoxypyrimidin-4-yl)-1,2-oxaborolan-2-ol; (R) ethyl 2-(6-(2-hydroxy-1,2-oxaborolan-4-yl)-2-(4-methoxy-3-propoxyphenyl)pyrimidin-4-yl)acetate; (S) ethyl 2-(6-(2-hydroxy-1,2-oxaborolan-4-yl)-2-(4-methoxy-3-propoxyphenyl)pyrimidin-4-yl)acetate; (R) 2-(6-(2-hydroxy-1,2-oxaborolan-4-yl)-2-(4-methoxy-3-propoxyphenyl)pyrimidin-4-yl)acetic acid; (S) 2-(6-(2-hydroxy-1,2-oxaborolan-4-yl)-2-(4-methoxy-3-propoxyphenyl)pyrimidin-4-yl)acetic acid; (R) 4-(5-fluoro-6-(4-methoxy-3-propoxyphenyl)pyridin-2-yl)-1,2-oxaborolan-2-ol; (S) 4-(5-fluoro-6-(4-methoxy-3-propoxyphenyl)pyridin-2-yl)-1,2-oxaborolan-2-ol; (R) 4-(6-(4-methoxy-3-propoxyphenyl)pyridazin-4-yl)-1,2-oxaborolan-2-ol; (S) 4-(6-(4-methoxy-3-propoxyphenyl)pyridazin-4-yl)-1,2-oxaborolan-2-ol; (R) 4-(4-(difluoromethyl)-5-(3-ethoxy-4-methoxyphenyl)pyridin-3-yl)-1,2-oxaborolan-2-ol; (S) 4-(4-(difluoromethyl)-5-(3-ethoxy-4-methoxyphenyl)pyridin-3-yl)-1,2-oxaborolan-2-ol; (R) 4-(5-(5-ethoxy-2-fluoro-4-methoxyphenyl)-4-methylpyridin-3-yl)-1,2-oxaborolan-2-ol; (S) 4-(5-(5-ethoxy-2-fluoro-4-methoxyphenyl)-4-methylpyridin-3-yl)-1,2-oxaborolan-2-ol; (R) 4-(5-(3-ethoxy-4-(methylthio)phenyl)pyridin-3-yl)-1,2-oxaborolan-2-ol; (S) 4-(5-(3-ethoxy-4-(methylthio)phenyl)pyridin-3-yl)-1,2-oxaborolan-2-ol; (R) 4-(5-(3-propoxyphenyl)pyridin-3-yl)-1,2-oxaborolan-2-ol; (S) 4-(5-(3-propoxyphenyl)pyridin-3-yl)-1,2-oxaborolan-2-ol; (R) 4-(5-(4-methoxy-3-propoxyphenyl)-1,2,4-thiadiazol-3-yl)-1,2-oxaborolan-2-ol; (S) 4-(5-(4-methoxy-3-propoxyphenyl)-1,2,4-thiadiazol-3-yl)-1,2-oxaborolan-2-ol; (R) 4-(5-(3-(cyclopentyloxy)-4-methoxyphenyl)pyridin-3-yl)-1,2-oxaborolan-2-ol; (S) 4-(5-(3-(cyclopentyloxy)-4-methoxyphenyl)pyridin-3-yl)-1,2-oxaborolan-2-ol; (R) 4-(2'-fluoro-4',5'-dimethoxy-[1,1'-biphenyl]-3-yl)-1,2-oxaborolan-2-ol; (S) 4-(2'-fluoro-4',5'-dimethoxy-[1,1'-biphenyl]-3-yl)-1,2-oxaborolan-2-ol; (R) 2-ethoxy-6-(6-(2-hydroxy-1,2-oxaborolan-4-yl)pyridin-2-yl)-3-methoxybenzonitrile; (S) 2-ethoxy-6-(6-(2-hydroxy-1,2-oxaborolan-4-yl)pyridin-2-yl)-3-methoxybenzonitrile; (R) 4-(3-(5,6-dimethoxypyridin-2-yl)phenyl)-1,2-oxaborolan-2-ol; (S) 4-(3-(5,6-dimethoxypyridin-2-yl)phenyl)-1,2-oxaborolan-2-ol; (R) 6-(5-(2-hydroxy-1,2-oxaborolan-4-yl)pyridin-3-yl)-2,3-dimethoxybenzonitrile; (S) 6-(5-(2-hydroxy-1,2-oxaborolan-4-yl)pyridin-3-yl)-2,3-dimethoxybenzonitrile; (R) 4-(2-(2-fluoro-4-methoxy-5-propoxyphenyl)-6-(hydroxymethyl)pyrimidin-4-yl)-1,2-oxaborolan-2-ol; (S) 4-(2-(2-fluoro-4-methoxy-5-propoxyphenyl)-6-(hydroxymethyl)pyrimidin-4-yl)-1,2-oxaborolan-2-ol; 4-(3-(5-methoxy-6-propoxypyridin-2-yl)phenyl)-1,2-oxaborol-2(5H)-ol; (R) 4-(3-(5-methoxy-6-propoxypyridin-2-yl)phenyl)-1,2-oxaborolan-2-ol; (S) 4-(3-(5-methoxy-6-propoxypyridin-2-yl)phenyl)-1,2-oxaborolan-2-ol; (R) 4-(3',4',5-trimethoxy-[1,1'-biphenyl]-3-yl)-1,2-oxaborolan-2-ol; (S) 4-(3',4',5-trimethoxy-[1,1'- biphenyl]-3-yl)-1,2-oxaborolan-2-ol; (R) 4-(6-(4-methoxy-3-propoxyphenyl)-4-methylpyridin-2-yl)-1,2-oxaborolan-2-ol; (S) 4-(6-(4-methoxy-3-propoxyphenyl)-4-methylpyridin-2-yl)-1,2-oxaborolan-2-ol; (R) 4-(2-(3,4-dimethoxyphenyl)thiazol-4-yl)-1,2-oxaborolan-2-ol; (S) 4-(2-(3,4-dimethoxyphenyl)thiazol-4-yl)-1,2-oxaborolan-2-ol; (R) 4-(3-(5,6-dimethoxypyridin-3-yl)phenyl)-1,2-oxaborolan-2-ol; (S) 4-(3-(5,6-dimethoxypyridin-3-yl)phenyl)-1,2-oxaborolan-2-ol; (R) 4-(6-(2-fluoro-3,4-dimethoxyphenyl)pyridin-2-yl)-1,2-oxaborolan-2-ol; (S) 4-(6-(2-fluoro-3,4-dimethoxyphenyl)pyridin-2-yl)-1,2-oxaborolan-2-ol; (R) 4-(5-(3-ethoxy-2,6-difluoro-4-methoxyphenyl)pyridin-3-yl)-1,2-oxaborolan-2-ol; (S) 4-(5-(3-ethoxy-2,6-difluoro-4-methoxyphenyl)pyridin-3-yl)-1,2-oxaborolan-2-ol; (R) 4-(3'-(cyclopropylmethoxy)-4'-methoxy-[1,1'-biphenyl]-3-yl)-1,2-oxaborolan-2-ol; (S) 4-(3'-(cyclopropylmethoxy)-4'-methoxy-[1,1'-biphenyl]-3-yl)-1,2-oxaborolan-2-ol; (R) 4-(3'-ethoxy-2'-fluoro-4'-methoxy-[1,1'-biphenyl]-3-yl)-1,2-oxaborolan-2-ol; (S) 4-(3'-ethoxy-2'-fluoro-4'-methoxy-[1,1'-biphenyl]-3-yl)-1,2-oxaborolan-2-ol; (R) 4-(5-(2,4-dimethoxy-3-propoxyphenyl)pyridin-3-yl)-1,2-oxaborolan-2-ol; (S) 4-(5-(2,4-dimethoxy-3-propoxyphenyl)pyridin-3-yl)-1,2-oxaborolan-2-ol; (R) 4-(5-(4-methoxy-3-((tetrahydro-2H-thiopyran-4-yl)oxy)phenyl)pyridin-3-yl)-1,2-oxaborolan-2-ol; (S) 4-(5-(4-methoxy-3-((tetrahydro-2H-thiopyran-4-yl)oxy)phenyl)pyridin-3-yl)-1,2-oxaborolan-2-ol; (R) 4-(5-(3-ethoxy-4-methoxyphenyl)-6-ethylpyridin-3-yl)-1,2-oxaborolan-2-ol; (S) 4-(5-(3-ethoxy-4-methoxyphenyl)-6-ethylpyridin-3-yl)-1,2-oxaborolan-2-ol; (R) 4-(3'-ethoxy-4'-(methylthio)-[1,1'-biphenyl]-3-yl)-1,2-oxaborolan-2-ol; (S) 4-(3'-ethoxy-4'-(methylthio)-[1,1'-biphenyl]-3-yl)-1,2-oxaborolan-2-ol; (R) 4-(5-(3-chloro-5-ethoxy-4-methoxyphenyl)pyridin-3-yl)-1,2-oxaborolan-2-ol; (S) 4-(5-(3-chloro-5-ethoxy-4-methoxyphenyl)pyridin-3-yl)-1,2-oxaborolan-2-ol; (R) 4-(3-(4,5-dimethoxypyridin-2-yl)phenyl)-1,2-oxaborolan-2-ol; (S) 4-(3-(4,5-dimethoxypyridin-2-yl)phenyl)-1,2-oxaborolan-2-ol; (R) 4-(4-(3-(cyclopentyloxy)-4-methoxyphenyl)-6-methoxypyrimidin-2-yl)-1,2-oxaborolan-2-ol; (S) 4-(4-(3-(cyclopentyloxy)-4-methoxyphenyl)-6-methoxypyrimidin-2-yl)-1,2-oxaborolan-2-ol; (R) 3'-(2-hydroxy-1,2-oxaborolan-4-yl)-3,4-dimethoxy-[1,1'-biphenyl]-2-carbonitrile; (S) 3'-(2-hydroxy-1,2-oxaborolan-4-yl)-3,4-dimethoxy-[1,1'-biphenyl]-2-carbonitrile; (R) 4-(5-methoxy-4-propoxy-[2,3'-bipyridin]-5'-yl)-1,2-oxaborolan-2-ol; (S) 4-(5-methoxy-4-propoxy-[2,3'-bipyridin]-5'-yl)-1,2-oxaborolan-2-ol; (R) 4-(2-(hydroxymethyl)-6-(4-methoxy-3-propoxyphenyl)pyridin-4-yl)-1,2-oxaborolan-2-ol; (S) 4-(2-(hydroxymethyl)-6-(4-methoxy-3-propoxyphenyl)pyridin-4-yl)-1,2-oxaborolan-2-ol; (R) 4-(5-(3-cyclopropoxy-4-methoxyphenyl)-1,2,4-thiadiazol-3-yl)-1,2-oxaborolan-2-ol; (S) 4-(5-(3-cyclopropoxy-4-methoxyphenyl)-1,2,4-thiadiazol-3-yl)-1,2-oxaborolan-2-ol; (R) 4-(4'-ethoxy-3'-methoxy-[1,1'-biphenyl]-3-yl)-1,2-oxaborolan-2-ol; (S) 4-(4'-ethoxy-3'-methoxy-[1,1'-biphenyl]-3-yl)-1,2-oxaborolan-2-ol; (R) 4-(3'-isobutoxy-4'-methoxy-[1,1'-biphenyl]-3-yl)-1,2-oxaborolan-2-ol; (S) 4-(3'-isobutoxy-4'-methoxy-[1,1'-biphenyl]-3-yl)-1,2-oxaborolan-2-ol; (R) 4-(3'-cyclobutoxy-4'-methoxy-[1,1'-biphenyl]-3-yl)-1,2-oxaborolan-2-ol: (S) 4-(3'-cyclobutoxy-4'-methoxy-[1,1'-biphenyl]-3-yl)-1,2-oxaborolan-2-ol; (R) 4-(2-(3-ethoxy-4-methoxyphenyl)-6-methoxypyrimidin-4-yl)-1,2-oxaborolan-2-ol; (S) 4-(2-(3-ethoxy-4-methoxyphenyl)-6-methoxypyrimidin-4-yl)-1,2-oxaborolan-2-ol; (R) 4-(5-(4-ethoxy-3-methoxyphenyl)pyridin-3-yl)-1,2-oxaborolan-2-ol; (S) 4-(5-(4-ethoxy-3-methoxyphenyl)pyridin-3-yl)-1,2-oxaborolan-2-ol; (R) 3-ethoxy-3'-(2-hydroxy-1,2-oxaborolan-4-yl)-4-methoxy-[1,1'-biphenyl]-2-carbonitrile; (S) 3-ethoxy-3'-(2-hydroxy-1,2-oxaborolan-4-yl)-4-methoxy-[1,1'-biphenyl]-2-carbonitrile; (R) 4-(6-(2-hydroxyethoxy)-2-(4-methoxy-3-propoxyphenyl)pyrimidin-4-yl)-1,2-oxaborolan-2-ol; (S) 4-(6-(2-hydroxyethoxy)-2-(4-methoxy-3-propoxyphenyl)pyrimidin-4-yl)-1,2-oxaborolan-2-ol; (R) 4-(6-(3,4-dimethoxyphenyl)pyridin-2-yl)-1,2-oxaborolan-2-ol; (S) 4-(6-(3,4-dimethoxyphenyl)pyridin-2-yl)-1,2-oxaborolan-2-ol; (R) 4-(4-(hydroxymethyl)-6-(4-methoxy-3-propoxyphenyl)pyrimidin-2-yl)-1,2-oxaborolan-2-ol; (S) 4-(4-(hydroxymethyl)-6-(4-methoxy-3-propoxyphenyl)pyrimidin-2-yl)-1,2-oxaborolan-2-ol; (R) 4-(6-(3-ethoxy-2-fluoro-4-methoxyphenyl)pyridin-2-yl)-1,2-oxaborolan-2-ol; (S) 4-(6-(3-ethoxy-2-fluoro-4-methoxyphenyl)pyridin-2-yl)-1,2-oxaborolan-2-ol; (R) 4-(1-(4-methoxy-3-propoxyphenyl)-1H-pyrazol-3-yl)-1,2-oxaborolan-2-ol; (S) 4-(1-(4-methoxy-3-propoxyphenyl)-1H-pyrazol-3-yl)-1,2-oxaborolan-2-ol; (R) 4-(5-(3-methoxy-4-(methylthio)phenyl)pyridin-3-yl)-1,2-oxaborolan-2-ol; (S) 4-(5-(3-methoxy-4-(methylthio)phenyl)pyridin-3-yl)-1,2-oxaborolan-2-ol; (R) 4-(6-(3-ethoxy-4-(methylthio)phenyl)pyridin-2-yl)-1,2-oxaborolan-2-ol; (S) 4-(6-(3-ethoxy-4-(methylthio)phenyl)pyridin-2-yl)-1,2-oxaborolan-2-ol; (R) 4-(5-(3-ethoxy-4-methoxyphenyl)-4,6-dimethylpyridin-3-yl)-1,2-oxaborolan-2-ol; (S) 4-(5-(3-ethoxy-4-methoxyphenyl)-4,6-dimethylpyridin-3-yl)-1,2-oxaborolan-2-ol; (R) 4-(3'-methoxy-4'-(methylthio)-[1,1'-biphenyl]-3-yl)-1,2-oxaborolan-2-ol; (S) 4-(3'-methoxy-4'-(methylthio)-[1,1'-biphenyl]-3-yl)-1,2-oxaborolan-2-ol; (R) 4-(3',4'-dimethoxy-5-methyl-[1,1'-biphenyl]-3-yl)-1,2-oxaborolan-2-ol; (S) 4-(3',4'-dimethoxy-5-methyl-[1,1'-biphenyl]-3-yl)-1,2-oxaborolan-2-ol; (R) 4-(2'-fluoro-3',4'-dimethoxy-[1,1'-biphenyl]-3-yl)-1,2-oxaborolan-2-ol; (S) 4-(2'-fluoro-3',4'-dimethoxy-[1,1'-biphenyl]-3-yl)-1,2-oxaborolan-2-ol; (R) 4-(2-(3-(cyclopentyloxy)-4-methoxyphenyl)pyridin-4-yl)-1,2-oxaborolan-2-ol; (S) 4-(2-(3-(cyclopentyloxy)-4-methoxyphenyl)pyridin-4-yl)-1,2-oxaborolan-2-ol; (R) 4-(2-(4-methoxy-3-propoxyphenyl)pyrimidin-4-yl)-1,2-oxaborolan-2-ol; (S) 4-(2-(4-methoxy-3-propoxyphenyl)pyrimidin-4-yl)-1,2-oxaborolan-2-ol; (R) 4-(6-(2-fluoro-4-methoxy-3-propoxyphenyl)pyridin-2-yl)-1,2-oxaborolan-2-ol; (S) 4-(6-(2-fluoro-4-methoxy-3-propoxyphenyl)pyridin-2-yl)-1,2-oxaborolan-2-ol; (R) 4-(6-(2-fluoro-4-methoxy-3-propoxyphenyl)pyrazin-2-yl)-1,2-oxaborolan-2-ol; (S) 4-(6-(2-fluoro-4-methoxy-3-propoxyphenyl)pyrazin-2-yl)-1,2-oxaborolan-2-ol; (R) 4-(5-(4-ethoxy-2-fluoro-3-methoxyphenyl)pyridin-3-yl)-1,2-oxaborolan-2-ol; (S) 4-(5-(4-ethoxy-2-fluoro-3-methoxyphenyl)pyridin-3-yl)-1,2-oxaborolan-2-ol; (R) 4-(6'-methoxy-2-methyl-5'-propoxy-[3,3'-bipyridin]-5-yl)-1,2-oxaborolan-2-ol; (S) 4-(6'-methoxy-2-methyl-5'-propoxy-[3,3'-bipyridin]-5-yl)-1,2-oxaborolan-2-ol; (R) 4-(6-(3-ethoxy-4-methoxyphenyl)-4-(trifluoromethyl)pyridin-2-yl)-1,2-oxaborolan-2-ol; (S) 4-(6-(3-ethoxy-4-methoxyphenyl)-4-(trifluoromethyl)pyridin-2-yl)-1,2-oxaborolan-2-ol; (R) 4-(6-ethoxy-2-(3-ethoxy-4-methoxyphenyl)pyrimidin-4-yl)-1,2-oxaborolan-2-ol; (S) 4-(6-ethoxy-2-(3-ethoxy-4-methoxyphenyl)pyrimidin-4-yl)-1,2-oxaborolan-2-ol; (R) 4-(6-methoxy-2-(4-methoxy-3-propoxyphenyl)pyrimidin-4-yl)-1,2-oxaborolan-2-ol; (S) 4-(6-methoxy-2-(4-methoxy-3-propoxyphenyl)pyrimidin-4-yl)-1,2-oxaborolan-2-ol; (R) 2-(cyclopentyloxy)-6-(6-(2-hydroxy-1,2-oxaborolan-4-yl)pyridin-2-yl)-3-methoxybenzonitrile; (S) 2-(cyclopentyloxy)-6-(6-(2-hydroxy-1,2-oxaborolan-4-yl)pyridin-2-yl)-3-methoxybenzonitrile; 4-(2-(3,4-dimethoxyphenyl)pyridin-4-yl)-1,2-oxaborol-2(5H)-ol; 4-(5-(3-ethoxy-4- methoxyphenyl)pyridin-3-yl)-1,2-oxaborol-2(5H)-ol; (R) 4-(3-fluoro-6-(4-methoxy-3-propoxyphenyl)pyridin-2-yl)-1,2-oxaborolan-2-ol; (S) 4-(3-fluoro-6-(4-methoxy-3-propoxyphenyl)pyridin-2-yl)-1,2-oxaborolan-2-ol; (R) 4-(5-methoxy-2'-methyl-6-propoxy-[2,3'-bipyridin]-5'-yl)-1,2-oxaborolan-2-ol; (S) 4-(5-methoxy-2'-methyl-6-propoxy-[2,3'-bipyridin]-5'-yl)-1,2-oxaborolan-2-ol; (R) 4-(3',4'-dimethoxy-[1,1'-biphenyl]-3-yl)-1,2-oxaborolan-2-ol; (S) 4-(3',4'-dimethoxy-[1,1'-biphenyl]-3-yl)-1,2-oxaborolan-2-ol; (R) 4-(6-(3-ethoxy-4-methoxyphenyl)pyridin-2-yl)-1,2-oxaborolan-2-ol; and (S) 4-(6-(3-ethoxy-4-methoxyphenyl)pyridin-2-yl)-1,2-oxaborolan-2-ol; or a pharmaceutically acceptable salt thereof.

In another embodiment, the present invention provides a pharmaceutical composition comprising a compound of Formula (I), Formula (IA), Formula (IB), or Formula (IC), or a pharmaceutically acceptable salt thereof, and at least one pharmaceutically acceptable excipient, diluent, or carrier.

In another embodiment, the present invention provides a method for treating or preventing an inflammatory disease in a human comprising administering to the human in need of such treatment a therapeutically effective amount of a compound of Formula (I), Formula (IA), Formula (IB), or Formula (IC), or a pharmaceutically acceptable salt thereof.

In another embodiment, the present invention provides a method for treating or preventing an inflammatory disease in a human comprising topically administering to the human in need of such treatment a therapeutically effective amount of a compound of Formula (I), Formula (IA), Formula (IB), or Formula (IC), or a pharmaceutically acceptable salt thereof, in the form of a transdermal patch, an ointment, a lotion, a cream, or a gel.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising administering to the human in need of such treatment a therapeutically effective amount of a compound of Formula (I), Formula (IA), Formula (IB), or Formula (IC), or a pharmaceutically acceptable salt thereof.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising topically administering to the human in need of such treatment a therapeutically effective amount of a compound of Formula (I), Formula (IA), Formula (IB), or Formula (IC), or a pharmaceutically acceptable salt thereof, in the form of a transdermal patch, an ointment, a lotion, a cream, or a gel.

In another embodiment, the present invention provides a method for treating or preventing arthritis, asthma, fibrosis, lupus, allergy, fibromyalgia, wound healing, or inflammation resulting from surgical complications in a human comprising administering to the human in need of such treatment a therapeutically effective amount of a compound of Formula (I), Formula (IA), Formula (IB), or Formula (IC), or a pharmaceutically acceptable salt thereof.

In another embodiment, the present invention provides a method for treating or preventing arthritis, asthma, fibrosis, lupus, allergy, fibromyalgia, wound healing, or inflammation resulting from surgical complications in a human comprising topically administering to the human in need of such treatment a therapeutically effective amount of a compound of Formula (I), Formula (IA), Formula (IB), or Formula (IC), or a pharmaceutically acceptable salt thereof in the form of a transdermal patch, an ointment, a lotion, a cream, or a gel.

In another embodiment, the present invention provides a method for treating or preventing inflammatory bowel disease, ulcerative colitis, or Crohn's disease in a human comprising administering to the human in need of such treatment a therapeutically effective amount of a compound of Formula (I), Formula (IA), Formula (IB), or Formula (IC), or a pharmaceutically acceptable salt thereof.

In another embodiment, the present invention provides the use of a compound of Formula (I), Formula (IA), Formula (IB), or Formula (IC), or a pharmaceutically acceptable salt thereof, in the manufacture of a medicament for treating an inflammatory disease in a human.

In another embodiment, the present invention provides the use of a compound of Formula (I), Formula (IA), Formula (IB), or Formula (IC), or a pharmaceutically acceptable salt thereof, in the manufacture of a medicament for treating atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human.

In another embodiment, the present invention provides the use of a compound of Formula (I), Formula (IA), Formula (IB), or Formula (IC), or a pharmaceutically acceptable salt thereof, in the manufacture of a medicament for treating arthritis, asthma, fibrosis, lupus, allergy, fibromyalgia, wound healing, or inflammation resulting from surgical complications in a human.

In another embodiment, the present invention provides the use of a compound of Formula (I), Formula (IA), Formula (IB), or Formula (IC), or a pharmaceutically acceptable salt thereof, in the manufacture of a medicament for treating inflammatory bowel disease, ulcerative colitis, or Crohn's disease in a human.

In another embodiment, the present invention provides crystalline (R)-4-(5-(3-ethoxy-4-methoxyphenyl)pyridin-3-yl)-1,2-oxaborolan-2-ol.

In another embodiment, the present invention provides crystalline (R)-4-(5-(3-ethoxy-4-methoxyphenyl)pyridin-3-yl)-1,2-oxaborolan-2-ol having an X-ray powder diffraction pattern comprising diffraction peaks 10.5±0.2, 18.3±0.2, and 24.9±0.2 degrees two theta.

In another embodiment, the present invention provides crystalline (R)-4-(5-(3-ethoxy-4-methoxyphenyl)pyridin-3-yl)-1,2-oxaborolan-2-ol having an X-ray powder diffraction pattern comprising diffraction peaks 10.5±0.2, 12.3±0.2, 13.5±0.2, 15.8±0.2, 16.0±0.2, 18.3±0.2, and 24.9±0.2 degrees two theta.

In another embodiment, the present invention provides crystalline (R)-4-(5-(3-ethoxy-4-methoxyphenyl)pyridin-3-yl)-1,2-oxaborolan-2-ol having an X-ray powder diffraction pattern comprising diffraction peaks 10.5±0.2, 12.3±0.2, 13.5±0.2, 15.8±0.2, 16.0±0.2, 18.3±0.2, 21.5±0.2, 22.9±0.2, 24.4±0.2, 24.9±0.2, 25.4±0.2, 26.5±0.2, 27.8±0.2, and 30.2±0.2 degrees two theta.

In another embodiment, the present invention provides crystalline (R)-4-(5-(3-ethoxy-4-methoxyphenyl)pyridin-3-yl)-1,2-oxaborolan-2-ol having an X-ray powder diffraction pattern comprising 3 to 10 diffraction peaks listed in Table 7.

In another embodiment, the present invention provides crystalline (R)-4-(5-(3-ethoxy-4-methoxyphenyl)pyridin-3-yl)-1,2-oxaborolan-2-ol having an X-ray powder diffraction pattern comprising the diffraction peaks listed in Table 7.

Figure 5:
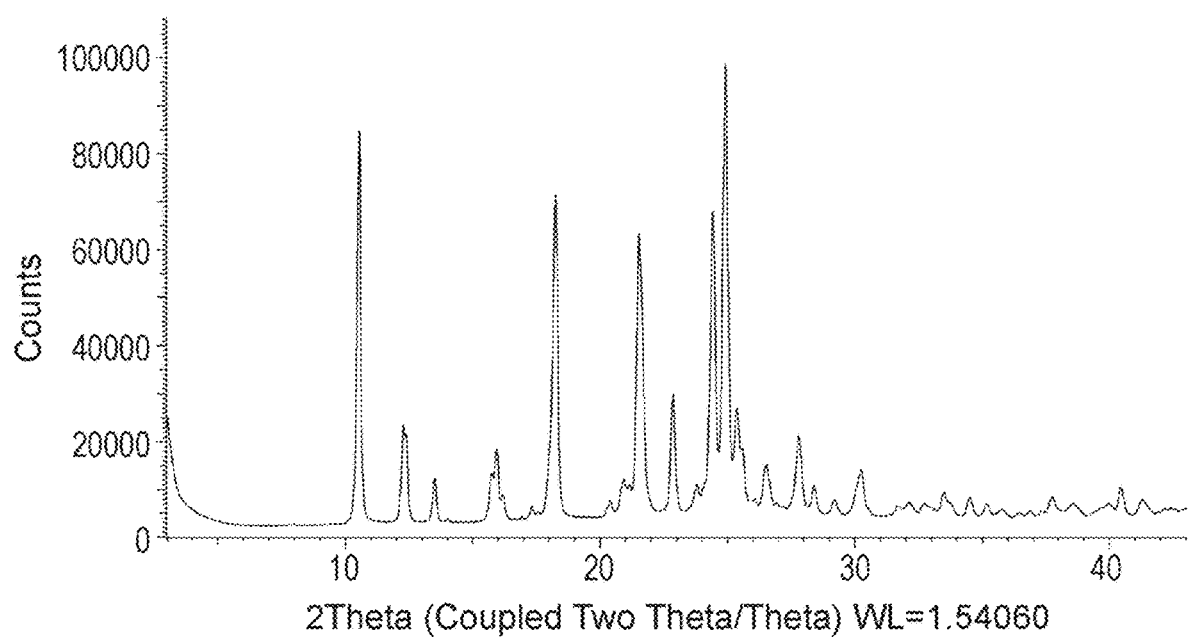
FIG. 5 is a powder X-ray diffraction analysis of crystalline (R)-4-(5-(3-ethoxy-4-methoxyphenyl)pyridin-3-yl)-1,2-oxaborolan-2-ol (Example 3).

In another embodiment, the present invention provides crystalline (R)-4-(5-(3-ethoxy-4-methoxyphenyl)pyridin-3-yl)-1,2-oxaborolan-2-ol having an X-ray powder diffraction pattern as depicted in FIG. 5.

In another embodiment, the present invention provides a pharmaceutical composition comprising crystalline (R)-4-(5-(3-ethoxy-4-methoxyphenyl)pyridin-3-yl)-1,2-oxaborolan-2-ol and at least one pharmaceutically acceptable excipient, diluent, or carrier.

In another embodiment, the present invention provides a method for treating or preventing an inflammatory disease in a human comprising administering to the human in need of such treatment a therapeutically effective amount of crystalline (R)-4-(5-(3-ethoxy-4-methoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human administering to the human in need of such treatment a therapeutically effective amount of crystalline (R)-4-(5-(3-ethoxy-4-methoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising topically administering to the human in need of such treatment a therapeutically effective amount of crystalline (R)-4-(5-(3-ethoxy-4-methoxyphenyl)pyridin-3-yl)-1,2-oxaborolan-2-ol in the form of a transdermal patch, an ointment, a lotion, a cream, or a gel.

In another embodiment, the present invention provides a method for treating or preventing an arthritis, asthma, fibrosis, lupus, allergy, fibromyalgia, wound healing, or inflammation resulting from surgical complications in a human comprising administering to the human in need of such treatment a therapeutically effective amount of crystalline (R)-4-(5-(3-ethoxy-4-methoxyphenyl)pyridin-3-yl)-1,2-oxaborolan-2-ol.

In another embodiment, the present invention provides a method for treating or preventing an arthritis, asthma, fibrosis, lupus, allergy, fibromyalgia, wound healing, or inflammation resulting from surgical complications in a human comprising topically administering to the human in need of such treatment a therapeutically effective amount of crystalline (R)-4-(5-(3-ethoxy-4-methoxyphenyl)pyridin-3-yl)-1,2-oxaborolan-2-ol in the form of a transdermal patch, an ointment, a lotion, a cream, or a gel.

In another embodiment, the present invention provides a method for treating or preventing inflammatory bowel disease, ulcerative colitis, or Crohn's disease in a human comprising administering to the human in need of such treatment a therapeutically effective amount of crystalline (R)-4-(5-(3-ethoxy-4-methoxyphenyl)pyridin-3-yl)-1,2-oxaborolan-2-ol.

In another embodiment, the present invention provides the use of crystalline (R)-4-(5-(3-ethoxy-4-methoxyphenyl)pyridin-3-yl)-1,2-oxaborolan-2-ol in the manufacture of a medicament for treating an inflammatory disease in a human.

In another embodiment, the present invention provides the use of crystalline (R)-4-(5-(3-ethoxy-4-methoxyphenyl)pyridin-3-yl)-1,2-oxaborolan-2-ol in the manufacture of a medicament for treating atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human.

In another embodiment, the present invention provides the use of crystalline (R)-4-(5-(3-ethoxy-4-methoxyphenyl)pyridin-3-yl)-1,2-oxaborolan-2-ol in the manufacture of a medicament for treating arthritis, asthma, fibrosis, lupus, allergy, fibromyalgia, wound healing, or inflammation resulting from surgical complications in a human.

In another embodiment, the present invention provides the use of crystalline (R)-4-(5-(3-ethoxy-4-methoxyphenyl)pyridin-3-yl)-1,2-oxaborolan-2-ol in the manufacture of a medicament for treating inflammatory bowel disease, ulcerative colitis, or Crohn's disease in a human.

In another embodiment, the present invention provides crystalline (R)-4-(5-(4-methoxy-3-propoxyphenyl)pyridin-3-yl)-1,2-oxaborolan-2-ol.

In another embodiment, the present invention provides crystalline (R)-4-(5-(4-methoxy-3-propoxyphenyl)pyridin-3-yl)-1,2-oxaborolan-2-ol having an X-ray powder diffraction pattern comprising diffraction peaks 11.0±0.2, 22.9±0.2, and 25.1±0.2 degrees two theta.

In another embodiment, the present invention provides crystalline (R)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 18.8±0.2, 22.9±0.2, 25.1±0.2, and 26.4±0.2 degrees two theta.

In another embodiment, the present invention provides crystalline (R)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 13.2±0.2, 15.1±0.2, 18.8±0.2, 21.3±0.2, 22.9±0.2, 25.1±0.2, and 26.4±0.2 degrees two theta.

In another embodiment, the present invention provides crystalline (R)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 13.2±0.2, 14.5±0.2, 15.1±0.2, 15.6±0.2, 15.9±0.2, 17.7±0.2, 18.8±0.2, 19.4±0.2, 19.7±0.2, 20.5±0.2, 21.3±0.2, and 22.9±0.2, degrees two theta.

In another embodiment, the present invention provides crystalline (R)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 13.2±0.2, 14.5±0.2, 15.1±0.2, 15.6±0.2, 15.9±0.2, 17.7±0.2, 18.8±0.2, 19.4±0.2, 19.7±0.2, 20.5±0.2, 21.3±0.2, 22.9±0.2, 25.1±0.2, 25.9±0.2, 26.4±0.2, 27.5±0.2, and 28.4±0.2 degrees two theta.

In another embodiment, the present invention provides crystalline (R)-4-(5-(4-methoxy-3-propoxyphenyl)pyridin-3-yl)-1,2-oxaborolan-2-ol having an X-ray powder diffraction pattern comprising 3 to 10 diffraction peaks listed in Table 8.

In another embodiment, the present invention provides crystalline (R)-4-(5-(4-methoxy-3-propoxyphenyl)pyridin-3-yl)-1,2-oxaborolan-2-ol having an X-ray powder diffraction pattern comprising the diffraction peaks listed in Table 8.

Figure 6:
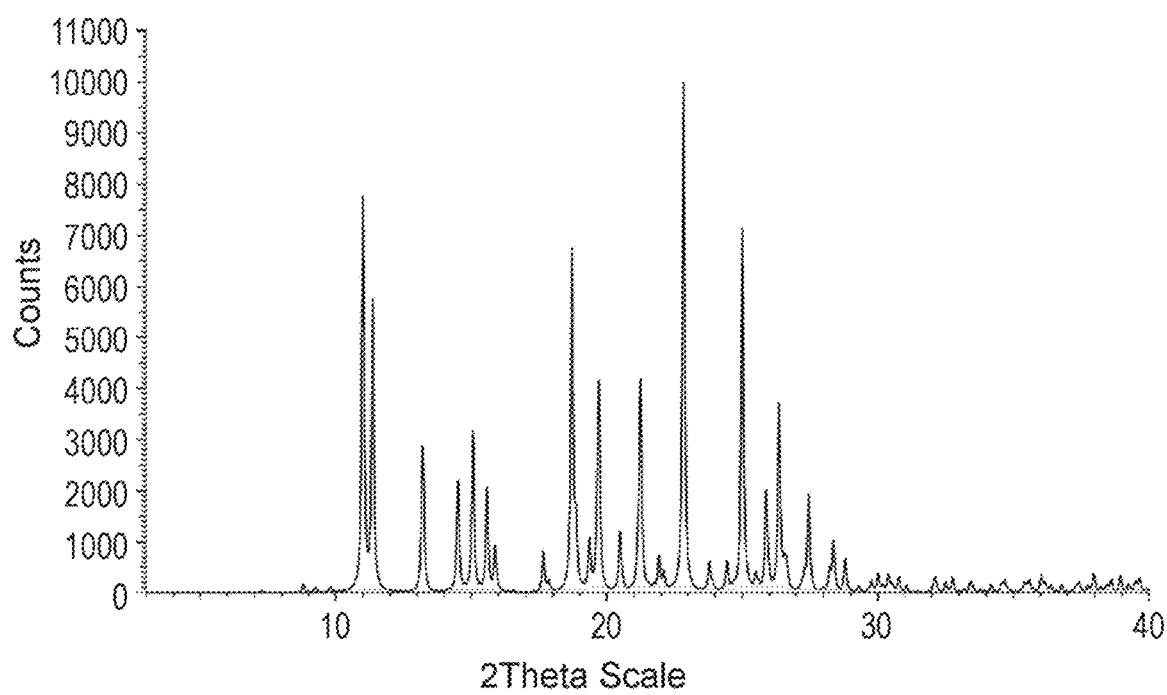
FIG. 6 is a powder X-ray diffraction analysis of crystalline (R)-4-(5-(4-methoxy-3-propoxyphenyl)pyridin-3-yl)-1,2-oxaborolan-2-ol (Example 4).

In another embodiment, the present invention provides crystalline (R)-4-(5-(4-methoxy-3-propoxyphenyl)pyridin-3-yl)-1,2-oxaborolan-2-ol having an X-ray powder diffraction pattern as depicted in FIG. 6.

In another embodiment, the present invention provides a pharmaceutical composition comprising crystalline (R)-4-(5-(4-methoxy-3-propoxyphenyl)pyridin-3-yl)-1,2-oxaborolan-2-ol and at least one pharmaceutically acceptable excipient, diluent, or carrier.

In another embodiment, the present invention provides a method for treating or preventing an inflammatory disease in a human comprising administering to the human in need of such treatment a therapeutically effective amount of crystalline (R)-4-(5-(4-methoxy-3-propoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising administering to the human in need of such treatment a therapeutically effective amount of crystalline (R)-4-(5-(4-methoxy-3-propoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising topically administering to the human in need of such treatment a therapeutically effective amount of crystalline (R)-4-(5-(4-methoxy-3-propoxyphenyl)pyridin-3-yl)-1,2-oxaborolan-2-ol in the form of a transdermal patch, an ointment, a lotion, a cream, or a gel.

In another embodiment, the present invention provides a method for treating or preventing an arthritis, asthma, fibrosis, lupus, allergy, fibromyalgia, wound healing, or inflammation resulting from surgical complications in a human comprising administering to the human in need of such treatment a therapeutically effective amount of crystalline (R)-4-(5-(4-methoxy-3-propoxyphenyl)pyridin-3-yl)-1,2-oxaborolan-2-ol.

In another embodiment, the present invention provides a method for treating or preventing an arthritis, asthma, fibrosis, lupus, allergy, fibromyalgia, wound healing, or inflammation resulting from surgical complications in a human comprising topically administering to the human in need of such treatment a therapeutically effective amount of crystalline (R)-4-(5-(4-methoxy-3-propoxyphenyl)pyridin-3-yl)-1,2-oxaborolan-2-ol in the form of a transdermal patch, an ointment, a lotion, a cream, or a gel.

In another embodiment, the present invention provides a method for treating or preventing inflammatory bowel disease, ulcerative colitis, or Crohn's disease in a human comprising administering to the human in need of such treatment a therapeutically effective amount of crystalline (R)-4-(5-(4-methoxy-3-propoxyphenyl)pyridin-3-yl)-1,2-oxaborolan-2-ol.

In another embodiment, the present invention provides the use of crystalline (R)-4-(5-(4-methoxy-3-propoxyphenyl)pyridin-3-yl)-1,2-oxaborolan-2-ol in the manufacture of a medicament for treating an inflammatory disease in a human.

In another embodiment, the present invention provides the use of crystalline (R)-4-(5-(4-methoxy-3-propoxyphenyl)pyridin-3-yl)-1,2-oxaborolan-2-ol in the manufacture of a medicament for treating atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human.

In another embodiment, the present invention provides the use of crystalline (R)-4-(5-(4-methoxy-3-propoxyphenyl)pyridin-3-yl)-1,2-oxaborolan-2-ol in the manufacture of a medicament for treating arthritis, asthma, fibrosis, lupus, allergy, fibromyalgia, wound healing, or inflammation resulting from surgical complications in a human.

In another embodiment, the present invention provides the use of crystalline (R)-4-(5-(4-methoxy-3-propoxyphenyl)pyridin-3-yl)-1,2-oxaborolan-2-ol in the manufacture of a medicament for treating inflammatory bowel disease, ulcerative colitis, or Crohn's disease in a human.

In another embodiment, the present invention provides crystalline (S)-4-(5-(4-methoxy-3-propoxyphenyl)pyridin-3-yl)-1,2-oxaborolan-2-ol.

In another embodiment, the present invention provides crystalline (S)-4-(5-(4-methoxy-3-propoxyphenyl)pyridin-3-yl)-1,2-oxaborolan-2-ol having an X-ray powder diffraction pattern comprising diffraction peaks 18.7±0.2, 22.8±0.2, and 25.0±0.2 degrees two theta.

In another embodiment, the present invention provides crystalline (S)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 13.2±0.2, 18.7±0.2, 22.8±0.2, and 25.0±0.2, degrees two theta.

In another embodiment, the present invention provides crystalline (S)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 13.2±0.2, 14.5±0.2, 15.1±0.2, 15.6±0.2, 18.7±0.2, 22.8±0.2, and 25.0±0.2, degrees two theta.

In another embodiment, the present invention provides crystalline (S)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 13.2±0.2, 14.5±0.2, 15.1±0.2, 15.6±0.2, 18.7±0.2, 19.7±0.2, 21.2±0.2, 22.8±0.2, 25.0±0.2, and 26.4±0.2 degrees two theta.

In another embodiment, the present invention provides crystalline (S)-4-(5-(4-methoxy-3-propoxyphenyl)pyridin-3-yl)-1,2-oxaborolan-2-ol having an X-ray powder diffraction pattern comprising diffraction peaks 11.0±0.2, 11.4±0.2, 13.2±0.2, 14.5±0.2, 15.1±0.2, 15.6±0.2, 18.7±0.2, 19.4±0.2, 19.7±0.2, 20.5±0.2, 21.2±0.2, 22.8±0.2, 25.0±0.2, 26.4±0.2, 27.4±0.2, and 28.3±0.2, degrees two theta.

In another embodiment, the present invention provides crystalline (S)-4-(5-(4-methoxy-3-propoxyphenyl)pyridin-3-yl)-1,2-oxaborolan-2-ol having an X-ray powder diffraction pattern comprising 3 to 10 diffraction peaks listed in Table 9.

In another embodiment, the present invention provides crystalline (S)-4-(5-(4-methoxy-3-propoxyphenyl)pyridin-3-yl)-1,2-oxaborolan-2-ol having an X-ray powder diffraction pattern comprising the diffraction peaks listed in Table 9.

Figure 7:
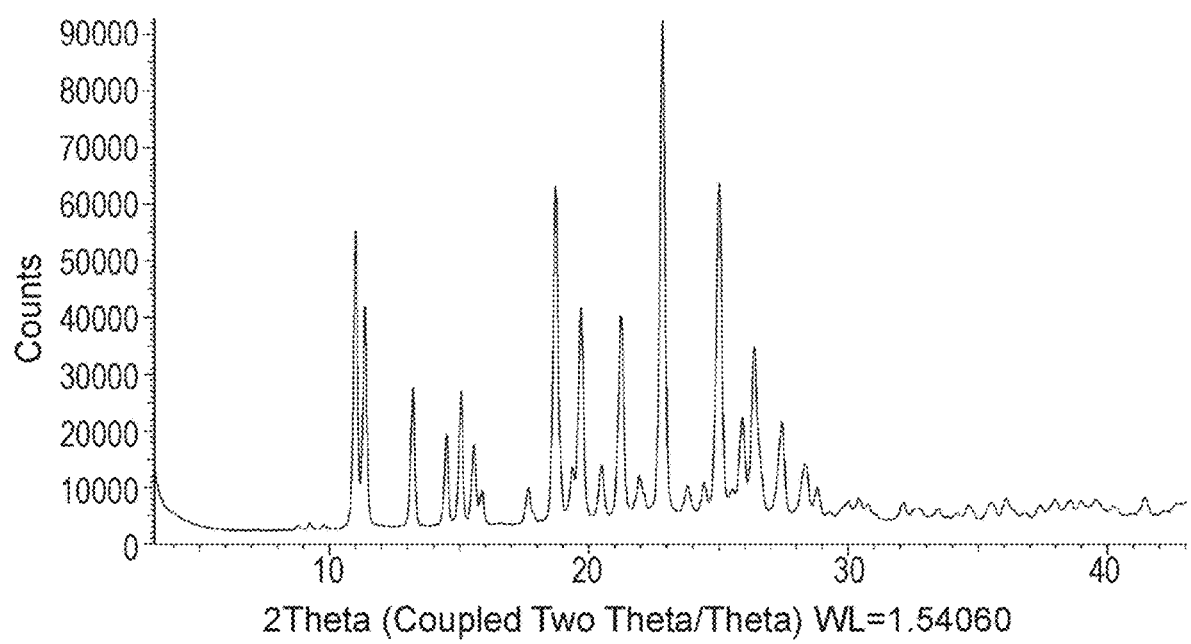
FIG. 7 is a powder X-ray diffraction analysis of crystalline (S)-4-(5-(4-methoxy-3-propoxyphenyl)pyridin-3-yl)-1,2-oxaborolan-2-ol (Example 5).

In another embodiment, the present invention provides crystalline (S)-4-(5-(4-methoxy-3-propoxyphenyl)pyridin-3-yl)-1,2-oxaborolan-2-ol having an X-ray powder diffraction pattern as depicted in FIG. 7.

In another embodiment, the present invention provides a pharmaceutical composition comprising crystalline (S)-4-(5-(4-methoxy-3-propoxyphenyl)pyridin-3-yl)-1,2-oxaborolan-2-ol and at least one pharmaceutically acceptable excipient, diluent, or carrier.

In another embodiment, the present invention provides a method for treating or preventing an inflammatory disease in a human comprising administering to the human in need of such treatment a therapeutically effective amount of crystalline (S)-4-(5-(4-methoxy-3-propoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising administering to the human in need of such treatment a therapeutically effective amount of crystalline (S)-4-(5-(4-methoxy-3-propoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koy-anagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising topically administering to the human in need of such treatment a therapeutically effective amount of crystalline (S)-4-(5-(4-methoxy-3-propoxyphenyl)pyridin-3-yl)-1,2-oxaborolan-2-ol in the form of a transdermal patch, an ointment, a lotion, a cream, or a gel.

In another embodiment, the present invention provides a method for treating or preventing an arthritis, asthma, fibrosis, lupus, allergy, fibromyalgia, wound healing, or inflammation resulting from surgical complications in a human comprising administering to the human in need of such treatment a therapeutically effective amount of crystalline (S)-4-(5-(4-methoxy-3-propoxyphenyl)pyridin-3-yl)-1,2-oxaborolan-2-ol.

In another embodiment, the present invention provides a method for treating or preventing an arthritis, asthma, fibrosis, lupus, allergy, fibromyalgia, wound healing, or inflammation resulting from surgical complications in a human comprising topically administering to the human in need of such treatment a therapeutically effective amount of crystalline (S)-4-(5-(4-methoxy-3-propoxyphenyl)pyridin-3-yl)-1,2-oxaborolan-2-ol in the form of a transdermal patch, an ointment, a lotion, a cream, or a gel.

In another embodiment, the present invention provides a method for treating or preventing inflammatory bowel disease, ulcerative colitis, or Crohn's disease in a human comprising administering to the human in need of such treatment a therapeutically effective amount of crystalline (S)-4-(5-(4-methoxy-3-propoxyphenyl)pyridin-3-yl)-1,2-oxaborolan-2-ol.

In another embodiment, the present invention provides the use of crystalline (S)-4-(5-(4-methoxy-3-propoxyphenyl)pyridin-3-yl)-1,2-oxaborolan-2-ol in the manufacture of a medicament for treating an inflammatory disease in a human.

In another embodiment, the present invention provides the use of crystalline (S)-4-(5-(4-methoxy-3-propoxyphenyl)pyridin-3-yl)-1,2-oxaborolan-2-ol in the manufacture of a medicament for treating atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koy-anagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human.

In another embodiment, the present invention provides the use of crystalline (S)-4-(5-(4-methoxy-3-propoxyphenyl)pyridin-3-yl)-1,2-oxaborolan-2-ol in the manufacture of a medicament for treating arthritis, asthma, fibrosis, lupus, allergy, fibromyalgia, wound healing, or inflammation resulting from surgical complications in a human.

In another embodiment, the present invention provides the use of crystalline (S)-4-(5-(4-methoxy-3-propoxyphenyl)pyridin-3-yl)-1,2-oxaborolan-2-ol in the manufacture of a medicament for treating inflammatory bowel disease, ulcerative colitis, or Crohn's disease in a human.

In another embodiment, the present invention provides crystalline (−) 4-(5-(2-(difluoromethyl)-3-ethoxy-4-methoxyphenyl)pyridin-3-yl)-1,2-oxaborolan-2-ol.

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern comprising diffraction peaks 12.8±0.2, 20.4±0.2, and 25.7±0.2 degrees two theta.

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern comprising diffraction peaks 12.8±0.2, 17.9±0.2, 20.4±0.2, 22.9±0.2, 23.1±0.2, and 25.7±0.2 degrees two theta.

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern comprising diffraction peaks 8.9±0.2, 12.0±0.2, 12.3±0.2, 12.8±0.2, 17.8±0.2, 20.4±0.2, 22.9±0.2, 23.1±0.2, and 25.7±0.2 degrees two theta.

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern comprising diffraction peaks 8.9±0.2, 12.0±0.2, 12.3±0.2, 12.8±0.2, 13.9±0.2, 14.2±0.2, 17.6±0.2, 17.8±0.2, 19.2±0.2, 19.4±0.2, 19.6±0.2, and 20.4±0.2 degrees two theta.

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern comprising diffraction peaks 8.9±0.2, 12.0±0.2, 12.3±0.2, 12.8±0.2, 13.9±0.2, 14.2±0.2, 17.6±0.2, 17.8±0.2, 19.2±0.2, 19.4±0.2, 19.6±0.2, 20.4±0.2, 21.4±0.2, 22.0±0.2, 22.3±0.2, 22.9±0.2, 23.1±0.2, and 25.7±0.2 degrees two theta.

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern comprising 3 to 10 diffraction peaks listed in Table 10.

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern comprising the diffraction peaks listed in Table 10.

Figure 8:
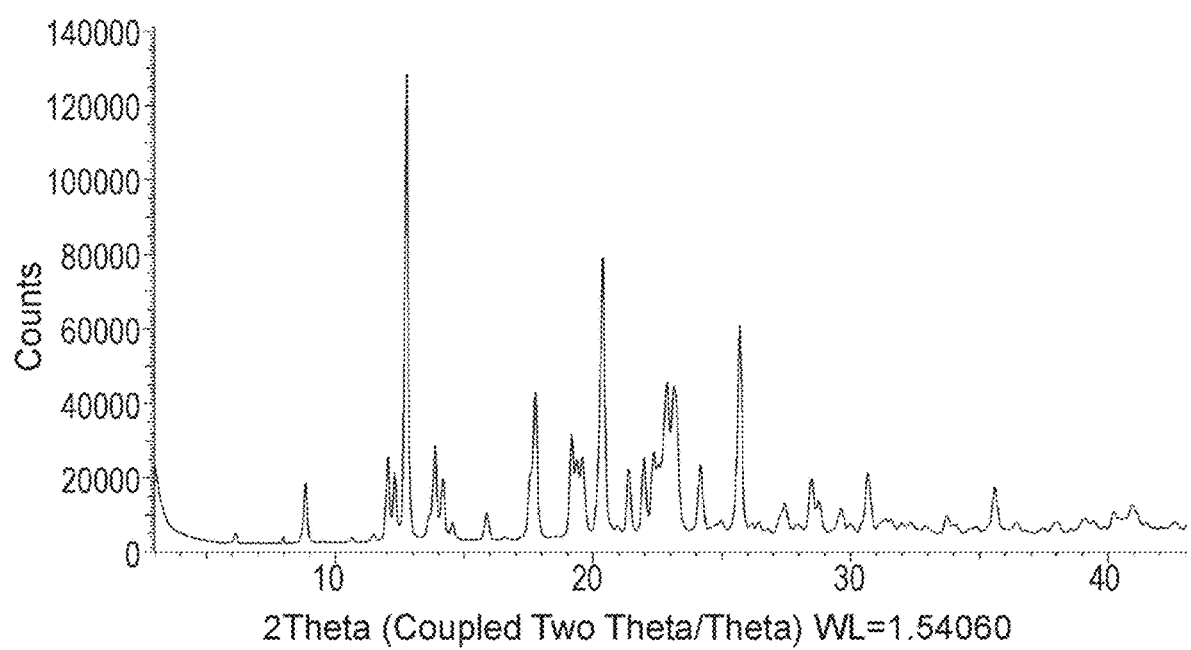
FIG. 8 is a powder X-ray diffraction analysis of crystalline (−) 4-(5-(2-(difluoromethyl)-3-ethoxy-4-methoxyphenyl)pyridin-3-yl)-1,2-oxaborolan-2-ol (Example 10).

In another embodiment, the present invention provides crystalline (−) 4-(5-(2-(difluoromethyl)-3-ethoxy-4-methoxyphenyl)pyridin-3-yl)-1,2-oxaborolan-2-ol having an X-ray powder diffraction pattern as depicted in FIG. 8.

In another embodiment, the present invention provides a pharmaceutical composition comprising crystalline (−) 4-(5-(2-(difluoromethyl)-3-ethoxy-4-methoxyphenyl)pyridin-3-yl)-1,2-oxaborolan-2-ol and at least one pharmaceutically acceptable excipient, diluent, or carrier.

In another embodiment, the present invention provides a method for treating or preventing an inflammatory disease in a human comprising administering to the human in need of such treatment a therapeutically effective amount of crystalline (−) 4-(5-(2-(difluoromethyl)-3-ethoxy-4-methoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising administering to the human in need of such treatment a therapeutically effective amount of crystalline (−) 4-(5-(2-(difluoromethyl)-3-ethoxy-4-methoxyphenyl)pyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising topically administering to the human in need of such treatment a therapeutically effective amount of crystalline (−) 4-(5-(2-(difluoromethyl)-3-ethoxy-4-methoxyphenyl)pyridin-3-yl)-1,2-oxaborolan-2-ol in the form of a transdermal patch, an ointment, a lotion, a cream, or a gel.

In another embodiment, the present invention provides a method for treating or preventing an arthritis, asthma, fibrosis, lupus, allergy, fibromyalgia, wound healing, or inflammation resulting from surgical complications in a human comprising administering to the human in need of such treatment a therapeutically effective amount of crystalline (−) 4-(5-(2-(difluoromethyl)-3-ethoxy-4-methoxyphenyl)pyridin-3-yl)-1,2-oxaborolan-2-ol.

In another embodiment, the present invention provides a method for treating or preventing an arthritis, asthma, fibrosis, lupus, allergy, fibromyalgia, wound healing, or inflammation resulting from surgical complications in a human comprising topically administering to the human in need of such treatment a therapeutically effective amount of crystalline (−) 4-(5-(2-(difluoromethyl)-3-ethoxy-4-methoxyphenyl)pyridin-3-yl)-1,2-oxaborolan-2-ol in the form of a transdermal patch, an ointment, a lotion, a cream, or a gel.

In another embodiment, the present invention provides a method for treating or preventing inflammatory bowel disease, ulcerative colitis, or Crohn's disease in a human comprising administering to the human in need of such treatment a therapeutically effective amount of crystalline (−) 4-(5-(2-(difluoromethyl)-3-ethoxy-4-methoxyphenyl)pyridin-3-yl)-1,2-oxaborolan-2-ol.

In another embodiment, the present invention provides the use of crystalline (−) 4-(5-(2-(difluoromethyl)-3-ethoxy-4-methoxyphenyl)pyridin-3-yl)-1,2-oxaborolan-2-ol in the manufacture of a medicament for treating an inflammatory disease in a human.

In another embodiment, the present invention provides the use of crystalline (−) 4-(5-(2-(difluoromethyl)-3-ethoxy-4-methoxyphenyl)pyridin-3-yl)-1,2-oxaborolan-2-ol in the manufacture of a medicament for treating atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human.

In another embodiment, the present invention provides the use of crystalline (−) 4-(5-(2-(difluoromethyl)-3-ethoxy-4-methoxyphenyl)pyridin-3-yl)-1,2-oxaborolan-2-ol in the manufacture of a medicament for treating arthritis, asthma, fibrosis, lupus, allergy, fibromyalgia, wound healing, or inflammation resulting from surgical complications in a human.

In another embodiment, the present invention provides the use of crystalline (−) 4-(5-(2-(difluoromethyl)-3-ethoxy-4-methoxyphenyl)pyridin-3-yl)-1,2-oxaborolan-2-ol in the manufacture of a medicament for treating inflammatory bowel disease, ulcerative colitis, or Crohn's disease in a human.

In another embodiment, the present invention provides crystalline (R) 4-(5-(3-ethoxy-4-methoxyphenyl)-6-methylpyridin-3-yl)-1,2-oxaborolan-2-ol.

In another embodiment, the present invention provides crystalline (R) 4-(5-(3-ethoxy-4-methoxyphenyl)-6-methylpyridin-3-yl)-1,2-oxaborolan-2-ol having an X-ray powder diffraction pattern comprising diffraction peaks 21.1±0.2, 22.7±0.2, and 23.8±0.2 degrees two theta.

In another embodiment, the present invention provides crystalline (R) 4-(5-(3-ethoxy-4-methoxyphenyl)-6-methylpyridin-3-yl)-1,2-oxaborolan-2-ol having an X-ray powder diffraction pattern comprising diffraction peaks 10.9±0.2, 11.3±0.2, 19.3±0.2, 21.1±0.2, 22.7±0.2, 23.8±0.2, and 30.4±0.2 degrees two theta.

In another embodiment, the present invention provides crystalline (R) 4-(5-(3-ethoxy-4-methoxyphenyl)-6-methylpyridin-3-yl)-1,2-oxaborolan-2-ol having an X-ray powder diffraction pattern comprising diffraction peaks 10.9±0.2, 11.3±0.2, 17.0±0.2, 17.3±0.2, 19.3±0.2, 21.1±0.2, 22.7±0.2, 23.8±0.2, and 30.4±0.2 degrees two theta.

In another embodiment, the present invention provides crystalline (R) 4-(5-(3-ethoxy-4-methoxyphenyl)-6-methylpyridin-3-yl)-1,2-oxaborolan-2-ol having an X-ray powder diffraction pattern comprising diffraction peaks 10.9±0.2, 11.3±0.2, 17.0±0.2, 17.3±0.2, 19.0±0.2, 19.3±0.2, 21.1±0.2, 22.7±0.2, 23.8±0.2, 25.4±0.2, 26.5±0.2, and 30.4±0.2 degrees two theta.

In another embodiment, the present invention provides crystalline (R) 4-(5-(3-ethoxy-4-methoxyphenyl)-6-methylpyridin-3-yl)-1,2-oxaborolan-2-ol having an X-ray powder diffraction pattern comprising 3 to 10 diffraction peaks listed in Table 11.

In another embodiment, the present invention provides crystalline (R) 4-(5-(3-ethoxy-4-methoxyphenyl)-6-methylpyridin-3-yl)-1,2-oxaborolan-2-ol having an X-ray powder diffraction pattern comprising the diffraction peaks listed in Table 11.

Figure 9:
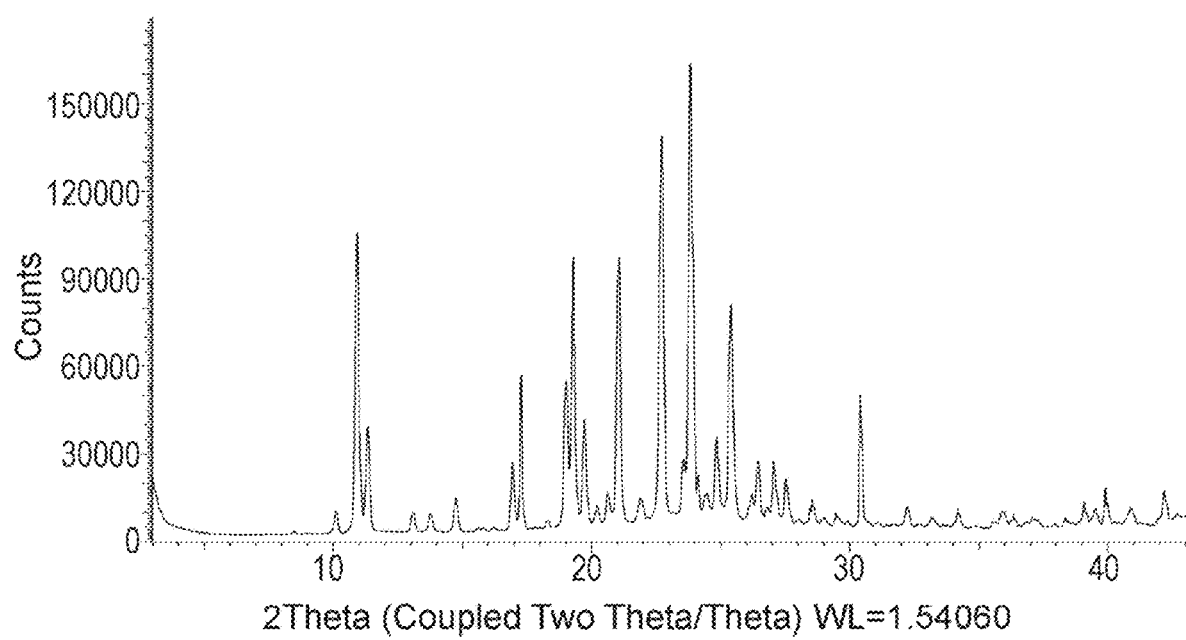
FIG. 9 is a powder X-ray diffraction analysis of crystalline (R)-4-(5-(3-ethoxy-4-methoxyphenyl)-6-methylpyridin-3-yl)-1,2-oxaborolan-2-ol (Example 19).
Figure 10:
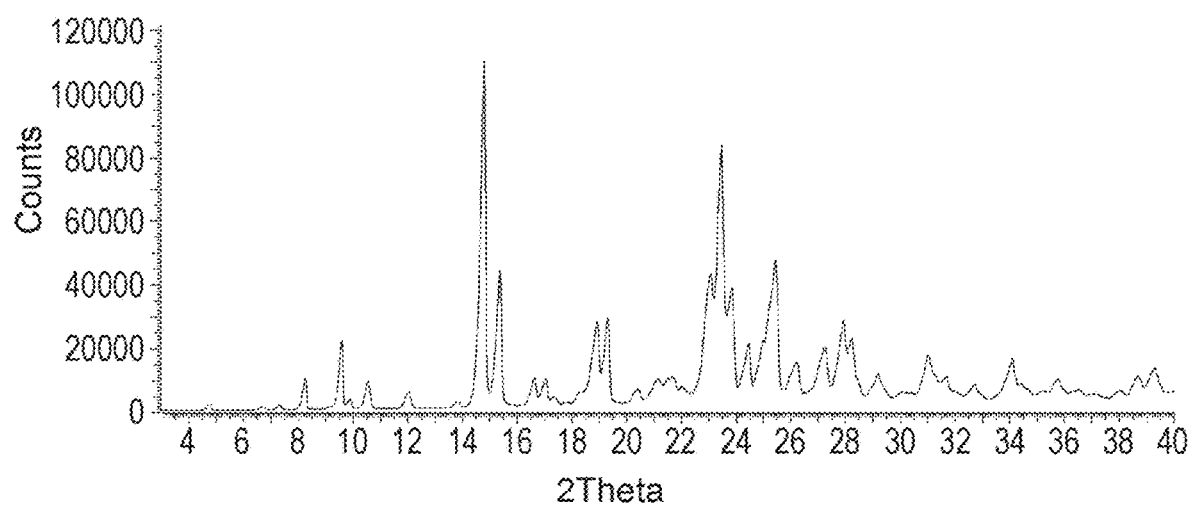
FIG. 10 is a powder X-ray diffraction analysis of crystalline (4-methoxy-3-propoxyphenyl)boronic acid.
Figure 11:
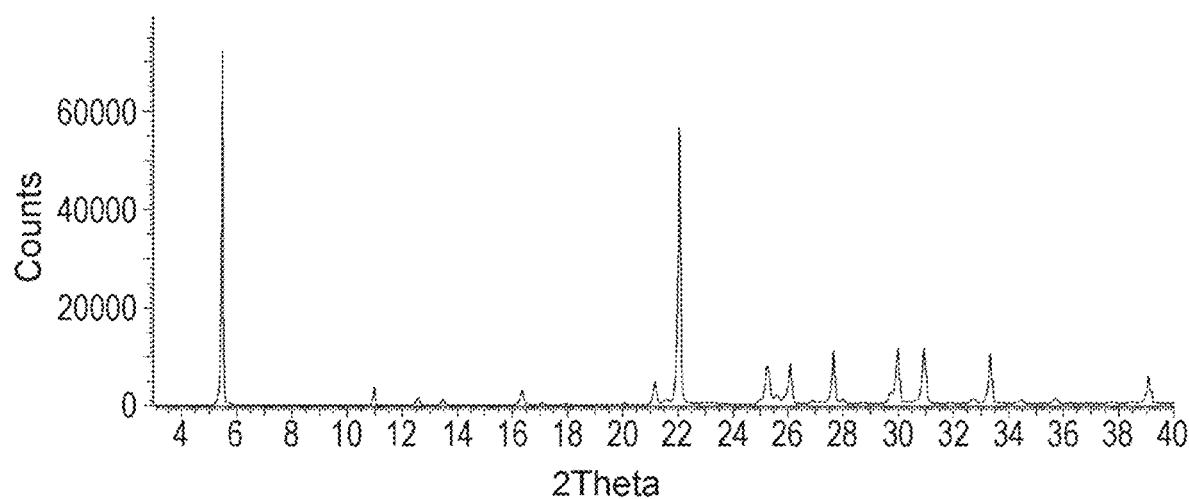
FIG. 11 is a powder X-ray diffraction analysis of crystalline 3-bromo-5-(4-methoxy-3-propoxyphenyl)pyridine.
Figure 12:
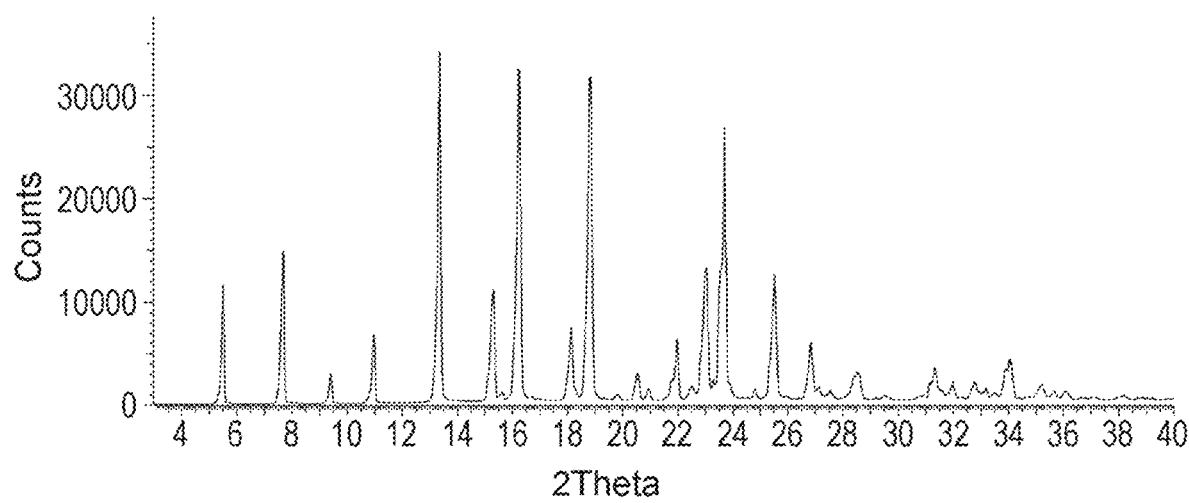
FIG. 12 is a powder X-ray diffraction analysis of crystalline 3-(3-(((tert-butyldimethylsilyl)oxy)prop-1-en-2-yl)-5-(4-methoxy-3-propoxyphenyl)pyridine.

In another embodiment, the present invention provides crystalline (R) 4-(5-(3-ethoxy-4-methoxyphenyl)-6-methylpyridin-3-yl)-1,2-oxaborolan-2-ol having an X-ray powder diffraction pattern as depicted in FIG. 9.

In another embodiment, the present invention provides a pharmaceutical composition comprising crystalline (R) 4-(5-(3-ethoxy-4-methoxyphenyl)-6-methylpyridin-3-yl)-1,2-oxaborolan-2-ol and at least one pharmaceutically acceptable excipient, diluent, or carrier.

In another embodiment, the present invention provides a method for treating or preventing an inflammatory disease in a human comprising administering to the human in need of such treatment a therapeutically effective amount of crystalline (R) 4-(5-(3-ethoxy-4-methoxyphenyl)-6-methylpyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising administering to the human in need of such treatment a therapeutically effective amount of crystalline (R) 4-(5-(3-ethoxy-4-methoxyphenyl)-6-methylpyridin-3-yl)-1,2-oxaborolan-2-ol.

In another embodiment, the present invention provides a method for treating or preventing atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human comprising topically administering to the human in need of such treatment a therapeutically effective amount of crystalline (R) 4-(5-(3-ethoxy-4-methoxyphenyl)-6-methylpyridin-3-yl)-1,2-oxaborolan-2-ol in the form of a transdermal patch, an ointment, a lotion, a cream, or a gel.

In another embodiment, the present invention provides a method for treating or preventing an arthritis, asthma, fibrosis, lupus, allergy, fibromyalgia, wound healing, or inflammation resulting from surgical complications in a human comprising administering to the human in need of such treatment a therapeutically effective amount of crystalline (R) 4-(5-(3-ethoxy-4-methoxyphenyl)-6-methylpyridin-3-yl)-1,2-oxaborolan-2-ol.

In another embodiment, the present invention provides a method for treating or preventing an arthritis, asthma, fibrosis, lupus, allergy, fibromyalgia, wound healing, or inflammation resulting from surgical complications in a human comprising topically administering to the human in need of such treatment a therapeutically effective amount of crystalline (R) 4-(5-(3-ethoxy-4-methoxyphenyl)-6-methylpyridin-3-yl)-1,2-oxaborolan-2-ol in the form of a transdermal patch, an ointment, a lotion, a cream, or a gel.

In another embodiment, the present invention provides a method for treating or preventing inflammatory bowel disease, ulcerative colitis, or Crohn's disease in a human comprising administering to the human in need of such treatment a therapeutically effective amount of crystalline (R) 4-(5-(3-ethoxy-4-methoxyphenyl)-6-methylpyridin-3-yl)-1,2-oxaborolan-2-ol.

In another embodiment, the present invention provides the use of crystalline (R) 4-(5-(3-ethoxy-4-methoxyphenyl)-6-methylpyridin-3-yl)-1,2-oxaborolan-2-ol in the manufacture of a medicament for treating an inflammatory disease in a human.

In another embodiment, the present invention provides the use of crystalline (R) 4-(5-(3-ethoxy-4-methoxyphenyl)-6-methylpyridin-3-yl)-1,2-oxaborolan-2-ol in the manufacture of a medicament for treating atopic dermatitis, hand dermatitis, contact dermatitis, allergic contact dermatitis, irritant contact dermatitis, neurodermatitis, perioral dermatitis, stasis dermatitis, dyshidrotic eczema, xerotic dermatitis, nummalar dermatitis, seborrheic dermatitis, eyelid dermatitis, diaper dermatitis, dermatomyositis, lichen planus, lichen sclerosis, alopecia areata, vitiligo, rosacea, epidermolysis bullosa, keratosis pilaris, pityriasis alba, pemphigus, vulvovaginitis, acne, chronic spontaneous urticaria, chronic idiopathic urticaria, chronic physical urticaria, vogt-koyanagi-harada disease, sutton nevus/nevi, post inflammatory hypopigmentation, senile leukoderma, chemical/drug-induced leukoderma, cutaneous lupus erythematosus, discoid lupus, palmoplantar pustulosis, pemphigoid, sweet's syndrome, hidradenitis suppurativa, psoriasis, plaque psoriasis, pustular psoriasis, nail psoriasis, flexural psoriasis, guttate psoriasis, psoriatic arthritis, erythrodermic psoriasis, or inverse psoriasis in a human.

In another embodiment, the present invention provides the use of crystalline (R) 4-(5-(3-ethoxy-4-methoxyphenyl)-6-methylpyridin-3-yl)-1,2-oxaborolan-2-ol in the manufacture of a medicament for treating arthritis, asthma, fibrosis, lupus, allergy, fibromyalgia, wound healing, or inflammation resulting from surgical complications in a human.

In another embodiment, the present invention provides the use of crystalline (R) 4-(5-(3-ethoxy-4-methoxyphenyl)-6-methylpyridin-3-yl)-1,2-oxaborolan-2-ol in the manufacture of a medicament for treating inflammatory bowel disease, ulcerative colitis, or Crohn's disease in a human.

In another embodiment, the present invention provides pharmaceutical combinations for topical administration comprising a compound of Formula (I), Formula (IA), Formula (IB), or Formula (IC), or a pharmaceutically acceptable salt thereof, in combination with another pharmaceutical agent for the treatment of the diseases, conditions and/or disorders described herein. Suitable pharmaceutical agents that may be used in combination with the compounds of the present invention for topical administration include, but are not limited to: a second compound of Formula (I), Formula (IA), Formula (IB), or Formula (IC); a PDE4 isoenzyme inhibitor including, but not limited to, crisaborole, apremilast, roflumilast, rolipram and piclamilast; a corticosteroid including, but not limited to, fluocinonide, desoximetasone, mometasone, triamcinolone, betamethasone, alclometasone, desonide, hydrocortisone and mapracorat; a calcineurin inhibitor including, but not limited to, tacrolimus, pimecrolimus and cyclosporine; a JAK inhibitor including, but not limited to, tofacitinib, ATI-502, SNA-152, SHR-0302, JTE052, BMS-986165, filgotinib, baricitinib, upadacitinib, ruxolitinib, peficitinib, PF-04965842, PF-06651600, PF-06700841, and PF06826647; an aryl hydrocarbon receptor agonist including, but not limited to, tapinarof; an IRAK4 inhibitor including, but not limited to, PF-06650833; a non-steroidal anti-inflammatory including, but not limited to, WBI-1001 and MRX-6; vitamin D analog such as calcipotriene; retinoic acid derivatives including, but not limited to, alitretinoin; a liver X receptor (LXR) selective agonist including, but not limited to, VTP-38543; a H4 receptor antagonists including, but not limited to, ZPL-389; a NKI receptor antagonists including, but not limited to, Aprepitant and Tradipitant; a CRTH2 receptor antagonists including, but not limited to, Fevipiprant and OC-459; a Chymase inhibitors including, but not limited to, SUN 13834; a GATA-3 inhibitors including, but not limited to, SB-011 and GR-MD-02; and a ROR inverse agonists including, but not limited to, VTP-43742, ARN6039, TAK-828 and JTE-451; immunomodulators such as PF-06763809, and inhibitors of SYK, BTK, and ITK, including but not limited to, R-348, cerdulatinib, ibrutinib, entospletinib, tirabrutinib, and JTE-051.

In another embodiment, the present invention provides pharmaceutical combinations for oral administration comprising a compound of Formula (I), Formula (IA), Formula (IB), or Formula (IC), or a pharmaceutically acceptable salt thereof, in combination with another pharmaceutical agent for the treatment of the diseases, conditions and/or disorders described herein. Suitable pharmaceutical agents that may be used in combination with the compounds of the present invention for oral administration include, but are not limited to: oral retinoic acid derivatives including, but not limited to, alitretinoin; oral liver X receptor (LXR) selective agonists including, but not limited to, VTP-38543; oral H4 receptor antagonists including, but not limited to, ZPL-389; oral NKI receptor antagonists including, but not limited to, Aprepitant and Tradipitant; oral CRTH2 receptor antagonists including, but not limited to, Fevipiprant and OC-459; oral Chymase inhibitors including, but not limited to, SUN 13834; oral GATA-3 inhibitors including, but not limited to, SB-011; oral ROR inverse agonists including, but not limited to, VTP-43742, ARN6039, TAK-828 and JTE-451; oral JAK inhibitors including, but not limited to, baricitinib, cerdulatinib, decernotinib, delgocitinib, fedratinib, filgotinib, gandotinib, ilginatinib, itacitinib, lestaurtinib, momelotinib, oclacitinib, pacritinib, peficitinib, ruxolitinib, tofacitinib, upadacitinib, ASN-002, AT9283, ATI-501, ATI-502, AZD1480, AZD4205, BMS-911543, BMS-986165, INCB-52793, INCB-54707, PF-04965842, PF-06263276, PF-06651600, PF-06700841, PF-06826647, SHR-0302, SNA-125, or TD-1473; immunomodulators and inhibitors of SYK, BTK, and ITK, including but not limited to, fostamatinib, ibrutinib, mastinib, mivavotinib, entospletinib, sperbrutinib, tirabrutinib, fenebrutinib, TOP-1288, R-348, cerdulatinib, SKI-O-703, TAS-05567, CG-806, R-343, CG-103065, PRT-2607, GSK-143, VRT-750018, UR-67767, PRN-1008, BMS-935177, PRN-473, ABBV-105, AS-550, M-7583, WXFL-10230486, LOU-064, AEG-42766, HCl-1401, KBP-7536, ARQ-531, GNE-4997, and GNE-9822; and oral IRAK4 inhibitors including, but not limited to, PF-06650833 and BAY-1830839.

In another embodiment, the present invention provides pharmaceutical combinations for injectable administration comprising a compound of Formula (I), Formula (IA), Formula (IB), or Formula (IC), or a pharmaceutically acceptable salt thereof, in combination with another pharmaceutical agent for the treatment of the diseases, conditions and/or disorders described herein. Suitable pharmaceutical agents that may be used in combination with the compounds of the present invention for injectable administration include, but are not limited to: TNFα inhibitors including, but not limited to, infliximab, adalimumab, golimumab, certolizumab pegol; injectable anti-IL4, IL-12, IL-17, IL-22, IL-23, IL-31, IL-33, IgE treatments such as dupilumab, lebrikizumab, nemolizumab, tralokinumab, etanercept, adalimumab, infliximab, ustekinumab, secukinumab, Oma-Zumilab, and CIM-331.

Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the Formulae (I), (IA), (IB), and (IC), another therapeutic agent or a pharmaceutically acceptable salt, ester or prodrug thereof, and at least one pharmaceutically acceptable excipient or carrier.

When used in the above or other treatments, a therapeutically effective amount of one of the compounds of the present invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the present invention means a sufficient amount of the compound to treat the diseases, conditions, or disorders indicated herein at a reasonable benefit/risk ratio applicable to any medical treatment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Pharmaceutical Compositions or Formulations

In another embodiment, the present invention provides pharmaceutical compositions, or formulations, comprising a therapeutically effective amount of a compound of the present invention and a pharmaceutically acceptable excipient, diluent or carrier. The pharmaceutical compositions, or formulations, of this invention may be administered to humans and other mammals topically, orally, parenterally, intracisternally, intravaginally, intraperitoneally, bucally, as an oral spray, as a nasal spray, rectally as a suppository, or in the form of a liposome.

A typical pharmaceutical composition or formulation is prepared by mixing a compound of the present invention and a carrier, diluent or excipient. Suitable carriers, diluents and excipients include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., for use in the preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent deposition method and disintegrants" J. Pharm. Pharmacol, 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical composition, or formulation, for application may be packaged in a variety of ways depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The term "pharmaceutically acceptable carrier" refers to carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Additional information concerning carriers can be found in Remington: The Science and Practice of Pharmacy, 21st Ed., Lippincott, Williams & Wilkins (2005) which is incorporated herein by reference. Further examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutically acceptable topical carrier" refers to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Compounds that are volatile in may require admixture with special formulating agents or with special packaging materials to assure proper dosage delivery. In addition, compounds of the present invention that have poor human skin permeability may require one or more permeability enhancers whereas compounds rapidly absorbed through the skin may require formulation with absorption-retarding agents or barriers.

The ointments, pastes, creams, lotions, gels, powders, and solutions, for topical administration may contain, in addition to an active compound of the present invention, pharmaceutically acceptable excipients such as animal and vegetable fats, oils, waxes, paraffins, starch, tragacanth, cellulose derivatives, polyethylene glycols, silicones, bentonites, silicic acid, talc, zinc oxide, preservatives, antioxidants, fragrances, emulsifiers, dyes, inert fillers, anti-irritants, tackifiers, fragrances, opacifiers, antioxidants, gelling agents, stabilizers, surfactants, emollients, coloring agents, preservatives, buffering agents, permeation enhancers, or mixtures thereof. Topical excipients should not interfere with the effectiveness of the biological activity of the active agent and not be deleterious to the epithelial cells or their function.

The terms "permeability enhancer," or "permeation enhancer," relates to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, J of Controlled Release, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Solid dosage forms for oral administration include capsules, tablets, pills, powders, and granules. In such solid dosage forms, the active compound is mixed with at least one inert pharmaceutically acceptable carrier such as sodium citrate or calcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

The term "parenterally," as used herein, refers to modes of administration which include intravenous, intramuscular, intraperitoneal, intrasternal, subcutaneous, intraarticular injection and infusion. Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Pharmaceutical compositions, or formulations, for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Compounds of the present invention may also be administered in the form of liposomes. Liposomes are generally derived from phospholipids or other lipid substances and are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Pharmaceutical compositions, or formulations, of the present invention may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

The pharmaceutical compositions, or formulations, of the invention may be suspensions. Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The pharmaceutical compositions also include solvates and hydrates of the compounds of the present invention. The term "solvate" refers to a molecular complex of a compound represented by Formulae (I), (IA), (IB), and (IC), including pharmaceutically acceptable salts thereof, with one or more solvent molecules. Such solvent molecules are those commonly used in the pharmaceutical art, which are known to be innocuous to the recipient, e.g., water, ethanol, ethylene glycol, (S)-propylene glycol, (R)-propylene glycol, and the like, The term "hydrate" refers to the complex where the solvent molecule is water. The solvates and/or hydrates preferably exist in crystalline form. Other solvents may be used as intermediate solvates in the preparation of more desirable solvates. Intermediate solvents include, but are not limited to, methanol, methyl t-butyl ether, ethyl acetate, methyl acetate, 1,4-butyne-diol, and the like.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.000001 to about 10 mg/kg/day. For purposes of oral administration, more preferable doses can be in the range of from about 0.001 to about 1 mg/kg/day. For topical administration, more preferable doses can be in the range of 0.00001 mg/kg/day to about 5 mg/kg/day. If desired, the effective daily dose can be divided into multiple doses for purposes of administration, e.g. two to four separate doses per day.

Definitions

As used throughout this specification and the appended claims, the following terms have the following meanings:

The term "$(C_2-C_6)$alkenyl" as used herein, means a straight or branched chain hydrocarbon containing from 2 to 6 carbons and containing at least one carbon-carbon double bond. Representative examples of $(C_2-C_6)$alkenyl include, but are not limited to, ethenyl, 2-propenyl, 2-methyl-2-propenyl, 3-butenyl, 4-pentenyl, and 5-hexenyl.

The term "$(C_2-C_6)$alkenyloxy" as used herein, means a $(C_2-C_6)$alkenyl group, as defined herein, appended to the parent molecular moiety through an oxygen atom.

The term "$(C_2-C_6)$alkenylthio" as used herein, means a $(C_2-C_6)$alkenyl group, as defined herein, appended to the parent molecular moiety through a sulfur atom.

The term "$(C_1-C_6)$alkoxy" as used herein, means a $(C_1-C_6)$alkyl group, as defined herein, appended to the parent molecular moiety through an oxygen atom. Representative examples of $(C_1-C_6)$alkoxy include, but are not limited to, methoxy, ethoxy, propoxy, 2-propoxy, butoxy, tert-butoxy, pentyloxy, and hexyloxy.

The term "$(C_1-C_6)$alkoxy-$d_1$-13" as used herein, means a $(C_1-C_6)$alkyl-$d_{1-13}$ group, as defined herein, appended to the parent molecular moiety through an oxygen atom.

Representative examples of $(C_1-C_6)$alkoxy-$d_{1-13}$ include, but are not limited to, methoxy-$d_3$, ethoxy-$d_5$, propoxy-$d_7$, 2-propoxy-$d_7$, butoxy-$d_8$, tert-butoxy-$d_9$, pentyloxy-$d_{11}$, and hexyloxy-$d_{13}$.

The term "$(C_1-C_6)$alkoxy$(C_1-C_6)$alkoxy" as used herein, means a $(C_1-C_6)$alkoxy group, as defined herein, appended to the parent molecular moiety through another $(C_1-C_6)$alkoxy group, as defined herein. Representative examples of $(C_1-C_6)$alkoxy$(C_1-C_6)$alkoxy include, but are not limited to, tert-butoxymethoxy, 2-ethoxyethoxy, 2-methoxyethoxy, and methoxymethoxy.

The term "$(C_1-C_6)$alkoxy$(C_1-C_6)$alkyl" as used herein, means a $(C_1-C_6)$alkoxy group, as defined herein, appended to the parent molecular moiety through a $(C_1-C_6)$alkyl group, as defined herein. Representative examples of $(C_1-C_6)$alkoxy$(C_1-C_6)$alkyl include, but are not limited to, tert-butoxymethyl, 2-ethoxyethyl, 2-methoxyethyl, and methoxymethyl.

The term "$(C_1-C_6)$alkoxycarbonyl" as used herein, means a $(C_1-C_6)$alkoxy group, as defined herein, appended to the parent molecular moiety through a carbonyl group, as defined herein. Representative examples of $(C_1-C_6)$alkoxycarbonyl include, but are not limited to, methoxycarbonyl, ethoxycarbonyl, and tert-butoxycarbonyl.

The term "$(C_1-C_3)$alkyl" as used herein, means a straight or branched chain hydrocarbon containing from 1 to 3 carbon atoms. Representative examples of $(C_1-C_3)$alkyl include methyl, ethyl, n-propyl, and iso-propyl.

The term "$(C_1-C_3)$alkyl-$d_{1-7}$" as used herein, means a straight or branched chain hydrocarbon containing from 1 to 3 carbon atoms wherein one to seven of the hydrogens have been exchanged for deuterium ($^2H$ or D). Representative examples of $(C_1-C_3)$alkyl-$d_{1-7}$ include methyl-$d_3$, ethyl-$d_5$, ethyl-2,2,2-$d_3$, propyl-$d_7$, and 2-propyl-$d_7$.

The term "$(C_1-C_6)$alkyl" as used herein, means a straight or branched chain hydrocarbon containing from 1 to 6 carbon atoms. Representative examples of $(C_1-C_6)$alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "$(C_1-C_6)$alkyl-$d_1$-13" as used herein, means a straight or branched chain hydrocarbon containing from 1 to 6 carbon atoms wherein one to thirteen of the hydrogens have been exchanged for deuterium ($^2H$ or D). Representative examples of $(C_1-C_6)$alkyl-$d_{1-13}$ include, but are not limited to, methyl-$d_3$, ethyl-$d_5$, ethyl-2,2,2-$d_3$, propyl-$d_7$, 2-propyl-$d_7$, butyl-$d_6$, tert-butyl-$d_9$, pentyl-$d_{11}$, and hexyl-$d_{13}$.

The term "$(C_1-C_6)$alkylcarbonyl" as used herein, means a $(C_1-C_6)$alkyl group, as defined herein, appended to the parent molecular moiety through a carbonyl group, as defined herein. Representative examples of $(C_1-C_6)$alkylcarbonyl include, but are not limited to, acetyl, 1-oxopropyl, 2,2-dimethyl-1-oxopropyl, 1-oxobutyl, and 1-oxopentyl.

The term "$(C_1-C_6)$alkylthio" as used herein, means a $(C_1-C_6)$alkyl group, as defined herein, appended to the parent molecular moiety through a sulfur atom. Representative examples of $(C_1-C_6)$alkylthio include, but are not limited to, methylthio, ethylthio, tert-butylthio, and hexylthio.

The term "$(C_1-C_6)$alkylthio$(C_1-C_6)$alkyl" as used herein, means a $(C_1-C_6)$alkylthio group, as defined herein, appended to the parent molecular moiety through a $(C_1-C_6)$alkyl group, as defined herein. Representative examples of $(C_1-C_6)$alkylthio$(C_1-C_6)$alkyl include, but are not limited to, methylthiomethyl and 2-(ethylthio)ethyl.

The term "$(C_2-C_6)$alkynyl" as used herein, means a straight or branched chain hydrocarbon group containing from 2 to 6 carbon atoms and containing at least one carbon-carbon triple bond. Representative examples of $(C_2-C_6)$alkynyl include, but are not limited to, to acetylenyl, 1-propynyl, 2-propynyl, 3-butynyl, 2-pentynyl, and 1-butynyl.

The term "$(C_2-C_6)$alkynyloxy" as used herein, means a $(C_2-C_6)$alkynyl group, as defined herein, appended to the parent molecular moiety through an oxygen atom.

The term "$(C_2-C_6)$alkynylthio" as used herein, means a $(C_2-C_6)$alkynyl group, as defined herein, appended to the parent molecular moiety through a sulfur atom.

The term "aryl," as used herein, means a phenyl or naphthyl group.

The term "aryl$(C_1-C_6)$alkoxy" as used herein, means an aryl group, as defined herein, appended to the parent molecular moiety through an $(C_1-C_6)$alkoxy group, as defined herein.

The term "aryl$(C_1-C_6)$alkyl" as used herein, means an aryl group, as defined herein, appended to the parent molecular moiety through an $(C_1-C_6)$alkyl group, as defined herein. Representative examples of aryl$(C_1-C_6)$alkyl include, but are not limited to, benzyl, 2-phenylethyl, 3-phenylpropyl, and 2-naphth-2-ylethyl.

The term "aryl$(C_1-C_6)$alkylthio" as used herein, means an aryl$(C_1-C_6)$alkyl group, as defined herein, appended to the parent molecular moiety through sulfur atom, as defined herein. Representative examples of aryl$(C_1-C_6)$alkylthio include, but are not limited to, benzylthio, phenylethylthio, 3-phenylpropylthio, and 2-naphth-2-ylethylthio.

The term "aryloxy" as used herein, means an aryl group, as defined herein, appended to the parent molecular moiety through an oxygen atom. Representative examples of aryloxy include, but are not limited to, phenoxy and naphthalenyloxy.

The term "arylthio" as used herein, means an aryl group, as defined herein, appended to the parent molecular moiety through a sulfur atom. Representative examples of arylthio include, but are not limited to, phenylthio and naphthalenylthio.

The term "carbonyl" as used herein, means a —C(O)— group.

The term "carboxy" as used herein, means a —C(O)OH group.

The term "carboxy$(C_1-C_6)$alkoxy" as used herein, means a carboxy group, as defined herein, is attached to the parent molecular moiety through a $(C_1-C_6)$alkoxy group, as defined herein.

The term "carboxy$(C_1-C_6)$alkyl" as used herein, means a carboxy group, as defined herein, is attached to the parent molecular moiety through a $(C_1-C_6)$alkyl group, as defined herein.

The term "cyano" as used herein, means a —CN group.

The term "$(C_3-C_8)$cycloalkyl" as used herein, means a saturated cyclic hydrocarbon group containing from 3 to 8 carbons, examples of $(C_3-C_8)$cycloalkyl include cyclopropyl, cyclobutyl, cyclopentyl, cyclohexyl, cycloheptyl, and cyclooctyl.

The term "($C_3$-$C_8$)cycloalkyl($C_1$-$C_6$)alkoxy" as used herein, means a ($C_3$-$C_8$)cycloalkyl group, as defined herein, appended to the parent molecular moiety through a ($C_1$-$C_6$) alkoxy group, as defined herein.

The term "($C_3$-$C_8$)cycloalkyl($C_1$-$C_6$)alkyl" as used herein, means a ($C_3$-$C_8$)cycloalkyl group, as defined herein, appended to the parent molecular moiety through a ($C_1$-$C_6$) alkyl group, as defined herein. Representative examples of ($C_3$-$C_8$)cycloalkyl($C_1$-$C_6$)alkyl include, but are not limited to, cyclopropylmethyl, 2-cyclobutylethyl, cyclopentylmethyl, cyclohexylmethyl, and 4-cycloheptylbutyl.

The term "($C_3$-$C_8$)cycloalkyl($C_1$-$C_6$)alkylthio" as used herein, means a ($C_3$-$C_8$)cycloalkyl($C_1$-$C_6$)alkyl group, as defined herein, appended to the parent molecular moiety through a sulfur atom.

The term "($C_3$-$C_8$)cycloalkyloxy" as used herein, means ($C_3$-$C_8$)cycloalkyl group, as defined herein, appended to the parent molecular moiety through an oxygen atom, as defined herein. Representative examples of ($C_3$-$C_8$)cycloalkyloxy include, but are not limited to, cyclopropyloxy, cyclobutyloxy, cyclopentyloxy, cyclohexyloxy, cycloheptyloxy, and cyclooctyloxy.

The term "($C_3$-$C_8$)cycloalkylthio" as used herein, means ($C_3$-$C_8$)cycloalkyl group, as defined herein, appended to the parent molecular moiety through a sulfur atom, as defined herein. Representative examples of ($C_3$-$C_8$)cycloalkylthio include, but are not limited to, cyclopropylthio, cyclobutylthio, cyclopentylthio, cyclohexylthio, cycloheptylthio, and cyclooctylthio.

The term "formyl" as used herein, means a —C(O)H group.

The term "halo" or "halogen" as used herein, means —C, —Br, —I or —F.

The term "halo($C_1$-$C_6$)alkoxy" as used herein, means at least one halogen, as defined herein, appended to the parent molecular moiety through a ($C_1$-$C_6$)alkoxy group, as defined herein. Representative examples of halo($C_1$-$C_6$)alkoxy include, but are not limited to, chloromethoxy, 2-fluoroethoxy, trifluoromethoxy, and pentafluoroethoxy.

The term "halo($C_1$-$C_6$)alkyl" as used herein, means at least one halogen, as defined herein, appended to the parent molecular moiety through a ($C_1$-$C_6$)alkyl group, as defined herein. Representative examples of halo($C_1$-$C_6$)alkyl include, but are not limited to, chloromethyl, 2-fluoroethyl, trifluoromethyl, pentafluoroethyl, and 2-chloro-3-fluoropentyl.

The term "halo($C_1$-$C_6$)alkylthio" as used herein, means a halo($C_1$-$C_6$)alkyl group, as defined herein, appended to the parent molecular moiety through a sulfur atom. Representative examples of halo($C_1$-$C_6$)alkylthio include, but are not limited to, trifluoromethylthio.

The term "(5-6 membered)heteroaryl," as used herein, means a 5 or 6 membered monocyclic heteroaryl. The 5 membered ring consists of two double bonds and one, two, three or four nitrogen atoms and/or optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl.

The term "(5-6 membered)heteroaryl($C_1$-$C_6$)alkoxy" as used herein, means a (5-6 membered)heteroaryl, as defined herein, appended to the parent molecular moiety through an ($C_1$-$C_6$)alkoxy group, as defined herein. Representative examples of heteroaryl($C_1$-$C_6$)alkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl) methoxy, (5-(cyano)pyridin-2-yl)methoxy, (2-(chloro) pyridin-4-yl)methoxy, pyrimidin-5-ylmethoxy, 2-(pyrimidin-2-yl)propoxy, thien-2-ylmethoxy, and thien-3-ylmethoxy.

The term "(5-6 membered)heteroaryl($C_1$-$C_6$)alkyl" as used herein, means a (5-6 membered)heteroaryl, as defined herein, appended to the parent molecular moiety through an ($C_1$-$C_6$)alkyl group, as defined herein. Representative examples of heteroaryl($C_1$-$C_6$)alkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "(5-6 membered)heteroaryl($C_1$-$C_6$)alkylthio" as used herein, means a (5-6 membered)heteroaryl($C_1$-$C_6$)alkyl group, as defined herein, appended to the parent molecular moiety through a sulfur atom. Representative examples of heteroaryl($C_1$-$C_6$)alkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)methylthio, (6-(cyano)pyridin-3-yl) methylthio, (2-(cyano)pyridin-4-yl)methylthio, (5-(cyano) pyridin-2-yl)methylthio, (2-(chloro)pyridin-4-yl) methylthio, pyrimidin-5-ylmethylthio, 2-(pyrimidin-2-yl) propylthio, thien-2-ylmethylthio, and thien-3-ylmethylthio.

The term "(5-6 membered)heteroaryloxy" as used herein, means a (5-6 membered)heteroaryl, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl) oxy, (6-(cyano)pyridin-3-yl) oxy, (2-(cyano)pyridin-4-yl) oxy, (5-(cyano)pyridin-2-yl)oxy, (2-(chloro)pyridin-4-yl) oxy, pyrimidin-5-yloxy, pyrimidin-2-yloxy, thien-2-yloxy, and thien-3-yloxy.

The term "(5-6 membered)heteroarylthio" as used herein, means a (5-6 membered)heteroaryl, as defined herein, appended to the parent molecular moiety through a sulfur atom. Representative examples of heteroarylthio include, but are not limited to, pyridin-3-ylthio and quinolin-3-ylthio.

The term "(4-7 membered)heterocycle" or "heterocyclic" as used herein, means a 4, 5, 6 or 7 membered ring containing at least one heteroatom independently selected from the group consisting of O, N, and S. The 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The heterocycle is connected to the parent molecular moiety through any carbon atom or any nitrogen atom contained within the heterocycle.

Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "(4-7 membered)heterocycle($C_1$-$C_6$)alkoxy" as used herein, means a (4-7 membered)heterocycle, as defined herein, appended to the parent molecular moiety through an ($C_1$-$C_6$)alkoxy group, as defined herein.

The term "(4-7 membered)heterocycle($C_1$-$C_6$)alkyl" as used herein, means a (4-7 membered)heterocycle, as defined herein, appended to the parent molecular moiety through an ($C_1$-$C_6$)alkyl group, as defined herein.

The term "(4-7 membered)heterocycle($C_1$-$C_6$)alkylthio" as used herein, means a (4-7 membered)heterocycle($C_1$-$C_6$) alkyl group, as defined herein, appended to the parent molecular moiety through a sulfur atom.

The term "(4-7 membered)heterocycleoxy" as used herein, means a (4-7 membered)heterocycle, as defined herein, appended to the parent molecular moiety through an oxygen atom. Representative examples of heteroaryloxy include, but are not limited to, pyridin-3-yloxy and pyrimidin-2-yloxy.

The term "(4-7 membered)heterocyclethio" as used herein, means a (4-7 membered)heterocycle, as defined herein, appended to the parent molecular moiety through a sulfur atom. Representative examples of heteroarylthio include, but are not limited to, pyridin-3-ylthio and pyrimidin-2-ylthio.

The term "hydroxy" as used herein, means an —OH group.

The term "hydroxy($C_1$-$C_6$)alkoxy" as used herein, means at least one hydroxy group, as defined herein, is appended to the parent molecular moiety through a ($C_1$-$C_6$)alkoxy group, as defined herein. Representative examples of hydroxy($C_1$-$C_6$)alkoxy include, but are not limited to, hydroxymethoxy, 2-hydroxyethoxy, 3-hydroxypropoxy, 2,3-dihydroxypentoxy, and 2-ethyl-4-hydroxyheptoxy.

The term "hydroxy($C_1$-$C_6$)alkyl" as used herein, means at least one hydroxy group, as defined herein, is appended to the parent molecular moiety through a ($C_1$-$C_6$)alkyl group, as defined herein. Representative examples of hydroxy($C_1$-$C_6$)alkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "thio($C_1$-$C_6$)alkyl" as used herein, means a sulfur atom appended to the parent molecular moiety through a ($C_1$-$C_6$)alkyl group, as defined herein. Representative examples of thio($C_1$-$C_6$)alkyl include, but are not limited to, thiomethyl, 2-thioethyl, 3-thiopropyl, and 4-thiobutyl.

The term "—$NR_AR_B$" as used herein, means two groups, $R_A$ and $R_B$ appended to the parent molecular moiety through a nitrogen atom. $R_A$ and $R_B$ are each independently hydrogen, ($C_1$-$C_6$)alkyl, or ($C_1$-$C_6$)alkylcarbonyl. Representative examples of —$NR_AR_B$ include, but are not limited to, amino, methylamino, dimethylamino, acetylamino, and acetylmethylamino.

The term "$NR_AR_B$ ($C_1$-$C_6$)alkoxy" as used herein, mean a $NR_AR_B$ group attached to the parent molecular moiety through a ($C_1$-$C_6$)alkoxy group.

The term "$NR_AR_B$ ($C_1$-$C_6$)alkyl" as used herein, mean a $NR_AR_B$ group attached to the parent molecular moiety through a ($C_1$-$C_6$)alkyl group.

The term "($NR_AR_B$)carbonyl" as used herein, means a $NR_AR_B$ group, as defined herein, appended to the parent molecular moiety through a carbonyl group, as defined herein.

Representative examples of ($NR_AR_B$)carbonyl include, but are not limited to, aminocarbonyl, (methylamino)carbonyl, (dimethylamino)carbonyl, and (ethylmethylamino)carbonyl.

The term "—$NR_CR_D$" as used herein, means two groups, $R_C$ and $R_D$ appended to the parent molecular moiety through a nitrogen atom. $R_C$ and $R_D$ are each independently hydrogen, ($C_1$-$C_6$)alkyl, or ($C_1$-$C_6$)alkylcarbonyl. Representative examples of —$NR_CR_D$ include, but are not limited to, amino, methylamino, dimethylamino, acetylamino, and acetylmethylamino.

The term "$NR_CR_D$($C_1$-$C_6$)alkoxy" as used herein, mean a $NR_CR_D$ group attached to the parent molecular moiety through a ($C_1$-$C_6$)alkoxy group.

The term "$NR_CR_D$($C_1$-$C_6$)alkyl" as used herein, mean a $NR_CR_D$ group attached to the parent molecular moiety through a ($C_1$-$C_6$)alkyl group.

The term "($NR_CR_D$)carbonyl" as used herein, means a $NR_CR_D$ group, as defined herein, appended to the parent molecular moiety through a carbonyl group, as defined herein.

The compounds of the present invention may form boron-oxygen dative bonds following exposure to water, alcohols (ROH, R is alkyl), and diols (ROH, R is hydroxyalkyl) as depicted in Scheme A.

Scheme A

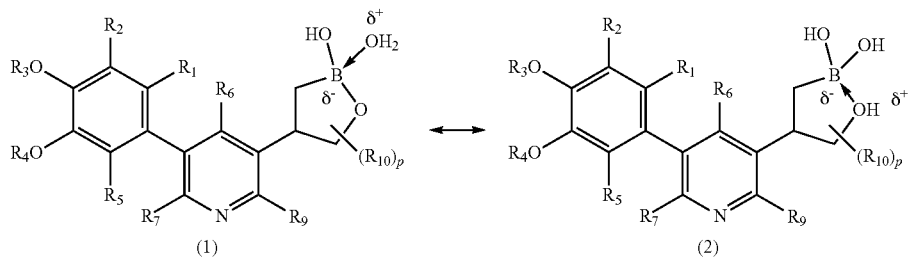

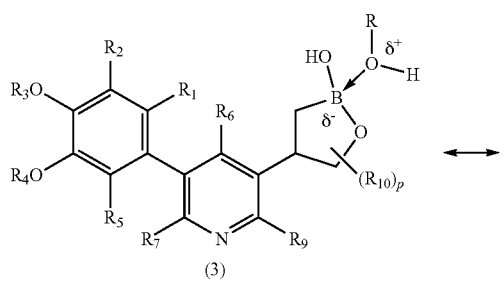 (3)
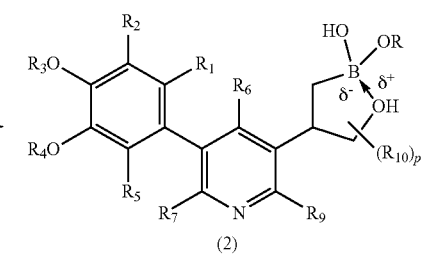 (2)

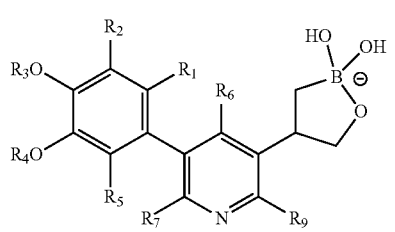 (5)
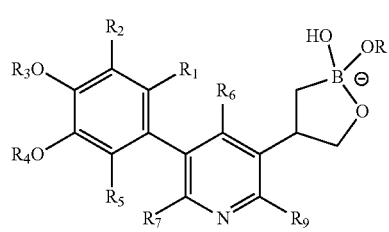 (6)

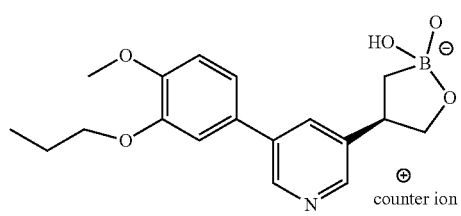 (7)
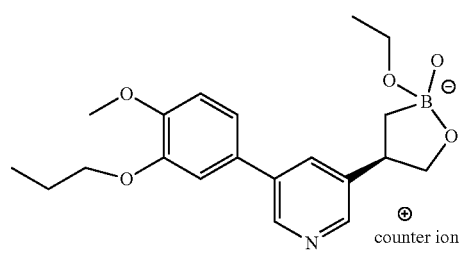 (8)

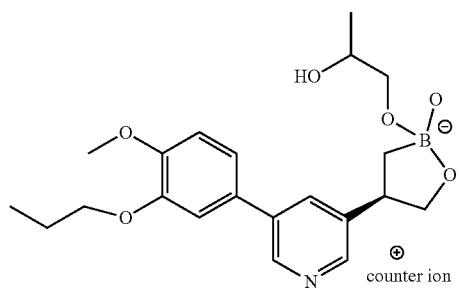 (9)
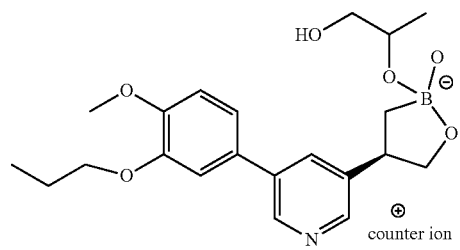 (10)

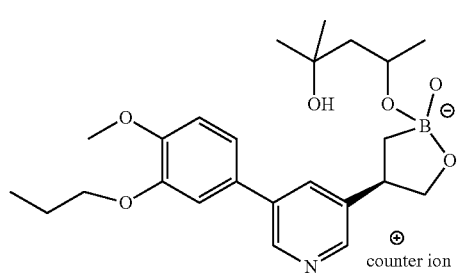 (11)
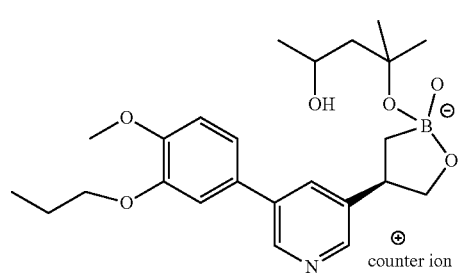 (12)

When a boron atom is covalently bonded to an oxygen atom and datively bonded to a second oxygen atom, the dative bond and covalent bond can interconvert or form a resonance hybrid as exemplified by structures (1), (2), (3), and (4) in Scheme A. Compounds of the present invention following exposure to water, alcohols, and diols may exist as neutral compounds, exemplified by compounds (1)-(4), or as negatively charged compounds depicted by compounds (5) and (6), wherein $R_1$, $R_2$, $R_3$, $R_4$, $R_5$, $R_6$, $R_7$, $R_9$, $R_{10}$ and p are as defined in the Summary section herein. In addition to oxygen, boron may form dative bonds with sulfur and nitrogen. It is to be understood that the present invention encompasses the compounds of Formula (I), Formula (IA), Formula (IB), and Formula (IC) that form dative bonds with oxygen, sulfur, and nitrogen including, but not limited to compounds (7)-(12). Suitable counter ions include, but are not limited to, lithium, sodium, potassium, ammonium, tetramethylammonium, tetraethylammonium, methylammonium, dimethylammonium, trimethylammonium, triethylammonium, diethylammonium, ethylammonium, calcium, magnesium, and aluminum.

The compounds of the present invention may form oxygen-linked dimers following exposure to water. Representative dimers of the present invention are shown in Scheme B wherein $R_1$, $R_2$, $R_3$, $R_4$, $R_5$, $R_6$, $R_7$, $R_9$, $R_{10}$, and p are as defined in the Summary section herein.

Scheme B

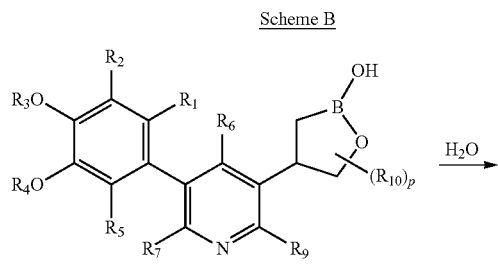

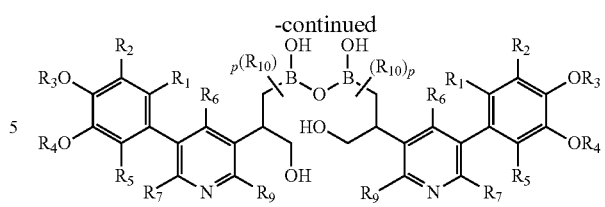

It is to be understood that the present invention encompasses the oxygen-linked dimers of Formula (I), Formula (IA), Formula (IB) and Formula (IC) including, but not limited to, bis((R)-3-hydroxy-2-(5-(4-methoxy-3-propoxyphenyl)pyridin-3-yl)propyl)diboronic acid and bis((S)-3-hydroxy-2-(5-(4-methoxy-3-propoxyphenyl)pyridin-3-yl)propyl)diboronic acid.

The compounds of the present invention may also form acyclic and cyclic trimers with exposure to water. Representative acyclic and cyclic trimers of the present invention are shown in Scheme C wherein $R_1$, $R_2$, $R_3$, $R_4$, $R_5$, $R_6$, $R_7$, $R_9$, $R_{10}$ and p are as defined in the Summary section herein.

Scheme C

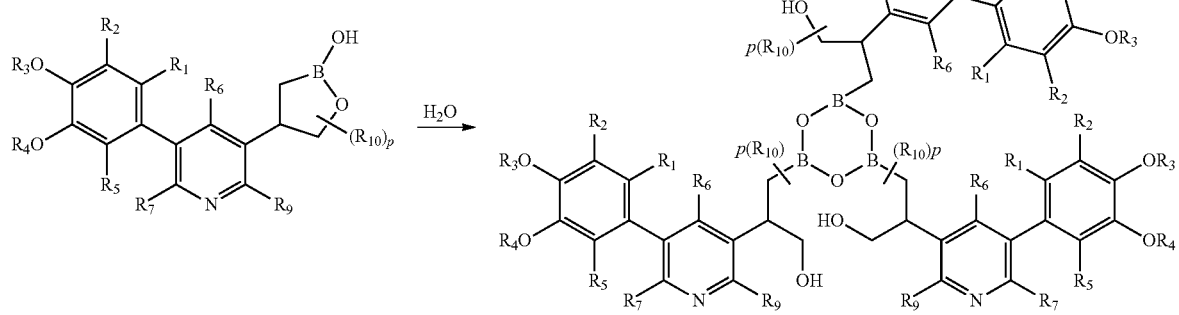

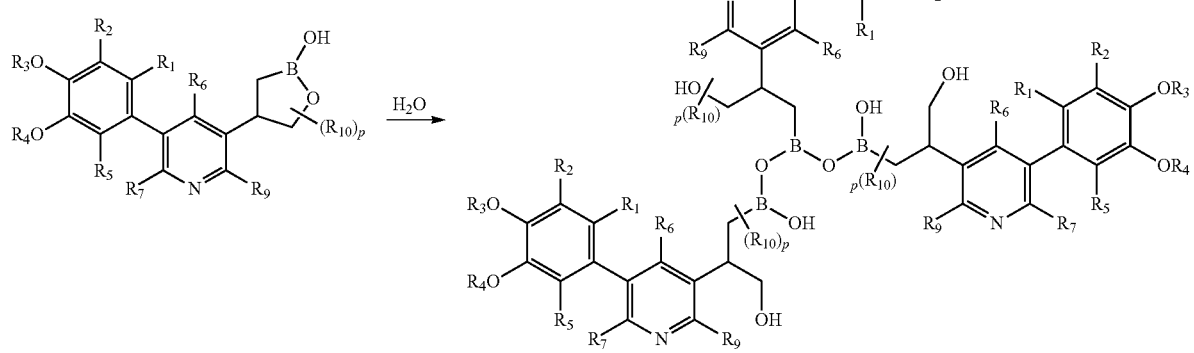

-continued

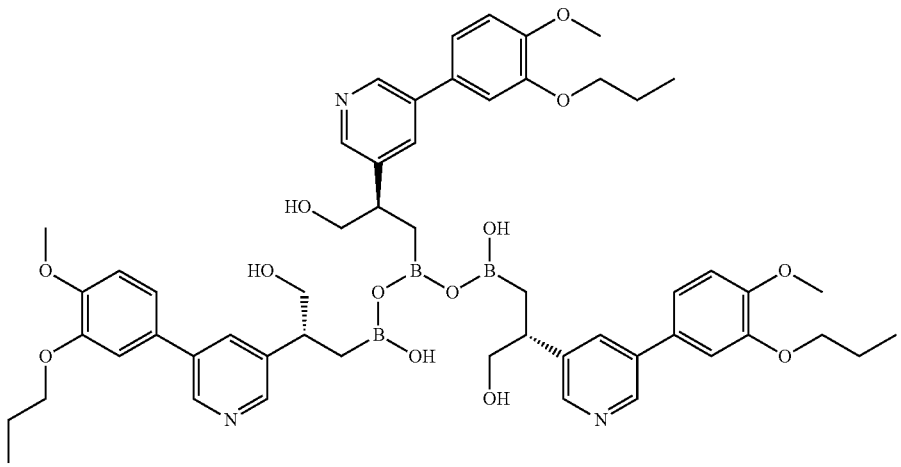

(13)

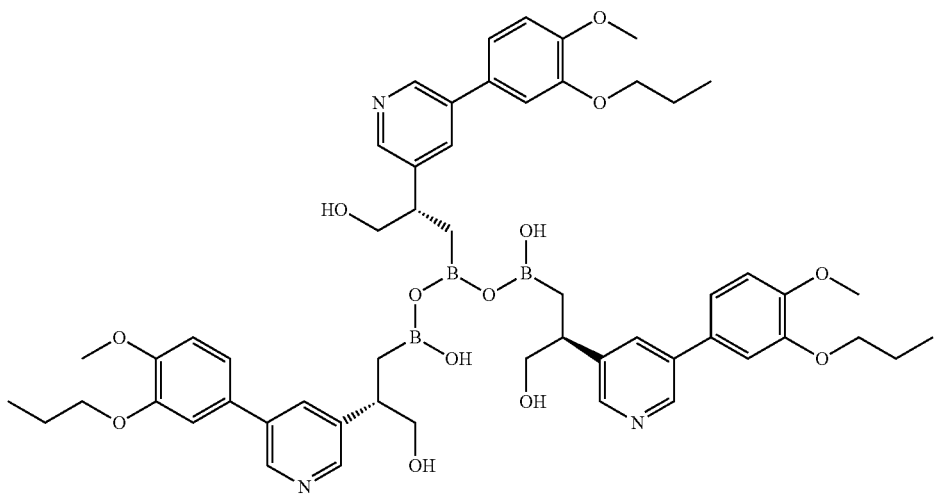

(14)

It is to be understood that the present invention encompasses acyclic and cyclic trimers of Formula (I), Formula (IA), Formula (IB) and Formula (IC) including, but not limited to, the acyclic trimers (13) and (14) shown in Scheme C and the cyclic trimers (2R,2'R,2"R)-3,3',3"-(1,3,5,2,4,6-trioxatriborinane-2,4,6-triyl)tris(2-(5-(4-methoxy-3-propoxyphenyl)pyridin-3-yl)propan-1-ol) and (2S,2'S,2"S)-3,3',3"-(1,3,5,2,4,6-trioxatriborinane-2,4,6-triyl)tris(2-(5-(4-methoxy-3-propoxyphenyl)pyridin-3-yl)propan-1-ol).

The present invention encompasses anhydrides of Formula (I), Formula (IA), Formula (IB) and Formula (IC) formed under dehydrating conditions. Representative anhydrides of the present invention are shown in Scheme D wherein $R_1$, $R_2$, $R_3$, $R_4$, $R_5$, Re, $R_7$, $R_8$, $R_{10}$, and p are as defined in the Summary section herein.

Scheme D

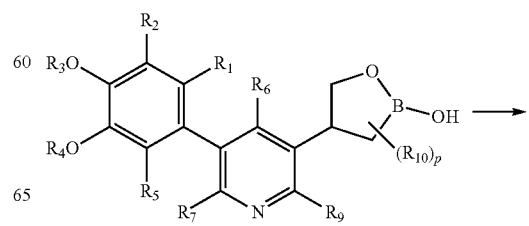

-continued

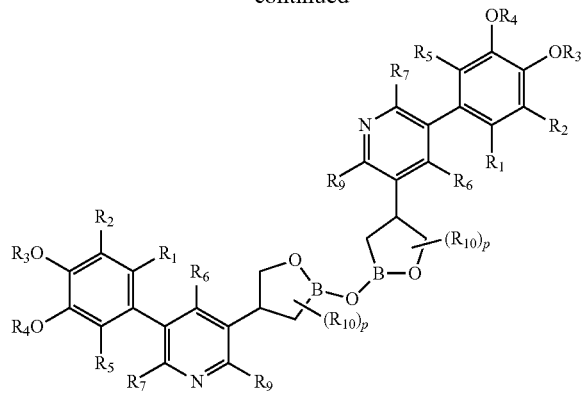

It is to be understood that the present invention encompasses the anhydrides of Formula (I), Formula (IA), Formula (IB) and Formula (IC) including, but not limited to, 5,5'-((4S,4'S)-oxybis(1,2-oxaborolane-2,4-diyl))bis(3-(4-methoxy-3-propoxyphenyl)pyridine) and 5,5'-((4R,4'R)-oxybis(1,2-oxaborolane-2,4-diyl))bis(3-(4-methoxy-3-propoxyphenyl)pyridine).

The compounds of the present invention may form poly- or multi-valent species assembled from a single species or from more than one species of the present invention. The polymeric constructs can be "homopolymeric" consisting of the same or related constructs, or "hetereropolymeric" consisting of multiple different constructs.

The present invention encompasses compounds that can be formulated with excipients such that one or more excipients interact with the compounds of the present invention to afford single, poly-, or multi-valent species, including, for example, species such as esters, dimers, trimers, tetramers and higher homologs. For example, compounds of Formula (I), Formula (IA), Formula (IB) and Formula (IC) may form boron-esters with propylene glycol or hexylene glycol under appropriate conditions. Representative esters of the present invention are shown in Scheme E wherein $R_1$, $R_2$, $R_3$, $R_4$, $R_5$, $R_6$, $R_7$, $R_8$, $R_{10}$, and p are as defined in the Summary section herein.

Scheme E

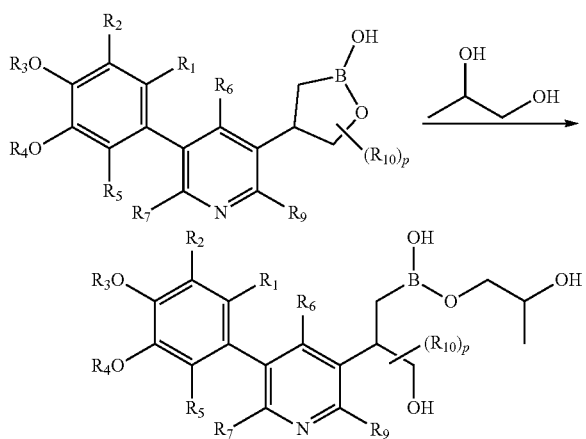

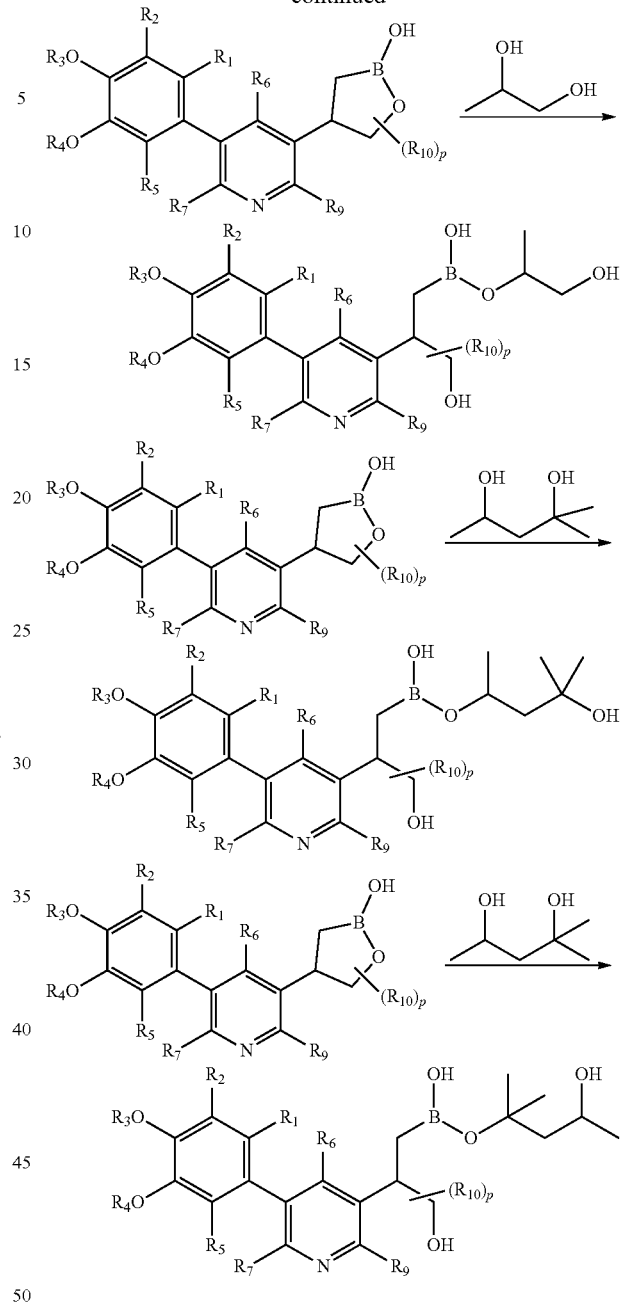

It is to be understood that the present invention encompasses boron-esters of Formula (I), Formula (IA), Formula (IB) and Formula (IC) including, but not limited to, 1-hydroxypropan-2-yl hydrogen ((R)-3-hydroxy-2-(5-(4-methoxy-3-propoxyphenyl)pyridin-3-yl)propyl)boronate, (S)-1-hydroxypropan-2-yl hydrogen ((R)-3-hydroxy-2-(5-(4-methoxy-3-propoxyphenyl)pyridin-3-yl)propyl)boronate, (R)-1-hydroxypropan-2-yl hydrogen ((R)-3-hydroxy-2-(5-(4-methoxy-3-propoxyphenyl)pyridin-3-yl)propyl)boronate, 2-hydroxypropyl hydrogen ((R)-3-hydroxy-2-(5-(4-methoxy-3-propoxyphenyl)pyridin-3-yl)propyl)boronate, (S)-2-hydroxypropyl hydrogen ((R)-3-hydroxy-2-(5-(4-methoxy-3-propoxyphenyl)pyridin-3-yl)propyl)boronate, (R)-2-hydroxypropyl hydrogen ((R)-3-hydroxy-2-(5-(4-methoxy-3-propoxyphenyl)pyridin-3-yl)propyl)boronate, 4-hydroxy-2-methylpentan-2-yl hydrogen ((R)-3- hydroxy-2-(5-(4-methoxy-3-propoxyphenyl)pyridin-3-yl)propyl)boronate, (S)-4-hydroxy-2-methylpentan-2-yl hydrogen ((R)-3-hydroxy-2-(5-(4-methoxy-3-propoxyphenyl)pyridin-3-yl)propyl)boronate, (R)-4-hydroxy-2-methylpentan-2-yl hydrogen ((R)-3-hydroxy-2-(5-(4-methoxy-3-propoxyphenyl)pyridin-3-yl)propyl)boronate, 4-hydroxy-4-methylpentan-2-yl hydrogen ((R)-3-hydroxy-2-(5-(4-methoxy-3-propoxyphenyl)pyridin-3-yl)propyl)boronate, (S)-4-hydroxy-4-methylpentan-2-yl hydrogen ((R)-3-hydroxy-2-(5-(4-methoxy-3-propoxyphenyl)pyridin-3-yl)propyl)boronate, (R)-4-hydroxy-4-methylpentan-2-yl hydrogen ((R)-3-hydroxy-2-(5-(4-methoxy-3-propoxyphenyl)pyridin-3-yl)propyl)boronate, 1-hydroxypropan-2-yl hydrogen ((S)-3-hydroxy-2-(5-(4-methoxy-3-propoxyphenyl)pyridin-3-yl)propyl)boronate, (S)-1-hydroxypropan-2-yl hydrogen ((S)-3-hydroxy-2-(5-(4-methoxy-3-propoxyphenyl)pyridin-3-yl)propyl)boronate, (R)-1-hydroxypropan-2-yl hydrogen ((S)-3-hydroxy-2-(5-(4-methoxy-3-propoxyphenyl)pyridin-3-yl)propyl)boronate, 2-hydroxypropyl hydrogen ((S)-3-hydroxy-2-(5-(4-methoxy-3-propoxyphenyl)pyridin-3-yl)propyl)boronate, (S)-2-hydroxypropyl hydrogen ((S)-3-hydroxy-2-(5-(4-methoxy-3-propoxyphenyl)pyridin-3-yl)propyl)boronate, (R)-2-hydroxypropyl hydrogen ((S)-3-hydroxy-2-(5-(4-methoxy-3-propoxyphenyl)pyridin-3-yl)propyl)boronate, 4-hydroxy-2-methylpentan-2-yl hydrogen ((S)-3-hydroxy-2-(5-(4-methoxy-3-propoxyphenyl)pyridin-3-yl)propyl)boronate, (S)-4-hydroxy-2-methylpentan-2-yl hydrogen ((S)-3-hydroxy-2-(5-(4-methoxy-3-propoxyphenyl)pyridin-3-yl)propyl)boronate, (R)-4-hydroxy-2-methylpentan-2-yl hydrogen ((S)-3-hydroxy-2-(5-(4-methoxy-3-propoxyphenyl)pyridin-3-yl)propyl)boronate, 4-hydroxy-4-methylpentan-2-yl hydrogen ((S)-3-hydroxy-2-(5-(4-methoxy-3-propoxyphenyl)pyridin-3-yl)propyl)boronate, (S)-4-hydroxy-4-methylpentan-2-yl hydrogen ((S)-3-hydroxy-2-(5-(4-methoxy-3-propoxyphenyl)pyridin-3-yl)propyl)boronate, and (R)-4-hydroxy-4-methylpentan-2-yl hydrogen ((S)-3-hydroxy-2-(5-(4-methoxy-3-propoxyphenyl)pyridin-3-yl)propyl)boronate.

The present invention also encompasses cyclic esters formed by interaction of compounds of Formula (I), Formula (IA), Formula (IB), and Formula (IC) with certain diols that include, but are not limited to, propylene glycol and hexylene glycol. Representative cyclic esters are shown in Scheme F wherein $R_1$, $R_2$, $R_3$, $R_4$, $R_5$, $R_6$, $R_7$, $R_9$, $R_{10}$, and p are as defined in the Summary section herein.

Scheme F

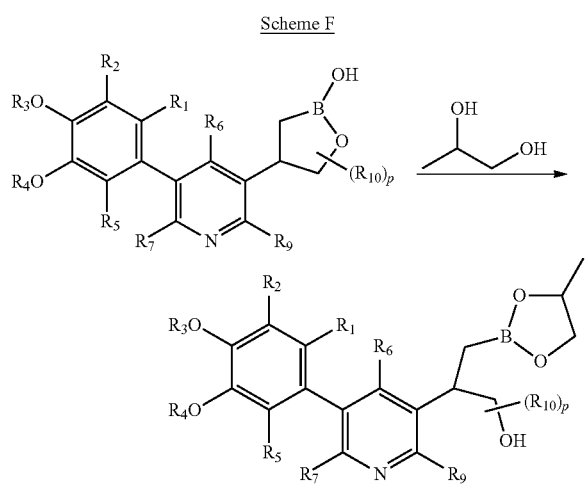

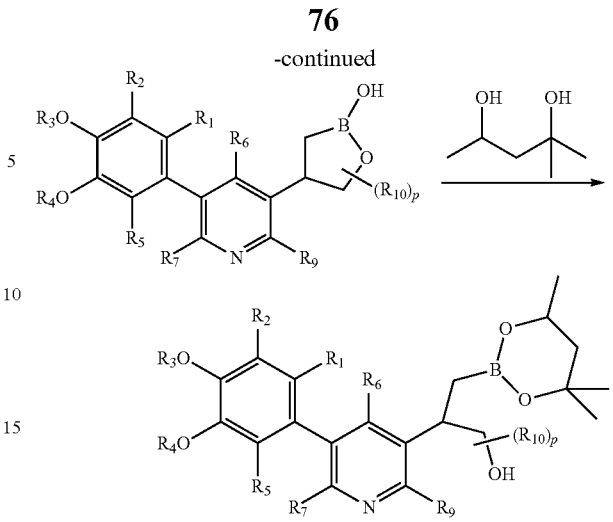

It is to be understood that the present invention encompasses cyclic boron-esters of Formula (I), Formula (IA), Formula (IB) and Formula (IC) including, but not limited to, (2R)-2-(5-(4-methoxy-3-propoxyphenyl)pyridin-3-yl)-3-(4-methyl-1,3,2-dioxaborolan-2-yl)propan-1-ol, (R)-2-(5-(4-methoxy-3-propoxyphenyl)pyridin-3-yl)-3-((S)-4-methyl-1,3,2-dioxaborolan-2-yl)propan-1-ol, (R)-2-(5-(4-methoxy-3-propoxyphenyl)pyridin-3-yl)-3-((R)-4-methyl-1,3,2-dioxaborolan-2-yl)propan-1-ol, (2R)-2-(5-(4-methoxy-3-propoxyphenyl)pyridin-3-yl)-3-(4,4,6-trimethyl-1,3,2-dioxaborinan-2-yl)propan-1-ol, (R)-2-(5-(4-methoxy-3-propoxyphenyl)pyridin-3-yl)-3-((S)-4,4,6-trimethyl-1,3,2-dioxaborinan-2-yl)propan-1-ol, (R)-2-(5-(4-methoxy-3-propoxyphenyl)pyridin-3-yl)-3-((R)-4,4,6-trimethyl-1,3,2-dioxaborinan-2-yl)propan-1-ol, (2S)-2-(5-(4-methoxy-3-propoxyphenyl)pyridin-3-yl)-3-(4-methyl-1,3,2-dioxaborolan-2-yl)propan-1-ol, (S)-2-(5-(4-methoxy-3-propoxyphenyl)pyridin-3-yl)-3-((S)-4-methyl-1,3,2-dioxaborolan-2-yl)propan-1-ol, (S)-2-(5-(4-methoxy-3-propoxyphenyl)pyridin-3-yl)-3-((R)-4-methyl-1,3,2-dioxaborolan-2-yl)propan-1-ol, (2S)-2-(5-(4-methoxy-3-propoxyphenyl)pyridin-3-yl)-3-(4,4,6-trimethyl-1,3,2-dioxaborinan-2-yl)propan-1-ol, (S)-2-(5-(4-methoxy-3-propoxyphenyl)pyridin-3-yl)-3-((S)-4,4,6-trimethyl-1,3,2-dioxaborinan-2-yl)propan-1-ol, and (S)-2-(5-(4-methoxy-3-propoxyphenyl)pyridin-3-yl)-3-((R)-4,4,6-trimethyl-1,3,2-dioxaborinan-2-yl)propan-1-ol.

The salts, esters, anhydrides, dimers, and trimers exemplified in Schemes A-F are prodrugs that can hydrolyze back to the parent compounds under aqueous conditions which include in vivo conditions reforming the oxaborole ring.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66:1-19, herein incorporated by reference. The salts can be prepared in situ during the final isolation and purification of the compounds of the present invention or separately by reacting a free base (basic nitrogen) with a suitable organic or inorganic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. In particular, the stereochemistry at the point of attachment of Y and Z, as shown in Formulae (I), (IA), and (IB) may independently be either (R) or (S), unless specifically noted otherwise. The enantiomers of the present invention indicated by (R), (S), or * are substantially free of the other enantiomer. "Substantially free" means that the enantiomeric excess is greater than about 90%, preferably greater than about 95%, and more preferably greater than about 99%. Within the context of enantiomeric excess, the term "about" means±1.0%. The symbol * designates a chiral carbon atom as either (R) or (S) stereochemistry depending on the configuration of substituents around the chiral carbon atom. The present invention contemplates various stereoisomers and mixtures thereof that are specifically included within the scope of this invention. Stereoisomers include enantiomers and mixtures of enantiomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution include, but are not limited to, (1) attachment of a chiral auxiliary to a mixture of enantiomers, separation of the resulting mixture of diastereomers by recrystallization or chromatography and liberation of the optically pure product from the auxiliary or (2) direct separation of the mixture of optical enantiomers on chiral chromatographic columns.

Compounds of the present invention not designated (R), (S), or * may exist as racemates (i.e. 50% (R) and 50% (S)) or as a mixture of two enantiomers wherein one enantiomer is in excess. For example, enantiomeric mixtures may include the (R) enantiomer in 51% and the (S) enantiomer in 49% or vice versa or any combination of (R) and (S) other than the racemic mixture of 50% (R) and 50% (S). The present invention includes racemates and enantiomeric mixtures of the compounds of the present invention.

Compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formulae (I), (IA), (IB), and (IC) and mixtures thereof.

Tautomers may exist in the compounds of the present invention and are specifically included within the scope of the present invention. The term "tautomer," as used herein, means a proton shift from one atom of a molecule to another atom of the same molecule wherein two or more structurally distinct compounds are in equilibrium with each other. Compounds of the present invention may exist as tautomers. The present invention contemplates tautomers due to proton shifts from one atom to another atom of the same molecule generating two or more distinct compounds that are in equilibrium with each other.

The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

Compounds of the present invention may exist in more than one crystal form.

Polymorphs of compounds of Formulae (I), (IA), (IB), and (IC) and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formulae (I), (IA), (IB), and (IC), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, chlorine, iodine, and fluorine, such as $^{2}H$, $^{3}H$, $^{13}C$, $^{14}C$, $^{15}N$, $^{18}O$, $^{17}O$, $^{35}S$, $^{36}Cl$, $^{125}I$, $^{129}I$, $^{18}F$, and $^{19}F$ respectively. Certain isotopically-labeled compounds of the present invention, for example those into which radioactive isotopes such as $^{3}H$ and $^{14}C$ are incorporated, are useful in drug and/or substrate tissue distribution assays. Tritiated (i.e., $^{3}H$), and carbon-14 (i.e., $^{14}C$), isotopes are particularly preferred for their ease of preparation and detectability. Further, substitution with heavier isotopes such as deuterium (i.e., $^{2}H$), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

In particular, the present invention includes deuterated compounds of Formula (I), (IA), (IB), and (IC). Any of the hydrogens contained on the compounds of the present invention may be exchanged for deuterium. Representative examples of deuterated compounds of the present invention include, but are not limited to, the compounds listed below wherein D is deuterium.

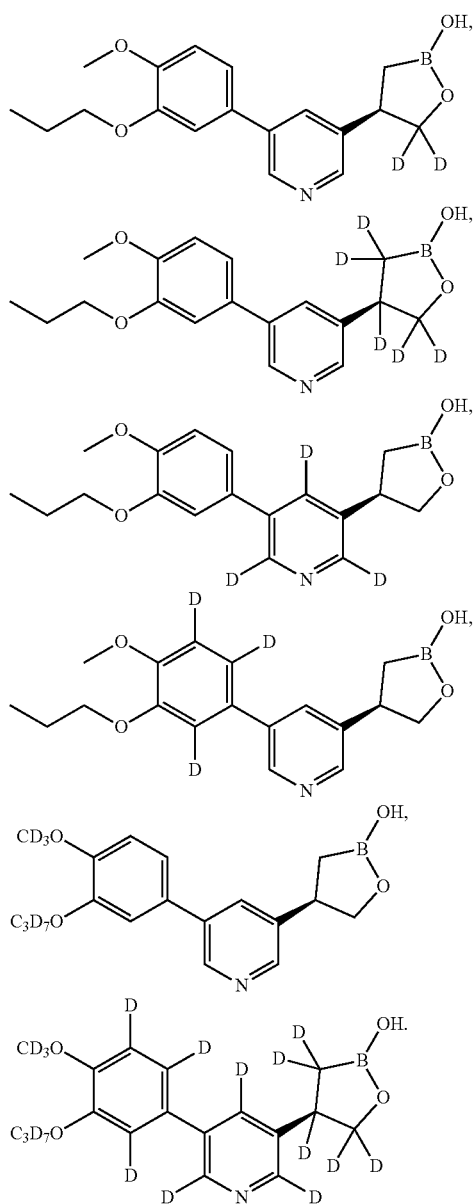

All patents, patent applications, and literature references cited in the specification are herein incorporated by reference in their entirety.

Compounds of the present invention were named by Chemdraw Professional version 15.0 or 16.0 or were given names which appeared to be consistent with Chemdraw nomenclature.

The present invention encompasses compounds of Formulae (I), (IA), (IB), and (IC) when prepared by synthetic processes or by metabolic processes. Preparation of the compounds of the invention by metabolic processes include those occurring in the human or animal body (in vivo) or processes occurring in vitro.

The present invention also contemplates pharmaceutically active metabolites formed by in vivo biotransformation of compounds of Formulae (I), (IA), (IB), and (IC). The term pharmaceutically active metabolite, as used herein, refers to a compound formed by the in vivo biotransformation of compounds of Formulae (I), (IA), (IB), and (IC). A thorough discussion of biotransformation is provided in (Goodman and Gilman's, The Pharmacological Basis of Therapeutics, seventh edition, MacMillan Publishing Company, New York, N.Y., (1985)).

Compounds of the present invention may be synthesized by synthetic routes that include processes analogous to those well-known in the chemical arts, particularly in light of the description contained herein. The starting materials are generally available from commercial sources or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as intermediates for preparing compounds of the present invention. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention protection of remote functionalities such as carboxylic acids, amines, and/or hydroxy groups of intermediates may be necessary. The need for such protection will vary depending on the nature of the remote functionality and the conditions of the preparation methods. Suitable amino-protecting groups (NH-PG) include acetyl, trifluoroacetyl, t-butoxycarbonyl (BOC), benzyloxycarbonyl (Cbz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-PG) include for example, allyl, acetyl, silyl, benzyl, para-methoxybenzyl, trityl, and the like. Carboxylic acid protecting groups include alkyl esters such as methy, ethyl, propyl, and tert-butyl. The need for such protection is readily determined by one skilled in the art. For a general description of protecting groups and their use, see T. W. Greene, Protective Groups in Organic Synthesis, John Wiley & Sons, New York, 1991.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1999). Suitable protecting groups include, but are not limited to, tert-butoxycarbonyl (BOC), trimethylsilylethanesulfonamide (SES), benzyloxycarbonyl (CBZ) and benzyl (Bn) protecting groups. The BOC protecting group may be removed by treatment with an acid such as trifluoroacetic acid or concentrated hydrochloric acid and the SES protecting group may be removed with a fluoride salt, such as cesium fluoride or tetrabutylammonium fluoride. The CBZ and Bn protection groups may be removed by catalytic hydrogenation. Additional suitable protecting groups for hydroxy substituents include, but are not limited to, t-butyldimethylsilyl (TBDMS), tetra-hydropyranyl (THP), or isopropyl (i-Pr) protecting groups. The TBDMS and THP protecting groups may be removed by treatment with an acid such as acetic acid or hydrochloric acid while the i-Pr protecting group may be removed by aluminum trichloride.

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low, medium, or high-pressure liquid chromatography, or a combination of these procedures. Specific illustrations of suitable separation and isolation procedures can be had by reference to the Examples herein below. However, other equivalent separation or isolation procedures could also be used.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formulae (I), (IA), (IB), and (IC). It will be further appreciated that it may be necessary or desirable to carry out the transformations in a different order from that described in the schemes, or to modify one or more of the transformations, to provide the desired compound of the invention.

The derivatives of Formulae (I), (IA), (IB), and (IC) can be prepared by the procedures described in the general methods presented below or by routine modifications thereof. The present invention also encompasses one or more of these processes for preparing the derivatives of Formulae (I), (IA), (IB), and (IC), in addition to any novel intermediates used therein. The person skilled in the art will appreciate that the following reactions may be heated thermally or under microwave irradiation.

The routes below, including those mentioned in the Examples and Preparations, illustrate methods of synthesising compounds of Formulae (I), (IA), (IB), and (IC). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by $R_C$ Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect alcohol, amino or carboxylic acid groups. The protecting groups used in the preparation of the compounds of the invention may be used in a conventional manner. See, for example, those described in 'Greene's Protective Groups in Organic Synthesis' by Theodora W Greene and Peter G M Wuts, fifth edition, (John Wiley and Sons, 2014), incorporated herein by reference, which also describes methods for the removal of such groups.

In the general synthetic methods below, unless otherwise specified, the substituents are as defined above with reference to the compounds of Formula (I) above. Where ratios of solvents are given, the ratios are by volume unless otherwise specified.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either. The skilled person will appreciate that the experimental conditions set forth in the schemes that follow are illustrative of suitable conditions for effecting the transformations shown, and that it may be necessary or desirable to vary the precise conditions employed for the preparation of compounds of Formula (I).

According to the first process, compounds of Formula (1D) (where $R_1$, $R_2$, $R_3$, $R_4$, $R_5$, $R_6$, $R_7$, $R_9$, $R_{10}$, and p are as defined in the Summary section herein and v=0, 1, 2, 3, 4, 5) may be prepared from compounds of Formula (II) and (III) as illustrated by Scheme 1.

Scheme 1

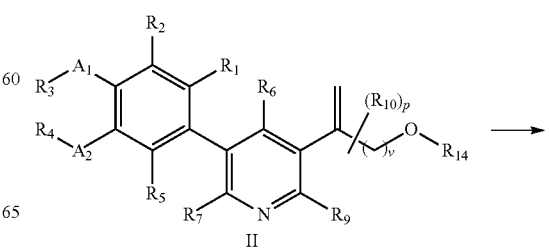

-continued

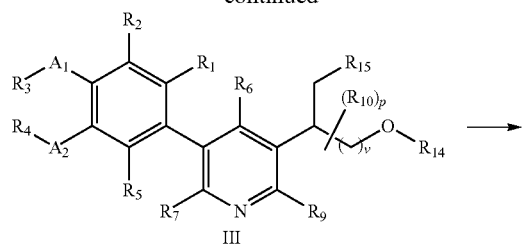

III

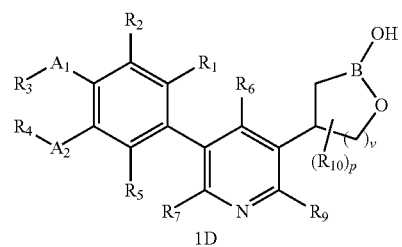

1D

In Scheme 1, compounds of the Formula (II), wherein $R_{14}$ is a suitable protecting group (preferably TBS), are converted to a compound of Formula (III) wherein $R_{15}$ is boronic acid (preferably) or 4,4,5,5-tetramethyl-1,3,2-dioxaborolane (Bpin) by treatment with a suitable hydroborating source such as catecolborane or bis(pinacolato)diboron, in the presence of a suitable catalyst (bis(1,5-cyclooctadiene) di-μ-methoxydiiridium(I) or (1.5-cycloocatdiene)(methoxy) iridium(I) dimer) and ligand (ethylenebis(diphenylphosphine), in a suitable solvent such as DCE or THF at an appropriate temperature (15° C. to 70° C.). A skilled person also knows alternative methods for hydroboration of alkenes are achievable using alternative reagents, solvents and temperatures. A compound of Formula (III) is converted into a compound of Formula (1D) under aqueous acidic conditions, treating with a suitable acid (acetic or hydrochloric) at a suitable temperature. It is well understood by a skilled person that a compound of the Formula (III) is prepared and isolated as described above or prepared in situ without isolation in a sequential reaction strategy leading to a compound of Formula (1D). In the case of compounds of Formula (III) and (1D) lead to the presence of a chiral center, it is well understood by a skilled person that the individual enantiomers can be obtained using a suitable separation method such as HPLC or SFC chromatography to afford both the (+) and (−) enantiomers of compounds of Formula (III) and (1D). It is well understood by a skilled person that an individual enantiomer of a compound of Formula (III) and (1D) is prepared and isolated as described above or isolated using an alternative separation technique such as HPLC or SFC using a suitable chiral stationary phase eluting with a suitable mobile phase as determined to be necessary to isolate the required enantiomers.

According to a second process, compounds of Formula (1E) or (1F) may be prepared from Formula (II) as illustrated in Scheme 2.

Scheme 2

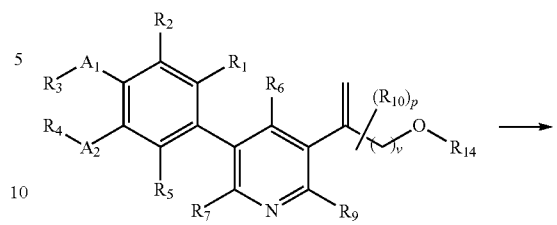

II

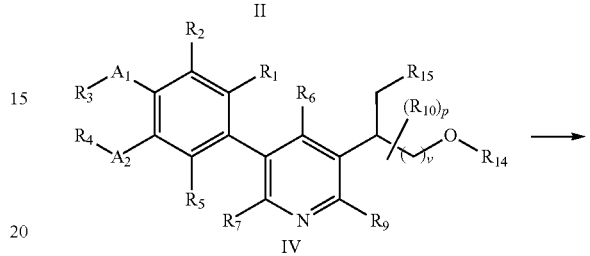

IV

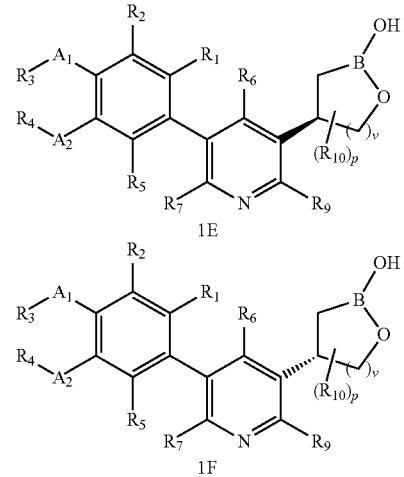

1E

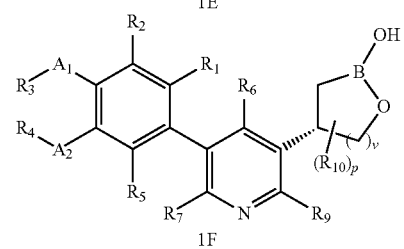

1F

In Scheme 2, compounds of Formula (1E) or (1F) may be prepared in a similar manner as in Scheme 1 using suitable chiral ligands such as (S,S)-[2-(4'-i-propyloxazolin-2-yl) ferrocynyl]diphenylphosphine or (R,R)-[2-(4'-i-propyloxazolin-2-yl)ferrocynyl]diphenylphosphine leading to chiral compounds of Formula (IV). A person of skill in the art knows that chiral hydroboration strategies can use alternative chiral ligands, catalysts, boron sources, solvents and temperature combinations. It is well understood by a skilled person that a compound of the Formula (IV) can be prepared and isolated as described above or prepared in situ without isolation in a sequential reaction strategy leading to a compound of Formula (1E) or (1F). A skilled person also knows that compounds of Formula (1E) or (1F) can be further enriched through crystallization techniques or chiral chromatography (HPLC or SFC) using a suitable chiral stationary phase eluting with a suitable mobile phase as determined to be necessary to isolate the required enantiomers.

According to a third process, compounds of Formula (1G) may be prepared from Formula (II) as illustrated in Scheme 3.

Scheme 3

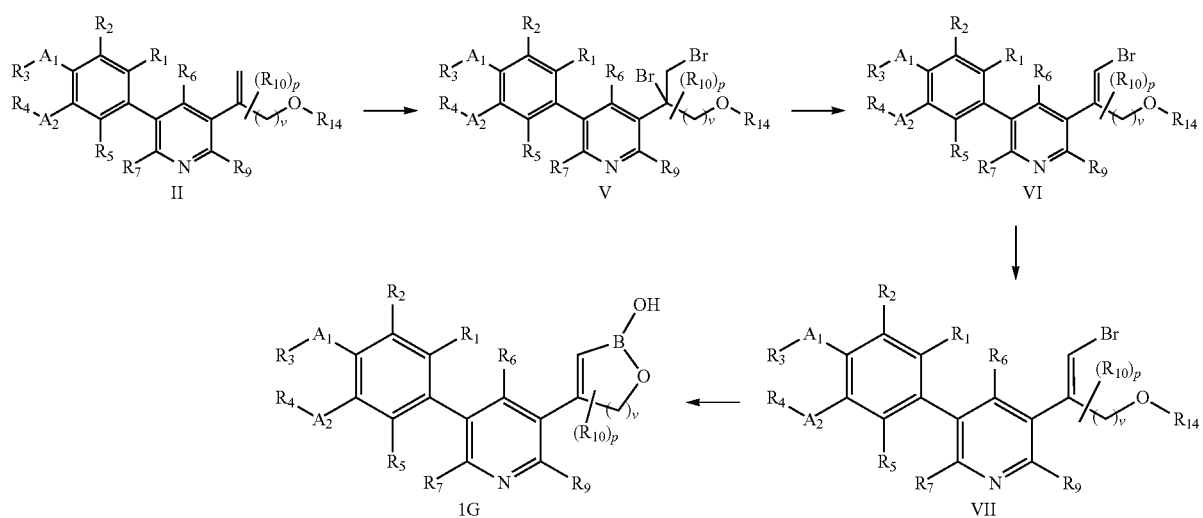

In Scheme 3, compounds of Formula (II) are converted to compounds of Formula (V) when treated with a halogenating agent such as pyridinium tribromide, in a suitable solvent, such as DCM, at an appropriate temperature such as 0° C. A skilled person also knows that alternative methods for specifically introducing a suitable halogen group such as Br are achievable using alternative reagents, solvents and temperatures. Compounds of Formula (VI) can be synthesized by this method or by the reaction of compounds of Formula (V) using DBU with a suitable solvent, such as DCM, at a suitable temperature, such as 25° C. Compounds of Formula (VI) can be converted to compounds of Formula (VII) (where $R_{15}$=Bpin) using Miyaura borylation conditions. Typical boronate ester formation conditions comprise of Pd(dppf)Cl$_2$.DCM and potassium acetate with bispinacolatoboron in 1,4-dioxane at a suitable temperature, such as 55° C. A compound of Formula (VII) can be converted into a compound of Formula (1G) under aqueous acidic conditions, treating with a suitable acid (acetic or hydrochloric) at a suitable temperature.

Compounds of Formula (II) may be prepared from compounds of Formulae (VIII), (IX), (X) and (XI) as illustrated by Scheme 4.

Scheme 4

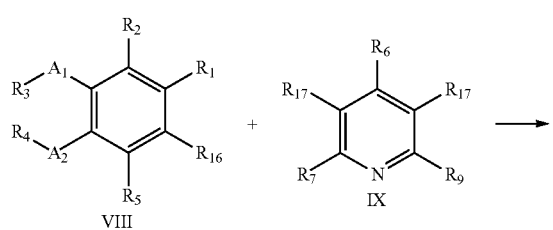

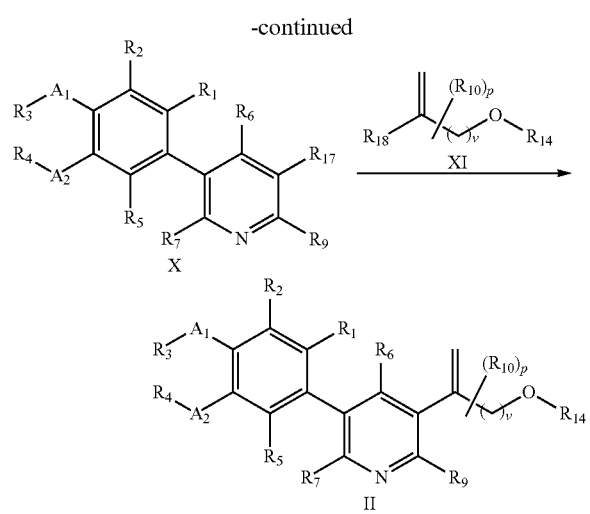

In Scheme 4, compounds of Formula (X), wherein $R_{17}$ is chloro, bromo or iodo may be prepared from compounds of Formula (VIII) and (IX) using a suitable organometallic cross-coupling reaction such as Suzuki cross-coupling reaction preceded if necessary by a boronic acid or ester formation. Typical Suzuki cross-coupling conditions comprise of a palladium catalyst containing suitable phosphine ligands, in the presence of an inorganic base, in aqueous dioxane or methanol, at elevated temperatures either thermally or under microwave irradiation. Preferred conditions comprise Pd(OAc)$_2$, Pd(dppf)Cl$_2$ or Pd(PPh$_3$)$_4$ with either sodium, cesium or potassium carbonate in aqueous dioxane or methanol at from room temperature to 120° C. A skilled person knows that organometallic cross-coupling reaction strategies can be used involving alternative metals, catalysts, ligands, bases, solvents and temperature combinations. Typical boronic ester formation conditions comprise of Pd(dppf)Cl$_2$ and potassium acetate with bispinacolatodiboron with compounds of Formula (VIII), where $R_{16}$=chloro, bromo or iodo, in dioxane at reflux. Compounds of Formula (VIII) may also be obtained commercially or be synthesized by those skilled in the art according to the literature or by analogy with the methods described herein.

Compounds of Formula (II) may be prepared from compounds of Formula (X) and (XI), (where $R_{18}$=boronic acid or Bpin) through an organometallic cross-coupling reaction, similar to the ones previously described. A skilled person knows that alternative organometallic cross-coupling reaction strategies can also be used involving alternative metals, catalysts, ligands, bases, solvents and temperature combinations. Preferred Suzuki conditions comprise of Pd(dppf)$Cl_2$ with potassium carbonate and potassium acetate in aqueous dioxane from room temperature to 120° C.

Alternatively, compounds of Formula (II) may be prepared from compounds of Formulae (VIII), (IX), (XI) and (XII), in a reverse sequence of that in Scheme 4, illustrated by Scheme 5.

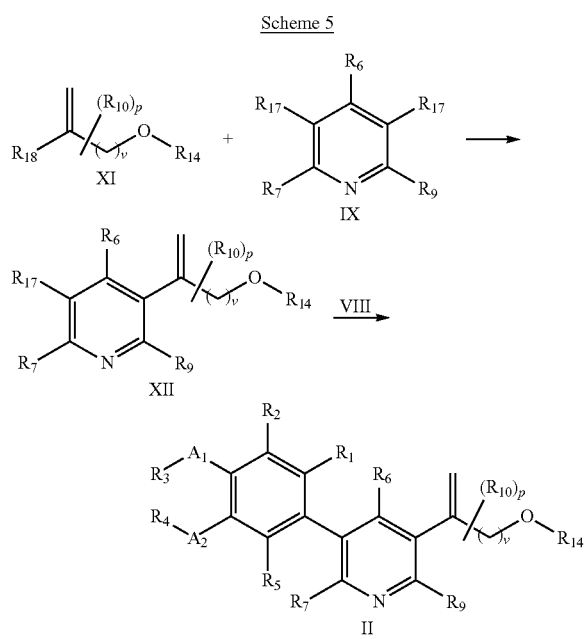

Compounds of Formula (XII) may be prepared from compounds of Formula (XI) (where $R_{18}$=boronic acid or pinacol) and (IX) (where $R_{17}$ is chloro, bromo or iodo) using an organometallic cross-coupling reaction as described in Scheme 4. Preferred conditions comprise of Pd(dppf)$Cl_2$ with potassium carbonate in aqueous dioxane from room temperature to 120° C. Compounds of Formula (XI) may be synthesized by those skilled in the art according to the literature or by analogy with the methods described herein. Compounds of Formula (XII) may be converted to compounds of Formula (II) using a similar method as previously described in Scheme 4, a Suzuki cross-coupling reaction preceded if necessary by a boronic acid or ester formation. A skilled person knows that alternative organometallic cross-coupling reaction strategies can also be used involving alternative metals, catalysts, ligands, bases, solvents and temperature combinations.

According to a sixth process, compounds of Formula (1H) may be prepared from Formula (XIII) and (XIV) as illustrated in Scheme 6.

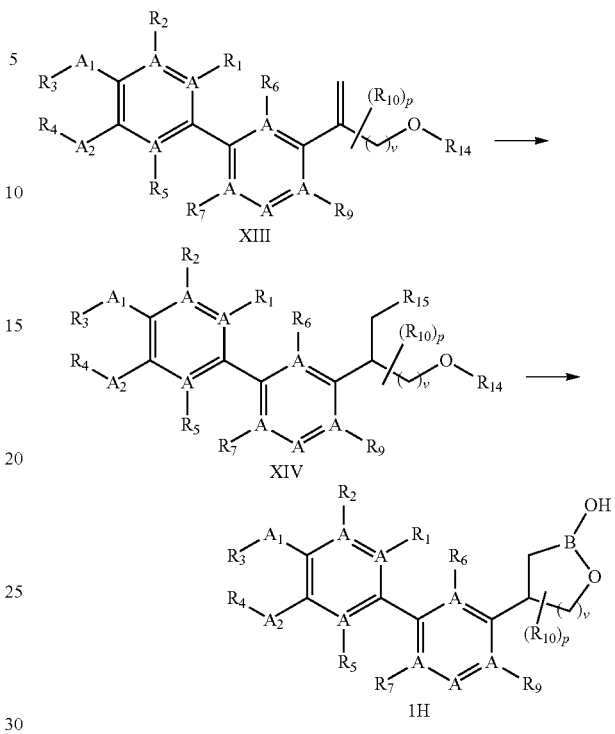

Compounds of Formula (1H), where A is carbon or nitrogen, may be prepared in an analogous manner as compounds of Formula (1D), (1E) or (1F) as described in Schemes 1-5. It is well understood by a skilled person that the individual enantiomers can be obtained using a suitable separation method such as HPLC or SFC chromatography to afford both the (+) and (−) enantiomers of compounds of Formula (XIV) and (1H). It is also well understood by a skilled person that an individual enantiomer of a compound of Formula (XIV) and (1H) is prepared and isolated as described above or isolated using an alternative separation technique such as HPLC or SFC using a suitable chiral stationary phase eluting with a suitable mobile phase as determined to be necessary to isolate the required enantiomers. Additionally, compounds of Formula (1H) in which the central ring is replaced by a substituted 5-membered heterocycle (exemplified by Y, in Formula (1)) can also be synthesized in an analogous manner by one skilled in the art.

The compounds and processes of the present invention will be better understood in connection with the following Examples which are intended as an illustration of and not a limitation upon the scope of the invention as defined in the appended claims.

Abbreviations which have been used in the descriptions of the schemes and the examples that follow are: Ac is acetyl; AcOH is acetic acid; $Ac_2O$ is acetic anhydride; Adam's catalyst is platinum (IV) oxide; $Br_2$ is bromine; n-BuLi is n-butyl lithium; ° C. is degrees celcius; $CDCl_3$ is deuterochloroform; $CD_3OD$ is deuteromethanol; $CO_2$ is carbon dioxide; $Cs_2CO_3$ is cesium carbonate; b is chemical shift; DAST is N,N-Diethylamino-S,S-difluorosulfinium tetrafluoroborate; DBU is 1,8-Diazabicyclo[5.4.0]undec-7-ene; DCE is 1,2-dichloroethane; DCM is dichloromethane or methylene chloride; DEA is diethylamine; DMAP is 4-dimethylaminopyridine; DMF is dimethylformamide; DMSO is dimethyl sulfoxide; DMSO-$d_6$ is deuterodimethylsulfoxide; Et$_2$O is diethyl ether; EtOAc is ethyl acetate; EtOH is ethanol; Et$_3$N is triethylamine; Fe is iron; g is gram; HCl is hydrochloric acid; HCO$_2$H is formic acid; HMTA is hexamethylenetetramine; HPLC is high pressure liquid chromatography; H$_2$ is hydrogen; H$_2$O is water; h is hours; Hr is hour; Hz is hertz; IPA is isopropyl alcohol; IPAm: is isopropylamine; [Ir(COD)Cl]$_2$ is bis(1,5 cyclooctadiene) diiridium(I) dichloride; [Ir(COD)OMe]$_2$ is (1.5-cycloocatdiene)(methoxy)iridium(I) dimer; K$_2$CO$_3$ is potassium carbonate; K$_3$PO$_4$ is potassium phosphate tribasic; KBr is potassium bromide; KMnO$_4$ is potassium permanganate; KOAc is potassium acetate; L is liter; LCMS is liquid chromatography mass spectrometry; LDA is lithium diisopropylamide; LiHMDS is lithium bis(trimethylsilyl)amide; LiOH is lithium hydroxide monohydrate; LTMP is lithium tetramethylpiperidine; M is molar; m-CPBA is meta-chloroperoxybenzoic acid; MeCN is acetonitrile; MeOH is methanol; MeNH$_2$ is methyl amine; mg is milligram; MgSO$_4$ is magnesium sulphate; MHz is mega Hertz; min is minutes; mL is milliliter; mm is millimeter; mmol is millimole; mol is mole; MS m/z is mass spectrum peak; MTBE is tert-butyl methyl ether; MsCl is mesyl chloride; NaBH$_4$ is sodium borohydride; Na$_2$CO$_3$ is sodium carbonate; NaOH is sodium hydroxide; NaOMe is sodium methoxide; Na$_2$SO$_4$ is sodium sulphate; NBS is N-bromo succinimide; NH$_3$ is ammonia; NH$_4$Cl is ammonium chloride; NH$_2$OH—HCl is hydroxylamine hydrochloride; NH$_4$OH is ammonium hydroxide; nM is nanomolar; PCls is phosphorus pentachloride; Pd/C is palladium on carbon; Pd(dppf)Cl$_2$ is [1,1'-bis(diphenylphosphino) ferrocene]dichloropalladium(II); Pd(dppf)Cl$_2$DCM is [1,1'-bis(diphenylphosphino) ferrocene]dichloropalladium(II), complex with dichloromethane; Pd(dppf)-tBu is [1,1'-bis(di-t-butylphosphino) ferrocene]dichloropalladium(II); Pd(OAc)$_2$ is palladium acetate; PPh$_3$ is triphenylphosphine; pet. ether is petroleum ether; pH is power of hydrogen; Pin$_2$B$_2$ is bis(pinacolato)diboron; PinBO-iPr is 2-isopropoxy-4,4,5,5-tetramethyl-1,3,2-dioxaborolane; psi is pounds per square inch; ppm is parts per million; POCl$_3$ is phosphorus oxychloride; PrOH is 1-propanol; PtO$_2$ is platinum (IV) oxide; rt is room temperature, RT is retention time; SEM-Cl is 2-(trimethylsilyl)ethoxymethyl chloride; SFC is supercritical fluid chromatography; TBS is t-butyldimethylsilyl; TBS-Cl is t-butyldimethylsilyl chloride; tBu$_3$P is tri-t-butylphosphine; TFA is trifluoroacetic acid; TFAA is trifluoroacetic anhydride; TiCl$_4$ is titanium tetrachloride; TfO is trifluoromethanesulfonyl; Tf$_2$O is trifluoromethanesulfonic anhydride; pTsOH is p-toluenesulfonic acid; Turbo Grignard is isopropylmagnesium chloride lithium chloride complex solution; Xantphos is 4,5-Bis(diphenylphosphino)-9,9-dimethylxanthene; XPhos-Pd-G2 is Chloro(2-dicyclohexylphosphino-2',4',6'-triisopropyl-1,1'-biphenyl)[2-(2'-amino-1,1'-biphenyl)]palladium(II). $^1$H and $^{19}$F Nuclear magnetic resonance (NMR) spectra were in all cases consistent with the proposed structures. Characteristic chemical shifts (6) are given in parts-per-million downfield from tetramethylsilane (for $^1$H-NMR) and upfield from trichloro-fluoro-methane (for $^{19}$F NMR) using conventional abbreviations for designation of major peaks: e.g. s, singlet; d, doublet; t, triplet; q, quartet; dd, doublet of doublets; dt, doublet of triplets; td, triplet of doublets; m, multiplet; br, broad. The following abbreviations have been used for common solvents: CDCl$_3$, deuterochloroform; DMSO-d$_6$, deuterodimethylsulphoxide; and CD$_3$OD, deuteromethanol.

Where appropriate, tautomers may be recorded within the NMR data; and some exchangeable protons may not be visible.

Mass spectra, MS (m/z), were recorded using either electrospray ionization (ESI) or atmospheric pressure chemical ionization (APCI).

Where relevant and unless otherwise stated the m/z data provided are for isotopes $^{19}$F, $^{35}$Cl, $^{79}$Br and $^{127}$I.

Wherein preparative TLC or column chromatography (silica) has been used, one skilled in the art may choose any combination of appropriate solvents to purify the desired compound.

Specific rotations based on the equation $[\alpha]=(100-\alpha)/(l \cdot c)$ are reported as unitless numbers where the concentration c is in g/100 mL and the path length l is in decimeters. The units of the specific rotation, (deg-mL)/g-dm) are implicit and are not included with the reported value.

The following are analytical and preparative chromatography methods used for the analysis and purification of compounds of the invention.

Preparative SFC Methods

Prep SFC Method A: Column: Chiralpak IC-H, 250 mm×30 mm, 5µ; Mobile Phase—Isocratic conditions: CO$_2$/EtOH, 60/40 (v/v); Flow rate: 65 mL/min Prep SFC Method B: Column: Lux Amylose-1 250 mm×30 mm, 5µ; Mobile Phase—Isocratic conditions: CO$_2$/MeOH+ 0.2% (7N ammonia in MeOH) 80/20 (v/v); Flow rate: 150 mL/min Prep SFC Method C: Column: Chiralpak IC-H, 250 mm×50 mm, 5µ; Mobile Phase—Isocratic conditions: CO$_2$/IPA 85/15 (v/v); Flow rate: 250 mL/min Prep SFC Method D: Column: Chiralcel OJ, 250 mm×30 mm, 5µ; Mobile Phase—Isocratic conditions: CO$_2$/IPA, 65/35 (v/v); Flow rate: 50 mL/min Prep SFC Method E: Column: Daicel Chiralpak AD, 250 mm×30 mm, 5µ; Mobile Phase—Isocratic conditions: CO$_2$/ EtOH (0.1% NH$_4$OH), 60/40 (v/v); Flow rate: 50 mL/min Prep SFC Method F: Column: Daicel Chiralpak IC, 250 mm×30 mm, 5µ; Mobile Phase—Isocratic conditions: CO$_2$/ EtOH (0.1% NH$_4$OH), 60/40 (v/v); Flow rate: 200 mL/min)

Prep SFC Method G: Column: Daicel Chiralpak AD, 250 mm×50 mm, 10µ; Mobile Phase—Isocratic conditions: CO$_2$/EtOH (0.1% NH$_4$OH), 55/45 (v/v); Flow rate: 200 mL/min Prep SFC Method H: Column: Chiralpak IC-H, 250 mm×30 mm, 5µ; Mobile Phase—Isocratic conditions: CO$_2$/EtOH (0.1% NH$_4$OH), 75/25 (v/v); Flow rate: 200 mL/min Prep SFC Method I: Column: Chiralpak IC, 250 mm×30 mm, 10µ; Mobile Phase—Isocratic conditions: CO$_2$/EtOH (0.1% NH$_4$OH), 60/40 (v/v); Flow rate: 60.0 mL/min Prep SFC Method J: Column: Chiralpak IC 250 mm×30 mm, 10µ; Mobile Phase—Isocratic conditions: CO$_2$/EtOH (0.1% NH$_4$OH), 80/20 (v/v); Flow rate: 60 mL/min Prep SFC Method K: Column: Chiralpak AD, 250 mm×30 mm, 5µ; Mobile Phase—Isocratic conditions: CO$_2$/MeOH (0.1% NH$_4$OH), 75/25 (v/v); Flow rate: 50.0 mL/min Prep SFC Method L: Column: Chiralpak AD, 250 mm×30 mm, 10µ; Mobile Phase—Isocratic conditions: CO$_2$/MeOH (0.1% NH$_4$OH), 75/25 (v/v); Flow rate: 200.0 mL/min Prep SFC Method M: Column: Chiralpak IC, 250 mm×30 mm, 5µ; Mobile Phase—Isocratic conditions: CO$_2$/EtOH (0.1% NH$_4$OH), 55/45 (v/v); Flow rate: 50.0 mL/min Prep SFC Method N: Column: Chiralpak IC, 250 mm×30 mm, 5µ; Mobile Phase—Isocratic conditions: CO$_2$/EtOH (0.1% NH$_4$OH), 75/25 (v/v); Flow rate: 60.0 mL/min Prep SFC Method O: Column: Daicel Chiralpak AD, 250 mm×50 mm, 10µ; Mobile Phase—Isocratic conditions: CO$_2$/MeOH, 60/40 (v/v); Flow rate: 200 mL/min Prep SFC Method P: Column: Chiralcel OJ-H, 250 mm×30 mm, 5μ; Mobile Phase—Isocratic conditions: $CO_2$/EtOH (0.1% $NH_4OH$), 85/15 (v/v); Flow rate: 50 mL/min Prep SFC Method Q: Column: Daicel Chiralpak AD, 250 mm×30 mm, 5μ; Mobile Phase—Isocratic conditions: $CO_2$/IPA (0.1% $NH_4OH$), 75/25 (v/v); Flow rate: 60 mL/min Prep SFC Method R: Column: Chiral Technologies AD-H, 250 mm×21 mm, 5μ; Mobile Phase—Isocratic conditions: $CO_2$/MeOH (0.2% $NH_4OH$), 80/20 (v/v); Flow rate: 75 mL/min Prep SFC Method S: Column: Princeton PPU, 250 mm×30 mm, 5μ; Mobile Phase—Isocratic conditions: $CO_2$/MeOH, 80/20 (v/v); Flow rate: 80 mL/min Analytical SFC Methods Analytical SFC Method A: Column: Chiralpak IC, 250 mm×4.6 mm, 5μ; Mobile Phase A: $CO_2$, Mobile Phase B: EtOH (0.05% isopropylamine); Gradient: A:B=65:35; Flow rate: 2.5 mL/min Analytical SFC Method B: Column: Lux Amylose-1, 250 mm×4.6 mm, 5μ; Mobile Phase A: $CO_2$, Mobile Phase B: MeOH (0.2% $MeNH_2$); Gradient Elution (time, % A, % B): (0 min, 95% A, 5% B), (1.0 min, 95% A, 5% B), (9.0 min, 40% A, 60% B), (10 min, 95% A, 5% B); Flow rate: 3.0 mL/min Analytical SFC Method C: Column: Chiralpak IC-3, 150 mm×4.6 mm, 3μ; Mobile Phase A: $CO_2$, Mobile Phase B: IPA (0.05% DEA); Gradient Elution (time, % A, % B): (0 min, 95% A, 5% B), (5.5 min, 60% A, 40% B), (8.5 min, 60% A, 40% B), (10 min, 95% A, 5% B), Flow rate: 2.5 mL/min Analytical SFC Method D: Column: Chiralpak AD-3, 150 mm×4.6 mm, 3μ; Mobile Phase A: $CO_2$, Mobile Phase B: EtOH (0.05% DEA); Gradient Elution (time, % A, % B): (0 min, 95% A, 5% B), (5.5 min, 60% A, 40% B), (8.5 min, 60% A, 40% B), (10 min, 95% A, 5% B), Flow rate: 2.5 mL/min Analytical SFC Method E: Column: Chiralpak IC-3, 150 mm×4.6 mm, 3μ; Mobile Phase A: $CO_2$, Mobile Phase B: EtOH (0.05% DEA); Gradient Elution (time, % A, % B): (0 min, 95% A, 5% B), (5.5 min, 60% A, 40% B), (8.5 min, 60% A, 40% B), (10 min, 95% A, 5% B), Flow rate: 2.5 mL/min Analytical SFC Method F: Column: Chiralpak AD-3, 50 mm×3.0 mm, 3μ; Mobile Phase—Isocratic conditions: $CO_2$/EtOH (0.05% DEA), 60/40 (v/v); Flow rate: 2.0 mL/min Analytical SFC Method G: Column: Chiralpak AD-3, 150 mm×4.6 mm, 3μ; Mobile phase A: $CO_2$, Mobile Phase B: MeOH (0.05% DEA); Gradient Elution (time, % A, % B): (0 min, 95% A, 5% B), (5.0 min, 60% A, 40% B), (7.5 min, 60% A, 40% B), (10 min, 95% A, 5% B), Flow rate: 2.5 mL/min Analytical SFC Method H: Column: Chiralcel OJ-3, 100 mm×4.6 mm, 3μ; Mobile Phase A: $CO_2$, Mobile Phase B: EtOH (0.05% DEA); Gradient Elution (time, % A, % B): (0 min, 95% A, 5% B), (5.0 min, 60% A, 40% B), (7.5 min, 60% A, 40% B), (8.5 min, 95% A, 5% B), Flow rate: 2.8 mL/min Analytical SFC Method I: Column: Chiralpak IC-3, 150 mm×4.6 mm, 3μ; Mobile Phase A: $CO_2$, Mobile Phase B: EtOH; Gradient Elution (time, % A, % B): (0 min, 95% A, 5% B), (5.5 min, 60% A, 40% B), (8.5 min, 60% A, 40% B), (10 min, 95% A, 5% B), Flow rate: 2.5 mL/min Analytical SFC Method J: Column: Chiralpak AD-3, 150 mm×4.6 mm, 3μ; Mobile Phase A: $CO_2$, Mobile Phase B: EtOH (0.05% DEA); Gradient Elution (time, % A, % B): (0 min, 95% A, 5% B), (5.0 min, 60% A, 40% B), (7.5 min, 60% A, 40% B), (10 min, 95% A, 5% B), Flow rate: 2.5 mL/min Analytical SFC Method K: Column: Chiral Technologies AD-H, 100 mm×4.6 mm, 3μ; Mobile Phase A: $CO_2$, Mobile Phase B: MeOH (0.2% $NH_4OH$); Gradient Elution (time, % A, % B): (5 min, 60% A, 40% B, [Flow rate: 1.5 mL/min Analytical SFC Method L: Column: ChiralCel OJ-H, 150 mm×4.6 mm, 5μ; Mobile Phase A: $CO_2$, Mobile Phase B: EtOH (0.05% DEA); Gradient Elution (time, % A, % B): (0 min, 95% A, 5% B), (5.0 min, 60% A, 40% B), (8.5 min, 60% A, 40% B), (10 min, 95% A, 5% B), Flow rate: 2.5 mL/min Analytical SFC Method M: Column: Chiral Tech IG, 250 mm×4.6 mm, 5μ; Mobile Phase A: $CO_2$, Mobile Phase B: MeOH (0.2% 7N NH3 in MeOH); Gradient Elution (time, % A, % B): (0 min, 95% A, 5% B), (1.0 min, 95% A, 5% B), (9.0 min, 40% A, 60% B), (9.5 min, 40% A, 60% B), (10 min, 95% A, 5% B), Flow rate: 3.0 mL/min Analytical SFC Method N: Column: Chiralcel OJ-H 250 mm×4.6 mm, 5μ; Mobile Phase A: $CO_2$, Mobile Phase B: IPA (0.05% IPAm), Gradient Elution: B in A from 10% to 40% in 10 minutes, Flow rate: 2.5 mL/min Analytical SFC Method O: Column: ChiralPak AY-3 150 mm×4.6 mm, 3μ; Mobile Phase: A: $CO_2$, Mobile Phase B: Methanol (0.05% DEA); Gradient Elution: (time, % A, % B): (0 min, 95% A, 5% B), (5.5 min, 60% A, 40% B), (8.5 min, 60% A, 40% B) (10 min, 95% A, 5% B), Flow rate: 2.5 mL/min Analytical SFC Method P: Column: Chiralcel OJ-3 100 mm×4.6 mm, 3μ; Mobile Phase: A: $CO_2$, Mobile Phase B: Methanol (0.05% DEA); Gradient Elution: (time, % A, % B): (0 min, 95% A, 5% B), (5.5 min, 60% A, 40% B), (7.5 min, 60% A, 40% B) (10 min, 95% A, 5% B), Flow rate: 2.8 mL/min Analytical SFC Method Q: Column: ChiralCel OD-3, 150 mm×4.6 mm, 3μ; Mobile Phase A: $CO_2$, Mobile Phase B: EtOH (0.05% DEA); Gradient Elution (time, % A, % B): (0 min, 95% A, 5% B), (5.0 min, 60% A, 40% B), (5.5 min, 95% A, 5% B), (7 min, 95% A, 5% B), Flow rate: 2.5 mL/min Analytical SFC Method R: Column: Chiralpak AD-3, 100 mm×4.6 mm, 3μ; Mobile Phase—Isocratic conditions: $CO_2$/EtOH (0.05% DEA), 60/40 (v/v); Flow rate: 2.08 mL/min Analytical SFC Method S: Column: Chiral Technologies OJ-H, 100 mm×4.6 mm, 5μ; Mobile Phase—Isocratic conditions: $CO_2$/EtOH (0.2% $NH_4OH$), 95/5 (v/v); Flow rate: 3.0 mL/min Analytical SFC Method T: Column: Chiralpak IC, 100 mm×4.6 mm, 3μ; Mobile Phase A: $CO_2$, Mobile Phase B: EtOH (0.05% DEA); Gradient Elution (time, % A, % B): (0 min, 95% A, 5% B), (0.5 min, 95% A, 5% B) (4.5 min, 60% A, 40% B), (7.0 min, 60% A, 40% B), (9.5 min, 95% A, 5% B), Flow rate: 1.5 mL/min Analytical SFC Method U: Column: Lux Amylose-2, 100 mm×4.6 mm, 5μ; Mobile Phase A: $CO_2$, Mobile Phase B: MeOH (0.2% $NH_4OH$); Gradient Elution (time, % A, % B): (0 min, 70% A, 30% B), (5.0 min, 70% A, 30% B); Flow rate: 1.5 mL/min Analytical SFC Method V: Column: Chiral Technologies AD-H, 100 mm×4.6 mm, 5μ; Mobile Phase A: $CO_2$, Mobile Phase B: MeOH (0.2% Ammonium hydroxide); Gradient Elution (time, % A, % B): (0 min, 85% A, 15% B) (10 min, 85% A, 15% B). Flow rate: 1.5 mL/min Analytical SFC Method W: Column: Chiral Tech IG, 250 mm×4.6 mm, 5μ; Mobile Phase A: $CO_2$, Mobile Phase B: EtOH; Gradient Elution (time, % A, % B): (0 min, 95% A, 5% B), (1.0 min, 95% A, 5% B), (9.0 min, 40% A, 60% B), (9.5 min, 40% A, 60% B), (10 min, 95% A, 5% B), Flow rate: 3.0 mL/min Analytical SFC Method X: Column: ChiralPak AY, 150 mm×4.6 mm, 3μ; Mobile Phase A: $CO_2$, Mobile Phase B: EtOH (0.05% DEA); Gradient Elution (time, % A, % B): (0 min, 95% A, 5% B), (5.0 min, 40% A, 60% B), (7.5 min, 40% A, 60% B), (10 min, 95% A, 5% B), Flow rate: 2.5 mL/min Analytical SFC Method Y: Column: Chiral Tech OJ-H, 100 mm×4.6 mm, 5μ; Mobile Phase A: $CO_2$, Mobile Phase B: MeOH (0.2% $NH_4OH$); Gradient Elution (time, % A, % B): (0 min, 95% A, 5% B), (10 min, 95% A, 5% B), Flow rate: 1.5 mL/min Analytical SFC Method Z: Column: Chiralcel OJ-3, 150 mm×4.6 mm, 3μ; Mobile Phase A: $CO_2$, Mobile Phase B: EtOH (0.05% DEA); Gradient Elution (time, % A, % B): (0 min, 95% A, 5% B), (5 min, 60% A, 40% B), (7.5 min, 60% A, 40% B), (10 min, 95% A, 5% B), Flow rate: 2.5 mL/min Analytical SFC Method AA: Column: ChiralPak AD-3 100 mm×4.6 mm, 3μ; Mobile Phase: A: $CO_2$, Mobile Phase B: MeOH (0.05% DEA); Gradient Elution: (time, % A, % B): (0 min, 60% A, 40% B), Flow rate: 2.8 mL/min Analytical SFC Method BA: Column: Chiralpak IC-3, 150 mm×4.6 mm, 3μ; Mobile Phase A: $CO_2$, Mobile Phase B: IPA (0.05% DEA); Gradient Elution (time, % A, % B): (0 min, 95% A, 5% B), (5 min, 60% A, 40% B), (7.5 min, 60% A, 40% B), (10 min, 95% A, 5% B), Flow rate: 2.5 mL/min Analytical SFC Method CA: Column: Lux Cellulose 100 mm×4.6 mm, 5μ; Mobile Phase: A: $CO_2$, Mobile Phase B: MeOH (0.2% $NH_4OH$); Gradient Elution: (time, % A, % B): (0 min, 70% A, 30% B), (5 min, 70% A, 30% B), Flow rate: 1.5 mL/min Analytical SFC Method DA: Column: Lux Cellulose-2, 150 mm×4.6 mm, 5μ; Mobile Phase A: $CO_2$, Mobile Phase B: MeOH (0.05% DEA); Gradient Elution (time, % A, % B): (0 min, 95% A, 5% B), (5.0 min, 60% A, 40% B), (8.5 min, 60% A, 40% B), (10 min, 95% A, 5% B), Flow rate: 2.5 mL/min Analytical SFC Method EA: Column: Chiralcel OJ-3, 150 mm×4.6 mm, 3μ; Mobile Phase—Isocratic conditions: $CO_2$/EtOH (0.05% DEA), 60/40 (v/v); Flow rate: 2.5 mL/min Analytical SFC Method FA: Column: ChiralPak AD-3, 250 mm×4.6 mm, 5μ; Mobile Phase A: $CO_2$, Mobile Phase B: EtOH (0.05% IPAm); Gradient Elution (time, % A, % B): (0 min, 65% A, 35% B), Flow rate: 2.5 mL/mi Analytical SFC Method GA: Column: Chiral Tech IC, 250 mm×4.6 mm, 5μ; Mobile Phase A: $CO_2$, Mobile Phase B: IPA (0.2% $NH_3$ in MeOH); Gradient Elution (time, % A, % B): (0 min, 95% A, 5% B), (1 min, 95% A, 5% B), (9 min, 40% A, 60% B), (9.5 min, 40% A, 60% B), (10 min, 95% A, 5% B), Flow rate: 2.5 mL/min Preparative HPLC Methods Prep HPLC Method A: Column: Xtimate C18, 150 mm×25 mm, 5μ; Mobile Phase A: water (0.05% $NH_4OH$ v/v), Mobile Phase B MeCN; B %: 18%-58%, 12 min; Flow rate: 25 mL/min Prep HPLC Method B: Column: Phenomenex XB-C18, 250 mm×21.2 mm, 5μ; Mobile Phase A: water (0.1% $HCO_2H$), Mobile Phase B: MeCN (0.1% $HCO_2H$); Gradient Elution (time, % A, % B): (0 min, 95% A, 5% B), (1.5 min, 95% A, 5% B), (10.0 min, 0% A, 100% B), (11 min, 0% A, 100% B), (12.5 min, 95% A, 5% B); Flow rate: 27 mL/min Prep HPLC Method C: Column: Waters Atlantis C18, 50 mm×4.6 mm, 5μ; Mobile Phase A: water (0.05% TFA), Mobile Phase B: MeCN (0.05% TFA); Gradient Elution (time, % A, % B): (0 min, 95% A, 5% B), (4 min, 5% A, 95% B), (5 min, 5% A, 95% B); Flow rate: 2 mL/min Prep HPLC Method D: Column: Xtimate C18, 150 mm×25 mm, 5μ; Mobile Phase A: water (0.05% ammonium hydroxide), Mobile Phase B: MeCN; B %: 25% to 65% in 12 min, Flow rate: 25 ml/min Prep HPLC Method E: Column: Waters Xbridge, 150 mm×25 mm, 5μ; Mobile Phase A: water (10 mM $NH_4HCO_3$), Mobile Phase B: MeCN; B %: 20%-50%, 12 min Prep HPLC Method F: Column: Phenomenex luna C18, 250 mm×80 mm, 10μ; Mobile Phase A: water (0.1% TFA), Mobile Phase B: MeCN; B %: 1%-25%, 20 min Prep HPLC Method G: Column: Phenomenex Synergi Max-RP, 250 mm×80 mm, 10μ; Mobile Phase A: water (0.1% TFA), Mobile Phase B: MeCN; B %: 10%-40%, 20 min Prep HPLC Method H: Column: Boston Green ODS, 150 mm×30 mm, 5μ; Mobile Phase A: water (0.225% $HCO_2H$), Mobile Phase B: MeCN; B %: 5%-53%, 11 min, Flow rate: 25 mL/min Prep HPLC Method I: Column: Agela Durashell C18, 150 mm×25 mm, 5μ; Mobile Phase A: water (0.225% $HCO_2H$), Mobile Phase B: MeCN; B %: 9%-39%, 12 min, flow rate: 25 mL/min Prep HPLC Method J: Column: Phenomenex Gemini C18, 250 mm×50 mm, 10μ; Mobile Phase A: water (0.05% ammonium hydroxide), Mobile Phase B: MeCN; B %: 5%-25%, 15 min, flow rate: 100 mL/min Prep HPLC Method K: Column: Agela Durashell C18, 150 mm×25 mm, 5μ; Mobile Phase A: water (0.225% $HCO_2H$), Mobile Phase B: MeCN; B %: 0%-32%, 11 min, Flow rate 25 mL/min Prep HPLC Method L: Column: Xtimate C18,150 mm×25 mm, 5μ; Mobile Phase A: water (0.05% $NH_4OH$ v/v), Mobile Phase B: MeCN; B %: 15%-55%, 12 min, Flow rate: 25 mL/min Prep HPLC Method M: Column: Agela Durashell 150 mm×25 mm, 5μ; Mobile Phase A: water (0.05% $NH_4OH$ v/v), Mobile Phase B: MeCN; B %: 30%-60%, 2.5 min, Flow rate: 25 mL/min Prep HPLC Method N: Column: Phenomenex luna C18, 250 mm×80 mm, 10μ; Mobile Phase A: water (0.1% TFA), Mobile Phase B: MeCN; B %: 25%-55%, 20 min, Flow rate: 25 mL/min Prep HPLC Method O: Column: Agela Durashell, 150 mm×25 mm, 5μ; Mobile Phase A: water (0.05% $NH_4OH$ v/v), Mobile Phase B: MeCN; B %: 25%-55%, 10 min, Flow rate: 25 mL/min Prep HPLC Method P: Column: Agela Durashell, 150 mm×25 mm, 5μ; Mobile Phase A: water (0.05% $NH_4OH$ v/v), Mobile Phase B: MeCN; B %: 30%-60%, 10 min, flow rate: 25 mL/min Prep HPLC Method Q: Column: Agela Durashell, 150 mm×25 mm, 5μ; Mobile Phase A: water (0.05% $NH_4OH$ v/v), Mobile Phase B: MeCN; B %: 23%-53%, 10 min, flow rate: 25 mL/min Prep HPLC Method R: Column: Phenomenex Gemini C18, 250 mm×50 mm, 10μ; Mobile Phase A: Water (0.05% $NH_4OH$ v/v), Mobile Phase B: MeCN; Gradient Elution (time, % A, % B): (0 min, 90% A, 10% B), (15 min, 60% A, 40% B), (18 min, 0% A, 100% B), Flow rate: 110 mL/min)

Prep HPLC Method S: Column: Phenomenex Gemini C18, 250 mm×50 mm, 10μ; Mobile Phase A: Water (0.05% $NH_4OH$ v/v), Mobile Phase B: MeCN; Gradient Elution (time, % A, % B): (0 min, 80% A, 20% B), (15 min, 60% A, 40% B), (18 min, 0% A, 100% B), Flow rate: 110 mL/min Prep HPLC Method T: Column: Phenomenex Gemini C18, 250 mm×50 mm, 10μ; Mobile Phase A: Water (0.05% NH₄OH v/v), Mobile Phase B: MeCN; B %: 20%-40%, 15 min, flow rate 110 ml/min Prep HPLC Method U: Column: Phenomenex Gemini C18, 250 mm×50 mm, 10μ; Mobile Phase A: Water (0.05% NH₄OH v/v), Mobile Phase B: MeCN; Gradient Elution (time, % A, % B): (0 min, 75% A, 25% B), (15 min, 55% A, 45% B), (18 min, 0% A, 100% B), Flow rate: 110 mL/min Prep HPLC Method V: Column: Phenomenex Synergi Max-RP, 150 mm×50 mm, 10μ; Mobile Phase A: Water (0.225% HCO₂H), Mobile Phase B: MeCN; B %: 0%-30%, 25 min, flow rate 120 mL/min Prep HPLC Method W: Column: Xtimate C18, 150 mm×25 mm, 5μ; Mobile Phase A: Water (0.05% NH₄OH v/v), Mobile Phase B: MeCN; B %: 17%-57%, 12 min, Flow rate: 25 mL/min Prep HPLC Method X: Column: Agela Durashell C18, 150 mm×30 mm, 5μ; Mobile Phase A: Water, Mobile Phase B: MeCN; Gradient Elution (time, % A, % B): (0 min, 82% A, 18% B), (10 min, 42% A, 58% B), (18 min, 0% A, 100% B), Flow rate: 25 mL/min Prep HPLC Method Y: Column: Boston Green ODS, 150 mm×30 mm, 5μ; Mobile Phase A: water (0.05% NH₄OH v/v), Mobile Phase B: MeCN; B %: 45%-65%, 9 min, Flow rate 25 mL/min Prep HPLC Method Z: Column: Phenomenex Gemini C18, 250 mm×50 mm, 10μ; Mobile Phase A: Water (0.05% NH₄OH v/v), Mobile Phase B: MeCN; Gradient Elution (time, % A, % B): (0 min, 80% A, 20% B), (15 min, 60% A, 40% B), (18 min, 0% A, 100% B), Flow rate: 110 mL/min Prep HPLC Method AA: Column: Gemini C18, 15 mm×21.2 mm, 5μ; Mobile Phase A: water (0.1% HCO₂H) Mobile Phase B: MeCN (0.1% HCO₂H); B % 25%-35%; 25 mL/min Prep HPLC Method BA: Column: Agela Durashell C18, 150 mm×30 mm, 5μ; Mobile Phase A: water (0.05% NH₄OH v/v), Mobile Phase B: MeCN; B %: 20%-55%, 15 min, Flow rate: 25 mL/min Prep HPLC Method CA: Column: Phenomenex Gemini C18, 250 mm×50 mm, 10μ; Mobile Phase A: Water (0.05% NH₄OH v/v), Mobile Phase B: MeCN; Gradient Elution (time, % A, % B): (0 min, 75% A, 25% B), (15 min, 55% A, 45% B), (18 min, 0% A, 100% B); Flow rate: 110 mL/min

EXAMPLES

Preparation 1: 3-(1-((tert-butyldimethylsilyl)oxy)-3-(4,4,5,5-tetramethyl-1,3,2-dioxaborolan-2-yl)propan-2-yl)-5-(3,4-dimethoxyphenyl)pyridine

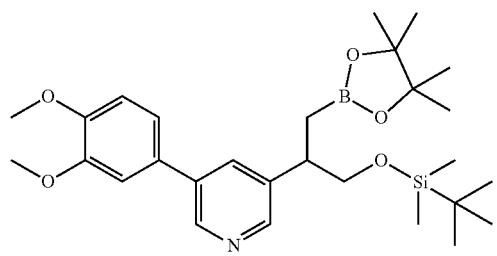

To a solution of 3-(3-((tert-butyldimethylsilyl)oxy)-1-(4,4,5,5-tetramethyl-1,3,2-dioxaborolan-2-yl)prop-1-en-2-yl)-5-(3,4-dimethoxyphenyl)pyridine (Preparation 2, 1.6 g, 3.13 mmol) in EtOAc (50 mL) was added Pd/C (0.5 g, 10% loading). The mixture was stirred under H₂ (5 psig) at 20° C. for about 3 h. The mixture was filtered and concentrated to afford 3-(1-((tert-butyldimethylsilyl)oxy)-3-(4,4,5,5-tetramethyl-1,3,2-dioxaborolan-2-yl)propan-2-yl)-5-(3,4-dimethoxyphenyl)pyridine (1.2 g), which was used directly without further purification. ¹H NMR (CDCl₃, 400 MHz): δ 8.69 (d, J=7.6 Hz, 1H), 8.48 (s, 1H), 7.78 (s, 1H), 7.32 (s, 1H), 7.18 (d, J=8.4 Hz, 1H), 7.12 (d, J=1.6 Hz, 1H), 7.04-7.01 (m, 1H), 4.15-4.20 (m, 1H), 4.00 (d, J=8.4 Hz, 6H), 3.75-3.79 (m, 1H), 2.10 (s, 12H), 1.31 (d, J=11.2 Hz, 9H), 1.15 (d, J=12.8 Hz, 1H), 0.88 (d, J=8.8 Hz, 1H), 0.01-0.02 (m, 6H). LCMS m/z=514 [MH]⁺.

Preparation 2: 3-(3-((tert-butyldimethylsilyl)oxy)-1-(4,4,5,5-tetramethyl-1,3,2-dioxaborolan-2-yl)prop-1-en-2-yl)-5-(3,4-dimethoxyphenyl)pyridine

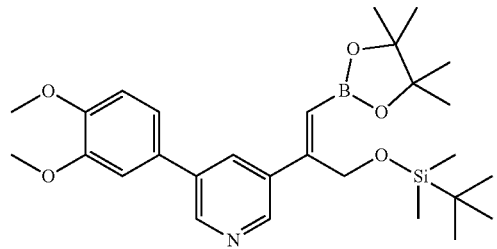 [SMILES: COc1ccc(-c2cncc(C(CO[Si](C)(C)C(C)(C)C)CB3OC(C)(C)C(C)(C)O3)c2)cc1OC]

A solution of 3-(1-bromo-3-((tert-butyldimethylsilyl)oxy)prop-1-en-2-yl)-5-(3,4-dimethoxyphenyl)pyridine (Preparation 37, 0.83 g, 1.79 mmol), Pd(dppf)Cl₂.DCM (73 mg, 89 umol), KOAc (263 mg, 2.68 mmol) and Pin₂B₂ (CAS 73183-34-3, 681 mg, 2.68 mmol) in 1,4-dioxane (10 mL) was heated to 55° C. under N₂ for 12 h. The mixture was concentrated and the residue was purified by column chromatography (silica) and eluted with pet. ether/EtOAc (3:1) to afford 3-(3-((tert-butyldimethylsilyl)oxy)-1-(4,4,5,5-tetramethyl-1,3,2-dioxaborolan-2-yl)prop-1-en-2-yl)-5-(3,4-dimethoxyphenyl)pyridine (900 mg, 98%). ¹H NMR (CDCl₃, 400 MHz): δ 8.74 (s, 1H), 8.71 (s, 1H), 8.03 (s, 1H), 7.13-7.16 (m, 1H), 7.09 (s, 1H), 6.98 (d, J=8.4 Hz, 1H), 5.90 (s, 1H), 4.97 (s, 2H), 3.96 (s, 3H), 3.94 (s, 3H). LCMS m/z=512 [MH]⁺.

Preparation 3: 3-(1-((tert-butyldimethylsilyl)oxy)-3-(4,4,5,5-tetramethyl-1,3,2-dioxaborolan-2-yl)propan-2-yl)-5-(3-ethoxy-4-methoxyphenyl)pyridine

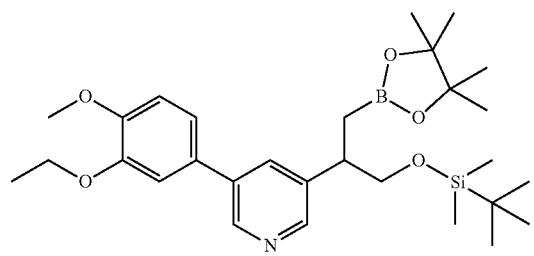 [SMILES: CCOc1cc(-c2cncc(C(CO[Si](C)(C)C(C)(C)C)CB3OC(C)(C)C(C)(C)O3)c2)ccc1OC]

3-(1-((tert-butyldimethylsilyl)oxy)-3-(4,4,5,5-tetramethyl-1,3,2-dioxaborolan-2-yl)propan-2-yl)-5-(3-ethoxy-4-methoxyphenyl)pyridine (3.8 g, 95%) was prepared in an analogous manner to Preparation 1 using 3-(1-bromo-3-((tert-butyldimethylsilyl)oxy)prop-1-en-2-yl)-5-(3-ethoxy-4-methoxyphenyl)pyridine (Preparation 4, 4.0 g, 7.6 mmol) which was used without further purification.

Preparation 4: 3-(3-((tert-butyldimethylsilyl)oxy)-1-(4,4,5,5-tetramethyl-1,3,2-dioxaborolan-2-yl)prop-1-en-2-yl)-5-(3-ethoxy-4-methoxyphenyl)pyridine

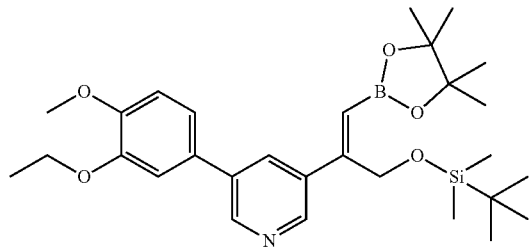 [SMILES: CCOc1cc(-c2cncc(/C(=C/B3OC(C)(C)C(C)(C)O3)CO[Si](C)(C)C(C)(C)C)c2)ccc1OC]

3-(3-((tert-butyldimethylsilyl)oxy)-1-(4,4,5,5-tetramethyl-1,3,2-dioxaborolan-2-yl)prop-1-en-2-yl)-5-(3-ethoxy-4-methoxyphenyl)pyridine (7.5 g, 97%) was prepared in an analogous manner to Preparation 2 using 3-(1-bromo-3-((tert-butyldimethylsilyl)oxy)prop-1-en-2-yl)-5-(3-ethoxy-4-methoxyphenyl)pyridine (Preparation 38, 7.0 g, 14.6 mmol). $^1$H NMR (CDCl$_3$, 400 MHz): δ 8.69-8.73 (m, 2H), 8.03 (s, 1H), 7.14 (dd, J=2.0, 8.4 Hz, 1H), 7.10 (s, 1H), 6.97 (d, J=8.4 Hz, 1H), 5.90 (s, 1H), 4.97 (s, 2H), 4.18 (q, J=7.2 Hz, 2H), 3.93 (s, 1H), 1.51 (t, J=7.2 Hz, 3H), 1.33 (s, 12H), 0.83 (s, 9H), 0.08 (s, 6H).

Preparation 5: 3-(1-((tert-butyldimethylsilyl)oxy)-3-(4,4,5,5-tetramethyl-1,3,2-dioxaborolan-2-yl)propan-2-yl)-5-(4-methoxy-3-propoxyphenyl)pyridine

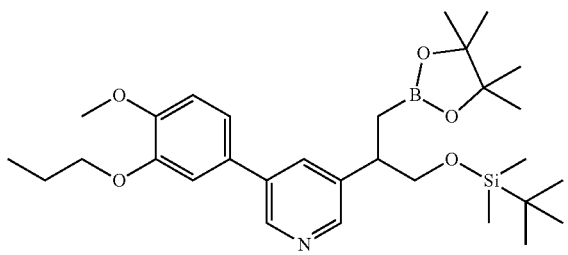 [SMILES: CCCOc1cc(-c2cncc(C(CO[Si](C)(C)C(C)(C)C)CB3OC(C)(C)C(C)(C)O3)c2)ccc1OC]

To a solution of 3-(3-((tert-butyldimethylsilyl)oxy)-1-(4,4,5,5-tetramethyl-1,3,2-dioxaborolan-2-yl)prop-1-en-2-yl)-5-(4-methoxy-3-propoxyphenyl)pyridine (Preparation 8, 4.00 g, 7.41 mmol) in EtOAc (100 mL) was added Pd/C (1.0 g, 10% loading) under N$_2$. The mixture was stirred under H$_2$ (14 psig) at about 25° C. for about 3 h. The mixture was filtered and concentrated to afford 3-(1-((tert-butyldimethylsilyl)oxy)-3-(4,4,5,5-tetramethyl-1,3,2-dioxaborolan-2-yl)propan-2-yl)-5-(4-methoxy-3-propoxyphenyl)pyridine (3.44 g, 86%), which was used without further purification.

Preparation 6: (R)-(3-((tert-butyldimethylsilyl)oxy)-2-(5-(4-methoxy-3-propoxyphenyl)pyridin-3-yl)propyl)boronic acid

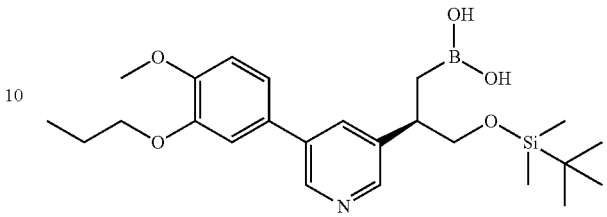

Method A:

To a mixture of 3-(3-((tert-butyldimethylsilyl)oxy)prop-1-en-2-yl)-5-(4-methoxy-3-propoxyphenyl)pyridine (Preparation 50, 50.00 g, 120.9 mmol), [Ir(COD)Cl]$_2$ (CAS 12112-67-3, 2.03 g, 3.02 mmol) and (S,S)-[2-(4'-i-propyloxazolin-2-yl)ferrocynyl]diphenylphosphine (CAS 163169-29-7, 3.20 g, 6.65 mmol) was added anhydrous THF (403 mL). The mixture was stirred for about 15 min at about 20° C. under N$_2$. The flask was chilled in an ice water bath until the solution temperature was about 0° C. Catecholborane (181.48 mL, 181 mmol, 1.0 M in THF) was added dropwise over 1 h. Once the catecholborane was added the flask was removed from the cooling bath and stirred at about 20° C. for about 3 h. The mixture was quenched with a dropwise addition of methanol (25 mL) at about 0° C. (ice bath). The solution was removed from the ice bath and stirred about 30 min. The solution was concentrated to afford (R)-(3-((tert-butyldimethylsilyl)oxy)-2-(5-(4-methoxy-3-propoxyphenyl)pyridin-3-yl)propyl)boronic acid (88 g), which is used directly without further purification. LCMS m/z=460 [MH]$^+$.

Method B:

To a solution of Turbo Grignard (180 mL, 117 mmol, 1.3 M in THF) was added 1,4-dioxane (19 mL) and stirred at about 20° C. for about 1 h. To the mixture was added slowly a solution of (R)-3-(1-((tert-butyldimethylsilyl)oxy)-3-iodopropan-2-yl)-5-(4-methoxy-3-propoxyphenyl)pyridine (Preparation 42, 46.8 g, 86.5 mmol) in anhydrous THF (270 mL), which was stirred at about 20° C. for about 20 min. A solution of trimethyl borate (96.4 mL, 865 mmol) in THF (107 mL) was added drop wise and stirred at about 20° C. for about 30 min. The mixture was concentrated and partitioned between water (500 mL) and EtOAc (200 mL). The aqueous layer was extracted with EtOAc (3×100 mL). The combined EtOAc layers were washed with brine, dried over Na$_2$SO$_4$, filtered and concentrated. The residue was purified by column chromatography (silica) and eluted with heptanes/EtOAc (80:20 to 0:100) followed by EtOAc/MeOH (100:0 to 90:10) to afford (R)-(3-((tert-butyldimethylsilyl)oxy)-2-(5-(4-methoxy-3-propoxyphenyl)pyridin-3-yl)propyl)boronic acid (29.0 g, 73%). $^1$H NMR (CD$_3$OD, 400 MHz): δ 8.51 (d, J=2.3 Hz, 1H), 8.30 (d, J=2.0 Hz, 1H), 7.85 (br s, 1H), 7.14-7.17 (m, 2H), 7.03 (d, J=7.8 Hz, 1H), 4.00 (t, J=6.6 Hz, 2H), 3.85 (s, 3H), 3.70-3.80 (m, 2H), 3.27 (br s, 2H), 3.07-3.14 (m, 1H), 1.76-1.85 (m, 2H), 1.10-1.33 (m, 2H), 1.03 (t, J=7.81 Hz, 3H), 0.79 (s, 9H), −0.08 (d, J=12.9 Hz, 6H). LCMS m/z=460 [MH]$^+$.

Preparation 7: (S)-(3-((tert-butyldimethylsilyl)oxy)-2-(5-(4-methoxy-3-propoxyphenyl)pyridin-3-yl)propyl)boronic acid

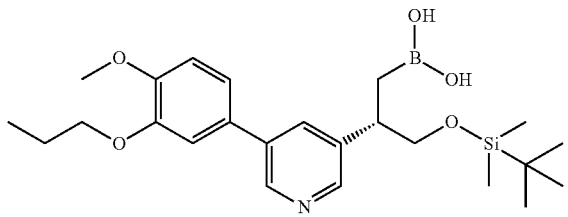 [SMILES: CCCOc1cc(-c2cncc([C@@H](CO[Si](C)(C)C(C)(C)C)CB(O)O)c2)ccc1OC]

To a mixture of 3-(3-((tert-butyldimethylsilyl)oxy)prop-1-en-2-yl)-5-(4-methoxy-3-propoxyphenyl)pyridine (Preparation 50, 1.0 g, 2.42 mmol), [Ir(COD)Cl]$_2$ (CAS 12112-67-3, 44.2 mg, 0.06 mmol) and (R,R)-[2-(4'-i-propyloxazolin-2-yl)ferrocynyl]diphenylphosphine (CAS 541540-70-9, 58.2 mg, 0.12 mmol) was added anhydrous THF (8.1 mL). The mixture was stirred at about 20° C. for about 10 min. The reaction was cooled to about 0° C. and catecholborane (6.04 mL, 6.04 mmol, 1.0 M in THF) was added dropwise. The reaction was warmed to about 20° C. and stirred for about 8 h. The reaction was cooled to about 5° C. and quenched with MeOH. The mixture was concentrated and purified by column chromatography (silica) and eluted with DCM/MeOH (100:0 to 90:10) to afford (S)-(3-((tert-butyldimethylsilyl)oxy)-2-(5-(4-methoxy-3-propoxyphenyl)pyridin-3-yl)propyl)boronic acid (889 mg, 80%). $^1$H NMR (CD$_3$OD, 400 MHz): δ 8.51 (d, J=2.3 Hz, 1H), 8.30 (d, J=2.0 Hz, 1H), 7.85 (br s, 1H), 7.14-7.17 (m, 2H), 7.03 (d, J=7.8 Hz, 1H), 4.00 (t, J=6.6 Hz, 2H), 3.85 (s, 3H), 3.70-3.80 (m, 2H), 3.27 (br s, 2H), 3.07-3.14 (m, 1H), 1.76-1.85 (m, 2H), 1.10-1.33 (m, 2H), 1.03 (t, J=7.81 Hz, 3H), 0.79 (s, 9H), −0.08 (d, J=12.9 Hz, 6H). LCMS m/z=460 [MH]$^+$.

Preparation 8: 3-(3-((tert-butyldimethylsilyl)oxy)-1-(4,4,5,5-tetramethyl-1,3,2-dioxaborolan-2-yl)prop-1-en-2-yl)-5-(4-methoxy-3-propoxyphenyl)pyridine

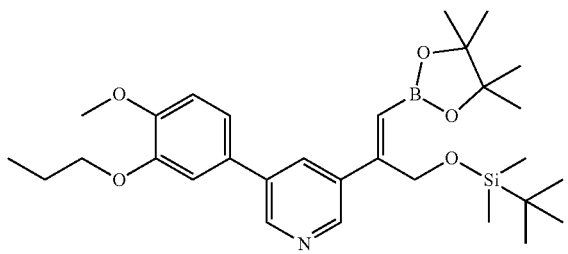 [SMILES: CCCOc1cc(-c2cncc(/C(=C/B3OC(C)(C)C(C)(C)O3)CO[Si](C)(C)C(C)(C)C)c2)ccc1OC]

3-(1-Bromo-3-((tert-butyldimethylsilyl)oxy)prop-1-en-2-yl)-5-(4-methoxy-3-propoxyphenyl)pyridine (Preparation 39, 5.60 g, 11.37 mmol), Pd(dppf)Cl$_2$ (415.98 mg, 568.50 umol), Pin$_2$B$_2$ (4.33 g, 17.06 mmol) and KOAc (2.23 g, 22.74 mmol) in dioxane (100 mL) was heated to about 60° C. under N$_2$ for about 16 h. The mixture was filtered and concentrated. The residue was purified by column chromatography (silica) and eluted with pet. ether/EtOAc (5:1) to afford 3-(3-((tert-butyldimethylsilyl)oxy)-1-(4,4,5,5-tetramethyl-1,3,2-dioxaborolan-2-yl)prop-1-en-2-yl)-5-(4-methoxy-3-propoxyphenyl)pyridine (6.10 g, 99%). $^1$H NMR (CDCl$_3$, 400 MHz): δ 8.70-8.73 (m, 2H), 8.03 (t, J=2.0 Hz, 1H), 7.14 (dd, J=2.0, 8.4 Hz, 1H), 7.10 (s, 1H), 6.97 (d, J=8.4 Hz, 1H), 5.90 (s, 1H), 4.97 (s, 2H), 4.06 (t, J=6.8 Hz, 2H), 3.93 (s, 1H), 1.87-1.96 (m, 2H), 1.33 (s, 12H), 1.08 (t, J=7.6 Hz, 3H), 0.83 (s, 9H), 0.07 (s, 6H).

Preparation 9: 3-(1-((tert-butyldimethylsilyl)oxy)-3-(4,4,5,5-tetramethyl-1,3,2-dioxaborolan-2-yl)propan-2-yl)-5-(3-isopropoxy-4-methoxyphenyl)pyridine

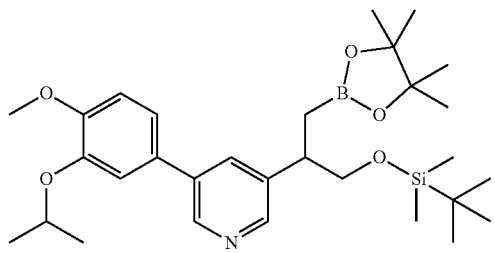 [SMILES: COc1ccc(-c2cncc(C(CO[Si](C)(C)C(C)(C)C)CB3OC(C)(C)C(C)(C)O3)c2)cc1OC(C)C]

Bis(1,5-cyclooctadiene)di-µ-methoxydiiridium(I) (CAS 12148-71-9, 96 mg, 0.15 mmol) and ethylenebis(diphenylphosphine) (CAS, 1663-45-2, 116 mg, 0.29 mmol) in anhydrous DCE (10 mL) were stirred for about 15 min under N$_2$ at about 15° C. 3-(3-((tert-butyldimethylsilyl)oxy)prop-1-en-2-yl)-5-(3-isopropoxy-4-methoxyphenyl)pyridine (Preparation 51, 600 mg, 1.45 mmol) was added to the mixture under N$_2$ at about 15° C. After stirring for about 5 min, 4,4,5,5-tetramethyl-1,3,2-dioxaborolane (CAS 25015-63-9, 913 mg, 7.13 mmol) was added at about 70° C. and stirred for an additional 15 min. The reaction was quenched with MeOH and concentrated. The residue was purified by column chromatography (silica) and eluted with pet. ether:EtOAc (100:0 to 85:15) to give afford 3-(1-((tert-butyldimethylsilyl)oxy)-3-(4,4,5,5-tetramethyl-1,3,2-dioxaborolan-2-yl)propan-2-yl)-5-(3-isopropoxy-4-methoxyphenyl)pyridine (750 mg, 96%). LCMS m/z=542 [MH]$^+$.

Preparation 10: 3-(1-((tert-butyldimethylsilyl)oxy)-3-(4,4,5,5-tetramethyl-1,3,2-dioxaborolan-2-yl)propan-2-yl)-5-(3-cyclopropoxy-4-methoxyphenyl)pyridine

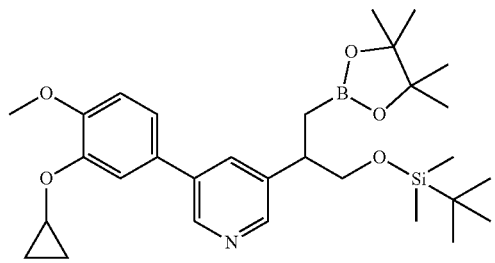 [SMILES: COc1ccc(-c2cncc(C(CO[Si](C)(C)C(C)(C)C)CB3OC(C)(C)C(C)(C)O3)c2)cc1OC1CC1]

3-(1-((tert-butyldimethylsilyl)oxy)-3-(4,4,5,5-tetramethyl-1,3,2-dioxaborolan-2-yl)propan-2-yl)-5-(3-cyclopropoxy-4-methoxyphenyl)pyridine (750 mg, 95%) was prepared in an analogous manner to Preparation 9 using 3-(3-((tert-butyldimethylsilyl)oxy)prop-1-en-2-yl)-5-(3-cyclopropoxy-4-methoxyphenyl)pyridine (Preparation 52, 600 mg, 1.46 mmol). LCMS m/z=540 [MH]$^+$.

Preparation 11: 3-(1-((tert-butyldimethylsilyl)oxy)-3-(4,4,5,5-tetramethyl-1,3,2-dioxaborolan-2-yl)propan-2-yl)-5-(3-(2-((tert-butyldimethylsilyl)oxy)ethoxy)-4-methoxyphenyl)pyridine

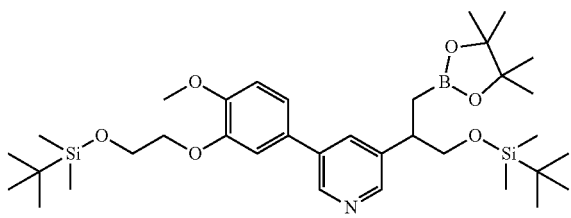 [SMILES: COc1ccc(-c2cncc(C(CO[Si](C)(C)C(C)(C)C)CB3OC(C)(C)C(C)(C)O3)c2)cc1OCCO[Si](C)(C)C(C)(C)C]

3-(1-((tert-butyldimethylsilyl)oxy)-3-(4,4,5,5-tetramethyl-1,3,2-dioxaborolan-2-yl)propan-2-yl)-5-(3-(2-((tert-butyldimethylsilyl)oxy)ethoxy)-4-methoxyphenyl)pyridine (2.0 g, 81%) was prepared in an analogous manner to Preparation 9 using 3-(3-(2-((tert-butyldimethylsilyl)oxy)ethoxy)-4-methoxyphenyl)-5-(3-((tert-butyldimethylsilyl)oxy)prop-1-en-2-yl)pyridine (Preparation 53, 2.0 g, 3.8 mmol). LCMS m/z=658 [MH]$^+$.

Preparation 12: 3-(1-((tert-butyldimethylsilyl)oxy)-3-(4,4,5,5-tetramethyl-1,3,2-dioxaborolan-2-yl)propan-2-yl)-5-(3-(3-((tert-butyldimethylsilyl)oxy)propoxy)-4-methoxyphenyl)pyridine

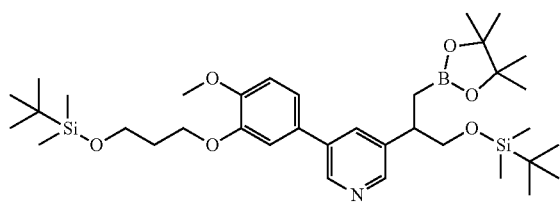 [SMILES: COc1ccc(-c2cncc(C(CO[Si](C)(C)C(C)(C)C)CB3OC(C)(C)C(C)(C)O3)c2)cc1OCCCO[Si](C)(C)C(C)(C)C]

3-(1-((tert-butyldimethylsilyl)oxy)-3-(4,4,5,5-tetramethyl-1,3,2-dioxaborolan-2-yl)propan-2-yl)-5-(3-(3-((tert-butyldimethylsilyl)oxy)propoxy)-4-methoxyphenyl)pyridine (12.0 g, 97%) was prepared in an analogous manner to Preparation 9 using 3-(3-((tert-butyldimethylsilyl)oxy)prop-1-en-2-yl)-5-(3-(3-((tert-butyldimethylsilyl)oxy)propoxy)-4-methoxyphenyl)pyridine (Preparation 54, 10.0 g, 18.4 mmol). LCMS m/z=671 [MH]$^+$.

Preparation 13: 3-(1-((tert-butyldimethylsilyl)oxy)-3-(4,4,5,5-tetramethyl-1,3,2-dioxaborolan-2-yl)propan-2-yl)-5-(3-(2-fluoroethoxy)-4-methoxyphenyl)pyridine

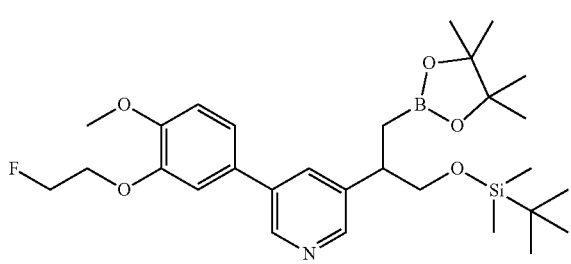 [SMILES: COc1ccc(-c2cncc(C(CO[Si](C)(C)C(C)(C)C)CB3OC(C)(C)C(C)(C)O3)c2)cc1OCCF]

3-(1-((tert-butyldimethylsilyl)oxy)-3-(4,4,5,5-tetramethyl-1,3,2-dioxaborolan-2-yl)propan-2-yl)-5-(3-(2-fluoroethoxy)-4-methoxyphenyl)pyridine (700 mg, 89%) was prepared in an analogous manner to Preparation 9 using 3-(3-((tert-butyldimethylsilyl)oxy)prop-1-en-2-yl)-5-(3-(2-fluoroethoxy)-4-methoxyphenyl)pyridine (Preparation 55, 600 mg, 1.4 mmol). LCMS m/z=433 [MH]$^+$.

Preparation 14: tert-butyl(2-(3'-(3-fluoropropoxy)-4'-methoxy-[1,1'-biphenyl]-3-yl)-3-(4,4,5,5-tetramethyl-1,3,2-dioxaborolan-2-yl)propoxy)dimethylsilane

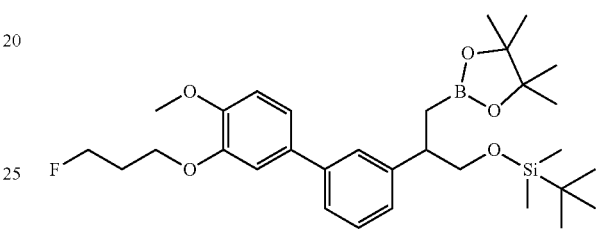

tert-butyl(2-(3'-(3-fluoropropoxy)-4'-methoxy-[1,1'-biphenyl]-3-yl)-3-(4,4,5,5-tetramethyl-1,3,2-dioxaborolan-2-yl)propoxy)dimethylsilane was prepared in an analogous manner to Preparation 9 using 3-(3-((tert-butyldimethylsilyl)oxy)prop-1-en-2-yl)-5-(3-(3-fluoropropoxy)-4-methoxyphenyl)pyridine (Preparation 56).

Preparation 15: 3-(1-((tert-butyldimethylsilyl)oxy)-3-(4,4,5,5-tetramethyl-1,3,2-dioxaborolan-2-yl)propan-2-yl)-5-(2-(difluoromethyl)-3-ethoxy-4-methoxyphenyl)pyridine

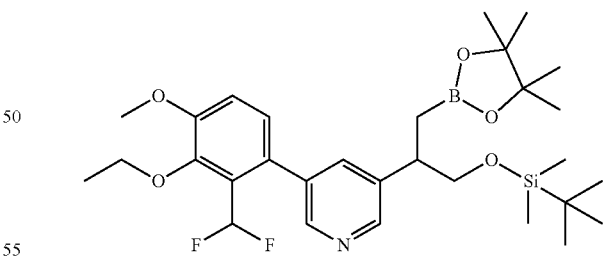

3-(1-((tert-butyldimethylsilyl)oxy)-3-(4,4,5,5-tetramethyl-1,3,2-dioxaborolan-2-yl)propan-2-yl)-5-(2-(difluoromethyl)-3-ethoxy-4-methoxyphenyl)pyridine (300 mg, 46%) was prepared in an analogous manner to Preparation 9 using 3-(3-((tert-butyldimethylsilyl)oxy)prop-1-en-2-yl)-5-(2-(difluoromethyl)-3-ethoxy-4-methoxyphenyl)pyridine (Preparation 57, 361 mg, 1.13 mmol). LCMS m/z=578 [MH]$^+$.

Preparation 16: 3-(1-((tert-butyldimethylsilyl)oxy)-3-(4,4,5,5-tetramethyl-1,3,2-dioxaborolan-2-yl)propan-2-yl)-5-(3-ethoxy-5-fluoro-4-methoxyphenyl)pyridine

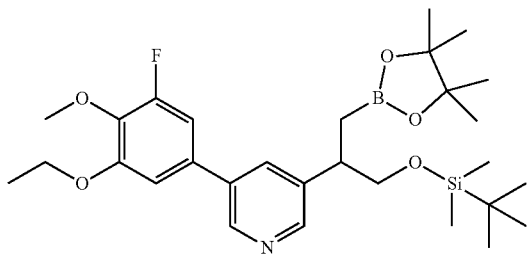 [SMILES: CCOc1cc(-c2cncc(C(CO[Si](C)(C)C(C)(C)C)CB3OC(C)(C)C(C)(C)O3)c2)cc(F)c1OC]

3-(1-((tert-butyldimethylsilyl)oxy)-3-(4,4,5,5-tetramethyl-1,3,2-dioxaborolan-2-yl)propan-2-yl)-5-(3-ethoxy-5-fluoro-4-methoxyphenyl)pyridine (650 mg, 75%) was prepared in an analogous manner to Preparation 9 using 3-(3-((tert-butyldimethylsilyl)oxy)prop-1-en-2-yl)-5-(3-ethoxy-5-fluoro-4-methoxyphenyl)pyridine (Preparation 58, 660 mg, 1.58 mmol). LCMS m/z=546 [MH]$^+$.

Preparation 17: 3-(1-((tert-butyldimethylsilyl)oxy)-3-(4,4,5,5-tetramethyl-1,3,2-dioxaborolan-2-yl)propan-2-yl)-5-(3-chloro-5-ethoxy-4-methoxyphenyl)pyridine

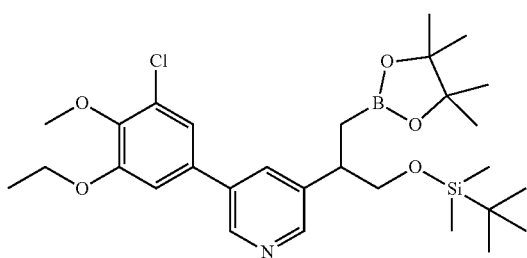 [SMILES: CCOc1cc(-c2cncc(C(CO[Si](C)(C)C(C)(C)C)CB3OC(C)(C)C(C)(C)O3)c2)cc(Cl)c1OC]

3-(1-((tert-butyldimethylsilyl)oxy)-3-(4,4,5,5-tetramethyl-1,3,2-dioxaborolan-2-yl)propan-2-yl)-5-(3-chloro-5-ethoxy-4-methoxyphenyl)pyridine (800 mg, 77%) was prepared in an analogous manner to Preparation 9 using 3-(3-((tert-butyldimethylsilyl)oxy)prop-1-en-2-yl)-5-(3-chloro-5-ethoxy-4-methoxyphenyl)pyridine (Preparation 59, 800 mg, 1.8 mmol). LCMS m/z=562 [MH]$^+$.

Preparation 18: 3-(1-((tert-butyldimethylsilyl)oxy)-3-(4,4,5,5-tetramethyl-1,3,2-dioxaborolan-2-yl)propan-2-yl)-5-(5-ethoxy-2-fluoro-4-methoxyphenyl)pyridine

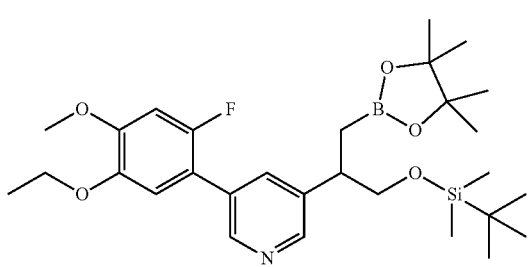 [SMILES: CCOc1cc(-c2cncc(C(CO[Si](C)(C)C(C)(C)C)CB3OC(C)(C)C(C)(C)O3)c2)c(F)cc1OC]

3-(1-((tert-butyldimethylsilyl)oxy)-3-(4,4,5,5-tetramethyl-1,3,2-dioxaborolan-2-yl)propan-2-yl)-5-(5-ethoxy-2-fluoro-4-methoxyphenyl)pyridine (2.0 g, 85%) was prepared in an analogous manner to Preparation 9 using 3-(3-((tert-butyldimethylsilyl)oxy)prop-1-en-2-yl)-5-(5-ethoxy-2-fluoro-4-methoxyphenyl)pyridine (Preparation 60, 1.80 g, 4.31 mmol). $^1$H NMR (CDCl$_3$, 400 MHz): δ 8.56 (t, J=1.7 Hz, 1H), 8.44 (d, J=2.0 Hz, 1H), 7.71 (m, 1H), 6.88 (d, J=7.5 Hz, 1H), 6.73 (d, J=11.5 Hz, 1H), 4.10 (q, J=7.0 Hz, 2H), 3.90 (s, 3H), 3.68-3.75 (m, 2H), 3.07-3.14 (m, 1H), 1.47 (t, J=7.0 Hz, 3H), 1.22-1.29 (m, 2H), 1.09 (d, J=13.1 Hz, 12H), 0.81 (s, 9H), −0.06 (d, J=6.5 Hz, 6H). LCMS m/z=546 [MH]$^+$.

Preparation 19: 3-(1-((tert-butyldimethylsilyl)oxy)-3-(4,4,5,5-tetramethyl-1,3,2-dioxaborolan-2-yl)propan-2-yl)-5-(2-chloro-5-ethoxy-4-methoxyphenyl)pyridine

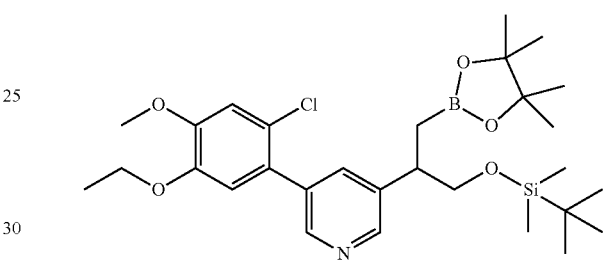

3-(1-((tert-butyldimethylsilyl)oxy)-3-(4,4,5,5-tetramethyl-1,3,2-dioxaborolan-2-yl)propan-2-yl)-5-(2-chloro-5-ethoxy-4-methoxyphenyl)pyridine (2.05 g, 73%) was prepared in an analogous manner to Preparation 9 using 3-(3-((tert-butyldimethylsilyl)oxy)prop-1-en-2-yl)-5-(2-chloro-5-ethoxy-4-methoxyphenyl)pyridine (Preparation 61, 2.17 g, 5.0 mmol). $^1$H NMR (CDCl$_3$, 400 MHz): δ 8.44 (m, 2H), 7.63 (t, J=2.0 Hz, 1H), 6.95 (s, 1H), 6.77 (s, 1H), 4.06 (q, J=7.0 Hz, 2H), 3.89 (s, 3H), 3.64-3.74 (m, 2H), 3.06-3.13 (m, 1H), 1.45 (t, J=7.0 Hz, 3H), 1.23-1.29 (m, 2H), 1.08 (d, J=13.6 Hz, 12H), 0.79 (s, 9H), −0.08 (d, J=6.8 Hz, 6H).

Preparation 20: 3-(1-((tert-butyldimethylsilyl)oxy)-3-(4,4,5,5-tetramethyl-1,3,2-dioxaborolan-2-yl)propan-2-yl)-5-(2-fluoro-4-methoxy-5-propoxyphenyl)pyridine

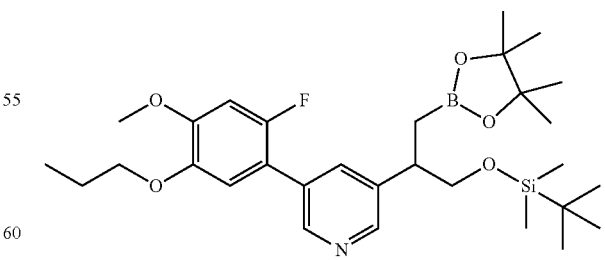

3-(1-((tert-butyldimethylsilyl)oxy)-3-(4,4,5,5-tetramethyl-1,3,2-dioxaborolan-2-yl)propan-2-yl)-5-(2-fluoro-4-methoxy-5-propoxyphenyl)pyridine (4.0 g, 86%) was prepared in an analogous manner to Preparation 9 using 3-(3-((tert-butyldimethylsilyl)oxy)prop-1-en-2-yl)-5-(2-fluoro-4-

Preparation 21: 3-(1-(((tert-butyldimethylsilyl)oxy)-3-(4,4,5,5-tetramethyl-1,3,2-dioxaborolan-2-yl)propan-2-yl)-5-(4-(difluoromethoxy)-3-propoxyphenyl)pyridine

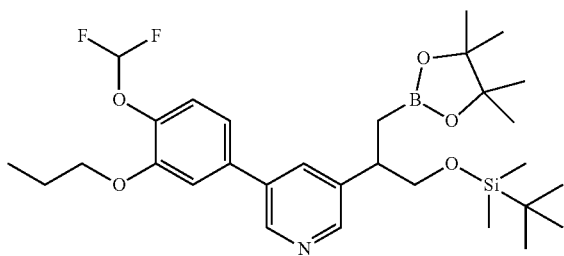 [SMILES: CCCOc1cc(-c2cncc(C(CO[Si](C)(C)C(C)(C)C)CB3OC(C)(C)C(C)(C)O3)c2)ccc1OC(F)F]

3-(1-((tert-butyldimethylsilyl)oxy)-3-(4,4,5,5-tetramethyl-1,3,2-dioxaborolan-2-yl)propan-2-yl)-5-(4-(difluoromethoxy)-3-propoxyphenyl)pyridine (2.25 g, 88%) was prepared in an analogous manner to Preparation 9 using 3-(3-((tert-butyldimethylsilyl)oxy)prop-1-en-2-yl)-5-(4-(difluoromethoxy)-3-propoxyphenyl)pyridine (Preparation 63, 2.0 g, 4.5 mmol). $^1$H NMR (CDCl$_3$, 400 MHz): δ 8.61 (d, J=2.2 Hz, 1H), 8.57 (d, J=2.1 Hz, 1H), 7.73 (t, J=2.1 Hz, 1H), 7.24 (d, J=8.0 Hz, 1H), 7.09-7.12 (m, 2H), 6.61 (t, J=75.3 Hz, 1H), 4.05 (t, J=6.5 Hz, 2H), 3.67-3.77 (m, 2H), 3.09-3.16 (m, 1H), 2.16 (s, 2H), 1.84-1.93 (2H), 1.06-1.11 (m, 15H), 0.81 (s, 9H), −0.07-−0.05 (d, J=5.8 Hz, 6H). LCMS m/z=578 [MH]$^+$.

Preparation 22: 5'-(1-(((tert-butyldimethylsilyl)oxy)-3-(4,4,5,5-tetramethyl-1,3,2-dioxaborolan-2-yl)propan-2-yl)-3-fluoro-5-methoxy-6-propoxy-2,3'-bipyridine

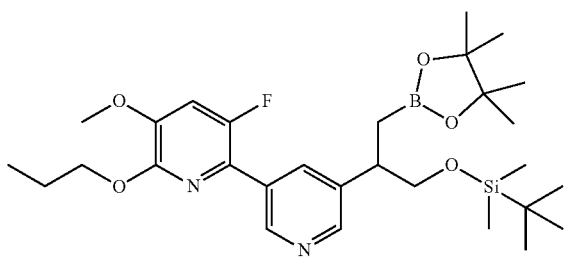 [SMILES: CCCOc1nc(-c2cncc(C(CO[Si](C)(C)C(C)(C)C)CB3OC(C)(C)C(C)(C)O3)c2)c(F)cc1OC]

5'-(1-(((tert-butyldimethylsilyl)oxy)-3-(4,4,5,5-tetramethyl-1,3,2-dioxaborolan-2-yl)propan-2-yl)-3-fluoro-5-methoxy-6-propoxy-2,3'-bipyridine (4.02 g, quant.) was prepared in an analogous manner to Preparation 9 using 5'-(3-((tert-butyldimethylsilyl)oxy)prop-1-en-2-yl)-3-fluoro-5-methoxy-6-propoxy-2,3'-bipyridine (Preparation 64, 3.1 g, 7.17 mmol). $^1$H NMR (CDCl$_3$, 400 MHz): δ 9.03 (s, 1H), 8.45 (d, J=2.3 Hz, 1H), 8.13-8.15 (m, 1H), 6.95 (d, J=11.3 Hz, 1H), 4.12 (t, J=7.0 Hz, 2H), 3.92 (s, 3H), 3.68-3.76 (m, 2H), 3.09-3.16 (m, 1H), 1.85-1.94 (m, 2H), 1.22-1.29 (m, 2H), 1.10 (d, J=11.5 Hz, 12H), 1.05 (t, J=7.5 Hz, 3H), 0.81 (s, 9H), −0.07-−0.06 (d, J=7.5 Hz, 6H). LCMS m/z=561 [MH]$^+$

Preparation 23: 5'-(1-(((tert-butyldimethylsilyl)oxy)-3-(4,4,5,5-tetramethyl-1,3,2-dioxaborolan-2-yl)propan-2-yl)-6-methoxy-5-propoxy-3,3'-bipyridine

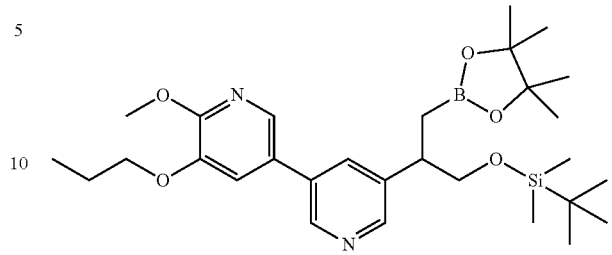

5'-(1-(((tert-butyldimethylsilyl)oxy)-3-(4,4,5,5-tetramethyl-1,3,2-dioxaborolan-2-yl)propan-2-yl)-6-methoxy-5-propoxy-3,3'-bipyridine (2.55 g, 81%) was prepared in an analogous manner to Preparation 9 using 5'-(3-((tert-butyldimethylsilyl)oxy)prop-1-en-2-yl)-6-methoxy-5-propoxy-3,3'-bipyridine (Preparation 65, 2.4 g, 5.8 mmol). LCMS m/z=543 [MH]$^+$.

Preparation 24: 5-(1-(((tert-butyldimethylsilyl)oxy)-3-(4,4,5,5-tetramethyl-1,3,2-dioxaborolan-2-yl)propan-2-yl)-3-(3-ethoxy-4-methoxyphenyl)-2-methylpyridine

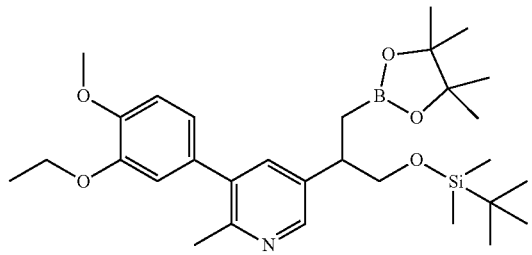 [SMILES: CCOc1cc(-c2cc(C(CO[Si](C)(C)C(C)(C)C)CB3OC(C)(C)C(C)(C)O3)cnc2C)ccc1OC]

5-(1-(((tert-butyldimethylsilyl)oxy)-3-(4,4,5,5-tetramethyl-1,3,2-dioxaborolan-2-yl)propan-2-yl)-3-(3-ethoxy-4-methoxyphenyl)-2-methylpyridine (700 mg, 91%) was prepared in an analogous manner to Preparation 9 using 5-(3-((tert-butyldimethylsilyl)oxy)prop-1-en-2-yl)-3-(3-ethoxy-4-methoxyphenyl)-2-methylpyridine (Preparation 66, 590 mg, 1.43 mmol). LCMS m/z=542 [MH]$^+$.

Preparation 25: 4-(1-(((tert-butyldimethylsilyl)oxy)-3-(4,4,5,5-tetramethyl-1,3,2-dioxaborolan-2-yl)propan-2-yl)-2-(4-methoxy-3-propoxyphenyl)-6-(trifluoromethyl)pyrimidine

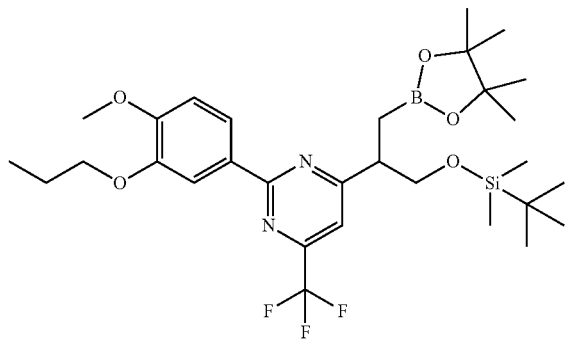 [SMILES: CCCOc1cc(-c2nc(C(CO[Si](C)(C)C(C)(C)C)CB3OC(C)(C)C(C)(C)O3)cc(C(F)(F)F)n2)ccc1OC]

4-(1-(((tert-butyldimethylsilyl)oxy)-3-(4,4,5,5-tetramethyl-1,3,2-dioxaborolan-2-yl)propan-2-yl)-2-(4-methoxy-3-propoxyphenyl)-6-(trifluoromethyl)pyrimidine (0.94 g, 59%) was prepared in an analogous manner to Preparation 9 using 4-(3-((tert-butyldimethylsilyl)oxy)prop-1-en-2-yl)-2-(4-methoxy-3-propoxyphenyl)-6-(trifluoromethyl)pyrimidine (Preparation 67, 1.27 g, 2.63 mmol). $^1$H NMR (CDCl$_3$, 400 MHz): δ 8.17-8.19 (m, 1H), 8.10 (d, J=2.1 Hz, 1H), 7.42 (s, 1H), 6.97 (d, J=8.6 Hz, 1H), 4.12-4.16 (m, 2H), 3.95 (s, 3H), 3.79-3.89 (m, 2H), 3.31-3.37 (m, 1H), 1.90-1.99 (m, 2H), 1.23-1.29 (m, 2H), 1.13 (s, 6H), 1.10 (t, J=7.5 Hz, 3H), 1.05 (s, 6H), 0.80-0.82 (s, 9H), −0.04 (t, J=3.1 Hz, 3H), −0.08 (t, J=3.1 Hz, 3H). LCMS m/z=611 [MH]$^+$.

Preparation 26: 2-(1-((tert-butyldimethylsilyl)oxy)-3-(4,4,5,5-tetramethyl-1,3,2-dioxaborolan-2-yl)propan-2-yl)-6-(3-ethoxy-4-methoxyphenyl)pyrazine

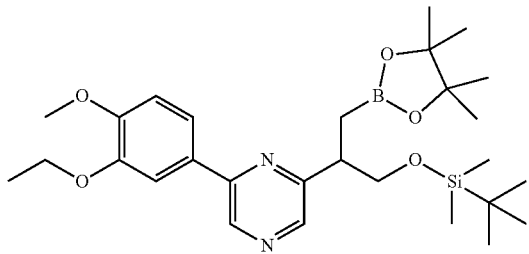 [SMILES: CCOc1cc(-c2cncc(C(CO[Si](C)(C)C(C)(C)C)CB3OC(C)(C)C(C)(C)O3)n2)ccc1OC]

2-(1-((tert-butyldimethylsilyl)oxy)-3-(4,4,5,5-tetramethyl-1,3,2-dioxaborolan-2-yl)propan-2-yl)-6-(3-ethoxy-4-methoxyphenyl)pyrazine (720 mg, 43%) was prepared in an analogous manner to Preparation 9 using 2-(3-((tert-butyldimethylsilyl)oxy)prop-1-en-2-yl)-6-(3-ethoxy-4-methoxyphenyl)pyrazine (Preparation 68, 1.26 g, 3.1 mmol). LCMS m/z=529 [MH]$^+$.

Preparation 27: 2-(6-(1-borono-3-((tert-butyldimethylsilyl)oxy)propan-2-yl)-2-(4-methoxy-3-propoxyphenyl)pyrimidin-4-yl)acetic acid

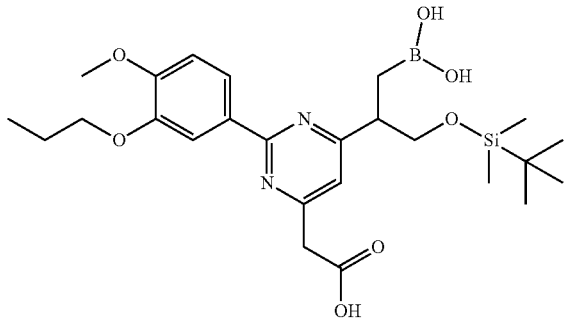 [SMILES: CCCOc1cc(-c2nc(CC(=O)O)cc(C(CO[Si](C)(C)C(C)(C)C)CB(O)O)n2)ccc1OC]

Ethyl 2-(6-(1-((tert-butyldimethylsilyl)oxy)-3-(4,4,5,5-tetramethyl-1,3,2-dioxaborolan-2-yl)propan-2-yl)-2-(4-methoxy-3-propoxyphenyl)pyrimidin-4-yl)acetate (Preparation 28, 758 mg, 1.21 mmol) was dissolved in MeCN (10 mL) and water (10 mL). To the solution was added LiOH—H$_2$O (101 mg, 2.41 mmol) in portions. The mixture was stirred at about 25° C. for about 1 h. The mixture was concentrated. The reaction mixture was used directly in the next step without further purification. LCMS m/z=519 [MH]$^+$.

Preparation 28: ethyl 2-(6-(1-((tert-butyldimethylsilyl)oxy)-3-(4,4,5,5-tetramethyl-1,3,2-dioxaborolan-2-yl)propan-2-yl)-2-(4-methoxy-3-propoxyphenyl)pyrimidin-4-yl)acetate

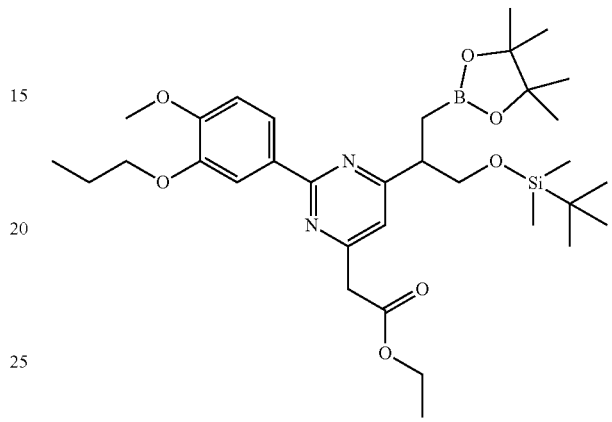

Ethyl 2-(6-(1-((tert-butyldimethylsilyl)oxy)-3-(4,4,5,5-tetramethyl-1,3,2-dioxaborolan-2-yl)propan-2-yl)-2-(4-methoxy-3-propoxyphenyl)pyrimidin-4-yl)acetate (437 mg, 70%) was prepared in an analogous manner to Preparation 9 using ethyl 2-(6-(3-((tert-butyldimethylsilyl)oxy)prop-1-en-2-yl)-2-(4-methoxy-3-propoxyphenyl)pyrimidin-4-yl)acetate (Preparation 69, 500 mg, 0.99 mmol). LCMS m/z=629 [MH]$^+$.

Preparation 29: 4-(1-((tert-butyldimethylsilyl)oxy)-3-(4,4,5,5-tetramethyl-1,3,2-dioxaborolan-2-yl)propan-2-yl)-6-(((tert-butyldimethylsilyl)oxy)methyl)-2-(4-methoxy-3-propoxyphenyl)pyrimidine

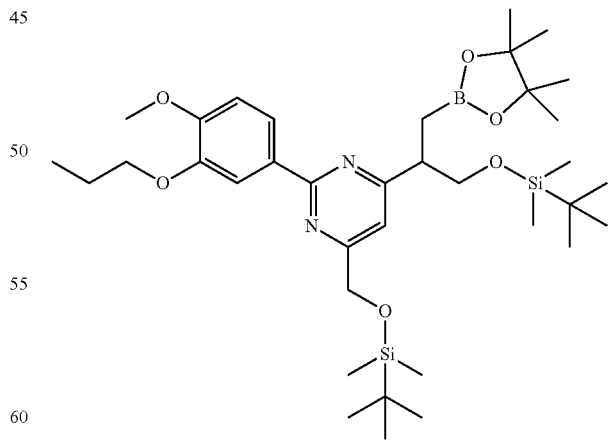

4-(1-((tert-butyldimethylsilyl)oxy)-3-(4,4,5,5-tetramethyl-1,3,2-dioxaborolan-2-yl)propan-2-yl)-6-(((tert-butyldimethylsilyl)oxy)methyl)-2-(4-methoxy-3-propoxyphenyl)pyrimidine (1.0 g, 58%) was prepared in an analogous manner to Preparation 9 using 4-(((tert-butyldimethylsilyl)oxy)methyl)-6-(3-((tert-butyldimethylsilyl)oxy)prop-1-en-2-yl)-2-(4-methoxy-3-propoxyphenyl)pyrimidine (Preparation 70, 1.4 g, 2.5 mmol). LCMS m/z=687 [MH]⁺.

Preparation 30: methyl (Z)-2-(2'-cyano-4'-methoxy-3'-propoxy-[1,1'-biphenyl]-3-yl)-3-(4,4,5,5-tetramethyl-1,3,2-dioxaborolan-2-yl)acrylate

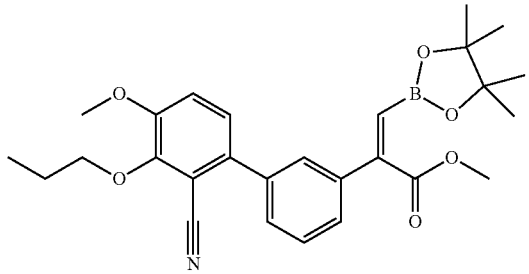 [SMILES: CCCOc1c(OC)ccc(-c2cccc(/C(=C/B3OC(C)(C)C(C)(C)O3)C(=O)OC)c2)c1C#N]

A mixture of methyl (Z)-2-(2'-cyano-4'-methoxy-3'-propoxy-[1,1'-biphenyl]-3-yl)-3-(((trifluoromethyl)sulfonyl)oxy)acrylate (Preparation 40, 15.00 g, 30.03 mmol), Pd(dppf)Cl₂ (1.10 g, 1.50 mmol), Pin₂B₂ (11.44 g, 45.05 mmol) and KOAc (4.42 g, 45.05 mmol) in 1,4-dioxane (200 mL) was stirred at about 80° C. for about 2 h under N₂. The mixture was filtered and concentrated. The residue was purified by column chromatography (silica) and eluted with pet. ether/EtOAc (5:1) to afford methyl (Z)-2-(2'-cyano-4'-methoxy-3'-propoxy-[1,1'-biphenyl]-3-yl)-3-(4,4,5,5-tetramethyl-1,3,2-dioxaborolan-2-yl)acrylate (13.6 g, 94%). ¹H NMR (CDCl₃, 400 MHz): δ 7.52 (s, 1H), 7.49-7.47 (m, 1H), 7.42-7.40 (m, 2H), 7.14-7.11 (m, 2H), 6.30 (s, 1H), 4.18-4.14 (m, 2H), 3.89 (s, 3H), 3.83 (s, 3H), 1.90-1.81 (m, 2H), 1.25 (s, 12H), 1.06 (t, J=3.6 Hz, 3H).

Preparation 31: 2-(4-((tert-butyldimethylsilyl)oxy)-1-(4,4,5,5-tetramethyl-1,3,2-dioxaborolan-2-yl)butan-2-yl)-6-(4-methoxy-3-propoxyphenyl)pyridine

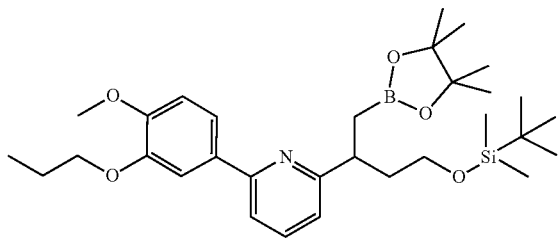 [SMILES: CCCOc1cc(-c2cccc(C(CCO[Si](C)(C)C(C)(C)C)CB3OC(C)(C)C(C)(C)O3)n2)ccc1OC]

2-(4-((tert-butyldimethylsilyl)oxy)-1-(4,4,5,5-tetramethyl-1,3,2-dioxaborolan-2-yl)butan-2-yl)-6-(4-methoxy-3-propoxyphenyl)pyridine (140 mg, 12%) was prepared in an analogous manner to Preparation 9 using 2-(4-((tert-butyldimethylsilyl)oxy)but-1-en-2-yl)-6-(4-methoxy-3-propoxyphenyl)pyridine (Preparation 71, 900 mg, 2.10 mmol). LCMS m/z=556 [MH]⁺.

Preparation 32: (E)-3-(1-((tert-butyldimethylsilyl)oxy)-3-(4,4,5,5-tetramethyl-1,3,2-dioxaborolan-2-yl)but-2-en-2-yl)-5-(4-methoxy-3-propoxyphenyl)pyridine

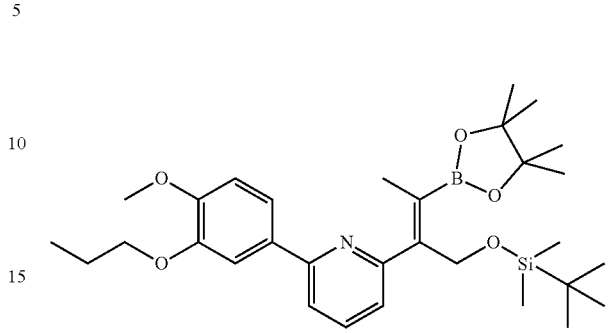

A solution of 2,2,6,6-tetramethylpiperidine (CAS 768-66-1, 1.08 mL, 6.41 mmol) in THF (2.5 mL) was cooled to about 0° C. (ice bath) under N₂. N-BuLi (2.56 mL, 6.41 mmol, 2.5 M in hexanes) was added dropwise to the solution and stirred for about 30 min at about 0° C. A solution of 2,2'-(ethane-1,1-diyl)bis(4,4,5,5-tetramethyl-1,3,2-dioxaborolane) (Preparation 149, 1810 mg, 6.41 mmol) in THF (2 mL) was added dropwise, which was stirred for about 5 min before cooling to about −78° C. A solution of 2-((tert-butyldimethylsilyl)oxy)-1-(5-(4-methoxy-3-propoxyphenyl)pyridin-3-yl)ethan-1-one (Preparation 75, 666 mg, 1.60 mmol) in THF (3.0 mL) added dropwise and stirred under N₂ at about −78° C. for about 1 h. The reaction was placed in an ice bath and stirred for an additional hour. The reaction was quenched with water and diluted with EtOAc. The EtOAc was separated, washed with brine and dried over MgSO₄. The solution was filtered and concentrated. The residue was purified by column chromatography (silica) and eluted with heptane/EtOAc (9:1) to afford (E)-3-(1-((tert-butyldimethylsilyl)oxy)-3-(4,4,5,5-tetramethyl-1,3,2-dioxaborolan-2-yl)but-2-en-2-yl)-5-(4-methoxy-3-propoxyphenyl)pyridine (400 mg, 45%). LCMS m/z=554 [MH]⁺.

Preparation 33: ethyl 2-(5-(4-methoxy-3-propoxyphenyl)pyridin-3-yl)-2-methyl-3-(4,4,5,5-tetramethyl-1,3,2-dioxaborolan-2-yl)propanoate

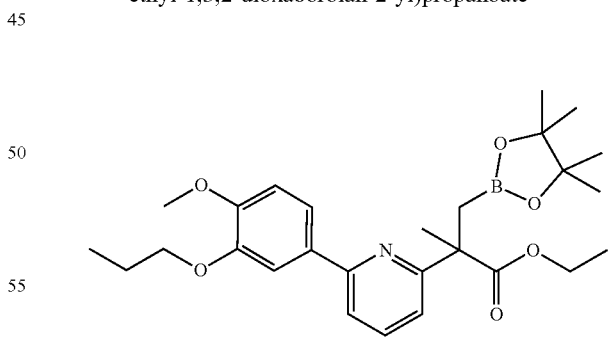

To a mixture of ethyl 2-(6-bromopyridin-2-yl)-2-methyl-3-(4,4,5,5-tetramethyl-1,3,2-dioxaborolan-2-yl)propanoate (Preparation 110, 249 mg, 0.625 mmol) and 2-(4-methoxy-3-propoxyphenyl)-4,4,5,5-tetramethyl-1,3,2-dioxaborolane (Preparation 114, 357 mg, 1.22 mmol) in 1,4-dioxane (8.5 mL) was added a solution of K₃PO₄ in water (2.0 M, 0.625 mL, 1.25 mmol). The mixture was degassed using N₂ at about 20° C. for about 10 min. Bis(tri-t-butylphosphine)palladium(0) (CAS 53199-31-8, 16.0 mg, 0.03 mmol) was added and the mixture was allowed to stir at about 20° C. for 2 h. The mixture was diluted with EtOAc, dried over Na$_2$SO$_4$, filtered, and concentrated. The residue was purified by column chromatography (silica) and eluted with heptane/EtOAc (100:0 to 0:100) to afford ethyl 2-(5-(4-methoxy-3-propoxyphenyl)pyridin-3-yl)-2-methyl-3-(4,4,5,5-tetramethyl-1,3,2-dioxaborolan-2-yl)propanoate (134 mg, 44%). $^1$H NMR (CDCl$_3$, 400 MHz): δ 7.40-7.56 (m, 1H), 7.23-7.38 (m, 4H), 7.07-7.13 (m, 4H), 6.96 (d, J=8.6 Hz, 2H), 5.33 (s, 1H), 4.02-4.22 (m, 7H), 3.93 (s, 6H), 1.83-2.08 (m, 4H), 1.71 (s, 4H), 1.49-1.67 (m, 9H), 1.37 (s, 1H), 1.17-1.29 (m, 19H), 1.09 (t, J=7.4 Hz, 7H). LCMS m/z=399 [MH]$^+$.

Preparation 34: 5-(3-((tert-butyldimethylsilyl)oxy)-1-(4,4,5,5-tetramethyl-1,3,2-dioxaborolan-2-yl)butan-2-yl)-3-(4-methoxy-3-propoxyphenyl)pyridazine

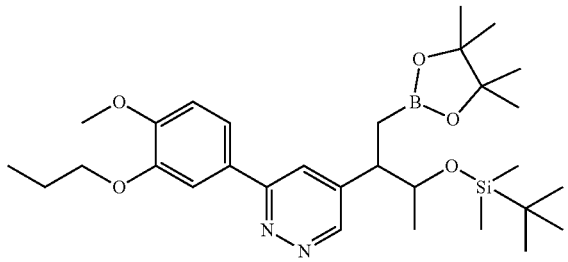 [SMILES: CCCOc1cc(-c2cc(C(CB3OC(C)(C)C(C)(C)O3)C(C)O[Si](C)(C)C(C)(C)C)cnn2)ccc1OC]

5-(3-((tert-butyldimethylsilyl)oxy)-1-(4,4,5,5-tetramethyl-1,3,2-dioxaborolan-2-yl)butan-2-yl)-3-(4-methoxy-3-propoxyphenyl)pyridazine (160 mg, 41%) was prepared in an analogous manner to Preparation 9 using 5-(3-((tert-butyldimethylsilyl)oxy)but-1-en-2-yl)-3-(4-methoxy-3-propoxyphenyl)pyridazine (Preparation 72, 300 mg, 0.7 mmol). LCMS m/z=557 [MH]$^+$.

Preparation 35: 3-(1-((tert-butyldimethylsilyl)oxy)-3-(4,4,5,5-tetramethyl-1,3,2-dioxaborolan-2-yl)propan-2-yl)-5-(3-ethoxy-4-methoxyphenyl)-4-methylpyridine

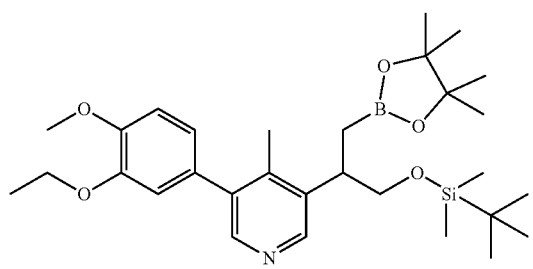 [SMILES: CCOc1cc(-c2cncc(C(CO[Si](C)(C)C(C)(C)C)CB3OC(C)(C)C(C)(C)O3)c2C)ccc1OC]

3-(1-((tert-butyldimethylsilyl)oxy)-3-(4,4,5,5-tetramethyl-1,3,2-dioxaborolan-2-yl)propan-2-yl)-5-(3-ethoxy-4-methoxyphenyl)-4-methylpyridine (0.28 g, 26%) was prepared in an analogous manner to Preparation 9 using 3-(3-((tert-butyldimethylsilyl)oxy)prop-1-en-2-yl)-5-(3-ethoxy-4-methoxyphenyl)-4-methylpyridine (Preparation 73, 0.8 g, 1.93 mmol). $^1$H NMR (CDCl$_3$, 400 MHz): δ 8.36 (s, 1H), 8.22 (s, 1H), 6.92 (d, J=8.3 Hz, 1H), 6.75-6.78 (m, 1H), 6.73 (d, J=2.0 Hz, 1H), 4.08 (q, J=7.0 Hz, 2H), 3.91 (s, 3H), 3.74-3.78 (m, 1H), 3.64-3.68 (m, 1H), 3.38-3.46 (m, 1H), 2.29 (s, 3H), 1.45 (t, J=7.0 Hz, 3H), 1.22-1.29 (m, 2H), 1.03-1.08 (m, 12H), 0.79 (s, 9H), −0.11-−0.08 (m, 6H). LCMS m/z=542 [MH]$^+$ Preparation 36: 4-(1-((tert-butyldimethylsilyl)oxy)-3-(4,4,5,5-tetramethyl-1,3,2-dioxaborolan-2-yl)propan-2-yl)-2-(3-ethoxy-4-methoxyphenyl)thiazole

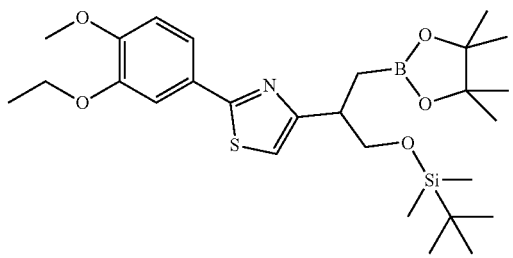 [SMILES: CCOc1cc(-c2nc(C(CO[Si](C)(C)C(C)(C)C)CB3OC(C)(C)C(C)(C)O3)cs2)ccc1OC]

4-(1-((tert-butyldimethylsilyl)oxy)-3-(4,4,5,5-tetramethyl-1,3,2-dioxaborolan-2-yl)propan-2-yl)-2-(3-ethoxy-4-methoxyphenyl)thiazole (0.41 g, 39%) was prepared in an analogous manner to Preparation 9 using 4-(3-((tert-butyldimethylsilyl)oxy)prop-1-en-2-yl)-2-(3-ethoxy-4-methoxyphenyl)thiazole (Preparation 74, 0.8 g, 1.97 mmol). $^1$H NMR (CDCl$_3$, 400 MHz): δ 7.53 (d, J=2.0 Hz, 1H), 7.46 (dd, J=2.0, 8.5 Hz, 1H), 6.91 (s, 1H), 6.89 (d, J=8.3 Hz, 1H), 4.20 (q, J=7.0 Hz, 2H), 3.88-3.92 (s, 4H), 3.77-3.81 (m, 1H), 3.27-3.34 (m, 1H), 1.51 (t, J=7.0 Hz, 3H), 1.27-1.30 (m, 2H), 1.15 (d, J=13.6, 12H), 0.85 (s, 9H), −0.03 (s, 6H). LCMS m/z=534 [MH]$^+$.

Preparation 37: 3-(1-bromo-3-((tert-butyldimethylsilyl)oxy)prop-1-en-2-yl)-5-(3,4-dimethoxyphenyl)pyridine

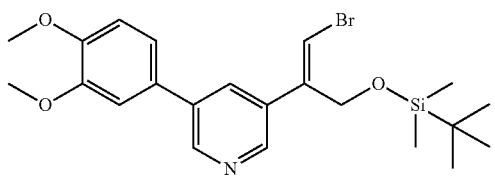 [SMILES: COc1ccc(-c2cncc(/C(=C/Br)CO[Si](C)(C)C(C)(C)C)c2)cc1OC]

To a solution of 3-(3-((tert-butyldimethylsilyl)oxy)prop-i-en-2-yl)-5-(3,4-dimethoxyphenyl)pyridine (Preparation 48, 30.00 g, 77.81 mmol) in DCM (500 mL) was added pyridinium tribromide (CAS 39416-48-3, 24.9 g, 77.8 mmol) in portions at about 0° C. The mixture was stirred at about 20° C. for about 1 h and poured into cold aqueous Na$_2$SO$_3$ (100 mL). The mixture was extracted with DCM (3×50 mL). The combined DCM extracts were washed with brine (50 mL), dried over Na$_2$SO$_4$ and concentrated. DBU (CAS 6674-22-2, 58.64 mL, 389.1 mmol) was added to the above mixture in DCM (500 mL) at about 20° C. The mixture was stirred at about 20° C. for about 16 h and poured into aqueous NH$_4$Cl (500 mL). The mixture was extracted with DCM (3×200 mL). The combined DCM extracts were washed with brine (200 mL), dried over Na$_2$SO$_4$ and concentrated. The residue was purified by column chromatography (silica) and eluted with pet. ether/EtOAc (15:1) to afford 3-(1-bromo-3-((tert-butyldimethylsilyl)oxy)prop-1-en-2-yl)-5-(3,4-dimethoxyphenyl)pyridine (27.0 g, 75%).

¹H NMR (CDCl₃, 400 MHz): δ 8.74 (d, J=2.4 Hz, 1H), 8.55 (d, J=3.0 Hz, 1H), 7.88 (t, J=2.0 Hz, 1H), 7.13-7.15 (m, 1H), 7.08 (d, J=3.0 Hz, 1H), 6.97 (d, J=7.2 Hz, 1H), 6.57 (s, 1H), 4.76 (s, 2H), 3.96 (s, 3H), 3.94 (s, 3H), 0.82 (s, 9H), 0.07 (s, 6H).

Preparation 38: 3-(1-bromo-3-((tert-butyldimethylsilyl)oxy)prop-1-en-2-yl)-5-(3-ethoxy-4-methoxyphenyl)pyridine

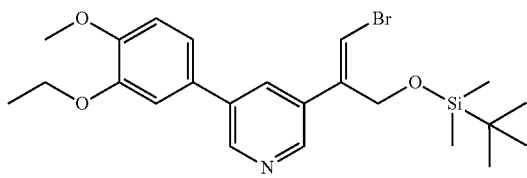 [SMILES: CCOc1cc(-c2cncc(/C(=C/Br)CO[Si](C)(C)C(C)(C)C)c2)ccc1OC]

A mixture of 3-(1,2-dibromo-3-((tert-butyldimethylsilyl)oxy)propan-2-yl)-5-(3-ethoxy-4-methoxyphenyl)pyridine (Preparation 47a, 11.0 g, 19.66 mmol) and DBU (CAS 6674-22-2, 5.99 g, 39.33 mmol, 5.93 mL) in DCM (150 mL) was stirred at about 25° C. for about 16 h. The mixture was washed with 1N HCl (300 mL), brine (300 mL), dried over Na₂SO₄, filtered and concentrated. The residue was purified by column chromatography (silica) and eluted with pet. ether/EtOAc (10:1) to afford 3-(1-bromo-3-((tert-butyldimethylsilyl)oxy)prop-1-en-2-yl)-5-(3-ethoxy-4-methoxyphenyl)pyridine (7.0 g, 74%). ¹H NMR (CDCl₃, 400 MHz): δ 8.74 (d, J=1.6 Hz, 1H), 8.55 (d, J=1.6 Hz, 1H), 7.87 (s, 1H), 7.14 (dd, J=1.6, 8.0 Hz, 1H), 7.09 (s, 1H), 6.98 (d, J=8.0 Hz, 1H), 6.57 (s, 1H), 4.77 (s, 2H), 4.18 (q, J=6.8 Hz, 2H), 3.94 (s, 3H), 1.51 (t, J=6.8 Hz, 3H), 0.82 (s, 9H), 0.08 (s, 6H).

Preparation 39: 3-(1-bromo-3-((tert-butyldimethylsilyl)oxy)prop-1-en-2-yl)-5-(4-methoxy-3-propoxyphenyl)pyridine

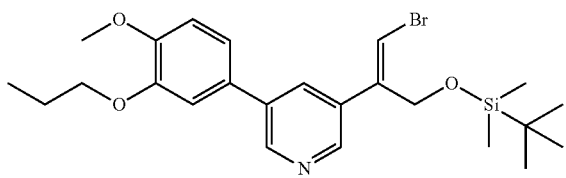 [SMILES: CCCOc1cc(-c2cncc(/C(=C/Br)CO[Si](C)(C)C(C)(C)C)c2)ccc1OC]

To a mixture of 3-(1,2-ibromo-3-((tert-butyldimethylsilyl)oxy)propan-2-yl)-5-(4-methoxy-3-propoxyphenyl)pyridine (Preparation 47b, 10.0 g, 17.44 mmol) in DCM (150 mL) was added DBU (CAS 6674-22-2, 5.26 mL, 34.88 mmol), which was stirred at about 25° C. for about 16 h under N₂. The mixture was washed with 1N HCl (400 mL), brine (400 mL), dried over Na₂SO₄ and concentrated. The residue was purified by column chromatography (silica) and eluted with pet. ether/EtOAc (10:1) to afford 3-(1-bromo-3-((tert-butyldimethylsilyl)oxy)prop-1-en-2-yl)-5-(4-methoxy-3-propoxyphenyl)pyridine (5.60 g, 65%). ¹H NMR (CDCl₃, 400 MHz): δ 8.74 (d, J=2.0 Hz, 1H), 8.55 (d, J=1.6 Hz, 1H), 7.87 (s, 1H), 7.13 (dd, J=1.6, 8.4 Hz, 1H), 7.09 (s, 1H), 6.98 (d, J=8.0 Hz, 1H), 6.57 (s, 1H), 4.77 (s, 2H), 4.06 (t, J=6.8 Hz, 2H), 3.93 (s, 3H), 1.87-1.96 (m, 2H), 1.08 (t, J=7.6 Hz, 3H), 0.82 (s, 9H), 0.08 (s, 6H).

Preparation 40: methyl 2-(2'-cyano-4'-methoxy-3'-propoxy-[1,1'-biphenyl]-3-yl)-3-(((trifluoromethyl)sulfonyl)oxy)acrylate

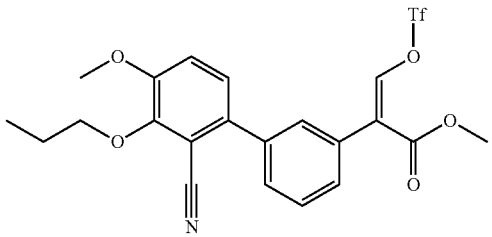

To a solution of methyl 2-(2'-cyano-4'-methoxy-3'-propoxy-[1,1'-biphenyl]-3-yl)-3-hydroxyacrylate (Preparation 41, 14.5 g, 39.47 mmol) in toluene (500 mL) was added LiOH (11.59 g, 276.27 mmol) in water (30 mL). To the mixture was added Tf₂O (CAS 358-23-8, 15.63 mL, 94.72 mmol) dropwise at about 0° C. The mixture was stirred at about 0° C. for about 1 h. The reaction was quenched with water (500 mL) and extracted with EtOAc (2×500 mL). The combined EtOAc extracts were washed with brine (2×300 mL), dried over anhydrous Na₂SO₄, filtered and concentrated. The residue was purified by column chromatography (silica) and eluted with pet. ether/EtOAc (15:1) to afford methyl 2-(2'-cyano-4'-methoxy-3'-propoxy-[1,1'-biphenyl]-3-yl)-3-(((trifluoromethyl)sulfonyl)oxy)acrylate (15.00 g, 74%). ¹H NMR (CDCl₃, 400 MHz): δ 7.56-7.59 (m, 1H), 7.48-7.52 (m, 2H), 7.39-7.41 (m, 1H), 7.13-7.18 (m, 3H), 4.19 (t, J=6.8 Hz, 2H), 3.93 (s, 3H), 3.91 (s, 3H), 1.83-1.92 (m, 2H), 1.09 (t, J=7.6 Hz, 3H).

Preparation 41: methyl 2-(2'-cyano-4'-methoxy-3'-propoxy-[1,1'-biphenyl]-3-yl)-3-hydroxyacrylate

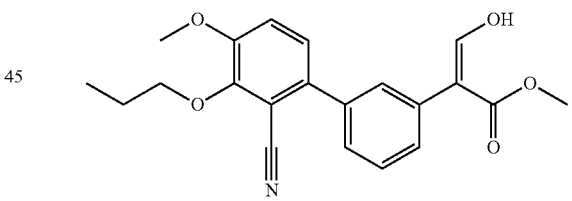

To a mixture of methyl 2-(2'-cyano-4'-methoxy-3'-propoxy-[1,1'-biphenyl]-3-yl)acetate (Preparation 85, 12.0 g, 35.36 mmol) and ethyl formate (11.39 mL, 141.43 mmol) in DCM (150 mL) was added TiCl₄ (13.41 g, 70.72 mmol, 7.62 mL) and Et₃N (8.59 g, 84.86 mmol, 11.76 mL) slowly at about 0° C. The mixture was stirred at about 20° C. for about 1 h. Water (150 mL) was added and the mixture was extracted with DCM (2×150 mL). The combined DCM extracts were washed with brine (150 mL), dried over Na₂SO₄ and concentrated to afford methyl 2-(2'-cyano-4'-methoxy-3'-propoxy-[1,1'-biphenyl]-3-yl)-3-hydroxyacrylate (14.50 g), which was used directly without further purification. ¹H NMR (CDCl₃, 400 MHz): δ 12.09 (d, J=12.4 Hz, 1H), 7.43-7.44 (m, 3H), 7.38-7.41 (m, 1H), 7.29-7.34 (m, 1H), 7.15 (s, 2H), 4.19 (t, J=6.8 Hz, 2H), 3.92 (s, 3H), 3.85 (s, 3H), 1.84-1.93 (m, 2H), 1.07-1.11 (m, 3H).

Preparation 42: (R)-3-(1-((tert-butyldimethylsilyl)oxy)-3-iodopropan-2-yl)-5-(4-methoxy-3-propoxyphenyl)pyridine

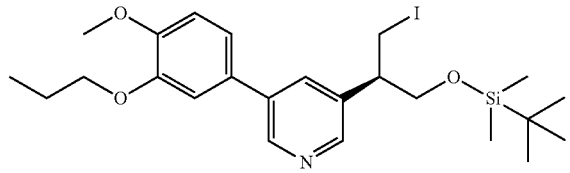 [SMILES: CCCOc1cc(-c2cncc([C@@H](CI)CO[Si](C)(C)C(C)(C)C)c2)ccc1OC]

A mixture of (R)-3-((tert-butyldimethylsilyl)oxy)-2-(5-(4-methoxy-3-propoxyphenyl)pyridin-3-yl)propyl methanesulfonate (Preparation 43, 45.5 g, 89.28 mmol) and lithium iodide (38.2 g, 286 mmol) in acetone (446 mL) was stirred at about 30° C. for 3 days. The reaction was heated to about 50° C. for about 45 min. The mixture was cooled to about 20° C. and concentrated to remove acetone. The residue was diluted with DCM and washed with water (2×100 mL). The DCM extract was dried over MgSO$_4$, filtered and concentrated. The residue was triturated in heptanes/EtOAc (1:1, 100 mL) for about 45 min. The solid material was filtered and purified by column chromatography (silica) and eluted with heptanes/EtOAc (85:15 to 30:70) to afford (R)-3-(1-((tert-butyldimethylsilyl)oxy)-3-iodopropan-2-yl)-5-(4-methoxy-3-propoxyphenyl)pyridine (41.2 g, 85%). 1H NMR (CDCl$_3$, 400 MHz): δ 8.71 (d, J=2.3 Hz, 1H), 8.43 (d, J=2.0 Hz, 1H), 7.71 (t, J=2.0 Hz, 1H), 7.09-7.15 (m, 2H), 6.98 (d, J=8.2 Hz, 1H), 4.06 (t, J=7.0 Hz, 2H), 3.98-4.02 (m, 1H), 3.93 (s, 3H), 3.84-3.88 (m, 1H), 3.68-3.72 (m, 1H), 3.43-3.47 (m, 1H), 3.09-3.15 (m, 1H), 1.87-1.96 (m, 2H), 1.08 (t, J=7.4 Hz, 3H), 0.89 (s, 9H), 0.05 (d, J=7.4 Hz, 6H). LCMS m/z=542 [MH]$^+$.

Preparation 43: (R)-3-((tert-butyldimethylsilyl)oxy)-2-(5-(4-methoxy-3-propoxyphenyl)pyridin-3-yl)propyl methanesulfonate

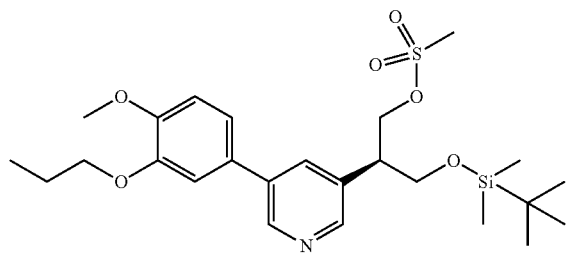 [SMILES: CCCOc1cc(-c2cncc([C@H](CO[Si](C)(C)C(C)(C)C)COS(C)(=O)=O)c2)ccc1OC]

To an ice cold solution of (S)-3-((tert-butyldimethylsilyl)oxy)-2-(5-(4-methoxy-3-propoxyphenyl)pyridin-3-yl)propan-1-ol (Preparation 44, 42.8 g, 99.2 mmol) in DCM (600 mL) was added Et$_3$N (25.1 mL, 178 mmol) and stirred for about 30 min. MsCl (9.98 mL, 129 mmol) was added dropwise and allowed to warm and stir at about 20° C. overnight. The mixture was washed with water, dried over MgSO$_4$, filtered, passed through a silica gel plug and concentrated to afford (R)-3-((tert-butyldimethylsilyl)oxy)-2-(5-(4-methoxy-3-propoxyphenyl)pyridin-3-yl)propyl methanesulfonate (45.5 g), which was used in Preparation 42. LCMS m/z=510 [MH]$^+$.

Preparation 44: (S)-3-((tert-butyldimethylsilyl)oxy)-2-(5-(4-methoxy-3-propoxyphenyl)pyridin-3-yl)propan-1-ol

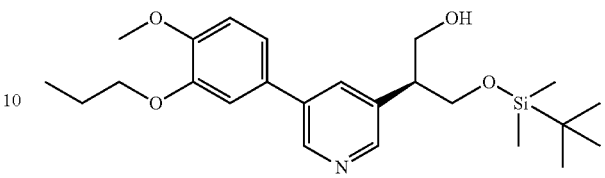

To an ice cold solution of (S)-3-((tert-butyldimethylsilyl)oxy)-2-(5-(4-methoxy-3-propoxyphenyl)pyridin-3-yl)propyl acetate (Preparation 45, 45.7 g, 96.5 mmol) in THF (400 mL) was added aqueous NaOH (154 mL, 1 N). The mixture was allowed to warm and stir at about 20° C. for 2 days. The organic phase was separated and concentrated. The residue was dissolved in DCM (300 mL). The aqueous layer was extracted with DCM. The combined DCM extracts were washed with water, brine, dried over Na$_2$SO$_4$, filtered and concentrated to afford (S)-3-((tert-butyldimethylsilyl)oxy)-2-(5-(4-methoxy-3-propoxyphenyl)pyridin-3-yl)propan-1-ol (42.8 g), which was used in Preparation 43. LCMS m/z=432 [MH]$^+$.

Preparation 45: (S)-3-((tert-butyldimethylsilyl)oxy)-2-(5-(4-methoxy-3-propoxyphenyl)pyridin-3-yl)propyl acetate

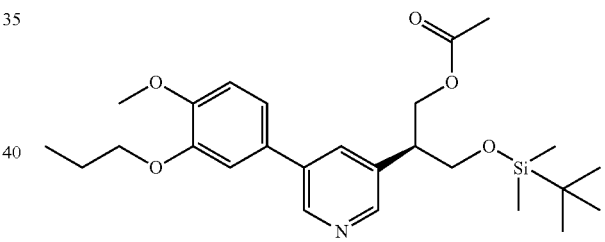

To an ice cold solution of (R)-3-hydroxy-2-(5-(4-methoxy-3-propoxyphenyl)pyridin-3-yl)propyl acetate (Preparation 46, 43.4 g, 121 mmol) in 2-MeTHF (1400 mL) was added DCM (800 mL), imidazole (41.1 g, 604 mmol) and TBS-Cl (91.0 g, 604 mmol). The reaction mixture was warmed to about 20° C. and stirred overnight. The mixture was filtered and the solids washed with EtOAc. The combined filtrates were washed with water, brine, dried over Na$_2$SO$_4$, filtered and concentrated. The residue was purified by column chromatography (silica) and eluted with heptanes/EtOAc (100:0 to 60:40) to afford (S)-3-((tert-butyldimethylsilyl)oxy)-2-(5-(4-methoxy-3-propoxyphenyl)pyridin-3-yl)propyl acetate (48.3 g, 85%). $^1$H NMR (CDCl$_3$, 400 MHz): δ 8.70 (d, J=2.0 Hz, 1H), 8.45 (d, J=2.3 Hz, 1H), 7.74 (t, J=2.3 Hz, 1H), 7.08-7.14 (m, 2H), 6.98 (d, J=8.2 Hz, 1H), 4.40-4.49 (m, 2H), 4.06 (t, J=7.0 Hz, 2H), 3.86-3.95 (m, 5H), 3.17-3.23 (m, 1H), 2.04 (s, 3H), 1.67-1.96 (m, 2H), 1.08 (t, J=7.4 Hz, 3H), 0.87 (s, 9H), 0.01 (d, J=2.3 Hz, 6H). LCMS m/z=474 [MH]$^+$.

Preparation 46: (R)-3-hydroxy-2-(5-(4-methoxy-3-propoxyphenyl)pyridin-3-yl)propyl acetate

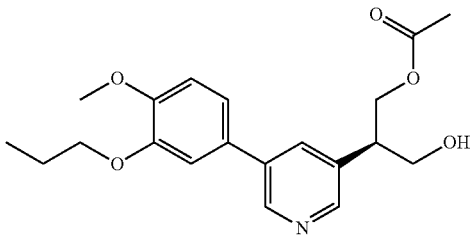 [SMILES: CCCOc1cc(-c2cncc([C@H](CO)COC(C)=O)c2)ccc1OC]

To a mixture of 2-(5-(4-methoxy-3-propoxyphenyl)pyridin-3-yl)propane-1,3-diol (Preparation 82, 38.3 g, 121 mmol) in 2-MeTHF (1088 mL) was added immobilized Rhizomucor miehei lipase (1.53 g, Lipozyme® RM IM, Novozymes A/S, Denmark). The mixture was stirred at about 20° C. for about 5 min. Vinyl acetate (89.0 mL, 965 mmol) was added to the mixture followed by 2-MeTHF (100 mL). The mixture was stirred at about 20° C. for about 39 h. The mixture was filtered and the filter cake was washed with 2-MeTHF (50 mL). The combined filtrates were concentrated to afford (R)-3-hydroxy-2-(5-(4-methoxy-3-propoxyphenyl)pyridin-3-yl)propyl acetate (36.0 g, 83%), which was used in Preparation 45.

Preparation 47a: 3-(1,2-dibromo-3-((tert-butyldimethylsilyl)oxy)propan-2-yl)-5-(3-ethoxy-4-methoxyphenyl)pyridine

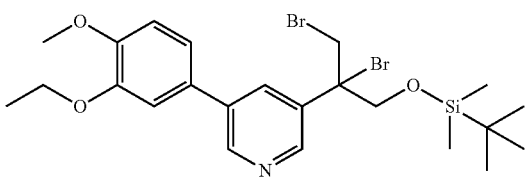 [SMILES: CCOc1cc(-c2cncc(C(Br)(CBr)CO[Si](C)(C)C(C)(C)C)c2)ccc1OC]

To a mixture of 3-(3-((tert-butyldimethylsilyl)oxy)prop-1-en-2-yl)-5-(3-ethoxy-4-methoxyphenyl)pyridine (Preparation 49, 8.00 g, 20.02 mmol) in DCM (150 mL) was added pyridinium tribromide (CAS 39416-48-3, 7.68 g, 24.02 mmol) in one portion at about 0° C. under $N_2$. The mixture was stirred at about 25° C. for about 3 h. The DCM mixture was washed with aqueous $Na_2SO_3$ (100 mL), brine (100 mL), dried over $Na_2SO_4$ and concentrated. The residue was purified by column chromatography (silica) and eluted with pet. ether/EtOAc (10:1) to afford 3-(1,2-dibromo-3-((tert-butyldimethylsilyl)oxy)propan-2-yl)-5-(3-ethoxy-4-methoxyphenyl)pyridine (11.00 g) which was used directly for the next step. $^1$H NMR (CDCl$_3$, 400 MHz): δ 8.72-8.74 (m, 2H), 7.99 (t, J=2.0 Hz, 1H), 7.14 (dd, J=2.0, 8.4 Hz, 1H), 7.09 (d, J=2.0 Hz, 1H), 7.00 (d, J=8.0 Hz, 1H), 4.37-4.40 (m, 2H), 4.28 (d, J=11.2 Hz, 1H), 4.21-4.26 (m, 3H), 3.93 (s, 3H), 1.52 (t, J=7.2 Hz, 3H), 0.94 (s, 9H), 0.14 (d, J=9.6 Hz, 6H).

Preparation 47b: 3-(1,2-dibromo-3-((tert-butyldimethylsilyl)oxy)propan-2-yl)-5-(4-methoxy-3-propoxyphenyl)pyridine

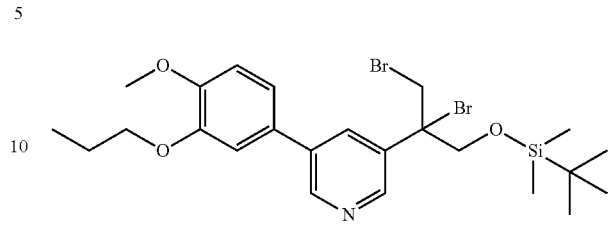

To a mixture of 3-(3-((tert-butyldimethylsilyl)oxy)prop-1-en-2-yl)-5-(4-methoxy-3-propoxyphenyl)pyridine (Preparation 50, 7.00 g, 16.92 mmol) in DCM (150 mL) was added pyridinium tribromide (CAS 39416-48-3, 6.49 g, 20.30 mmol) in one portion at about 0° C. under $N_2$. The mixture was stirred at about 25° C. for about 3 h. The DCM mixture was washed with aqueous $Na_2SO_3$ (100 mL), brine (100 mL), dried over $Na_2SO_4$ and concentrated. The residue was purified by column chromatography (silica) and eluted with pet. ether/EtOAc (10:1) to afford 3-(1,2-dibromo-3-((tert-butyldimethylsilyl)oxy)propan-2-yl)-5-(4-methoxy-3-propoxyphenyl)pyridine (10.00 g), which was used directly for the next step. $^1$H NMR (CDCl$_3$, 400 MHz): δ 8.72-8.75 (m, 2H), 7.99 (t, J=2.0 Hz, 1H), 7.14 (dd, J=2.0, 8.0 Hz, 1H), 7.09 (d, J=2.0 Hz, 1H), 7.00 (d, J=8.4 Hz, 1H), 4.39 (d, J=10.8 Hz, 2H), 4.28 (d, J=10.8 Hz, 1H), 4.20 (d, J=10.4 Hz, 1H), 4.07 (t, J=6.8 Hz, 2H), 3.93 (s, 3H), 1.97-1.87 (m, 1H), 1.08 (t, J=7.2 Hz, 3H), 0.93 (s, 9H), 0.14 (d, J=9.6 Hz, 6H).

Preparation 48: 3-(3-((tert-butyldimethylsilyl)oxy)prop-1-en-2-yl)-5-(3,4-dimethoxyphenyl)pyridine

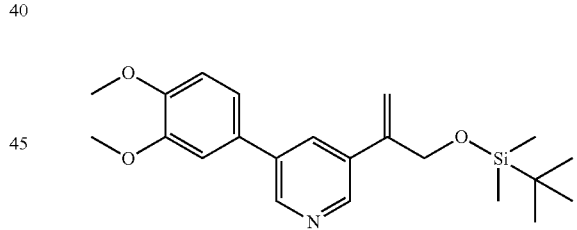

A mixture of 3-(3,4-dimethoxyphenyl)-5-(4,4,5,5-tetramethyl-1,3,2-dioxaborolan-2-yl)pyridine (Preparation 91a, 2.0 g, 5.86 mmol), 2-bromallyloxy-tert-butyl-dimethyl-silane (Preparation 227, 1.47 g, 5.86 mmol), Pd(dppf)Cl$_2$DCM (239.34 mg, 293 umol), Na$_2$CO$_3$ (621.26 mg, 5.86 mmol) and KOAc (1.15 g, 11.72 mmol) in 1,4-dioxane (50 mL) and water (5 mL) were heated to about 90° C. for about 12 h. The mixture was filtered and the filtrate concentrated. The residue was purified by column chromatography (silica) and eluted with DCM/MeCN (5:1) to afford 3-(3-((tert-butyldimethylsilyl)oxy)prop-1-en-2-yl)-5-(3,4-dimethoxyphenyl)pyridine (2.10 g, 5.45 mmol, 93%). $^1$H NMR (CDCl$_3$, 400 MHz): δ 8.72 (d, J=2.0 Hz, 1H), 8.61 (d, J=2.0 Hz, 1H), 7.85 (t, J=2.0 Hz, 1H), 7.14-7.16 (m, 1H), 7.08 (d, J=2.0 Hz, 1H), 6.99 (d, J=8.4 Hz, 1H), 5.52 (d, J=12.0 Hz, 2H), 4.56 (s, 2H), 3.97 (s, 3H), 3.95 (s, 3H), 0.93 (s, 9H), 0.12 (s, 6H).

Preparation 49: 3-(3-((tert-butyldimethylsilyl)oxy) prop-1-en-2-yl)-5-(3-ethoxy-4-methoxyphenyl)pyridine

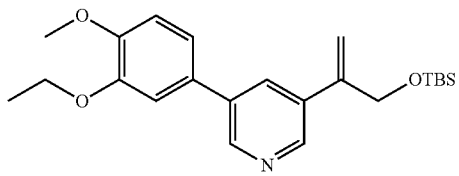 [SMILES: C=C(CO[Si](C)(C)C(C)(C)C)c1cncc(-c2ccc(OC)c(OCC)c2)c1]

A mixture of 3-bromo-5-(3-ethoxy-4-methoxyphenyl) pyridine (Preparation 92, 20 g, 64.9 mmol), tert-butyldimethyl((2-(4,4,5,5-tetramethyl-1,3,2-dioxaborolan-2-yl)allyl) oxy)silane (Preparation 146, 23.23 g, 77.88 mmol), Pd(dppf) Cl$_2$ (1.42 g, 1.95 mmol), K$_2$CO$_3$ (17.94 g, 129.8 mmol) and KOAc (9.55 g, 97.35 mmol) in 1,4-dioxane (300 mL) and water (10 mL) was degassed and heated to about 90° C. for about 16 h under N$_2$. The mixture was filtered and concentrated. The residue was purified by column chromatography (silica) and eluted with pet. ether/EtOAc (3:1) to afford 3-(3-((tert-butyldimethylsilyl)oxy)prop-1-en-2-yl)-5-(3-ethoxy-4-methoxyphenyl)pyridine (18.0 g, 69%). $^1$H NMR (CDCl$_3$, 400 MHz): δ 8.71 (d, J=2.0 Hz, 1H), 8.60 (d, J=2.0 Hz, 1H), 7.84 (t, J=2.0 Hz, 1H), 7.14 (dd, J=2.0, 8.4 Hz, 1H), 7.09 (d, J=2.4 Hz, 1H), 6.99 (d, J=8.0 Hz, 1H), 5.54 (s, 1H), 5.50 (s, 1H), 4.56 (s, 2H), 4.19 (q, J=7.2 Hz, 2H), 3.94 (s, 3H), 1.52 (t, J=7.2 Hz, 3H), 0.93 (s, 9H), 0.12 (s, 6H).

Preparation 50: 3-(3-((tert-butyldimethylsilyl)oxy) prop-1-en-2-yl)-5-(4-methoxy-3-propoxyphenyl) pyridine

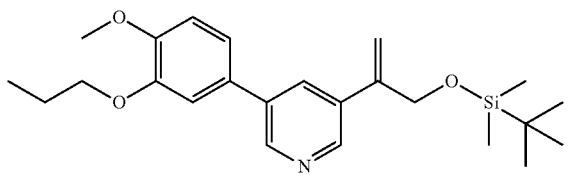 [SMILES: C=C(CO[Si](C)(C)C(C)(C)C)c1cncc(-c2ccc(OC)c(OCCC)c2)c1]

A mixture of 3-bromo-5-(4-methoxy-3-propoxyphenyl) pyridine (Preparation 93a, 15.0 g, 46.55 mmol), tert-butyldimethyl((2-(4,4,5,5-tetramethyl-1,3,2-dioxaborolan-2-yl)allyl)oxy)silane (Preparation 146, 18.05 g, 60.51 mmol), Pd(dppf)Cl$_2$ (1.70 g, 2.33 mmol), K$_2$CO$_3$ (12.87 g, 93.10 mmol) and KOAc (6.85 g, 69.83 mmol) in 1,4-dioxane (250 mL) and water (5 mL) was degassed and heated to about 90° C. for about 16 h under N$_2$. The mixture was filtered and concentrated. The residue was purified by column chromatography (silica) and eluted with pet. ether/EtOAc (3:1) to afford 3-(3-((tert-butyldimethylsilyl)oxy)prop-1-en-2-yl)-5-(4-methoxy-3-propoxyphenyl)pyridine (13.50 g, 70%). $^1$H NMR (CDCl$_3$, 400 MHz): δ 8.71 (d, J=2.4 Hz, 1H), 8.60 (d, J=2.0 Hz, 1H), 7.84 (t, J=2.0 Hz, 1H), 7.13 (dd, J=2.4, 8.4 Hz, 1H), 7.10 (d, J=2.4 Hz, 1H), 6.99 (d, J=8.4 Hz, 1H), 5.53 (d, J=1.2 Hz, 1H), 5.50 (d, J=1.2 Hz, 1H), 4.56 (s, 2H), 4.06 (t, J=6.8 Hz, 2H), 3.93 (s, 3H), 1.87-1.96 (m, 2H), 1.08 (t, J=7.2 Hz, 3H), 0.93 (s, 9H), 0.13 (s, 6H).

Preparation 51: 3-(3-((tert-butyldimethylsilyl)oxy) prop-1-en-2-yl)-5-(3-isopropoxy-4-methoxyphenyl) pyridine

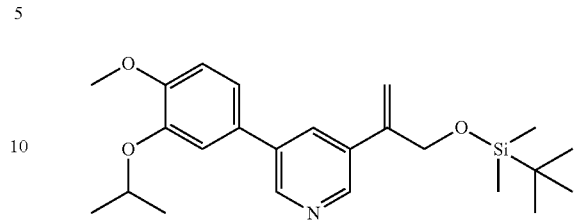

3-(3-((tert-butyldimethylsilyl)oxy)prop-1-en-2-yl)-5-(3-isopropoxy-4-methoxyphenyl)pyridine (1.1 g, 75%) was prepared in an analogous manner to Preparation 50 using 3-bromo-5-(3-isopropoxy-4-methoxyphenyl)pyridine (Preparation 94, 1.15 g, 3.6 mmol) at about 90° C. for about 2 h. LCMS m/z=414 [MH]$^+$.

Preparation 52: 3-(3-((tert-butyldimethylsilyl)oxy) prop-1-en-2-yl)-5-(3-cyclopropoxy-4-methoxyphenyl)pyridine

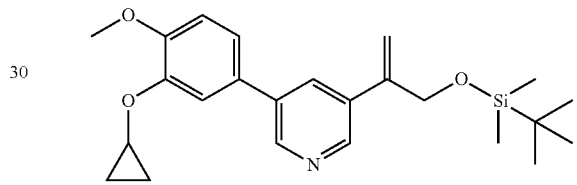

3-(3-((tert-butyldimethylsilyl)oxy)prop-1-en-2-yl)-5-(3-cyclopropoxy-4-methoxyphenyl)pyridine (730 mg, 76%) was prepared in an analogous manner to Preparation 50 using 3-bromo-5-(3-cyclopropoxy-4-methoxyphenyl)pyridine (Preparation 95, 0.75 g, 2.34 mmol). $^1$H NMR (CDCl$_3$, 400 MHz): δ 8.74 (d, J=2.0 Hz, 1H), 8.61 (d, J=2.5 Hz, 1H), 7.85 (t, J=2.3 Hz, 1H), 7.47 (d, J=2.0 Hz, 1H), 7.14-7.22 (m, 1H), 6.98 (d, J=8.5 Hz, 1H), 5.53 (dd, J=1.3, 10.3 Hz, 2H), 4.50-4.62 (m, 2H), 3.92 (s, 3H), 3.84 (tt, J=3.2, 6.1 Hz, 1H), 0.81-0.96 (m, 13H), 0.11-0.14 (m, 6H). LCMS m/z=412 [MH]$^+$.

Preparation 53: 3-(3-(2-((tert-butyldimethylsilyl) oxy)ethoxy)-4-methoxyphenyl)-5-(3-((tert-butyldimethylsilyl)oxy)prop-1-en-2-yl)pyridine

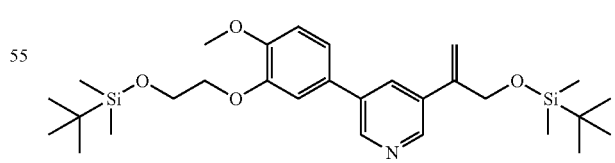

3-(3-(2-((tert-butyldimethylsilyl)oxy)ethoxy)-4-methoxyphenyl)-5-(3-((tert-butyldimethylsilyl)oxy)prop-1-en-2-yl)pyridine (6.7 g, 62%) was prepared in an analogous manner to Preparation 50 using 3-bromo-5-(3-(2-((tert-butyldimethylsilyl)oxy)ethoxy)-4-methoxyphenyl)pyridine (Preparation 96, 9.3 g, 21 mmol). $^1$H NMR (CDCl$_3$, 400 MHz): δ 8.71 (d, J=2.0 Hz, 1H), 8.60 (d, J=2.0 Hz, 1H), 7.83

(t, J=2.0 Hz, 1H), 7.13-7.18 (m, 2H), 6.96-7.01 (m, 1H), 5.52 (dd, J=1.3, 10.3 Hz, 2H), 4.56 (s, 2H), 4.16-4.22 (m, 2H), 4.02-4.07 (m, 2H), 3.92 (s, 3H), 0.92-0.95 (m, 9H), 0.90 (s, 9H), 0.12 (s, 6H), 0.10 (s, 6H). LCMS m/z=530 [MH]+.

Preparation 54: 3-(3-((tert-butyldimethylsilyl)oxy)prop-1-en-2-yl)-5-(3-(3-((tert-butyldimethylsilyl)oxy)propoxy)-4-methoxyphenyl)pyridine

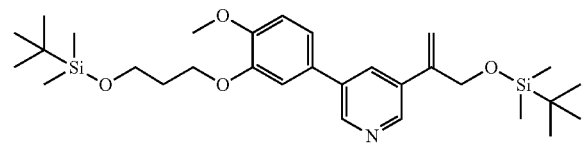 [SMILES: C=C(CO[Si](C)(C)C(C)(C)C)c1cncc(-c2ccc(OC)c(OCCCO[Si](C)(C)C(C)(C)C)c2)c1]

3-(3-((tert-butyldimethylsilyl)oxy)prop-1-en-2-yl)-5-(3-(3-((tert-butyldimethylsilyl)oxy)propoxy)-4-methoxyphenyl)pyridine (12.9 g, 99%) was prepared in an analogous manner to Preparation 50 using 3-bromo-5-(3-(3-((tert-butyldimethylsilyl)oxy)propoxy)-4-methoxyphenyl)pyridine (Preparation 97, 10.8 g, 23.8 mmol). $^1$H NMR (CDCl$_3$, 400 MHz): δ 8.71 (d, J=2.5 Hz, 1H), 8.60 (d, J=2.0 Hz, 1H), 7.83 (t, J=2.2 Hz, 1H), 7.11-7.16 (m, 2H), 6.98 (d, J=8.3 Hz, 1H), 5.49-5.54 (m, 2H), 4.56 (t, J=1.5 Hz, 2H), 4.21 (t, J=6.4 Hz, 2H), 3.92 (s, 3H), 3.85 (t, J=5.9 Hz, 2H), 2.05-2.13 (m, 2H), 0.92-0.94 (m, 9H), 0.89 (s, 9H), 0.12 (s, 6H), 0.05 (s, 6H). LCMS m/z=544 [MH]+.

Preparation 55: 3-(3-((tert-butyldimethylsilyl)oxy)prop-1-en-2-yl)-5-(3-(2-fluoroethoxy)-4-methoxyphenyl)pyridine

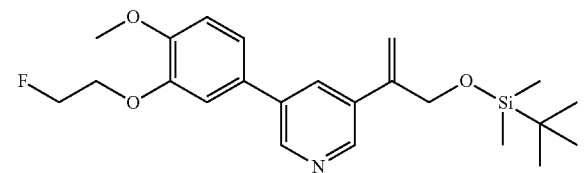 [SMILES: C=C(CO[Si](C)(C)C(C)(C)C)c1cncc(-c2ccc(OC)c(OCCF)c2)c1]

3-(3-((tert-butyldimethylsilyl)oxy)prop-1-en-2-yl)-5-(3-(2-fluoroethoxy)-4-methoxyphenyl)pyridine (1.6 g, 78%) was prepared in an analogous manner to Preparation 50 using 3-bromo-5-(3-(2-fluoroethoxy)-4-methoxyphenyl)pyridine (Preparation 98, 1.4 g, 4.7 mmol). $^1$H NMR (CDCl$_3$, 400 MHz): δ 8.92 (d, J=2.5 Hz, 1H), 8.70-8.73 (m, 1H), 7.73 (t, J=8.6 Hz, 1H), 6.84-6.90 (m, 1H), 6.07 (d, J=1.5 Hz, 1H), 5.76 (d, J=1.5 Hz, 1H), 4.76 (t, J=1.7 Hz, 2H), 4.06 (t, J=6.9 Hz, 2H), 3.94 (s, 3H), 1.81-1.86 (m, 2H), 1.03-1.09 (m, 3H), 0.95 (s, 9H), 0.14 (s, 6H). LCMS m/z=433 [MH]+.

Preparation 56: 3-(3-((tert-butyldimethylsilyl)oxy)prop-1-en-2-yl)-5-(3-(3-fluoropropoxy)-4-methoxyphenyl)pyridine

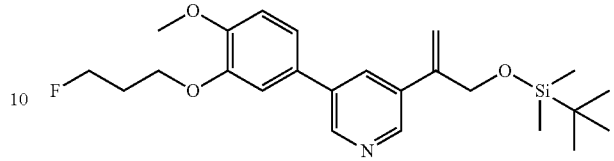

3-(3-((tert-butyldimethylsilyl)oxy)prop-1-en-2-yl)-5-(3-(3-fluoropropoxy)-4-methoxyphenyl)pyridine was prepared in an analogous manner to Preparation 50 using 3-bromo-5-(3-(3-fluoropropoxy)-4-methoxyphenyl)pyridine (Preparation 99).

Preparation 57: 3-(3-((tert-butyldimethylsilyl)oxy)prop-1-en-2-yl)-5-(2-(difluoromethyl)-3-ethoxy-4-methoxyphenyl)pyridine

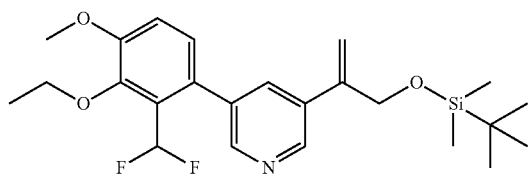 [SMILES: C=C(CO[Si](C)(C)C(C)(C)C)c1cncc(-c2ccc(OC)c(OCC)c2C(F)F)c1]

A solution of 2-(5-(2-(difluoromethyl)-3-ethoxy-4-methoxyphenyl)pyridin-3-yl)prop-2-en-1-ol (Preparation 76, 321 mg, 0.71 mmol) and imidazole (97.2 mg, 1.43 mmol) in DCM (20 mL) was added TBS-Cl (129 mg, 0.86 mmol) at about 0° C. The reaction mixture was stirred at about 20° C. for about 15 h. Additional TBS-Cl (129 mg, 0.86 mmol) was added and the reaction mixture was stirred at about 20° C. for about 20 h. The reaction mixture was concentrated and purified by column chromatography (silica) and eluted with pet. ether/EtOAc (100:0 to 60:40) to afford 3-(3-((tert-butyldimethylsilyl)oxy)prop-1-en-2-yl)-5-(2-(difluoromethyl)-3-ethoxy-4-methoxyphenyl)pyridine (361 mg, 75%). $^1$H NMR (CDCl$_3$, 400 MHz): δ 8.66 (d, J=2.0 Hz, 1H), 8.51 (d, J=2.0 Hz, 1H), 7.71 (t, J=2.3 Hz, 1H), 7.05-7.10 (m, 1H), 6.78-7.03 (m, 2H), 5.51 (dd, J=1.5, 14.1 Hz, 2H), 4.55 (t, J=1.5 Hz, 2H), 4.17 (q, J=7.0 Hz, 2H), 3.93 (s, 3H), 1.43 (t, J=7.0 Hz, 3H), 0.88-0.94 (m, 9H), 0.09-0.13 (m, 6H). LCMS m/z=450 [MH]+.

Preparation 58: 3-(3-((tert-butyldimethylsilyl)oxy)prop-1-en-2-yl)-5-(3-ethoxy-5-fluoro-4-methoxyphenyl)pyridine

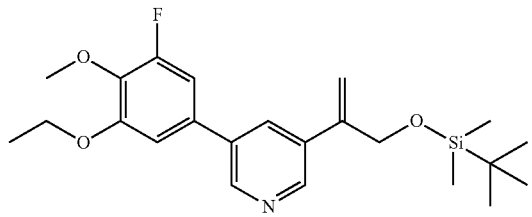 [SMILES: C=C(CO[Si](C)(C)C(C)(C)C)c1cncc(-c2cc(F)c(OC)c(OCC)c2)c1]

To a mixture of 3-bromo-5-(3-((tert-butyldimethylsilyl)oxy)prop-1-en-2-yl)pyridine (Preparation 86, 795 mg, 2.42 mmol), 2-(3-ethoxy-5-fluoro-4-methoxyphenyl)-4,4,5,5-tetramethyl-1,3,2-dioxaborolane (Preparation 132, 652 mg, 2.2 mmol), Pd(dppf)Cl$_2$-DCM and K$_2$CO$_3$ (760 mg, 5.5 mmol) was suspended in 1,4-dioxane (20 mL) and water (0.7 mL). The mixture was degassed and heated to about 85° C. under N$_2$ for about 9 h. The mixture was concentrated and MTBE (50 mL) was added, stirring for about 20 min. The mixture was filtered and the filtrate was concentrated. The residue was purified by column chromatography (silica) and eluted with pet. ether/EtOAc (100:0 to 80:20) to afford 3-(3-((tert-butyldimethylsilyl)oxy)prop-1-en-2-yl)-5-(3-ethoxy-5-fluoro-4-methoxyphenyl)pyridine (660 mg, 72%). $^1$H NMR (CDCl$_3$, 400 MHz): δ 8.66 (dd, J=2.2, 15.4 Hz, 2H), 7.82 (t, J=2.0 Hz, 1H), 6.94 (dd, J=2.2, 11.0 Hz, 1H), 6.88 (t, J=1.7 Hz, 1H), 5.50-5.57 (m, 2H), 4.54-4.57 (m, 2H), 4.18 (q, J=7.0 Hz, 2H), 3.98 (s, 3H), 1.50 (t, J=7.1 Hz, 3H), 0.92 (s, 9H), 0.12 (s, 6H). LCMS m/z=418 [MH]$^+$.

Preparation 59: 3-(3-((tert-butyldimethylsilyl)oxy) prop-1-en-2-yl)-5-(3-chloro-5-ethoxy-4-methoxy-phenyl)pyridine

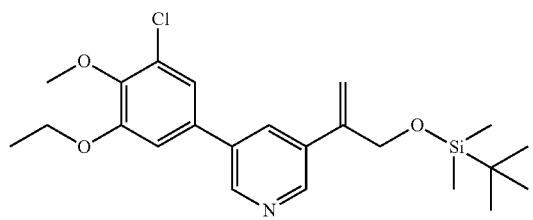

3-(3-((tert-butyldimethylsilyl)oxy) prop-1-en-2-yl)-5-(3-chloro-5-ethoxy-4-methoxyphenyl)pyridine (840 mg, 61%) was prepared in an analogous manner to Preparation 58 using 2-(3-chloro-5-ethoxy-4-methoxyphenyl)-4,4,5,5-tetramethyl-1,3,2-dioxaborolane (Preparation 133, 1.0 g, 3.2 mmol). $^1$H NMR (CDCl$_3$, 400 MHz): δ 8.66 (dd, J=2.2, 11.5 Hz, 2H), 7.83 (t, J=2.2 Hz, 1H), 7.19 (d, J=2.0 Hz, 1H), 6.99 (d, J=2.0 Hz, 1H), 5.53 (dd, J=1.5, 12.2 Hz, 2H), 4.52-4.63 (m, 2H), 4.17 (q, J=7.2 Hz, 2H), 3.94 (s, 3H), 1.51 (t, J=6.9 Hz, 3H), 0.90-0.97 (m, 9H), 0.08-0.15 (m, 6H).

Preparation 60: 3-(3-((tert-butyldimethylsilyl)oxy) prop-1-en-2-yl)-5-(5-ethoxy-2-fluoro-4-methoxyphenyl)pyridine

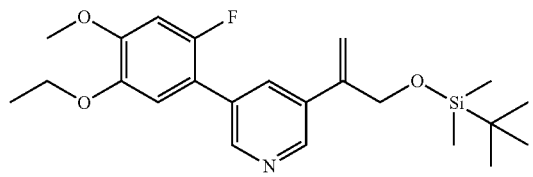 [SMILES: C=C(CO[Si](C)(C)C(C)(C)C)c1cncc(-c2cc(OCC)c(OC)cc2F)c1]

3-(3-((tert-butyldimethylsilyl)oxy)prop-1-en-2-yl)-5-(5-ethoxy-2-fluoro-4-methoxyphenyl)pyridine (400 mg, 89%) was prepared in an analogous manner to Preparation 50 using 3-bromo-5-(5-ethoxy-2-fluoro-4-methoxyphenyl) pyridine (Preparation 101, 350 mg, 1.07 mmol). $^1$H NMR (CDCl$_3$, 400 MHz): δ 8.66 (t, J=1.7 Hz, 1H), 8.62 (d, J=2.2 Hz, 1H), 7.84-7.86 (m, 1H), 6.91 (d, J=7.3 Hz, 1H), 6.75 (d, J=11.7 Hz, 1H), 5.50-5.53 (m, 2H), 4.56 (t, J=1.3 Hz, 2H), 4.12 (q, J=7.0 Hz, 2H), 3.92 (s, 3H), 1.48 (t, J=7.0 Hz, 3H), 0.92 (s, 9H), 0.11 (s, 6H). LCMS m/z=418 [MH]$^+$.

Preparation 61: 3-(3-((tert-butyldimethylsilyl)oxy) prop-1-en-2-yl)-5-(2-chloro-5-ethoxy-4-methoxy-phenyl)pyridine

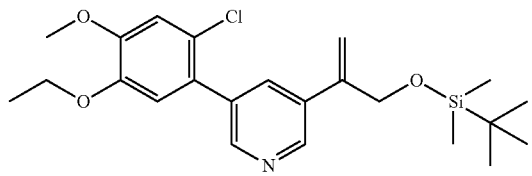 [SMILES: C=C(CO[Si](C)(C)C(C)(C)C)c1cncc(-c2cc(OCC)c(OC)cc2Cl)c1]

3-(3-((tert-butyldimethylsilyl)oxy)prop-1-en-2-yl)-5-(2-chloro-5-ethoxy-4-methoxyphenyl)pyridine (2.1 g, 48%) was prepared in an analogous manner to Preparation 58 using 2-(2-chloro-5-ethoxy-4-methoxyphenyl)-4,4,5,5-tetramethyl-1,3,2-dioxaborolane (Preparation 135, 3.13 g, 10.0 mmol). LCMS m/z=434 [MH]$^+$.

Preparation 62: 3-(3-((tert-butyldimethylsilyl)oxy) prop-1-en-2-yl)-5-(2-fluoro-4-methoxy-5-propoxy-phenyl)pyridine

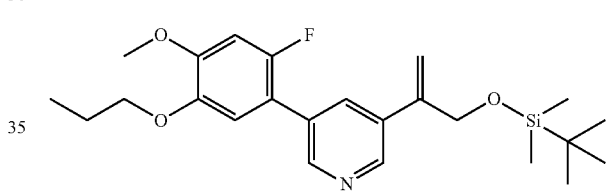

3-(3-((tert-butyldimethylsilyl)oxy)prop-1-en-2-yl)-5-(2-fluoro-4-methoxy-5-propoxyphenyl)pyridine (5.0 g, 99%) was prepared in an analogous manner to Preparation 50 using 3-bromo-5-(2-fluoro-4-methoxy-5-propoxyphenyl) pyridine (Preparation 102, 7.0 g, 9.0 mmol). $^1$H NMR (CDCl$_3$, 400 MHz): δ 8.66 (s, 1H), 8.62 (d, J=2.0 Hz, 1H), 7.85 (d, J=1.5 Hz, 1H), 6.92 (d, J=7.3 Hz, 1H), 6.76 (d, J=11.7 Hz, 1H), 5.52 (d, J=9.8 Hz, 2H), 4.55 (s, 2H), 4.00 (t, J=6.8 Hz, 2H), 3.91 (s, 3H), 1.84-1.93 (m, 2H), 1.06 (t, J=7.3 Hz, 3H), 0.94-0.92 (m, 9H), 0.12-0.11 (m, 6H). LCMS m/z=432 [MH]$^+$.

Preparation 63: 3-(3-((tert-butyldimethylsilyl)oxy) prop-1-en-2-yl)-5-(4-(difluoromethoxy)-3-propoxy-phenyl)pyridine

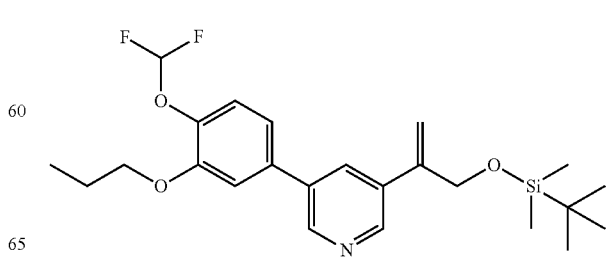

3-(3-((tert-butyldimethylsilyl)oxy)prop-1-en-2-yl)-5-(4-(difluoromethoxy)-3-propoxyphenyl)pyridine (2.1 g, 62%) was prepared in an analogous manner to Preparation 58 using 2-(4-(difluoromethoxy)-3-propoxyphenyl)-4,4,5,5-tetramethyl-1,3,2-dioxaborolane (Preparation 142, 2.46 g, 7.5 mmol). $^1$H NMR (CDCl$_3$, 400 MHz): δ 8.66-8.71 (m, 2H), 7.85 (d, J=2.1 Hz, 1H), 7.27-7.29 (m, 1H), 7.12-7.14 (m, 2H) 6.63 (t, J=75.3 Hz, 1H), 5.53 (d, J=12.0 Hz, 2H), 4.56 (s, 2H), 4.07 (t, J=6.4 Hz, 2H), 1.85-1.94 (m, 2H), 1.09 (t, J=7.4 Hz, 3H), 0.92 (s, 9H), 0.12 (s, 6H). LCMS m/z=450 [MH]$^+$.

Preparation 64: 5'-(3-((tert-butyldimethylsilyl)oxy)prop-1-en-2-yl)-3-fluoro-5-methoxy-6-propoxy-2,3'-bipyridine

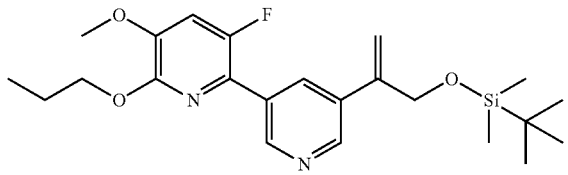 [SMILES: C=C(CO[Si](C)(C)C(C)(C)C)c1cncc(-c2nc(OCCC)c(OC)cc2F)c1]

To a mixture of 5'-chloro-3-fluoro-5-methoxy-6-propoxy-2,3'-bipyridine (Preparation 103, 3.0 g, 10.11 mmol) and tert-butyldimethyl((2-(4,4,5,5-tetramethyl-1,3,2-dioxaborolan-2-yl)allyl)oxy)silane (Preparation 146, 12.1 g, 40.4 mmol) in 1,4-dioxane (300 mL) was added Xphos Pd G2 (CAS 1310584-14-5, 0.64 g, 0.81 mmol), Pd(dppf)-tBu (0.66 g, 1.01 mmol), K$_2$CO$_3$ (2.79 g, 20.2 mmol) and KOAc (0.50 g, 5.06 mmol). The mixture was degassed, heated to about 70° C. for about 16 h under N$_2$. The mixture was diluted with EtOAc (50 mL), dried over MgSO$_4$, filtered and concentrated. The residue was purified by column chromatography (silica) and eluted with pet. ether/EtOAc (100:0 to 85:15) to afford 5'-(3-((tert-butyldimethylsilyl)oxy)prop-1-en-2-yl)-3-fluoro-5-methoxy-6-propoxy-2,3'-bipyridine (3.1 g, 71%). $^1$H NMR (CDCl$_3$, 400 MHz): δ 9.13-9.14 (m, 1H), 8.62 (d, J=2.1 Hz, 1H), 8.28 (t, J=2.1 Hz, 1H), 6.97 (d, J=11.4 Hz, 1H), 5.51-5.54 (m, 2H), 4.57 (t, J=1.5 Hz, 2H), 4.44 (t, J=7.0 Hz, 2H), 3.93 (s, 3H), 1.86-1.95 (m, 2H), 1.06 (t, J=7.5 Hz, 3H), 0.93 (s, 9H), 0.12 (s, 6H). LCMS m/z=433 [MH]$^+$.

Preparation 65: 5'-(3-((tert-butyldimethylsilyl)oxy)prop-1-en-2-yl)-6-methoxy-5-propoxy-3,3'-bipyridine

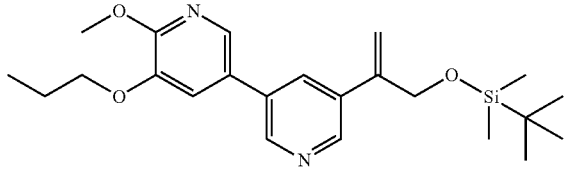 [SMILES: C=C(CO[Si](C)(C)C(C)(C)C)c1cncc(-c2cnc(OC)c(OCCC)c2)c1]

5'-(3-((tert-butyldimethylsilyl)oxy)prop-1-en-2-yl)-6-methoxy-5-propoxy-3,3'-bipyridine (4.85 g, 87%) was prepared in an analogous manner to Preparation 58 using 2-methoxy-3-propoxy-5-(4,4,5,5-tetramethyl-1,3,2-dioxaborolan-2-yl)pyridine (Preparation 124, 3.95 g, 13.5 mmol). $^1$H NMR (CDCl$_3$, 400 MHz): δ 8.67 (dd, J=2.2, 16.9 Hz, 2H), 7.9 (d, J=2.2 Hz, 1H), 7.83 (t, J=2.2 Hz, 1H), 7.23 (d, J=2.0 Hz, 1H), 5.47-5.60 (m, 2H), 4.56 (t, J=1.3 Hz, 2H), 4.03-4.08 (m, 5H), 1.90-1.99 (m, 2H), 1.04-1.13 (m, 3H), 0.92 (s, 9H), 0.10-0.13 (m, 6H).

Preparation 66: 5-(3-((tert-butyldimethylsilyl)oxy)prop-1-en-2-yl)-3-(3-ethoxy-4-methoxyphenyl)-2-methylpyridine

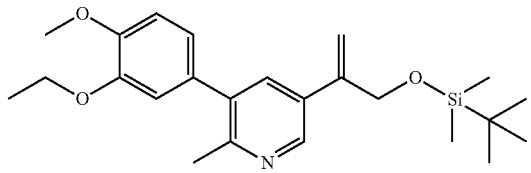 [SMILES: C=C(CO[Si](C)(C)C(C)(C)C)c1cnc(C)c(-c2ccc(OC)c(OCC)c2)c1]

3-Bromo-5-(3-((tert-butyldimethylsilyl)oxy)prop-1-en-2-yl)-2-methylpyridine (Preparation 87, 1.28 g, 3.7 mmol) and 2-(3-ethoxy-4-methoxyphenyl)-4,4,5,5-tetramethyl-1,3,2-dioxaborolane (Preparation 113, 1.25 g, 4.49 mmol), Pd(dppf)Cl$_2$ (274 mg, 0.374 mmol) and K$_2$CO$_3$ (1.29 g, 9.35 mmol) was suspended in 1,4-dioxane (60 mL) and water (2 mL). The mixture was degassed and heated to about 80° C. under N$_2$ for about 5 h. The mixture was concentrated and to the residue was added MTBE (100 mL), which was stirred for about 20 min. The mixture was filtered and the filter cake was washed with MTBE (50 mL). The combined filtrates were dried and concentrated. The residue was purified column chromatography (silica) and eluted with pet. ether/EtOAc (100:0 to 85:15) to afford 5-(3-((tert-butyldimethylsilyl)oxy)prop-1-en-2-yl)-3-(3-ethoxy-4-methoxyphenyl)-2-methylpyridine (640 mg, 41%). $^1$H NMR (CDCl$_3$, 400 MHz): δ 8.54 (d, J=2.5 Hz, 1H), 7.54 (d, J=2.0 Hz, 1H), 6.94-6.97 (m, 1H), 6.85-6.88 (m, 1H), 6.83-6.84 (m, 1H), 5.48 (d, J=1.5 Hz, 1H), 5.43-5.45 (m, 1H), 4.52 (t, J=1.5 Hz, 2H), 4.12 (q, J=7.0 Hz, 2H), 3.93 (s, 3H), 2.51 (s, 3H), 1.49 (t, J=7.0 Hz, 3H), 0.90-0.93 (m, 9H), 0.09-0.11 (m, 6H). LCMS m/z=414 [MH]$^+$.

Preparation 67: 4-(3-((tert-butyldimethylsilyl)oxy)prop-1-en-2-yl)-2-(4-methoxy-3-propoxyphenyl)-6-(trifluoromethyl)pyrimidine

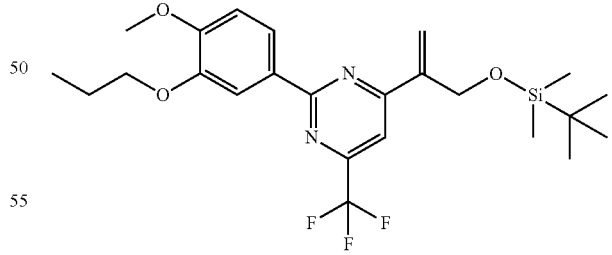

To a mixture of 4-(3-((tert-butyldimethylsilyl)oxy)prop-1-en-2-yl)-2-chloro-6-(trifluoromethyl)pyrimidine (Preparation 90, 1.33 g, 3.77 mmol) in 1,4-dioxane (40 mL) was added 2-(4-methoxy-3-propoxyphenyl)-4,4,5,5-tetramethyl-1,3,2-dioxaborolane (Preparation 114, 1.32 g, 4.52 mmol), K$_3$PO$_4$ (3.01 g, 11.3 mmol) and Pd(dppf)Cl$_2$ (0.41 g, 0.57 mmol). The mixture was degassed and heated to about 90° C. for about 5 h under N$_2$. The mixture was concentrated and the residue was purified by column chromatography (silica)

and eluted with pet. ether:EtOAc (100:0 to 90:10) to afford 4-(3-((tert-butyldimethylsilyl)oxy)prop-1-en-2-yl)-2-(4-methoxy-3-propoxyphenyl)-6-(trifluoromethyl)pyrimidine (1.27 g, 70%). ¹H NMR (CDCl₃, 400 MHz): δ 8.13-8.16 (m, 1H), 8.07 (d, J=2.0 Hz, 1H), 7.61 (s, 1H), 6.99 (d, J=8.6 Hz, 1H), 6.31 (d, J=1.1 Hz, 1H), 5.95 (d, J=1.0 Hz, 1H), 4.65 (t, J=1.6 Hz, 2H), 4.13 (t, J=6.9 Hz, 2H), 3.96 (s, 3H), 1.90-1.99 (m, 2H), 1.10 (t, J=7.5 Hz, 3H), 0.97 (s, 9H), 0.13 (s, 6H). LCMS m/z=483 [MH]⁺.

Preparation 68: 2-(3-((tert-butyldimethylsilyl)oxy)prop-1-en-2-yl)-6-(3-ethoxy-4-methoxyphenyl)pyrazine

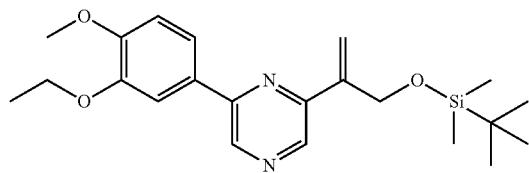 [SMILES: C=C(CO[Si](C)(C)C(C)(C)C)c1cncc(-c2ccc(OC)c(OCC)c2)n1]

2-(3-((tert-butyldimethylsilyl)oxy)prop-1-en-2-yl)-6-(3-ethoxy-4-methoxyphenyl)pyrazine (1.26 g, 65%) was prepared in an analogous manner to Preparation 50 using 2-bromo-6-(3-ethoxy-4-methoxyphenyl)pyrazine (Preparation 104, 1.5 g, 4.9 mmol). ¹H NMR (CDCl₃, 400 MHz): δ 8.77-8.90 (m, 1H), 8.68 (s, 1H), 7.69 (d, J=2.0 Hz, 1H), 7.60 (dd, J=2.1, 8.44 Hz, 1H), 6.99 (d, J=8.3 Hz, 1H), 6.07 (q, J=1.4 Hz, 1H), 5.77 (q, J=1.9 Hz, 1H), 4.80 (t, J=1.7 Hz, 2H), 4.23 (q, J=7.0 Hz, 2H), 3.96 (s, 3H), 1.53 (t, J=7.0 Hz, 3H), 0.90-0.98 (m, 9H), 0.13-0.18 (m, 6H). LCMS m/z=401 [MH]⁺.

Preparation 69: ethyl 2-(6-(3-((tert-butyldimethylsilyl)oxy)prop-1-en-2-yl)-2-(4-methoxy-3-propoxyphenyl)pyrimidin-4-yl)acetate

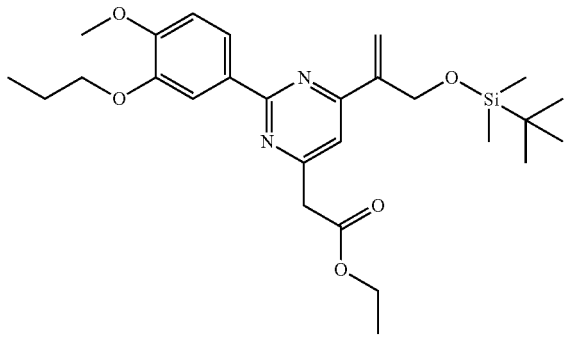 [SMILES: C=C(CO[Si](C)(C)C(C)(C)C)c1cc(CC(=O)OCC)nc(-c2ccc(OC)c(OCCC)c2)n1]

Ethyl 2-(6-(3-((tert-butyldimethylsilyl)oxy)prop-1-en-2-yl)-2-(4-methoxy-3-propoxyphenyl)pyrimidin-4-yl)acetate (5.6 g, 82%) was prepared in an analogous manner to Preparation 50 using ethyl 2-(6-chloro-2-(4-methoxy-3-propoxyphenyl)pyrimidin-4-yl)acetate (Preparation 105, 5 g, 13.7 mmol). ¹H NMR (CD₃OD, 400 MHz): δ 8.05 (dd, J=2.1, 8.4 Hz, 1H), 8.01-8.03 (m, 1H), 7.46 (s, 1H), 7.05 (d, J=8.6 Hz, 1H), 6.24 (d, J=1.2 Hz, 1H), 5.81 (d, J=1.5 Hz, 1H), 4.81 (t, J=1.6 Hz, 2H), 4.21 (q, J=7.1 Hz, 2H), 4.05 (t, J=6.6 Hz, 2H), 3.91 (s, 3H), 3.88 (s, 2H), 1.80-1.92 (m, 2H), 1.26-1.31 (m, 3H), 1.08 (t, J=7.5 Hz, 3H), 0.95 (s, 9H), 0.13-0.16 (m, 6H). LCMS m/z=501 [MH]⁺.

Preparation 70: 4-(((tert-butyldimethylsilyl)oxy)methyl)-6-(3-((tert-butyldimethylsilyl)oxy)prop-1-en-2-yl)-2-(4-methoxy-3-propoxyphenyl)pyrimidine

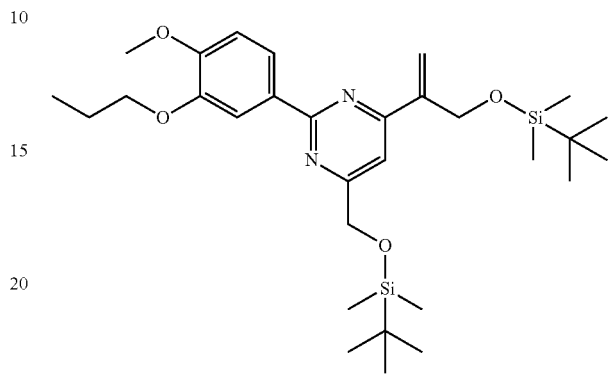

4-(((tert-butyldimethylsilyl)oxy)methyl)-6-(3-((tert-butyldimethylsilyl)oxy)prop-1-en-2-yl)-2-(4-methoxy-3-propoxyphenyl)pyrimidine (1 g, 77%) was prepared in an analogous manner to Preparation 58 using 4-(((tert-butyldimethylsilyl)oxy)methyl)-6-(3-((tert-butyldimethylsilyl)oxy)prop-1-en-2-yl)-2-chloropyrimidine (Preparation 89, 2.0 g, 5.2 mmol) and 2-(4-methoxy-3-propoxyphenyl)-4,4,5,5-tetramethyl-1,3,2-dioxaborolane (Preparation 114, 0.817 g, 2.8 mmol) at about 90° C. and substituting K₃PO₄ (1.55 g, 5.80 mmol) for K₂CO₃. ¹H NMR (CDCl₃, 400 MHz): δ 8.02-8.08 (m, 2H), 7.52 (s, 1H), 6.94-6.99 (m, 1H), 6.20 (d, J=1.5 Hz, 1H), 5.84 (d, J=1.5 Hz, 1H), 4.80-4.86 (m, 4H), 4.09-4.15 (m, 2H), 3.93-3.96 (m, 3H), 1.91-1.98 (m, 2H), 1.09 (t, J=7.5 Hz, 3H), 1.00 (s, 9H), 0.97 (s, 9H), 0.17 (s, 6H), 0.15 (s, 6H). LCMS m/z=559 [MH]⁺.

Preparation 71: 2-(4-((tert-butyldimethylsilyl)oxy)but-1-en-2-yl)-6-(4-methoxy-3-propoxyphenyl)pyridine

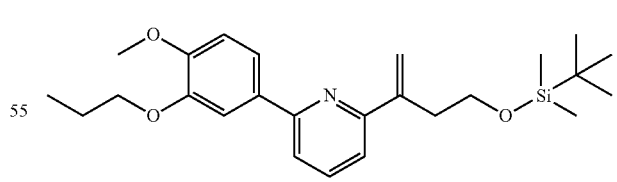

2-(4-((tert-butyldimethylsilyl)oxy)but-1-en-2-yl)-6-(4-methoxy-3-propoxyphenyl)pyridine (900 mg, 68%) was prepared in an analogous manner to Preparation 50 using 2-bromo-6-(4-methoxy-3-propoxyphenyl)pyridine (Preparation 93b, 1000 mg, 3.10 mmol) and tert-butyldimethyl((3-(4,4,5,5-tetramethyl-1,3,2-dioxaborolan-2-yl)but-3-en-1-yl)oxy)silane (Preparation 148, 969 mg, 3.10 mmol). LCMS m/z=428 [MH]⁺.

Preparation 72: 5-(3-((tert-butyldimethylsilyl)oxy)but-1-en-2-yl)-3-(4-methoxy-3-propoxyphenyl)pyridazine

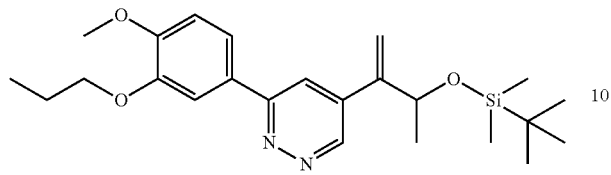

5-(3-((tert-butyldimethylsilyl)oxy)but-1-en-2-yl)-3-(4-methoxy-3-propoxyphenyl)pyridazine (3.0 g, 89%) was prepared in an analogous manner to Preparation 50 using 5-chloro-3-(4-methoxy-3-propoxyphenyl)pyridazine (Preparation 107, 2.2 g, 7.9 mmol) and tert-butyldimethyl((3-(4,4,5,5-tetramethyl-1,3,2-dioxaborolan-2-yl)but-3-en-2-yl)oxy)silane (Preparation 147, 4.9 g, 15.8 mmol). $^1$H NMR (CDCl$_3$, 400 MHz): δ 9.14 (d, J=2.0 Hz, 1H), 7.91 (d, J=2.0 Hz, 1H), 7.86 (d, J=2.0 Hz, 1H), 7.53 (dd, J=2.0, 8.3 Hz, 1H), 7.00 (d, J=8.3 Hz, 1H), 5.58 (s, 1H), 5.53 (s, 1H), 4.08-4.18 (m, 3H), 3.95 (s, 3H), 1.86-1.99 (m, 2H), 1.29 (d, J=6.9 Hz, 3H), 1.08 (t, J=7.3 Hz, 3H), 0.93 (s, 9H), 0.12 (d, J=19.6 Hz, 6H). LCMS m/z=429 [MH]$^+$.

Preparation 73: 3-(3-((tert-butyldimethylsilyl)oxy)prop-1-en-2-yl)-5-(3-ethoxy-4-methoxyphenyl)-4-methylpyridine

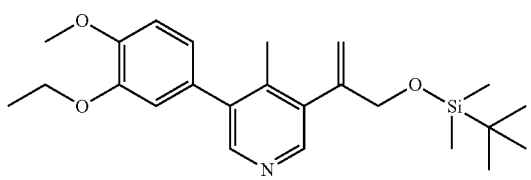 [SMILES: C=C(CO[Si](C)(C)C(C)(C)C)c1cncc(-c2ccc(OC)c(OCC)c2)c1C]

3-(3-((tert-butyldimethylsilyl)oxy)prop-1-en-2-yl)-5-(3-ethoxy-4-methoxyphenyl)-4-methylpyridine (0.8 g, 77%) was prepared in an analogous manner to Preparation 50 using 3-bromo-5-(3-ethoxy-4-methoxyphenyl)-4-methylpyridine (Preparation 108, 0.81 g, 3.28 mmol) and tert-butyldimethyl((2-(4,4,5,5-tetramethyl-1,3,2-dioxaborolan-2-yl)allyl)oxy)silane (Preparation 146, 0.98 g, 3.28 mmol). $^1$H NMR (CDCl$_3$, 400 MHz): δ 8.35 (s, 1H), 8.26 (s, 1H), 6.95 (d, J=8.2 Hz, 1H), 6.83-6.86 (m, 1H), 6.78 (d, J=2.0 Hz, 1H), 5.61-5.63 (m 1H), 5.10-5.12 (m, 1H), 4.31-4.32 (m, 2H), 4.12 (q, J=7.0 Hz, 2H), 3.93 (s, 3H), 2.21 (s, 3H), 1.48 (t, J=7.0 Hz, 3H), 0.91 (s, 9H), 0.08 (s, 6H). LCMS m/z=414 [MH]$^+$.

Preparation 74: 4-(3-((tert-butyldimethylsilyl)oxy)prop-1-en-2-yl)-2-(3-ethoxy-4-methoxyphenyl)thiazole

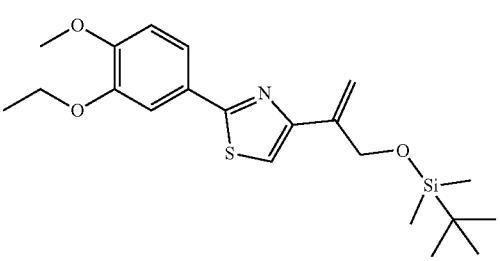 [SMILES: C=C(CO[Si](C)(C)C(C)(C)C)c1csc(-c2ccc(OC)c(OCC)c2)n1]

4-(3-((tert-butyldimethylsilyl)oxy)prop-1-en-2-yl)-2-(3-ethoxy-4-methoxyphenyl)thiazole was prepared (0.8 g, 91%) in an analogous manner to Preparation 50 using 4-bromo-2-(3-ethoxy-4-methoxyphenyl)thiazole (Preparation 109, 0.68 g, 2.16 mmol) and tert-butyldimethyl((2-(4,4,5,5-tetramethyl-1,3,2-dioxaborolan-2-yl)allyl)oxy)silane (Preparation 146, 0.84 g, 2.81 mmol). $^1$H NMR (CDCl$_3$, 400 MHz): δ 7.57 (d, J=2.3 Hz, 1H), 7.58 (dd, J=2.3, 8.3 Hz, 1H), 7.17 (s, 1H), 6.91 (d, J=8.3 Hz, 1H), 6.07-6.08 (m, 1H), 5.50-5.52 (m, 1H), 4.60-4.61 (m, 1H), 4.22 (q, J=7.0 Hz, 2H), 3.93 (s, 3H), 1.52 (t, J=7.0 Hz, 3H), 0.99 (s, 1H), 0.95 (s, 9H), 0.13 (s, 6H). LCMS m/z=406 [MH]$^+$.

Preparation 75: 2-((tert-butyldimethylsilyl)oxy)-1-(6-(4-methoxy-3-propoxyphenyl)pyridin-2-yl)ethan-1-one

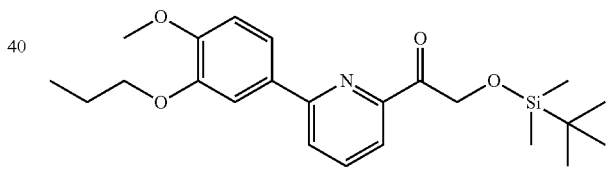

To a mixture of 1-(6-bromopyridin-2-yl)-2-((tert-butyldimethylsilyl)oxy)ethan-1-one (Preparation 88, 1270 mg, 4.36 mmol), K$_2$CO$_3$ (1000 mg, 7.27 mmol), KOAc (357 mg, 3.63 mmol), Pd(dppf)Cl$_2$-DCM (151 mg, 0.182 mmol) and a solution of 2-(4-methoxy-3-propoxyphenyl)-4,4,5,5-tetramethyl-1,3,2-dioxaborolane (Preparation 114, 1200 mg, 3.633 mmol) in 1,4-dioxane (24 mL) was added water (2.4 mL). The mixture was degassed and heated to about 90° C. for about 16 h under N$_2$. The reaction was filtered through a pad of MgSO$_4$ and silica gel, washing with DCM and EtOAc. The filtrate was concentrated and the residue was purified by column chromatography (silica) and eluted with heptane/EtOAc (100:0 to 95:5) to afford 2-((tert-butyldimethylsilyl)oxy)-1-(6-(4-methoxy-3-propoxyphenyl)pyridin-2-yl)ethan-1-one (1.21 g, 80%). $^1$H NMR (CDCl$_3$, 400 MHz): δ 7.84-7.93 (m, 3H), 7.72 (d, J=2.0 Hz, 1H), 7.58 (dd, J=2.0, 8.6 Hz, 1H), 7.00 (d, J=8.6 Hz, 1H), 5.42 (s, 2H), 4.12 (t, J=6.8 Hz, 2H), 3.95 (s, 3H), 1.90-2.00 (m, 2H), 1.10 (t, J=7.4 Hz, 3H), 1.00 (s, 9H), 0.16-0.20 (m, 6H). LCMS m/z=416 [MH]$^+$.

Preparation 76: 2-(5-(2-(difluoromethyl)-3-ethoxy-4-methoxyphenyl)pyridin-3-yl)prop-2-en-1-ol

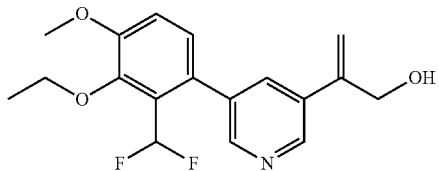 [SMILES: C=C(CO)c1cncc(-c2ccc(OC)c(OCC)c2C(F)F)c1]

2-(5-(2-(difluoromethyl)-3-ethoxy-4-methoxyphenyl)pyridin-3-yl)prop-2-en-1-ol (321 mg, 61%) was prepared in an analogous manner to Preparation 50 using 3-bromo-5-(2-(difluoromethyl)-3-ethoxy-4-methoxyphenyl)pyridine (Preparation 100, 558 mg, 1.56 mmol) at about 100° C. for about 15 h. $^1$H NMR (CDCl$_3$, 400 MHz): δ 8.70 (d, J=2.0 Hz, 1H), 8.52 (d, J=2.0 Hz, 1H), 7.76-7.79 (m, 1H), 7.07 (d, J=8.6 Hz, 1H), 7.01 (d, J=8.6 Hz, 1H), 6.96 (t, J=54.4 Hz, 1H), 5.60 (s, 1H), 5.49 (s, 1H), 4.58 (s, 2H), 4.12-4.22 (m, 2H), 3.93 (s, 3H), 1.75 (br s, 1H), 1.43 (t, J=7.0 Hz, 3H). LCMS m/z=336 [MH]$^+$.

Preparation 77: 3-(5-(iodomethyl)-2,2-dimethyl-1,3-dioxan-5-yl)-5-(4-methoxy-3-propoxyphenyl)pyridine

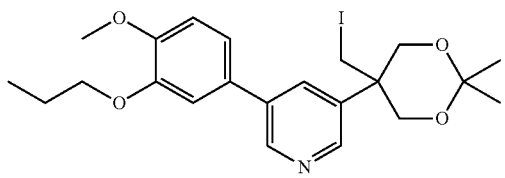 [SMILES: CCCOc1cc(-c2cncc(C3(CI)COC(C)(C)OC3)c2)ccc1OC]

To a solution of (5-(5-(4-methoxy-3-propoxyphenyl)pyridin-3-yl)-2,2-dimethyl-1,3-dioxan-5-yl)methyl methanesulfonate (Preparation 78, 140 mg, 0.30 mmol) in acetone (1.20 mL) was added lithium iodide (201 mg, 1.50 mmol). The solution was stirred at about 50° C. for about 16 h. The reaction was cooled to about 50° C., diluted with EtOAc, washed with water, dried over Na$_2$SO$_4$, filtered and concentrated. The residue was purified by column chromatography (silica) and eluted with heptane/EtOAc (100:0 to 0:100) to afford 3-(5-(iodomethyl)-2,2-dimethyl-1,3-dioxan-5-yl)-5-(4-methoxy-3-propoxyphenyl)pyridine (138 mg, 92%). $^1$H NMR (CDCl$_3$, 400 MHz): δ 8.74 (d, J=2.0 Hz, 1H), 8.45 (d, J=2.3 Hz, 1H), 7.66 (t, J=2.0 Hz, 1H), 7.08-7.17 (m, 2H), 7.00 (d, J=8.2 Hz, 1H), 4.25-4.37 (m, 2H), 4.14-4.23 (m, 2H), 4.07 (t, J=6.8 Hz, 2H), 3.93 (s, 3H), 3.81 (s, 2H), 1.92 (qd, J=7.2, 14.3 Hz, 2H), 1.49 (d, J=18.3 Hz, 6H), 1.08 (t, J=7.4 Hz, 3H). LCMS m/z=498 [MH]$^+$.

Preparation 78: (5-(5-(4-methoxy-3-propoxyphenyl)pyridin-3-yl)-2,2-dimethyl-1,3-dioxan-5-yl)methyl methanesulfonate

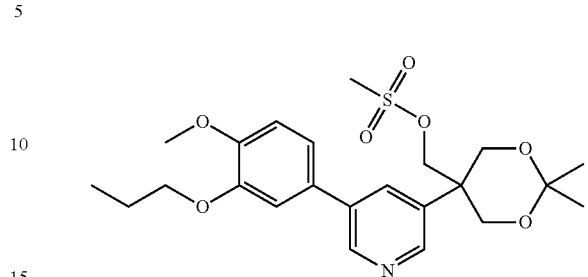

To a mixture of (5-(5-(4-methoxy-3-propoxyphenyl)pyridin-3-yl)-2,2-dimethyl-1,3-dioxan-5-yl)methanol (Preparation 79, 128 mg, 0.33 mmol) in DCM (7.0 mL) was added Me$_3$N (84 μL, 0.60 mmol), followed by MsCl (33 μL, 0.43 mmol). The solution was stirred at about 20° C. for about 3.5 h. The mixture was concentrated and the residue was purified by column chromatography (silica) and eluted with heptane/EtOAc (100:0 to 0:100) to afford (5-(5-(4-methoxy-3-propoxyphenyl)pyridin-3-yl)-2,2-dimethyl-1,3-dioxan-5-yl)methyl methanesulfonate (144 mg, 94%). $^1$H NMR (CDCl$_3$, 400 MHz): δ 8.75 (d, J=2.0 Hz, 1H), 8.47 (d, J=2.0 Hz, 1H), 7.72 (t, J=2.1 Hz, 1H), 7.08-7.17 (m, 2H), 6.99 (d, J=8.2 Hz, 1H), 4.78 (s, 2H), 4.20-4.28 (m, 2H), 4.03-4.18 (m, 4H), 3.93 (s, 3H), 2.92-3.01 (m, 3H), 1.87-1.96 (m, 2H), 1.51 (d, J=4.3 Hz, 6H), 1.08 (t, J=7.4 Hz, 3H).

Preparation 79: (5-(5-(4-methoxy-3-propoxyphenyl)pyridin-3-yl)-2,2-dimethyl-1,3-dioxan-5-yl)methanol

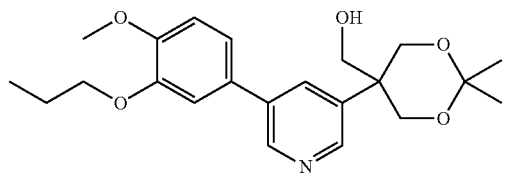 [SMILES: CCCOc1cc(-c2cncc(C3(CO)COC(C)(C)OC3)c2)ccc1OC]

To a solution of 2-(hydroxymethyl)-2-(5-(4-methoxy-3-propoxyphenyl)pyridin-3-yl)propane-1,3-diol (Preparation 80, 406 mg, 1.17 mmol) in DCM (12 mL) was added 2,2-dimethoxypropane (0.43 mL, 3.51 mmol) and pTSOH (33 mg, 0.18 mmol). The solution was stirred at about 40° C. for about 24 h and about 20° C. for about 4 days. The solution was concentrated and the residue was purified by column chromatography (silica) and eluted with heptane/EtOAc (100:0 to 0:100 gradient) to afford (5-(5-(4-methoxy-3-propoxyphenyl)pyridin-3-yl)-2,2-dimethyl-1,3-dioxan-5-yl)methanol (129 mg, 28%). $^1$H NMR (CDCl$_3$, 400 MHz): δ 8.71 (d, J=2.3 Hz, 1H), 8.50 (d, J=2.0 Hz, 1H), 7.75 (t, J=2.1 Hz, 1H), 7.05-7.15 (m, 2H), 6.99 (d, J=8.6 Hz, 1H), 4.19 (d, J=5.5 Hz, 3H), 4.12-4.17 (m, 3H), 4.06 (t, J=6.8 Hz, 2H), 3.93 (s, 3H), 1.91 (qd, J=7.2, 14.4 Hz, 2H), 1.62-1.64 (m, 1H), 1.49 (d, J=5.1 Hz, 6H), 1.08 (t, J=7.4 Hz, 3H). LCMS m/z=388 [MH]$^+$.

Preparation 80: 2-(hydroxymethyl)-2-(5-(4-methoxy-3-propoxyphenyl)pyridin-3-yl)propane-1,3-diol

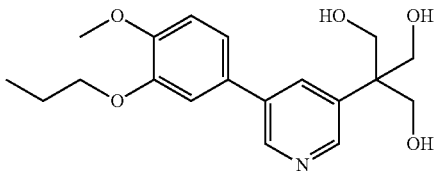 [SMILES: CCCOc1cc(-c2cncc(C(CO)(CO)CO)c2)ccc1OC]

To a solution of methyl 3-hydroxy-2-(hydroxymethyl)-2-(5-(4-methoxy-3-propoxyphenyl)pyridin-3-yl)propanoate (Preparation 81, 250 mg, 0.67 mmol) in methanol (2.0 mL) was added LiBH$_4$ (17.5 mg, 0.80 mmol). The solution was stirred at about 20° C. for about 21 h. The mixture was treated with saturated aqueous NH$_4$Cl and extracted with DCM. The DCM extracts were washed with brine, dried over Na$_2$SO$_4$, filtered and concentrated to afford 2-(hydroxymethyl)-2-(5-(4-methoxy-3-propoxyphenyl)pyridin-3-yl)propane-1,3-diol (55 mg, 24%). $^1$H NMR (CDCl$_3$, 400 MHz): δ 8.49 (br s, 1H), 8.28 (br s, 1H), 7.90 (br s, 1H), 6.83-7.00 (m, 2H), 6.77 (d, J=8.6 Hz, 1H), 4.78 (br s, 2H), 4.04 (br s, 5H), 3.74-3.99 (m, 6H), 1.74-1.91 (m, 2H), 1.26 (s, 1H), 1.00 (t, J=7.4 Hz, 3H). LCMS m/z=348 [MH]$^+$.

Preparation 81: methyl 3-hydroxy-2-(hydroxymethyl)-2-(5-(4-methoxy-3-propoxyphenyl)pyridin-3-yl)propanoate

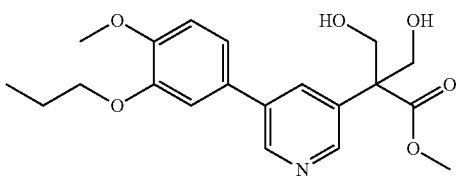 [SMILES: CCCOc1cc(-c2cncc(C(CO)(CO)C(=O)OC)c2)ccc1OC]

To a solution of methyl 2-(5-(4-methoxy-3-propoxyphenyl)pyridin-3-yl)acetate (Preparation 84, 65 g, 210 mmol) in DMSO (200 mL) was added paraformaldehyde (6.81 g, 227 mmol), followed by DMSO (300 mL). NaOMe (2.23 g, 41.2 mmol) was added, followed by another 100 mL of DMSO. The mixture was stirred at about 20° C. for about 18 h. The mixture was diluted with water (1200 mL) and extracted with diethyl ether and EtOAc. The diethyl ether and EtOAc combined extracts were washed with water, brine, dried over MgSO$_4$, filtered and concentrated. The residue was stirred with EtOH (200 mL) at about 65° C. until the residue was dissolved. The solution was cooled to about 20° C. with stirring for about 2 h. The mixture was cooled to about 0° C. (ice water bath) for an additional 1 h. The mixture was filtered, and the filter cake was washed with ice-cold EtOH. The combined EtOH filtrates were concentrated and the residue purified by column chromatography (silica) eluting with EtOAc/MeOH (95:5) to afford methyl 3-hydroxy-2-(hydroxymethyl)-2-(5-(4-methoxy-3-propoxyphenyl)pyridin-3-yl)propanoate (5.46 g, 7%). $^1$H NMR (CDCl$_3$, 400 MHz): δ 8.64 (d, J=2.0 Hz, 1H), 8.40 (d, J=2.0 Hz, 1H), 7.71 (t, J=2.0 Hz, 1H), 7.25 (s, 1H), 6.98-7.10 (m, 2H), 6.94 (t, J=7.3 Hz, 1H), 4.36 (d, J=11.3 Hz, 2H), 4.24 (d, J=11.3 Hz, 2H), 4.02 (t, J=6.6 Hz, 2H), 3.90 (s, 3H), 3.79 (s, 3H), 2.03 (s, 1H), 1.78-1.97 (m, 2H), 1.05 (t, J=7.4 Hz, 3H).

Preparation 82: 2-(5-(4-methoxy-3-propoxyphenyl)pyridin-3-yl)propane-1,3-diol

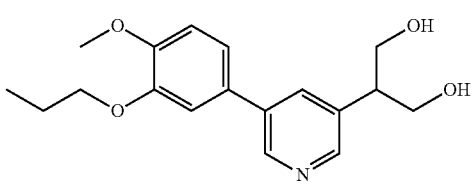 [SMILES: CCCOc1cc(-c2cncc(C(CO)CO)c2)ccc1OC]

To an ice cold solution of methyl 3-hydroxy-2-(5-(4-methoxy-3-propoxyphenyl)pyridin-3-yl)propanoate (Preparation 83, 26.4 g, 73.5 mmol) in MeOH (350 mL) was added LiBH$_4$ (3.2 g, 147 mmol) in 3 portions. The mixture was stirred for about 1 h. The mixture was concentrated and diluted with DCM. The mixture was washed with 2N NaOH. The DCM layer was separated, dried over Na$_2$SO$_4$, filtered and concentrated. The residue was purified by column chromatography (silica) and eluted with DCM/MeOH (100:0 to 90:10) to afford 2-(5-(4-methoxy-3-propoxyphenyl)pyridin-3-yl)propane-1,3-diol (20.3 g, 87%). $^1$H NMR (DMSO-d$_6$, 400 MHz): δ 8.68 (d, J=2.3 Hz, 1H), 8.37 (d, J=2.0 Hz, 1H), 7.84 (t, J=2.3 Hz, 1H), 7.21-7.25 (m, 2H), 7.06 (d, J=8.2 Hz, 1H), 4.64 (t, J=5.4 Hz, 2H), 4.03 (t, J=6.6 Hz, 2H), 3.81 (s, 3H), 3.65-3.79 (m, 4H), 2.89-2.95 (m, 1H), 1.72-1.80 (m, 2H), 1.00 (t, J=7.4 Hz, 3H). LCMS m/z=318 [MH]$^+$.

Preparation 83: methyl 3-hydroxy-2-(5-(4-methoxy-3-propoxyphenyl)pyridin-3-yl)propanoate

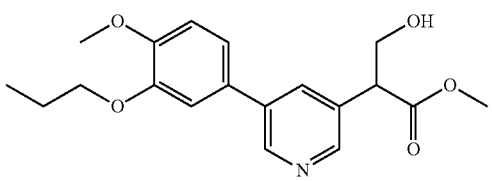 [SMILES: CCCOc1cc(-c2cncc(C(CO)C(=O)OC)c2)ccc1OC]

A mixture of methyl 2-(5-(4-methoxy-3-propoxyphenyl)pyridin-3-yl)acetate (Preparation 84, 30.0 g, 95 mmol), paraformaldehyde (3.14 g, 105 mmol) and NaOMe (1.03 g, 19.0 mmol) in anhydrous DMSO (317 mL) was stirred at about 20° C. for about 16 h. The mixture was diluted with water (1200 mL) and extracted with diethyl ether and EtOAc. The combined diethyl ether and EtOAc extracts were washed with water, brine, dried over MgSO$_4$, filtered and concentrated. The residue was dissolved in hot EtOH (120 mL). The solution was cooled to about 20° C. with stirring. Further cooling, to about 0° C. (ice bath) affording a precipitate which was filtered to afford methyl 3-hydroxy-2-(5-(4-methoxy-3-propoxyphenyl)pyridin-3-yl)propanoate (15.6 g). The filtrate was concentrated and purified by column chromatography (silica) to provide additional solid (10.8 g). The solids were combined to afford methyl 3-hydroxy-2-(5-(4-methoxy-3-propoxyphenyl)pyridin-3-yl)propanoate (26.4 g, 78%). $^1$H NMR (CDCl$_3$, 400 MHz): δ 8.72 (d, J=2.0 Hz, 1H), 8.45 (d, J=2.3 Hz, 1H), 7.76 (t, J=2.0 Hz, 1H), 7.07-7.12 (m, 2H), 6.97 (d, J=8.6 Hz, 1H), 4.16-4.22

(m, 1H), 4.05 (t, J=7.0 Hz, 2H), 3.91-3.99 (m, 5H), 3.76 (s, 3H), 2.66-2.70 (m, 1H), 1.67-1.95 (m, 2H), 1.08 (t, J=7.4 Hz, 3H). LCMS m/z=346 [MH]+.

Preparation 84: methyl 2-(5-(4-methoxy-3-propoxyphenyl)pyridin-3-yl)acetate

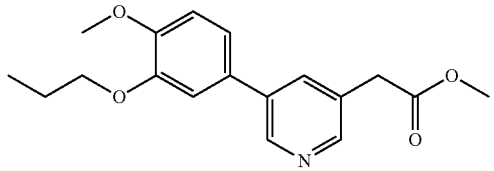 [SMILES: CCCOc1cc(-c2cncc(CC(=O)OC)c2)ccc1OC]

A mixture of methyl 2-(5-bromopyridin-3-yl)acetate (55.5 g, 241.0 mmol), 2-(4-methoxy-3-propoxyphenyl)-4,4,5,5-tetramethyl-1,3,2-dioxaborolane (Preparation 114, 84.7 g, 290 mmol) and anhydrous Na₂CO₃ (51.1 g, 482 mmol) in 1,4-dioxane (700 mL) and water (180 mL) was degassed and stirred at about 20° C. for about 20 min under N₂. Pd(dppf)Cl₂ (9.85 g, 12.1 mmol) was added to the mixture, which was heated to about 85° C. for about 18 h under N₂. The reaction was cooled to about 20° C. and concentrated. The residue was partitioned between water and EtOAc. The aqueous layer was extracted with EtOAc. The combined EtOAc extracts were washed with water, brine, dried over Na₂SO₄, filtered and concentrated. The residue was purified by column chromatography (silica) eluting with heptane/EtOAc (85:15 to 40:60) to afford methyl 2-(5-(4-methoxy-3-propoxyphenyl)pyridin-3-yl)acetate (75.4 g, 88%). ¹H NMR (CDCl₃, 400 MHz): δ 8.72 (d, J=2.0 Hz, 1H), 8.46 (d, J=2.0 Hz, 1H), 7.77 (t, J=2.0 Hz, 1H), 7.13 (dd, J=2.3, 8.6 Hz, 1H), 7.09 (d, J=2.3 Hz, 1H), 6.98 (d, J=8.6 Hz, 1H), 4.06 (t, J=6.8 Hz, 2H), 3.92 (s, 3H), 3.70 (s, 2H), 2.94 (s, 3H), 1.86-1.95 (m, 2H), 1.08 (t, J=7.4 Hz, 3H). LCMS m/z=316 [MH]+.

Preparation 85: methyl 2-(2'-cyano-4'-methoxy-3'-propoxy-[1,1'-biphenyl]-3-yl)acetate

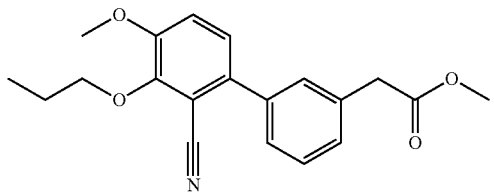 [SMILES: CCCOc1c(OC)ccc(-c2cccc(CC(=O)OC)c2)c1C#N]

To a solution of 6-bromo-3-methoxy-2-propoxybenzonitrile (Preparation 171, 10.0 g, 37.02 mmol), (3-(2-methoxy-2-oxoethyl)phenyl)boronic acid (7.18 g, 37.02 mmol), Pd(dppf)Cl₂ (1.35 g, 1.85 mmol), KOAc (3.63 g, 37.02 mmol) and Na₂CO₃ (7.85 g, 74.04 mmol) in 1,4-dioxane (100 mL) and water (5 mL) was degassed and heated to about 90° C. for about 5 h under N₂. The mixture was filtered and concentrated. The residue was purified by column chromatography (silica) and eluted with pet. ether/EtOAc (4:1) to afford methyl 2-(2'-cyano-4'-methoxy-3'-propoxy-[1,1'-biphenyl]-3-yl)acetate (12.0 g, 96%). ¹H NMR (CDCl₃, 400 MHz): δ 7.40-7.44 (m, 3H), 7.33 (d, J=6.8 Hz, 1H), 7.15 (d, J=8.8 Hz, 2H), 4.18 (t, J=6.8 Hz, 2H), 3.92 (s, 3H), 3.71 (d, J=5.6 Hz, 5H), 1.83-1.92 (m, 2H), 1.09 (t, J=7.2 Hz, 3H).

Preparation 86: 3-bromo-5-(3-((tert-butyldimethylsilyl)oxy)prop-1-en-2-yl)pyridine

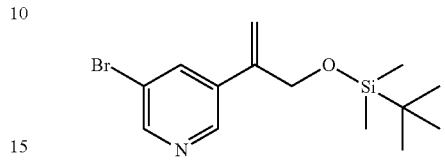

A mixture of tert-butyldimethyl((2-(4,4,5,5-tetramethyl-1,3,2-dioxaborolan-2-yl)allyl)oxy)silane (Preparation 146, 14.9 g, 50 mmol), 3,5-dibromopyridine (12.4 g, 52.5 mmol), Pd(dppf)Cl₂ (1.83 g, 2.5 mmol) and K₂CO₃ (20.7 g, 150 mmol) were suspended in 1,4-dioxane (300 mL) and water (20 mL). The mixture was degassed and heated to about 85° C. for about 5 h under N₂. The mixture was removed from heat and allowed to stand over the weekend. The mixture was concentrated, MTBE (100 mL) was added and stirred for about 20 min. The mixture was filtered and the filter cake was washed with MTBE (50 mL). The combined MTBE filtrates were dried and concentrated. The residue was purified by column chromatography (silica) eluting with pet. ether/EtOAc (100:0 to 95:5) to afford 3-bromo-5-(3-((tert-butyldimethylsilyl)oxy)prop-1-en-2-yl)pyridine (8.5 g, 51.8%). ¹H NMR (CDCl₃, 400 MHz): δ 8.55-8.63 (m, 2H), 7.84-7.93 (m, 1H), 5.44-5.55 (m, 2H), 4.49 (t, J=1.5 Hz, 2H), 0.91 (s, 9H), 0.10 (s, 6H). LCMS m/z=329 [MH]+.

Preparation 87: 3-bromo-5-(3-((tert-butyldimethylsilyl)oxy)prop-1-en-2-yl)-2-methylpyridine

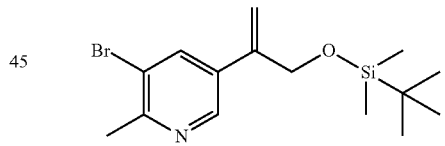

A mixture of tert-butyldimethyl((2-(4,4,5,5-tetramethyl-1,3,2-dioxaborolan-2-yl)allyl)oxy)silane (Preparation 146, 4.2 g, 14.08 mmol), 3,5-dibromo-2-methylpyridine (3.71 g, 14.8 mmol), Pd(dppf)Cl₂ (1030 mg, 1.41 mmol) and K₂CO₃ (5.84 g, 42.2 mmol) were suspended in 1,4-dioxane (150 mL) and water (5 mL). The mixture was degassed and heated to about 80° C. for about 5 h under N₂. The mixture was concentrated and MTBE (100 mL) was added, stirring for about 20 min. The mixture was filtered and the filter cake was washed with MTBE (50 mL). The combined MTBE filtrates were concentrated and the residue was purified by column chromatography (silica) eluting with pet. ether/EtOAc (100:0 to 95:5) to afford 3-bromo-5-(3-((tert-butyldimethylsilyl)oxy)prop-1-en-2-yl)-2-methylpyridine (930 mg, 19.3%). ¹H NMR (CDCl₃, 400 MHz): δ 8.46-8.53 (m, 1H), 7.86 (d, J=2.0 Hz, 1H), 5.41-5.50 (m, 2H), 4.43-4.54 (m, 2H), 2.66 (s, 3H), 0.92 (s, 9H), 0.10 (s, 6H).

137

Preparation 88: 1-(6-bromopyridin-2-yl)-2-((tert-butyldimethylsilyl)oxy)ethan-1-one

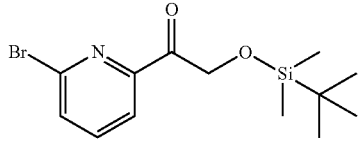 [SMILES: CC(C)(C)[Si](C)(C)OCC(=O)c1cccc(Br)n1]

A solution of 1-(6-bromopyridin-2-yl)-2-hydroxyethan-1-one (Preparation 237, 977 mg, 4.52 mmol) and DCM (30 mL) cooled to about 0° C., was added imidazole (770 mg, 11.3 mmol) and TBS-Cl (750 mg, 4.97 mmol). The mixture was stirred at about 0° C. for about 2.5 h. The reaction was quenched with water and the layers were separated. The DCM layer was washed with water and brine. The DCM layer was passed through a pad of MgSO₄ and silica gel. The filtrate was concentrated to afford 1-(6-bromopyridin-2-yl)-2-((tert-butyldimethylsilyl)oxy)ethan-1-one (1.35 g, 90%). ¹H NMR (CDCl₃, 400 MHz): δ 7.93-8.04 (m, 1H), 7.62-7.78 (m, 2H), 5.21 (s, 2H), 0.97 (s, 9H), 0.15 (s, 6H).

Preparation 89: 4-(((tert-butyldimethylsilyl)oxy)methyl)-6-(3-((tert-butyldimethylsilyl)oxy)prop-1-en-2-yl)-2-chloropyrimidine

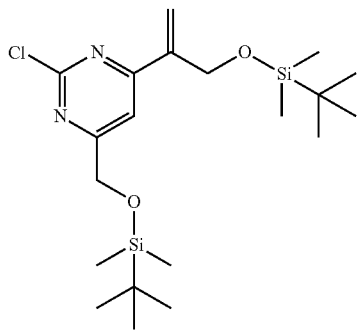 [SMILES: C=C(CO[Si](C)(C)C(C)(C)C)c1cc(CO[Si](C)(C)C(C)(C)C)nc(Cl)n1]

4-(((tert-butyldimethylsilyl)oxy)methyl)-6-(3-((tert-butyldimethylsilyl)oxy)prop-1-en-2-yl)-2-chloropyrimidine (0.9 g, 34%) was prepared in an analogous manner to Preparation 50 using 4-(((tert-butyldimethylsilyl)oxy)methyl)-2,6-dichloropyrimidine (Preparation 230, 1.65 g, 5.5 mmol) and K₃PO₄ as base. ¹H NMR (CDCl₃, 400 MHz): δ 7.63 (s, 1H), 6.23 (d, J=1.5 Hz, 1H), 5.87 (d, J=1.5 Hz, 1H), 4.76 (d, J=1.0 Hz, 2H), 4.62-4.66 (m, 2H), 0.97-0.99 (m, 9H), 0.94 (s, 9H), 0.12-0.16 (m, 12H). LCMS m/z=429 [MH]⁺.

138

Preparation 90: 4-(3-((tert-butyldimethylsilyl)oxy)prop-1-en-2-yl)-2-chloro-6-(trifluoromethyl)pyrimidine

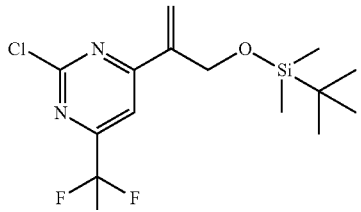

4-(3-((tert-butyldimethylsilyl)oxy)prop-1-en-2-yl)-2-chloro-6-(trifluoromethyl)pyrimidine (1.33 g, 66%) was prepared in an analogous manner to Preparation 50 using 2,4-dichloro-6-(trifluoromethyl)pyrimidine (CAS 16097-64-6, 1.24 g, 5.72 mmol) and substituting K₃PO₄ (4.57 g, 17.1 mmol) for K₂CO₃. ¹H NMR (CDCl₃, 400 MHz): δ 7.77 (s, 1H), 6.38-6.39 (m, 1H), 5.99-6.00 (m, 1H), 4.65 (t, J=1.5 Hz, 2H), 0.92-0.94 (m, 9H), 0.13 (s, 6H). LCMS m/z=353 [MH]⁺.

Preparation 91a: 3-(3,4-dimethoxyphenyl)-5-(4,4,5,5-tetramethyl-1,3,2-dioxaborolan-2-yl)pyridine

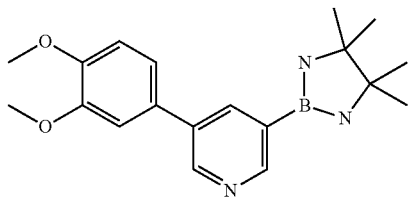

A mixture of 3-bromo-5-(3,4-dimethoxyphenyl)pyridine (Preparation 91b, 12.20 g, 41.48 mmol), Pin₂B₂ (21.07 g, 82.96 mmol), KOAc (8.14 g, 82.96 mmol) and Pd(dppf)Cl₂ (607 mg, 830 umol) in 1,4-dioxane (500 mL) was degassed and stirred at about 110° C. for about 4 h under N₂. The mixture was concentrated and the residue was purified by column chromatography (silica) eluting with pet. ether/EtOAc (100:1 to 10:1) to afford 3-(3,4-dimethoxyphenyl)-5-(4,4,5,5-tetramethyl-1,3,2-dioxaborolan-2-yl)pyridine (6.00 g, 42%). ¹H NMR (CDCl₃, 400 MHz): δ 8.97 (d, J=2.3 Hz, 1H), 8.71 (d, J=1.0 Hz, 1H), 8.14 (s, 1H), 7.27 (s, 1H), 7.22-7.26 (m, 1H), 7.06 (d, J=8.3 Hz, 1H), 3.86 (s, 3H), 3.80 (s, 3H), 1.33 (s, 13H).

Preparation 91b: 3-bromo-5-(3,4-dimethoxyphenyl)pyridine

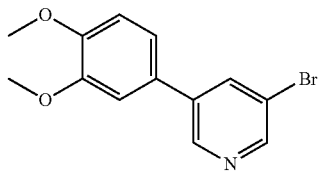 [SMILES: COc1ccc(-c2cncc(Br)c2)cc1OC]

A mixture of 3,5-dibromopyridine (17.90 g, 75.56 mmol), (3,4-dimethoxyphenyl) boronic acid (CAS 122775-35-3, 12.50 g, 68.69 mmol), Na₂CO₃ (10.92 g, 103.0 mmol), KOAc (10.11 g, 103.03 mmol) and Pd(dppf)Cl₂ (1.01 g, 1.37 mmol) in 1,4-dioxane (20 mL) was degassed and stirred at about 90° C. for about 8 h under N₂. The mixture was filtered and concentrated The residue was purified by column chromatography (silica) and eluted with pet. ether/EtOAc (20:1 to 1:1) to afford 3-bromo-5-(3,4-dimethoxyphenyl)pyridine (20.2 g, 59%). ¹H NMR (DMSO-d₆, 400 MHz): δ 8.88 (d, J=1.8 Hz, 1H), 8.61 (d, J=1.8 Hz, 1H), 8.35 (t, J=2.0 Hz, 1H), 7.28-7.35 (m, 2H), 7.05 (d, J=7.9 Hz, 1H), 3.85 (s, 3H), 3.79 (s, 3H). LCMS m/z=294 [MH]⁺.

Preparation 92:
3-Bromo-5-(3-ethoxy-4-methoxyphenyl)pyridine

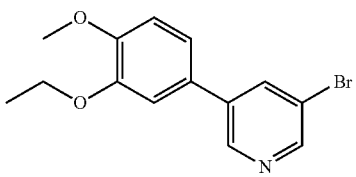 [SMILES: CCOc1cc(-c2cncc(Br)c2)ccc1OC]

A mixture of 2-(3-ethoxy-4-methoxyphenyl)-4,4,5,5-tetramethyl-1,3,2-dioxaborolane (Preparation 113, 20.0 g, 71.9 mmol), 3,5-dibromopyridine (34.07 g, 143.8 mmol), K₂CO₃ (19.87 g, 143.8 mmol), KOAc (10.58 g, 107.9 mmol) and Pd(dppf)Cl₂ (2.10 g, 2.88 mmol) in 1,4-dioxane (600 mL) and water (10 mL) was degassed and heated to about 100° C. for about 5 h under N₂. The mixture was filtered and concentrated. The residue was purified by column chromatography (silica) and eluted with pet. ether/EtOAc (5:1) to afford 3-bromo-5-(3-ethoxy-4-methoxyphenyl)pyridine (20 g, 90%). ¹H NMR (CDCl₃, 400 MHz): δ 8.71 (s, 1H), 8.60 (s, 1H), 7.96 (s, 1H), 7.11 (dd, J=2.0, 8.4 Hz, 1H), 7.05 (s, 1H), 6.97 (t, J=4.0 Hz, 1H), 4.18 (q, J=6.8 Hz, 2H), 3.92 (s, 3H), 1.49 (t, J=6.8 Hz, 3H).

Preparation 93a:
3-bromo-5-(4-methoxy-3-propoxyphenyl)pyridine

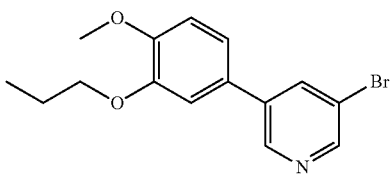 [SMILES: CCCOc1cc(-c2cncc(Br)c2)ccc1OC]

2-(4-Methoxy-3-propoxyphenyl)-4,4,5,5-tetramethyl-1,3,2-dioxaborolane (Preparation 114, 28.00 g, 95.83 mmol), 3,5-dibromopyridine (45.40 g, 191.66 mmol), K₂CO₃ (19.87 g, 143.75 mmol), KOAc (14.11 g, 143.75 mmol) and Pd(dppf)Cl₂ (3.51 g, 4.79 mmol) in 1,4-dioxane (600 mL) and water (10 mL) was degassed and heated to about 100° C. for about 5 h under N₂. The mixture was filtered and concentrated. The residue was purified by column chromatography (silica) and eluted with pet. ether/EtOAc (5:1) to afford 3-bromo-5-(4-methoxy-3-propoxyphenyl)pyridine (15.00 g, 49%). ¹H NMR (CDCl₃, 400 MHz): δ 8.72 (d, J=2.0 Hz, 1H), 8.61 (d, J=2.0 Hz, 1H), 7.97 (t, J=2.0 Hz, 1H), 7.12 (dd, J=2.0, 8.4 Hz, 1H), 7.06 (d, J=2.4 Hz, 1H), 6.98 (d, J=8.4 Hz, 1H), 4.06 (t, J=6.8 Hz, 2H), 3.93 (s, 3H), 1.87-1.96 (m, 2H), 1.08 (t, J=7.2 Hz, 3H).

Preparation 93b:
2-bromo-6-(4-methoxy-3-propoxyphenyl)pyridine

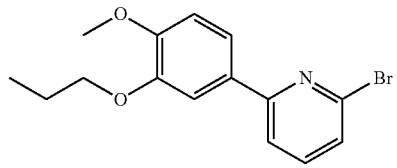 [SMILES: CCCOc1cc(-c2cccc(Br)n2)ccc1OC]

2-(4-Methoxy-3-propoxyphenyl)-4,4,5,5-tetramethyl-1,3,2-dioxaborolane (Preparation 114, 10.6 g, 36.3 mmol), 2,6-dibromopyridine (9.0 g, 38.0 mmol), K₃PO₄ (16.1 g, 76.0 mmol) and Pd(dppf)Cl₂ (1.55 g, 1.90 mmol) in dioxane (6 mL) and water (1.5 mL) was degassed and heated to about 80° C. overnight. The mixture was diluted with brine (150 mL) and EtOAc (150 mL). The layers were separated and the EtOAc layer was washed with brine (75 mL), dried over Na₂SO₄, filtered and concentrated. The residue was purified by column chromatography (silica) and eluted with heptane/EtOAc (100:0 to 3:1) to afford 2-bromo-6-(4-methoxy-3-propoxyphenyl)pyridine (5.34 g, 44%). ¹H NMR (CDCl₃, 400 MHz): δ 7.81-8.72 (m, 2H), 7.51-7.57 (m, 2H), 7.35 (d, J=7.4 Hz, 1H), 6.95 (d, J=8.2 Hz, 1H), 4.11 (t, J=6.6 Hz, 2H), 3.93 (s, 3H), 1.86-1.97 (m, 2H), 1.09 (t, J=7.4 Hz, 3H).

Preparation 94:
3-bromo-5-(3-isopropoxy-4-methoxyphenyl)pyridine

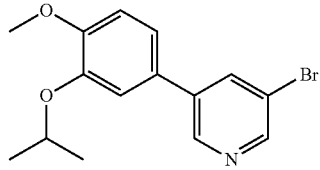 [SMILES: COc1ccc(-c2cncc(Br)c2)cc1OC(C)C]

3-bromo-5-(3-isopropoxy-4-methoxyphenyl)pyridine (1.15 g, 52%) was prepared in an analogous manner to Preparation 93a using 2-(3-isopropoxy-4-methoxyphenyl)-4,4,5,5-tetramethyl-1,3,2-dioxaborolane (Preparation 115, 2 g, 6.8 mmol) at about 120° C. for about 2 h. ¹H NMR (CDCl₃, 400 MHz): δ8.71 (d, J=1.5 Hz, 1H), 8.61 (d, J=2.5 Hz, 1H), 7.95-7.98 (m, 1H), 7.12-7.16 (m, 1H), 7.09 (d, J=2.5 Hz, 1H), 6.99 (d, J=8.5 Hz, 1H), 4.58-4.67 (m, 1H), 3.92 (s, 3H), 1.42 (d, J=6.0 Hz, 6H). LCMS m/z=323 [MH]⁺.

Preparation 95:
3-bromo-5-(3-cyclopropoxy-4-methoxyphenyl)pyridine

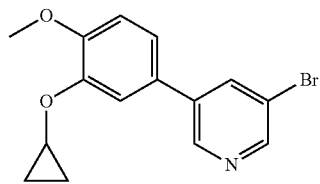 [SMILES: COc1ccc(-c2cncc(Br)c2)cc1OC1CC1]

3-bromo-5-(3-cyclopropoxy-4-methoxyphenyl)pyridine (860 mg, 52%) was prepared in an analogous manner to Preparation 93a using 2-(3-cyclopropoxy-4-methoxyphenyl)-4,4,5,5-tetramethyl-1,3,2-dioxaborolane (Preparation 117, 1.5 g, 5.2 mmol) at about 120° C. for about 2 h. $^1$H NMR (CDCl$_3$, 400 MHz): δ 8.74 (d, J=2.0 Hz, 1H), 8.62 (d, J=2.5 Hz, 1H), 7.99 (t, J=2.2 Hz, 1H), 7.43 (d, J=2.0 Hz, 1H), 7.14 (dd, J=2.5, 8.3 Hz, 1H), 6.97 (d, J=8.3 Hz, 1H), 3.92 (s, 3H), 3.81-3.87 (m, 1H), 0.83-0.96 (m, 4H). LCMS m/z=321 [MH]$^+$.

Preparation 96: 3-bromo-5-(3-(2-((tert-butyldimethylsilyl)oxy)ethoxy)-4-methoxyphenyl)pyridine
3-bromo-5-(3-(2-((tert-butyldimethylsilyl)oxy)ethoxy)-4-methoxyphenyl)pyridine

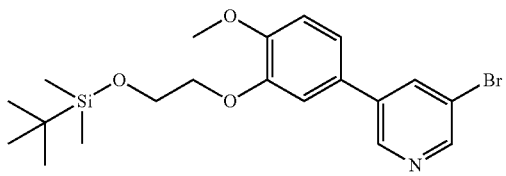 [SMILES: COc1ccc(-c2cncc(Br)c2)cc1OCCO[Si](C)(C)C(C)(C)C]

3-bromo-5-(3-(2-((tert-butyldimethylsilyl)oxy)ethoxy)-4-methoxyphenyl)pyridine 3-bromo-5-(3-(2-((tert-butyldimethylsilyl)oxy)ethoxy)-4-methoxyphenyl)pyridine (6.8 g, 32%) was prepared in an analogous manner to Preparation 93a using tert-butyl(2-(2-methoxy-5-(4,4,5,5-tetramethyl-1,3,2-dioxaborolan-2-yl)phenoxy)ethoxy)dimethylsilane (Preparation 120, 20 g, 49 mmol) at about 120° C. for about 3 h. $^1$H NMR (CDCl$_3$, 400 MHz): δ 8.69-8.78 (m, 1H), 8.61 (d, J=2.2 Hz, 1H), 7.97 (t, J=2.1 Hz, 1H), 7.13 (qd, J=2.2, 4.4 Hz, 2H), 6.98 (d, J=8.8 Hz, 1H), 4.16-4.23 (m, 2H), 4.02-4.09 (m, 2H), 3.92 (s, 3H), 0.88-0.93 (m, 9H), 0.10 (s, 6H). LCMS m/z=439 [MH]$^+$.

Preparation 97: 3-bromo-5-(3-(3-((tert-butyldimethylsilyl)oxy)propoxy)-4-methoxyphenyl)pyridine

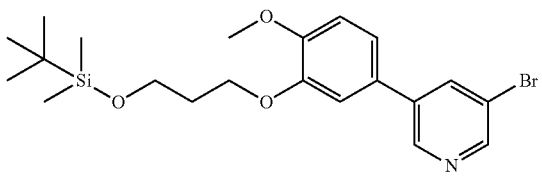 [SMILES: COc1ccc(-c2cncc(Br)c2)cc1OCCCO[Si](C)(C)C(C)(C)C]

3-bromo-5-(3-(3-((tert-butyldimethylsilyl)oxy)propoxy)-4-methoxyphenyl)pyridine (12.4 g, 64%) was prepared in an analogous manner to Preparation 93a using tert-butyl(3-(2-methoxy-5-(4,4,5,5-tetramethyl-1,3,2-dioxaborolan-2-yl)phenoxy)propoxy)dimethylsilane (Preparation 121, 18 g, 42.6 mmol). $^1$H NMR (CDCl$_3$, 400 MHz): δ 8.68 (d, J=2.0 Hz, 1H), 8.58 (d, J=2.5 Hz, 1H), 7.94-8.01 (m, 1H), 7.10 (dd, J=2.5, 8.3 Hz, 1H), 7.07 (d, J=2.0 Hz, 1H), 6.96 (d, J=8.3 Hz, 1H), 4.19 (t, J=6.4 Hz, 2H), 3.90 (s, 3H), 3.80-3.86 (m, 2H), 2.03-2.11 (m, 2H), 0.85-0.90 (m, 9H), 0.04 (s, 6H). LCMS m/z=454 [MH]$^+$.

Preparation 98: 3-bromo-5-(3-(2-fluoroethoxy)-4-methoxyphenyl)pyridine

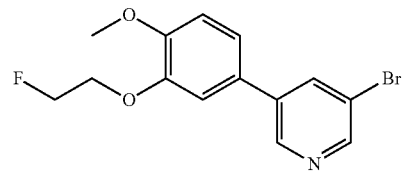 [SMILES: COc1ccc(-c2cncc(Br)c2)cc1OCCF]

3-Bromo-5-(3-(2-fluoroethoxy)-4-methoxyphenyl)pyridine (1.8 g, 74%) was prepared in an analogous manner to Preparation 93a using 2-(3-(2-fluoroethoxy)-4-methoxyphenyl)-4,4,5,5-tetramethyl-1,3,2-dioxaborolane (Preparation 122, 2.2 g, 7.4 mmol) at about 120° C. for about 2 h. $^1$H NMR (CDCl$_3$, 400 MHz): δ 8.68-8.76 (m, 1H), 8.58-8.65 (m, 1H), 7.97 (t, J=2.3 Hz, 1H), 7.18 (dd, J=2.0, 8.5 Hz, 1H), 7.12 (d, J=2.0 Hz, 1H), 7.00 (d, J=8.5 Hz, 1H), 4.83-4.92 (m, 1H), 4.72-4.81 (m, 1H), 4.37-4.44 (m, 1H), 4.25-4.36 (m, 1H), 3.88-3.97 (m, 3H). LCMS m/z=325 [MH]$^+$.

Preparation 99: 3-bromo-5-(3-(3-fluoropropoxy)-4-methoxyphenyl)pyridine

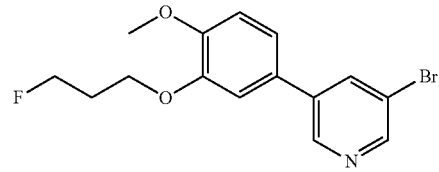 [SMILES: COc1ccc(-c2cncc(Br)c2)cc1OCCCF]

3-Bromo-5-(3-(3-fluoropropoxy)-4-methoxyphenyl)pyridine was prepared in an analogous manner to Preparation 93a using 2-(3-(3-fluoropropoxy)-4-methoxyphenyl)-4,4,5,5-tetramethyl-1,3,2-dioxaborolane (Preparation 123).

Preparation 100: 3-bromo-5-(2-(difluoromethyl)-3-ethoxy-4-methoxyphenyl)pyridine

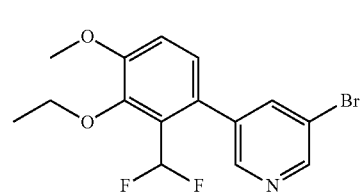 [SMILES: CCOc1c(OC)ccc(-c2cncc(Br)c2)c1C(F)F]

3-Bromo-5-(2-(difluoromethyl)-3-ethoxy-4-methoxyphenyl)pyridine (1000 mg, 28%) was prepared in an analogous manner to Preparation 93a using 2-(2-(difluoromethyl)-3-ethoxy-4-methoxyphenyl)-4,4,5,5-tetramethyl-1,3,2-dioxaborolane (Preparation 127, 4.09 g, 12.46 mmol) heated to about 100° C. for about 15 h. $^1$H NMR (400 MHz, CDCl$_3$): δ 8.67 (d, J=2.0 Hz, 1H), 8.52 (d, J=1.5 Hz, 1H), 7.86 (t, J=2.0 Hz, 1H), 6.84-7.13 (m, 4H), 4.17 (q, J=7.4 Hz, 2H), 3.93 (s, 3H), 1.42 (t, J=7.0 Hz, 3H). LCMS m/z=359 [MH]$^+$.

Preparation 101: 3-bromo-5-(5-ethoxy-2-fluoro-4-methoxyphenyl)pyridine

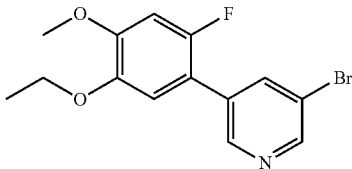 [SMILES: CCOc1cc(-c2cncc(Br)c2)c(F)cc1OC]

3-Bromo-5-(5-ethoxy-2-fluoro-4-methoxyphenyl)pyridine (350 mg, 27%) was prepared as in an analogous manner to Preparation 93a using 2-(5-ethoxy-2-fluoro-4-methoxyphenyl)-4,4,5,5-tetramethyl-1,3,2-dioxaborolane (Preparation 134, 1.2 g, 4.05 mmol). $^1$H NMR (CDCl$_3$, 400 MHz): δ 8.68 (t, J=1.7 Hz, 1H), 8.63 (d, J=2.1 Hz, 1H), 7.98-8.00 (m, 1H), 6.88 (d, J=7.3 Hz, 1H), 6.75 (d, J=11.7 Hz, 1H), 4.12 (q, J=7.0 Hz, 2H), 3.92 (s, 3H), 1.49 (t, J=7.0 Hz, 3H). LCMS m/z=327 [MH]$^+$.

Preparation 102: 3-bromo-5-(2-fluoro-4-methoxy-5-propoxyphenyl)pyridine

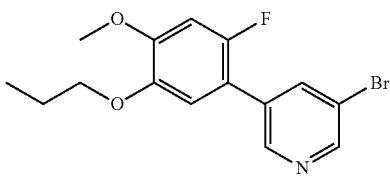 [SMILES: CCCOc1cc(-c2cncc(Br)c2)c(F)cc1OC]

3-Bromo-5-(2-fluoro-4-methoxy-5-propoxyphenyl)pyridine (3.4 g, 31%) was prepared as in an analogous manner to Preparation 93a using 2-(2-fluoro-4-methoxy-5-propoxyphenyl)-4,4,5,5-tetramethyl-1,3,2-dioxaborolane (Preparation 138, 10 g, 32 mmol). $^1$H NMR (CDCl$_3$, 400 MHz): δ 8.68 (t, J=1.5 Hz, 1H), 8.63 (d, J=2.4 Hz, 1H), 7.99 (q, J=2.0 Hz, 1H), 6.88 (d, J=7.8 Hz, 1H), 6.75 (d, J=11.7 Hz, 1H), 4.00 (t, J=6.8 Hz, 2H), 3.91 (s, 3H), 1.84-1.93 (m, 2H), 1.06 (t, J=7.6 Hz, 3H). LCMS m/z=339 [MH]$^+$.

Preparation 103: 5'-chloro-3-fluoro-5-methoxy-6-propoxy-2,3'-bipyridine

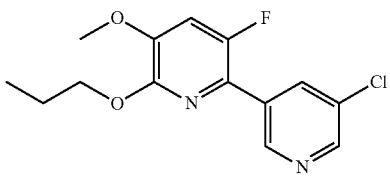 [SMILES: CCCOc1nc(-c2cncc(Cl)c2)c(F)cc1OC]

5'-Chloro-3-fluoro-5-methoxy-6-propoxy-2,3'-bipyridine (3.11 g, 78%) was prepared in an analogous manner to Preparation 93a using 3-fluoro-2-iodo-5-methoxy-6-propoxypyridine (Preparation 220, 4.18 g, 13.44 mmol) and (5-chloropyridin-3-yl)boronic acid (2.11 g, 13.4 mmol) at about 90° C. for about 16 h. $^1$H NMR (CDCl$_3$, 400 MHz): δ 9.13 (s, 1H), 8.53 (d, J=2.5 Hz, 1H), 8.27 (t, J=2.1 Hz, 1H), 6.97 (d, J=11.5 Hz, 1H), 4.43 (t, J=6.9 Hz, 2H), 3.93 (s, 3H), 1.86-1.95 (m, 2H), 1.07 (t, J=7.5 Hz, 3H). LCMS m/z=328 [MH]$^+$.

Preparation 104: 2-bromo-6-(3-ethoxy-4-methoxyphenyl)pyrazine

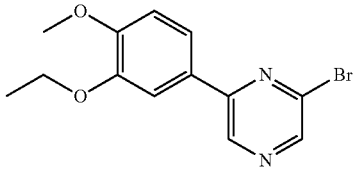 [SMILES: CCOc1cc(-c2cncc(Br)n2)ccc1OC]

2-Bromo-6-(3-ethoxy-4-methoxyphenyl)pyrazine (2.9 g, 52%) was prepared in an analogous manner to Preparation 93a using 2-(3-ethoxy-2-fluoro-4-methoxyphenyl)-4,4,5,5-tetramethyl-1,3,2-dioxaborolane (Preparation 113, 5 g, 18 mmol) and 2,6-dibromopyrazine (6.4 g, 27 mmol) at about 110° C. for about 16 h. $^1$H NMR (CDCl$_3$, 400 MHz): δ 8.86-8.92 (m, 1H), 8.53 (s, 1H), 7.61 (d, J=2.0 Hz, 1H), 7.57 (dd, J=2.2, 8.3 Hz, 1H), 6.98 (d, J=8.3 Hz, 1H), 4.23 (q, J=6.9 Hz, 2H), 3.95 (s, 3H), 1.53 (t, J=7.0 Hz, 3H). LCMS m/z=309 [MH]$^+$.

Preparation 105: ethyl 2-(6-chloro-2-(4-methoxy-3-propoxyphenyl)pyrimidin-4-yl)acetate

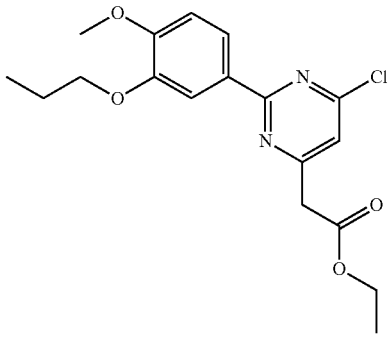 [SMILES: CCCOc1cc(-c2nc(Cl)cc(CC(=O)OCC)n2)ccc1OC]

POCl$_3$ (253 mL, 2716 mmol) was added to ethyl 2-(2-(4-methoxy-3-propoxyphenyl)-6-oxo-1,6-dihydropyrimidin-4-yl)acetate (Preparation 106, 42.98 g, 124.08 mmol), followed by pyridine hydrochloride (14.3 g, 124 mmol) at about 25° C. The resulting mixture was heated to about 80° C. for about 0.5 h. The mixture was diluted with EtOAc (200 mL) and added into water dropwise. The EtOAc layer was treated with NaHCO$_3$. The EtOAc layer was washed with brine, dried with Na$_2$SO$_4$, filtered and concentrated. The residue was purified by column chromatography on a reversed-phase column eluting with MeCN/water (0:100 to 100:0) to afford ethyl 2-(6-chloro-2-(4-methoxy-3-propoxyphenyl)pyrimidin-4-yl)acetate (22.07 g, 49%). $^1$H NMR (CDCl$_3$, 400 MHz): δ 8.08 (dd, J=2.1, 8.4 Hz, 1H), 7.98 (d, J=2.0 Hz, 1H), 7.20 (s, 1H), 6.95 (d, J=8.6 Hz, 1H), 4.24 (q, J=7.2 Hz, 2H), 4.11 (t, J=6.9 Hz, 2H), 3.95 (s, 3H), 3.85 (s, 2H), 1.89-1.96 (m, 2H), 1.31 (t, J=7.2 Hz, 3H), 1.09 (t, J=7.5 Hz, 3H). LCMS m/z=365 [MH]$^+$.

Preparation 106: ethyl 2-(2-(4-methoxy-3-propoxyphenyl)-6-oxo-1,6-dihydropyrimidin-4-yl)acetate

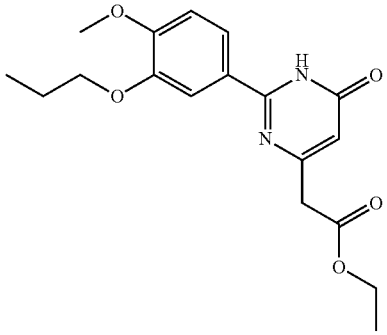 [SMILES: CCCOc1cc(-c2nc(CC(=O)OCC)cc(=O)[nH]2)ccc1OC]

A mixture of 4-methoxy-3-propoxybenzimidamide (Preparation 233, 25.3 g, 121 mmol), NaHCO$_3$ (12.2 mg, 146 mmol) and diethyl 1,3-acetonedicarboxylate (CAS 105-50-0, 29.4 g, 146 mmol) in EtOH (500 mL) was stirred at about 100° C. for about 24 h. The mixture was filtered, and the filter cake was washed with MTBE (200 mL), MeOH (100 mL) and DCM (50 mL) to afford ethyl 2-(2-(4-methoxy-3-propoxyphenyl)-6-oxo-1,6-dihydropyrimidin-4-yl)acetate (34.34 g, 82%). $^1$H NMR (CDCl$_3$, 400 MHz): δ 12.44 (br s, 1H), 7.73-7.86 (m, 2H), 6.99 (d, J=8.3 Hz, 1H), 6.33 (s, 1H), 4.23 (q, J=7.3 Hz, 2H), 4.16 (t, J=6.9 Hz, 2H), 3.96 (s, 3H), 3.66 (s, 2H), 1.92-1.97 (m, 2H), 1.30 (t, J=7.2 Hz, 3H), 1.10 (t, J=7.5 Hz, 3H). LCMS m/z=346 [MH]$^+$.

Preparation 107: 5-chloro-3-(4-methoxy-3-propoxyphenyl)pyridazine

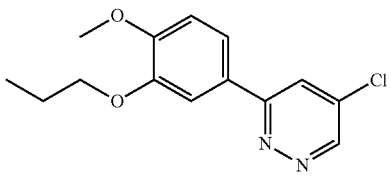 [SMILES: CCCOc1cc(-c2cc(Cl)cnn2)ccc1OC]

5-chloro-3-(4-methoxy-3-propoxyphenyl)pyridazine (2.9 g, 52%) was prepared in an analogous manner to Preparation 93a using 2-(4-methoxy-3-propoxyphenyl)-4,4,5,5-tetramethyl-1,3,2-dioxaborolane (Preparation 114, 4.3 g, 14.7 mmol) and 3,5-dichloropyridazine (2.3 g, 15.5 mmol). $^1$H NMR (CDCl$_3$, 400 MHz): δ 9.08 (d, J=2.5 Hz, 1H), 7.84 (d, J=2.5 Hz, 1H), 7.51 (dd, J=2.2, 8.6 Hz, 1H), 7.00 (d, J=8.3 Hz, 1H), 4.12 (t, J=6.9 Hz, 2H), 3.95 (s, 3H), 1.92-1.97 (m, 2H), 1.08 (t, J=7.3 Hz, 3H). LCMS m/z=278 [MH]$^+$.

Preparation 108: 3-bromo-5-(3-ethoxy-4-methoxyphenyl)-4-methylpyridine

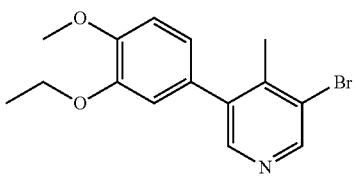

3-bromo-5-(3-ethoxy-4-methoxyphenyl)-4-methylpyridine (0.82 g, 35%) was prepared in an analogous manner to Preparation 93a using 2-(3-ethoxy-4-methoxyphenyl)-4,4,5,5-tetramethyl-1,3,2-dioxaborolane (Preparation 113, 2.0 g, 7.19 mmol) and 3,5-dibromo-4-methylpyridine (2.71 g, 10.8 mmol) at about 120° C. for about 2 h. $^1$H NMR (CDCl$_3$, 400 MHz): δ 8.61 (s, 1H), 8.32 (s, 1H), 6.94 (d, J=8.0 Hz, 1H), 6.81-6.83 (m, 1H), 6.78 (d, J=2.3 Hz, 1H), 4.10 (q, J=7.0 Hz, 2H), 3.92 (s, 3H), 2.34 (s, 3H), 1.47 (t, J=7.0 Hz, 3H). LCMS m/z=323 [MH]$^+$.

Preparation 109: 4-bromo-2-(3-ethoxy-4-methoxyphenyl)thiazole

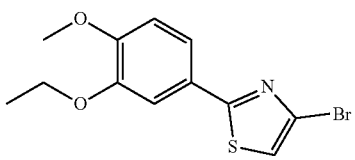 [SMILES: CCOc1cc(-c2nc(Br)cs2)ccc1OC]

To a mixture of Pd(OAc)$_2$ (CAS 3375-31-3, 40.4 mg, 0.18 mmol) and Xantphos (CAS 161265-03-8, 208.0 mg, 0.36 mmol), stirring for about 10 min., was added 2-(3-ethoxy-4-methoxyphenyl)-4,4,5,5-tetramethyl-1,3,2-dioxaborolane (Preparation 113, 1.0 g, 3.60 mmol), 2,4-dibromothiazole (0.83 g, 3.42 mmol) and K$_3$PO$_4$ (2.44 g, 11.5 mmol). The combined mixture was degassed and heated to about 60° C. for about 16 h. The mixture was concentrated and the residue was purified by column chromatography (silica) eluting with pet. ether:EtOAc (100:0 to 85:15) to afford 4-bromo-2-(3-ethoxy-4-methoxyphenyl)thiazole (0.68 g, 60%). $^1$H NMR (CDCl$_3$, 400 MHz): δ 7.51 (d, J=2.3 Hz, 1H), 7.45 (dd, J=2.3, 8.3 Hz, 1H), 7.14 (s, 1H), 6.90 (d, J=8.3 Hz, 1H), 4.20 (q, J=7.0 Hz, 2H), 3.93 (s, 3H), 1.51 (t, J=7.0 Hz, 3H). LCMS m/z=315 [MH]$^+$.

Preparation 110: ethyl 2-(6-bromopyridin-2-yl)-2-methyl-3-(4,4,5,5-tetramethyl-1,3,2-dioxaborolan-2-yl)propanoate

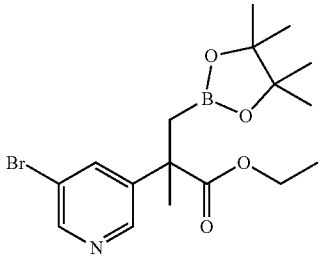 [SMILES: CCOC(=O)C(C)(CB1OC(C)(C)C(C)(C)O1)c1cncc(Br)c1]

To a mixture of sodium iodide (1.05 g, 6.98 mmol) and acetone (1.50 mL) was added 2-(chloromethyl)-4,4,5,5-tetramethyl-1,3,2-dioxaborolane (187 mg, 1.06 mmol) and was stirred at about 20° C. for about 30 min. The mixture was filtered through a pad of Celite® and the filtrate concentrated. The residue was dissolved and concentrated with anhydrous THF (3×5 mL). The residue was dissolved in THF (6.0 mL) and added to a cold suspension of NaH (60% dispersion in mineral oil, 349 mg, 8.73 mmol) and ethyl 2-(6-bromopyridin-2-yl)propanoate (Preparation 111, 1.502 g, 5.819 mmol) in THF (13.0 mL), which had been degassed under N$_2$. The combined mixture was stirred at about 20° C. for about 18 h. The mixture was treated with saturated aqueous NH$_4$Cl and extracted with EtOAc. The combined EtOAc extracts were washed with brine, dried over Na$_2$SO$_4$, filtered and concentrated. The residue was dissolved in DMSO (5 mL) and was purified by preparative HPLC (Biotage C18 RP column, 60 g) eluting with MeCN (0.1% NH$_4$CO$_2$H)/water (0:100 to 100:0) to afford ethyl 2-(6-bromopyridin-2-yl)-2-methyl-3-(4,4,5,5-tetramethyl-1,3,2-dioxaborolan-2-yl)propanoate (339 mg, 14%). $^1$H NMR (CDCl$_3$, 500 MHz): δ 7.44-7.48 (m, 1H), 7.31 (m, 1H), 7.25-7.29 (m, 2H), 4.15 (q, J=7.1 Hz, 2H), 1.67-1.70 (m, 3H), 1.54 (s, 2H), 1.23-1.25 (m, 7H), 1.20 (d, J=3.9 Hz, 13H). LCMS m/z=399 [MH]$^+$.

Preparation 111: ethyl 2-(6-bromopyridin-2-yl)propanoate

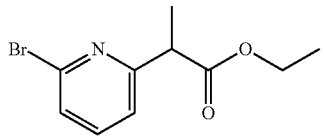

To a solution of ethyl 2-(6-bromopyridin-2-yl)acetate (Preparation 112, 5.72 g, 23.4 mmol) in THF (117 mL) cooled to about −78° C. was added a solution of LiHMDS in THF (1.0 M, 29.3 mL, 29.3 mmol). The solution was stirred for about 1 h and iodomethane (3.33 g, 23.4 mmol, 1.46 mL) was added dropwise. The reaction was allowed to warm to about 20° C. over about 19 h. The reaction mixture was diluted with EtOAc. The mixture was washed with saturated aqueous NH$_4$Cl, brine, dried over MgSO$_4$ and Na$_2$SO$_4$, filtered and concentrated. The residue was purified by column chromatography (silica) and eluted with heptanes/EtOAc (100:0 to 80:20) to afford ethyl 2-(6-bromopyridin-2-yl)acetate (5.06 g, 84%). $^1$H NMR (CDCl$_3$, 400 MHz): δ 7.50-7.57 (m, 1H), 7.39 (d, J=7.8 Hz, 1H), 7.26-7.31 (m, 1H), 4.19 (q, J=7.0 Hz, 2H), 3.93 (q, J=7.0 Hz, 1H), 1.57 (d, J=7.4 Hz, 3H), 1.25 (t, J=7.0 Hz, 3H). LCMS m/z=259 [MH]$^+$.

Preparation 112: ethyl 2-(6-bromopyridin-2-yl)acetate

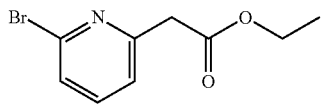

To a solution of 2-bromo-6-methylpyridine (CAS 5315-25-3, 10.2 g, 59.1 mmol) in THF (62 mL) was cooled to about −78° C. under N$_2$ was added a solution of LDA in THF (2.0 M, 59 mL, 118 mmol) slowly while stirring. The solution was stirred at about −78° C. for about 30 min.

To the mixture was added diethyl carbonate (8.6 mL, 70.9 mmol) at about −78° C. The mixture was allowed to warm to about 20° C. over overnight. The reaction was cooled to about 0° C. and diluted with saturated aqueous NH$_4$Cl solution. The aqueous layer was extracted with DCM and the combined DCM extracts were washed with water, brine, dried over Na$_2$SO$_4$, filtered and concentrated. The residue was purified by column chromatography (silica) and eluted with heptanes/EtOAc (100:0 to 60:40) to afford ethyl 2-(6-bromopyridin-2-yl)acetate (7.7 g, 53%). $^1$H NMR (CDCl$_3$, 400 MHz): δ 7.55 (t, J=7.8 Hz, 1H), 7.42 (d, J=8.2 Hz, 1H), 7.28-7.34 (m, 1H), 4.21 (q, J=7.2 Hz, 2H), 3.85 (s, 2H), 1.26-1.34 (m, 3H). LCMS m/z=245 [MH]$^+$.

Preparation 113: 2-(3-ethoxy-4-methoxyphenyl)-4,4,5,5-tetramethyl-1,3,2-dioxaborolane

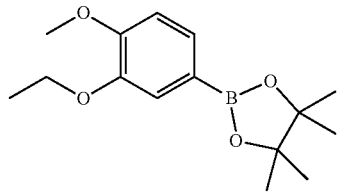 [SMILES: CCOc1cc(B2OC(C)(C)C(C)(C)O2)ccc1OC]

A mixture of 4-bromo-2-ethoxy-1-methoxybenzene (Preparation 150, 48.0 g, 207.7 mmol), Pd(dppf)Cl$_2$ (4.56 g, 6.23 mmol), Pin$_2$B$_2$ (58.0 g, 228.5 mmol) and KOAc (40.8 g, 415.4 mmol) in 1,4-dioxane (500 mL) was degassed and heated to about 90° C. for about 16 h under N$_2$. The mixture was filtered and concentrated. The residue was purified by column chromatography (silica) and eluted with pet. ether/EtOAc (10:1) to afford 2-(3-ethoxy-4-methoxyphenyl)-4,4,5,5-tetramethyl-1,3,2-dioxaborolane (50.0 g, 86%). $^1$H NMR (CDCl$_3$, 400 MHz): δ 7.41 (d, J=8.0 Hz, 1H), 7.30 (s, 1H), 6.89 (d, J=8.0 Hz, 1H), 4.16 (q, J=7.2 Hz, 2H), 3.90 (s, 3H), 1.47 (t, J=7.2 Hz, 3H), 1.34 (s, 12H).

Preparation 114: 2-(4-methoxy-3-propoxyphenyl)-4,4,5,5-tetramethyl-1,3,2-dioxaborolane

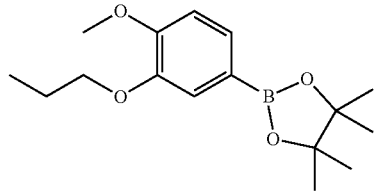 [SMILES: CCCOc1cc(B2OC(C)(C)C(C)(C)O2)ccc1OC]

A mixture of 4-bromo-1-methoxy-2-propoxybenzene (Preparation 151, 43.00 g, 175.43 mmol), KOAc (34.43 g, 350.86 mmol), Pin$_2$B$_2$ (49.00 g, 192.97 mmol) and Pd(dppf)Cl$_2$-DCM (4.30 g, 5.26 mmol) in 1,4-dioxane (500 mL) was degassed and stirred at about 80° C. for about 16 h. The solid was removed by filtration and the filtrate was concentrated. The residue was purified by column chromatography (silica) and eluted with pet. ether/EtOAc (10:1) to afford 2-(4-methoxy-3-propoxyphenyl)-4,4,5,5-tetramethyl-1,3,2-dioxaborolane (51.0 g, 99%). $^1$H NMR (CDCl$_3$, 400 MHz): δ 7.40-7.42 (m, 1H), 7.30 (d, J=1.2 Hz, 1H), 6.89 (d, J=8.0 Hz, 1H), 4.03 (t, J=7.0 Hz, 2H), 3.89 (s, 3H), 1.84-1.93 (m, 2H), 1.34 (s, 12H), 1.05 (t, J=7.4 Hz, 3H).

The following compounds were prepared using the appropriate bromide and 4,4,4',4',5,5,5',5'-octamethyl-2,2'-bi(1,3,2-dioxaborolane), following the procedure described in Preparation 114.

| Preparation No. | Structure/Name | Source | Analytical Data |
|---|---|---|---|
| 115 | 2-(3-isopropoxy-4-methoxyphenyl)-4,4,5,5-tetramethyl-1,3,2-dioxaborolane | Preparation 152 | $^1$H NMR (CDCl$_3$, 400 MHz): δ 7.40-7.44 (m, 1H), 7.33 (d, J = 1.5 Hz, 1H), 6.87-6.91 (m, 1H), 4.62 (td, J = 6.1, 12.2 Hz, 1H), 3.88 (s, 3H), 1.36-1.39 (m, 6H), 1.34 (s, 12H). LCMS m/z = 293 [MH]$^+$. |
| 116 | 2-(3-isobutoxy-4-methoxyphenyl)-4,4,5,5-tetramethyl-1,3,2-dioxaborolane | Preparation 153 | $^1$H NMR (CDCl$_3$, 400 MHz): δ 7.41 (dd, J = 1.2, 8.1 Hz, 1H), 7.29 (d, J = 1.0 Hz, 1H), 6.89 (d, J = 7.8 Hz, 1H), 3.89 (s, 3H), 3.82 (d, J = 6.9 Hz, 2H), 2.16-2.23 (m, 1H), 1.33-1.37 (m, 12H), 1.05 (d, J = 6.4 Hz, 6H). LCMS m/z = 307 [MH]$^+$. |
| 117 | 2-(3-cyclopropoxy-4-methoxyphenyl)-4,4,5,5-tetramethyl-1,3,2-dioxaborolane | Preparation 154 | $^1$H NMR (CDCl$_3$, 400 MHz): δ 7.62 (d, J = 1.0 Hz, 1H), 7.40-7.48 (m, 1H), 6.83-6.91 (m, 1H), 3.87 (s, 3H), 3.81-3.86 (m, 1H), 1.33-1.36 (m, 12H), 0.80-0.88 (m, 4H). LCMS m/z = 291 [MH]$^+$. |
| 118 | 2-(4-methoxy-3-((tetrahydrothiophen-3-yl)oxy)phenyl)-4,4,5,5-tetramethyl-1,3,2-dioxaborolane | Preparation 155 | $^1$H NMR (CDCl$_3$, 400 MHz): δ 7.43-7.51 (m, 1H), 7.37 (d, J = 1.5 Hz, 1H), 6.88-6.92 (m, 1H), 5.13.5.15 (m, 1H), 3.87 (s, 3H), 3.09-3.18 (m, 3H), 2.89-2.96 (m, 1H), 2.39-2.47 (m, 1H), 2.04-2.07 (m, 1H), 1.34 (s, 12H). LCMS m/z = 337 [MH]$^+$. |
| 119 | 2-(4-methoxy-3-((tetrahydro-2H-thiopyran-4-yl)oxy)phenyl)-4,4,5,5-tetramethyl-1,3,2-dioxaborolane | Preparation 156 | $^1$H NMR (CDCl$_3$, 400 MHz): δ 7.41-7.48 (m, 1H), 7.32 (d, J = 1.5 Hz, 1H), 6.86-6.93 (m, 1H), 4.26-4.37 (m, 1H), 3.86 (s, 3H), 2.87-3.01 (m, 2H), 2.51-2.62 (m, 2H), 2.13-2.25 (m, 2H), 1.98-2.10 (m, 2H), 1.29-1.36 (m, 12H). |

-continued

| Preparation No. | Structure/Name | Source | Analytical Data |
|---|---|---|---|
| 120 | tert-butyl(2-(2-methoxy-5-(4,4,5,5-tetramethyl-1,3,2-dioxaborolan-2-yl)phenoxy)ethoxy)dimethylsilane | Preparation 157 | $^1$H NMR (CDCl$_3$, 400 MHz): δ 7.42 (dd, J = 1.5, 7.8 Hz, 1H), 7.34 (d, J = 1.5 Hz, 1H), 6.86-6.90 (m, 1H), 4.10-4.18 (m, 2H), 3.99-4.03 (m, 2H), 3.88 (s, 3H), 1.34 (s, 12H), 0.90-0.92 (m, 9H), 0.09-0.11 (m, 6H). LCMS m/z = 409 [MH]$^+$. |
| 121 | tert-butyl(3-(2-methoxy-5-(4,4,5,5-tetramethyl-1,3,2-dioxaborolan-2-yl)phenoxy)propoxy)dimethylsilane | Preparation 158 | $^1$H NMR (CDCl$_3$, 400 MHz): δ 7.40-7.43 (m, 1H), 7.33 (d, J = 1.5 Hz, 1H), 6.86-6.89 (m, 1H), 4.18 (t, J = 6.6 Hz, 2H), 3.88 (s, 3H), 3.81-3.85 (m, 2H), 2.05-2.09 (m, 2H), 1.34 (s, 12H), 0.90 (s, 9H), 0.05-0.06 (m, 6H). LCMS m/z = 423 [MH]$^+$. |
| 122 | 2-(3-(2-fluoroethoxy)-4-methoxyphenyl)-4,4,5,5-tetramethyl-1,3,2-dioxaborolane | Preparation 159 | $^1$H NMR (CDCl$_3$, 400 MHz): δ 7.46 (dd, J = 1.5, 7.8 Hz, 1H), 7.32 (d, J = 1.0 Hz, 1H), 6.89-6.93 (m, 1H), 4.83-4.88 (m, 1H), 4.71-4.75 (m, 1H), 4.34-4.38 (m, 1H), 4.27-4.31 (m, 1H), 3.90 (s, 3H), 1.34 (s, 12H). LCMS m/z = 297 [MH]$^+$. |
| 123 | 2-(3-(3-fluoropropoxy)-4-methoxyphenyl)-4,4,5,5-tetramethyl-1,3,2-dioxaborolane | Preparation 160 | $^1$H NMR (CDCl$_3$, 400 MHz): δ 7.44 (dd, J = 1.5, 7.8 Hz, 1H), 7.33 (d, J = 1.5 Hz, 1H), 6.89 (d, J = 7.8 Hz, 1H), 4.74 (t, J = 5.9 Hz, 1H), 4.62 (t, J = 5.9 Hz, 1H), 4.20 (t, J = 6.4 Hz, 2H), 3.89 (s, 3H), 2.27-2.30 (m, 1H), 2.20-2.23 (m, 1H), 1.32-1.37 (m, 12H). LCMS m/z = 311 [MH]$^+$. |
| 124 | 2-methoxy-3-propoxy-5-(4,4,5,5-tetramethyl-1,3,2-dioxaborolan-2-yl)pyridine | Preparation 215 | $^1$H NMR (CDCl$_3$, 400 MHz): δ 8.12 (d, J = 1.5 Hz, 1H), 7.34 (d, J = 1.5 Hz, 1H), 4.03 (s, 3H), 3.98-4.02 (m, 2H), 1.85-1.94 (m, 2H), 1.35 (s, 12H), 1.05 (t, J = 7.5 Hz, 3H). LCMS m/z = 294 [MH]$^+$. |

| Preparation No. | Structure/Name | Source | Analytical Data |
|---|---|---|---|
| 125 | 2,3-dimethoxy-6-(4,4,5,5-tetramethyl-1,3,2-dioxaborolan-2-yl)benzonitrile | Preparation 162 | $^1$H NMR (CDCl$_3$, 400 MHz): δ 7.57 (d, J = 8.4 Hz, 1H), 7.07 (d, J = 8.4 Hz, 1H), 4.00-3.96 (m, 3H), 3.93-3.89 (m, 3H), 1.37 (s, 12H). |
| 126 | 2-(3-ethoxy-2-fluoro-4-methoxyphenyl)-4,4,5,5-tetramethyl-1,3,2-dioxaborolane | Preparation 170a | $^1$H NMR (CDCl$_3$, 400 MHz): δ 7.35-7.44 (m, 1H), 6.69 (dd, J = 0.9, 8.4 Hz, 1H), 4.07-4.16 (m, 2H), 3.88 (s, 3H), 1.33-1.40 (m, 15H). |
| 127 | 2-(2-(difluoromethyl)-3-ethoxy-4-methoxyphenyl)-4,4,5,5-tetramethyl-1,3,2-dioxaborolane | Preparation 168 | $^1$H NMR (CDCl$_3$, 400 MHz): δ 7.15-7.18 (m, 1H), 7.11 (s, 1H), 4.14 (q, J = 7.0 Hz, 2H), 3.96 (d, J = 1.3 Hz, 3H), 1.46 (t, J = 7.0 Hz, 3H), 1.34 (s, 12H). $^{19}$F NMR (CDCl$_3$, 376 MHz): δ -114.25 (br s, 1F). LCMS m/z = 296 [MH]$^+$. |
| 128 | 2-(2-fluoro-4-methoxy-3-propoxyphenyl)-4,4,5,5-tetramethyl-1,3,2-dioxaborolane | Preparation 170b | LCMS m/z = 311 [MH]$^+$. |
| 129 | 3-methoxy-2-propoxy-6-(4,4,5,5-tetramethyl-1,3,2-dioxaborolan-2-yl)benzonitrile | Preparation 171 | $^1$H NMR (CDCl$_3$, 400 MHz): δ 7.54 (d, J = 8.1 Hz, 1H), 7.05 (d, J = 8.3 Hz, 1H), 4.06-4.11 (m, 2H), 3.89 (s, 3H), 1.79-1.90 (m, 2H), 1.35-1.38 (m, 12H), 1.03-1.08 (m, 3H). LCMS m/z = 318 [MH]$^+$. |

-continued

| Preparation No. | Structure/Name | Source | Analytical Data |
|---|---|---|---|
| 130 | 2-(2,4-dimethoxy-3-propoxyphenyl)-4,4,5,5-tetramethyl-1,3,2-dioxaborolane | Preparation 210 | $^1$H NMR (CDCl$_3$, 400 MHz): δ 7.42 (d, J = 8.5 Hz, 1H), 6.69 (d, J = 8.3 Hz, 1H), 3.92-3.99 (m, 2H), 3.82-3.87 (m, 6H), 1.73-1.84 (m, 2H), 1.33-1.38 (m, 12H), 1.00-1.08 (m, 3H). LCMS m/z = 345 [M + Na]$^+$. |
| 131 | 2-(cyclopentyloxy)-3-methoxy-6-(4,4,5,5-tetramethyl-1,3,2-dioxaborolan-2-yl)benzonitrile | Preparation 207 | $^1$H NMR (CDCl$_3$, 400 MHz): δ 7.52 (d, J = 8.3 Hz, 1H), 7.00-7.10 (m, 1H), 4.98-5.11 (m, 1H), 3.88 (s, 3H), 1.91-2.01 (m, 4H), 1.65-1.76 (m, 2H), 1.53-1.64 (m, 2H), 1.37 (s, 12H). LCMS m/z = 344 [MH]$^+$. |
| 132 | 2-(3-ethoxy-5-fluoro-4-methoxyphenyl)-4,4,5,5-tetramethyl-1,3,2-dioxaborolane | Preparation 172 | $^1$H NMR (CDCl$_3$, 400 MHz): δ 7.17 (dd, J = 1.0, 10.5 Hz, 1H), 7.11 (s, 1H), 4.14 (q, J = 7.0 Hz, 2H), 3.96 (d, J = 1.0 Hz, 3H), 1.56 (s, 6H), 1.46 (t, J = 7.0 Hz, 3H), 1.34 (s, 12H). LCMS m/z = 297 [MH]$^+$. |
| 133 | 2-(3-chloro-5-ethoxy-4-methoxyphenyl)-4,4,5,5-tetramethyl-1,3,2-dioxaborolane | Preparation 177 | $^1$H NMR (CDCl$_3$, 400 MHz): δ 7.44 (d, J = 1.0 Hz, 1H), 7.22 (d, J = 1.0 Hz, 1H), 4.10-4.17 (m, 2H), 3.91 (s, 3H), 1.46 (t, J = 7.0 Hz, 3H), 1.34 (s, 12H). LCMS m/z = 312 [MH]$^+$. |
| 134 | 2-(5-ethoxy-2-fluoro-4-methoxyphenyl)-4,4,5,5-tetramethyl-1,3,2-dioxaborolane | Preparation 182 | $^1$H NMR (CDCl$_3$, 400 MHz): δ 7.14 (d, J = 5.5 Hz, 1H), 6.59 (d, J = 10.0 Hz, 1H), 4.02-4.16 (m, 2H), 3.86 (s, 3H), 1.40-1.52 (m, 3H), 1.34 (s, 12H). LCMS m/z = 297 [MH]$^+$. |

-continued

| Preparation No. | Structure/Name | Source | Analytical Data |
|---|---|---|---|
| 135 | 2-(2-chloro-5-ethoxy-4-methoxyphenyl)-4,4,5,5-tetramethyl-1,3,2-dioxaborolane | Preparation 183 | $^1$H NMR (CDCl$_3$, 400 MHz): δ 7.18 (s, 1H), 6.86 (s, 1H), 4.12 (q, J = 7.0 Hz, 2H), 3.87 (s, 3H), 1.46 (t, J = 7.0 Hz, 3H), 1.36 (s, 12H). LCMS m/z = 312 [MH]$^+$. |
| 136 | 2-(5-ethoxy-4-methoxy-2-methylphenyl)-4,4,5,5-tetramethyl-1,3,2-dioxaborolane | Preparation 187 | $^1$H NMR (CDCl$_3$, 400 MHz): δ 7.28 (s, 1H), 6.69 (s, 1H), 4.13 (q, J = 6.9 Hz, 2H), 3.88 (s, 3H), 2.50 (s, 3H), 1.46 (t, J = 7.1 Hz, 3H), 1.33 (s, 12H). LCMS m/z = 292 [MH]$^+$. |
| 137 | 2-(3-ethoxy-2,6-difluoro-4-methoxyphenyl)-4,4,5,5-tetramethyl-1,3,2-dioxaborolane | Preparation 193 | $^1$H NMR (CDCl$_3$, 400 MHz): δ 6.34-6.48 (m, 1H), 4.04 (q, J = 7.0 Hz, 2H), 3.85 (s, 3H), 1.32-1.42 (m, 15H). LCMS m/z = 315 [MH]$^+$. |
| 138 | 2-(2-fluoro-4-methoxy-5-propoxyphenyl)-4,4,5,5-tetramethyl-1,3,2-dioxaborolane | Preparation 188 | $^1$H NMR (CDCl$_3$, 400 MHz): δ 7.15 (d, J = 5.9 Hz, 1H), 6.59 (d, J = 10.8 Hz, 1H), 3.98 (t, J = 6.8 Hz, 2H), 3.87 (s, 3H), 1.81-1.90 (m, 2H), 1.25-1.30 (m, 12H), 1.05 (t, J = 7.6 Hz, 3H). |
| 139 | 2-(4-ethoxy-3-methoxyphenyl)-4,4,5,5-tetramethyl-1,3,2-dioxaborolane | Preparation 198 | $^1$H NMR (CDCl$_3$, 400 MHz): δ 7.41 (dd, J = 1.2, 8.1 Hz, 1H), 7.29 (d, J = 1.5 Hz, 1H), 6.88 (d, J = 8.3 Hz, 1H), 4.14 (q, J = 7.0 Hz, 2H), 3.92 (s, 3H), 1.48 (t, J = 6.9 Hz, 3H), 1.34-1.36 (m, 12H). LCMS m/z = 279 [MH]$^+$. |

-continued

| Preparation No. | Structure/Name | Source | Analytical Data |
|---|---|---|---|
| 140 | 2-(4-ethoxy-2-fluoro-3-methoxyphenyl)-4,4,5,5-tetramethyl-1,3,2-dioxaborolane | Preparation 199 | $^1$H NMR (CDCl$_3$, 400 MHz): δ 7.37 (dd, J = 6.4, 8.3 Hz, 1H), 6.64-6.73 (m, 1H), 4.07-4.18 (m, 2H), 3.90 (d, J = 1.0 Hz, 3H), 1.46 (t, J = 6.9 Hz, 3H), 1.35 (s, 12H). LCMS m/z = 297 [MH]$^+$. |
| 141 | 2-(3,4-diethoxyphenyl)-4,4,5,5-tetramethyl-1,3,2-dioxaborolane | Preparation 197 | $^1$H NMR (400 MHz, CDCl$_3$) δ 7.39 (dd, J = 1.2, 8.1 Hz, 1H), 7.30 (d, J = 1.0 Hz, 1H), 6.88 (d, J = 8.3 Hz, 1H), 4.08-4.17 (m, 4H), 1.41-1.49 (m, 6H), 1.33 (s, 12H). LCMS m/z = 293 [MH]$^+$. |
| 142 | 2-(4-(difluoromethoxy)-3-propoxyphenyl)-4,4,5,5-tetramethyl-1,3,2-dioxaborolane | Preparation 223 | $^1$H NMR (CDCl$_3$, 400 MHz): δ 7.40 (d, J = 1.2 Hz, 1H), 7.38 (s, 1H), 7.15 (dd, J = 0.7, 7.6 Hz, 1H), 6.41-6.82 (m, 1H), 4.04 (t, J = 6.5 Hz, 2H), 1.80-1.91 (m, 2H), 1.33-1.37 (m, 12H), 1.06 (t, J = 7.3 Hz, 3H). |
| 143 | 2-(3-methoxy-4-(methylthio)phenyl)-4,4,5,5-tetramethyl-1,3,2-dioxaborolane | Preparation 203 | $^1$H NMR (CDCl$_3$, 400 MHz): δ 7.43 (dd, J = 1.1, 7.7 Hz, 1H), 7.22 (s, 1H), 7.13 (d, J = 7.8 Hz, 1H), 3.95 (s, 3H), 2.45 (s, 3H), 1.35 (s, 12H). LCMS m/z = 281 [MH]$^+$. |
| 144 | 2-(3-ethoxy-4-(methylthio)phenyl)-4,4,5,5-tetramethyl-1,3,2-dioxaborolane | Preparation 204 | $^1$H NMR (MeOD-d$_3$, 400 MHz): δ 7.34 (dd, J = 0.7, 7.6 Hz, 1H), 7.19 (s, 1H), 7.12-7.16 (m, 1H), 4.10 (q, J = 7.1 Hz, 2H), 2.39 (d, J = 1.0 Hz, 3H), 1.39-1.44 (m, 3H), 1.34 (s, 12H). LCMS m/z = 295 [MH]$^+$. |

| Preparation No. | Structure/Name | Source | Analytical Data |
|---|---|---|---|
| 145 | 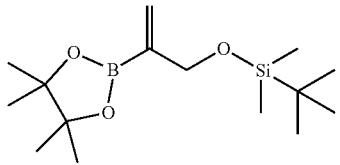<br>2-(3-(cyclopentyloxy)-4-(methylthio)phenyl)-4,4,5,5-tetramethyl-1,3,2-dioxaborolane | Preparation 205 | $^1$H NMR (CDCl$_3$, 400 MHz): δ 7.39 (dd, J = 1.0, 7.8 Hz, 1H), 7.22 (s, 1H), 7.06-7.11 (m, 1H),4.94-4.98 (m, 1H), 2.41 (s, 3H), 1.82-1.96 (m, 6H), 1.61-1.67 (m, 2H), 1.32-1.37 (m, 12H). LCMS m/z = 335 [MH]$^+$. |

Preparation 146: tert-butyldimethyl((2-(4,4,5,5-tetramethyl-1,3,2-dioxaborolan-2-yl)allyl)oxy)silane

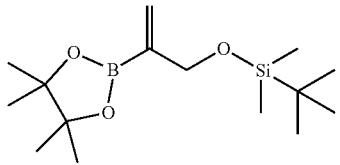 [SMILES: C=C(CO[Si](C)(C)C(C)(C)C)B1OC(C)(C)C(C)(C)O1]

Method A:

Five reactions were carried out in parallel. A mixture of ((2-bromoallyl)oxy)(tert-butyl)dimethylsilane (Preparation 227, 300 g, 1.19 mol), KOAc (234 g, 2.39 mol), 4,4,4',4',5,5,5',5'-octamethyl-2,2'-bi(1,3,2-dioxaborolane) (333 g, 1.31 mol) and Pd(PPh)$_2$Cl$_2$ (16.7 g, 0.023 mol) in 1,4-dioxane (1.5 L) was degassed and stirred at about 80° C. for about 16 h. The solids were removed by filtration and the filtrate was concentrated. The residue was purified by column chromatography (silica) and eluted with pet. ether/EtOAc (1:0) to afford tert-butyldimethyl((2-(4,4,5,5-tetramethyl-1,3,2-dioxaborolan-2-yl)allyl)oxy)silane (520 g, 30%). GC (Column: Agilent J&W HP-5MS 30M×0.25 mm ID×0.25 um film thickness; injector temp. 250° C.; split ratio 100:1; ion source temp 230° C.; interface temp. 250° C.; Column temp. 50° C. 1 min to 100° C. @ 30° C./min to 250° C. @ 10° C./min.; run time 17.67 min.; Flow rate 1.5 mL/min; RT=11.67 min. $^1$H NMR (CDCl$_3$, 400 MHz): δ 5.97 (d, J=1.3 Hz, 1H), 5.88 (td, J=1.8, 3.9 Hz, 1H), 4.29 (t, J=2.0 Hz, 2H), 1.21-1.30 (m, 12H), 0.93 (s, 9H), 0.07 (s, 6H).

Method B:

To a mixture of tert-butyldimethyl(prop-2-yn-1-yloxy) silane (250 mg, 1.47 mmol), sodium t-butoxide (21.2 mg, 0.220 mmol), copper (I) chloride (14.5 mg, 0.10 mmol) and 4,4,4',4',5,5,5',5'-octamethyl-2,2'-bi(1,3,2-dioxaborolane) (410 mg, 1.61 mmol) under N$_2$ was added dropwise a solution of tBusP (1.0M solution in toluene, 0.176 mL, 0.12 mmol) in anhydrous toluene (2.5 mL). MeOH (94 mg, 2.94 mmol) was added to the mixture dropwise and the mixture was stirred at about 20° C. overnight. The reaction was quenched with MeOH (20 mL) and concentrated. The residue was purified by column chromatography (silica) and eluted with pet. ether/EtOAc (100:0 to 80:20) to afford tert-butyldimethyl((2-(4,4,5,5-tetramethyl-1,3,2-dioxaborolan-2-yl)allyl)oxy)silane (2.2 g, 50%). $^1$H NMR (CDCl$_3$, 400 MHz): δ 5.97 (br s, 1H), 5.88 (d, J=1.6 Hz, 1H), 4.29 (s, 2H), 1.25-1.33 (m, 12H), 0.93 (s, 9H), 0.08 (s, 6H).

Preparation 147: tert-butyldimethyl((3-(4,4,5,5-tetramethyl-1,3,2-dioxaborolan-2-yl)but-3-en-2-yl)oxy)silane

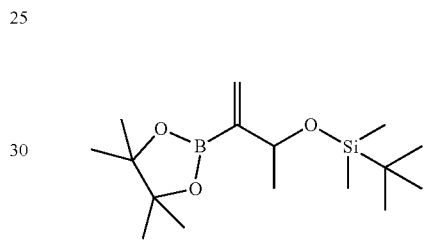

To a mixture of (but-3-yn-2-yloxy)(tert-butyl)dimethylsilane (CAS 193812-02-1, 10 g, 54.24 mmol), sodium t-butoxide (782 mg, 8.41 mmol), copper (I) chloride (537 mg, 5.42 mmol) and Pin$_2$B$_2$ (15.2 g, 59.7 mmol) in toluene (120 mL) under N$_2$ was added a solution of tBusP (13.2 g, 6.51 mmol) in anhydrous toluene (10 mL) drop-wise. MeOH (3.48 g, 108 mmol) was added dropwise and the mixture was stirred at about 20° C. for about 16 h. The reaction was quenched with MeOH (10 mL) and concentrated. The residue was purified by column chromatography (silica) and eluted with pet. ether/EtOAc (100:0 to 97:3) to afford tert-butyldimethyl((3-(4,4,5,5-tetramethyl-1,3,2-dioxaborolan-2-yl)but-3-en-2-yl)oxy)silane (8.2 g, 48.4%). $^1$H NMR (CDCl$_3$, 400 MHz): δ 5.88-6.02 (m, 1H), 5.79 (dd, J=1.5, 3.5 Hz, 1H), 4.40-4.56 (m, 1H), 1.27 (d, J=3.5 Hz, 12H), 1.24 (d, J=6.5 Hz, 3H), 0.91 (s, 9H), 0.05 (d, J=5.5 Hz, 6H).

Preparation 148: tert-butyldimethyl((3-(4,4,5,5-tetramethyl-1,3,2-dioxaborolan-2-yl)but-3-en-1-yl)oxy)silane

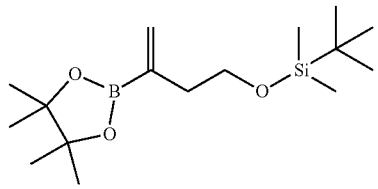 [SMILES: C=C(CCO[Si](C)(C)C(C)(C)C)B1OC(C)(C)C(C)(C)O1]

A mixture of ((3-bromobut-3-en-1-yl)oxy)(tert-butyl)dimethylsilane (Preparation 229, 2.0 g, 7.54 mmol), Pin$_2$B$_2$ (2.87 g, 11.3 mmol) and KOAc (0.74 g, 7.54 mmol) was suspended in anhydrous 1,4-dioxane (10 mL). The mixture was degassed for about 10 min at about 18° C. under N$_2$. Pd(PPh$_3$)$_2$Cl$_2$ (106 mg, 0.15 mmol) was added and the mixture was heated to about 90° C. for 16 h. The reaction was cooled to about 20° C. and filtered. The filter cake was washed with 1,4-dioxane and the combined filtrates were concentrated. The residue was purified by column chromatography (silica) and eluted with heptane/EtOAc (100:0 to 80:20) to afford tert-butyldimethyl((3-(4,4,5,5-tetramethyl-1,3,2-dioxaborolan-2-yl)but-3-en-1-yl)oxy)silane (1.15 g, 49%). LCMS m/z=313 [MH]$^+$.

Preparation 149: 2,2'-(ethane-1,1-diyl)bis(4,4,5,5-tetramethyl-1,3,2-dioxaborolane)

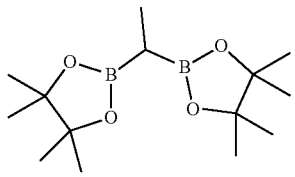

A mixture of 1,1-dibromoethane (14.9 g, 58.6 mmol), lithium methoxide (3.03 g, 79.8 mmol) and copper (I) iodide (5.07 g, 26.6 mmol) was suspended in DMF (150 mL) under N$_2$. Additional lithium methoxide (5.0 g, 2.43 mL) in DMF (10 mL) was added to the mixture. The reaction mixture was warmed to about 40° C. and stirred for about 48 h under N$_2$. The solution was cooled to about 20° C. and extracted with heptane (3×300 mL). The heptane extracts were washed with water (100 mL), brine (100 mL) and passed through a pad of MgSO$_4$ and silica gel. The pad was washed with DCM (100 mL). The combined filtrates were concentrated. The residue was purified by column chromatography (silica) and eluted with DCM to afford 2,2'-(ethane-1,1-diyl)bis(4,4,5,5-tetramethyl-1,3,2-dioxaborolane (3.6 g, 48%). $^1$H NMR (CDCl$_3$, 400 MHz): δ 1.23 (d, J=3.1 Hz, 24H), 1.05 (d, J=7.4 Hz, 3H), 0.72 (q, J=7.0 Hz, 1H).

Preparation 150: 4-bromo-2-ethoxy-1-methoxybenzene

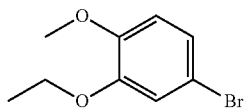

A mixture of 5-bromo-2-methoxyphenol (40.0 g, 197.0 mmol), iodoethane (23.6 mL, 295.5 mmol) and Cs$_2$CO$_3$ (96.3 g, 295.5 mmol) in DMF (350 mL) was stirred at about 25° C. for about 16 h. The mixture was filtered and water (500 mL) was added to the filtrate. The mixture was extracted with EtOAc (2×400 mL). The combined EtOAc extracts were washed with brine (100 mL), dried over Na$_2$SO$_4$ and concentrated. The residue was purified by column chromatography (silica) and eluted with pet. ether/EtOAc (10:1) to afford 4-bromo-2-ethoxy-1-methoxybenzene (48.0 g), which was used directly in the next step. $^1$H NMR (CDCl$_3$, 400 MHz): δ 7.02 (dd, J=2.4, 8.4 Hz, 1H), 6.98 (d, J=2.4 Hz, 1H), 6.76-6.73 (m, 1H), 4.08 (q, J=7.2 Hz, 2H), 3.88 (s, 3H), 1.47 (t, J=7.2 Hz, 3H).

Preparation 151: 4-bromo-1-methoxy-2-propoxybenzene

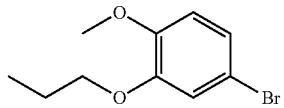

To a solution of 5-bromo-2-methoxyphenol (40.0 g, 197.0 mmol) and K$_2$CO$_3$ (54.5 g, 394 mmol) in DMF (200 mL) was added 1-iodopropane (28.9 mL, 295 mmol) in portions at about 20° C. The mixture was stirred at about 20° C. for about 1 h. The mixture was poured into ice water (500 mL) and extracted with EtOAc (3×300 mL). The combined EtOAc extracts were washed with brine (200 mL), dried over Na$_2$SO$_4$ and concentrated. The residue was purified by column chromatography (silica) and eluted with pet. ether/EtOAc (40:1) to afford 4-bromo-1-methoxy-2-propoxybenzene (43.0 g, crude). $^1$H NMR (CDCl$_3$, 400 MHz): δ 7.27 (s, 1H), 6.99-7.03 (m, 1H), 6.74 (d, J=8.4 Hz, 1H), 3.96 (t, J=6.8 Hz, 2H), 3.85 (s, 3H), 1.83-1.92 (m, 2H), 1.05 (t, J=7.6 Hz, 3H).

Preparation 152: 4-bromo-2-isopropoxy-1-methoxybenzene

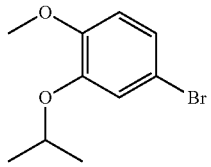

4-bromo-2-isopropoxy-1-methoxybenzene (16 g, 95%) was prepared in an analogous manner to Preparation 150 using 2-bromopropane (12.7 g, 103.4 mmol). $^1$H NMR (CDCl$_3$, 400 MHz): δ 7.00-7.05 (m, 2H), 6.75 (d, J=8.3 Hz, 1H), 4.50-4.54 (m, 1H), 3.83 (s, 3H), 1.35-1.40 (m, 6H). LCMS m/z=245 [MH]$^+$.

Preparation 153: 4-bromo-2-isobutoxy-1-methoxybenzene

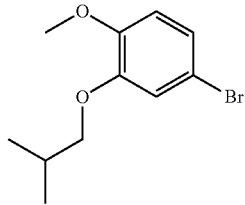

To a solution of 5-bromo-2-methoxyphenol (25 g, 120 mmol), 2-methylpropan-1-ol (11.0 g, 148 mmol), PPh$_3$ (48.4 g, 185 mmol) in anhydrous DCM (400 mL) at about 0° C. was added DIAD (37.3 g, 185 mmol) dropwise under N$_2$.

The mixture was stirred at about 0° C. for about 2 h. Additional DIAD (2.53 g, 12.5 mmol) and 2-methylpropan-1-ol (1.03 g, 13.9 mmol) were added and the mixture was stirred at about 10° C. for about 5 days then filtered. The filtrate was concentrated under reduced pressure. MTBE (500 mL) was added and the mixture was stirred at about 10° C. for about 20 min. A white precipitate was filtered. The filtrate was concentrated. The residue was dissolved in water (200 mL) and extracted with MTBE (2×300 mL). The combined MTBE extracts were concentrated and the residue was purified by column chromatography (silica) and eluted with pet. ether/EtOAc (100:1 to 90:10) to afford 4-bromo-2-isobutoxy-1-methoxybenzene (22 g, 69%). $^1$H NMR (CDCl$_3$, 400 MHz): δ 6.99-7.03 (m, 1H), 6.96-6.99 (m, 1H), 6.74 (d, J=8.5 Hz, 1H), 3.84 (s, 3H), 3.75 (d, J=7.0 Hz, 2H), 2.11-2.22 (m, 1H), 1.04 (d, J=6.5 Hz, 6H).

Preparation 154:
4-bromo-2-cyclopropoxy-1-methoxybenzene

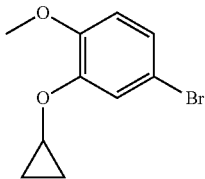

4-bromo-2-cyclopropoxy-1-methoxybenzene (6.15 g, 64%) was prepared in an analogous manner to Preparation 150 using bromocyclopropane (8.0 g, 39 mmol). $^1$H NMR (CDCl$_3$, 400 MHz): δ 7.36 (d, J=2.5 Hz, 1H), 7.05 (dd, J=2.5, 8.5 Hz, 1H), 6.74 (d, J=8.5 Hz, 1H), 3.84 (s, 3H), 3.70-3.77 (m, 1H), 0.80-0.90 (m, 4H).

Preparation 155:
3-(5-bromo-2-methoxyphenoxy)tetrahydrothiophene

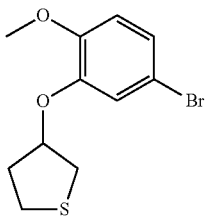

To a solution of 5-bromo-2-methoxyphenol (1.6 g, 7.88 mmol), tetrahydrothiophen-3-ol (0.903 g, 8.67 mmol), PPh$_3$ (3.10 g, 11.8 mmol) in anhydrous DCM (20 mL) at about 0° C. was added DIAD (2.39 g, 11.8 mmol) dropwise under N$_2$. The mixture was stirred at about 0° C. for about 2 h. The mixture was stirred for about 3 days. The mixture was filtered and the filtrate was concentrated. To the residue was added MTBE (50 mL) and stirred at about 10° C. for about 20 min. A white precipitate was filtered. The filtrate was concentrated again. The residue was dissolved in water (20 mL) and extracted with MTBE (2×30 mL). The combined MTBE extracts were concentrated and the residue was purified by column chromatography (silica) and eluted with pet. ether/EtOAc (100:1 to 90:10) to afford 3-(5-bromo-2-methoxyphenoxy)tetrahydrothiophene (2.0 g, 88%). $^1$H NMR (CDCl$_3$, 400 MHz): δ 7.05-7.11 (m, 2H), 6.74-6.79 (m, 1H), 5.06-5.09 (m, 1H), 3.82 (s, 3H), 3.04-3.15 (m, 3H), 2.93 (ddd, J=3.7, 7.3, 10.5 Hz, 1H), 2.38-2.47 (m, 1H), 2.03-2.05 (m, 1H).

Preparation 156: 4-(5-bromo-2-methoxyphenoxy)
tetrahydro-2H-thiopyran

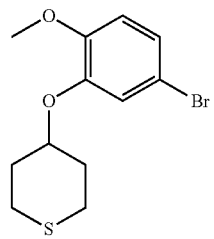 [SMILES: COc1ccc(Br)cc1OC1CCSCC1]

4-(5-bromo-2-methoxyphenoxy) tetrahydro-2H-thiopyran (5.1 g, 68%) was prepared in an analogous manner to Preparation 155 using tetrahydro-2H-thiopyran-4-ol (3.2 g, 27.1 mmol). $^1$H NMR (CDCl$_3$, 400 MHz): δ 7.03-7.08 (m, 1H), 7.01 (d, J=2.5 Hz, 1H), 6.73-6.77 (m, 1H), 4.21-4.29 (m, 1H), 3.81-3.84 (m, 3H), 2.87-2.96 (m, 2H), 2.52-2.62 (m, 2H), 2.15-2.25 (m, 2H), 1.98-2.08 (m, 2H).

Preparation 157: (2-(5-bromo-2-methoxyphenoxy)
ethoxy)(tert-butyl)dimethylsilane

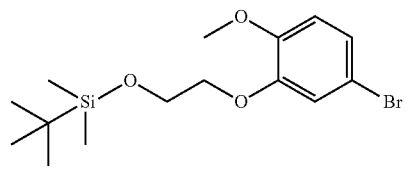 [SMILES: COc1ccc(Br)cc1OCCO[Si](C)(C)C(C)(C)C]

(2-(5-bromo-2-methoxyphenoxy)ethoxy)(tert-butyl)dimethylsilane (60 g, 86%) was prepared in an analogous manner to Preparation 155 using 2-((tert-butyldimethylsilyl)oxy)ethan-1-ol (34 g, 190 mmol). $^1$H NMR (CDCl$_3$, 400 MHz): δ 7.07 (d, J=2.2 Hz, 1H), 7.00-7.05 (m, 1H), 6.71-6.76 (m, 1H), 4.06-4.11 (m, 2H), 3.96-4.02 (m, 2H), 3.81-3.85 (m, 3H), 0.88-0.93 (m, 9H), 0.08-0.12 (m, 6H).

Preparation 158: (3-(5-bromo-2-methoxyphenoxy)
propoxy)(tert-butyl)dimethylsilane

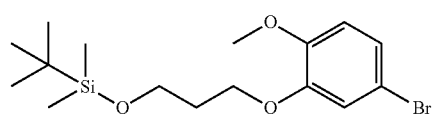 [SMILES: COc1ccc(Br)cc1OCCCO[Si](C)(C)C(C)(C)C]

(3-(5-bromo-2-methoxyphenoxy)propoxy)(tert-butyl)dimethylsilane(19.8 g, 86%) was prepared in an analogous manner to Preparation 155 using 3-((tert-butyldimethylsilyl)oxy)propan-1-ol (Preparation 236, 12.5 g, 61.6 mmol). $^1$H NMR (CDCl$_3$, 400 MHz): δ 6.99-7.03 (m, 1H), 6.71-6.75 (m, 1H), 4.08-4.13 (m, 2H), 3.83 (s, 3H), 3.81 (t, J=5.9 Hz, 2H), 2.00-2.07 (m, 2H), 0.88-0.91 (m, 9H), 0.04-0.07 (m, 6H).

Preparation 159: 4-bromo-2-(2-fluoroethoxy)-1-methoxybenzene

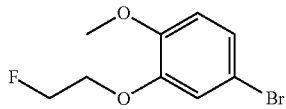

4-bromo-2-(2-fluoroethoxy)-1-methoxybenzene (12 g, 98%) was prepared in an analogous manner to Preparation 155 using 2-fluoroethan-1-ol (3.79 g, 59 mmol). $^1$H NMR (CDCl$_3$, 400 MHz): δ 7.08 (dd, J=2.5, 8.8 Hz, 1H), 7.03 (d, J=2.5 Hz, 1H), 6.75-6.79 (m, 1H), 4.82-4.87 (m, 1H), 4.71-4.74 (m, 1H), 4.27-4.31 (m, 1H), 4.20-4.24 (m, 1H), 3.86 (s, 3H).

Preparation 160: 4-bromo-2-(3-fluoropropoxy)-1-methoxybenzene

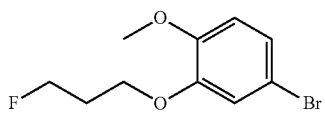

4-bromo-2-(3-fluoropropoxy)-1-methoxybenzene (10 g, 100%) was prepared in an analogous manner to Preparation 155 using 3-fluoropropan-1-ol (3.69 g, 47.3 mmol). $^1$H NMR (CDCl$_3$, 400 MHz): δ 7.03-7.07 (m, 1H), 7.01-7.03 (m, 1H), 6.75 (d, J=8.3 Hz, 1H), 4.72 (t, J=5.6 Hz, 1H), 4.61 (t, J=5.6 Hz, 1H), 4.13 (t, J=6.1 Hz, 2H), 3.84 (s, 3H), 2.26-2.28 (m, 1H), 2.19-2.22 (m, 1H).

Preparation 161: 1-bromo-2-fluoro-3,4-dimethoxybenzene

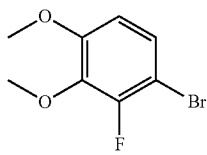

A mixture of 1-fluoro-2,3-dimethoxybenzene (35.0 g, 224.1 mmol) and NBS (43.9 g, 246.6 mmol) in DCM (300 mL) was degassed and stirred at about 15° C. for about 12 h under N$_2$. The reaction mixture was quenched with water (300 mL) and extracted with DCM (2×300 mL). The combined DCM extracts were washed with brine (2×100 mL), dried over Na$_2$SO$_4$, filtered and concentrated. The residue was purified by column chromatography (silica) and eluted with pet. ether/EtOAc (10:1) to afford 1-bromo-2-fluoro-3,4-dimethoxybenzene (35.0 g, 66%). $^1$H NMR (CDCl$_3$, 400 MHz): δ 7.17-7.21 (m, 1H), 6.60-6.63 (m, 1H), 3.93 (s, 3H), 3.87 (s, 3H).

Preparation 162: 6-bromo-2,3-dimethoxybenzonitrile

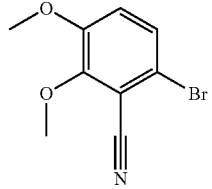

To a solution of 6-bromo-2,3-dimethoxybenzaldehyde oxime (Preparation 163, 30.0 g, 115 mmol) in DCM (500 mL) was added TFAA (24.0 mL, 173 mmol) and Et$_3$N (48.0 mL, 346.0 mmol). The mixture was stirred at about 20° C. for about 2 h. The mixture was quenched with water (200 mL) at about 0° C. and extracted with DCM (300 mL). The combined DCM extracts were washed with brine, dried over Na$_2$SO$_4$, filtered and concentrated. The residue was purified by column chromatography (silica) and eluted with pet. ether/EtOAc (10:1 to 3:1) to afford 6-bromo-2,3-dimethoxybenzonitrile (25.0 g, 90%). $^1$H NMR (CDCl$_3$, 400 MHz): δ 7.34-7.29 (m, 1H), 6.99 (d, J=8.8 Hz, 1H), 4.04-4.01 (m, 3H), 3.90-3.88 (m, 3H).

Preparation 163: 6-bromo-2,3-dimethoxybenzaldehyde oxime

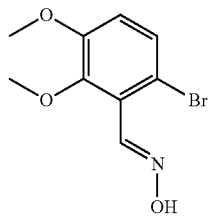

To a solution of 6-bromo-2,3-dimethoxybenzaldehyde (Preparation 164, 15.0 g, 61.2 mmol) in EtOH (150 mL) was added NaHCO$_3$ (7.7 g, 91.8 mmol) and NH$_2$OH—HCl (6.4 g, 91.8 mmol). The mixture was stirred at about 20° C. for about 2 h. The mixture was quenched by the addition of water (300 mL) at about 0° C. and extracted with EtOAc (200 mL). The EtOAc layer was washed with brine, dried over Na$_2$SO$_4$, filtered and concentrated to afford 6-bromo-2,3-dimethoxybenzaldehyde oxime (15.0 g), which was used in Preparation 162. $^1$H NMR (CDCl$_3$, 400 MHz): δ 7.27-7.34 (m, 1H), 6.99 (d, J=9.2 Hz, 1H), 4.00-4.03 (m, 3H), 3.87-3.90 (m, 3H).

Preparation 164: 6-bromo-2,3-dimethoxybenzaldehyde

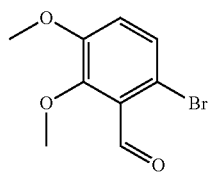

6-bromo-2,3-dimethoxybenzaldehyde (35.0 g, 82.5%) was prepared in an analogous manner to Preparation 172 using 6-bromo-2-hydroxy-3-methoxybenzaldehyde (Preparation 165, 40 g, 173.1 mmol) and iodomethane (36.8 g, 259.7 mmol). ¹H NMR (CDCl₃, 400 MHz): δ 10.35 (s, 1H), 7.33-7.37 (m, 1H), 6.97 (d, J=8.8 Hz, 1H), 3.94 (s, 3H), 3.90 (s, 3H).

Preparation 165:
6-bromo-2-hydroxy-3-methoxybenzaldehyde

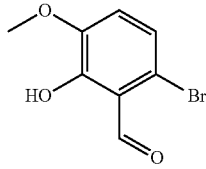

To a solution of 3-bromo-2-formyl-6-methoxyphenyl acetate (Preparation 166, 40.0 g, 146.5 mmol) in MeOH (400 mL) and water (50 mL) was added NaHCO₃ (13.5 g, 161.1 mmol) and LiOH (12.3 g, 293.0 mmol). The mixture was stirred at about 20° C. for about 12 h. The reaction was adjusted to pH 5-6 and extracted with DCM. The DCM layer was concentrated to afford 6-bromo-2-hydroxy-3-methoxybenzaldehyde (40.0 g), which was used in Preparation 164. ¹H NMR (CDCl₃, 400 MHz): δ 12.21 (s, 1H), 10.22 (s, 1H), 7.03 (d, J=8.4 Hz, 1H), 6.85 (d, J=8.8 Hz, 1H), 3.81-3.85 (m, 3H).

Preparation 166:
3-bromo-2-formyl-6-methoxyphenyl acetate

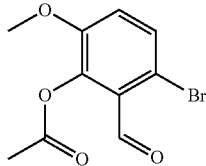

To a solution of 2-formyl-6-methoxyphenyl acetate (Preparation 167, 50.0 g, 257.5 mmol) in water (500 mL) was added Br₂ (53.5 g, 334.7 mmol) and KBr (46.0 g, 386.2 mmol). The mixture was stirred at about 20° C. for about 10 h. The precipitate was filtered, rinsed with ethyl acetate and recrystallized from EtOAc/pet. ether to afford 3-bromo-2-formyl-6-methoxyphenyl acetate (40.0 g, 57%). ¹H NMR (CDCl₃, 400 MHz): δ 10.28 (s, 1H), 7.53 (d, J=8.8 Hz, 1H), 7.07 (d, J=8.8 Hz, 1H), 3.87 (s, 3H), 2.40 (s, 3H).

Preparation 167: 2-formyl-6-methoxyphenyl acetate

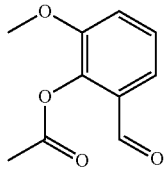

To a solution of 2-hydroxy-3-methoxybenzaldehyde (50.0 g, 328.6 mmol) in DCM (200 mL) was added Ac₂O (33.5 g, 329 mmol), DMAP (4.0 g, 32.8 mmol) and Et₃N (33.2 g, 329 mmol). The mixture was stirred at about 20° C. for about 2 h. The reaction mixture was quenched with saturated aqueous NH₄Cl (100 mL) and extracted with DCM (2×100 mL). The combined DCM extracts were washed with HCl (100 mL, 1 M), brine (300 mL), dried over Na₂SO₄, filtered and concentrated to afford 2-formyl-6-methoxyphenyl acetate (60.0 g, 94%). ¹H NMR (CDCl₃, 400 MHz): δ 10.12-10.17 (m, 1H), 7.46 (dd, J=1.6, 7.8 Hz, 1H), 7.34 (t, J=8.0 Hz, 1H), 7.22 (dd, J=1.6, 8.2 Hz, 1H), 3.88 (s, 3H), 2.41 (s, 3H).

Preparation 168: 1-bromo-2-(difluoromethyl)-3-ethoxy-4-methoxybenzene

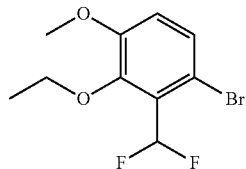

To a mixture of DAST (CAS 38078-09-0, 17.8 mL, 143.0 mmol) in DCM (100 mL) was added a solution of 6-bromo-2-ethoxy-3-methoxybenzaldehyde (Preparation 169, 4.64 g, 17.9 mmol) in DCM (20 mL) at about −20° C. The reaction mixture was warmed to about 25° C. over 0.5 h and then at about 25° C. for about 15 h. The reaction was quenched with saturated aqueous NaHCO₃ (200 mL) at about 0° C. and the mixture was extracted with DCM (2×100 mL). The combined DCM extracts were concentrated and the residue was purified by column chromatography (silica) and eluted with pet. ether/EtOAc (100:0 to 97:3) to afford 1-bromo-2-(difluoromethyl)-3-ethoxy-4-methoxybenzene (4.77 g, 95%). ¹H NMR (CDCl₃, 400 MHz): δ 7.31 (d, J=8.8 Hz, 1H), 7.10 (t, J=54.0 Hz, 1H), 6.87 (d, J=8.8 Hz, 1H), 4.11 (q, J=7.0 Hz, 2H), 3.87 (s, 3H), 1.40 (t, J=7.0 Hz, 3H).

Preparation 169: 6-bromo-2-ethoxy-3-methoxybenzaldehyde

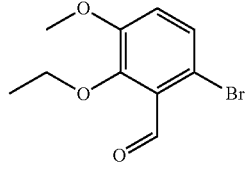

To a mixture of 6-bromo-2-hydroxy-3-methoxybenzaldehyde (Preparation 165, 5 g, 21.64 mmol) and K₂CO₃ (5.98 g, 43.3 mmol) in MeCN (100 mL) was added iodoethane (16.9 g, 108 mmol). The mixture was warmed to 60° C. and stirred for 4 h, followed by heating to 100° C. for 19 h. The mixture was cooled to r.t and condensed under reduced pressure. The residue was purified by column chromatography (silica) and eluted with pet. ether:EtOAc (100:0 to 90:10) to afford 6-bromo-2-ethoxy-3-methoxybenzaldehyde (5.1 g, 92%) as a light yellow oil. ¹H NMR (CDCl₃, 400 MHz): δ 10.37 (s, 1H), 7.34 (d, J=8.8 Hz, 1H), 6.96 (d, J=8.8 Hz, 1H), 4.15 (q, J=7.0 Hz, 2H), 3.88 (s, 3H), 1.40 (t, J=7.0 Hz, 3H).

Preparation 170a:
1-bromo-3-ethoxy-2-fluoro-4-methoxybenzene

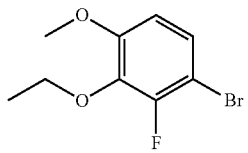

1-bromo-3-ethoxy-2-fluoro-4-methoxybenzene (25 g, 58%) was prepared in an analogous manner to Preparation 155 using 3-bromo-2-fluoro-6-methoxyphenol (38 g, 170 mmol) and iodoethane (40.2 g, 258 mmol). $^1$H NMR (CDCl$_3$, 400 MHz): δ 7.14-7.20 (m, 1H), 6.58-6.63 (m, 1H), 4.02 (t, J=6.7 Hz, 2H), 3.86 (s, 3H), 1.75-1.80 (m, 2H), 1.03 (t, J=7.5 Hz, 3H).

Preparation 170b:
1-bromo-2-fluoro-4-methoxy-3-propoxybenzene

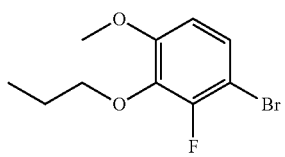

1-bromo-2-fluoro-4-methoxy-3-propoxybenzene (10.2 g 57%) was prepared in an analogous manner to Preparation 155 using 3-bromo-2-fluoro-6-methoxyphenol (15 g, 68.2 mmol) and 1-bromopropane (10.8 g, 88.6 mmol). $^1$H NMR (CDCl$_3$, 400 MHz): δ 7.14-7.20 (m, 1H), 6.58-6.63 (m, 1H), 4.02 (t, J=6.7 Hz, 2H), 3.86 (s, 3H), 1.75-1.80 (m, 2H), 1.03 (t, J=7.5 Hz, 3H).

Preparation 171:
6-bromo-3-methoxy-2-propoxybenzonitrile

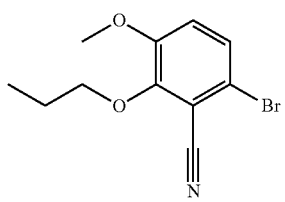

6-bromo-3-methoxy-2-propoxybenzonitrile (10.9 g 92%) was prepared in an analogous manner to Preparation 155 using 6-bromo-2-hydroxy-3-methoxybenzonitrile (10 g, 44 mmol) and 1-bromopropane (7 g, 57 mmol). $^1$H NMR (CDCl$_3$, 400 MHz): δ 7.27-7.30 (m, 1H), 6.96 (d, J=8.8 Hz, 1H), 4.15 (t, J=6.6 Hz, 2H), 3.86 (s, 3H), 1.78-1.87 (m, 2H), 1.06 (t, J=7.5 Hz, 3H). LCMS m/z=270 [MH]$^+$.

Preparation 172:
5-bromo-1-ethoxy-3-fluoro-2-methoxybenzene

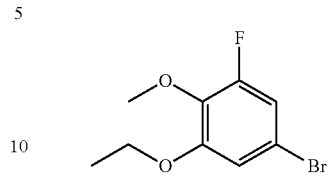

To a mixture of 5-bromo-3-fluoro-2-methoxyphenol (Preparation 173, 2.21 g, 10.0 mmol) and iodoethane (3.12 g, 20.0 mmol) dissolved in MeCN (30 mL) was added K$_2$CO$_3$ (2.07 g, 15 mmol). The mixture was warmed to about 50° C. and stirred for about 5 h. The mixture was cooled to about 20° C. and was filtered. The filtrate was concentrated and the residue was triturated with MTBE (20 mL) for about 20 min. The mixture was filtered and the filtrate was concentrated to afford 5-bromo-1-ethoxy-3-fluoro-2-methoxybenzene (1.85 g, 74%). $^1$H NMR (CDCl$_3$, 400 MHz): δ 6.88-6.91 (m, 1H), 6.82-6.83 (m, 1H), 4.07 (q, J=7.0 Hz, 2H), 3.90 (d, J=0.7 Hz, 3H), 1.46 (t, J=7.0 Hz, 3H).

Preparation 173:
5-bromo-3-fluoro-2-methoxyphenol

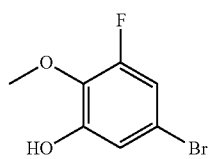

To a mixture 5-bromo-3-fluoro-2-methoxyphenyl formate (Preparation 174, 4.98 g, 20.0 mmol) in MeOH (30 mL) and water (30 mL) was added LiOH (1.68 g, 40.0 mmol) in portions.

The mixture was stirred at about 25° C. for about 16 h. The mixture was concentrated. The resulting aqueous phase was diluted with water and NaHCO$_3$ was added until pH 8. The aqueous phase was washed with MTBE (2×30 mL) and the combine MTBE extracts were concentrated. The residue was purified by column chromatography (silica) and eluted with pet. ether/EtOAc (100:0 to 85:15) to afford 5-bromo-3-fluoro-2-methoxyphenol (2.4 g, 54% over 2 steps). $^1$H NMR (CDCl$_3$, 400 MHz): δ 6.91-6.92 (m, 1H), 6.81-6.84 (m, 1H), 5.82 (s, 1H), 4.00 (d, J=1.8 Hz, 3H).

Preparation 174:
5-bromo-3-fluoro-2-methoxyphenyl formate

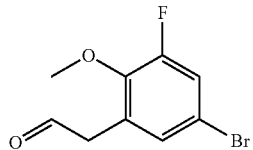

To a mixture of 5-bromo-3-fluoro-2-methoxybenzaldehyde (Preparation 175, 3.50 g, 15.0 mmol) in DCM (50 mL)

was added m-CPBA (4.85 g, 22.5 mmol). The resulting mixture was stirred at about 25° C. for about 16 h. The reaction was concentrated to afford 2-(5-bromo-3-fluoro-2-methoxyphenyl)acetaldehyde (3.74 g), which was used in Preparation 173.

Preparation 175:
5-bromo-3-fluoro-2-methoxybenzaldehyde

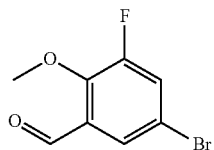

To a mixture of 5-bromo-3-fluoro-2-hydroxybenzaldehyde (Preparation 176, 18.6 g, 85.0 mmol) in MeCN (150 mL) was added K$_2$CO$_3$ (17.6 g, 128.0 mmol) and iodomethane (24.1 g, 170.0 mmol). The mixture was warmed to about 50° C. for about 16 h. The reaction was filtered and the filtrate was concentrated. The residue was triturated in MTBE (50 mL) and the resulting solid was filtered to afford 5-bromo-3-fluoro-2-methoxybenzaldehyde (4.9 g, 25%). $^1$H NMR (CDCl$_3$, 400 MHz): δ 10.33 (s, 1H), 7.73-7.74 (m, 1H), 7.47-7.51 (m, 1H), 4.10 (d, J=3.0 Hz, 3H).

Preparation 176:
5-bromo-3-fluoro-2-hydroxybenzaldehyde

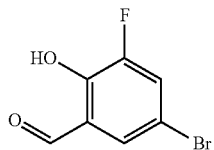 [SMILES: O=Cc1cc(Br)cc(F)c1O]

To a mixture of 4-bromo-2-fluorophenol (20.0 g, 104.7 mmol) dissolved in TFA (100 mL) was added HMTA (CAS 100-97-0, 29.4 g, 209.0 mmol) in portions. The mixture was heated at about 90° C. for about 16 h. The mixture was poured into water (800 mL) and a solid formed which was filtered. The cake was washed with water (2×150 mL) and dried to afford 5-bromo-3-fluoro-2-hydroxybenzaldehyde (18.9 g, 82%). $^1$H NMR (CDCl$_3$, 400 MHz): δ 10.90 (s, 1H), 9.88 (d, J=2.0 Hz, 1H), 7.49-7.53 (m, 2H).

Preparation 177:
5-bromo-1-chloro-3-ethoxy-2-methoxybenzene

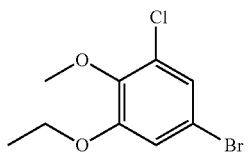

5-bromo-1-chloro-3-ethoxy-2-methoxybenzene (1.25 g, 86%) was prepared in an analogous manner to Preparation 172 using 5-bromo-3-chloro-2-methoxyphenol (Preparation 178, 1.3 g, 5.47 mmol). $^1$H NMR (CDCl$_3$, 400 MHz): δ 7.12 (d, J=2.3 Hz, 1H), 6.93 (d, J=2.3 Hz, 1H), 4.06 (q, J=7.0 Hz, 2H), 3.86 (s, 3H), 1.46 (t, J=7.0 Hz, 3H).

Preparation 178:
5-bromo-3-chloro-2-methoxyphenol

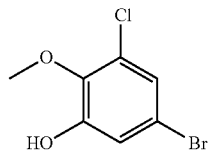

To a mixture of 5-bromo-3-chloro-2-methoxyphenyl formate (Preparation 179, 15.6 g, 58.76 mmol) in MeOH (100 mL) and water (100 mL) was added LiOH (4.93 g, 118.0 mmol) in portions. The mixture was stirred at about 25° C. for about 16 h. The mixture was concentrated and the resulting aqueous phase was diluted with aqueous NaHCO$_3$ (50 mL). The solution was extracted with MTBE (2×30 mL) and the combined MTBE extracts were dried and concentrated. The residue was purified by column chromatography (silica) and eluted with pet. ether:EtOAc (100:0 to 90:10) to afford 5-bromo-3-chloro-2-methoxyphenol (1.3 g, 7% over 2 steps). $^1$H NMR (CDCl$_3$, 400 MHz): δ 7.07 (d, J=2.3 Hz, 1H), 7.05 (d, J=2.3 Hz, 1H), 5.79 (s, 1H), 3.92 (s, 3H).

Preparation 179:
5-bromo-3-chloro-2-methoxyphenyl formate

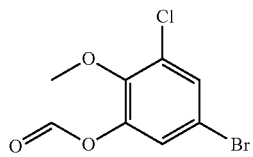

To a mixture of 5-bromo-3-chloro-2-methoxybenzaldehyde (Preparation 180, 20.0 g, 80.16 mmol) in DCM (200 mL) was added m-CPBA (25.9 g, 120 mmol). The mixture was stirred at about 25° C. for about 16 h. The white solid was filtered and the filtrate was concentrated to afford 5-bromo-3-chloro-2-methoxyphenyl formate (15.0 g, 70%), which was used in Preparation 178. LCMS m/z=266 [MH]-.

Preparation 180:
5-bromo-3-chloro-2-methoxybenzaldehyde

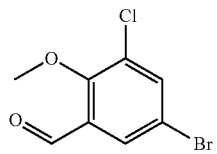

To a mixture of 5-bromo-3-chloro-2-hydroxybenzaldehyde (Preparation 181, 10 g, 42.5 mmol) dissolved in MeCN (150 mL) was added iodomethane (24.1 g, 170 mmol) and K$_2$CO$_3$ (11.7 g, 84.9 mmol). The mixture was warmed to about 50° C. and stirred for about 24 h. The mixture was cooled to about 20° C., filtered. The filtrate was concentrated and the residue was triturated with MTBE (30 mL) for about 20 min. before filtering. The filtrate was concentrated and the residue was diluted with water (20 mL) and extracted with EtOAc (2×100 mL). The combined EtOAc extracts were concentrated to afford 5-bromo-3-chloro-2-methoxybenzaldehyde (8.9 g, 84%), which was used in Preparation 179. $^1$H NMR (CDCl$_3$, 400 MHz): δ 10.30 (s, 1H), 7.87 (d, J=2.5 Hz, 1H), 7.77 (d, J=2.5 Hz, 1H), 4.01 (s, 3H).

Preparation 181:
5-bromo-3-chloro-2-hydroxybenzaldehyde

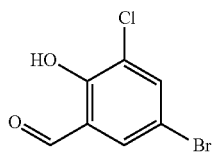 [SMILES: O=Cc1cc(Br)cc(Cl)c1O]

To a mixture of 4-bromo-2-chlorophenol (20.0 g, 94.41 mmol) in TFA (150 mL) was added HMTA (CAS 100-97-0, 27.0 g, 193 mmol) in portions. The mixture was stirred at about 90° C. for about 16 h. The mixture was poured into water (800 mL) forming a precipitate. The precipitate was filtered, washed with water (2×150 mL) and dried to afford 5-bromo-3-chloro-2-hydroxybenzaldehyde (22.7 g), which was used in Preparation 180. $^1$H NMR (CDCl$_3$, 400 MHz): δ 11.40 (br s, 1H), 9.86 (s, 1H), 7.75 (d, J=2.3 Hz, 1H), 7.63 (d, J=2.3 Hz, 1H).

Preparation 182:
1-bromo-5-ethoxy-2-fluoro-4-methoxybenzene

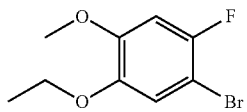

1-bromo-5-ethoxy-2-fluoro-4-methoxybenzene (7.1 g, 90%) was prepared in an analogous manner to Preparation 172 using 5-bromo-4-fluoro-2-methoxyphenol (Preparation 192, 7.0 g, 32.0 mmol). $^1$H NMR (CDCl$_3$, 400 MHz): δ6.96-6.98 (m, 1H), 6.69-6.71 (m, 1H), 4.02-4.07 (m, 2H), 3.84 (s, 3H), 1.41-1.52 (m, 3H).

Preparation 183:1-bromo-2-chloro-5-ethoxy-4-methoxybenzene

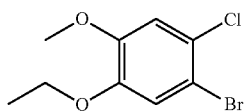

1-bromo-2-chloro-5-ethoxy-4-methoxybenzene (5.7 g, 98%) was prepared in an analogous manner to Preparation 172 using 5-bromo-4-chloro-2-methoxyphenol (Preparation 184, 5.2 g, 21.9 mmol). $^1$H NMR (CDCl$_3$, 400 MHz): δ 7.05 (s, 1H), 6.94 (s, 1H), 4.06 (q, J=7.0 Hz, 2H), 3.86 (s, 3H), 1.47 (t, J=7.0 Hz, 3H).

Preparation 184:5-bromo-4-chloro-2-methoxyphenol

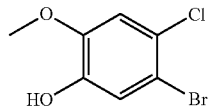

To a mixture of 5-bromo-4-chloro-2-methoxyphenyl formate (Preparation 185, 3.2 g, 12.05 mmol) in MeOH (50 mL) and water (50 mL) was added NaOH (0.72 g, 18.1 mmol). The mixture was stirred at about 20° C. for about 1 h. The mixture was acidified using 1N HCl to pH 3. The mixture was concentrated and the remaining aqueous phase was extracted with EtOAc (3×100 mL). The combined EtOAc extracts were washed with brine (200 mL), dried with anhydrous Na$_2$SO4, filtered and concentrated to afford 5-bromo-4-chloro-2-methoxyphenol (2.8 g, 98%). $^1$H NMR (CDCl$_3$, 400 MHz): δ 7.16 (s, 1H), 6.93 (s, 1H), 5.58 (s, 1H), 3.28 (s, 3H).

Preparation 185:
5-bromo-4-chloro-2-methoxyphenyl formate

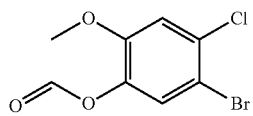

To a mixture of 5-bromo-4-chloro-2-methoxybenzaldehyde (Preparation 186, 12.2 g, 48.9 mmol) in DCM (300 mL) was added m-CPBA (21.1 g, 97.8 mmol). The mixture was stirred at about 18° C. for about 16 h. The mixture was partitioned between DCM (400 mL) and saturated sodium metabisulfite solution (200 mL). The separated DCM layer was washed with water (400 mL), brine (400 mL), dried over MgSO$_4$ and concentrated. The residue was purified by column chromatography (silica) and eluted with pet. ether/EtOAc (100:0 to 90:10) to afford 5-bromo-4-chloro-2-methoxyphenyl formate (3.2 g, 25%). $^1$H NMR (CDCl$_3$, 400 MHz): δ 8.22 (s, 1H), 7.36 (s, 1H), 7.09 (s, 1H), 3.85 (s, 3H).

Preparation 186:
5-bromo-4-chloro-2-methoxybenzaldehyde

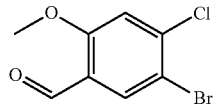

To a mixture of 1-bromo-2-chloro-4-methoxybenzene (15.0 g, 67.73 mmol) in TFA (100 mL) was added HMTA (CAS 100-97-0, 14.2 g, 102 mmol) in portions. The mixture was stirred at about 80° C. for about 12 h. The mixture was poured into water (1000 mL) and stirred at about 20° C. for about 1 h, forming a precipitate. The precipitate was filtered, dissolved in EtOAc (200 mL), dried over Na$_2$SO$_4$, filtered and concentrated. The residue was purified by column chromatography (silica) and eluted with pet. ether/EtOAc (100:0 to 90:10) to afford 5-bromo-4-chloro-2-methoxybenzaldehyde (6.7 g, 40%). $^1$H NMR (CDCl$_3$, 400 MHz): δ 10.33 (s, 1H), 8.03 (s, 1H), 7.12 (s, 1H), 3.94 (s, 3H).

Preparation 187:
1-bromo-5-ethoxy-4-methoxy-2-methylbenzene

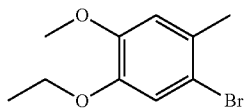

1-bromo-5-ethoxy-4-methoxy-2-methylbenzene (8.0 g, 99%) was prepared in an analogous manner to Preparation 172 using 5-bromo-2-methoxy-4-methylphenol (Preparation 189, 7.16 g, 33.0 mmol). $^1$H NMR (CDCl$_3$, 400 MHz): δ 7.01 (s, 1H), 6.74 (s, 1H), 4.05 (q, J=7.0 Hz, 2H), 3.85 (s, 3H), 2.33 (s, 3H) 1.46 (t, J=7.0 Hz, 3H).

Preparation 188:
1-bromo-2-fluoro-4-methoxy-5-propoxybenzene

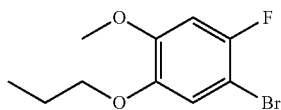

1-bromo-2-fluoro-4-methoxy-5-propoxybenzene (13.5 g, 95%) was prepared in an analogous manner to Preparation 172 using 5-bromo-4-fluoro-2-methoxyphenol (Preparation 192, 12 g, 109 mmol) and 1-iodopropane (18.5 g, 109 mmol). $^1$H NMR (CDCl$_3$, 400 MHz): δ 6.98 (d, J=6.8 Hz, 1H), 6.70 (d, J=9.8 Hz, 1H), 3.93 (t, J=6.8 Hz, 2H), 3.84 (s, 3H), 1.81-1.90 (m 2H), 1.04 (t, J=7.6 Hz, 3H).

Preparation 189:
5-bromo-2-methoxy-4-methylphenol

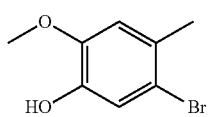

To a mixture of 5-bromo-2-methoxy-4-methylphenyl formate (Preparation 190, 19.3 g, 78.58 mmol) in MeOH (100 mL) and water (100 mL) was added NaOH (4.72 g, 118.1 mmol). The mixture was stirred at about 20° C. for about 1 h. The mixture was acidified using 1N HCl to pH 3. The mixture was concentrated and the remaining aqueous phase was extracted with EtOAc (3×150 mL). The combined EtOAc extracts were dried, filtered and concentrated. The residue was purified by column chromatography (silica) and eluted with pet. ether/EtOAc (100:0 to 80:20) to afford 5-bromo-2-methoxy-4-methylphenol (10.25 g, 60% over 2 steps). $^1$H NMR (CDCl$_3$, 400 MHz): δ 7.10 (s, 1H), 6.72 (s, 1H), 5.46 (br s, 1H), 3.87 (s, 3H), 2.33 (s, 3H).

Preparation 190:
5-bromo-2-methoxy-4-methylphenyl formate

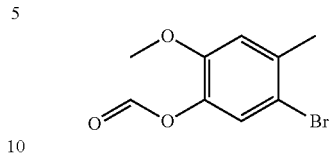

To a mixture of 5-bromo-2-methoxy-4-methylbenzaldehyde (Preparation 191, 18.0 g, 78.58 mmol) in DCM (200 mL) was added m-CPBA (33.9 g, 157.0 mmol). The mixture was stirred at about 18° C. for about 16 h. The mixture was filtered and the filtrate was concentrated. The residue was washed with aqueous sodium metabisulfite solution (1N, 200 mL), aqueous Na$_2$CO$_3$ (1N, 100 mL) and water. The residue afforded 5-bromo-2-methoxy-4-methylphenyl formate (19.3 g), which was used in Preparation 189.

Preparation 191:
5-bromo-2-methoxy-4-methylbenzaldehyde

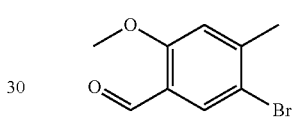

To a mixture of 1-bromo-4-methoxy-2-methylbenzene (25.1 g, 125.0 mmol) in TFA (120 mL) was added HMTA (26.3 g, 188 mmol) in portions. The mixture was stirred at about 80° C. for about 12 h. The mixture was poured into water (500 mL) and stirred at about 20° C. for about 2 h, forming a precipitate. The precipitate was filtered, suspended in water at about 60° C. for about 20 min, cooled to about 20° C. and filtered. The precipitate was dissolved in EtOAc (300 mL), dried over Na$_2$SO$_4$, filtered and concentrated to afford 5-bromo-2-methoxy-4-methylbenzaldehyde (18.0 g, 63%). $^1$H NMR (CDCl$_3$, 400 MHz): δ 10.34 (s, 1H), 7.95 (s, 1H), 6.88 (s, 1H), 3.92 (s, 3H), 2.45 (s, 3H).

Preparation 192: 5-bromo-4-fluoro-2-methoxyphenol

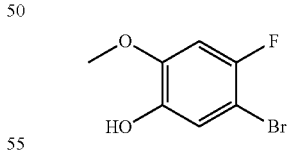

To a solution of 4-fluoro-2-methoxyphenol (5 g, 40 mmol) and Fe powder (98.2 mg, 1.76 mmol) in DCM (230 mL) was added a solution of Br$_2$ (6.18 g, 38.7 mmol) in DCM (20 mL). The solution was stirred for about 16 h at about 20° C. The mixture was washed with water (3×200 mL) and NaOH (1N). The DCM layer was dried (Na$_2$SO$_4$) and concentrated. The residue was purified by column chromatography (silica) and eluted with pet. ether/EtOAc (100:0 to 90:10) to afford 5-bromo-4-fluoro-2-methoxyphenol (6.0 g, 77%). $^1$H NMR (CDCl$_3$, 400 MHz): δ 7.07 (d, J=6.8 Hz, 1H), 6.68 (d, J=9.6 Hz, 1H), 5.47 (s, 1H), 3.87 (s, 3H).

Preparation 193: 2-ethoxy-1,5-difluoro-3-methoxybenzene

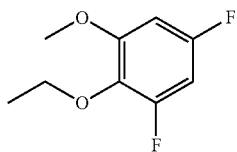

To a mixture of 2-ethoxy-3,5-difluorophenol (6.0 g, 34.45 mmol) and iodomethane (Preparation 194, 24.5 g, 172.0 mmol) in MeCN (100 mL) was added $K_2CO_3$ (9.52 g, 68.9 mmol). The mixture was warmed to about 60° C. and stirred for about 5 h. The mixture was cooled to about 20° C., filtered and concentrated. The residue was dissolved in EtOAc (200 mL). The EtOAc layer was washed with water (80 mL), brine (50 mL), dried over MgSO4, filtered and concentrated to afford 2-ethoxy-1,5-difluoro-3-methoxybenzene (5.0 g, 77%), which was used in Preparation 137. $^1$H NMR (CDCl$_3$, 400 MHz): δ 6.43-6.50 (m, 2H), 4.07 (q, J=7.0 Hz, 2H), 3.85 (s, 3H), 1.36 (t, J=7.0 Hz, 3H).

Preparation 194: 2-ethoxy-3,5-difluorophenol

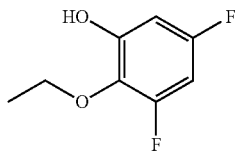

To a mixture of 2-(2-ethoxy-3,5-difluorophenyl)-4,4,5,5-tetramethyl-1,3,2-dioxaborolane (Preparation 195, 13.0 g, 45.76 mmol) in THF (100 mL) was added $H_2O_2$ (30%, 7.78 g, 68.6 mmol) and aqueous NaOH (1M, 48.0 mL, 48.0 mmol) at about 0° C. The mixture was allowed to warm to about 25° C. for about 2 h. The mixture was acidified with 1N HCl to pH 5. Brine (100 mL) was added and the mixture was extracted with EtOAc (2×200 mL). The combined EtOAc extracts were dried over NaSO$_4$, filtered and concentrated. The residue was purified by column chromatography (silica) and eluted with pet. ether/EtOAc (10:1) to afford 2-ethoxy-3,5-difluorophenol (6.0 g, 75%). $^1$H NMR (CDCl$_3$, 400 MHz): δ 6.49-6.52 (m, 1H), 6.37-6.43 (m, 1H), 5.95 (d, J=1.5 Hz, 1H), 4.18 (q, J=7.0 Hz, 2H), 1.39 (t, J=7.0 Hz, 3H).

Preparation 195: 2-(2-ethoxy-3,5-difluorophenyl)-4,4,5,5-tetramethyl-1,3,2-dioxaborolane

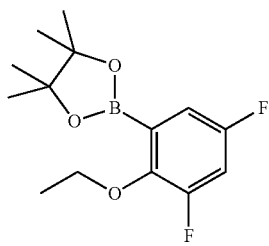 [SMILES: CCOc1c(F)cc(F)cc1B1OC(C)(C)C(C)(C)O1]

A combined mixture of 1-bromo-2-ethoxy-3,5-difluorobenzene (Preparation 196, 11.0 g, 46.4 mmol), Pin$_2$B$_2$ (6.53 g, 51.0 mmol) Pd(dppf)Cl$_2$ (1.7 g, 2.32 mmol) and KOAc (9.11 g, 92.8 mmol) in anhydrous 1,4-dioxane (200 mL) was degassed, heated and stirred at about 80° C. for about 24 h under N$_2$. The suspension was filtered and the filtrate was concentrated. The residue was purified by column chromatography (silica) and eluted with pet. ether/EtOAc (100:0 to 70:30) to afford 2-(2-ethoxy-3,5-difluorophenyl)-4,4,5,5-tetramethyl-1,3,2-dioxaborolane (13.0 g, 99%). $^1$H NMR (CDCl$_3$, 400 MHz): δ 7.14-7.17 (m, 1H), 6.90-6.95 (m, 1H), 4.06 (q, J=7.1 Hz, 2H), 1.41 (t, J=7.1 Hz, 3H), 1.37 (s, 12H). LCMS m/z=285 [MH]$^+$.

Preparation 196: 1-bromo-2-ethoxy-3,5-difluorobenzene

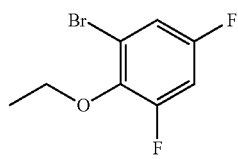

To a mixture of 2-bromo-4,6-difluorophenol (10.0 g, 47.85 mmol) and iodoethane (14.9 g, 95.7 mmol) in MeCN (200 mL) was added $K_2CO_3$ (13.2 g, 95.7 mmol). The mixture was warmed to about 60° C. and stirred for about 16 h. The mixture was cooled to about 20° C., filtered and the filtrate concentrated. The residue was dissolved in EtOAc (200 mL). The EtOAc layer was washed with water (80 mL), brine (50 mL), dried over MgSO$_4$, filtered and concentrated to afford 1-bromo-2-ethoxy-3,5-difluorobenzene (11.0 g, 97%), which was used in Preparation 195. $^1$H NMR (CDCl$_3$, 400 MHz): δ 7.09-7.12 (m, 1H), 6.82-6.88 (m, 1H), 4.12 (q, J=7.0 Hz, 2H), 1.43 (t, J=7.0 Hz, 3H).

Preparation 197: 4-bromo-1,2-diethoxybenzene

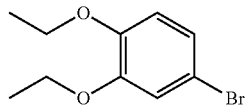

4-bromo-1,2-diethoxybenzene (6.3 g, 97%) was prepared in an analogous manner to Preparation 172 using 4-bromobenzene-1,2-diol (5.0 g, 26 mmol). $^1$H NMR (CDCl$_3$, 400 MHz): δ 6.96-7.01 (m, 2H), 6.71-6.76 (m, 1H), 4.06 (dq, J=3.5, 7.0 Hz, 4H), 1.40-1.48 (m, 6H).

Preparation 198: 4-bromo-1-ethoxy-2-methoxybenzene

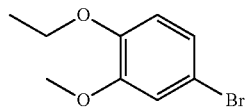

4-bromo-1-ethoxy-2-methoxybenzene (5.1 g, 98%) was prepared in an analogous manner to Preparation 172 using 4-bromo-2-methoxyphenol (4.57 g, 22.5 mmol). $^1$H NMR (CDCl$_3$, 400 MHz): δ 6.99-7.03 (m, 1H), 6.97-6.99 (m, 1H), 6.74 (d, J=8.8 Hz, 1H), 4.07 (q, J=6.9 Hz, 2H), 3.86 (s, 3H), 1.46 (t, J=6.9 Hz, 3H). LCMS m/z=231 [MH]$^+$.

Preparation 199:
1-bromo-4-ethoxy-2-fluoro-3-methoxybenzene

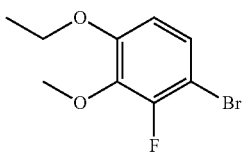

1-bromo-4-ethoxy-2-fluoro-3-methoxybenzene was prepared as a yellow oil (6.3 g, 99%) in an analogous manner to Preparation 172 using 3-bromo-6-ethoxy-2-fluorophenol (Preparation 200, 6 g, 25.5 mmol) and iodomethane (10.9 g, 76.6 mmol). $^1$H NMR (CDCl$_3$, 400 MHz): δ 7.13-7.19 (m, 1H), 6.60 (dd, J=2.0, 9.3 Hz, 1H), 4.08 (q, J=7.2 Hz, 2H), 3.93 (d, J=1.0 Hz, 3H), 1.46 (t, J=7.1 Hz, 3H).

Preparation 200:3-bromo-6-ethoxy-2-fluorophenol

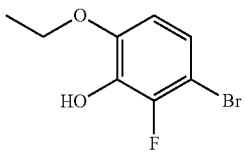

To a solution of 2-(3-bromo-6-ethoxy-2-fluorophenyl)-4,4,5,5-tetramethyl-1,3,2-dioxaborolane (Preparation 201, 15.2 g, 44.1 mmol) in THF (150 mL) was added H$_2$O$_2$ (30%, 7.49 g, 66.1 mmol) and aqueous NaOH (1M, 46.3 mL, 46.3 mmol) at about 0° C. The mixture was allowed to warm to about 25° C. for about 1.5 h. The mixture was acidified with 1N HCl to pH 5. Brine (150 mL) was added and the mixture was extracted with EtOAc (2×200 mL). The combined EtOAc extracts were dried over Na$_2$SO$_4$, filtered and concentrated to afford 3-bromo-6-ethoxy-2-fluorophenol (10.0 g, 97%). $^1$H NMR (CDCl$_3$, 400 MHz): δ 6.99 (dd, J=7.0, 9.0 Hz, 1H), 6.53-6.62 (m, 1H), 4.07-4.20 (m, 3H), 1.46 (t, J=7.0 Hz, 3H).

Preparation 201:2-(3-bromo-6-ethoxy-2-fluorophenyl)-4,4,5,5-tetramethyl-1,3,2-dioxaborolane

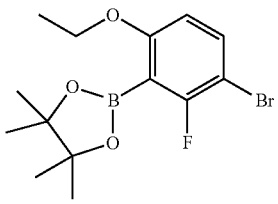 [SMILES: CCOc1ccc(Br)c(F)c1B1OC(C)(C)C(C)(C)O1]

To a solution of 1-bromo-4-ethoxy-2-fluorobenzene (Preparation 202, 11.0 g, 50.2 mmol) in THF (250 mL) was added dropwise a solution of LDA (37.7 mL, 75.3 mmol, 2 M in THF) at about −78° C. The solution was stirred at about −78° C. for about 1 h, PinBO-Pr (14.0 g, 75.3 mmol) was added dropwise. After stirring at about −78° C. for about 2 h, the solution was quenched with aqueous NH$_4$Cl (1 M, 100 mL) and extracted with MTBE (3×300 mL). The combined MTBE extracts were washed with brine (200 mL), dried over Na$_2$SO$_4$, and concentrated. The residue was purified by column chromatography (silica) and eluted with pet. ether/EtOAc (10:1) to afford 2-(3-bromo-6-ethoxy-2-fluorophenyl)-4,4,5,5-tetramethyl-1,3,2-dioxaborolane (15.2 g, 88%). $^1$H NMR (CDCl$_3$, 400 MHz): δ 7.43 (t, J=8.6 Hz, 1H), 6.51 (d, J=8.8 Hz, 1H), 3.99 (q, J=6.9 Hz, 2H), 1.35-1.45 (m, 16H).

Preparation 202: 1-bromo-4-ethoxy-2-fluorobenzene

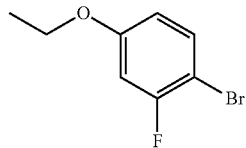

1-bromo-4-ethoxy-2-fluorobenzene (11 g, 96%) was prepared in an analogous manner to Preparation 172 using 4-bromo-2-methoxyphenol (10 g, 52 mmol). $^1$H NMR (CDCl$_3$, 400 MHz): δ 7.33-7.45 (m, 1H), 6.69 (dd, J=2.9, 10.8 Hz, 1H), 6.60 (ddd, J=1.0, 2.9, 8.8 Hz, 1H), 4.00 (q, J=7.2 Hz, 2H), 1.42 (t, J=6.9 Hz, 3H).

Preparation 203:
(4-bromo-2-methoxyphenyl)(methyl)sulfane

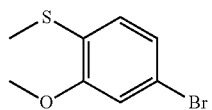

To a solution of dimethyl disulfide (35 g, 371 mmol) and isopentyl nitrite (57.9 g, 495 mmol) in THF (600 mL) was added 4-bromo-2-methoxybenzenamine (50 g, 247.46 mmol) slowly. The mixture was stirred at about 70° C. for about 3 h. The reaction mixture was concentrated. The residue was purified by column chromatography (silica) and eluted with pet. ether/EtOAc (100:0 to 90:10) to afford (4-bromo-2-methoxyphenyl)(methyl)sulfane (50 g, 87%). $^1$H NMR (CDCl$_3$, 400 MHz): δ 7.07-7.12 (m, 1H), 6.99-7.03 (m, 1H), 6.96 (d, J=2.0 Hz, 1H), 3.90 (s, 3H), 2.42 (s, 3H). LCMS m/z=233.0 [MH]$^+$.

Preparation 204:
(4-bromo-2-ethoxyphenyl)(methyl)sulfane

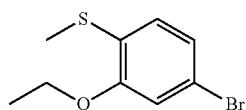

(4-bromo-2-ethoxyphenyl)(methyl)sulfane (35.0 g, 83%) was prepared in an analogous manner to Preparation 172 using 5-bromo-2-(methylthio)phenol (Preparation 20, 16 g, 73 mmol). $^{1}$H NMR (CDCl$_{3}$, 400 MHz): δ 7.05-7.09 (m, 1H), 6.97-7.01 (m, 1H), 6.94 (d, J=2.0 Hz, 1H), 4.09 (q, J=7.1 Hz, 2H), 2.41 (s, 3H), 1.47 (t, J=7.0 Hz, 3H).

Preparation 205: (4-bromo-2-(cyclopentyloxy)phenyl)(methyl)sulfane

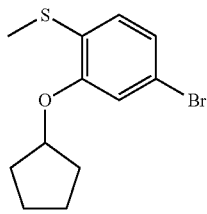

(4-bromo-2-(cyclopentyloxy)phenyl)(methyl)sulfane (6.0 g, 92%) was prepared in an analogous manner to Preparation 153 using 5-bromo-2-(methylthio)phenol (5 g, 22.8 mmol) and cyclopentanol (2.36 g, 27.4 mmol). $^{1}$H NMR (CDCl$_{3}$, 400 MHz): δ 7.05 (dd, J=2.0, 8.3 Hz, 1H), 6.93-6.98 (m, 2H), 4.80-4.84 (m, 1H), 2.38 (s, 3H), 1.79-1.95 (m, 6H), 1.60-1.68 (m, 2H).

Preparation 206: 5-bromo-2-(methylthio)phenol

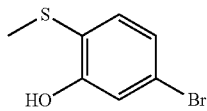

To a solution of (4-bromo-2-methoxyphenyl)(methyl)sulfane (19.0 g, 81.5 mmol) in DCM (300 mL) at about −78° C. was added BBr$_{3}$ (179 mL, 179 mmol, 1 M in DCM) dropwise under N$_{2}$ atmosphere. The reaction mixture was allowed to warm to about 20° C. and stirred for about 2 h. The mixture was quenched with MeOH at about 0° C. and concentrated. The residue was purified by column chromatography (silica) and eluted with pet. ether/EtOAc (100:0 to 70:30) to afford 5-bromo-2-(methylthio)phenol (16.3 g, 91%). $^{1}$H NMR (CDCl$_{3}$, 400 MHz): δ 7.35 (d, J=8.3 Hz, 1H), 7.17 (d, J=2.2 Hz, 1H), 7.03 (dd, J=2.2, 8.3 Hz, 1H), 6.67 (br s, 1H), 2.32 (s, 3H).

Preparation 207: 6-bromo-2-(cyclopentyloxy)-3-methoxybenzonitrile

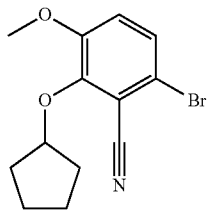 [SMILES: COc1ccc(Br)c(C#N)c1OC1CCCC1]

A mixture of 6-bromo-2-(cyclopentyloxy)-3-methoxybenzaldehyde oxime (Preparation 208, 7 g, 22.3 mmol), TFAA (7.16 g, 33.45 mmol) and Et$_{3}$N (6.76 g, 66.9 mmol) in DCM (100 mL) was stirred at about 20° C. for about 16 h. Water (200 mL) was added to the mixture and extracted with DCM (2×200 mL). The combined DCM extracts were washed with brine (200 mL), dried and concentrated. The residue was purified by column chromatography (silica) and eluted with pet. ether/EtOAc (10:1) to afford 6-bromo-2-(cyclopentyloxy)-3-methoxybenzonitrile (1.6 g, 24%). $^{1}$H NMR (CDCl$_{3}$, 400 MHz): δ 7.26-7.30 (m, 1H), 6.96 (d, J=8.8 Hz, 1H), 5.11-5.17 (m, 1H), 3.87 (s, 3H), 1.89-2.02 (m, 4H), 1.70-1.80 (m, 2H), 1.59-1.68 (m, 2H).

Preparation 208: 6-bromo-2-(cyclopentyloxy)-3-methoxybenzaldehyde oxime

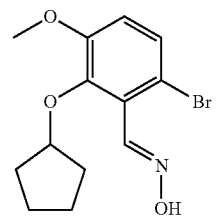 [SMILES: COc1ccc(Br)c(/C=N/O)c1OC1CCCC1]

To a solution of 6-bromo-2-(cyclopentyloxy)-3-methoxybenzaldehyde (Preparation 209, 6.8 g, 22.7 mmol) in EtOH (100 mL) was added NaHCO$_{3}$ (3.8 g, 45.4 mmol) and NH$_{2}$OH—HCl (2.35 g, 34 mmol). The mixture was stirred at about 20° C. for about 2 h. The reaction mixture was concentrated to afford 6-bromo-2-(cyclopentyloxy)-3-methoxybenzaldehyde oxime (7 g), which was used in Preparation 207.

Preparation 209: 6-bromo-2-(cyclopentyloxy)-3-methoxybenzaldehyde

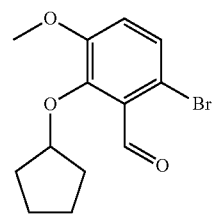 [SMILES: COc1ccc(Br)c(C=O)c1OC1CCCC1]

6-bromo-2-(cyclopentyloxy)-3-methoxybenzaldehyde (6.8 g, 90%) was prepared in an analogous manner to Preparation 172 using 6-bromo-2-hydroxy-3-methoxybenzaldehyde (Preparation 165, 6 g, 30 mmol) and bromocyclopentane (4.26 g, 28.6 mmol) at about 60° C. for about 3 h. $^{1}$H NMR (CDCl$_{3}$, 400 MHz): δ 10.31-10.38 (m, 1H), 7.31 (d, J=8.8 Hz, 1H), 6.94 (d, J=8.8 Hz, 1H), 4.95-5.01 (m, 1H), 3.87 (s, 3H), 1.70-1.93 (m, 7H), 1.62 (d, J=5.4 Hz, 2H). LCMS m/z=323 [M+Na]$^{+}$.

Preparation 210:
1-bromo-2,4-dimethoxy-3-propoxybenzene

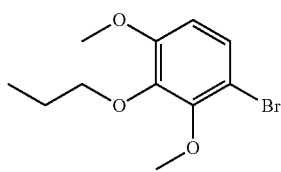

1-bromo-2,4-dimethoxy-3-propoxybenzene (10 g, 85%) was prepared in an analogous manner to Preparation 172 using 3-bromo-2,6-dimethoxyphenol (Preparation 211, 10 g, 43 mmol) and 1-iodopropane (14.6 g, 86 mmol). $^1$H NMR (CDCl$_3$, 400 MHz): δ 7.17-7.22 (m, 1H), 6.58 (d, J=8.8 Hz, 1H), 3.95-3.99 (m, 2H), 3.90 (s, 3H), 3.84 (s, 3H), 1.73-1.85 (m, 2H), 1.01-1.07 (m, 4H). LCMS m/z=276 [MH]$^+$.

Preparation 211:3-bromo-2,6-dimethoxyphenol

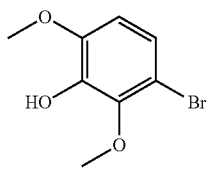

To a stirring solution of 2,6-dimethoxyphenol (1 g, 6.5 mmol) in CCl$_4$ (35 mL) at about −10° C. was added Br$_2$ (1.04 g, 6.5 mmol) and stirred for about 2 h. The reaction mixture was diluted with CCl$_4$ (20 mL), washed with water (3×60 mL) and the CCl$_4$ layer was washed with brine, dried over Na$_2$SO$_4$ and concentrated. The residue was purified by column chromatography (silica) and eluted with pet. ether/EtOAc (100:0 to 80:20) to afford 3-bromo-2,6-dimethoxyphenol (1.46 g, 97%). $^1$H NMR (CDCl$_3$, 400 MHz): δ 7.02 (d, J=8.8 Hz, 1H), 6.57 (d, J=8.8 Hz, 1H), 5.66 (s, 1H), 3.93 (s, 3H), 3.89 (s, 3H).

Preparation 212:
6-iodo-3-methoxy-2-propoxypyridine

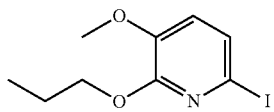

6-iodo-3-methoxy-2-propoxypyridine was (11 g, 95%) prepared in an analogous manner to Preparation 172 using 6-iodo-2-propoxypyridin-3-ol (Preparation 213, 11 g, 39 mmol) and 1-iodomethane (57 g, 402 mmol) at about 15° C. for about 6 h. $^1$H NMR (CDCl$_3$, 400 MHz): δ 7.24 (d, J=8.0 Hz, 1H), 6.91 (d, J=8.0 Hz, 1H), 4.25 (t, J=6.8 Hz, 2H), 3.83 (s, 3H), 1.73-1.90 (m, 2H), 1.04 (t, J=7.5 Hz, 3H). LCMS m/z=293 [MH]$^+$.

Preparation 213: 6-iodo-2-propoxypyridin-3-ol

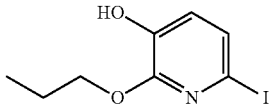

Sodium propan-1-olate (21.8 g, 265 mmol) was added to 2-bromo-6-iodopyridin-3-ol (Preparation 214, 26.5 g, 88.4 mmol) in DMF (200 mL), and the reaction mixture was stirred for about 16 h at about 110° C. under N$_2$. After cooling to about 20° C., the reaction mixture was partitioned between brine (200 mL) and EtOAc (250 mL). The aqueous layer was extracted with EtOAc (200 mL). The combined EtOAc extracts were dried (Na$_2$SO$_4$) and concentrated. The residue was purified by column chromatography (silica) and eluted with pet. ether/EtOAc (100:0 to 80:20) to afford 6-iodo-2-propoxypyridin-3-ol (11.2 g, 45%). $^1$H NMR (CDCl$_3$, 400 MHz): δ 7.17 (d, J=8.0 Hz, 1H), 6.81 (d, J=8.0 Hz, 1H), 5.47 (s, 1H), 4.31 (dt, J=0.9, 6.7 Hz, 2H), 1.74-1.86 (m, 2H), 0.98-1.05 (m, 3H).

Preparation 214:2-bromo-6-iodopyridin-3-ol

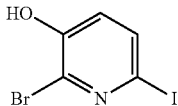

To a solution of 2-bromo-3-hydroxy pyridine (20.0 g, 114.95 mmol) in water (250 mL) was added K$_2$CO$_3$ (31.8 g, 230 mmol) and I$_2$ (29.2 g, 115 mmol). The mixture was stirred at about 20° C. for about 5 h. The mixture was cooled to 0° C. and treated with concentrated HCl. The precipitate was filtered to afford 2-bromo-6-iodopyridin-3-ol (30 g, 87%). $^1$H NMR (DMSO-d$_6$, 400 MHz): δ 11.10 (br s, 1H), 7.62 (d, J=8.1 Hz, 1H), 7.03 (d, J=8.3 Hz, 1H). LCMS m/z=299 [MH]$^+$.

Preparation 215:5-bromo-2-methoxy-3-propoxypyridine

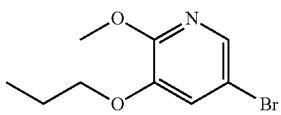

To a solution of 2-methoxy-3-propoxypyridine (Preparation 216, 5.68 g, 34 mmol) dissolved in DCM (60 mL) was added HOAc (2.04 g, 34 mmol). To the mixture, NBS (6.35 g, 35.7 mmol) was added in portions while stirring. The mixture was stirred at about 12° C. for about 16 h. The mixture was concentrated. The residue was diluted with water (200 mL) and extracted with EtOAc (2×100 mL) The combined EtOAc extracts were dried and concentrated. The residue was purified by column chromatography (silica) and eluted with pet. ether/EtOAc (100:0 to 85:15) to afford a mixture of 6-bromo-2-methoxy-3-propoxypyridine and 5-bromo-2-methoxy-3-propoxypyridine. The mixture was chilled to about −10° C. overnight. A precipitate formed which was separated from the oil by centrifugation (3×5 min @ 3000 rpm) to afford 5-bromo-2-methoxy-3-propoxypyridine (3 g, 53%). $^1$H NMR (CDCl$_3$, 400 MHz): δ 7.76 (d, J=2.0 Hz, 1H), 7.13 (d, J=2.0 Hz, 1H), 3.98 (s, 3H), 3.95 (t, J=6.8 Hz, 2H), 1.85-1.94 (m, 2H), 1.05 (t, J=7.5 Hz, 3H).

Preparation 216: 2-methoxy-3-propoxypyridine

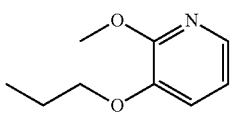

2-methoxy-3-propoxypyridine (5.7 g, 85%) was prepared in an analogous manner to Preparation 172 using 2-methoxypyridin-3-ol (5 g, 40 mmol) and 1-iodopropane (13.6 g, 80 mmol). $^1$H NMR (CDCl$_3$, 400 MHz): δ 7.73 (dd, J=1.5, 4.9 Hz, 1H), 7.05 (dd, J=1.5, 7.82 Hz, 1H), 6.83 (dd, J=5.0, 7.7 Hz, 1H), 4.02 (s, 3H), 3.97 (t, J=6.9 Hz, 2H), 1.86-1.93 (m, 2H), 1.05 (t, J=7.5 Hz, 3H).

Preparation 217:
2-bromo-5-methoxy-4-propoxypyridine

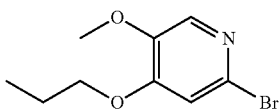

To a solution of 2-bromo-4-iodo-5-methoxypyridine (Preparation 218, 4.0 g, 13 mmol) in DMF (30 mL) was added NaH (765 mg, 19.1 mmol, 60%) and 1-propanol (1.53 g, 25.5 mmol) in DMF (25 mL) at about 20° C. The mixture was heated to about 60° C. for about 1 h. The solution was quenched with aqueous NH$_4$Cl (1 M, 30 mL) and extracted with EtOAc (3×100 mL). The combined EtOAc extracts were washed with brine (100 mL), dried over Na$_2$SO$_4$ and concentrated. The residue was purified by column chromatography (silica) and eluted with pet. ether/EtOAc (100:0 to 89:11) to afford 2-bromo-5-methoxy-4-propoxypyridine (2 g, 64%). $^1$H NMR (CDCl$_3$, 400 MHz): δ 7.84 (s, 1H), 6.91 (s, 1H), 4.00 (t, J=6.9 Hz, 2H), 3.90 (s, 3H), 1.83-1.92 (m, 2H), 1.05 (t, J=7.3 Hz, 3H). LCMS m/z=247.8 [MH]$^+$.

Preparation 218:
2-bromo-4-iodo-5-methoxypyridine

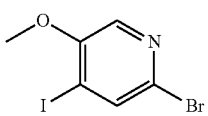

Sodium hydride (1.27 g, 31.8 mmol, 60%) was suspended in MeOH (2.55 g, 79.5 mmol) and DMF (80 mL) at about 25° C. The mixture was added to a solution of 2-bromo-5-fluoro-4-iodopyridine (Preparation 219, 8 g, 26.50 mmol) in DMF (10 mL) at about 0° C. The mixture was stirred at about 0° C. for about 1 h. The solution was quenched with aqueous NH$_4$Cl (1 M, 60 mL) and extracted with MBTE (3×200 mL). The combined MTBE extracts were washed with brine (100 mL), dried over Na$_2$SO$_4$, and concentrated. The residue was purified by column chromatography (silica) and eluted with pet. ether/EtOAc (100:0 to 90:10) to afford 2-bromo-4-iodo-5-methoxypyridine (4 g, 48.1%). $^1$H NMR (CDCl$_3$, 400 MHz): δ 7.88 (s, 1H), 7.85 (s, 1H), 3.97 (s, 3H).

Preparation 219: 2-bromo-5-fluoro-4-iodopyridine

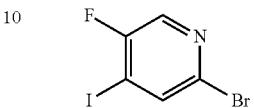

A solution of 2-bromo-5-fluoropyridine (24.6 g, 140 mmol) in THF (300 mL) was cooled to about −78° C. LDA (2 M in THF, 90.9 mL, 182 mmol) was added dropwise and the mixture was stirred for about 20 min. To the mixture was added a solution of iodine (49.7 g, 196 mmol) in THF (100 mL) dropwise. The reaction mixture was warmed to about 0° C. and stirred for about 30 min. The reaction was quenched with 10% aq. Na$_2$S$_2$O$_3$ solution and was extracted with EtOAc (3×500 mL). The combined EtOAc extracts were washed with brine (500 mL), dried over Na$_2$SO$_4$, filtered and concentrated. The residue was purified by column chromatograph (silica) and eluted with pet. ether/EtOAc (10:1) to afford 2-bromo-5-fluoro-4-iodopyridine (50 g, 67% purity). The material was further purified by preparative HPLC (Column: Phenomenex Synergi Max-RP 150 mm×50 mm, 10μ; Mobile Phase: [water (0.225% HCO$_2$H)-ACN]; B %: 30%-60%, 25 min. Flow rate 120 mL/min.) to afford 2-bromo-5-fluoro-4-iodopyridine (16.8 g, 40%). $^1$H NMR (CDCl$_3$, 400 MHz): δ 8.15 (s, 1H), 7.92 (s, 1H). LCMS m/z=303 [MH]$^+$.

Preparation 220: 3-fluoro-2-iodo-5-methoxy-6-propoxypyridine

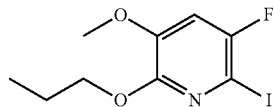

To a solution of 5-fluoro-3-methoxy-2-propoxypyridine (Preparation 221, 2.80 g, 15.1 mmol) in EtOH (50 mL) was added Ag$_2$SO$_4$ (7.07 g, 22.7 mmol) and I2 (5.76 g, 22.7 mmol). The reaction mixture was stirred at about 10° C. for about 16 h. The mixture was and the solution was partitioned between EtOAc (3×100 mL) and water (100 mL). The EtOAc extracts were dried with Na$_2$SO$_4$, filtered and concentrated to afford 3-fluoro-2-iodo-5-methoxy-6-propoxypyridine (4.38 g, 93%). $^1$H NMR (CDCl$_3$, 400 MHz): δ 7.58-7.74 (m, 1H), 4.30 (t, J=6.7 Hz, 2H), 3.92 (s, 3H), 1.75-1.91 (m, 2H), 1.05 (t, J=7.3 Hz, 3H). LCMS m/z=311 [MH]$^+$.

Preparation 221:
5-fluoro-3-methoxy-2-propoxypyridine

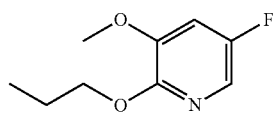

A mixture of tBuXPhos-Pd-G3 (CAS 14447963-75-8, 443 mg, 0.557 mmol), PrOH (803 mg, 13.4 mmol), 2-chloro-5-fluoro-3-methoxypyridine (Preparation 222, 1800 mg, 11.14 mmol) and Cs$_2$CO$_3$ (7260 mg, 22.3 mmol) was dissolved in PrOH (40 mL) under a N$_2$. The mixture was heated at about 90° C. for about 16 h. The mixture was dried and concentrated. The residue was purified by column chromatography (silica) and eluted with pet. ether/EtOAc (100:0 to 90:10) to afford 5-fluoro-3-methoxy-2-propoxypyridine (1280 mg, 77%). $^1$H NMR (CDCl$_3$, 400 MHz): δ 7.57 (d, J=2.5 Hz, 1H), 6.87 (dd, J=2.7, 9.3 Hz, 1H), 4.31 (t, J=7.0 Hz, 2H), 3.87 (s, 3H), 1.77-1.93 (m, 2H), 0.98-1.08 (m, 3H). LCMS m/z=185 [MH]$^+$.

Preparation 222: 2-chloro-5-fluoro-3-methoxypyridine

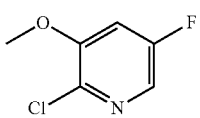

2-chloro-5-fluoro-3-methoxypyridine (1.8 g, 72%) was prepared in an analogous manner to Preparation 153 using 2-chloro-5-fluoropyridin-3-ol (2.3 g, 16 mmol) and methanol (5 g, 156 mmol). $^1$H NMR (CDCl$_3$, 400 MHz): δ 7.89 (d, J=2.70 Hz, 1H), 7.00 (dd, J=2.5, 9.1 Hz, 1H), 3.93 (s, 3H).

Preparation 223: 4-bromo-1-(difluoromethoxy)-2-propoxybenzene

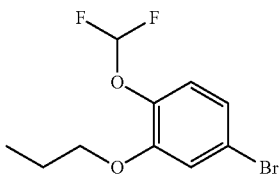

Powdered KOH (1.34 g, 23.8 mmol) was added to a stirring solution of 4-bromo-2-propoxyphenol (Preparation 224, 5.5 g, 23.8 mmol) in NMP (150 mL) at about 15° C. under N$_2$. The mixture was heated at about 50° C. for about 45 min then cooled to about 15° C. Difluorochloromethane was bubbled through the reaction mixture (approximately 20 min) until saturation and the mixture was stirred for an additional 20 min. Potassium hydroxide (2.68 g in 3 mL of water) was added dropwise, maintaining the temperature below 33° C. The mixture was stirred for an additional 40 min. Additional potassium hydroxide (1.34 g, in 3 mL of water) was added dropwise and the mixture was stirred for 1 h. N$_2$ was bubbled through the reaction and water was added. The pH of the resulting mixture was adjusted to 8 by the addition of potassium hydroxide (aqueous) and the mixture was extracted using MTBE (2×100 mL). The combined MBTE extracts were washed with water (50 mL), brine (3×100 mL), dried over Na$_2$SO$_4$, filtered, and concentrated. The residue was purified by column chromatography (silica) and eluted with pet. ether/EtOAc (100:0 to 90:10) to afford 4-bromo-1-(difluoromethoxy)-2-propoxybenzene (4.8 g, 72%). $^1$H NMR (CDCl$_3$, 400 MHz): δ 7.09 (d, J=1.3 Hz, 1H), 7.03-7.06 (m, 2H), 6.33-6.74 (m, 1H), 3.93-4.01 (m, 2H), 1.80-1.92 (m, 2H), 1.06 (t, J=7.4 Hz, 3H).

Preparation 224: 4-bromo-2-propoxyphenol

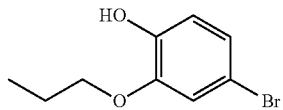

To a solution of 4-bromo-2-propoxyphenyl formate (Preparation 225, 10.9 g, 42 mmol) in MeOH (75 mL) and water (75 mL) was added NaOH (4200 mg, 105 mmol). The mixture was stirred at about 10° C. for about 1 h. The mixture was allowed to stand overnight. The mixture was acidified by HCl (1N) to pH 3. The mixture was concentrated and filtered. The filter cake was washed with water (20 mL). The cake was dissolved in MTBE (200 mL) and EtOAc (50 mL). The combined MTBE and EtOAc extracts were dried over Na$_2$SO$_4$, filtered and concentrated. The residue was purified by column chromatography (silica) and eluted with pet. ether/EtOAc (100:0 to 75:25) to afford 4-bromo-2-propoxyphenol (6.11 g, 63%). $^1$H NMR (CDCl$_3$, 400 MHz): δ 6.94-7.06 (m, 2H), 6.81 (d, J=8.5 Hz, 1H), 3.99 (t, J=6.8 Hz, 2H), 1.79-1.95 (m, 2H), 1.06 (t, J=7.5 Hz, 3H).

Preparation 225: 4-bromo-2-propoxyphenyl formate

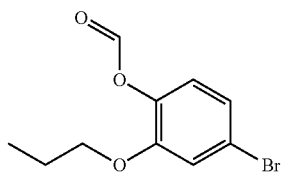

To a solution of 4-bromo-2-propoxybenzaldehyde (Preparation 226, 10.2 g, 42 mmol) dissolved in DCM (150 mL) was added m-CPBA (18.1 g, 84 mmol). The mixture was stirred at about 18° C. for about 16 h, then allowed to stand over the weekend. The mixture was filtered and concentrated to afford 4-bromo-2-propoxyphenyl formate (10.9 g), which was used in Preparation 224. LCMS m/z=248 [MH]$^+$.

Preparation 226: 4-bromo-2-propoxybenzaldehyde

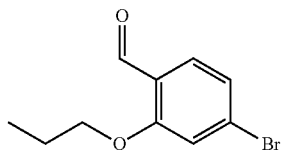

4-bromo-2-propoxybenzaldehyde (11.5 g, 95%) was prepared in an analogous manner to Preparation 172 using 4-bromo-2-hydroxybenzaldehyde (10 g, 50 mmol) and 1-iodopropane (11 g, 65 mmol). $^1$H NMR (CDCl$_3$, 400 MHz): δ 10.45 (d, J=0.7 Hz, 1H), 7.69 (d, J=8.1 Hz, 1H), 7.11-7.22 (m, 2H), 4.04 (t, J=6.5 Hz, 2H), 1.80-2.02 (m, 2H), 1.09 (t, J=7.3 Hz, 3H).

Preparation 227: ((2-bromoallyl)oxy)(tert-butyl)dimethylsilane

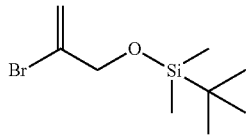

Five reactions were carried out in parallel. To a solution of 2-bromoprop-2-en-1-ol (Preparation 60, 150 g, 1.10 mol) and imidazole (Preparation 228, 74.6 g, 0.985 mol) in DMF (900 mL) was added TBS-Cl (140 g, 0.93 mol) in portions at about 30° C. Then the mixture was stirred at about 35° C. for 1 h. The mixture was poured into water (5.0 L). The combined mixtures were extracted with MTBE (3×2.5 L). The organic layer was washed with brine (2.0 L), dried over Na$_2$SO$_4$ and concentrated to afford ((2-bromoallyl)oxy)(tert-butyl)dimethylsilane (1250 g, 92%). $^1$H NMR (CDCl$_3$, 400 MHz): δ 5.96 (d, J=1.8 Hz, 1H), 5.54 (d, J=1.8 Hz, 1H), 4.22 (t, J=1.5 Hz, 2H), 0.89-0.97 (m, 9H), 0.11 (s, 6H).

Preparation 228: 2-bromoprop-2-en-1-ol

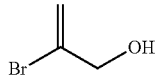

Five reactions were carried out in parallel: To a solution of 2,3-dibromoprop-1-ene (300 g, 1.50 mol) in DMF (900 mL) was added KOAc (221 g, 2.25 mol) in portions with stirring at about 20° C. The mixture was stirred at about 20° C. for about 12 h. A solution of LiOH (126 g, 3.01 mol) in MeOH (900 mL) and H$_2$O (300 mL) was added dropwise to the above mixture with stirring at about 20° C. The mixture was stirred at about 20° C. for about 1 h. The mixture was concentrated and poured into ice-water (2.0 L). The mixture was extracted with EtOAc (3×1.5 L). The EtOAc extracts were washed with brine (1.0 L), dried over Na$_2$SO$_4$ and concentrated to afford 2-bromoprop-2-en-1-ol (750 g, 72%). $^1$H NMR (CDCl$_3$, 400 MHz): δ 5.87-6.02 (m, 1H), 5.45-5.62 (m, 1H), 4.17 (s, 2H), 3.70 (br s, 1H).

Preparation 229: ((3-bromobut-3-en-1-yl)oxy)(tert-butyl)dimethylsilane

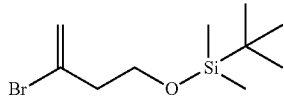

To a mixture of 3-bromobut-3-en-1-ol (CAS 76334-36-6, 10.0 g, 66.2 mmol) in anhydrous DCM (65 mL) was added imidazole (5.41 g, 79.5 mmol) and TBS-Cl (9.98 g, 66.2 mmol). The mixture was stirred at about 18° C. for about 16 h. The reaction was poured into ice water and extracted with EtOAc (2×200 mL). The combined EtOAc extracts were washed with brine, dried over Na$_2$SO$_4$ and filtered. The filtrate was concentrated. The residue was purified by column chromatography (silica) and eluted with pet. ether to afford ((3-bromobut-3-en-1-yl)oxy)(tert-butyl)dimethylsilane (16.0 g, 91%). $^1$H NMR (CDCl$_3$, 400 MHz): δ 5.64 (s, 1H), 5.46 (d, J=1.6 Hz, 1H), 3.80 (t, J=6.4 Hz, 2H), 2.63 (t, J=6.2 Hz, 2H), 0.90 (s, 9H), -0.08 (s, 6H).

Preparation 230: 4-(((tert-butyldimethylsilyl)oxy)methyl)-2,6-dichloropyrimidine

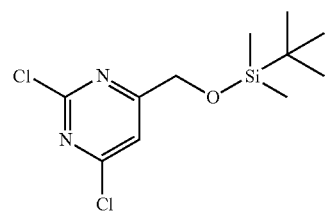 [SMILES: CC(C)(C)[Si](C)(C)OCc1cc(Cl)nc(Cl)n1]

To a solution of 2,6-dichloropyrimidin-4-yl)methanol (Preparation 231, 3.5 g, 19.55 mmol) and imidazole (1.6 g, 23.5 mmol) in DMF (60 mL) was added TBS-Cl (3.24 g, 22.4 mol) in portions at about 0° C. The mixture was stirred at about 0° C. for about 2 h. The mixture was poured into ice water (50 mL) and extracted with EtOAc (3×50 mL). The combined EtOAc extracts were washed with brine (2×30 mL), dried over Na$_2$SO$_4$, filtered and concentrated. The residue was purified by column chromatography (silica) and eluted with pet. ether/EtOAc (100:0 to 90:10) to afford 4-(((tert-butyldimethylsilyl)oxy)methyl)-2,6-dichloropyrimidine (3.1 g, 54%). $^1$H NMR (CDCl$_3$, 400 MHz): δ 7.48-7.57 (m, 1H), 4.72-4.82 (m, 2H), 0.93-1.03 (m, 9H), 0.14 (s, 6H). LCMS m/z=293 [MH]$^+$.

Preparation 231: 2,6-dichloropyrimidin-4-yl)methanol

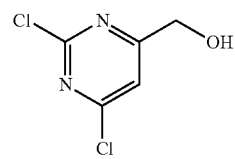

2,6-Dichloropyrimidine-4-carbonyl chloride (Preparation 232, 10 g, 47.3 mmol) was dissolved in a mixture of MeCN (60 mL) and THF (70 mL). The mixture was cooled to about −78° C. and treated with a solution of NaBH$_4$ (3.58 g, 94.6 mmol) in DMF (30 mL) dropwise. The mixture was stirred at about −78° C. for about 2 h and diluted with aqueous HCl solution (1 M, 10 mL). The mixture was diluted with saturated aqueous NaHCO$_3$ and extracted with EtOAc (2×100 mL). The combined EtOAc extracts were dried over MgSO$_4$, filtered and concentrated to afford 2,6-dichloropyrimidin-4-yl)methanol (8 g, 95%), which was used in Preparation 230. $^1$H NMR (CDCl$_3$, 400 MHz): δ 7.51 (s, 1H), 4.78 (s, 2H).

Preparation 232: 2,6-dichloropyrimidine-4-carbonyl chloride

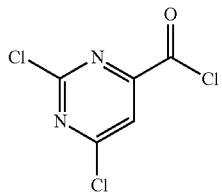 [SMILES: O=C(Cl)c1cc(Cl)nc(Cl)n1]

A solution of 2,6-dioxo-1,2,3,6-tetrahydropyrimidine-4-carboxylic acid (50 g, 0.32 mol) and $PCl_5$ (220 g, 1.06 mol) in $POCl_3$ (250 mL) was heated to reflux (120° C.) for about 16 h. The resulting mixture was concentrated and distilled under reduced pressure (120° C., 10 mm Hg) to afford 2,6-dichloropyrimidine-4-carbonyl chloride (21 g, 31%), which was used in Preparation 231.

Preparation 233: 4-methoxy-3-propoxybenzimidamide

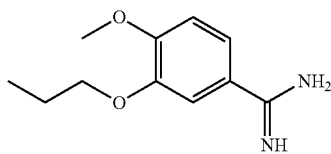

Ethyl 4-methoxy-3-propoxybenzimidate (Preparation 234, 37.6 g, 158.45 mmol) was dissolved in EtOH (226 mL). Ammonia in methanol (226 mL) was added to the reaction mixture. The reaction mixture was stirred at about 28° C. for about 24 h. After concentration, MTBE (150 mL) was poured into the residue, stirred for 1 h, and filtered and concentrated to afford 4-methoxy-3-propoxybenzimidamide (33.8 g, 100%). $^1$H NMR ($CD_3OD$, 400 MHz): δ 7.46 (dd, J=2.2, 8.6 Hz, 1H), 7.36 (d, J=2.2 Hz, 1H), 7.14 (d, J=8.6 Hz, 1H), 4.04 (t, J=6.5 Hz, 2H), 3.93 (s, 3H), 1.81-1.90 (m, 2H), 1.07 (t, J=7.6 Hz, 3H). LCMS m/z=209 [MH]$^+$.

Preparation 234: ethyl 4-methoxy-3-propoxybenzimidate

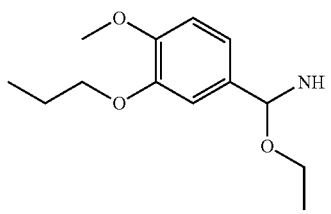 [SMILES: CCCOc1cc(C(N)OCC)ccc1OC]

Acetyl chloride (69.0 g, 879 mmol) was added dropwise to a solution of 4-methoxy-3-propoxybenzonitrile (Preparation 235, 21.0 g, 110 mmol) in dry EtOH (60.7 g, 1320 mmol), which was stirred at about 30° C. for about 12 h. The mixture was concentrated and to the residue was added MTBE (150 mL). The mixture was stirred for about 1 h and filtered to afford ethyl 4-methoxy-3-propoxybenzimidate (26.1 g, 100%). $^1$H NMR ($CDCl_3$, 400 MHz): δ 12.28 (br s, 1H), 11.56 (br s, 1H), 8.01 (d, J=2.2 Hz, 1H), 7.98 (dd, J=2.2, 8.6 Hz, 1H), 7.0 (d, J=8.6 Hz, 1H), 4.91 (q, J=7.0 Hz, 2H), 4.21 (t, J=6.6 Hz, 2H), 3.96 (s, 3H), 1.85-1.96 (m, 2H), 1.61 (t, J=7.0 Hz, 2H), 1.08 (t, J=7.5 Hz, 3H). LCMS m/z=238 [MH]$^+$.

Preparation 235: 4-methoxy-3-propoxybenzonitrile

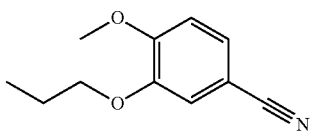

4-methoxy-3-propoxybenzonitrile (32.10 g, 100%) was prepared in an analogous manner to Preparation 172 using 3-hydroxy-4-methoxybenzonitrile (25 g, 170 mmol) and 1-iodopropane (57 g, 335 mmol). $^1$H NMR ($CDCl_3$, 400 MHz): δ 7.25-7.29 (m, 1H), 7.08 (d, J=2.0 Hz, 1H), 6.90 (d, J=8.3 Hz, 1H), 3.99 (t, J=6.9 Hz, 2H), 3.92 (s, 3H), 1.84-1.93 (m, 2H), 1.03-1.09 (m, 3H). LCMS m/z=191 [MH]$^+$.

Preparation 236: 3-((tert-butyldimethylsilyl)oxy)propan-1-ol

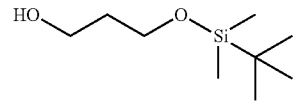

Propane-1,3-diol (20 g, 260 mmol), tert-butylchlorodimethylsilane (47.5 g, 315 mmol), $Et_3N$ (76.0 mL, 526 mmol) and DMAP (1.610 g, 13.1 mmol) were suspended in DCM (300 mL).

The mixture was stirred at about 18° C. overnight. The reaction mixture was partitioned between DCM (3×300 mL) and water (300 mL). The combined DCM extracts were concentrated. The residue was purified by column chromatography (silica) and eluted with pet. ether/EtOAc (100:0 to 97:3) to afford 3-((tert-butyldimethylsilyl)oxy)propan-1-ol (50 g, 100%), which was used in Preparation 158.

Preparation 237: 1-(6-bromopyridin-2-yl)-2-hydroxyethan-1-one

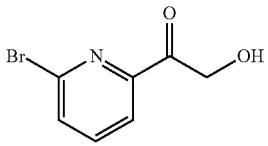 [SMILES: O=C(CO)c1cccc(Br)n1]

Step 1: A solution of 1-(6-bromopyridin-2-yl)ethanone (CAS 49669-13-8, 5.0 g, 25.0 mmol) in AcOH (12 mL) was heated to about 70° C. Bromine (1.4 mL, 27.5 mmol) was added dropwise over 30 min. The solution was stirred at about 70° C. for about 19 h. The solution was cooled EtOAc (50 mL) and hexanes (50 mL) were added. The precipitate was filtered and washed with heptane (2×50 mL). The combined filtrates were washed with brine (30 mL), dried over MgSO4, filtered, and concentrated to give a 2-bromo-1-(6-bromopyridin-2-yl)ethan-1-one (6.85 g), which was used directly in the next step.

Step 2: To a solution of 2-bromo-1-(6-bromopyridin-2-yl)ethanone (6.74 g) in DMF (30 mL) was added sodium nitrite (2.00 g). The solution was stirred at about 20° C. for about 22 h. The reaction was diluted with EtOAc (100 mL) and washed with water (100 mL). The water layers extracted with EtOAc. The combined EtOAc extracts were washed with brine (20 mL), dried with MgSO$_4$, filtered and concentrated. The residue was purified by column chromatography (silica) and eluted with heptane/EtOAc (90:10 to 70:30) to afford 1-(6-bromopyridin-2-yl)-2-hydroxyethan-1-one (977 mg), which was used in Preparation 88. $^1$H NMR (CDCl$_3$, 400 MHz): δ 7.99-8.11 (m, 1H), 7.68-7.83 (m, 2H), 5.08 (d, J=5.1 Hz, 2H).

Example 1: 4-(5-(3,4-dimethoxyphenyl)pyridin-3-yl)-1,2-oxaborolan-2-ol, enantiomer 1

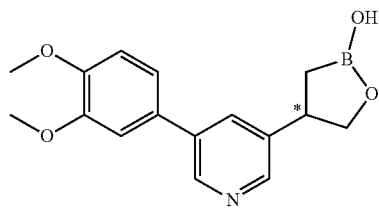 [SMILES: COc1ccc(-c2cncc(C3COB(O)C3)c2)cc1OC]

4-(5-(3,4-dimethoxyphenyl)pyridin-3-yl)-1,2-oxaborolan-2-ol (Example 32, 500 mg, 1.67 mmol) was further purified by preparative SFC (Prep SFC Method A) to afford 4-(5-(3,4-dimethoxyphenyl)pyridin-3-yl)-1,2-oxaborolan-2-ol, enantiomer 1 (233 mg, 46%). $^1$H NMR (DMSO-d$_6$, 400 MHz): δ 8.72 (d, J=2.8 Hz, 2H), 8.43 (d, J=2.0 Hz, 1H), 7.95 (t, J=2.0 Hz, 1H), 7.25-7.29 (m, 1H), 7.06 (d, J=8.4 Hz, 2H), 4.28 (t, J=4.28 Hz, 1H), 3.84-3.88 (m, 4H), 3.80 (s, 3H), 3.46-3.54 (m, 1H), 1.28-1.34 (m, 1H), 1.12-1.18 (m, 1H). LCMS m/z=300 [MH]$^+$; RT [Analytical SFC Method A]=5.20 min.

Example 2: (S)-4-(5-(3-ethoxy-4-methoxyphenyl)pyridin-3-yl)-1,2-oxaborolan-2-ol

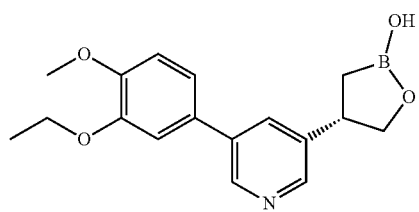 [SMILES: CCOc1cc(-c2cncc([C@H]3COB(O)C3)c2)ccc1OC]

4-(5-(3-ethoxy-4-methoxyphenyl)pyridin-3-yl)-1,2-oxaborolan-2-ol (Example 33, 2.3 g, 7.3 mmol) was further purified by preparative SFC (Prep SFC Method B). The solids were recrystallized from EtOAc (442 mg in 2 mL) to afford 4-(5-(3-ethoxy-4-methoxyphenyl)pyridin-3-yl)-1,2-oxaborolan-2-ol, enantiomer 1 (253 mg, 11%) as a crystalline solid. $^1$H NMR (DMSO-d$_6$, 400 MHz): δ 8.70 (d, J=2.3 Hz, 1H), 8.68 (s, 1H), 8.42 (d, J=1.6 Hz, 1H), 7.92-7.94 (m, 1H), 7.23-7.29 (m, 2H), 7.06 (d, J=8.2 Hz, 1H), 4.28 (t, J=8.2 Hz, 1H), 4.13 (q, J=6.8 Hz, 2H), 3.86 (t, J=9.0 Hz, 1H), 3.80 (s, 3H), 3.45-3.55 (m, 1H), 1.28-1.39 (m, 4H), 1.10-1.20 (m, 1H). LCMS m/z=314 [MH]+; RT [Analytical SFC Method B]=6.59 min. [α]$^{20}_D$ +19.5 (c=0.3, EtOH).

Example 3: (R)-4-(5-(3-ethoxy-4-methoxyphenyl)pyridin-3-yl)-1,2-oxaborolan-2-ol

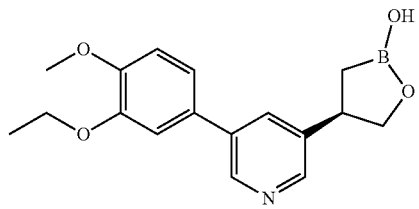 [SMILES: CCOc1cc(-c2cncc([C@@H]3COB(O)C3)c2)ccc1OC]

Further elution of the preparative SFC column (Prep SFC Method B) described in Example 2 provided enantiomer 2 that was recrystallization from EtOAc to afford (R) 4-(5-(3-ethoxy-4-methoxyphenyl)pyridin-3-yl)-1,2-oxaborolan-2-ol (610 mg, 27%) as a crystalline solid. $^1$H NMR (DMSO-d$_6$, 400 MHz): δ 8.70 (d, J=2.3 Hz, 1H), 8.68 (s, 1H), 8.42 (d, J=1.6 Hz, 1H), 7.92-7.94 (m, 1H), 7.23-7.29 (m, 2H), 7.06 (d, J=8.2 Hz, 1H), 4.28 (t, J=8.2 Hz, 1H), 4.13 (q, J=6.8 Hz, 2H), 3.86 (t, J=9.0 Hz, 1H), 3.80 (s, 3H), 3.45-3.55 (m, 1H), 1.28-1.39 (m, 4H), 1.10-1.20 (m, 1H). LCMS m/z=314 [MH]$^+$; RT [Analytical SFC Method B]=7.07 min. [α]$^{20}_D$ -22.5 (c=0.2, EtOH).

Example 4: (R)-4-(5-(4-methoxy-3-propoxyphenyl)pyridin-3-yl)-1,2-oxaborolan-2-ol

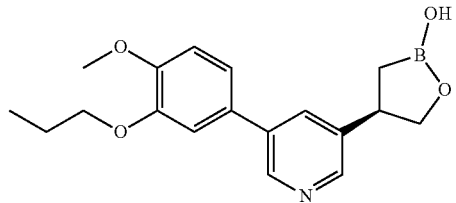 [SMILES: CCCOc1cc(-c2cncc([C@@H]3COB(O)C3)c2)ccc1OC]

Method A:
To a mixture of (R)-(3-((tert-butyldimethylsilyl)oxy)-2-(5-(4-methoxy-3-propoxyphenyl)pyridin-3-yl)propyl)boronic acid (Preparation 6, 55 g, 120 mmol) in IPA (247 mL) was added 5 M hydrogen chloride in IPA (37 mL, 185 mmol) at about 20° C. The mixture was stirred for about 3 h and concentrated. The residue was diluted with EtOAc (500 mL) and 1N HCl (500 mL) was added. The layers were separated and the EtOAc layer was extracted with 0.5 N HCl (2×200 mL). The aqueous extracts were combined with the separated acidic aqueous layer and washed with EtOAc (3×250 mL). The combined acidic aqueous layers were treated with K$_3$PO$_4$ to pH 5-6. The mixture was extracted with EtOAc (1×500 mL, 2×200 mL). The combined EtOAc extracts were washed with brine, dried over Na$_2$SO$_4$, filtered and concentrated to afford (R)-4-(5-(4-methoxy-3-propoxyphenyl)pyridin-3-yl)-1,2-oxaborolan-2-ol (34.5 g, 88%). This was further purified by preparative SFC (Prep SFC Method C) to afford 29 g as a crude product. The crude product was dissolved in methanol (250 mL) and water (50 mL) and stirred at 20° C. for about 30 min before concentrating. The concentrated solution was partitioned between brine and EtOAc. The aqueous layer was separated and extracted with EtOAc. The EtOAc extracts were combined with the separate EtOAc layer and were washed with brine, dried over Na$_2$SO$_4$ and concentrated. The residue was dissolved in degassed EtOAc (200 mL) and degassed heptane (100 mL) was added slowly. Heptane was added until a precipitate was observed and the resulting mixture was stirred overnight under N$_2$. The solid was filtered to afford 8.08 g of product. The filtrate was concentrated and the residue dissolved in EtOAc (50 mL). Heptane (25 mL) was slowly added and the mixture stirred overnight open to air. The solid was filtered to afford a second batch (6.16 g). This was repeated a second time to afford 3.0 g. The filtrate was stirred overnight to afford additional batches (2.09 g and 3.1 g) respectively. The solid batches were combined to afford (R)-4-(5-(4-methoxy-3-propoxyphenyl)pyridin-3-yl)-1,2-oxaborolan-2-ol (22.3 g, 57%) as a crystalline solid. $^1$H NMR (DMSO-d$_6$, 400 MHz): δ 8.70 (d, J=2.3 Hz, 1H), 8.68 (s, 1H), 8.42 (d, J=2.0 Hz, 1H), 7.93 (s, 1H), 7.27 (d, J=2.0 Hz, 1H), 7.23-7.26 (m, 1H), 7.06 (d, J=8.2 Hz, 1H), 4.28 (t, J=8.2 Hz, 1H), 4.03 (t, J=6.4 Hz, 2H), 3.86 (t, J=9.0 Hz, 1H), 3.81 (s, 3H), 3.46-3.54 (m, 1H), 1.71-1.80 (m, 2H), 1.28-1.35 (m, 1H), 1.15 (dd, J=10.5, 16.4 Hz, 1H), 1.00 (t, J=7.4 Hz, 3H). LCMS m/z=328 [MH]$^+$, RT [Analytical SFC Method B]=7.30 min. [α]$^{20}_D$ −23.7 (c=0.9, EtOH). Elemental analysis calculated (%) for C$_{18}$H$_{22}$BN$_4$: C 66.08, H 6.78, N 4.28. Found: C 65.86, H 6.59, N 4.18.

Method B:

Step 1: To THF (18.0 mL) was added 3-(3-((tert-butyldimethylsilyl)oxy)prop-1-en-2-yl)-5-(4-methoxy-3-propoxyphenyl)pyridine (Preparation 50, 3.0 g, 7.25 mmol), [Ir(COD)Cl]$_2$ (CAS 12112-67-3, 36.9 mg, 0.054 mmol) and (S)[(Sp)-2-(diphenylphosphino)ferrocenyl]-4-isopropyloxazoline (CAS 163169-29-7, 52.4 mg, 0.109 mmol). Additional THF (6.0 mL) was added to the mixture which was warmed to about 50° C. for about 5 min. Catecholborane (10.9 mL, 1.0M in THF) was added to the mixture and stirred at about 50° C. for about 1 h. The mixture was cooled to about 20° C. and treated with HCl (12.2 M, 1.51 mL) over 1 min. The mixture was held at about 20° C. for about 1 h, after which a precipitate had formed. The mixture was cooled to about 10° C. and filtered. The filtered solid was washed with THF (6.0 mL) and dried overnight at 35° C. under vacuum to afford (R)-4-(5-(4-methoxy-3-propoxyphenyl)pyridine-3-yl)-1,2-oxaborolan-2-ol hydrochloride monohydrate (3.98 g, 91%) as a crystalline solid. $^1$H NMR (CD$_3$OD, 400 MHz): δ 8.98 (d, J=1.5 Hz, 1H), 8.75 (s, 1H), 8.67 (d, J=1.3 Hz, 1H), 7.37-7.43 (m, 2H), 7.15 (d, J=8.3 Hz, 1H), 4.09 (t, J=6.5 Hz, 2H), 3.89-3.92 (m, 1H), 3.86-3.95 (m, 5H), 3.46 (br s, 1H), 1.85 (m, 2H), 1.31-1.42 (m, 2H), 1.08 (t, J=7.4 Hz, 3H). LCMS m/z=328 [MH]$^+$.

Step 2: To a solution of (R)-4-(5-(4-methoxy-3-propoxyphenyl)pyridine-3-yl)-1,2-oxaborolan-2-ol hydrochloride monohydrate (2.0 g, 5.24 mmol) in water (60 mL) was added EtOAc (20 mL). To the stirred mixture was added NaOH (1N) dropwise to adjust the pH of the aqeuous layer to 7-8. The mixture was stirred at about 20° C. for about 5 min. The layers were separated and the aqueous layer was extracted with EtOAc (2×10 mL). The combined EtOAc extracts were concentrated. The residue was dissolved in THF/MTBE (1:3, 22 mL) and stirred at about 20° C. overnight. The precipitate was filtered and dried under vacuum to afford (R)-4-(5-(4-methoxy-3-propoxyphenyl)pyridine-3-yl)-1,2-oxaborolan-2-ol (1.17 g, 68%) as a crystalline solid. $^1$H NMR (DMSO-d$_6$, 400 MHz): δ 8.70 (d, J=2.3 Hz, 1H), 8.68 (s, 1H), 8.42 (d, J=2.0 Hz, 1H), 7.93 (s, 1H), 7.27 (d, J=2.0 Hz, 1H), 7.23-7.26 (m, 1H), 7.06 (d, J=8.2 Hz, 1H), 4.28 (t, J=8.2 Hz, 1H), 4.03 (t, J=6.4 Hz, 2H), 3.86 (t, J=9.0 Hz, 1H), 3.81 (s, 3H), 3.46-3.54 (m, 1H), 1.71-1.80 (m, 2H), 1.28-1.35 (m, 1H), 1.15 (dd, J=10.5, 16.4 Hz, 1H), 1.00 (t, J=7.4 Hz, 3H). LCMS m/z=328 [MH]$^+$.

Method C:

To a solution of (R)-(3-((tert-butyldimethylsilyl)oxy)-2-(5-(4-methoxy-3-propoxyphenyl)pyridin-3-yl)propyl)boronic acid (Preparation 6, 29.0 g, 63.1 mmol) in THF (66 mL) was added aqueous HCl (84.2 mL, 252 mmol, 3.0 M) and stirred at 20° C. for about 1.5 h.

The mixture was concentrated. The mixture was diluted with 1 M HCl and extracted with EtOAc (3×100 mL). The combined EtOAc extracts were washed with 1 M HCl (3×50 mL). The combined aqueous extracts were neutralized with K$_3$PO$_4$ to pH 7-8 and extracted with EtOAc (3×100 mL). The combined EtOAc extracts were dried over Na$_2$SO$_4$, filtered and concentrated to afford (R)-4-(5-(4-methoxy-3-propoxyphenyl)pyridin-3-yl)-1,2-oxaborolan-2-ol (19.0 g, 92%). This was further purified by preparative SFC (Prep SFC Method C) to afford 18 g of the crude product. The crude product was dissolved in MeOH (100 mL) and water (50 mL). The mixture was partitioned between brine and EtOAc. The layers were separated and the aqueous layer was extracted with EtOAc. The combined EtOAc extracts were washed with brine, dried over Na$_2$SO$_4$ and concentrated to afford 15 g of product. The residue was dissolved in EtOAc (60 mL) and heptane (30 mL) was slowly added over about 3 h. The mixture was stirred at about 20° C. overnight. The precipitate was filtered and dried to afford (8.08 g). This process was repeated 2 more times to afford additional batches (2.01 g and 1.03 g), respectively. The three batches were combined in heptane (100 mL), chilled to about −78° C. for about 10 min, filtered and dried to afford (R)-4-(5-(4-methoxy-3-propoxyphenyl)pyridin-3-yl)-1,2-oxaborolan-2-ol (10.4 g, 51%) as a crystalline solid. $^1$H NMR (DMSO-d$_6$, 400 MHz): δ 8.70 (d, J=2.3 Hz, 1H), 8.68 (s, 1H), 8.42 (d, J=2.0 Hz, 1H), 7.93 (s, 1H), 7.27 (d, J=2.0 Hz, 1H), 7.23-7.26 (m, 1H), 7.06 (d, J=8.2 Hz, 1H), 4.28 (t, J=8.2 Hz, 1H), 4.03 (t, J=6.4 Hz, 2H), 3.86 (t, J=9.0 Hz, 1H), 3.81 (s, 3H), 3.46-3.54 (m, 1H), 1.71-1.80 (m, 2H), 1.28-1.35 (m, 1H), 1.15 (dd, J=10.5, 16.4 Hz, 1H), 1.00 (t, J=7.4 Hz, 3H). LCMS m/z=328 [MH]$^+$.

Example 5: (S)-4-(5-(4-methoxy-3-propoxyphenyl)pyridin-3-yl)-1,2-oxaborolan-2-ol

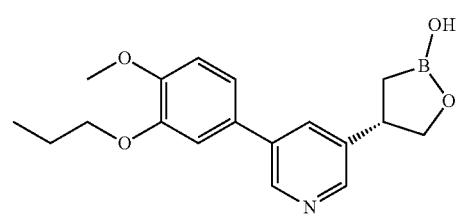 [SMILES: CCCOc1cc(-c2cncc([C@H]3COB(O)C3)c2)ccc1OC]

A mixture of 3-(3-((tert-butyldimethylsilyl)oxy)prop-1-en-2-yl)-5-(4-methoxy-3-propoxyphenyl)pyridine (Preparation 50, 30 g, 73 mmol), [Ir(COD)Cl]$_2$ (CAS 12112-67-3, 1.22 g, 1.81 mmol), (R,R)-[2-(4'-i-propyloxazolin-2-yl)ferrocenyl]diphenylphosphine (CAS 541540-70-9, 1.75 g, 3.63 mmol) and THF (240 mL) was cooled in an ice bath for about 30 min. A solution of catecholborane (109 mL, 109 mmol, 1.0 M in THF) was added slowly over about 20 min, after which the mixture was stirred at about 20° C. for about 3 h. The reaction was quenched with MeOH (30 mL). The mixture was concentrated and dried overnight. The residue was treated with 3 M aqueous HCl/THF (1:1, v/v) for about 2 h and washed with EtOAc. The aqueous layer was separated and neutralized to pH 7-8 and extracted with EtOAc. The EtOAc extract was dried over Na$_2$SO$_4$, filtered and concentrated. The residue was dissolved in THF/MTBE (1:1, 180 mL) and stirred with Biotage MP-TMT resin (28 g, Biotage P/N 801470) at about 20° C., under N$_2$, overnight. The mixture was filtered and the resin was washed with THF (2×50 mL). The combined THF/MTBE filtrates were concentrated to afford (S)-4-(5-(4-methoxy-3-propoxyphenyl)pyridin-3-yl)-1,2-oxaborolan-2-ol (23.5 g, 71%). This was further purified via SFC purification (Prep SFC Method C) to afford 12 g of a crude product. The crude product was dissolved in MeOH (35 mL) and water (15 mL). The mixture was partitioned between brine and EtOAc. The layers were separated and the aqueous phase was extracted with EtOAC. The combined EtOAc extracts were dried over Na$_2$SO$_4$, filtered and concentrated. The residue was dissolved in EtOAc (30 mL) and heptane was added until just cloudy. The mixture was stirred overnight. The precipitate was filtered and dried to afford (S)-4-(5-(4-methoxy-3-propoxyphenyl)pyridin-3-yl)-1,2-oxaborolan-2-ol (5.39 g, 45%) as a crystalline solid. $^1$H NMR (DMSO-d$_6$, 400 MHz): δ 8.70 (d, J=2.3 Hz, 1H), 8.68 (s, 1H), 8.42 (d, J=2.0 Hz, 1H), 7.93 (s, 1H), 7.27 (d, J=2.0 Hz, 1H), 7.23-7.26 (m, 1H), 7.06 (d, J=8.2 Hz, 1H), 4.28 (t, J=8.2 Hz, 1H), 4.03 (t, J=6.4 Hz, 2H), 3.86 (t, J=9.0 Hz, 1H), 3.81 (s, 3H), 3.46-3.54 (m, 1H), 1.71-1.80 (m, 2H), 1.28-1.35 (m, 1H), 1.15 (dd, J=10.5, 16.4 Hz, 1H), 1.00 (t, J=7.4 Hz, 3H). LCMS m/z=328 [MH]$^+$, RT [Analytical SFC Method B]=6.35 min. [α]$^{20}_D$ +27.3 (c=0.6, EtOH). Elemental analysis calculated (%) for C$_{18}$H$_{22}$BNO$_4$: C 66.08, H 6.78, N 4.28. Found: C 66.01, H 6.52, N 4.15.

Example 6: 4-(5-(3-isopropoxy-4-methoxyphenyl)pyridin-3-yl)-1,2-oxaborolan-2-ol, enantiomer 1

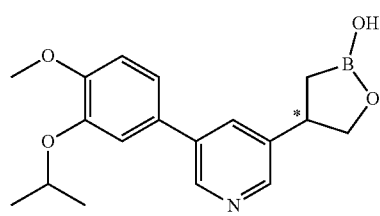 [SMILES: COc1ccc(-c2cncc(C3COB(O)C3)c2)cc1OC(C)C]

4-(5-(3-isopropoxy-4-methoxyphenyl)pyridin-3-yl)-1,2-oxaborolan-2-ol (Example 35, 90 mg, 0.28 mmol) was further purified by preparative SFC (Prep SFC Method D) followed by preparative HPLC (Method A) to afford 4-(5-(3-isopropoxy-4-methoxyphenyl)pyridin-3-yl)-1,2-oxaborolan-2-ol, enantiomer 1 (17 mg, 19%). $^1$H NMR (DMSO-d$_6$, 400 MHz): δ 8.72 (s, 1H), 8.69 (d, J=2.0 Hz, 1H), 8.42 (d, J=2.0 Hz, 1H), 7.92 (t, J=2.0 Hz, 1H), 7.29-7.24 (m, 2H), 7.07 (d, J=8.0 Hz, 1H), 4.68-4.74 (m, 1H), 4.27 (t, J=8.3 Hz, 1H), 3.86 (t, J=9.0 Hz, 1H), 3.79 (s, 3H), 3.47-3.55 (m, 1H), 1.26-1.35 (m, 7H), 1.10-1.18 (m, 1H). LCMS m/z=328 [MH]$^+$. RT [Analytical SFC Method C]=5.425 min.

Example 7: 4-(5-(3-cyclopropoxy-4-methoxyphenyl)pyridin-3-yl)-1,2-oxaborolan-2-ol, enantiomer 2

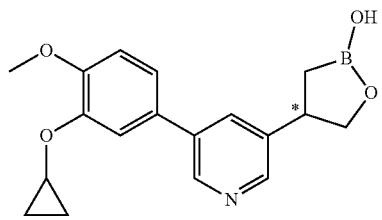 [SMILES: COc1ccc(-c2cncc(C3COB(O)C3)c2)cc1OC1CC1]

4-(5-(3-cyclopropoxy-4-methoxyphenyl)pyridin-3-yl)-1,2-oxaborolan-2-ol (Example 36, 5.0 g, 4.54 mmol) was further purified by preparative SFC (Prep SFC Method E) to afford 4-(5-(3-(2-hydroxyethoxy)-4-methoxyphenyl)pyridin-3-yl)-1,2-oxaborolan-2-ol, enantiomer 2 (205 mg, 41%). $^1$H NMR (DMSO-d$_6$, 400 MHz): δ 8.69-8.72 (m, 2H), 8.44 (d, J=2.0 Hz, 1H), 7.91 (t, J=2.0 Hz, 1H), 7.53 (d, J=2.0 Hz, 1H), 7.28 (dd, J=2.4, 8.3 Hz, 1H), 7.07 (d, J=8.8 Hz, 1H), 4.25-4.31 (m, 1H), 3.97-4.01 (m, 1H), 3.86 (t, J=8.8 Hz, 1H), 3.78 (s, 3H), 3.46-3.57 (m, 1H), 1.32 (dd, J=8.1, 16.4 Hz, 1H), 1.14 (dd, J=10.3, 16.1 Hz, 1H), 0.76-0.83 (m, 2H), 0.67-0.72 (m, 2H). LCMS m/z=326 [MH]$^+$. RT [Analytical SFC Method D]=5.736 min.

Example 8: (−) 4-(5-(3-(2-hydroxyethoxy)-4-methoxyphenyl)pyridin-3-yl)-1,2-oxaborolan-2-ol, enantiomer 1

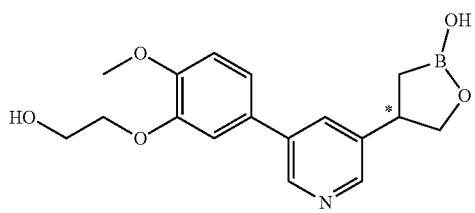 [SMILES: COc1ccc(-c2cncc(C3COB(O)C3)c2)cc1OCCO]

4-(5-(3-(2-hydroxyethoxy)-4-methoxyphenyl)pyridin-3-yl)-1,2-oxaborolan-2-ol (Example 37, 1.5 g, 4.56 mmol) was further purified by preparative SFC (Prep SFC Method F) to afford 4-(5-(3-(2-hydroxyethoxy)-4-methoxyphenyl)pyridin-3-yl)-1,2-oxaborolan-2-ol, enantiomer 1 (261 mg, 27%). $^1$H NMR (DMSO-d$_6$, 400 MHz): δ 8.70-8.72 (m, 2H), 8.42 (d, J=2.0 Hz, 1H), 7.94 (t, J=2.2 Hz, 1H), 7.30 (d, J=2.0 Hz, 1H), 7.26 (dd, J=2.1, 8.4 Hz, 1H), 7.07 (d, J=8.6 Hz, 1H), 4.88 (t, J=5.4 Hz, 1H), 4.25-4.30 (m, 1H), 4.09 (t, J=5.0 Hz, 2H), 3.86 (t, J=9.0 Hz, 1H), 3.81 (s, 3H), 3.75 (q, J=5.2 Hz, 2H), 3.46-3.53 (m, 1H), 1.28-1.34 (m, 1H), 1.15 (dd, J=10.5, 16.1 Hz, 1H). LCMS m/z=348 [MH+H$_2$O]$^+$; RT [Analytical SFC Method D]=3.357 min. [α]$^{20}_D$ −25.9 (c=0.1, EtOH).

Example 9: (−) 4-(5-(3-(3-hydroxypropoxy)-4-methoxyphenyl)pyridin-3-yl)-1,2-oxaborolan-2-ol, enantiomer 2

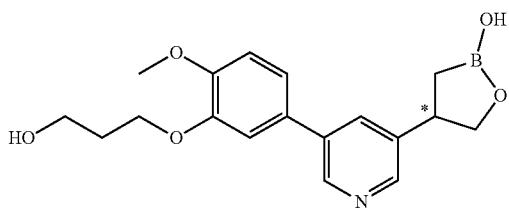 [SMILES: COc1ccc(-c2cncc(C3COB(O)C3)c2)cc1OCCCO]

4-(5-(3-(3-hydroxypropoxy)-4-methoxyphenyl)pyridin-3-yl)-1,2-oxaborolan-2-ol (Example 38, 1.2 g, 7.28 mmol) was further purified by preparative SFC (Prep SFC Method G) to afford 4-(5-(3-(3-hydroxypropoxy)-4-methoxyphenyl)pyridin-3-yl)-1,2-oxaborolan-2-ol, enantiomer 2 (639 mg, 35%). $^1$H NMR (DMSO-$d_6$, 400 MHz): δ 8.68-8.72 (m, 2H), 8.43 (d, J=2.0 Hz, 1H), 7.94 (t, J=2.0 Hz, 1H), 7.29 (d, J=2.0 Hz, 1H), 7.23-7.27 (m, 1H), 7.06 (d, J=8.5 Hz, 1H), 4.55 (t, J=5.1 Hz, 1H), 4.27 (t, J=8.3 Hz, 1H), 4.14 (t, J=6.4 Hz, 2H), 3.86 (t, J=9.0 Hz, 1H), 3.80 (s, 3H), 3.58 (q, J=6.0 Hz, 2H), 3.44-3.55 (m, 1H), 1.86-1.92 (m, 2H), 1.27-1.35 (m, 1H), 1.11-1.19 (m, 1H). LCMS m/z=344 [MH]$^+$; RT [Analytical SFC Method F]=1.060 min. $[α]^{20}_D$ −19.5 (c=0.02, EtOH).

Example 10: (−) 4-(5-(2-(difluoromethyl)-3-ethoxy-4-methoxyphenyl)pyridin-3-yl)-1,2-oxaborolan-2-ol, enantiomer 1

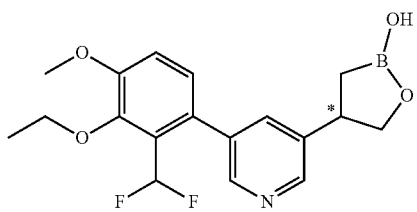 [SMILES: CCOc1c(OC)ccc(-c2cncc(C3COB(O)C3)c2)c1C(F)F]

4-(5-(2-(difluoromethyl)-3-ethoxy-4-methoxyphenyl)pyridin-3-yl)-1,2-oxaborolan-2-ol (Example 41, 800 mg, 2.20 mmol) was further purified by preparative SFC (Prep SFC Method H) to afford 4-(5-(2-(difluoromethyl)-3-ethoxy-4-methoxyphenyl)pyridin-3-yl)-1,2-oxaborolan-2-ol, enantiomer 1 (308 mg, 39%). The material was recrystallized from EtOAc/heptane (1:1, v/v) to afford a crystalline solid. $^1$H NMR (DMSO-$d_6$, 400 MHz): δ 8.69 (s, 1H), 8.48 (d, J=2.0 Hz, 1H), 8.34 (d, J=1.5 Hz, 1H), 7.61 (s, 1H), 7.31 (d, J=8.8 Hz, 1H), 6.80-7.14 (m, 2H), 4.27 (t, J=8.3 Hz, 1H), 4.08 (q, J=6.8 Hz, 2H), 3.89 (s, 3H), 3.80 (t, J=8.8 Hz, 1H), 3.45-3.54 (m, 1H), 1.25-1.38 (m, 4H), 1.00-1.12 (m, 1H). LCMS m/z=364 [MH]$^+$; RT [Analytical SFC Method E]=3.640 min. $[α]^{23}_D$ −27.5 (c=0.2, EtOH).

Example 11: (+) 4-(5-(2-(difluoromethyl)-3-ethoxy-4-methoxyphenyl)pyridin-3-yl)-1,2-oxaborolan-2-ol, enantiomer 2

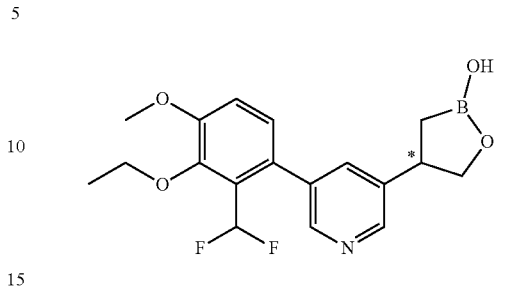

Further elution of the preparative SFC column (Prep SFC Method H) described in Example 10 provided 4-(5-(2-(difluoromethyl)-3-ethoxy-4-methoxyphenyl)pyridin-3-yl)-1,2-oxaborolan-2-ol, enantiomer 2 (259 mg, 32%). $^1$H NMR (DMSO-$d_6$, 400 MHz): δ 8.69 (s, 1H), 8.48 (d, J=2.0 Hz, 1H), 8.34 (d, J=1.5 Hz, 1H), 7.61 (s, 1H), 7.31 (d, J=8.8 Hz, 1H), 6.80-7.14 (m, 2H), 4.27 (t, J=8.3 Hz, 1H), 4.08 (q, J=6.8 Hz, 2H), 3.89 (s, 3H), 3.80 (t, J=8.8 Hz, 1H), 3.45-3.54 (m, 1H), 1.25-1.38 (m, 4H), 1.00-1.12 (m, 1H). LCMS m/z=364 [MH]$^+$; RT [Analytical SFC Method E]=4.050 min. $[α]^{23}_D$ +18.3 (c=0.2, EtOH).

Example 12: 4-(5-(3-ethoxy-5-fluoro-4-methoxyphenyl)pyridin-3-yl)-1,2-oxaborolan-2-ol, enantiomer 1

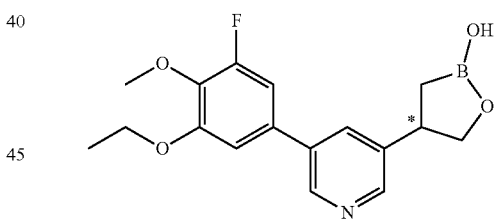

4-(5-(3-Ethoxy-5-fluoro-4-methoxyphenyl)pyridin-3-yl)-1,2-oxaborolan-2-ol (Example 44, 60 mg, 0.18 mmol) was further purified by preparative SFC (Prep SFC Method I) to afford 4-(5-(3-ethoxy-5-fluoro-4-methoxyphenyl)pyridin-3-yl)-1,2-oxaborolan-2-ol, enantiomer 1 (18 mg, 30%). $^1$H NMR (DMSO-$d_6$, 400 MHz): δ8.75 (d, J=2.0 Hz, 1H), 8.71 (s, 1H), 8.47 (d, J=1.47 Hz, 1H), 8.00 (s, 1H), 7.27 (dd, J=2.0, 11.7 Hz, 1H), 7.20 (s, 1H), 4.27 (t, J=8.3 Hz, 1H), 4.21 (q, J=6.9 Hz, 2H), 3.82-3.90 (m, 3H), 3.45-3.56 (m, 2H), 1.39 (t, J=6.9 Hz, 3H), 1.26-1.34 (m, 1H), 1.12-1.20 (m, 1H). LCMS m/z=350 [MH+H$_2$O]$^+$; RT [Analytical SFC Method D]=4.282 min.

Example 13: 4-(5-(3-chloro-5-ethoxy-4-methoxyphenyl)pyridin-3-yl)-1,2-oxaborolan-2-ol enantiomer 1

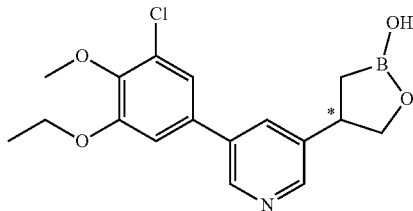 [SMILES: CCOc1cc(-c2cncc(C3COB(O)C3)c2)cc(Cl)c1OC]

4-(5-(3-Chloro-5-ethoxy-4-methoxyphenyl)pyridin-3-yl)-1,2-oxaborolan-2-ol (Example 45, 150 mg, 0.43 mmol) was further purified by preparative SFC (Prep SFC Method J) to afford 4-(5-(3-chloro-5-ethoxy-4-methoxyphenyl)pyridin-3-yl)-1,2-oxaborolan-2-ol, enantiomer 1 (411.3 mg, 37%). $^1$H NMR (DMSO-$d_6$, 400 MHz): δ 8.75 (d, J=2.0 Hz, 1H), 8.70 (s, 1H), 8.48 (d, J=2.0 Hz, 1H), 8.02 (t, J=2.2 Hz, 1H), 7.42 (d, J=2.0 Hz, 1H), 7.34 (d, J=2.0 Hz, 1H), 4.18-4.30 (m, 3H), 3.83-3.91 (m, 1H), 3.81 (s, 3H), 3.44-3.57 (m, 1H), 1.39 (t, J=6.9 Hz, 3H), 1.26-1.34 (m, 1H), 1.12-1.22 (m, 1H). LCMS m/z=348 [MH]$^+$; RT [Analytical SFC Method D]=4.932 min.

Example 14: 4-(5-(5-ethoxy-2-fluoro-4-methoxyphenyl)pyridin-3-yl)-1,2-oxaborolan-2-ol, enantiomer 2

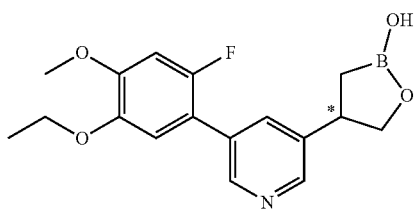 [SMILES: CCOc1cc(-c2cncc(C3COB(O)C3)c2)c(F)cc1OC]

4-(5-(5-ethoxy-2-fluoro-4-methoxyphenyl)pyridin-3-yl)-1,2-oxaborolan-2-ol (Example 46, 385 mg, 1.16 mmol) was further purified by preparative SFC (Prep SFC Method K) to afford 4-(5-(5-ethoxy-2-fluoro-4-methoxyphenyl)pyridin-3-yl)-1,2-oxaborolan-2-ol, enantiomer 2 (122 mg, 32%). $^1$H NMR (DMSO-$d_6$, 400 MHz): δ 8.72 (s, 1H), 8.58 (s, 1H), 8.46 (s, 1H), 7.83 (s, 1H), 7.09 (d, J=7.7 Hz, 1H), 7.03 (d, J=12.4 Hz, 1H), 4.28 (t, J=8.2 Hz, 1H), 4.07 (q, J=7.0 Hz, 2H), 3.82-3.86 (m, 4H), 3.46-3.55 (m, 1H), 1.29-1.34 (m, 4H), 1.07-1.14 (m, 1H). LCMS m/z=332 [MH]$^+$; RT [Analytical SFC Method D]=4.111 min.

Example 15: (−) 4-(5-(2-chloro-5-ethoxy-4-methoxyphenyl)pyridin-3-yl)-1,2-oxaborolan-2-ol, enantiomer 2

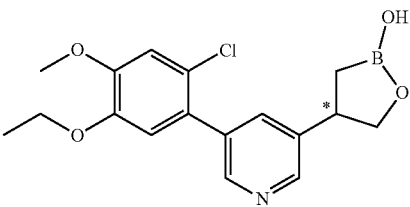 [SMILES: CCOc1cc(-c2cncc(C3COB(O)C3)c2)c(Cl)cc1OC]

4-(5-(2-chloro-5-ethoxy-4-methoxyphenyl)pyridin-3-yl)-1,2-oxaborolan-2-ol (Example 47, 1.6 g, 4.60 mmol) was further purified by preparative SFC (Prep SFC Method L) to afford 4-(5-(2-chloro-5-ethoxy-4-methoxyphenyl)pyridin-3-yl)-1,2-oxaborolan-2-ol, enantiomer 2 (550 mg, 34%). $^1$H NMR (DMSO-$d_6$, 400 MHz): δ 8.71 (s, 1H), 8.48 (t, J=2.0 Hz, 2H), 7.76 (t, J=2.2 Hz, 1H), 7.15 (s, 1H), 7.01 (s, 1H), 4.26-4.30 (m, 1H), 4.06 (q, J=7.0 Hz, 2H), 3.81-3.85 (m, 4H), 3.47-3.55 (m, 1H), 1.29-1.35 (m, 4H), 1.06-1.12 (m, 1H). LCMS m/z=348 [MH]$^+$; RT [Analytical SFC Method G]=4.089 min. $[α]^{20}_D$ −18.0 (c=0.1, EtOH).

Example 16: (−) 4-(3-fluoro-5-methoxy-6-propoxy-[2,3'-bipyridin]-5'-yl)-1,2-oxaborolan-2-ol, enantiomer 1

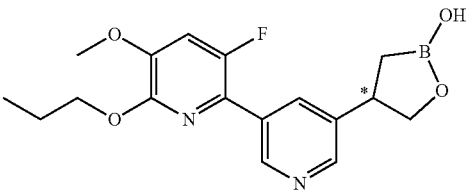 [SMILES: CCCOc1nc(-c2cncc(C3COB(O)C3)c2)c(F)cc1OC]

4-(3-fluoro-5-methoxy-6-propoxy-[2,3'-bipyridin]-5'-yl)-1,2-oxaborolan-2-ol (Example 48, 770 mg, 2.22 mmol) was further purified by preparative SFC (Prep SFC Method M) to afford 4-(3-fluoro-5-methoxy-6-propoxy-[2,3'-bipyridin]-5'-yl)-1,2-oxaborolan-2-ol, enantiomer 1 (298 mg, 39%). $^1$H NMR (DMSO-$d_6$, 400 MHz): δ 8.89 (s, 1H), 8.73 (s, 1H), 8.49 (d, J=2.0 Hz, 1H), 8.09 (s, 1H), 7.49 (d, J=12.0 Hz, 1H), 4.28-4.33 (m, 3H), 3.87 (s, 3H), 3.82 (t, J=8.7 Hz, 1H), 3.49-3.57 (m, 1H), 1.73-1.81 (m, 2H), 1.31-1.37 (m, 1H), 1.03-1.09 (m, 1H), 0.98 (t, J=7.5 Hz, 3H). LCMS m/z=347 [MH]$^+$; RT [Analytical SFC Method D]=4.347 min. $[α]^{20}_D$ −12.1 (c=0.1, EtOH).

Example 17: (−) 4-(5-(4-(difluoromethoxy)-3-propoxyphenyl)pyridin-3-yl)-1,2-oxaborolan-2-ol, enantiomer 1

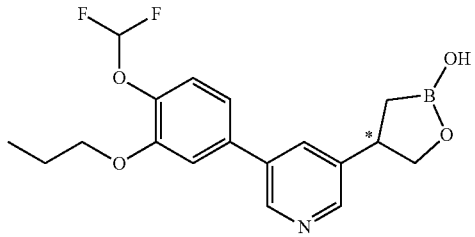 [SMILES: CCCOc1cc(-c2cncc(C3COB(O)C3)c2)ccc1OC(F)F]

4-(5-(4-(difluoromethoxy)-3-propoxyphenyl)pyridin-3-yl)-1,2-oxaborolan-2-ol (Example 50, 506 mg, 1.39 mmol) was further purified by preparative SFC (Prep SFC Method N) to afford 4-(5-(4-(difluoromethoxy)-3-propoxyphenyl)pyridin-3-yl)-1,2-oxaborolan-2-ol, enantiomer 1 (165 mg, 33%). $^1$H NMR (DMSO-$d_6$, 400 MHz): δ 8.74 (d, J=2.1 Hz, 1H), 8.72 (s, 1H), 8.49 (d, J=2.0 Hz, 1H), 8.00 (t, J=2.0 Hz, 1H), 7.45 (d, J=1.6 Hz, 1H), 7.28-7.31 (m, 2H), 7.09 (t, J=74.5 Hz, 1H), 4.28 (t, J=8.3 Hz, 1H), 4.12 (t, J=6.4 Hz, 2H), 3.87 (t, J=9.1 Hz, 1H), 3.47-3.56 (m, 1H), 1.73-1.82 (m, 2H), 1.29-1.35 (m, 1H), 1.12-1.19 (m, 1H), 1.01 (t, J=7.5 Hz, 3H). LCMS m/z=381 [MH+H$_2$O]$^+$; RT [Analytical SFC Method E]=3.402 min. [α]$^{20}_D$ −21.2 (c=0.1, EtOH).

Example 18: (−) 4-(6′-methoxy-5′-propoxy-[3,3′-bipyridin]-5-yl)-1,2-oxaborolan-2-ol, enantiomer 1

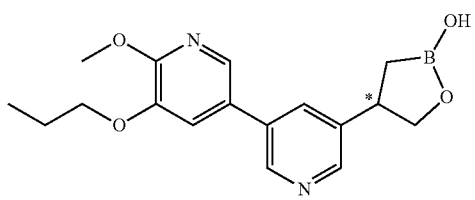 [SMILES: CCCOc1cc(-c2cncc(C3COB(O)C3)c2)cnc1OC]

4-(6′-Methoxy-5′-propoxy-[3,3′-bipyridin]-5-yl)-1,2-oxaborolan-2-ol (Example 51, 1.1 g, 3.4 mmol) was further purified by preparative SFC (Prep SFC Method O) to afford 4-(6′-methoxy-5′-propoxy-[3,3′-bipyridin]-5-yl)-1,2-oxaborolan-2-ol, enantiomer 1 (411 mg, 37%). $^1$H NMR (DMSO-$d_6$, 400 MHz): δ 8.76 (d, J=2.2 Hz, 1H), 8.72 (s, 1H), 8.48 (d, J=2.0 Hz, 1H), 8.06 (d, J=2.0 Hz, 1H), 8.01 (t, J=2.2 Hz, 1H), 7.61 (d, J=2.2 Hz, 1H), 4.26-4.31 (m, 1H), 4.08 (t, J=6.6 Hz, 2H), 3.92 (s, 3H), 3.87 (t, J=9.1 Hz, 1H), 3.48-3.56 (m, 1H), 1.73-1.82 (m, 2H), 1.28-1.35 (m, 1H), 1.13-1.21 (m, 1H), 1.00 (t, J=7.5 Hz, 3H). LCMS m/z=347 [MH+H$_2$]$^+$; RT [Analytical SFC Method G]=4.231 min. [α]$^{20}_D$ −27.2 (c=0.1, EtOH).

Example 19: (R)-4-(5-(3-ethoxy-4-methoxyphenyl)-6-methylpyridin-3-yl)-1,2-oxaborolan-2-ol, enantiomer 1

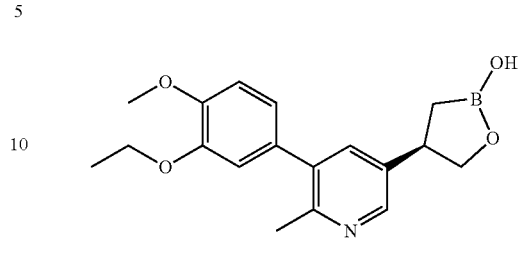

4-(5-(3-ethoxy-4-methoxyphenyl)-6-methylpyridin-3-yl)-1,2-oxaborolan-2-ol (Example 52, 171.7 mg, 0.53 mmol) was further purified by preparative SFC (Prep SFC Method P) to afford 4-(5-(3-ethoxy-4-methoxyphenyl)-6-methylpyridin-3-yl)-1,2-oxaborolan-2-ol, enantiomer 1, (66 mg, 36%). The material was recrystallized from EtOAc/heptane to afford a crystalline solid. $^1$H NMR (DMSO-$d_6$, 400 MHz): δ 8.67 (s, 1H), 8.33 (d, J=2.0 Hz, 1H), 7.47 (d, J=2.0 Hz, 1H), 7.03 (d, J=8.3 Hz, 1H), 6.94 (d, J=2.0 Hz, 1H), 6.88 (dd, J=2.0, 7.8 Hz, 1H), 4.24 (t, J=8.1 Hz, 1H), 4.04 (q, J=6.9 Hz, 2H), 3.76-3.83 (m, 4H), 3.39-3.50 (m, 1H), 2.40 (s, 3H), 1.24-1.36 (m, 4H), 1.01-1.10 (m, 1H). LCMS m/z=328 [MH]$^+$; RT [Analytical SFC Method H]=1.768 min. [α]$^{20}_D$ −20.0 (c=0.4, EtOH).

Example 20: (S)-4-(5-(3-ethoxy-4-methoxyphenyl)-6-methylpyridin-3-yl)-1,2-oxaborolan-2-ol, enantiomer 2

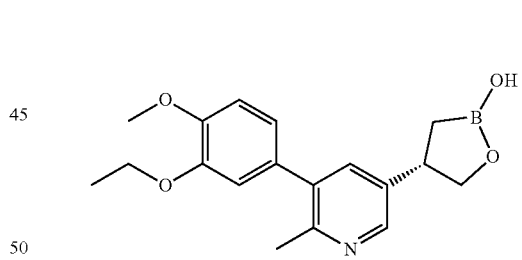

Further elution of the preparative SFC column (Prep SFC Method P) described in Example 19 provided 4-(5-(3-ethoxy-4-methoxyphenyl)-6-methylpyridin-3-yl)-1,2-oxaborolan-2-ol, enantiomer 2, (69 mg, 40%). $^1$H NMR (DMSO-$d_6$, 400 MHz): δ 8.67 (s, 1H), 8.33 (d, J=2.0 Hz, 1H), 7.47 (d, J=2.0 Hz, 1H), 7.03 (d, J=8.3 Hz, 1H), 6.94 (d, J=2.0 Hz, 1H), 6.88 (dd, J=2.0, 7.8 Hz, 1H), 4.24 (t, J=8.1 Hz, 1H), 4.04 (q, J=6.9 Hz, 2H), 3.76-3.83 (m, 4H), 3.39-3.50 (m, 1H), 2.40 (s, 3H), 1.24-1.36 (m, 4H), 1.01-1.10 (m, 1H). LCMS m/z=328 [MH]$^+$; RT [Analytical SFC Method H]=2.168 min.

Example 21: 4-(5-(3-ethoxy-4-methoxyphenyl)-4-methylpyridin-3-yl)-1,2-oxaborolan-2-ol, enantiomer 1

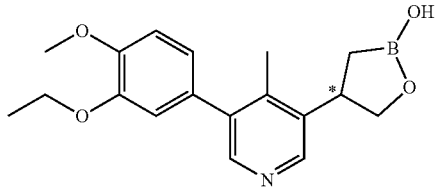 [SMILES: CCOc1cc(-c2cncc(C3COB(O)C3)c2C)ccc1OC]

4-(5-(3-ethoxy-4-methoxyphenyl)-4-methylpyridin-3-yl)-1,2-oxaborolan-2-ol (Example 53, 45 mg, 0.14 mmol) was further purified by preparative SFC (Prep SFC Method I) to afford 4-(5-(3-ethoxy-4-methoxyphenyl)-4-methylpyridin-3-yl)-1,2-oxaborolan-2-ol, enantiomer 1 (12.5 mg, 28%). $^1$H NMR (DMSO-$d_6$, 400 MHz): δ 8.71 (s, 1H), 8.43 (s, 1H), 8.21 (s, 1H), 7.04 (d, J=8.0 Hz, 1H), 6.90 (d, J=2.3 Hz, 1H), 6.82-6.85 (m, 1H), 4.24-4.28 (m, 1H), 4.03 (q, J=7.0 Hz, 2H), 3.90-3.95 (m, 1H), 3.80 (s, 3H), 3.63-3.71 (m, 1H), 2.22 (s, 3H), 1.30-1.36 (m, 4H), 1.04-1.10 (m, 1H). LCMS m/z=328 [MH]$^+$; RT [Analytical SFC Method 1]=5.208 min.

Example 22: (−) 4-(2-(4-methoxy-3-propoxyphenyl)-6-methylpyrimidin-4-yl)-1,2-oxaborolan-2-ol, enantiomer 2

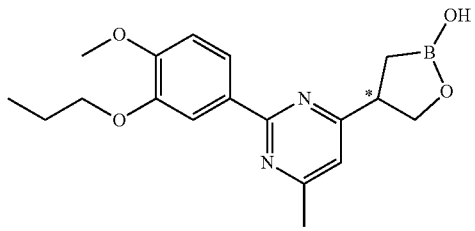 [SMILES: CCCOc1cc(-c2nc(C)cc(C3COB(O)C3)n2)ccc1OC]

4-(2-(4-methoxy-3-propoxyphenyl)-6-methylpyrimidin-4-yl)-1,2-oxaborolan-2-ol (Example 54, 2.5 g, 7.28 mmol) was further purified by preparative SFC (Prep SFC Method Q) to afford 4-(2-(4-methoxy-3-propoxyphenyl)-6-methylpyrimidin-4-yl)-1,2-oxaborolan-2-ol, enantiomer 2 (68 mg, 22%). $^1$H NMR (CD$_3$OD, 400 MHz): δ 8.03 (dd, J=2.0, 8.6 Hz, 1H), 8.00 (d, J=2.0 Hz, 1H), 7.07 (s, 1H), 7.05 (d, J=8.3 Hz, 1H), 4.17 (br s, 1H), 4.07 (t, J=6.5 Hz, 2H), 4.00 (br s, 1H), 3.91 (s, 2H), 3.41 (br s, 1H), 2.52 (s, 2H), 1.84-1.89 (m, 2H), 1.29-1.38 (m, 1H), 1.21-1.29 (m, 1H), 1.09 (t, J=7.3 Hz, 3H). LCMS m/z=343 [MH]$^+$; RT [Analytical SFC Method J]=3.148 min. [α]$^{20}_D$ −23.2 (c=0.1, EtOH).

Example 23: (−) 4-(2-(4-methoxy-3-propoxyphenyl)-6-(trifluoromethyl)pyrimidin-4-yl)-1,2-oxaborolan-2-ol, enantiomer 2

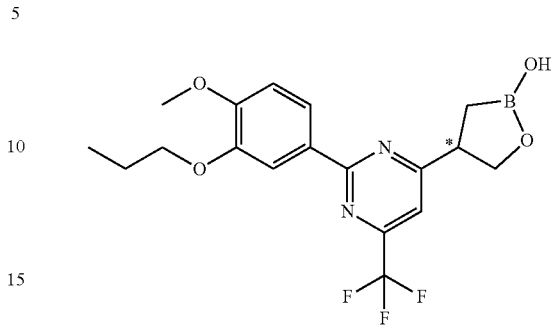

4-(2-(4-methoxy-3-propoxyphenyl)-6-(trifluoromethyl)pyrimidin-4-yl)-1,2-oxaborolan-2-ol (Example 55, 572 mg, 1.45 mmol) was further purified by preparative SFC (Prep SFC Method M) to afford 4-(2-(4-methoxy-3-propoxyphenyl)-6-(trifluoromethyl)pyrimidin-4-yl)-1,2-oxaborolan-2-ol, enantiomer 2 (100 mg, 18%). $^1$H NMR (DMSO-$d_6$, 400 MHz): δ 8.72 (s, 1H), 8.03 (dd, J=2.0, 8.6 Hz, 1H), 7.95 (d, J=2.0 Hz, 1H), 7.77 (s, 1H), 7.13 (d, J=8.6 Hz, 1H), 4.32 (dd, J=7.4, 9.0 Hz, 1H), 3.98-4.09 (m, 3H), 3.86 (s, 3H), 3.73-3.82 (m, 1H), 1.73-1.84 (m, 1H), 1.31-1.41 (m, 1H), 1.18-1.26 (m, 2H), 1.01 (t, J=7.4 Hz, 3H). LCMS m/z=397 [MH]$^+$; RT [Analytical SFC Method E]=4.765 min. [α]$^{20}_D$ −12.6 (c=0.4, EtOH).

Example 24: 4-(6-(3-ethoxy-4-methoxyphenyl)pyrazin-2-yl)-1,2-oxaborolan-2-ol, enantiomer 2

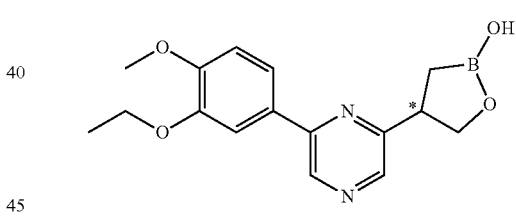

4-(6-(3-Ethoxy-4-methoxyphenyl)pyrazin-2-yl)-1,2-oxaborolan-2-ol (Example 56, 20 mg, 0.06 mmol) was further purified by preparative SFC (Prep SFC Method R) to afford 4-(6-(3-ethoxy-4-methoxyphenyl)pyrazin-2-yl)-1,2-oxaborolan-2-ol, enantiomer 2 (6.4 mg, 34%). LCMS m/z=315 [MH]$^+$. RT [Analytical SFC Method K]=3.23 min.

Example 25: 4-(5-(4-methoxy-3-propoxyphenyl)pyridin-3-yl)-1,2-oxaborol-2(5H)-ol

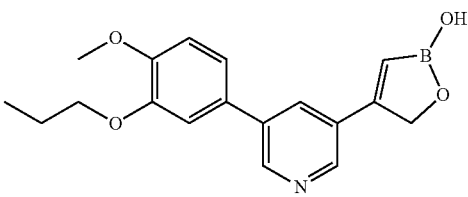 [SMILES: CCCOc1cc(-c2cncc(C3=CB(O)OC3)c2)ccc1OC]

A mixture of 3-(3-((tert-butyldimethylsilyl)oxy)-1-(4,4,5,5-tetramethyl-1,3,2-dioxaborolan-2-yl)prop-1-en-2-yl)-5-(4-methoxy-3-propoxyphenyl)pyridine (Preparation 8, 1.30 g, 2.41 mmol) in AcOH (10 mL) and water (5 mL) was stirred at about 50° C. for about 1 h. The mixture was concentrated and EtOH (10 mL) was added. The mixture was stirred at about 0° C. for about 15 min and filtered. The solid was washed with water (15 mL) and dried to afford 4-(5-(4-methoxy-3-propoxyphenyl)pyridin-3-yl)-1,2-oxaborol-2(5H)-ol (560 mg, 68%). $^1$H NMR (DMSO-$d_6$, 400 MHz): δ 8.86 (d, J=2.0 Hz, 1H), 8.77 (s, 1H), 8.73 (d, J=2.0 Hz, 1H), 8.14 (t, J=2.0 Hz, 1H), 7.31-7.34 (m, 2H), 7.08 (d, J=8.0 Hz, 1H), 6.46 (s, 1H), 5.02 (s, 2H), 4.05 (t, J=6.4 Hz, 2H), 3.82 (s, 3H), 1.72-1.81 (m, 2H), 1.01 (t, J=7.6 Hz, 3H). LCMS m/z=326 [MH]$^+$.

Example 26: 4-(6-(4-methoxy-3-propoxyphenyl)pyridin-2-yl)-1,2-oxaborinan-2-ol

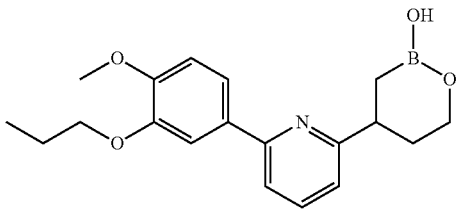 [SMILES: CCCOc1cc(-c2cccc(C3CCOB(O)C3)n2)ccc1OC]

2-(4-((tert-butyldimethylsilyl)oxy)-1-(4,4,5,5-tetramethyl-1,3,2-dioxaborolan-2-yl)butan-2-yl)-6-(4-methoxy-3-propoxyphenyl)pyridine (Preparation 31, 140 mg, 0.25 mmol) was dissolved in AcOH (4.3 mL) and water (0.2 mL) and stirred at about 20° C. for about 16 h. The mixture was concentrated and the residue was purified by preparative HPLC (Prep HPLC Method B) to afford 4-(6-(4-methoxy-3-propoxyphenyl)pyridin-2-yl)-1,2-oxaborinan-2-ol (60 mg, 70%). $^1$H NMR (DMSO-$d_6$, 400 MHz): δ 7.71-7.76 (m, 4H), 7.64-7.66 (m, 1H), 7.15-7.17 (m, 1H), 7.03 (d, J=8.6 Hz, 1H), 4.02 (t, J=6.6 Hz, 2H), 3.64-3.98 (m, 2H), 3.81 (m, 3H), 3.13-3.20 (m, 1H), 1.92-2.00 (m, 1H), 1.72-1.82 (m, 3H), 1.09 (d, J=7.0 Hz, 2H), 1.00 (t, J=7.4 Hz, 3H). LCMS m/z=342 [MH]$^+$.

Example 27: 4-(6-(4-methoxy-3-propoxyphenyl)pyridin-2-yl)-3-methyl-1,2-oxaborolan-2-ol

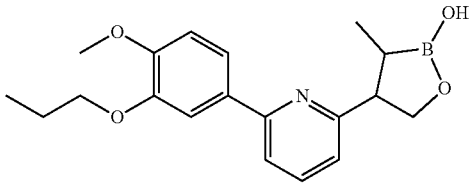 [SMILES: CCCOc1cc(-c2cccc(C3COB(O)C3C)n2)ccc1OC]

A mixture of 4-(6-(4-methoxy-3-propoxyphenyl)pyridin-2-yl)-3-methyl-1,2-oxaborol-2(5H)-ol (Example 28, 50 mg, 0.15 mmol) and Adam's catalyst (10.0 mg, 0.044 mmol) in EtOAc (1.5 mL) was hydrogenated at 20 psig at about 40° C. for about 2 h. The reaction was filtered through a Celite® pad and the filtrate was concentrated. The residue was purified by column chromatography (silica) and eluted with heptane/EtOAc (80:20 to 0:100) followed by DCM/MeOH (90:10) to afford 4-(6-(4-methoxy-3-propoxyphenyl)pyridin-2-yl)-3-methyl-1,2-oxaborolan-2-ol (40 mg, 80%). $^1$H NMR (CDCl$_3$, 400 MHz): δ 7.73 (br s, 1H), 7.51-7.66 (m, 4H), 6.92-7.00 (m, 2H), 4.36 (d, J=3.1 Hz, 2H), 4.12 (t, J=6.8 Hz, 2H), 3.92 (s, 3H), 3.56 (br s, 1H), 1.87-1.96 (m, 2H), 1.70-1.80 (m, 1H), 1.08 (t, J=7.4 Hz, 3H), 0.80 (d, J=7.0 Hz, 3H). LCMS m/z=342 [MH]$^+$.

Example 28: 4-(6-(4-methoxy-3-propoxyphenyl)pyridin-2-yl)-3-methyl-1,2-oxaborol-2(5H)-ol

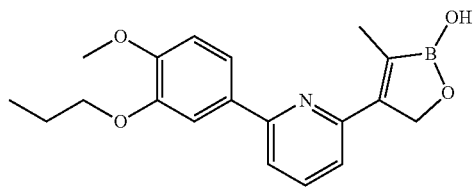 [SMILES: CCCOc1cc(-c2cccc(C3=C(C)B(O)OC3)n2)ccc1OC]

4-(6-(4-methoxy-3-propoxyphenyl)pyridin-2-yl)-3-methyl-1,2-oxaborol-2(5H)-ol (105 mg, 46%) was prepared in an analogous manner to Example 25 using 3-(1-((tert-butyldimethylsilyl)oxy)-3-(4,4,5,5-tetramethyl-1,3,2-dioxaborolan-2-yl)but-2-en-2-yl)-5-(4-methoxy-3-propoxyphenyl)pyridine (Preparation 32, 370 mg, 0.668 mmol). $^1$H NMR (DMSO-$d_6$, 400 MHz): δ 8.71 (s, 1H), 7.86-7.91 (m, 2H), 7.75 (d, J=2.0 Hz, 1H), 7.67 (dd, J=2.0, 8.6 Hz, 1H), 7.36-7.44 (m, 1H), 7.07 (d, J=8.6 Hz, 1H), 4.95 (d, J=2.0 Hz, 2H), 4.02 (t, J=6.6 Hz, 2H), 3.82 (s, 3H), 2.15 (s, 3H), 1.71-1.85 (m, 2H), 1.01 (t, J=7.4 Hz, 3H). LCMS m/z=340 [MH]$^+$.

Example 29: 4-(6-(4-methoxy-3-propoxyphenyl)pyridin-2-yl)-4-methyl-1,2-oxaborolan-2-ol

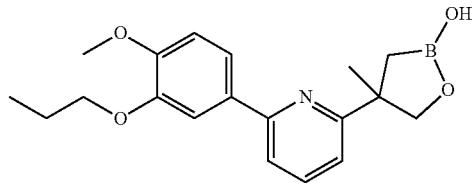 [SMILES: CCCOc1cc(-c2cccc(C3(C)COB(O)C3)n2)ccc1OC]

To a solution of ethyl 2-(5-(4-methoxy-3-propoxyphenyl)pyridin-3-yl)-2-methyl-3-(4,4,5,5-tetramethyl-1,3,2-dioxaborolan-2-yl)propanoate (Preparation 33, 134 mg, 0.277 mmol) in THF (3.0 mL) at about 20° C. was added LiBH$_4$ (6.0 mg, 0.28 mmol), followed by water (0.10 mL). The reaction mixture was stirred at about 20° C. for about 3 h. Another portion of LiBH$_4$ (25 mg, 1.15 mmol) and water (0.2 mL) was added. The mixture was stirred at about 20° C. for about 5 min. Another portion of LiBH$_4$ (25 mg, 1.15 mmol) and water (0.3 mL) was added and stirred at about 20° C. for about 10 min. The mixture was diluted with water and extracted with EtOAc. The EtOAc extract was washed with brine and dried over Na$_2$SO$_4$. The mixture was filtered, concentrated and dissolved in THF (3 mL) and water (1 mL). The solution was treated with excess LiBH$_4$ at about 20° C. for about 3 h. The mixture was diluted with water and extracted with EtOAc. The EtOAc extract was washed with brine, dried over Na$_2$SO$_4$, filtered and concentrated. The residue was purified by preparative HPLC (Prep HPLC Method C) to afford 4-(6-(4-methoxy-3-propoxyphenyl)pyridin-2-yl)-4-methyl-1,2-oxaborolan-2-ol (46.1 mg, 49%). $^1$H NMR (CD$_3$OD, 500 MHz): δ 7.80 (br s, 1H), 7.74 (d, J=1.5 Hz, 1H), 7.67 (d, J=8.1 Hz, 1H), 7.62 (m, 1H), 7.32 (d, J=7.1 Hz, 1H), 7.07 (d, J=8.3 Hz, 1H), 5.51 (s, 1H), 4.29 (d, J=8.8 Hz, 1H), 4.07-4.16 (m, 3H), 3.92 (s, 3H), 3.47 (m, 1H), 3.19 (m, 1H), 1.88 (m, 2H), 1.55 (d, J=16.1 Hz, 1H), 1.51 (s, 3H), 1.20 (d, J=15.7 Hz, 1H), 1.10 (t, J=7.3 Hz, 3H). LCMS m/z=342 [MH]$^+$.

Example 30: 4-(6-(4-methoxy-3-propoxyphenyl)pyridazin-4-yl)-5-methyl-1,2-oxaborolan-2-ol

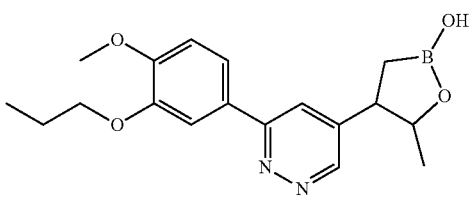 [SMILES: CCCOc1cc(-c2cc(C3CB(O)OC3C)cnn2)ccc1OC]

A mixture of 5-(3-((tert-butyldimethylsilyl)oxy)-1-(4,4,5,5-tetramethyl-1,3,2-dioxaborolan-2-yl)butan-2-yl)-3-(4-methoxy-3-propoxyphenyl)pyridazine (Preparation 34, 160 mg, 0.29 mmol) in AcOH (6 mL) and water (1 mL) was stirred at about 70° C. for about 21 h. The mixture was concentrated, dissolved in MeCN (15 mL) and concentrated again. The mixture was purified by preparative HPLC (Prep HPLC Method D) to afford 4-(6-(4-methoxy-3-propoxyphenyl)pyridazin-4-yl)-5-methyl-1,2-oxaborolan-2-ol (10.6 mg, 11%). $^1$H NMR (DMSO-d$_6$, 400 MHz): δ 9.12 (s, 1H), 9.05 (d, J=2.0 Hz, 1H), 8.77 (s, 1H), 8.69 (s, 1H), 8.13 (s, 1H), 7.98 (s, 1H), 7.68-7.81 (m, 3H), 7.07-7.16 (m, 2H), 4.64 (t, J=6.5 Hz, 1H), 4.25-4.35 (m, 1H), 4.04 (t, J=6.5 Hz, 3H), 3.84 (s, 5H), 3.64 (d, J=9.0 Hz, 1H), 2.92-3.01 (m, 1H), 1.74-1.83 (m, 3H), 1.48 (dd, J=10.0, 16.1 Hz, 1H), 1.24-1.39 (m, 2H), 1.17 (d, J=6.0 Hz, 3H), 1.01 (t, J=7.0 Hz, 6H), 0.77 (d, J=7.0 Hz, 1H). LCMS m/z=343 [MH]$^+$.

Example 31: 4-(hydroxymethyl)-4-(5-(4-methoxy-3-propoxyphenyl)pyridin-3-yl)-1,2-oxaborolan-2-ol

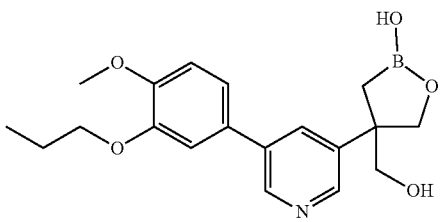 [SMILES: CCCOc1cc(-c2cncc(C3(CO)COB(O)C3)c2)ccc1OC]

Turbo Grignard (0.5 mL, 1.3 M in THF) was stirred with anhydrous 1,4-dioxane (0.05 mL) at about 20° C. under N$_2$ for about 30 min to afford a mixture which was used directly in the following procedure (Reagent A). To a solution of 3-(5-(iodomethyl)-2,2-dimethyl-1,3-dioxan-5-yl)-5-(4-methoxy-3-propoxyphenyl)pyridine (Preparation 77, 120 mg, 0.25 mmol) in THF (0.50 mL) under N$_2$ was added Reagent A. The mixture was stirred at about 20° C. for about 1 h. Trimethyl borate (0.33 mL, 2.98 mmol) was added and stirred at about 20° C. under N$_2$ for about 1 h. The cooled mixture was treated with HCl in IPA (5.5 M, 0.45 mL, 2.48 mmol) for about 1 h. The mixture was diluted with 1 M HCl and washed with EtOAc. The EtOAc layer was extracted with 1 M HCl (2×5 mL). The combined aqueous extracts were neutralized to pH 6-7 with K$_3$PO$_4$. The aqueous extract was extracted with EtOAc (3×10 mL). The combined EtOAc extracts were dried over Na$_2$SO$_4$, filtered and concentrated. The residue was purified by preparative SFC (Prep SFC Method S) to afford 4-(hydroxymethyl)-4-(5-(4-methoxy-3-propoxyphenyl)pyridin-3-yl)-1,2-oxaborolan-2-ol (38 mg, 43%). $^1$H NMR (DMSO-d$_6$, 400 MHz): δ 8.69 (d, J=2.0 Hz, 1H), 8.63 (s, 1H), 8.37 (d, J=2.0 Hz, 1H), 7.75 (m, 1H), 7.19-7.28 (m, 2H), 7.08 (d, J=8.6 Hz, 1H), 4.99 (m, 1H), 4.39 (d, J=9.0 Hz, 1H), 4.00-4.13 (m, 4H), 3.82 (s, 3H), 3.47 (br s, 2H), 1.77 (m, 2H), 1.28-1.38 (m, 1H), 1.14-1.22 (m, 1H), 0.96-1.08 (m, 3H). LCMS m/z=358 [MH]$^+$.

Example 32: 4-(5-(3,4-dimethoxyphenyl)pyridin-3-yl)-1,2-oxaborolan-2-ol

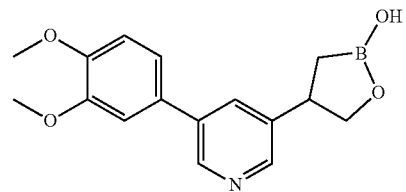 [SMILES: COc1ccc(-c2cncc(C3COB(O)C3)c2)cc1OC]

A mixture of 3-(1-((tert-butyldimethylsilyl)oxy)-3-(4,4,5,5-tetramethyl-1,3,2-dioxaborolan-2-yl)propan-2-yl)-5-(3,4-dimethoxyphenyl)pyridine (Preparation 1, 1.0 g, 1.95 mmol) in AcOH (15 mL), THF (5 mL) and water (5 mL) was stirred at about 55° C. for about 6 h. The mixture was concentrated and the residue was purified by preparative HPLC (Prep HPLC Method E) to afford 4-(5-(3,4-dimethoxyphenyl)pyridin-3-yl)-1,2-oxaborolan-2-ol (98 mg, 17%). $^1$H NMR (DMSO-d$_6$, 400 MHz): δ 8.72 (d, J=2.8 Hz, 2H), 8.43 (d, J=2.0 Hz, 1H), 7.95 (t, J=2.0 Hz, 1H), 7.25-7.29 (m, 1H), 7.06 (d, J=8.4 Hz, 2H), 4.28 (t, J=4.28 Hz, 1H), 3.84-3.88 (m, 4H), 3.80 (s, 3H), 3.46-3.54 (m, 1H), 1.28-1.34 (m, 1H), 1.12-1.18 (m, 1H). LCMS m/z=300 [MH]$^+$.

Example 33: 4-(5-(3-ethoxy-4-methoxyphenyl)pyridin-3-yl)-1,2-oxaborolan-2-ol

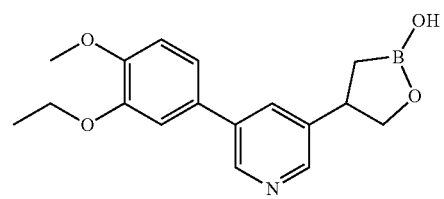 [SMILES: CCOc1cc(-c2cncc(C3COB(O)C3)c2)ccc1OC]

A mixture of 3-(1-((tert-butyldimethylsilyl)oxy)-3-(4,4,5,5-tetramethyl-1,3,2-dioxaborolan-2-yl)propan-2-yl)-5-(3-ethoxy-4-methoxyphenyl)pyridine (Preparation 3, 3.80 g, 7.20 mmol) in AcOH (60 mL) and water (10 mL) was stirred at about 50° C. for about 1 h. The mixture was concentrated and the residue was purified by preparative HPLC (Prep HPLC Method F) to afford 4-(5-(3-ethoxy-4-methoxyphenyl)pyridin-3-yl)-1,2-oxaborolan-2-ol (810 mg, 34%). $^1$H NMR (DMSO-d$_6$, 400 MHz): δ 8.70 (d, J=2.3 Hz, 1H), 8.68 (s, 1H), 8.42 (d, J=1.6 Hz, 1H), 7.92-7.94 (m, 1H), 7.23-7.29

Example 34: 4-(5-(4-methoxy-3-propoxyphenyl)pyridin-3-yl)-1,2-oxaborolan-2-ol

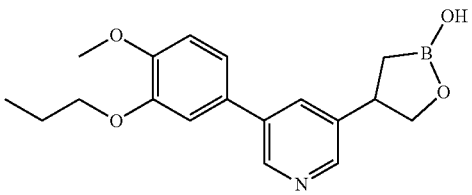 [SMILES: CCCOc1cc(-c2cncc(C3COB(O)C3)c2)ccc1OC]

A mixture of 3-(1-((tert-butyldimethylsilyl)oxy)-3-(4,4,5,5-tetramethyl-1,3,2-dioxaborolan-2-yl)propan-2-yl)-5-(4-methoxy-3-propoxyphenyl)pyridine (Preparation 5, 3.44 g, 6.35 mmol) in AcOH (60 mL) and water (10 mL) was stirred at about 50° C. for about 1 h. The mixture was concentrated and the residue was purified by preparative HPLC (Prep HPLC Method G) to afford 4-(5-(4-methoxy-3-propoxyphenyl)pyridin-3-yl)-1,2-oxaborolan-2-ol (1.04 g, 49%). $^1$H NMR (DMSO-$d_6$, 400 MHz): δ 8.70 (d, J=2.3 Hz, 1H), 8.68 (s, 1H), 8.42 (d, J=2.0 Hz, 1H), 7.93 (s, 1H), 7.27 (d, J=2.0 Hz, 1H), 7.23-7.26 (m, 1H), 7.06 (d, J=8.2 Hz, 1H), 4.28 (t, J=8.2 Hz, 1H), 4.03 (t, J=6.4 Hz, 2H), 3.86 (t, J=9.0 Hz, 1H), 3.81 (s, 3H), 3.46-3.54 (m, 1H), 1.71-1.80 (m, 2H), 1.28-1.35 (m, 1H), 1.15 (dd, J=10.5, 16.4 Hz, 1H), 1.00 (t, J=7.4 Hz, 3H). LCMS m/z=328 [MH]$^+$.

Example 35: 4-(5-(3-isopropoxy-4-methoxyphenyl)pyridin-3-yl)-1,2-oxaborolan-2-ol

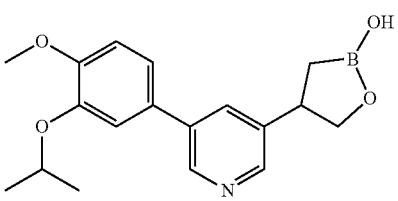 [SMILES: COc1ccc(-c2cncc(C3COB(O)C3)c2)cc1OC(C)C]

4-(5-(3-isopropoxy-4-methoxyphenyl)pyridin-3-yl)-1,2-oxaborolan-2-ol (103 mg, 43%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-isopropoxy-4-methoxyphenyl)pyridine (Preparation 9, 400 mg, 0.74 mmol) and purified by preparative HPLC (Prep HPLC Method H). $^1$H NMR (DMSO-$d_6$, 400 MHz): δ 8.72 (s, 1H), 8.69 (d, J=2.0 Hz, 1H), 8.42 (d, J=2.0 Hz, 1H), 7.92 (t, J=2.0 Hz, 1H), 7.29-7.24 (m, 2H), 7.07 (d, J=8.0 Hz, 1H), 4.68-4.74 (m, 1H), 4.27 (t, J=8.3 Hz, 1H), 3.86 (t, J=9.0 Hz, 1H), 3.79 (s, 3H), 3.47-3.55 (m, 1H), 1.26-1.35 (m, 7H), 1.10-1.18 (m, 1H). LCMS m/z=328 [MH]$^+$.

Example 36: 4-(5-(3-cyclopropoxy-4-methoxyphenyl)pyridin-3-yl)-1,2-oxaborolan-2-ol

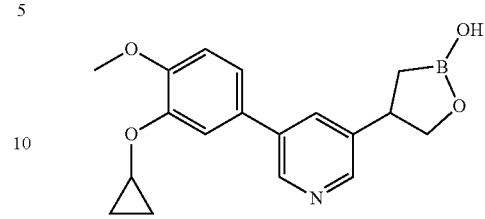

4-(5-(3-cyclopropoxy-4-methoxyphenyl)pyridin-3-yl)-1,2-oxaborolan-2-ol (45 mg, 10%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-cyclopropoxy-4-methoxyphenyl)pyridine (Preparation 10, 750 mg, 1.39 mmol) and purified by preparative HPLC (Prep HPLC Method I). $^1$H NMR (DMSO-$d_6$, 400 MHz): δ 8.69-8.72 (m, 2H), 8.44 (d, J=2.0 Hz, 1H), 7.91 (t, J=2.0 Hz, 1H), 7.53 (d, J=2.0 Hz, 1H), 7.28 (dd, J=2.4, 8.3 Hz, 1H), 7.07 (d, J=8.8 Hz, 1H), 4.25-4.31 (m, 1H), 3.97-4.01 (m, 1H), 3.86 (t, J=8.8 Hz, 1H), 3.78 (s, 3H), 3.46-3.57 (m, 1H), 1.32 (dd, J=8.1, 16.4 Hz, 1H), 1.14 (dd, J=10.3, 16.1 Hz, 1H), 0.76-0.83 (m, 2H), 0.67-0.72 (m, 2H). LCMS m/z=326 [MH]$^+$.

Example 37: 4-(5-(3-(2-hydroxyethoxy)-4-methoxyphenyl)pyridin-3-yl)-1,2-oxaborolan-2-ol

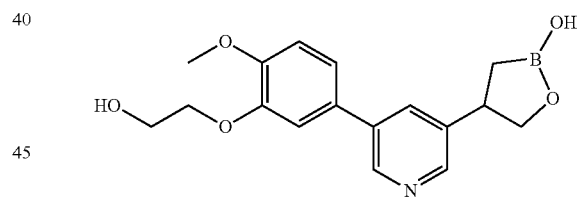

4-(5-(3-(2-hydroxyethoxy)-4-methoxyphenyl)pyridin-3-yl)-1,2-oxaborolan-2-ol (1.5 g, 75%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-(2-((tert-butyldimethylsilyl)oxy)ethoxy)-4-methoxyphenyl)pyridine (Preparation 11, 4.0 g, 6.1 mmol) and purified by preparative HPLC (Prep HPLC Method J). $^1$H NMR (DMSO-$d_6$, 400 MHz): δ 8.70-8.72 (m, 2H), 8.42 (d, J=2.0 Hz, 1H), 7.94 (t, J=2.2 Hz, 1H), 7.30 (d, J=2.0 Hz, 1H), 7.26 (dd, J=2.1, 8.4 Hz, 1H), 7.07 (d, J=8.6 Hz, 1H), 4.88 (t, J=5.4 Hz, 1H), 4.25-4.30 (m, 1H), 4.09 (t, J=5.0 Hz, 2H), 3.86 (t, J=9.0 Hz, 1H), 3.81 (s, 3H), 3.75 (q, J=5.2 Hz, 2H), 3.46-3.53 (m, 1H), 1.28-1.34 (m, 1H), 1.15 (dd, J=10.5, 16.1 Hz, 1H). LCMS m/z=330 [MH]$^+$.

Example 38: 4-(5-(3-(3-hydroxypropoxy)-4-methoxyphenyl)pyridin-3-yl)-1,2-oxaborolan-2-ol

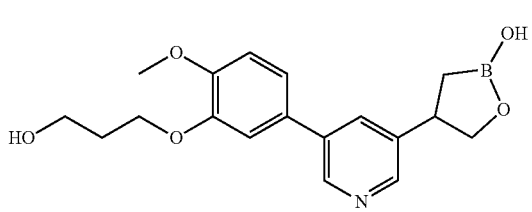 [SMILES: COc1ccc(-c2cncc(C3COB(O)C3)c2)cc1OCCCO]

4-(5-(3-(3-hydroxypropoxy)-4-methoxyphenyl)pyridin-3-yl)-1,2-oxaborolan-2-ol (2.5 g, 41%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-(3-((tert-butyldimethylsilyl)oxy)propoxy)-4-methoxyphenyl)pyridine (Preparation 12, 12 g, 18.0 mmol) and purified by preparative HPLC (Prep HPLC Method K). $^1$H NMR (DMSO-$d_6$, 400 MHz): δ 8.68-8.72 (m, 2H), 8.43 (d, J=2.0 Hz, 1H), 7.94 (t, J=2.0 Hz, 1H), 7.29 (d, J=2.0 Hz, 1H), 7.23-7.27 (m, 1H), 7.06 (d, J=8.5 Hz, 1H), 4.55 (t, J=5.1 Hz, 1H), 4.27 (t, J=8.3 Hz, 1H), 4.14 (t, J=6.4 Hz, 2H), 3.86 (t, J=9.0 Hz, 1H), 3.80 (s, 3H), 3.58 (q, J=6.0 Hz, 2H), 3.44-3.55 (m, 1H), 1.86-1.92 (m, 2H), 1.27-1.35 (m, 1H), 1.11-1.19 (m, 1H). LCMS m/z=344 [MH]$^+$.

Example 39: 4-(5-(3-(2-fluoroethoxy)-4-methoxyphenyl)pyridin-3-yl)-1,2-oxaborolan-2-ol

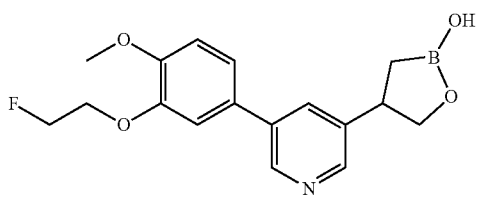 [SMILES: COc1ccc(-c2cncc(C3COB(O)C3)c2)cc1OCCF]

4-(5-(3-(2-fluoroethoxy)-4-methoxyphenyl)pyridin-3-yl)-1,2-oxaborolan-2-ol (122 mg, 29%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-(2-fluoroethoxy)-4-methoxyphenyl)pyridine (Preparation 13, 700 mg, 1.28 mmol) and purified by preparative HPLC (Prep HPLC Method L). $^1$H NMR (DMSO-$d_6$, 400 MHz): δ 8.71-8.78 (m, 2H), 8.44 (d, J=1.5 Hz, 1H), 7.96 (t, J=2.0 Hz, 1H), 7.30-7.37 (m, 2H), 7.10 (d, J=8.0 Hz, 1H), 4.81-4.87 (m, 1H), 4.70-4.75 (m, 1H), 4.38-4.43 (m, 1H), 4.30-4.34 (m, 1H), 4.27 (d, J=8.5 Hz, 1H), 3.87 (t, J=9.0 Hz, 1H), 3.83 (s, 3H), 3.47-3.57 (m, 1H), 1.32 (dd, J=8.3, 16.3 Hz, 1H), 1.10-1.21 (m, 1H). LCMS m/z=332 [MH]$^+$.

Example 40: 4-(3'-(3-fluoropropoxy)-4'-methoxy-[1,1'-biphenyl]-3-yl)-1,2-oxaborolan-2-ol

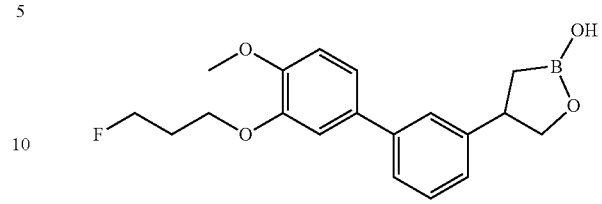

4-(3'-(3-fluoropropoxy)-4'-methoxy-[1,1'-biphenyl]-3-yl)-1,2-oxaborolan-2-ol was prepared in an analogous manner Example 33 using tert-butyl(2-(3'-(3-fluoropropoxy)-4'-methoxy-[1,1'-biphenyl]-3-yl)-3-(4,4,5,5-tetramethyl-1,3,2-dioxaborolan-2-yl)propoxy)dimethylsilane (Preparation 14). $^1$H NMR (DMSO-$d_6$, 400 MHz): δ 7.50 (br s, 1H), 7.46 (d, J=7.8 Hz, 1H), 7.35 (t, J=7.8 Hz, 1H) 7.18-7.25 (m, 3H), 7.04 (d, J=8.2 Hz, 1H), 4.69 (t, J=5.9 Hz, 1H), 4.57 (t, J=5.9 Hz, 1H), 4.26 (t, J=7.8 Hz, 1H), 4.02-4.18 (m, 3H), 3.80 (s, 3H), 3.42-3.51 (m, 1H), 2.07-2.19 (m, 2H), 1.22-1.32 (m, 1H), 1.05-1.12 (m, 1H). LCMS m/z=345 [MH]$^+$.

Example 41: 4-(5-(2-(difluoromethyl)-3-ethoxy-4-methoxyphenyl)pyridin-3-yl)-1,2-oxaborolan-2-ol

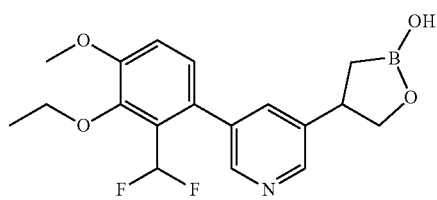 [SMILES: CCOc1c(OC)ccc(-c2cncc(C3COB(O)C3)c2)c1C(F)F]

4-(5-(2-(difluoromethyl)-3-ethoxy-4-methoxyphenyl)pyridin-3-yl)-1,2-oxaborolan-2-ol was prepared (80 mg, 42%) in an analogous manner to Example 33 using 3-(1-((tert-butyldimethylsilyl)oxy)-3-(4,4,5,5-tetramethyl-1,3,2-dioxaborolan-2-yl)propan-2-yl)-5-(2-(difluoromethyl)-3-ethoxy-4-methoxyphenyl)pyridine (Preparation 15, 300 mg, 0.519 mmol) and purified by preparative HPLC (Prep HPLC Method M). $^1$H NMR (DMSO-$d_6$, 400 MHz): δ 8.69 (s, 1H), 8.48 (d, J=2.0 Hz, 1H), 8.34 (d, J=1.5 Hz, 1H), 7.61 (s, 1H), 7.31 (d, J=8.8 Hz, 1H), 6.80-7.14 (m, 2H), 4.27 (t, J=8.3 Hz, 1H), 4.08 (q, J=6.8 Hz, 2H), 3.89 (s, 3H), 3.80 (t, J=8.8 Hz, 1H), 3.45-3.54 (m, 1H), 1.25-1.38 (m, 4H), 1.00-1.12 (m, 1H). LCMS m/z=364 [MH]$^+$.

Example 42: 3'-(2-hydroxy-1,2-oxaborolan-4-yl)-4-methoxy-3-propoxy-[1,1'-biphenyl]-2-carbonitrile

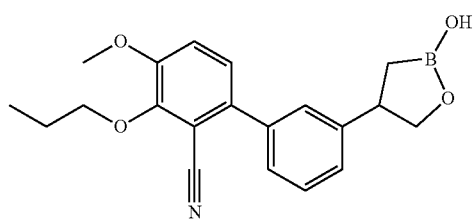 [SMILES: CCCOc1c(OC)ccc(-c2cccc(C3COB(O)C3)c2)c1C#N]

To a solution of 3'-(2-hydroxy-2,5-dihydro-1,2-oxaborol-4-yl)-4-methoxy-3-propoxy-[1,1'-biphenyl]-2-carbonitrile (Example 43, 500 mg, 1.43 mmol) in EtOAc (15 mL) was added PtO$_2$ (16 mg, 72 umol) under N$_2$. The mixture was stirred under H$_2$ (15 psi) at about 0° C. for about 2 h. The mixture was filtered and concentrated. The residue was purified by preparative HPLC (Prep HPLC Method N) to afford 3'-(2-hydroxy-1,2-oxaborolan-4-yl)-4-methoxy-3-propoxy-[1,1'-biphenyl]-2-carbonitrile (284 mg, 55%). $^1$H NMR (DMSO-d$_6$, 400 MHz): δ 7.45 (d, J=8.8 Hz, 2H), 7.41 (d, J=7.2 Hz, 1H), 7.34 (t, J=7.2 Hz, 2H), 7.26 (d, J=8.8 Hz, 1H), 4.26 (t, J=8.0 Hz, 1H), 4.12 (t, J=6.0 Hz, 2H), 3.89 (s, 3H), 3.81 (t, J=8.8 Hz, 1H), 3.43-3.52 (m, 1H), 1.69-1.78 (m, 2H), 1.29 (q, J=8.0 Hz, 1H). 1.07-1.11 (m, 1H), 1.01 (t, J=7.6 Hz, 3H). LCMS m/z=352 [MH]$^+$.

Example 43: 3'-(2-hydroxy-2,5-dihydro-1,2-oxaborol-4-yl)-4-methoxy-3-propoxy-[1,1'-biphenyl]-2-carbonitrile

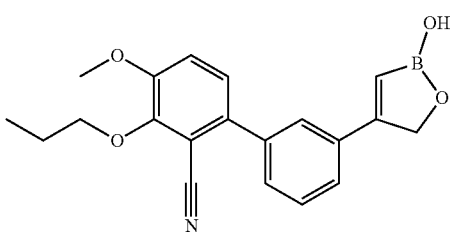 [SMILES: CCCOc1c(OC)ccc(-c2cccc(C3=CB(O)OC3)c2)c1C#N]

To a mixture of methyl 2-(2'-cyano-4'-methoxy-3'-propoxy-[1,1'-biphenyl]-3-yl)-3-(4,4,5,5-tetramethyl-1,3,2-dioxaborolan-2-yl)acrylate (Preparation 30, 13.6 g, 28.5 mmol) in THF (150 mL) and MeOH (5 mL) was added NaBH$_4$ (754 mg, 19.9 mmol) slowly at about 0° C. The mixture was stirred at about 20° C. for about 1 h. Water (150 mL) was added and the mixture was extracted with EtOAc (2×150 mL). The combined EtOAc extracts were washed with brine (150 mL), dried with Na$_2$SO$_4$, filtered and concentrated. The residue was purified by column chromatography (silica) and eluted with pet. ether/EtOAc (10:1), then re-crystallized from EtOH (30 mL) at about 0° C. to afford 3'-(2-hydroxy-2,5-dihydro-1,2-oxaborol-4-yl)-4-methoxy-3-propoxy-[1,1'-biphenyl]-2-carbonitrile (2.60 g, 26%). $^1$H NMR (DMSO-d$_6$, 400 MHz): δ 8.71 (s, 1H), 7.70 (s, 1H), 7.64-7.65 (m, 1H), 7.53 (d, J=4.4 Hz, 2H), 7.48 (d, J=8.4 Hz, 1H), 7.33 (d, J=8.4 Hz, 1H), 6.27 (s, 1H), 4.95 (s, 2H), 4.13 (t, J=6.4 Hz, 2H), 3.91 (s, 3H), 1.69-1.77 (m, 2H), 1.02 (t, J=7.2 Hz, 3H). LCMS m/z=350 [MH]$^+$.

Example 44: 4-(5-(3-ethoxy-5-fluoro-4-methoxyphenyl)pyridin-3-yl)-1,2-oxaborolan-2-ol

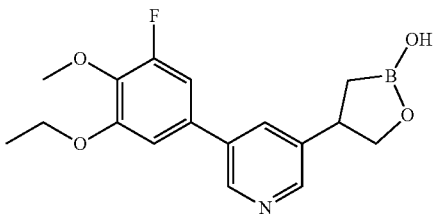 [SMILES: CCOc1cc(-c2cncc(C3COB(O)C3)c2)cc(F)c1OC]

4-(5-(3-ethoxy-5-fluoro-4-methoxyphenyl)pyridin-3-yl)-1,2-oxaborolan-2-ol (90 mg, 25%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-ethoxy-5-fluoro-4-methoxyphenyl)pyridine (Preparation 16, 600 mg, 1.1 mmol) and purified by preparative HPLC (Prep HPLC Method O). $^1$H NMR (DMSO-d$_6$, 400 MHz): δ 8.75 (d, J=2.0 Hz, 1H), 8.71 (s, 1H), 8.47 (d, J=1.47 Hz, 1H), 8.00 (s, 1H), 7.27 (dd, J=2.0, 11.7 Hz, 1H), 7.20 (s, 1H), 4.27 (t, J=8.3 Hz, 1H), 4.21 (q, J=6.9 Hz, 2H), 3.82-3.90 (m, 3H), 3.45-3.56 (m, 2H), 1.39 (t, J=6.9 Hz, 3H), 1.26-1.34 (m, 1H), 1.12-1.20 (m, 1H). LCMS m/z=332 [MH]$^+$.

Example 45: 4-(5-(3-chloro-5-ethoxy-4-methoxyphenyl)pyridin-3-yl)-1,2-oxaborolan-2-ol

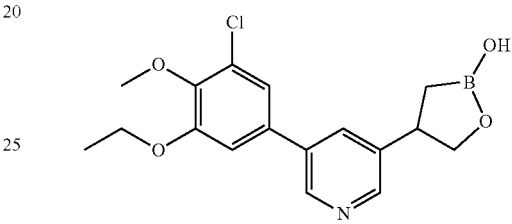

4-(5-(3-chloro-5-ethoxy-4-methoxyphenyl)pyridin-3-yl)-1,2-oxaborolan-2-ol (150 mg, 30%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-chloro-5-ethoxy-4-methoxyphenyl)pyridine (Preparation 17, 800 mg, 1.42 mmol) and purified by preparative HPLC (Prep HPLC Method P). $^1$H NMR (DMSO-d$_6$, 400 MHz): δ 8.75 (d, J=2.0 Hz, 1H), 8.70 (s, 1H), 8.48 (d, J=2.0 Hz, 1H), 8.02 (t, J=2.2 Hz, 1H), 7.42 (d, J=2.0 Hz, 1H), 7.34 (d, J=2.0 Hz, 1H), 4.18-4.30 (m, 3H), 3.83-3.91 (m, 1H), 3.81 (s, 3H), 3.44-3.57 (m, 1H), 1.39 (t, J=6.9 Hz, 3H), 1.26-1.34 (m, 1H), 1.12-1.22 (m, 1H). LCMS m/z=347 [MH]$^+$.

Example 46: 4-(5-(5-ethoxy-2-fluoro-4-methoxyphenyl)pyridin-3-yl)-1,2-oxaborolan-2-ol

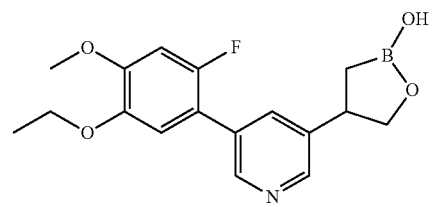 [SMILES: CCOc1cc(-c2cncc(C3COB(O)C3)c2)c(F)cc1OC]

4-(5-(5-ethoxy-2-fluoro-4-methoxyphenyl)pyridin-3-yl)-1,2-oxaborolan-2-ol (385 mg, 32%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(5-ethoxy-2-fluoro-4-methoxyphenyl)pyridine (Preparation 18, 2.0 g, 3.67 mmol) and purified by preparative HPLC (Prep HPLC Method Q). $^1$H NMR (DMSO-d$_6$, 400 MHz): δ 8.72 (s, 1H), 8.58 (s, 1H), 8.46 (s, 1H), 7.83 (s, 1H), 7.09 (d, J=7.7 Hz, 1H), 7.03 (d, J=12.4 Hz, 1H), 4.28 (t, J=8.2 Hz, 1H), 4.07 (q, J=7.0 Hz, 2H), 3.82-3.86 (m, 4H), 3.46-3.55 (m, 1H), 1.29-1.34 (m, 4H), 1.07-1.14 (m, 1H). LCMS m/z=332 [MH]$^+$.

Example 47: 4-(5-(2-chloro-5-ethoxy-4-methoxy-phenyl)pyridin-3-yl)-1,2-oxaborolan-2-ol

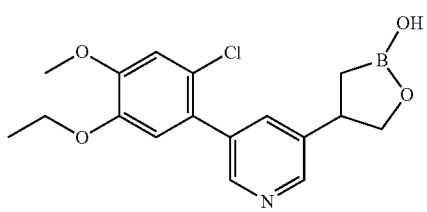 [SMILES: CCOc1cc(-c2cncc(C3COB(O)C3)c2)c(Cl)cc1OC]

4-(5-(2-chloro-5-ethoxy-4-methoxyphenyl)pyridin-3-yl)-1,2-oxaborolan-2-ol (1.6 g, 65%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(2-chloro-5-ethoxy-4-methoxyphenyl)pyridine (Preparation 19, 4.1 g, 7.30 mmol) and purified by preparative HPLC (Prep HPLC Method R). $^1$H NMR (DMSO-d$_6$, 400 MHz): δ 8.71 (s, 1H), 8.48 (t, J=2.0 Hz, 2H), 7.76 (t, J=2.2 Hz, 1H), 7.15 (s, 1H), 7.01 (s, 1H), 4.26-4.30 (m, 1H), 4.06 (q, J=7.0 Hz, 2H), 3.81-3.85 (m, 4H), 3.47-3.55 (m, 1H), 1.29-1.35 (m, 4H), 1.06-1.12 (m, 1H). LCMS m/z=348 [MH]$^+$.

Example 48: 4-(3-fluoro-5-methoxy-6-propoxy-[2,3'-bipyridin]-5'-yl)-1,2-oxaborolan-2-ol

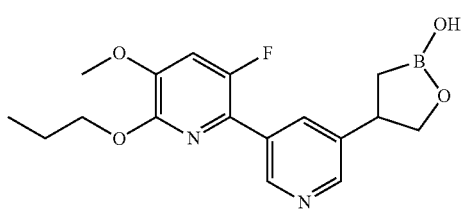 [SMILES: CCCOc1nc(-c2cncc(C3COB(O)C3)c2)c(F)cc1OC]

4-(3-fluoro-5-methoxy-6-propoxy-[2,3'-bipyridin]-5'-yl)-1,2-oxaborolan-2-ol (780 mg, 49%) was prepared in an analogous manner to Example 33 using 5'-(1-((tert-butyldimethylsilyl)oxy)-3-(4,4,5,5-tetramethyl-1,3,2-dioxaborolan-2-yl)propan-2-yl)-3-fluoro-5-methoxy-6-propoxy-2,3'-bipyridine (Preparation 22, 4.02 g, 7.14 mmol) and purified by preparative HPLC (Prep HPLC Method S). $^1$H NMR (DMSO-d$_6$, 400 MHz): δ 8.89 (s, 1H), 8.73 (s, 1H), 8.49 (d, J=2.0 Hz, 1H), 8.09 (s, 1H), 7.49 (d, J=12.0 Hz, 1H), 4.28-4.33 (m, 3H), 3.87 (s, 3H), 3.82 (t, J=8.7 Hz, 1H), 3.49-3.57 (m, 1H), 1.73-1.81 (m, 2H), 1.31-1.37 (m, 1H), 1.03-1.09 (m, 1H), 0.98 (t, J=7.5 Hz, 3H). LCMS m/z=347 [MH]$^+$.

Example 49: 4-(5-(2-fluoro-4-methoxy-5-propoxy-phenyl)pyridin-3-yl)-1,2-oxaborolan-2-ol

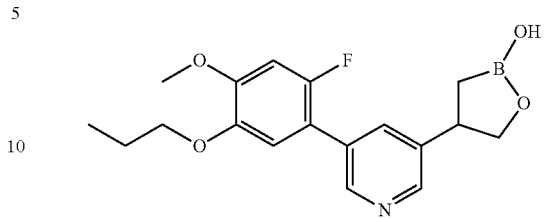

4-(5-(2-fluoro-4-methoxy-5-propoxyphenyl)pyridin-3-yl)-1,2-oxaborolan-2-ol (1.2 g, 49%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(2-fluoro-4-methoxy-5-propoxyphenyl)pyridine (Preparation 20, 4.0 g, 7.1 mmol) and purified by preparative HPLC (Prep HPLC Method T). $^1$H NMR (DMSO-d$_6$, 400 MHz): δ 8.89 (s, 1H), 8.74 (s, 1H), 8.49 (d, J=2.0 Hz, 1H), 8.09 (s, 1H), 7.47-7.53 (m, 1H), 4.27-4.36 (m, 3H), 3.87 (s, 3H), 3.82 (t, J=8.7 Hz, 1H), 3.50-3.56 (m, 1H), 1.75-1.80 (m, 2H), 1.34 (dd, J=8.2, 16.3 Hz, 1H), 1.01-1.12 (m, 1H), 0.98 (t, J=7.3 Hz, 3H). LCMS m/z=347 [MH]$^+$.

Example 50: 4-(5-(4-(difluoromethoxy)-3-propoxy-phenyl)pyridin-3-yl)-1,2-oxaborolan-2-ol

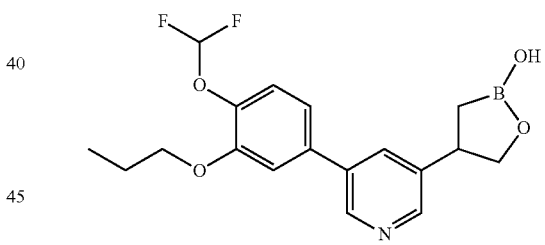

4-(5-(4-(difluoromethoxy)-3-propoxyphenyl)pyridin-3-yl)-1,2-oxaborolan-2-ol (0.51 g, 31%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(4-(difluoromethoxy)-3-propoxyphenyl)pyridine (Preparation 21, 2.6 g, 4.50 mmol) and purified by preparative HPLC (Prep HPLC Method U). $^1$H NMR (DMSO-d$_6$, 400 MHz): δ 8.74 (d, J=2.1 Hz, 1H), 8.72 (s, 1H), 8.49 (d, J=2.0 Hz, 1H), 8.00 (t, J=2.0 Hz, 1H), 7.45 (d, J=1.6 Hz, 1H), 7.28-7.31 (m, 2H), 7.09 (t, J=74.5 Hz, 1H), 4.28 (t, J=8.3 Hz, 1H), 4.12 (t, J=6.4 Hz, 2H), 3.87 (t, J=9.1 Hz, 1H), 3.47-3.56 (m, 1H), 1.73-1.82 (m, 2H), 1.29-1.35 (m, 1H), 1.12-1.19 (m, 1H), 1.01 (t, J=7.5 Hz, 3H). LCMS m/z=382 [MH+H$_2$O]$^+$.

Example 51: 4-(6'-methoxy-5'-propoxy-[3,3'-bipyridin]-5-yl)-1,2-oxaborolan-2-ol

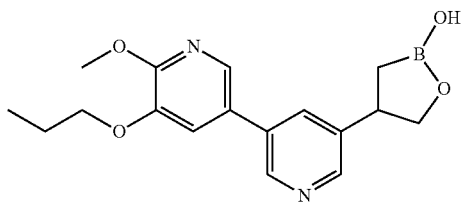 [SMILES: CCCOc1cc(-c2cncc(C3COB(O)C3)c2)cnc1OC]

4-(6'-methoxy-5'-propoxy-[3,3'-bipyridin]-5-yl)-1,2-oxaborolan-2-ol was prepared (720 mg, 25%) in an analogous manner to Example 33 using 5'-(1-((tert-butyldimethylsilyl)oxy)-3-(4,4,5,5-tetramethyl-1,3,2-dioxaborolan-2-yl)propan-2-yl)-6-methoxy-5-propoxy-3,3'-bipyridine (Preparation 23, 1.034 g, 1.9 mmol) and purified by preparative HPLC (Prep HPLC Method V). $^1$H NMR (DMSO-$d_6$, 400 MHz): δ 8.76 (d, J=2.2 Hz, 1H), 8.72 (s, 1H), 8.48 (d, J=2.0 Hz, 1H), 8.06 (d, J=2.0 Hz, 1H), 8.01 (t, J=2.2 Hz, 1H), 7.61 (d, J=2.2 Hz, 1H), 4.26-4.31 (m, 1H), 4.08 (t, J=6.6 Hz, 2H), 3.92 (s, 3H), 3.87 (t, J=9.1 Hz, 1H), 3.48-3.56 (m, 1H), 1.73-1.82 (m, 2H), 1.28-1.35 (m, 1H), 1.13-1.21 (m, 1H), 1.00 (t, J=7.5 Hz, 3H). LCMS m/z=329 [MH]$^+$.

Example 52: 4-(5-(3-ethoxy-4-methoxyphenyl)-6-methylpyridin-3-yl)-1,2-oxaborolan-2-ol

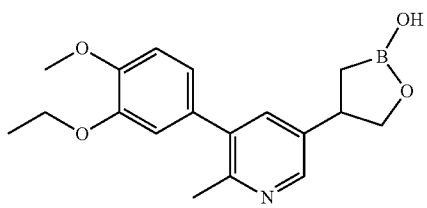 [SMILES: CCOc1cc(-c2cc(C3COB(O)C3)cnc2C)ccc1OC]

4-(5-(3-ethoxy-4-methoxyphenyl)-6-methylpyridin-3-yl)-1,2-oxaborolan-2-ol (182 mg, 43%) was prepared in an analogous manner to Example 33 using 5-(1-((tert-butyldimethylsilyl)oxy)-3-(4,4,5,5-tetramethyl-1,3,2-dioxaborolan-2-yl)propan-2-yl)-3-(3-ethoxy-4-methoxyphenyl)-2-methylpyridine (Preparation 24, 700 mg, 1.29 mmol) and purified by preparative HPLC (Prep HPLC Method WV). $^1$H NMR (DMSO-$d_6$, 400 MHz): δ 8.67 (s, 1H), 8.33 (d, J=2.0 Hz, 1H), 7.47 (d, J=2.0 Hz, 1H), 7.03 (d, J=8.3 Hz, 1H), 6.94 (d, J=2.0 Hz, 1H), 6.88 (dd, J=2.0, 7.8 Hz, 1H), 4.24 (t, J=8.1 Hz, 1H), 4.04 (q, J=6.9 Hz, 2H), 3.76-3.83 (m, 4H), 3.39-3.50 (m, 1H), 2.40 (s, 3H), 1.24-1.36 (m, 4H), 1.01-1.10 (m, 1H). LCMS m/z=328 [MH]$^+$.

Example 53: 4-(5-(3-ethoxy-4-methoxyphenyl)-4-methylpyridin-3-yl)-1,2-oxaborolan-2-ol

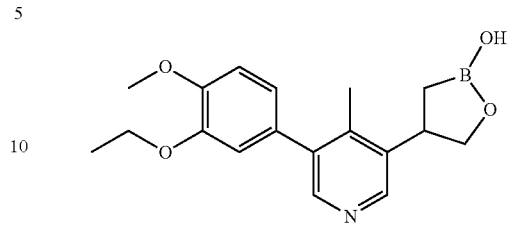

4-(5-(3-ethoxy-4-methoxyphenyl)-4-methylpyridin-3-yl)-1,2-oxaborolan-2-ol (0.06 g, 33%) was prepared in an analogous manner to Example 33 using 3-(1-((tert-butyldimethylsilyl)oxy)-3-(4,4,5,5-tetramethyl-1,3,2-dioxaborolan-2-yl)propan-2-yl)-5-(3-ethoxy-4-methoxyphenyl)-4-methylpyridine (Preparation 35, 0.28 g, 0.51 mmol) and purified by preparative HPLC (Prep HPLC Method X). $^1$H NMR (DMSO-$d_6$, 400 MHz): δ 8.71 (s, 1H), 8.43 (s, 1H), 8.21 (s, 1H), 7.04 (d, J=8.0 Hz, 1H), 6.90 (d, J=2.3 Hz, 1H), 6.82-6.85 (m, 1H), 4.24-4.28 (m, 1H), 4.03 (q, J=7.0 Hz, 2H), 3.90-3.95 (m, 1H), 3.80 (s, 3H), 3.63-3.71 (m, 1H), 2.22 (s, 3H), 1.30-1.36 (m, 4H), 1.04-1.10 (m, 1H). LCMS m/z=328 [MH]$^+$.

Example 54: 4-(2-(4-methoxy-3-propoxyphenyl)-6-methylpyrimidin-4-yl)-1,2-oxaborolan-2-ol

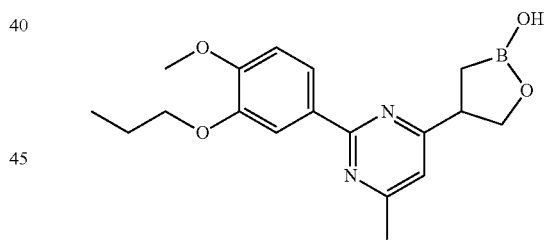

4-(2-(4-methoxy-3-propoxyphenyl)-6-methylpyrimidin-4-yl)-1,2-oxaborolan-2-ol (314 mg, 95%) was prepared in an analogous manner to Example 33 using ethyl 2-(6-(1-((tert-butyldimethylsilyl)oxy)-3-(4,4,5,5-tetramethyl-1,3,2-dioxaborolan-2-yl)propan-2-yl)-2-(4-methoxy-3-propoxyphenyl)pyrimidin-4-yl)acetate (Preparation 28, 500 mg, 0.96 mmol) and purified by preparative HPLC (Prep HPLC Method Y). $^1$H NMR (CD$_3$OD, 400 MHz): δ 8.03 (dd, J=2.0, 8.6 Hz, 1H), 8.00 (d, J=2.0 Hz, 1H), 7.07 (s, 1H), 7.05 (d, J=8.3 Hz, 1H), 4.17 (br s, 1H), 4.07 (t, J=6.5 Hz, 2H), 4.00 (br s, 1H), 3.91 (s, 2H), 3.41 (br s, 1H), 2.52 (s, 2H), 1.84-1.89 (m, 2H), 1.29-1.38 (m, 1H), 1.21-1.29 (m, 1H), 1.09 (t, J=7.3 Hz, 3H). LCMS m/z=343 [MH]$^+$.

Example 55: 4-(2-(4-methoxy-3-propoxyphenyl)-6-(trifluoromethyl)pyrimidin-4-yl)-1,2-oxaborolan-2-ol

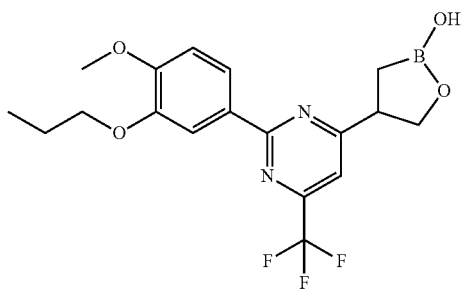 [SMILES: CCCOc1cc(-c2nc(C3COB(O)C3)cc(C(F)(F)F)n2)ccc1OC]

4-(2-(4-methoxy-3-propoxyphenyl)-6-(trifluoromethyl) pyrimidin-4-yl)-1,2-oxaborolan-2-ol (582 mg, 36%) was prepared in an analogous manner to Example 33 using 4-(1-((tert-butyldimethylsilyl)oxy)-3-(4,4,5,5-tetramethyl-1,3,2-dioxaborolan-2-yl)propan-2-yl)-2-(4-methoxy-3-propoxyphenyl)-6-(trifluoromethyl)pyrimidine (Preparation 25, 2.5 g, 4.09 mmol) and purified by preparative HPLC (Prep HPLC Method Z). $^1$H NMR (DMSO-$d_6$, 400 MHz): δ 8.72 (s, 1H), 8.03 (dd, J=2.0, 8.6 Hz, 1H), 7.95 (d, J=2.0 Hz, 1H), 7.77 (s, 1H), 7.13 (d, J=8.6 Hz, 1H), 4.32 (dd, J=7.4, 9.0 Hz, 1H), 3.98-4.09 (m, 3H), 3.86 (s, 3H), 3.73-3.82 (m, 1H), 1.73-1.84 (m, 1H), 1.31-1.41 (m, 1H), 1.18-1.26 (m, 2H), 1.01 (t, J=7.4 Hz, 3H). LCMS m/z=397 [MH]$^+$.

Example 56: 4-(6-(3-ethoxy-4-methoxyphenyl)pyrazin-2-yl)-1,2-oxaborolan-2-ol

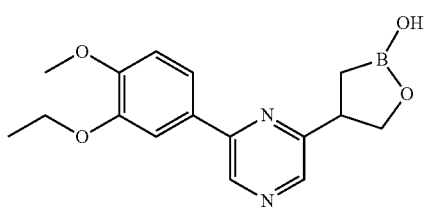 [SMILES: CCOc1cc(-c2cncc(C3COB(O)C3)n2)ccc1OC]

4-(6-(3-ethoxy-4-methoxyphenyl)pyrazin-2-yl)-1,2-oxaborolan-2-ol (30 mg, 7%) was prepared in an analogous manner to Example 33 using 2-(1-((tert-butyldimethylsilyl)oxy)-3-(4,4,5,5-tetramethyl-1,3,2-dioxaborolan-2-yl)propan-2-yl)-6-(3-ethoxy-4-methoxyphenyl)pyrazine (Preparation 26, 720 mg, 1.36 mmol) and purified by preparative HPLC (Prep HPLC Method AA). $^1$H NMR (DMSO-$d_6$, 400 MHz): δ 9.06 (s, 1H), 8.67 (s, 1H), 8.44 (s, 1H), 8.37-8.50 (m, 1H), 7.65-7.79 (m, 2H), 7.08 (d, J=8.8 Hz, 1H), 4.30 (t, J=8.2 Hz, 1H), 4.12 (q, J=6.9 Hz, 2H), 3.98 (dd, J=6.5, 8.9 Hz, 1H), 3.83 (s, 3H), 3.66-3.70 (m, 1H), 1.37 (t, J=7.0 Hz, 3H), 1.27-1.34 (m, 1H), 1.14-1.22 (m, 1H). LCMS m/z=315 [MH]$^+$.

Example 57: 4-(6-(hydroxymethyl)-2-(4-methoxy-3-propoxyphenyl)pyrimidin-4-yl)-1,2-oxaborolan-2-ol

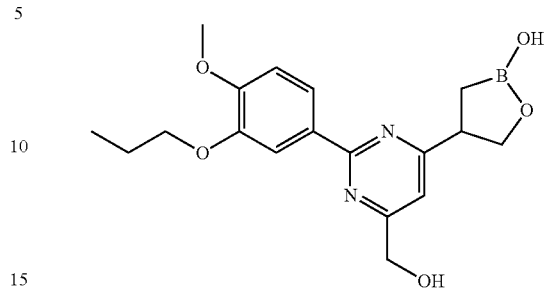

4-(6-(hydroxymethyl)-2-(4-methoxy-3-propoxyphenyl) pyrimidin-4-yl)-1,2-oxaborolan-2-ol (0.2 g, 38.4%) was prepared in an analogous manner to Example 33 using 4-(1-((tert-butyldimethylsilyl)oxy)-3-(4,4,5,5-tetramethyl-1,3,2-dioxaborolan-2-yl)propan-2-yl)-6-(((tert-butyldimethylsilyl)oxy)methyl)-2-(4-methoxy-3-propoxyphenyl)pyrimidine (Preparation 29, 1.0 g, 1.5 mmol) and purified by preparative HPLC (Prep HPLC Method BA). $^1$H NMR (DMSO-$d_6$, 400 MHz): δ 8.71 (s, 1H), 8.00 (dd, J=2.0, 8.0 Hz, 1H), 7.96 (d, J=2.0 Hz, 1H), 7.52 (s, 1H), 7.27-7.31 (m, 1H), 7.06 (d, J=8.5 Hz, 1H), 5.60-5.66 (m, 1H), 4.59 (d, J=6.0 Hz, 2H), 4.31 (dd, J=7.0, 9.0 Hz, 1H), 3.96-4.04 (m, 2H), 3.83 (s, 3H), 3.57-3.65 (m, 1H), 1.75-1.82 (m, 2H), 1.25-1.35 (m, 1H), 1.12-1.21 (m, 1H), 0.96-1.07 (m, 3H). LCMS m/z=359 [MH]$^+$.

Example 58: 4-(2-(3-ethoxy-4-methoxyphenyl)thiazol-4-yl)-1,2-oxaborolan-2-ol

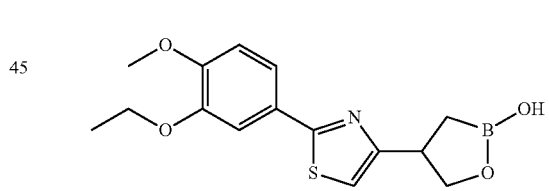

4-(2-(3-ethoxy-4-methoxyphenyl)thiazol-4-yl)-1,2-oxaborolan-2-ol (0.31 g, 37%) was prepared in an analogous manner to Example 33 using 4-(1-((tert-butyldimethylsilyl)oxy)-3-(4,4,5,5-tetramethyl-1,3,2-dioxaborolan-2-yl)propan-2-yl)-2-(3-ethoxy-4-methoxyphenyl)thiazole (Preparation 36, 1.42 g, 2.66 mmol) and purified by preparative HPLC (Prep HPLC Method CA). $^1$H NMR (DMSO-$d_6$, 400 MHz): δ 8.66 (br s, 1H), 7.42-7.46 (m, 2H), 7.30 (s, 1H), 7.05 (d, J=8.3 Hz, 1H), 4.24-4.28 (m, 1H), 4.09 (q, J=7.0 Hz, 2H), 3.90-3.95 (m, 1H), 3.82 (s, 3H), 3.55-3.63 (m, 1H), 1.36 (t, J=7.0 Hz, 3H), 1.25-1.31 (m, 1H), 1.11-1.18 (m, 1H). LCMS m/z=320 [MH]$^+$.

Example 59: (2R)-2-(5-(4-methoxy-3-propoxyphenyl)pyridin-3-yl)-3-(4,4,6-trimethyl-1,3,2-dioxaborinan-2-yl)propan-1-ol

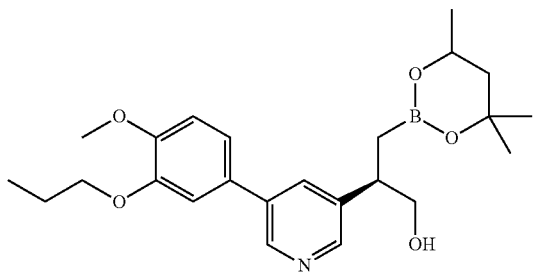 [SMILES: CCCOc1cc(-c2cncc([C@H](CO)CB3OC(C)CC(C)(C)O3)c2)ccc1OC]

To hexylene glycol (1.0 g, 8.46 mmol) was added-4-(5-(4-methoxy-3-propoxyphenyl)pyridin-3-yl)-1,2-oxaborolan-2-ol (Example 4, 0.051 g, 0.16 mmol) at about 20° C. The mixture was stirred until homogeneous to afford (2R)-2-(5-(4-methoxy-3-propoxyphenyl)pyridin-3-yl)-3-(4,4,6-trimethyl-1,3,2-dioxaborinan-2-yl)propan-1-ol (5 wt % solution in hexyleneglycol) as a mixture of diastereomers (1:1 ratio). $^1$H NMR (DMSO-$d_6$, 400 MHz): δ 8.64 (d, J=2.2 Hz, 1H), 8.32 (d, J=1.9 Hz, 1H), 7.77 (t, J=2.2 Hz, 1H), 7.23 (s, 1H), 7.17-7.25 (m, 1H), 7.06 (d, J=8.1 Hz, 1H), 4.61 (H, 1H), 4.02 (t, J=6.6 Hz, 2H), 3.97-4.07 (m, 1H), 3.80 (s, 3H), 3.46-3.58 (m, 2H), 2.84-2.98 (m, 1H), 1.69-1.83 (m, 3H), 1.14 (m, 1H), 1.02-1.09 (m, 10H), 1.00 (t, J=7.4 Hz, 3H), 0.83 (dd, J=9.0, 15.0 Hz, 1H). LCMS m/z=428 [MH]=.

The following compounds, Example 60-, were prepared similarly using methods described above. Examples containing an asterisk (*), designates a single enantiomer obtained through chiral purification methods. For those examples characterized by HPLC retention time (RT), the analytical HPLC methods are described.

| Example No. | Structure and Name | Analytical Data |
|---|---|---|
| 60 | 4-(5-methoxy-6-propoxy-[2,3'-bipyridin]-5'-yl)-1,2-oxaborolan-2-ol | $^1$H NMR (DMSO-$d_6$, 400 MHz): δ 9.04 (d, J = 2.0 Hz, 1H), 8.71 (s, 1H), 8.45 (d, J = 2.0 Hz, 1H), 8.22 (t, J = 2.2 Hz, 1H), 7.61 (d, J = 7.8 Hz, 1H), 7.37 (d, J = 8.3 Hz, 1H), 4.36 (t, J = 6.6 Hz, 2H), 4.26-4.32 (m, 1H), 3.80-3.88 (m, 4H), 3.45-3.58 (m, 1H), 1.75-1.84 (m, 2H), 1.33 (dd, J = 8.3, 16.1 Hz, 1H), 1.06-1.17 (m, 1H), 1.00 (t, J = 7.3 Hz, 3H). LCMS m/z = 329 [MH]$^+$. |
| 61 | 4-(5-methoxy-6-propoxy-[2,3'-bipyridin]-5'-yl)-1,2-oxaborolan-2-ol, enantiomer 1 | $^1$H NMR (DMSO-$d_6$, 400 MHz): δ 9.04 (d, J = 2.0 Hz, 1H), 8.71 (s, 1H), 8.45 (d, J = 2.0 Hz, 1H), 8.22 (t, J = 2.2 Hz, 1H), 7.61 (d, J = 7.8 Hz, 1H), 7.37 (d, J = 8.3 Hz, 1H), 4.36 (t, J = 6.6 Hz, 2H), 4.26-4.32 (m, 1H), 3.80-3.88 (m, 4H), 3.45-3.58 (m, 1H), 1.75-1.84 (m, 2H), 1.33 (dd, J = 8.3, 16.1 Hz, 1H), 1.06-1.17 (m, 1H), 1.00 (t, J = 7.3 Hz, 3H). LCMS m/z = 329 [MH]$^+$. RT [Analytical SFC Method I] = 4.57 min. |
| 62 | 4-(5-methoxy-6-propoxy-[2,3'-bipyridin]-5'-yl)-1,2-oxaborolan-2-ol, enantiomer 2 | $^1$H NMR (DMSO-$d_6$, 400 MHz): δ 9.04 (d, J = 2.0 Hz, 1H), 8.71 (s, 1H), 8.45 (d, J = 2.0 Hz, 1H), 8.22 (t, J = 2.2 Hz, 1H), 7.61 (d, J = 7.8 Hz, 1H), 7.37 (d, J = 8.3 Hz, 1H), 4.36 (t, J = 6.6 Hz, 2H), 4.26-4.32 (m, 1H), 3.80-3.88 (m, 4H), 3.45-3.58 (m, 1H), 1.75-1.84 (m, 2H), 1.33 (dd, J = 8.3, 16.1 Hz, 1H), 1.06-1.17 (m, 1H), 1.00 (t, J = 7.3 Hz, 3H). LCMS m/z = 329 [MH]$^+$. RT [Analytical SFC Method I] = 4.98 min. |
| 63 | 4-(3'-(2-fluoroethoxy)-4'-methoxy-[1,1'-biphenyl]-3-yl)-1,2-oxaborolan-2-ol | $^1$H NMR (DMSO-$d_6$, 400 MHz): δ 7.51 (br s, 1H), 7.46 (d, J = 7.8 Hz, 1H), 7.35 (t, J = 7.8 Hz, 1H), 7.18-7.23 (m, 3H), 7.06 (d, J = 8.2 Hz, 1H), 4.81-4.83 (m, 1H), 4.69-4.71 (m, 1H), 4.36-4.38 (m, 1H), 4.24-4.30 (m, 2H), 3.79-3.83 (m, 4H), 3.42-3.51 (m, 1H), 1.26-1.32 (m, 1H), 1.05-1.12 (m, 1H). LCMS m/z = 331 [MH]$^+$. |

| Example No. | Structure and Name | Analytical Data |
|---|---|---|
| 64 | 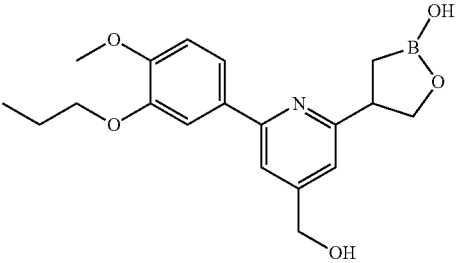<br>4-(4-(hydroxymethyl)-6-(4-methoxy-3-propoxphenyl)pyridin-2-yl)-1,2-oxaborolan-2-ol | $^1$H NMR (DMSO-$d_6$, 400 MHz): δ 8.59 (br s, 1H), 7.69 (d, J = 2.0 Hz, 1H), 7.57-7.66 (m, 2H), 7.11 (s, 1H), 7.00-7.06 (m, 1H), 5.41 (br s, 1H), 4.56 (s, 2H), 4.28 (dd, J = 7.3, 8.78 Hz, 1H), 3.94-4.03 (m, 3H), 3.80 (s, 3H), 3.52-3.62 (m, 1H), 1.70-1.82 (m, 2H), 1.13-1.30 (m, 2H), 1.00 (t, J = 7.5 Hz, 3H). LCMS m/z = 376 [MH + H$_2$O]$^+$. |
| 65 | 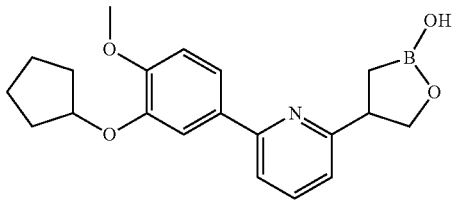<br>4-(6-(3-(cyclopentyloxy)-4-methoxyphenyl)pyridin-2-yl)-1,2-oxaborolan-2-ol | $^1$H NMR (DMSO-$d_6$, 400 MHz): δ 8.59 (s, 1H), 7.70-7.75 (m, 3H), 7.62 (dd, J = 2.0, 8.3 Hz, 1H), 7.10-7.20 (m, 1H), 7.03 (d, J = 8.6 Hz, 1H), 4.90 (t, J = 5.9 Hz, 1H), 4.29 (t, J = 8.2 Hz, 1H), 3.99 (dd, J = 7.0, 8.9 Hz, 1H), 3.79 (s, 3H), 3.56-3.63 (m, 1H), 1.87-2.04 (m, 2H), 1.68-1.81 (m, 4H), 1.59 (br s, 2H), 1.16-1.30 (m, 2H). LCMS m/z = 372 [MH + H$_2$O]$^+$. |
| 66 | 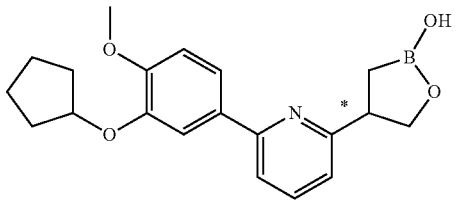 [SMILES: COc1ccc(-c2cccc(C3COB(O)C3)n2)cc1OC1CCCC1]<br>4-(6-(3-(cyclopentyloxy)-4-methoxyphenyl)pyridin-2-yl)-1,2-oxaborolan-2-ol, enantiomer 1 | LCMS m/z = 354 [MH]$^+$. RT [Analytical SFC Method V] = 3.60 min. |
| 67 | 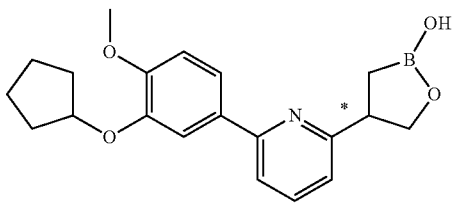 [SMILES: COc1ccc(-c2cccc(C3COB(O)C3)n2)cc1OC1CCCC1]<br>4-(6-(3-(cyclopentyloxy)-4-methoxyphenyl)pyridin-2-yl)-1,2-oxaborolan-2-ol, enantiomer 2 | LCMS m/z = 354 [M + H]$^+$. RT [Analytical SFC Method V] = 3.93 min. |
| 68 | 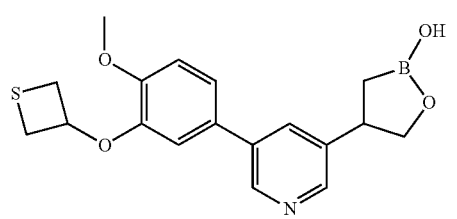 [SMILES: COc1ccc(-c2cncc(C3COB(O)C3)c2)cc1OC1CSC1]<br>4-(5-(4-methoxy-3-(thietan-3-yloxy)phenyl)pyridin-3-yl)-1,2-oxaborolan-2-ol | $^1$H NMR (DMSO-$d_6$, 400 MHz): δ 8.72 (s, 1H), 8.70 (d, J = 2.0 Hz, 1H), 8.42 (d, J = 2.0 Hz, 1H), 7.92 (t, J = 2.0 Hz, 1H), 7.31 (dd, J = 2.3, 8.3 Hz, 1H), 7.22 (d, J = 2.5 Hz, 1H), 7.09 (d, J = 8.5 Hz, 1H), 5.44-5.53 (m, 1H), 4.27 (t, J = 8.3 Hz, 1H), 3.86 (t, J = 9.0 Hz, 1H), 3.81 (s, 3H), 3.47 (dd, J = 3.8, 7.8 Hz, 5H), 1.31 (dd, J = 8.3, 16.3 Hz, 1H), 1.11 1.19 (m, 1H). LCMS m/z = 358 [MH]$^+$. |

| Example No. | Structure and Name | Analytical Data |
|---|---|---|
| 69 | 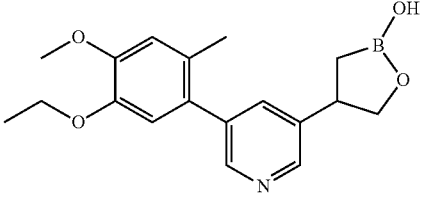 [SMILES: CCOc1cc(-c2cncc(C3COB(O)C3)c2)c(C)cc1OC]<br>4-(5-(5-ethoxy-4-methoxy-2-methylphenyl)pyridin-3-yl)-1,2-oxaborolan-2-ol | $^1$H NMR (MeOD-d$_3$, 400 MHz): δ 8.40 (d, J = 2.0 Hz, 1H), 8.31 (d, J = 2.5 Hz, 1H), 7.69 (t, J = 2.0 Hz, 1H), 6.92 (s, 1H), 6.80 (s, 1H), 4.06 (q, J = 6.9 Hz, 2H), 3.83-3.90 (m, 4H), 3.33-3.40 (m, 1H), 2.21 (s, 3H), 1.39 (t, J = 6.9 Hz, 3H), 1.16-1.33 (m, 2H) LCMS m/z = 328 [MH]$^+$. |
| 70 | 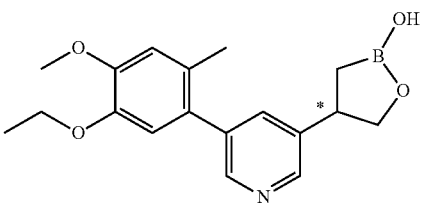<br>4-(5-(5-ethoxy-4-methoxy-2-methylphenyl)pyridin-3-yl)-1,2-oxaborolan-2-ol, enantiomer 1 | $^1$H NMR (DMSO-d$_6$, 400 MHz): δ 8.69 (br s, 1H), 8.31-8.49 (m, 2H), 7.66 (br s, 1H), 6.91 (br s, 1H), 6.81 (br s, 1H), 4.27 (br s, 1H), 4.01 (d, J = 5.9 Hz, 2H), 3.73-3.90 (m, 4H), 3.49 (br s, 1H), 2.18 (br s, 3H), 1.30 (br s, 3H), 0.99-1.16 (m, 2H). LCMS m/z = 346 [MH + H$_2$O]$^+$. RT [Analytical SFC Method L] = 2.67 min. |
| 71 | 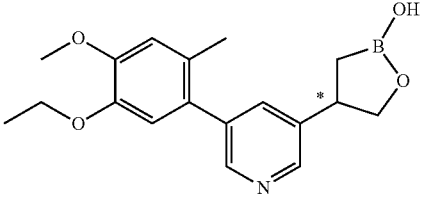 [SMILES: CCOc1cc(-c2cncc(C3COB(O)C3)c2)c(C)cc1OC]<br>4-(5-(5-ethoxy-4-methoxy-2-methylphenyl)pyridin-3-yl)-1,2-oxaborolan-2-ol, enantiomer 2 | $^1$H NMR (DMSO-d$_6$, 400 MHz): δ 8.69 (br s, 1H), 8.31-8.49 (m, 2H), 7.66 (br s, 1H), 6.91 (br s, 1H), 6.81 (br s, 1H), 4.27 (br s, 1H), 4.01 (d, J = 5.9 Hz, 2H), 3.73-3.90 (m, 4H), 3.49 (br s, 1H), 2.18 (br s, 3H), 1.30 (br s, 3H), 0.99-1.16 (m, 2H). LCMS m/z = 327 [MH]$^+$. RT [Analytical SFC Method L] = 2.91 min. |
| 72 | 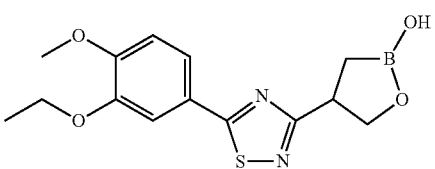 [SMILES: CCOc1cc(-c2nc(C3COB(O)C3)ns2)ccc1OC]<br>4-(5-(3-ethoxy-4-methoxyphenyl)-1,2,4-thiadiazol-3-yl)-1,2-oxaborolan-2-ol | $^1$H NMR (DMSO-d$_6$, 400 MHz): δ 7.58 (dd, J = 1.8, 8.4 Hz, 1H), 7.46 (d, J = 1.71 Hz, 1H), 7.12 (d, J = 8.6 Hz, 1H), 4.27-4.37 (m, 1H), 4.07-4.16 (m, 3H), 3.85 (s, 3H), 3.76-3.83 (m, 1H), 1.23-1.43 (m, 5H). LCMS m/z = 321.1 [MH]$^+$. |
| 73 | 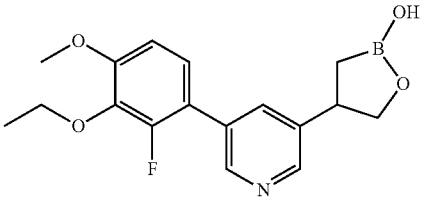 [SMILES: CCOc1c(OC)ccc(-c2cncc(C3COB(O)C3)c2)c1F]<br>4-(5-(3-ethoxy-2-fluoro-4-methoxyphenyl)pyridin-3-yl)-1,2-oxaborolan-2-ol | $^1$H NMR (DMSO-d$_6$, 400 MHz): δ 8.70 (s, 1H), 8.54 (s, 1H), 8.48 (d, J = 2.0 Hz, 1H), 7.81 (d, J = 1.5 Hz, 1H), 7.26 (t, J = 8.8 Hz, 1H), 7.01 (dd, J = 1.0, 8.8 Hz, 1H), 4.28 (t, J = 8.3 Hz, 1H), 4.06 (q, J = 7.3 Hz, 2H), 3.80-3.90 (m, 4H), 3.44-3.58 (m, 1H), 1.24-1.39 (m, 4H), 0.99-1.16 (m, 1H). LCMS m/z = 332 [MH]$^+$. |

| Example No. | Structure and Name | Analytical Data |
|---|---|---|
| 74 | 4-(5-(3-ethoxy-2-fluoro-4-methoxyphenyl)pyridin-3-yl)-1,2-oxaborolan-2-ol, enantiomer 2 | $^1$H NMR (DMSO-d$_6$, 400 MHz): δ 8.70 (s, 1H), 8.54 (s, 1H), 8.48 (d, J = 2.0 Hz, 1H), 7.81 (d, J = 1.5 Hz, 1H), 7.26 (t, J = 8.8 Hz, 1H), 7.01 (dd, J = 1.0, 8.8 Hz, 1H), 4.28 (t, J = 8.3 Hz, 1H), 4.06 (q, J = 7.3 Hz, 2H), 3.80-3.90 (m, 4H), 3.44-3.58 (m, 1H), 1.24-1.39 (m, 4H), 0.99-1.16 (m, 1H). LCMS m/z = 332 [MH]$^+$. RT [Analytical SFC Method GA] = 6.58 min. |
| 75 | 4-(3'-isopropoxy-4'-methoxy-[1,1'-biphenyl]-3-yl)-1,2-oxaborolan-2-ol | $^1$H NMR (DMSO-d$_6$, 400 MHz): δ 7.48 (s, 1H), 7.43 (d, J = 7.6 Hz, 1H), 7.34 (t, J = 7.6 Hz, 1H), 7.14-7.24 (m, 3H), 7.00-7.06 (m, 1H), 4.61-4.71 (m, 1H), 4.22-4.29 (m, 1H), 3.77-3.85 (m, 3H), 3.37-3.53 (m, 1H), 1.22-1.31 (m, 7H), 0.99-1.12 (m, 3H). LCMS m/z = 327 [MH]$^+$. |
| 76 | (−) 4-(6-(hydroxymethyl)-2-(4-methoxy-3-propoxyphenyl)pyrimidin-4-yl)-1,2-oxaborolan-2-ol, enantiomer 1 | $^1$H NMR (DMSO-d$_6$, 400 MHz): δ 8.71 (s, 1H), 8.00 (dd, J = 2.0, 8.0 Hz, 1H), 7.96 (d, J = 2.0 Hz, 1H), 7.52 (s, 1H), 7.27-7.31 (m, 1H), 7.06 (d, J = 8.5 Hz, 1H), 5.60-5.66 (m, 1H), 4.59 (d, J = 6.0 Hz, 2H), 4.31 (dd, J = 7.0, 9.0 Hz, 1H), 3.96-4.04 (m, 2H), 3.83 (s, 3H), 3.57-3.65 (m, 1H), 1.75-1.82 (m, 2H), 1.25-1.35 (m, 1H), 1.12-1.21 (m, 1H), 0.96-1.07 (m, 3H). LCMS m/z = 359 [MH]$^+$. [α]$^{20}_D$ −10.0 (c = 0.1, EtOH). |
| 77 | 4-(3'-ethoxy-4'-methoxy-[1,1'-biphenyl]-3-yl)-1,2-oxaborolan-2-ol | $^1$H NMR (DMSO-d$_6$, 400 MHz): δ 8.65 (s, 1H), 7.50 (s, 1H), 7.45 (d, J = 7.6 Hz, 1H), 7.34 (t, J = 7.7 Hz, 1H), 7.21 (d, J = 7.6 Hz, 1H), 7.18 (s, 1H), 7.16 (d, J = 1.71 Hz, 1H), 7.02 (d, J = 8.1 Hz, 1H), 4.26 (t, J = 8.3 Hz, 1H), 4.10 (q, J = 6.9 Hz, 2H), 3.77-3.84 (m, 4H), 3.42-3.49 (m, 1H), 1.35 (t, J = 7.0 Hz, 3H), 1.28 (dd, J = 8.2, 16.3 Hz, 1H), 1.08 (dd, J = 10.0, 16.4 Hz, 1H). LCMS m/z = 313 [MH]$^+$. |
| 78 | 4-(5-(4-methoxy-3-((tetrahydrothiophen-3-yl)oxy)phenyl)pyridin-3-yl)-1,2-oxaborolan-2-ol | $^1$H NMR (DMSO-d$_6$, 400 MHz): δ 8.73 (s, 1H), 8.70 (d, J = 2.0 Hz, 1H), 8.43 (d, J = 2.0 Hz, 1H), 7.93 (t, J = 2.0 Hz, 1H), 7.36 (d, J = 2.0 Hz, 1H), 7.30-7.34 (m, 1H), 7.10 (d, J = 8.0 Hz, 1H), 5.30 (br s, 1H), 4.27 (t, J = 8.3 Hz, 1H), 3.86 (t, J = 9.0 Hz, 1H), 3.81 (s, 3H), 3.46-3.55 (m, 1H), 3.13 (dd, J = 4.8, 11.8 Hz, 1H), 2.85-3.00 (m, 3H), 2.27-2.34 (m, 1H), 1.90-2.00 (m, 1H), 1.31 (dd, J = 8.3, 16.3 Hz, 1H), 1.14 (dd, J = 10.3, 16.3 Hz, 1H). LCMS m/z = 372 [MH]$^+$. |

| Example No. | Structure and Name | Analytical Data |
|---|---|---|
| 79 | 4-(5-(4-methoxy-3-((tetrahydrothiophen-3-yl)oxy)phenyl)pyridin-3-yl)-1,2-oxaborolan-2-ol, diastereomer 1 | $^1$H NMR (DMSO-d$_6$, 400 MHz): δ 8.73 (s, 1H), 8.70 (d, J = 2.0 Hz, 1H), 8.43 (d, J = 2.0 Hz, 1H), 7.93 (t, J = 2.0 Hz, 1H), 7.36 (d, J = 2.0 Hz, 1H), 7.30-7.34 (m, 1H), 7.10 (d, J = 8.0 Hz, 1H), 5.30 (br s, 1H), 4.27 (t, J = 8.3 Hz, 1H), 3.86 (t, J = 9.0 Hz, 1H), 3.81 (s, 3H), 3.46-3.55 (m, 1H), 3.13 (dd, J = 4.8, 11.8 Hz, 1H), 2.85-3.00 (m, 3H), 2.27-2.34 (m, 1H), 1.90-2.00 (m, 1H), 1.31 (dd, J = 8.3, 16.3 Hz, 1H), 1.14 (dd, J = 10.3, 16.3 Hz, 1H). LCMS m/z = 372.3 [MH]$^+$. RT [Analytical SFC Method EA] = 3.30 min. |
| 80 | 4-(5-(4-methoxy-3-((tetrahydrothiophen-3-yl)oxy)phenyl)pyridin-3-yl)-1,2-oxaborolan-2-ol, diastereomer 2 | $^1$H NMR (DMSO-d$_6$, 400 MHz): δ 8.73 (s, 1H), 8.70 (d, J = 2.0 Hz, 1H), 8.43 (d, J = 2.0 Hz, 1H), 7.93 (t, J = 2.0 Hz, 1H), 7.36 (d, J = 2.0 Hz, 1H), 7.30-7.34 (m, 1H), 7.10 (d, J = 8.0 Hz, 1H), 5.30 (br s, 1H), 4.27 (t, J = 8.3 Hz, 1H), 3.86 (t, J = 9.0 Hz, 1H), 3.81 (s, 3H), 3.46-3.55 (m, 1H), 3.13 (dd, J = 4.8, 11.8 Hz, 1H), 2.85-3.00 (m, 3H), 2.27-2.34 (m, 1H), 1.90-2.00 (m, 1H), 1.31 (dd, J = 8.3, 16.3 Hz, 1H), 1.14 (dd, J = 10.3, 16.3 Hz, 1H). LCMS m/z = 372.1 [MH]$^+$. RT [Analytical SFC Method EA] = 4.18 min. |
| 81 | 4-(5-(2-fluoro-4-methoxy-3-propoxphenyl)pyridin-3-yl)-1,2-oxaborolan-2-ol | $^1$H NMR (DMSO-d$_6$, 400 MHz): δ 8.71 (s, 1H), 8.54 (t, J = 2.0 Hz, 1H), 8.48 (d, J = 2.0 Hz, 1H), 7.82 (d, J = 1.5 Hz, 1H), 7.26 (t, J = 8.7 Hz, 1H), 7.01 (dd, J = 1.5, 8.8 Hz, 1H), 4.24-4.32 (m, 1H), 3.97 (t, J = 6.6 Hz, 2H), 3.87 (s, 3H), 3.80-3.86 (m, 1H), 3.44-3.57 (m, 1H), 1.63-1.72 (m, 2H), 1.31 (dd, J = 8.2, 16.3 Hz, 1H), 1.10 (dd, J = 10.3, 16.1 Hz, 1H), 0.98 (t, J = 7.3 Hz, 3H). LCMS m/z = 346 [MH]$^+$. |
| 82 | 4-(5-(2-fluoro-4-methoxy-3-propoxphenyl)pyridin-3-yl)-1,2-oxaborolan-2-ol, enantiomer 2 | $^1$H NMR (DMSO-d$_6$, 400 MHz): δ 8.71 (s, 1H), 8.54 (d, J = 2.0 Hz, 1H), 8.48 (d, J = 2.0 Hz, 1H), 7.82 (d, J = 1.5 Hz, 1H), 7.26 (t, J = 8.7 Hz, 1H), 7.01 (dd, J = 1.5, 8.8 Hz, 1H), 4.24-4.32 (m, 1H), 3.97 (t, J = 6.6 Hz, 2H), 3.87 (s, 3H), 3.80-3.86 (m, 1H), 3.44-3.57 (m, 1H), 1.63-1.72 (m, 2H), 1.31 (dd, J = 8.2, 16.3 Hz, 1H), 1.10 (dd, J = 10.3, 16.1 Hz, 1H), 0.98 (t, J = 7.3 Hz, 3H). LCMS m/z = 372 [MH]$^+$. RT [Analytical SFC Method E] = 4.76 min. |

| Example No. | Structure and Name | Analytical Data |
|---|---|---|
| 83 | 4-(6-(1-hydroxyethyl)-2-(4-methoxy-3-propoxyphenyl)pyrimidin-4-yl)-1,2-oxaborolan-2-ol, diastereomer 1 | $^1$H NMR (DMSO-$d_6$, 400 MHz): δ 8.68 (s, 1H), 8.00 (dd, J = 2.0, 8.3 Hz, 1H), 7.97 (d, J = 2.0 Hz, 1H), 7.32 (s, 1H), 7.07 (d, J = 8.3 Hz, 1H), 5.57 (d, J = 4.9 Hz, 1H), 4.65-4.75 (m, 1H), 4.30 (dd, J = 7.3, 9.3 Hz, 1H), 3.96-4.03 (m, 3H), 3.83 (s, 3H), 3.61 (s, 1H), 1.71-1.83 (m, 2H), 1.43 (d, J = 6.4 Hz, 3H), 1.27 (dd, J = 1.5, 8.3 Hz, 1H), 1.11-1.20 (m, 1H), 1.01 (t, J = 7.6 Hz, 3H). LCMS m/z = 391 [MH + H$_2$O]$^+$. RT [Analytical SFC Method E] = 4.07 min. |
| 80 | 4-(5-(4-methoxy-3-propoxyphenyl)-4-methylpyridin-3-yl)-1,2-oxaborolan-2-ol | $^1$H NMR (DMSO-$d_6$, 400 MHz): δ 8.71 (s, 1H), 8.43 (s, 1H), 8.21 (s, 1H), 7.04 (d, J = 7.8 Hz, 1H), 6.90 (d, J = 2.0 Hz, 1H), 6.84 (dd, J = 2.0, 8.3 Hz, 1H), 4.26 (dd, J = 7.3, 8.8 Hz, 1H), 3.89-3.97 (m, 3H), 3.80 (s, 3H), 3.67 (t, J = 8.1 Hz, 1H), 2.21 (s, 3H), 1.68-1.77 (m, 2H), 1.33 (dd, J = 8.3, 16.1 Hz, 1H), 1.08 (dd, J = 8.6, 16.4 Hz, 1H), 0.97 (t, J = 7.3 Hz, 3H). LCMS m/z = 342 [MH]$^+$. |
| 85 | (+) 4-(5-(4-methoxy-3-propoxyphenyl)-4-methylpyridin-3-yl)-1,2-oxaborolan-2-ol, enantiomer 1 | $^1$H NMR (DMSO-$d_6$, 400 MHz): δ 8.71 (s, 1H), 8.43 (s, 1H), 8.21 (s, 1H), 7.04 (d, J = 7.8 Hz, 1H), 6.90 (d, J = 2.0 Hz, 1H), 6.84 (dd, J = 2.0, 8.3 Hz, 1H), 4.26 (dd, J = 7.3, 8.8 Hz, 1H), 3.89-3.97 (m, 3H), 3.80 (s, 3H), 3.67 (t, J = 8.1 Hz, 1H), 2.21 (s, 3H), 1.68-1.77 (m, 2H), 1.33 (dd, J = 8.3, 16.1 Hz, 1H), 1.08 (dd, J = 8.6, 16.4 Hz, 1H), 0.97 (t, J = 7.3 Hz, 3H). LCMS m/z = 342 [MH]$^+$. [α]$^{20}_D$ −14.7 (c = 0.1, EtOH). |
| 86 | 6-(6-(2-hydroxy-1,2-oxaborolan-4-yl)pyridin-2-yl)-3-methoxy-2-propoxybenzonitrile | $^1$H NMR (DMSO-$d_6$, 400 MHz): δ 8.58 (s, 1H), 7.85 (t, J = 7.7 Hz, 1H), 7.60 (d, J = 7.8 Hz, 1H), 7.56-7.52 (m, 1H), 7.44-7.49 (m, 1H), 7.32 (d, J = 7.6 Hz, 1H), 4.24-4.31 (m, 1H), 4.06-4.14 (m, 3H), 3.91 (s, 3H), 3.60-3.68 (m, 1H), 1.70-1.79 (m, 2H), 1.20-1.37 (m, 2H), 1.02 (t, J = 7.5 Hz, 3H). LCMS m/z = 353 [MH]$^+$. |
| 87 | 6-(6-(2-hydroxy-1,2-oxaborolan-4-yl)pyridin-2-yl)-3-methoxy-2-propoxybenzonitrile, enantiomer 2 | $^1$H NMR (DMSO-$d_6$, 400 MHz): δ 8.58 (s, 1H), 7.85 (t, J = 7.7 Hz, 1H), 7.60 (d, J = 7.8 Hz, 1H), 7.56-7.52 (m, 1H), 7.44-7.49 (m, 1H), 7.32 (d, J = 7.6 Hz, 1H), 4.24-4.31 (m, 1H), 4.06-4.14 (m, 3H), 3.91 (s, 3H), 3.60-3.68 (m, 1H), 1.70-1.79 (m, 2H), 1.20-1.37 (m, 2H), 1.02 (t, J = 7.5 Hz, 3H). LCMS m/z = 353.3 [MH]$^+$. RT [Analytical SFC Method M] = 5.79 min. |

| Example No. | Structure and Name | Analytical Data |
|---|---|---|
| 88 | 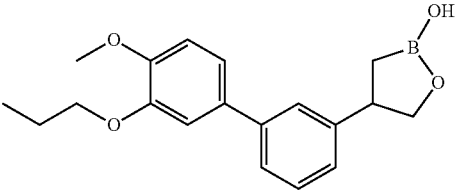 [SMILES: CCCOc1cc(-c2cccc(C3COB(O)C3)c2)ccc1OC]<br>4-(4'-methoxy-3'-propoxy-[1,1'-biphenyl]-3-yl)-1,2-oxaborolan-2-ol | 1H NMR (DMSO-$d_6$, 400 MHz): δ 8.66 (s, 1H), 7.44-7.49 (m, 2H), 7.35 (m, 1H), 7.16-7.22 (m, 3H), 7.02 (d, J = 8.0 Hz, 1H), 4.26 (t, J = 8.0 Hz, 1H), 4.01 (t, J = 6.8 Hz, 2H), 3.79-3.83 (m, 4H), 3.34-3.51 (m, 1H), 1.73-1.79 (m, 2H), 1.25-1.29 (m, 1H), 1.07-1.11 (m, 1H), 0.99 (t, J = 7.6 Hz, 3H). LCMS m/z = 327 [MH]$^+$. |
| 89 | 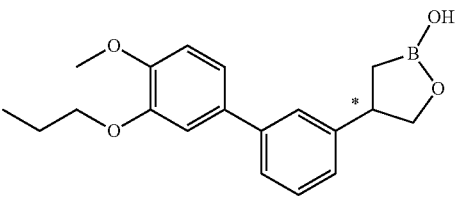 [SMILES: CCCOc1cc(-c2cccc(C3COB(O)C3)c2)ccc1OC]<br>4-(4'-methoxy-3'-propoxy-[1,1'-biphenyl]-3-yl)-1,2-oxaborolan-2-ol, enantiomer 1 | 1H NMR (DMSO-$d_6$, 400 MHz): δ 8.66 (s, 1H), 7.44-7.49 (m, 2H), 7.35 (m, 1H), 7.16-7.22 (m, 3H), 7.02 (d, J = 8.0 Hz, 1H), 4.26 (t, J = 8.0 Hz, 1H), 4.01 (t, J = 6.8 Hz, 2H), 3.79-3.83 (m, 4H), 3.34-3.51 (m, 1H), 1.73-1.79 (m, 2H), 1.25-1.29 (m, 1H), 1.07-1.11 (m, 1H), 0.99 (t, J = 7.6 Hz, 3H). LCMS m/z = 327 [MH]$^+$. RT [Analytical SFC Method N] = 3.76 min. |
| 90 | 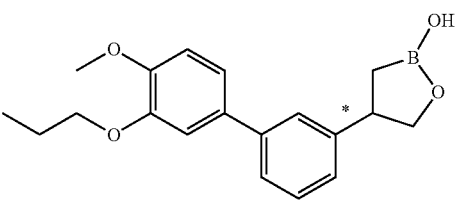 [SMILES: CCCOc1cc(-c2cccc(C3COB(O)C3)c2)ccc1OC]<br>4-(4'-methoxy-3'-propoxy-[1,1'-biphenyl]-3-yl)-1,2-oxaborolan-2-ol, enantiomer 2 | 1H NMR (DMSO-$d_6$, 400 MHz): δ 8.66 (s, 1H), 7.44-7.49 (m, 2H), 7.35 (m, 1H), 7.16-7.22 (m, 3H), 7.02 (d, J = 8.0 Hz, 1H), 4.26 (t, J = 8.0 Hz, 1H), 4.01 (t, J = 6.8 Hz, 2H), 3.79-3.83 (m, 4H), 3.34-3.51 (m, 1H), 1.73-1.79 (m, 2H), 1.25-1.29 (m, 1H), 1.07-1.11 (m, 1H), 0.99 (t, J = 7.6 Hz, 3H). LCMS m/z = 327 [MH]$^+$. RT [Analytical SFC Method N] = 3.97 min. |
| 91 | 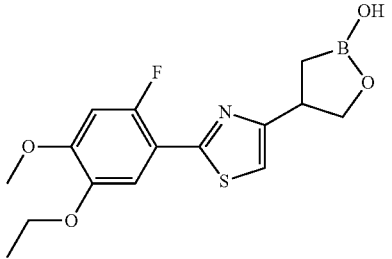 [SMILES: CCOc1cc(-c2nc(C3COB(O)C3)cs2)c(F)cc1OC]<br>4-(2-(5-ethoxy-2-fluoro-4-methoxyphenyl)thiazol-4-yl)-1,2-oxaborolan-2-ol | $^1$H NMR (DMSO-$d_6$, 400 MHz): δ 8.66 (s, 1H), 7.62 (d, J = 7.0 Hz, 1H), 7.41 (s, 1H), 7.05-7.10 (m, 1H), 4.26 (dd, J = 7.5, 8.5 Hz, 1H), 4.05 (q, J = 6.9 Hz, 2H), 3.93 (dd, J = 7.5, 9.0 Hz, 1H), 3.83 (s, 3H), 3.57-3.66 (m, 1H), 1.34 (t, J = 7.0 Hz, 3H), 1.25-1.32 (m, 1H), 1.12-1.20 (m, 1H). LCMS m/z = 338 [MH]$^+$. |
| 92 | 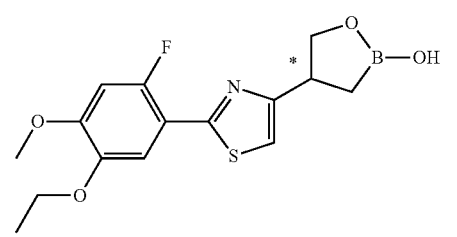 [SMILES: CCOc1cc(-c2nc(C3COB(O)C3)cs2)c(F)cc1OC]<br>(−) 4-(2-(5-ethoxy-2-fluoro-4-methoxyphenyl)thiazol-4-yl)-1,2-oxaborolan-2-ol enantiomer 2 | $^1$H NMR (DMSO-$d_6$, 400 MHz): δ8.66 (s, 1H), 7.62 (d, J = 7.0 Hz, 1H), 7.41 (s, 1H), 7.05-7.10 (m, 1H), 4.26 (dd, J = 7.5, 8.5 Hz, 1H), 4.05 (q, J = 6.9 Hz, 2H), 3.93 (dd, J = 7.5, 9.0 Hz, 1H), 3.83 (s, 3H), 3.57-3.66 (m, 1H), 1.34 (t, J = 7.0 Hz, 3H), 1.25-1.32 (m, 1H), 1.12-1.20 (m, 1H). LCMS m/z = 338 [MH]$^+$. RT [Analytical SFC Method O] = 4.13 min. $[α]^{20}_D$ −37.9 (c = 0.1, EtOH). |

| Example No. | Structure and Name | Analytical Data |
|---|---|---|
| 93 | 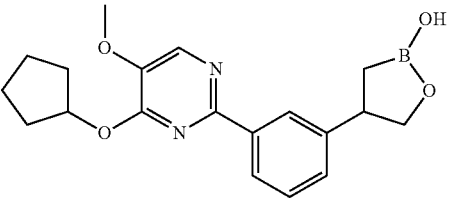 [SMILES: COc1cnc(-c2cccc(C3COB(O)C3)c2)nc1OC1CCCC1]<br>4-(3-(4-(cyclopentyloxy)-5-methoxypyrimidin-2-yl)phenyl)-1,2-oxaborolan-2-ol | $^1$H NMR (DMSO-d$_6$, 400 MHz): δ 8.67 (br s, 1H), 8.30 (s, 1H), 8.18 (s, 1H), 8.10-8.15 (m, 1H), 7.39-7.45 (m, 1H), 7.34-7.38 (m, 1H), 5.56-5.63 (m, 1H), 4.26-4.32 (m, 1H), 3.89 (s, 3H), 3.80 (t, J = 8.6 Hz, 1H), 3.48-3.55 (m, 1H), 2.04-2.15 (m, 2H), 1.60-1.85 (m, 6H), 1.33 (dd, J = 8.3, 16.1 Hz, 1H), 0.99-1.08 (m, 1H). LCMS m/z = 355 [MH]$^+$. |
| 94 | 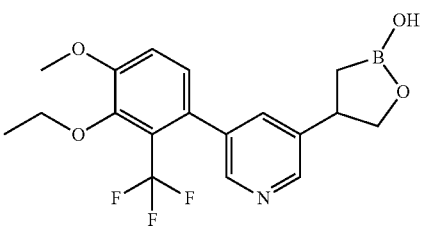 [SMILES: CCOc1c(OC)ccc(-c2cncc(C3COB(O)C3)c2)c1C(F)(F)F]<br>4-(5-(3-ethoxy-4-methoxy-2-(trifluoromethyl)phenyl)pyridin-3-yl)-1,2-oxaborolan-2-ol | $^1$H NMR (DMSO-d$_6$, 400 MHz): δ 8.70 (d, J = 2.5 Hz, 1H), 8.48 (d, J = 2.0 Hz, 1H), 8.26-8.32 (m, 1H), 7.58 (d, J = 2.0 Hz, 1H), 7.37-7.43 (m, 1H), 7.05 (d, J = 9.0 Hz, 1H), 4.19-4.34 (m, 1H), 4.09 (td, J = 3.1, 9.9 Hz, 2H), 3.87-3.95 (m, 3H), 3.72-3.83 (m, 1H), 3.46-3.55 (m, 1H), 1.26-1.37 (m, 4H), 1.00-1.13 (m, 1H). LCMS m/z = 382 [MH]$^+$. |
| 95 | 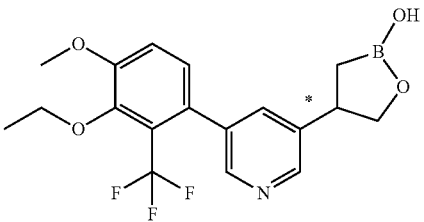 [SMILES: CCOc1c(OC)ccc(-c2cncc(C3COB(O)C3)c2)c1C(F)(F)F]<br>4-(5-(3-ethoxy-4-methoxy-2-(trifluoromethyl)phenyl)pyridin-3-yl)-1,2-oxaborolan-2-ol, enantiomer 1 | $^1$H NMR (DMSO-d$_6$, 400 MHz): δ 8.70 (d, J = 2.5 Hz, 1H), 8.48 (d, J = 2.0 Hz, 1H), 8.26-8.32 (m, 1H), 7.58 (d, J = 2.0 Hz, 1H), 7.37-7.43 (m, 1H), 7.05 (d, J = 9.0 Hz, 1H), 4.19-4.34 (m, 1H), 4.09 (td, J = 3.1, 9.9 Hz, 2H), 3.87-3.95 (m, 3H), 3.72-3.83 (m, 1H), 3.46-3.55 (m, 1H), 1.26-1.37 (m, 4H), 1.00-1.13 (m, 1H). LCMS m/z = 382 [MH]$^+$. RT [Analytical SFC Method E] = 3.14 min. |
| 96 | 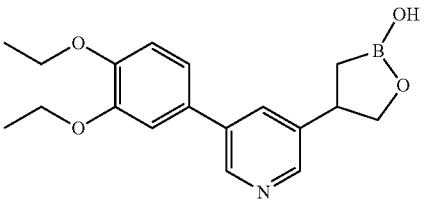 [SMILES: CCOc1ccc(-c2cncc(C3COB(O)C3)c2)cc1OCC]<br>4-(5-(3,4-diethoxyphenyl)pyridin-3-yl)-1,2-oxaborolan-2-ol | $^1$H NMR (DMSO-d$_6$, 400 MHz): δ 8.68-8.75 (m, 2H), 8.42 (d, J = 1.5 Hz, 1H), 7.93 (s, 1H), 7.27 (d, J = 2.0 Hz, 1H), 7.23 (dd, J = 1.8, 8.3 Hz, 1H), 7.04 (d, J = 8.5 Hz, 1H), 4.27 (t, J = 8.3 Hz, 1H), 4.13 (q, J = 6.9 Hz, 2H), 4.06 (q, J = 7.0 Hz, 2H), 3.86 (t, J = 8.8 Hz, 1H), 3.45-3.54 (m, 1H), 1.26-1.39 (m, 7H), 1.14 (dd, J = 10.5, 16.1 Hz, 1H). LCMS m/z = 328 [MH]$^+$. |
| 97 | 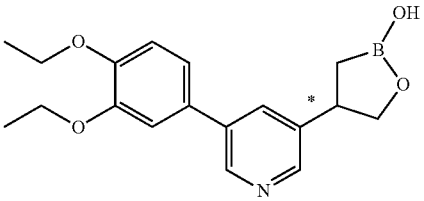 [SMILES: CCOc1ccc(-c2cncc(C3COB(O)C3)c2)cc1OCC]<br>4-(5-(3,4-diethoxyphenyl)pyridin-3-yl)-1,2-oxaborolan-2-ol, enantiomer 2 | $^1$H NMR (DMSO-d$_6$, 400 MHz): δ 8.68-8.75 (m, 2H), 8.42 (d, J = 1.5 Hz, 1H), 7.93 (s, 1H), 7.27 (d, J = 2.0 Hz, 1H), 7.23 (dd, J = 1.8, 8.3 Hz, 1H), 7.04 (d, J = 8.5 Hz, 1H), 4.27 (t, J = 8.3 Hz, 1H), 4.13 (q, J = 6.9 Hz, 2H), 4.06 (q, J = 7.0 Hz, 2H), 3.86 (t, J = 8.8 Hz, 1H), 3.45-3.54 (m, 1H), 1.26-1.39 (m, 7H), 1.14 (dd, J = 10.5, 16.1 Hz, 1H). LCMS m/z = 345 [MH + H$_2$O]$^+$. RT [Analytical SFC Method D] = 5.73 min. |

-continued

| Example No. | Structure and Name | Analytical Data |
|---|---|---|
| 98 | 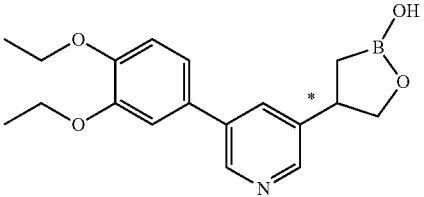 [SMILES: CCOc1ccc(-c2cncc(C3COB(O)C3)c2)cc1OCC]<br>4-(5-(3,4-diethoxyphenyl)pyridin-3-yl)-1,2-oxaborolan-2-ol, enantiomer 1 | ¹H NMR (DMSO-d₆, 400 MHz): δ 8.68-8.75 (m, 2H), 8.42 (d, J = 1.5 Hz, 1H), 7.93 (s, 1H), 7.27 (d, J = 2.0 Hz, 1H), 7.23 (dd, J = 1.8, 8.3 Hz, 1H), 7.04 (d, J = 8.5 Hz, 1H), 4.27 (t, J = 8.3 Hz, 1H), 4.13 (q, J = 6.9 Hz, 2H), 4.06 (q, J = 7.0 Hz, 2H), 3.86 (t, J = 8.8 Hz, 1H), 3.45-3.54 (m, 1H), 1.26-1.39 (m, 7H), 1.14 (dd, J = 10.5, 16.1 Hz, 1H). LCMS m/z = 328 [MH]⁺. RT [Analytical SFC Method D] = 5.37 min. |
| 99 | 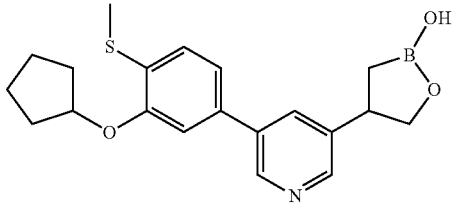 [SMILES: CSc1ccc(-c2cncc(C3COB(O)C3)c2)cc1OC1CCCC1]<br>4-(5-(3-(cyclopentyloxy)-4-(methylthio)phenyl)pyridin-3-yl)-1,2-oxaborolan-2-ol | ¹H NMR (DMSO-d₆, 400 MHz): δ 8.73 (s, 2H), 8.44-8.48 (m, 1H), 7.96 (s, 1H), 7.28-7.33 (m, 1H), 7.26 (s, 1H), 7.19-7.24 (m, 1H), 5.10 (t, J = 5.5 Hz, 1H), 4.28 (t, J = 8.3 Hz, 1H), 3.83-3.91 (m, 1H), 3.49-3.57 (m, 1H), 2.39 (s, 3H), 1.87-1.96 (m, 2H), 1.75 (d, J = 4.5 Hz, 4H), 1.56-1.66 (m, 2H), 1.32 (dd, J = 8.3, 16.3 Hz, 1H), 1.10-1.19 (m, 1H). LCMS m/z = 370 [MH]⁺. |
| 100 | 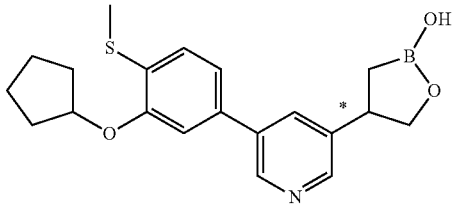<br>4-(5-(3-(cyclopentyloxy)-4-(methylthio)phenyl)pyridin-3-yl)-1,2-oxaborolan-2-ol enantiomer 1 | 1H NMR (DMSO-d₆, 400 MHz): δ 8.73 (s, 2H), 8.44-8.48 (m, 1H), 7.96 (s, 1H), 7.28-7.33 (m, 1H), 7.26 (s, 1H), 7.19-7.24 (m, 1H), 5.10 (t, J = 5.5 Hz, 1H), 4.28 (t, J = 8.3 Hz, 1H), 3.83-3.91 (m, 1H), 3.49-3.57 (m, 1H), 2.39 (s, 3H), 1.87-1.96 (m, 2H), 1.75 (d, J = 4.5 Hz, 4H), 1.56-1.66 (m, 2H), 1.32 (dd, J = 8.3, 16.3 Hz, 1H), 1.10-1.19 (m, 1H). LCMS m/z = 388 [MH + H₂O]⁺. RT [Analytical SFC Method P] = 3.83 min. |
| 101 | 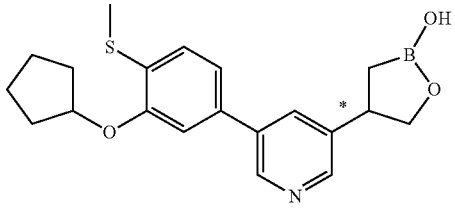<br>4-(5-(3-(cyclopentyloxy)-4-(methylthio)phenyl)pyridin-3-yl)-1,2-oxaborolan-2-ol, enantiomer 2 | ¹H NMR (DMSO-d₆, 400 MHz): δ 8.73 (s, 2H), 8.44-8.48 (m, 1H), 7.96 (s, 1H), 7.28-7.33 (m, 1H), 7.26 (s, 1H), 7.19-7.24 (m, 1H), 5.10 (t, J = 5.5 Hz, 1H), 4.28 (t, J = 8.3 Hz, 1H), 3.83-3.91 (m, 1H), 3.49-3.57 (m, 1H), 2.39 (s, 3H), 1.87-1.96 (m, 2H), 1.75 (d, J = 4.5 Hz, 4H), 1.56-1.66 (m, 2H), 1.32 (dd, J = 8.3, 16.3 Hz, 1H), 1.10-1.19 (m, 1H). LCMS m/z = 388 [MH + H₂O]⁺. RT [Analytical SFC Method P] = 4.17 min. |
| 102 | 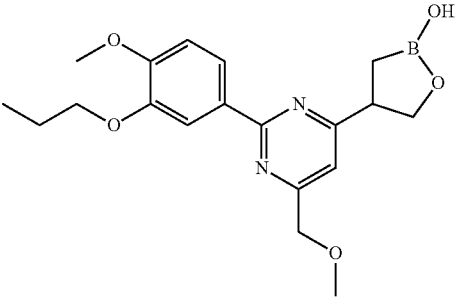<br>4-(2-(4-methoxy-3-propoxyphenyl)-6-(methoxymethyl)pyrimidin-4-yl)-1,2-oxaborolan-2-ol | ¹H NMR (DMSO-d₆, 400 MHz): δ 8.69 (br s, 1H), 7.99 (dd, J = 1.9, 8.4 Hz, 1H), 7.95 (d, J = 1.8 Hz, 1H), 7.22 (s, 1H), 7.07 (d, J = 8.8 Hz, 1H), 4.54 (s, 2H), 4.30 (dd, J = 7.5, 8.8 Hz, 1H), 3.96-4.03 (m, 3H), 3.83 (s, 3H), 3.58-3.65 (m, 1H), 3.43 (s, 3H), 1.73-1.81 (m, 2H), 1.24-1.34 (m, 1H), 1.12-1.21 (m, 1H), 0.96-1.06 (m, 3H). LCMS m/z = 391 [MH + H₂O]⁺. |

| Example No. | Structure and Name | Analytical Data |
|---|---|---|
| 103 | 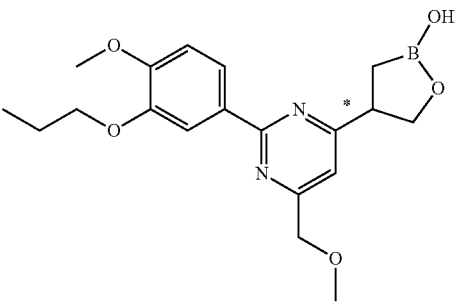<br>(−) 4-(2-(4-methoxy-3-propoxyphenyl)-6-(methoxymethyl)pyrimidin-4-yl)-1,2-oxaborolan-2-ol, enantiomer 2 | $^1$H NMR (DMSO-$d_6$, 400 MHz): δ 8.69 (br s, 1H), 7.99 (dd, J = 1.9, 8.4 Hz, 1H), 7.95 (d, J = 1.8 Hz, 1H), 7.22 (s, 1H), 7.07 (d, J = 8.8 Hz, 1H), 4.54 (s, 2H), 4.30 (dd, J = 7.5, 8.8 Hz, 1H), 3.96-4.03 (m, 3H), 3.83 (s, 3H), 3.58-3.65 (m, 1H), 3.43 (s, 3H), 1.73-1.81 (m, 2H), 1.24-1.34 (m, 1H), 1.12-1.21 (m, 1H), 0.96-1.06 (m, 3H). LCMS m/z = 391 [MH + H$_2$O]$^+$. RT [Analytical SFC Method Q] = 3.25 min. [α]$^{20}_D$ −38.3 (c = 0.1, EtOH). |
| 104 | 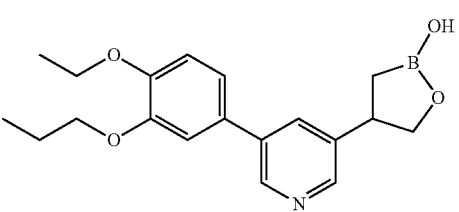 [SMILES: CCCOc1cc(-c2cncc(C3COB(O)C3)c2)ccc1OCC]<br>4-(5-(4-ethoxy-3-propoxyphenyl)pyridin-3-yl)-1,2-oxaborolan-2-ol | $^1$H NMR (DMSO-$d_6$, 400 MHz): δ 8.71 (s, 1H), 8.70 (d, J = 1.5 Hz, 1H), 8.42 (d, J = 1.5 Hz, 1H), 7.93 (t, J = 2.0 Hz, 1H), 7.28 (d, J = 2.0 Hz, 1H), 7.23 (dd, J = 2.0, 8.0 Hz, 1H), 7.03-7.07 (m, 1H), 4.27 (t, J = 8.3 Hz, 1H), 4.00-4.11 (m, 4H), 3.86 (t, J = 9.0 Hz, 1H), 3.45-3.55 (m, 1H), 1.70-1.80 (m, 3H), 1.27-1.37 (m, 3H), 1.10-1.19 (m, 1H), 1.00 (t, J = 7.5 Hz, 3H). LCMS m/z = 342 [MH]$^+$. |
| 105 | 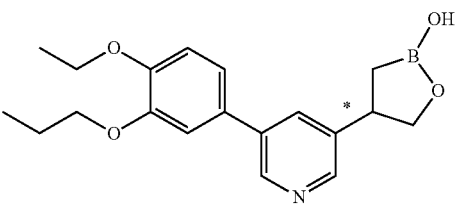 [SMILES: CCCOc1cc(-c2cncc(C3COB(O)C3)c2)ccc1OCC]<br>4-(5-(4-ethoxy-3-propoxyphenyl)pyridin-3-yl)-1,2-oxaborolan-2-ol, enantiomer 2 | $^1$H NMR (DMSO-$d_6$, 400 MHz): δ 8.71 (s, 1H), 8.70 (d, J = 1.5 Hz, 1H), 8.42 (d, J = 1.5 Hz, 1H), 7.93 (t, J = 2.0 Hz, 1H), 7.28 (d, J = 2.0 Hz, 1H), 7.23 (dd, J = 2.0, 8.0 Hz, 1H), 7.03-7.07 (m, 1H), 4.27 (t, J = 8.3 Hz, 1H), 4.00-4.11 (m, 4H), 3.86 (t, J = 9.0 Hz, 1H), 3.45-3.55 (m, 1H), 1.70-1.80 (m, 3H), 1.27-1.37 (m, 3H), 1.10-1.19 (m, 1H), 1.00 (t, J = 7.5 Hz, 3H). LCMS m/z = 342 [MH]$^+$. RT [Analytical SFC Method R] = 3.48 min. |
| 106 | 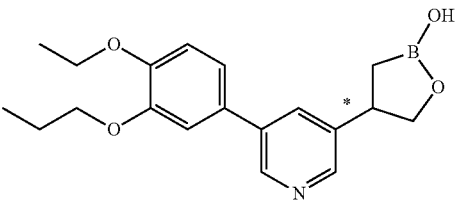 [SMILES: CCCOc1cc(-c2cncc(C3COB(O)C3)c2)ccc1OCC]<br>4-(5-(4-ethoxy-3-propoxyphenyl)pyridin-3-yl)-1,2-oxaborolan-2-ol, enantiomer 1 | $^1$H NMR (DMSO-$d_6$, 400 MHz): δ 8.71 (s, 1H), 8.70 (d, J = 1.5 Hz, 1H), 8.42 (d, J = 1.5 Hz, 1H), 7.93 (t, J = 2.0 Hz, 1H), 7.28 (d, J = 2.0 Hz, 1H), 7.23 (dd, J = 2.0, 8.0 Hz, 1H), 7.03-7.07 (m, 1H), 4.27 (t, J = 8.3 Hz, 1H), 4.00-4.11 (m, 4H), 3.86 (t, J = 9.0 Hz, 1H), 3.45-3.55 (m, 1H), 1.70-1.80 (m, 3H), 1.27-1.37 (m, 3H), 1.10-1.19 (m, 1H), 1.00 (t, J = 7.5 Hz, 3H). LCMS m/z = 342 [MH]$^+$. RT [Analytical SFC Method R] = 2.25 min. |

| Example No. | Structure and Name | Analytical Data |
|---|---|---|
| 107 | 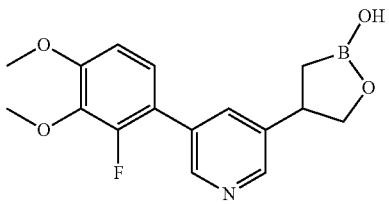 [SMILES: COc1ccc(-c2cncc(C3COB(O)C3)c2)c(F)c1OC]<br>4-(5-(2-fluoro-3,4-dimethoxyphenyl)pyridin-3-yl)-1,2-oxaborolan-2-ol | $^1$H NMR (DMSO-$d_6$, 400 MHz): δ 8.72 (s, 1H), 8.56 (dd, J = 2.0, 8.8 Hz, 1H), 8.48 (d, J = 2.0 Hz, 1H), 7.82 (s, 1H), 7.25-7.29 (m, 1H), 7.02 (d, J = 8.8 Hz, 1H), 4.28 (t, J = 8.4 Hz, 1H), 3.81-3.87 (m, 7H), 3.41-3.55 (m, 1H), 1.29-1.35 (m, 1H), 1.06-1.13 (m, 1H). LCMS m/z = 318 [MH]$^+$. |
| 108 | 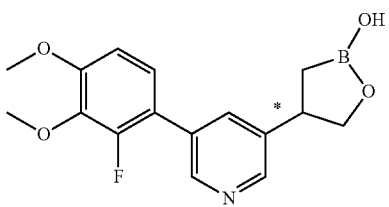<br>4-(5-(2-fluoro-3,4-dimethoxyphenyl)pyridin-3-yl)-1,2-oxaborolan-2-ol, enantiomer 1 | LCMS m/z = 332 [MH + H$_2$O]$^+$. RT [Analytical SFC Method S] = 5.28 min. |
| 109 | 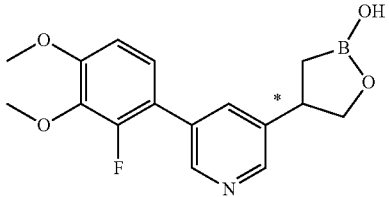 [SMILES: COc1ccc(-c2cncc(C3COB(O)C3)c2)c(F)c1OC]<br>4-(5-(2-fluoro-3,4-dimethoxyphenyl)pyridin-3-yl)-1,2-oxaborolan-2-ol, enantiomer 2 | LCMS m/z = 318 [MH]$^+$. RT [Analytical SFC Method S] = 5.35 min. |
| 110 | 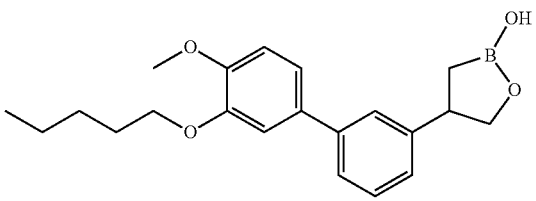 [SMILES: CCCCCOc1cc(-c2cccc(C3COB(O)C3)c2)ccc1OC]<br>4-(4'-methoxy-3'-(pentyloxy)-[1,1'-biphenyl]-3-yl)-1,2-oxaborolan-2-ol | LCMS m/z = 355 [MH]$^+$. |
| 111 | 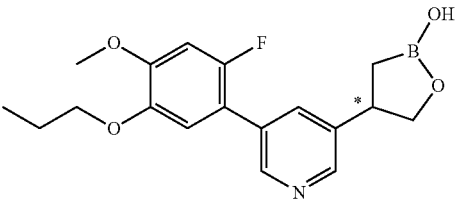 [SMILES: CCCOc1cc(-c2cncc(C3COB(O)C3)c2)c(F)cc1OC]<br>(−)-4-(5-(2-fluoro-4-methoxy-5-propoxyphenyl)pyridin-3-yl)-1,2-oxaborolan-2-ol, enantiomer 1 | $^1$H NMR (DMSO-$d_6$, 400 MHz): δ 8.89 (s, 1H), 8.74 (s, 1H), 8.49 (d, J = 2.0 Hz, 1H), 8.09 (s, 1H), 7.47-7.53 (m, 1H), 4.27-4.36 (m, 3H), 3.87 (s, 3H), 3.82 (t, J = 8.7 Hz, 1H), 3.50-3.56 (m, 1H), 1.75-1.80 (m, 2H), 1.34 (dd, J = 8.2, 16.3 Hz, 1H), 1.01-1.12 (m, 1H), 0.98 (t, J = 7.3 Hz, 3H). LCMS m/z = 346 [MH]$^+$. [α]$^{20}_D$ −17.7 (c = 0.15, EtOH). |

| Example No. | Structure and Name | Analytical Data |
|---|---|---|
| 112 | 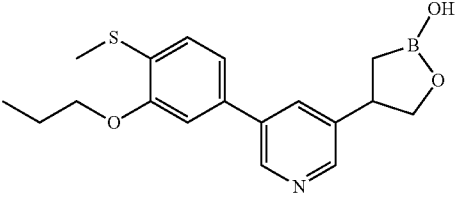 [SMILES: CCCOc1cc(-c2cncc(C3COB(O)C3)c2)ccc1SC]<br>4-(5-(4-(methylthio)-3-propoxyphenyl)pyridin-3-yl)-1,2-oxaborolan-2-ol | $^1$H NMR (DMSO-$d_6$, 400 MHz): δ 8.74 (d, J = 2.5 Hz, 1H), 8.73 (s, 1H), 8.46 (d, J = 2.0 Hz, 1H), 7.98 (t, J = 2.0 Hz, 1H), 7.30-7.34 (m, 1H), 7.26 (d, J = 1.5 Hz, 1H), 7.22 (d, J = 8.0 Hz, 1H), 4.28 (t, J = 8.3 Hz, 1H), 4.11 (t, J = 6.3 Hz, 2H), 3.87 (t, J = 9.0 Hz, 1H), 3.46-3.57 (m, 1H), 2.41 (s, 3H), 1.71-1.82 (m, 2H), 1.27-1.36 (m, 1H), 1.11-1.20 (m, 1H), 1.03 (t, J = 7.5 Hz, 3H). LCMS m/z = 344 [MH]$^+$. |
| 113 | 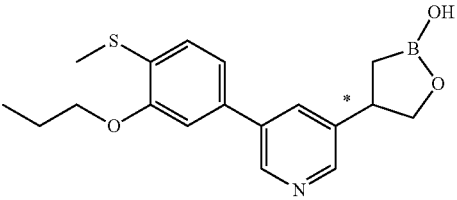<br>4-(5-(4-(methylthio)-3-propoxyphenyl)pyridin-3-yl)-1,2-oxaborolan-2-ol, enantiomer 1 | $^1$H NMR (DMSO-$d_6$, 400 MHz): δ 8.74 (d, J = 2.5 Hz, 1H), 8.73 (s, 1H), 8.46 (d, J = 2.0 Hz, 1H), 7.98 (t, J = 2.0 Hz, 1H), 7.30-7.34 (m, 1H), 7.26 (d, J = 1.5 Hz, 1H), 7.22 (d, J = 8.0 Hz, 1H), 4.28 (t, J = 8.3 Hz, 1H), 4.11 (t, J = 6.3 Hz, 2H), 3.87 (t, J = 9.0 Hz, 1H), 3.46-3.57 (m, 1H), 2.41 (s, 3H), 1.71-1.82 (m, 2H), 1.27-1.36 (m, 1H), 1.11-1.20 (m, 1H), 1.03 (t, J = 7.5 Hz, 3H). LCMS m/z = 343 [MH]$^+$. RT = 5.23 min. |
| 114 | 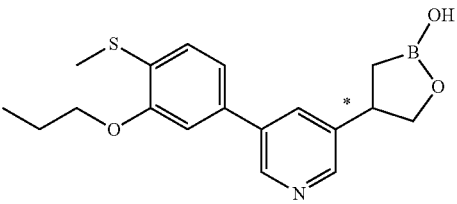 [SMILES: CCCOc1cc(-c2cncc(C3COB(O)C3)c2)ccc1SC]<br>4-(5-(4-(methylthio)-3-propoxyphenyl)pyridin-3-yl)-1,2-oxaborolan-2-ol, enantiomer 2 | $^1$H NMR (DMSO-$d_6$, 400 MHz): δ 8.74 (d, J = 2.5 Hz, 1H), 8.73 (s, 1H), 8.46 (d, J = 2.0 Hz, 1H), 7.98 (t, J = 2.0 Hz, 1H), 7.30-7.34 (m, 1H), 7.26 (d, J = 1.5 Hz, 1H), 7.22 (d, J = 8.0 Hz, 1H), 4.28 (t, J = 8.3 Hz, 1H), 4.11 (t, J = 6.3 Hz, 2H), 3.87 (t, J = 9.0 Hz, 1H), 3.46-3.57 (m, 1H), 2.41 (s, 3H), 1.71-1.82 (m, 2H), 1.27-1.36 (m, 1H), 1.11-1.20 (m, 1H), 1.03 (t, J = 7.5 Hz, 3H). LCMS m/z = 343 [MH]$^+$. RT = 5.63 min. |
| 115 | 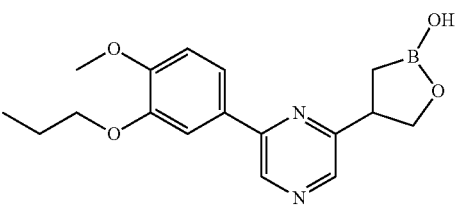 [SMILES: CCCOc1cc(-c2cncc(C3COB(O)C3)n2)ccc1OC]<br>4-(6-(4-methoxy-3-propoxyphenyl)pyrazin-2-yl)-1,2-oxaborolan-2-ol | $^1$H NMR (DMSO-$d_6$, 400 MHz): δ 9.06 (s, 1H), 8.67 (s, 1H), 8.44 (s, 1H), 7.73 (br s, 2H), 7.08 (d, J = 8.8 Hz, 1H), 4.30 (t, J = 8.2 Hz, 1H), 3.94-4.06 (m, 3H), 3.83 (s, 3H), 3.61-3.74 (m, 1H), 1.71-1.83 (m, 2H), 1.26-1.36 (m, 1H), 1.14-1.22 (m, 1H), 1.00 (t, J = 7.3 Hz, 3H). LCMS m/z = 329 [MH]$^+$. |
| 116 | 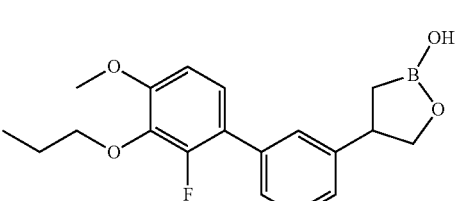<br>4-(2'-fluoro-4'-methoxy-3'-propoxy-[1,1'-biphenyl]-3-yl)-1,2-oxaborolan-2-ol | $^1$H NMR (DMSO-$d_6$, 400 MHz): δ 8.65 (s, 1H), 7.36-7.40 (m, 2H), 7.26-7.32 (m, 2H), 7.16 (t, J = 8.4 Hz, 1H), 6.97 (d, J = 8.8 Hz, 1H), 4.25 (t, J = 8.0 Hz, 1H), 3.96 (t, J = 4.2 Hz, 2H), 3.86 (s, 3H), 3.79 (t, J = 8.8 Hz, 1H), 3.34-3.49 (m, 1H), 1.65-1.71 (m, 2H), 1.26-1.28 (m, 1H), 1.02-1.08 (m, 1H), 0.98 (t, J = 8.0 Hz, 3H). LCMS m/z = 343 [MH]$^-$. |

| Example No. | Structure and Name | Analytical Data |
|---|---|---|
| 117 | 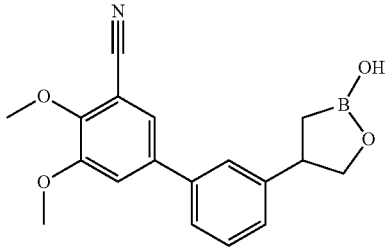 [SMILES: COc1cc(-c2cccc(C3COB(O)C3)c2)cc(C#N)c1OC]<br>3'-(2-hydroxy-1,2-oxaborolan-4-yl)-4,5-dimethoxy-[1,1'-biphenyl]-3-carbonitrile | $^1$H NMR (DMSO-$d_6$, 400 MHz): δ 7.47 (d, J = 8.8 Hz, 1H), 7.44 (s, 1H), 7.41 (d, J = 7.2 Hz, 1H), 7.32-7.37 (m, 2H), 7.29 (d, J = 8.6 Hz, 1H), 4.23-4.29 (m, 1H), 3.94 (s, 3H), 3.91 (s, 3H), 3.81 (t, J = 8.8 Hz, 1H), 1.29 (dd, J = 8.4, 16.2 Hz, 1H), 1.08 (dd, J = 10.0, 16.2 Hz, 1H). LCMS m/z = 324 [MH]$^+$. |
| 118 | 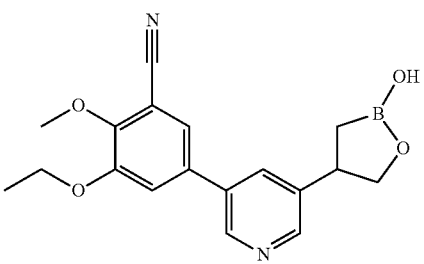 [SMILES: CCOc1cc(-c2cncc(C3COB(O)C3)c2)cc(C#N)c1OC]<br>3-ethoxy-5-(5-(2-hydroxy-1,2-oxaborolan-4-yl)pyridin-3-yl)-2-methoxybenzonitrile | $^1$H NMR (DMSO-$d_6$, 400 MHz): δ 7.47 (d, J = 8.8 Hz, 1H), 7.44 (s, 1H), 7.41 (d, J = 7.2 Hz, 1H), 7.32-7.37 (m, 2H), 7.29 (d, J = 8.6 Hz, 1H), 4.23-4.29 (m, 1H), 3.94 (s, 3H), 3.91 (s, 3H), 3.81 (t, J = 8.8 Hz, 1H), 1.29 (dd, J = 8.4, 16.2 Hz, 1H), 1.08 (dd, J = 10.0, 16.2 Hz, 1H). LCMS m/z = 339 [MH]$^+$. |
| 119 | 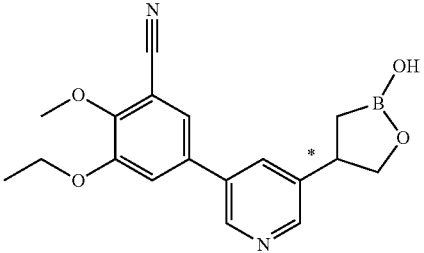 [SMILES: CCOc1cc(-c2cncc(C3COB(O)C3)c2)cc(C#N)c1OC]<br>3-ethoxy-5-(5-(2-hydroxy-1,2-oxaborolan-4-yl)pyridin-3-yl)-2-methoxybenzonitrile, enantiomer 1 | $^1$H NMR (DMSO-$d_6$, 400 MHz): δ 7.47 (d, J = 8.8 Hz, 1H), 7.44 (s, 1H), 7.41 (d, J = 7.2 Hz, 1H), 7.32-7.37 (m, 2H), 7.29 (d, J = 8.6 Hz, 1H), 4.23-4.29 (m, 1H), 3.94 (s, 3H), 3.91 (s, 3H), 3.81 (t, J = 8.8 Hz, 1H), 1.29 (dd, J = 8.4, 16.2 Hz, 1H), 1.08 (dd, J = 10.0, 16.2 Hz, 1H). LCMS m/z = 339.1 [MH]$^+$. RT [Analytical SFC Method T] = 4.71 min. |
| 120 | 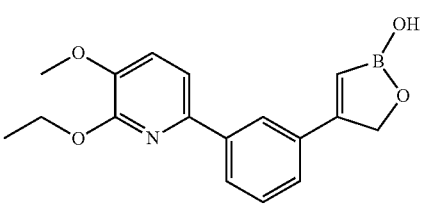<br>4-(3-(6-ethoxy-5-methoxypyridin-2-yl)phenyl)-1,2-oxaborol-2(5H)-ol | $^1$H NMR (DMSO-$d_6$, 400 MHz): δ 8.68 (s, 1H), 8.13 (s, 1H), 8.02 (d, J = 7.6 Hz, 1H), 7.60 (d, J = 8.4 Hz, 1H), 7.54 (d, J = 7.6 Hz, 1H), 7.48 (t, J = 7.6 Hz, 1H), 7.35 (d, J = 8.0 Hz, 1H), 6.27 (s, 1H), 4.97 (s, 2H), 4.47 (q, J = 7.2 Hz, 2H), 3.83 (s, 3H), 1.39 (t, J = 6.8 Hz, 3H). LCMS m/z = 312 [MH]$^+$. |
| 121 | 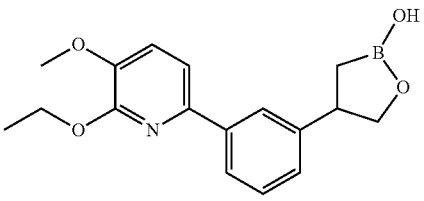 [SMILES: CCOc1nc(-c2cccc(C3COB(O)C3)c2)ccc1OC]<br>4-(3-(6-ethoxy-5-methoxypyridin-2-yl)phenyl)-1,2-oxaborolan-2-ol | $^1$H NMR (DMSO-$d_6$, 400 MHz): δ 8.65 (s, 1H), 7.88 (s, 1H), 7.83 (d, J = 7.6 Hz, 1H), 7.49 (d, J = 8.0 Hz, 1H), 7.32-7.36 (m, 2H), 7.24 (d, J = 7.2 Hz, 1H), 4.44 (q, J = 7.2 Hz, 2H), 4.27 (t, J = 8.0 Hz, 1H), 3.82 (m, 4H), 3.43-3.51 (m, 1H) 1.38 (t, J = 6.8 Hz, 3H), 1.30 (q, J = 8.0 Hz, 1H), 1.03-1.10 (m, 1H). LCMS m/z = 314 [MH]$^+$. |

| Example No. | Structure and Name | Analytical Data |
|---|---|---|
| 122 | 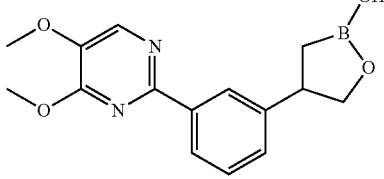<br>4-(3-(4,5-dimethoxypyrimidin-2-yl)phenyl)-1,2-oxaborolan-2-ol | $^1$H NMR (DMSO-$d_6$, 400 MHz): δ 8.67 (br s, 1H), 8.33 (s, 1H), 8.12-8.27 (m, 2H), 7.31-7.50 (m, 2H), 4.24-4.34 (m, 1H), 4.06 (s, 3H), 3.90 (s, 3H), 1.32 (br dd, J = 8.4, 16.2 Hz, 1H), 1.04 (br dd, J = 9.6, 16.1 Hz, 1H). LCMS m/z = 317 [MH]$^+$. |
| 123 | 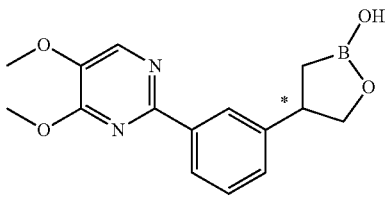 [SMILES: COc1cnc(-c2cccc(C3COB(O)C3)c2)nc1OC]<br>4-(3-(4,5-dimethoxypyrimidin-2-yl)phenyl)-1,2-oxaborolan-2-ol, enantiomer 1 | RT [Analytical SFC Method U] = 1.64 min. |
| 124 | 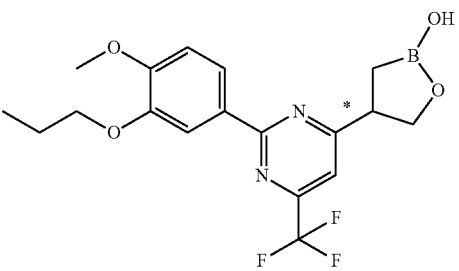 [SMILES: CCCOc1cc(-c2nc(C3COB(O)C3)cc(C(F)(F)F)n2)ccc1OC]<br>(+) 4-(2-(4-methoxy-3-propoxyphenyl)-6-(trifluoromethyl)pyrimidin-4-yl)-1,2-oxaborolan-2-ol, enantiomer 1 | $^1$H NMR (DMSO-$d_6$, 400 MHz): δ 8.72 (s, 1H), 8.03 (dd, J = 2.0, 8.6 Hz, 1H), 7.95 (d, J = 2.0 Hz, 1H), 7.77 (s, 1H), 7.13 (d, J = 8.6 Hz, 1H), 4.32 (dd, J = 7.4, 9.0 Hz, 1H), 3.98-4.09 (m, 3H), 3.86 (s, 3H), 3.73-3.82 (m, 1H), 1.73-1.84 (m, 1H), 1.31-1.41 (m, 1H), 1.18-1.26 (m, 2H), 1.01 (t, J = 7.4 Hz, 3H). LCMS m/z = 397 [MH + H$_2$O]$^+$. [α]$^{20}_D$ +19.4 (c = 0.1, EtOH). |
| 125 | 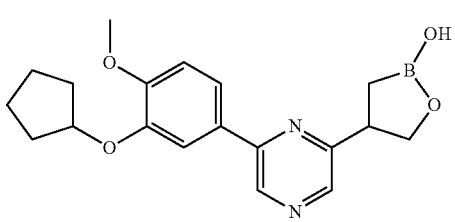 [SMILES: COc1ccc(-c2cncc(C3COB(O)C3)n2)cc1OC1CCCC1]<br>4-(6-(3-(cyclopentyloxy)-4-methoxyphenyl)pyrazin-2-yl)-1,2-oxaborolan-2-ol | $^1$H NMR (DMSO-$d_6$, 400 MHz): δ 9.05 (s, 1H), 8.68 (s, 1H), 8.44 (s, 1H), 7.70-7.73 (m, 2H), 7.05-7.10 (m, 1H), 4.92 (t, J = 6.1 Hz, 1H), 4.31 (dd, J = 7.3, 9.3 Hz, 1H), 3.99 (dd, J = 6.6, 9.0 Hz, 1H), 3.81 (s, 3H), 3.64-3.72 (m, 1H), 1.94 (d, J = 6.4 Hz, 2H), 1.68-1.81 (m, 4H), 1.55-1.64 (m, 2H), 1.27-1.36 (m, 1H), 1.14-1.23 (m, 1H). LCMS m/z = 355 [MH]$^+$. |
| 126 | 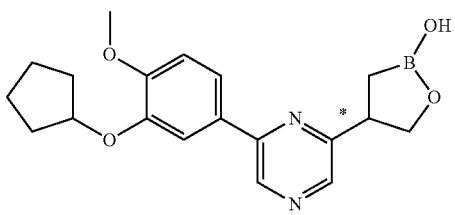 [SMILES: COc1ccc(-c2cncc(C3COB(O)C3)n2)cc1OC1CCCC1]<br>4-(6-(3-(cyclopentyloxy)-4-methoxyphenyl)pyrazin-2-yl)-1,2-oxaborolan-2-ol, enantiomer 1 | $^1$H NMR (DMSO-$d_6$, 400 MHz): δ 9.05 (s, 1H), 8.68 (s, 1H), 8.44 (s, 1H), 7.70-7.73 (m, 2H), 7.05-7.10 (m, 1H), 4.92 (t, J = 6.1 Hz, 1H), 4.31 (dd, J = 7.3, 9.3 Hz, 1H), 3.99 (dd, J = 6.6, 9.0 Hz, 1H), 3.81 (s, 3H), 3.64-3.72 (m, 1H), 1.94 (d, J = 6.4 Hz, 2H), 1.68-1.81 (m, 4H), 1.55-1.64 (m, 2H), 1.27-1.36 (m, 1H), 1.14-1.23 (m, 1H). LCMS m/z = 355 [MH]$^+$. RT [Analytical SFC Method C] = 7.2 min. |

| Example No. | Structure and Name | Analytical Data |
|---|---|---|
| 127 | 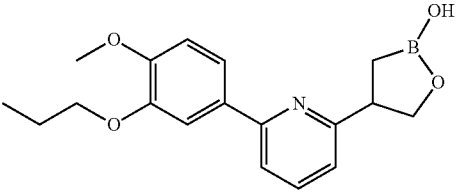<br>4-(6-(4-methoxy-3-propoxyphenyl)pyridin-2-yl)-1,2-oxaborolan-2-ol | $^1$H NMR (DMSO-d$_6$, 400 MHz): δ 8.59 (s, 1H), 7.70-7.76 (m, 3H), 7.64 (d, J = 8.3 Hz, 1H), 7.16 (dd, J = 2.8, 5.3 Hz, 1H), 7.04 (d, J = 8.3 Hz, 1H), 4.29 (t, J = 8.1 Hz, 1H), 3.94-4.05 (m, 3H), 3.81 (s, 3H), 3.55-3.63 (m, 1H), 1.72-1.84 (m, 2H), 1.22-1.31 (m, 1H), 1.14-1.21 (m, 1H), 1.01 (t, J = 7.5 Hz, 3H). LCMS m/z = 346 [MH]$^+$. |
| 128 | 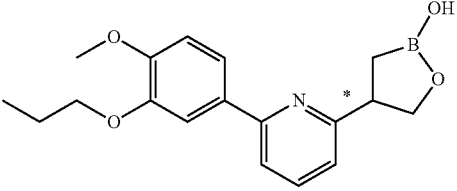 [SMILES: CCCOc1cc(-c2cccc(C3COB(O)C3)n2)ccc1OC]<br>(−) 4-(6-(4-methoxy-3-propoxyphenyl)pyridin-2-yl)-1,2-oxaborolan-2-ol, enantiomer 1 | $^1$H NMR (DMSO-d$_6$, 400 MHz): δ 8.59 (s, 1H), 7.70-7.76 (m, 3H), 7.64 (d, J = 8.3 Hz, 1H), 7.16 (dd, J = 2.8, 5.3 Hz, 1H), 7.04 (d, J = 8.3 Hz, 1H), 4.29 (t, J = 8.1 Hz, 1H), 3.94-4.05 (m, 3H), 3.81 (s, 3H), 3.55-3.63 (m, 1H), 1.72-1.84 (m, 2H), 1.22-1.31 (m, 1H), 1.14-1.21 (m, 1H), 1.01 (t, J = 7.5 Hz, 3H). LCMS m/z = 328 [MH]$^+$. [α]$^{20}_D$ −39.5 (c = 3.8, EtOH). |
| 129 | 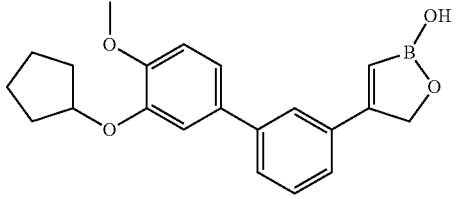 [SMILES: COc1ccc(-c2cccc(C3=CB(O)OC3)c2)cc1OC1CCCC1]<br>4-(3'-(cyclopentyloxy)-4'-methoxy-[1,1'-biphenyl]-3-yl)-1,2-oxaborol-2(5H)-ol | $^1$H NMR (DMSO-d$_6$, 400 MHz): δ 7.71 (s, 1H), 7.62 (d, J = 7.2 Hz, 1H), 7.51-7.53 (m, 1H), 7.44-7.48 (m, 1H), 7.21-7.24 (m, 2H), 7.04 (d, J = 8.0 Hz, 1H), 6.27 (s, 1H), 4.94-4.98 (m, 3H), 3.79 (s, 3H), 1.87-1.94 (m, 2H), 1.74-1.78 (m, 4H), 1.54-1.62 (m, 2H). LCMS m/z = 351 [MH]$^+$. |
| 130 | 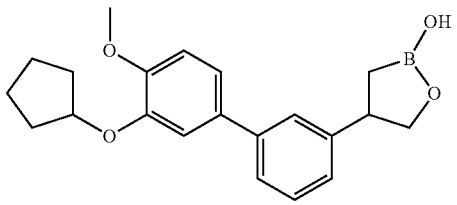 [SMILES: COc1ccc(-c2cccc(C3COB(O)C3)c2)cc1OC1CCCC1]<br>4-(3'-(cyclopentyloxy)-4'-methoxy-[1,1'-biphenyl]-3-yl)-1,2-oxaborolan-2-ol | $^1$H NMR (DMSO-d$_6$, 400 MHz): δ 7.48 (s, 1H), 7.43 (d, J = 7.6 Hz, 1H), 7.35 (t, J = 7.6 Hz, 1H), 7.21 (d, J = 7.6 Hz, 1H), 7.15-7.17 (m, 2H), 7.02 (d, J = 8.8 Hz, 1H), 4.91-4.94 (m, 1H), 4.26 (t, J = 8.0 Hz, 1H), 3.81 (t, J = 8.8 Hz, 1H), 3.77 (s, 3H), 3.42-3.51 (m, 1H), 1.88-1.92 (m, 2H), 1.73-1.76 (m, 4H), 1.58 (m, 2H), 1.29 (q, J = 8.0 Hz, 1H), 1.05-1.11 (m, 1H). LCMS m/z = 353 [MH]$^+$. |
| 131 | 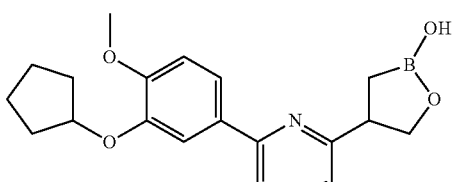<br>4-(6-(3-(cyclopentyloxy)-4-methoxyphenyl)-5-fluoropyridin-2-yl)-1,2-oxaborolan-2-ol | $^1$H NMR (DMSO-d$_6$, 400 MHz): δ 8.61 (s, 1H), 7.68 (dd, J = 8.3, 11.8 Hz, 1H), 7.58 (s, 1H), 7.50-7.55 (m, 1H), 7.27 (dd, J = 3.3, 8.3 Hz, 1H), 7.07 (d, J = 8.5 Hz, 1H), 4.81-4.86 (m, 1H), 4.28 (dd, J = 7.5, 9.0 Hz, 1H), 3.97 (dd, J = 7.3, 8.8 Hz, 1H), 3.81 (s, 3H), 3.58-3.66 (m, 1H), 1.92 (d, J = 6.5 Hz, 2H), 1.68-1.80 (m, 4H), 1.59 (br s, 2H), 1.23-1.31 (m, 1H), 1.12-1.20 (m, 1H). LCMS m/z = 344 [MH]$^+$. |

-continued

| Example No. | Structure and Name | Analytical Data |
|---|---|---|
| 132 | 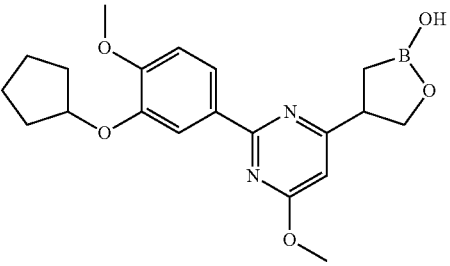 [SMILES: COc1cc(C2COB(O)C2)nc(-c2ccc(OC)c(OC3CCCC3)c2)n1]<br>4-(2-(3-(cyclopentyloxy)-4-methoxyphenyl)-6-methoxypyrimidin-4-yl)-1,2-oxaborolan-2-ol | $^1$H NMR (DMSO-$d_6$, 400 MHz): δ 8.66 (br s, 1H), 7.98 (d, J = 2.0 Hz, 1H), 7.96 (s, 1H), 7.05 (d, J = 8.5 Hz, 1H), 6.64 (s, 1H), 4.83-4.90 (m, 1H), 4.26 (dd, J = 7.5, 9.0 Hz, 1H), 3.92-4.01 (m, 4H), 3.81 (s, 3H), 3.50 (td, J = 7.3, 14.9 Hz, 1H), 1.94 (d, J = 6.5 Hz, 2H), 1.68-1.82 (m, 4H), 1.59 (br s, 2H), 1.20-1.29 (m, 1H), 1.09-1.18 (m, 1H). LCMS m/z = 385 [MH]$^+$. |
| 133 | 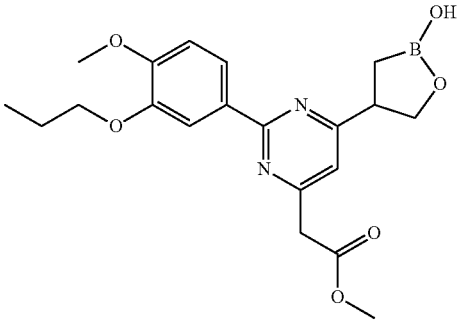<br>ethyl 2-(6-(2-hydroxy-1,2-oxaborolan-4-yl)-2-(4-methoxy-3-propoxyphenyl)pyrimidin-4-yl)acetate | $^1$H NMR (DMSO-$d_6$, 400 MHz): δ 8.69 (s, 1H), 7.98 (dd, J = 2.0, 8.3 Hz, 1H), 7.93 (d, J = 2.0 Hz, 1H), 7.23 (s, 1H), 7.07 (d, J = 8.6 Hz, 1H), 4.30 (dd, J = 7.5, 8.9 Hz, 1H), 4.14 (q, J = 7.1 Hz, 2H), 3.95-4.02 (m, 3H), 3.88 (s, 2H), 3.83 (s, 3H), 3.54-3.62 (m, 1H), 1.73-1.81 (m, 2H), 1.25-1.33 (m, 1H), 1.21 (t, J = 7.1 Hz, 3H), 1.12-1.19 (m, 1H), 1.00 (t, J = 7.3 Hz, 3H). LCMS m/z = 433 [MH + H$_2$O]$^+$. |
| 134 | 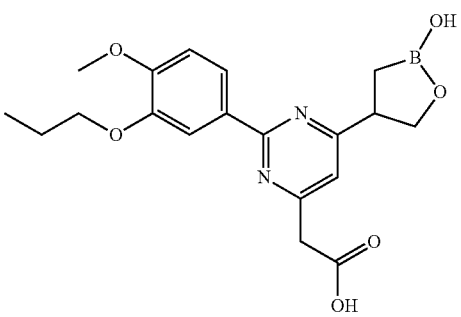 [SMILES: CCCOc1cc(-c2nc(CC(=O)O)cc(C3COB(O)C3)n2)ccc1OC]<br>2-(6-(2-hydroxy-1,2-oxaborolan-4-yl)-2-(4-methoxy-3-propoxyphenyl)pyrimidin-4-yl)acetic acid | $^1$H NMR (CD$_3$OD, 400 MHz): δ 8.05 (s, 2H), 7.18 (s, 1H), 7.03 (d, J = 8.6 Hz, 1H), 4.16-4.22 (m, 1H), 4.07 (t, J = 6.5 Hz, 2H), 3.96-4.02 (m, 1H), 3.90 (s, 3H), 3.70 (s, 2H), 3.40-3.46 (m, 1H), 1.81-1.90 (m, 2H), 1.15-1.31 (m, 2H), 1.08 (t, J = 7.3 Hz, 3H). LCMS m/z = 387 [MH]$^+$. |
| 135 | 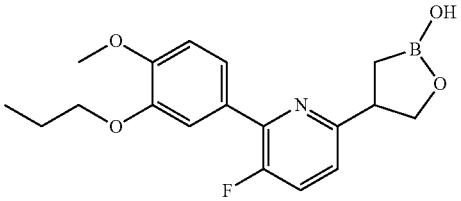 [SMILES: CCCOc1cc(-c2nc(C3COB(O)C3)ccc2F)ccc1OC]<br>4-(5-fluoro-6-(4-methoxy-3-propoxyphenyl)pyridin-2-yl)-1,2-oxaborolan-2-ol | $^1$H NMR (DMSO-$d_6$, 400 MHz): δ 8.61 (s, 1H), 7.68 (dd, J = 8.8, 11.7 Hz, 1H), 7.58 (s, 1H), 7.53 (d, J = 8.8 Hz, 1H), 7.27 (dd, J = 3.4, 8.3 Hz, 1H), 7.08 (d, J = 8.3 Hz, 1H), 4.27 (dd, J = 7.3, 8.8 Hz, 1H), 3.92-4.01 (m, 3H), 3.82 (s, 3H), 3.58-3.65 (m, 1H), 1.71-1.80 (m, 2H), 1.23-1.31 (m, 1H), 1.11-1.19 (m, 1H), 0.99 (t, J = 7.3 Hz, 3H). LCMS m/z = 346 [MH]$^+$. |

| Example No. | Structure and Name | Analytical Data |
|---|---|---|
| 136 | 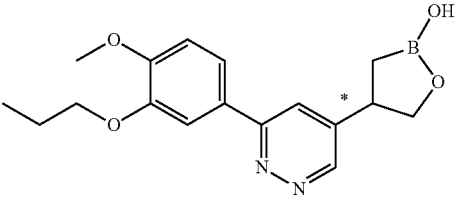<br>4-(6-(4-methoxy-3-propoxyphenyl)pyridazin-4-yl)-1,2-oxaborolan-2-ol, enantiomer 1 | LCMS m/z = 342.3 [MH]$^+$. RT [Analytical SFC Method V] = 6.90 min. |
| 137 | 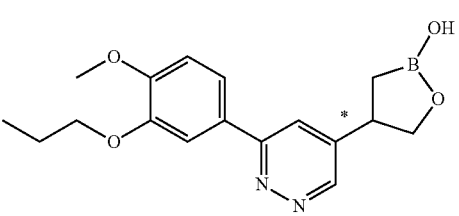<br>4-(6-(4-methoxy-3-propoxyphenyhpyridazin-4-yl)-1,2-oxaborolan-2-ol, enantiomer 2 | LCMS m/z = 342.3 [MH + H$_2$O]$^+$. RT [Analytical SFC Method V] = 7.90 min. |
| 138 | 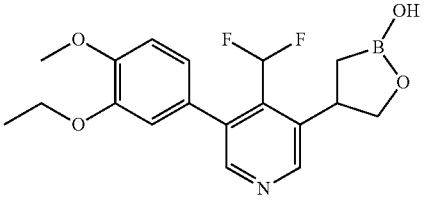 [SMILES: CCOc1cc(-c2cncc(C3COB(O)C3)c2C(F)F)ccc1OC]<br>4-(4-(difluoromethyl)-5-(3-ethoxy-4-methoxyphenyl)pyridin-3-yl)-1,2-oxaborolan-2-ol | LCMS m/z = 364.4 [MH]$^+$. RT [Prep HPLC Method C] = 2.30 min. |
| 139 | 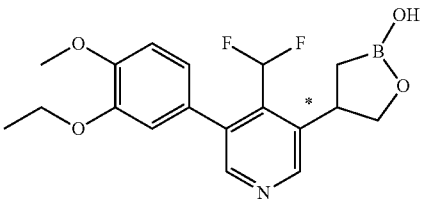 [SMILES: CCOc1cc(-c2cncc(C3COB(O)C3)c2C(F)F)ccc1OC]<br>4-(4-(difluoromethyl)-5-(3-ethoxy-4-methoxyphenyl)pyridin-3-yl)-1,2-oxaborolan-2-ol, enantiomer 1 | $^1$H NMR (CDCl$_3$, 400 MHz): δ 8.72-8.92 (m, 1H), 8.50 (br s, 1H), 6.95-7.01 (m, 1H), 6.86 (dd, J = 2.3, 8.2 Hz, 1H), 6.51-6.83 (m, 2H), 4.48 (t, J = 8.2 Hz, 1H), 4.02-4.27 (m, 4H), 3.94 (s, 3H), 3.74 (s, 1H), 1.63 (dt, J = 8.6, 16.6 Hz, 2H), 1.49 (t, J = 7.0 Hz, 2H), 1.23-1.38 (m, 1H). LCMS m/z = 364 [MH]$^+$. RT [Analytical SFC Method W] = 3.95 min. |
| 140 | 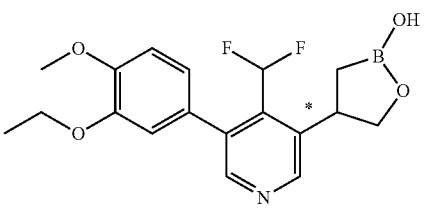 [SMILES: CCOc1cc(-c2cncc(C3COB(O)C3)c2C(F)F)ccc1OC]<br>4-(4-(difluoromethyl)-5-(3-ethoxy-4-methoxyphenyl)pyridin-3-yl)-1,2-oxaborolan-2-ol, enantiomer 2 | $^1$H NMR (CDCl$_3$, 400 MHz): δ 8.72-8.92 (m, 1H), 8.50 (br s, 1H), 6.95-7.01 (m, 1H), 6.86 (dd, J = 2.3, 8.2 Hz, 1H), 6.51-6.83 (m, 2H), 4.48 (t, J = 8.2 Hz, 1H), 4.02-4.27 (m, 4H), 3.94 (s, 3H), 3.74 (s, 1H), 1.63 (dt, J = 8.6, 16.6 Hz, 2H), 1.49 (t, J = 7.0 Hz, 2H), 1.23-1.38 (m, 1H). LCMS m/z = 364 [MH]$^+$. RT [Analytical SFC Method W] = 3.95 min. |

| Example No. | Structure and Name | Analytical Data |
|---|---|---|
| 141 | 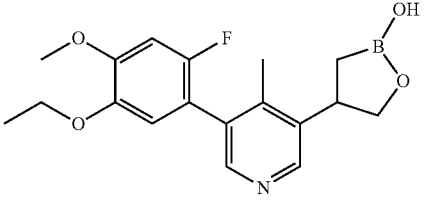 [SMILES: CCOc1cc(-c2cncc(C3COB(O)C3)c2C)c(F)cc1OC]<br>4-(5-(5-ethoxy-2-fluoro-4-methoxyphenyl)-4-methylpyridin-3-yl)-1,2-oxaborolan-2-ol | $^1$H NMR (CD$_3$OD, 400 MHz): δ 8.40 (s, 1H), 8.16 (s, 1H), 6.91 (d, J = 11.0 Hz, 1H), 6.82 (d, J = 7.0 Hz, 1H), 4.04 (q, J = 6.9 Hz, 3H), 3.89 (s, 4H), 3.64 (br s, 1H), 2.25 (d, J = 1.0 Hz, 3H), 1.39 (t, J = 7.0 Hz, 3H), 1.16-1.34 (m, 2H). LCMS m/z = 346 [MH]$^+$. |
| 142 | 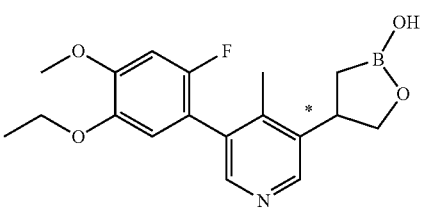 [SMILES: CCOc1cc(-c2cncc(C3COB(O)C3)c2C)c(F)cc1OC]<br>(−) 4-(5-(5-ethoxy-2-fluoro-4-methoxyphenyl)-4-methylpyridin-3-yl)-1,2-oxaborolan-2-ol, enantiomer 2 | $^1$H NMR (DMSO-d$_6$, 400 MHz): δ 8.72 (s, 1H), 8.48 (s, 1H), 8.22 (s, 1H), 7.02 (d, J = 11.5 Hz, 1H), 6.86 (d, J = 7.5 Hz, 1H), 4.26 (t, J = 8.3 Hz, 1H), 4.00 (q, J = 7.0 Hz, 2H), 3.93 (br s, 1H), 3.82 (s, 3H), 3.64-3.72 (m, 1H), 2.14 (s, 3H), 1.27-1.38 (m, 4H), 0.98-1.12 (m, 1H). LCMS m/z = 346 [MH]$^+$. [α]$^{20}_D$ −8.83 (c = 0.1, EtOH). |
| 143 | 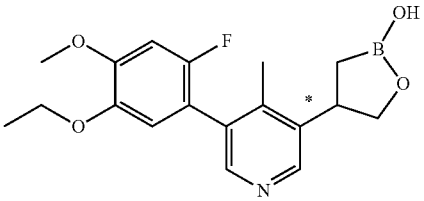 [SMILES: CCOc1cc(-c2cncc(C3COB(O)C3)c2C)c(F)cc1OC]<br>4-(5-(5-ethoxy-2-fluoro-4-methoxyphenyl)-4-methylpyridin-3-yl)-1,2-oxaborolan-2-ol, enantiomer 1 | $^1$H NMR (DMSO-d$_6$, 400 MHz): δ 8.72 (s, 1H), 8.48 (s, 1H), 8.22 (s, 1H), 7.02 (d, J = 11.5 Hz, 1H), 6.86 (d, J = 7.5 Hz, 1H), 4.26 (t, J = 8.3 Hz, 1H), 4.00 (q, J = 7.0 Hz, 2H), 3.93 (br s, 1H), 3.82 (s, 3H), 3.64-3.72 (m, 1H), 2.14 (s, 3H), 1.27-1.38 (m, 4H), 0.98-1.12 (m, 1H). LCMS m/z = 346.2 [MH]$^+$. RT [Analytical SFC Method X] = 3.52 min. |
| 144 | 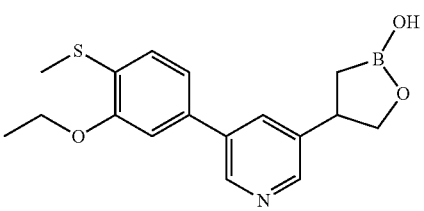 [SMILES: CCOc1cc(-c2cncc(C3COB(O)C3)c2)ccc1SC]<br>4-(5-(3-ethoxy-4-(methylthio)phenyl)pyridin-3-yl)-1,2-oxaborolan-2-ol | $^1$H NMR (DMSO-d$_6$, 400 MHz): δ 8.66 (s, 1H), 7.54 (s, 1H), 7.49 (d, J = 7.6 Hz, 1H), 7.37 (t, J = 7.6 Hz, 1H), 7.26 (br s, 1H), 7.18-7.25 (m, 2H), 7.18 (s, 1H), 4.26 (t, J = 8.2 Hz, 1H), 4.19 (q, J = 7.1 Hz, 2H), 3.81 (t, J = 8.9 Hz, 1H), 3.43-3.52 (m, 1H), 2.40 (s, 3H), 1.36 (t, J = 7.0 Hz, 2H), 1.29 (dd, J = 8.2, 16.3 Hz, 1H), 1.09 (dd, J = 10.1, 16.3 Hz, 1H). LCMS m/z = 329 [MH]$^+$. |
| 145 | 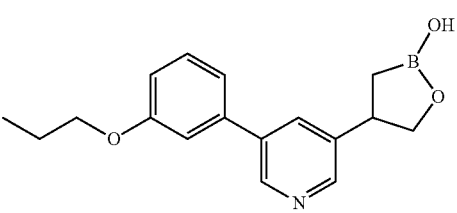 [SMILES: CCCOc1cccc(-c2cncc(C3COB(O)C3)c2)c1]<br>4-(5-(3-propoxphenyl)pyridin-3-yl)-1,2-oxaborolan-2-ol | $^1$H NMR (DMSO-d$_6$, 400 MHz): δ 8.67-8.79 (m, 2H), 8.48 (d, J = 2.0 Hz, 1H), 7.99 (s, 1H), 7.37-7.46 (m, 1H), 7.24-7.33 (m, 2H), 6.98 (d, J = 6.5 Hz, 1H), 4.28 (t, J = 8.3 Hz, 1H), 4.02 (t, J = 6.5 Hz, 2H), 3.87 (t, J = 9.0 Hz, 1H), 3.45-3.60 (m, 1H), 1.69-1.86 (m, 2H), 1.25-1.38 (m, 1H), 1.16 (dd, J = 10.5, 16.1 Hz, 1H), 1.01 (t, J = 7.5 Hz, 3H). LCMS m/z = 298 [MH]$^+$. |

| Example No. | Structure and Name | Analytical Data |
|---|---|---|
| 146 | (−) 4-(5-(3-propoxyphenyl)pyridin-3-yl)-1,2-oxaborolan-2-ol, enantiomer 2 | $^1$H NMR (DMSO-d$_6$, 400 MHz): δ 8.67-8.79 (m, 2H), 8.48 (d, J = 2.0 Hz, 1H), 7.99 (s, 1H), 7.37-7.46 (m, 1H), 7.24-7.33 (m, 2H), 6.98 (d, J = 6.5 Hz, 1H), 4.28 (t, J = 8.3 Hz, 1H), 4.02 (t, J = 6.5 Hz, 2H), 3.87 (t, J = 9.0 Hz, 1H), 3.45-3.60 (m, 1H), 1.69-1.86 (m, 2H), 1.25-1.38 (m, 1H), 1.16 (dd, J = 10.5, 16.1 Hz, 1H), 1.01 (t, J = 7.5 Hz, 3H). LCMS m/z = 298 [MH]$^+$. [α]$^{20}_D$ −25.7 (c = 0.1, EtOH). |
| 147 | 4-(5-(4-methoxy-3-propoxyphenyl)-1,2,4-thiadiazol-3-yl)-1,2-oxaborolan-2-ol | $^1$H NMR (DMSO-d$_6$, 400 MHz): δ 8.70 (br s, 1H), 7.56-7.64 (m, 1H), 7.47 (d, J = 2.2 Hz, 1H), 7.12 (d, J = 8.3 Hz, 1H), 4.29-4.35 (m, 1H), 4.12 (dd, J = 6.7, 9.2 Hz, 1H), 4.01 (t, J = 6.5 Hz, 2H), 3.85 (s, 3H), 3.81 (t, J = 7.7 Hz, 1H), 1.72-1.81 (m, 2H), 1.27-1.40 (m, 2H), 1.00 (t, J = 7.5 Hz, 3H). LCMS m/z = 335 [MH]$^+$. |
| 148 | (−) 4-(5-(4-methoxy-3-propoxyphenyl)-1,2,4-thiadiazol-3-yl)-1,2-oxaborolan-2-ol, enantiomer 2 | $^1$H NMR (DMSO-d$_6$, 400 MHz): δ 8.70 (br s, 1H), 7.56-7.64 (m, 1H), 7.47 (d, J = 2.2 Hz, 1H), 7.12 (d, J = 8.3 Hz, 1H), 4.29-4.35 (m, 1H), 4.12 (dd, J = 6.7, 9.2 Hz, 1H), 4.01 (t, J = 6.5 Hz, 2H), 3.85 (s, 3H), 3.81 (t, J = 7.7 Hz, 1H), 1.72-1.81 (m, 2H), 1.27-1.40 (m, 2H), 1.00 (t, J = 7.5 Hz, 3H). LCMS m/z = 335 [MH]$^+$. [α]$^{20}_D$ −10.3 (c = 0.1, EtOH). |
| 149 | 4-(5-(3-(cyclopentyloxy)-4-methoxyphenyl)pyridin-3-yl)-1,2-oxaborolan-2-ol | $^1$H NMR (DMSO-d$_6$, 400 MHz): δ 8.65-8.74 (m, 2H), 8.43 (d, J = 1.7 Hz, 1H), 7.91 (t, J = 2.0 Hz, 1H), 7.17-7.30 (m, 2H), 7.05 (d, J = 8.8 Hz, 1H), 4.96 (t, J = 5.7 Hz, 1H), 4.27 (t, J = 8.3 Hz, 1H), 3.86 (t, J = 9.0 Hz, 1H), 3.79 (s, 3H), 3.41-3.59 (m, 1H), 1.90 (d, J = 6.4 Hz, 2H), 1.66-1.80 (m, 4H), 1.58 (br s, 2H), 1.29 (d, J = 8.3 Hz, 1H), 1.14 (dd, J = 10.4, 16.3 Hz, 1H). LCMS m/z = 354 [MH]$^+$. |
| 150 | 4-(2-fluoro-4',5-dimethoxy-[1,1'-biphenyl]-3-yl)-1,2-oxaborolan-2-ol | $^1$H NMR (DMSO-d$_6$, 400 MHz): δ 8.66 (s, 1H), 7.33-7.44 (m, 3H), 7.26 (d, J = 6.4 Hz, 1H), 6.94-7.05 (m, 2H), 4.23-4.28 (m, 1H), 3.74-3.85 (m, 6H), 3.45-3.50 (m, 1H), 1.29 (dd, J = 16.0, 8.0 Hz, 1H), 1.05 (dd, J = 16.0, 10.0 Hz, 1H), 1.02-1.09 (m, 1H). LCMS m/z = 317 [MH]$^+$. |

| Example No. | Structure and Name | Analytical Data |
|---|---|---|
| 151 | 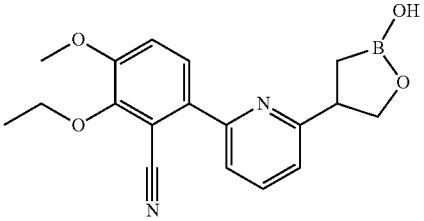 [SMILES: CCOc1c(OC)ccc(-c2cccc(C3COB(O)C3)n2)c1C#N]<br>2-ethoxy-6-(6-(2-hydroxy-1,2-oxaborolan-4-yl)pyridin-2-yl)-3-methoxybenzonitrile | $^1$H NMR (DMSO-d$_6$, 400 MHz): δ 8.58 (s, 1H), 7.85 (t, J = 7.7 Hz, 1H), 7.60 (d, J = 7.6 Hz, 1H), 7.53-7.58 (m, 1H), 7.43-7.50 (m, 1H), 7.33 (d, J = 7.8 Hz, 1H), 4.25-4.31 (m, 1H), 4.20 (q, J = 7.1 Hz, 2H), 4.09 (t, J = 8.7 Hz, 1H), 3.91 (s, 3H), 3.60-3.68 (m, 1H), 1.21-1.38 (m, 5H). LCMS m/z = 339 [MH]$^+$. |
| 152 | 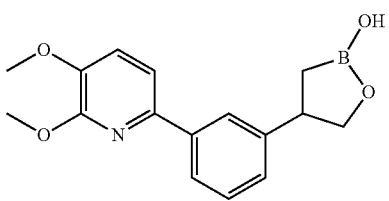 [SMILES: COc1ccc(-c2cccc(C3COB(O)C3)c2)nc1OC]<br>4-(3-(5,6-dimethoxypyridin-2-yl)phenyl)-1,2-oxaborolan-2-ol | $^1$H NMR (DMSO-d$_6$, 400 MHz): δ 8.66 (s, 1H), 7.91 (s, 1H), 7.85 (d, J = 8.0 Hz, 1H), 7.51 (d, J = 8.4 Hz, 1H), 7.38-7.33 (m, 2H), 7.24 (d, J = 7.6 Hz, 1H), 4.27 (t, J = 8.0 Hz, 1H), 3.97 (s, 3H), 3.80-3.82 (m, 4H), 3.43-3.52 (m, 1H), 1.27-1.33 (m, 1H), 1.04-1.10 (m, 1H). LCMS m/z = 300 [MH]$^+$. |
| 153 | 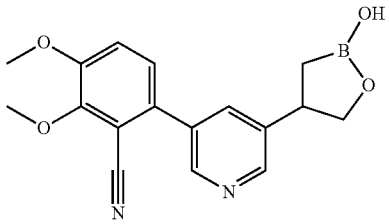 [SMILES: COc1ccc(-c2cncc(C3COB(O)C3)c2)c(C#N)c1OC]<br>6-(5-(2-hydroxy-1,2-oxaborolan-4-yl)pyridin-3-yl)-2,3-dimethoxybenzonitrile | $^1$H NMR (DMSO-d$_6$, 400 MHz): δ 8.72 (s, 1H), 8.57 (d, J = 2.0 Hz, 1H), 8.55 (d, J = 1.7 Hz, 1H), 7.93 (s, 1H), 7.51 (d, J = 8.6 Hz, 1H), 7.38 (d, J = 8.6 Hz, 1H), 4.28 (t, J = 8.3 Hz, 1H), 3.95 (s, 3H), 3.92 (s, 3H), 3.84 (t, J = 9.0 Hz, 1H), 3.49-3.57 (m, 1H), 1.32 (dd, J = 8.2, 16.3 Hz, 1H), 1.12 (dd, J = 10.4, 16.3 Hz, 1H). LCMS m/z = 325 [MH]$^+$. |
| 154 | 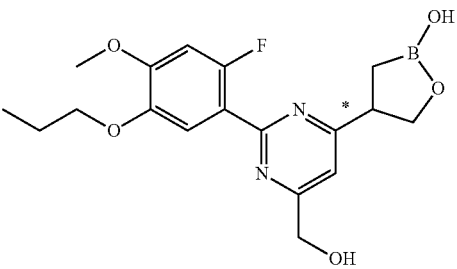 [SMILES: CCCOc1cc(-c2nc(CO)cc(C3COB(O)C3)n2)c(F)cc1OC]<br>(−) 4-(2-(2-fluoro-4-methoxy-5-propoxyphenyl)-6-(hydroxymethyl)pyrimidin-4-yl)-1,2-oxaborolan-2-ol, enantiomer 2 | $^1$H NMR (DMSO-d$_6$, 400 MHz): δ 8.66 (s, 1H), 7.57 (d, J = 7.8 Hz, 1H), 7.34 (s, 1H), 6.95 (d, J = 12.7 Hz, 1H), 5.62 (t, J = 5.6 Hz, 1H), 4.57 (d, J = 5.9 Hz, 2H), 4.26-4.33 (m, 1H), 4.00 (dd, J = 7.1, 9.0 Hz, 1H), 3.93 (t, J = 6.6 Hz, 2H), 3.84 (s, 3H), 3.58-3.66 (m, 1H), 1.69-1.78 (m, 2H), 1.25-1.34 (m, 1H), 1.12-1.21 (m, 1H), 0.98 (t, J = 7.3 Hz, 3H). LCMS m/z = 377 [MH]$^+$. [α]$^{20}_D$ −11.9 (c = 0.1, EtOH). |
| 155 | 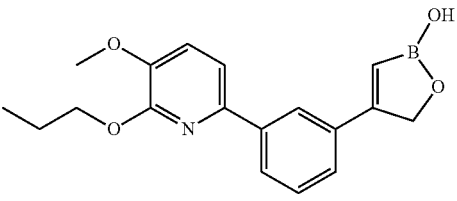<br>4-(3-(5-methoxy-6-propoxypyridin-2-yl)phenyl)-1,2-oxaborol-2(5H)-ol | $^1$H NMR (DMSO-d$_6$, 400 MHz): δ 8.68 (s, 1H), 8.13 (s, 1H), 8.01 (d, J = 7.2 Hz, 1H), 7.60 (d, J = 8.0 Hz, 1H), 7.54 (d, J = 8.0 Hz, 1H), 7.48 (t, J = 7.6 Hz, 1H), 7.36 (d, J = 8.0 Hz, 1H), 6.26 (s, 1H), 4.97 (s, 2H), 4.37 (t, J = 6.8 Hz, 2H), 3.83 (s, 3H), 1.80 (q, J = 6.8 Hz, 2H), 1.00 (t, J = 6.8 Hz, 3H). LCMS m/z = 326 [MH]$^+$. |

| Example No. | Structure and Name | Analytical Data |
|---|---|---|
| 156 | 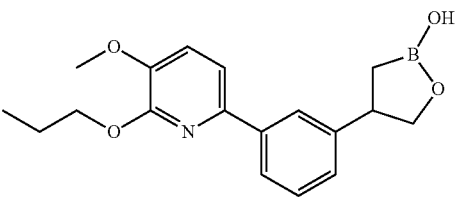 [SMILES: CCCOc1nc(-c2cccc(C3COB(O)C3)c2)ccc1OC]<br>4-(3-(5-methoxy-6-propoxypyridin-2-yl)phenyl)-1,2-oxaborolan-2-ol | $^1$H NMR (DMSO-$d_6$, 400 MHz): δ 8.68 (s, 1H), 8.13 (s, 1H), 8.01 (d, J = 7.2 Hz, 1H), 7.60 (d, J = 8.0 Hz, 1H), 7.54 (d, J = 8.0 Hz, 1H), 7.48 (t, J = 7.6 Hz, 1H), 7.36 (d, J = 8.0 Hz, 1H), 6.26 (s, 1H), 4.97 (s, 2H), 4.37 (t, J = 6.8 Hz, 2H), 3.83 (s, 3H), 1.80 (q, J = 6.8 Hz, 2H), 1.00 (t, J = 6.8 Hz, 3H). LCMS m/z = 328 [MH]$^+$. |
| 157 | 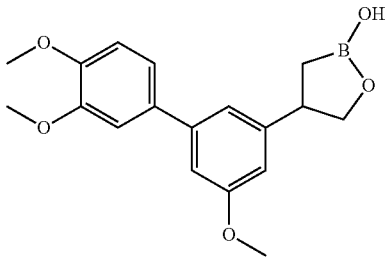 [SMILES: COc1cc(-c2ccc(OC)c(OC)c2)cc(C2COB(O)C2)c1]<br>4-(3',4',5-trimethoxy-[1,1'-biphenyl]-3-yl)-1,2-oxaborolan-2-ol | $^1$H NMR (DMSO-$d_6$, 400 MHz): δ 8.65 (s, 1H), 7.12-7.22 (m, 2H), 7.09 (s, 1H), 6.95-7.05 (m, 3H), 6.79 (s, 1H), 4.24 (t, J = 8.2 Hz, 1H), 3.84 (s, 3H), 3.79 (d, J = 8.0 Hz, 7H), 3.40-3.50 (m, 1H), 1.19-1.33 (m, 1H), 1.08 (dd, J = 10.0, 16.1 Hz, 1H), 1.01-1.13 (m, 1H). LCMS m/z = 329 [MH]$^+$. |
| 158 | 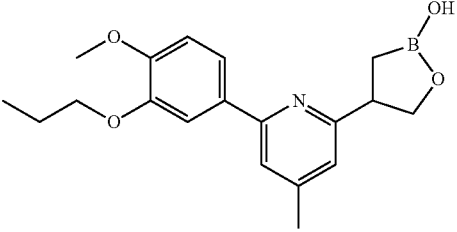<br>4-(6-(4-methoxy-3-propoxyphenyl)-4-methylpyridin-2-yl)-1,2-oxaborolan-2-ol | $^1$H NMR (DMSO-$d_6$, 400 MHz): δ 8.58 (br s, 1H), 7.69 (d, J = 1.5 Hz, 1H), 7.63 (d, J = 8.3 Hz, 1H), 7.59 (s, 1H), 7.02 (d, J = 8.3 Hz, 1H), 6.99 (s, 1H), 4.26 (t, J = 8.1 Hz, 1H), 4.00 (t, J = 6.6 Hz, 2H), 3.96 (dd, J = 6.8, 8.8 Hz, 1H), 3.80 (s, 3H), 3.49-3.57 (m, 1H), 2.34 (s, 3H), 1.72-1.80 (m, 2H), 1.20-1.28 (m, 1H), 1.13-1.20 (m, 1H), 1.00 (t, J = 7.3 Hz, 3H). LCMS m/z = 342 [MH]$^+$. |
| 159 | 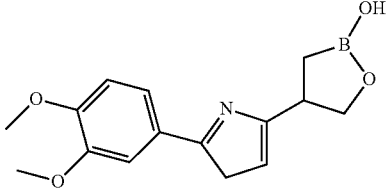<br>4-(2-(3,4-dimethoxyphenyl)thiazol-4-yl)-1,2-oxaborolan-2-ol | $^1$H NMR (DMSO-$d_6$, 400 MHz): δ 8.64 (s, 1H), 7.42-7.48 (m, 2H), 7.31 (s, 1H), 7.05 (d, J = 8.1 Hz, 1H), 4.26 (dd, J = 7.7, 8.7 Hz, 1H), 3.93 (dd, J = 7.6, 8.8 Hz, 1H), 3.84 (s, 3H), 3.81 (s, 3H), 3.56-3.62 (m, 1H), 1.24-1.34 (m, 1H), 1.12-1.20 (m, 1H). LCMS m/z = 306 [MH]$^+$. |
| 160 | 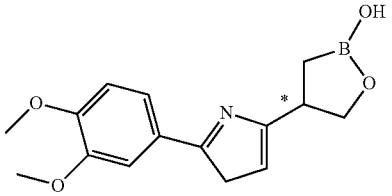<br>4-(2-(3,4-dimethoxyphenyl)thiazol-4-yl)-1,2-oxaborolan-2-ol, enantiomer 2 | LCMS m/z = 319.9 [MH]$^+$. RT [Analytical SFC Method Y] = 5.76 min. |

| Example No. | Structure and Name | Analytical Data |
|---|---|---|
| 161 | 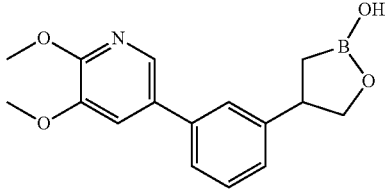 [SMILES: COc1cc(-c2cccc(C3COB(O)C3)c2)cnc1OC]<br>4-(3-(5,6-dimethoxypyridin-3-yl)phenyl)-1,2-oxaborolan-2-ol | $^1$H NMR (DMSO-d$_6$, 400 MHz): δ 7.98 (s, 1H), 7.55-7.57 (m, 1H), 7.50-7.52 (m, 2H), 7.39-7.41 (m, 1H), 7.28-7.37 (m, 1H), 4.26 (t, J = 8.0 Hz, 1H), 3.89 (s, 3H), 3.88 (s, 3H), 3.82 (t, J = 8.0 Hz, 1H), 3.32-3.79 (m, 1H), 1.28-1.32 (m, 1H), 1.03-1.14 (m, 1H). LCMS m/z = 300 [MH]$^+$. |
| 162 | 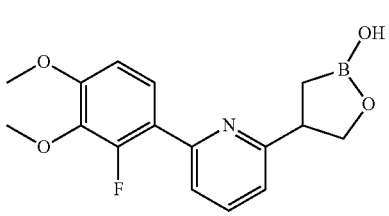 [SMILES: COc1ccc(-c2cccc(C3COB(O)C3)n2)c(F)c1OC]<br>4-(6-(2-fluoro-3,4-dimethoxyphenyl)pyridin-2-yl)-1,2-oxaborolan-2-ol | $^1$H NMR (DMSO-d$_6$, 400 MHz): δ 8.59 (s, 1H), 7.78 (t, J = 8.0 Hz, 1H), 7.67 (t, J = 8.8 Hz, 1H), 7.54-7.57 (m, 1H), 7.25 (d, J = 8.0 Hz, 1H), 7.02 (d, J = 9.2 Hz, 1H), 4.26-4.30 (m, 1H), 4.01-4.97 (m, 1H), 3.88 (s, 3H), 3.82 (s, 3H), 3.32-3.65 (m, 1H), 1.18-1.30 (m, 2H). LCMS m/z = 318 [MH]$^+$. |
| 163 | 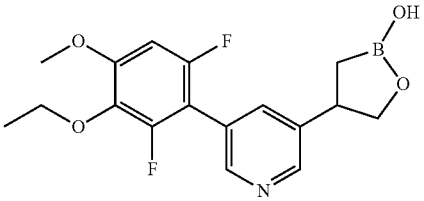 [SMILES: CCOc1c(OC)cc(F)c(-c2cncc(C3COB(O)C3)c2)c1F]<br>4-(5-(3-ethoxy-2,6-difluoro-4-methoxyphenyl)pyridin-3-yl)-1,2-oxaborolan-2-ol | $^1$H NMR (DMSO-d$_6$, 400 MHz): δ 8.71 (s, 1H), 8.52 (d, J = 2.0 Hz, 1H), 8.46 (s, 1H), 7.78 (s, 1H), 7.06 (d, J = 12.2 Hz, 1H), 4.28 (t, J = 8.3 Hz, 1H), 4.02 (q, J = 7.3 Hz, 2H), 3.88 (s, 3H), 3.81 (t, J = 8.8 Hz, 1H), 3.47-3.55 (m, 1H), 1.22-1.38 (m, 4H), 1.00-1.13 (m, 1H). LCMS m/z = 350 [MH]$^+$. |
| 164 | 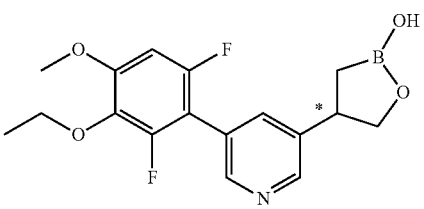<br>(−) 4-(5-(3-ethoxy-2,6-difluoro-4-methoxyphenyl)pyridin-3-yl)-1,2-oxaborolan-2-ol, enantiomer 1 | $^1$H NMR (DMSO-d$_6$, 400 MHz): δ 8.71 (s, 1H), 8.52 (d, J = 2.0 Hz, 1H), 8.46 (s, 1H), 7.78 (s, 1H), 7.06 (d, J = 12.2 Hz, 1H), 4.28 (t, J = 8.3 Hz, 1H), 4.02 (q, J = 7.3 Hz, 2H), 3.88 (s, 3H), 3.81 (t, J = 8.8 Hz, 1H), 3.47-3.55 (m, 1H), 1.22-1.38 (m, 4H), 1.00-1.13 (m, 1H). LCMS m/z = 318 [MH]$^+$. [α]$^{20}_D$ −20.6 (c = 0.22, EtOH). |
| 165 | 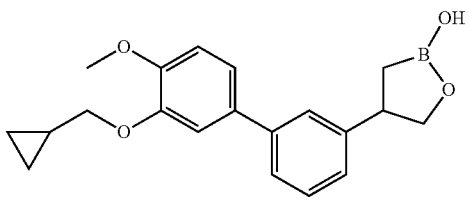 [SMILES: COc1ccc(-c2cccc(C3COB(O)C3)c2)cc1OCC1CC1]<br>4-(3'-(cyclopropylmethoxy)-4'-methoxy-[1,1'-biphenyl]-3-yl)-1,2-oxaborolan-2-ol | |

| Example No. | Structure and Name | Analytical Data |
|---|---|---|
| 166 | 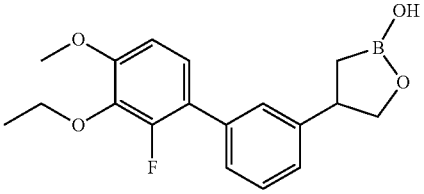 [SMILES: CCOc1c(OC)ccc(-c2cccc(C3COB(O)C3)c2)c1F]<br>4-(3'-ethoxy-2'-fluoro-4'-methoxy-[1,1'-biphenyl]-3-yl)-1,2-oxaborolan-2-ol | $^1$H NMR (DMSO-$d_6$, 400 MHz): δ 7.36-7.39 (m, 2H), 7.31-7.32 (m, 1H), 7.27 (d, J = 7.6 Hz, 1H), 7.15-7.19 (m, 1H), 6.96 (d, J = 8.8 Hz, 1H), 4.25 (t, J = 8.0 Hz, 1H), 4.05 (q, J = 7.2 Hz, 2H), 3.85 (s, 3H), 3.79 (t, J = 8.8 Hz, 1H), 3.41-3.50 (m, 1H), 1.26-1.32 (m, 4H), 1.02-1.08 (m, 1H). LCMS m/z = 331 [MH]$^+$. |
| 167 | 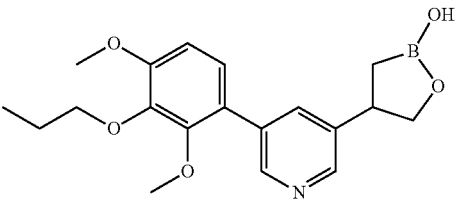 [SMILES: CCCOc1c(OC)ccc(-c2cncc(C3COB(O)C3)c2)c1OC]<br>4-(5-(2,4-dimethoxy-3-propoxphenyl)pyridin-3-yl)-1,2-oxaborolan-2-ol | $^1$H NMR (DMSO-$d_6$, 400 MHz): δ 8.70 (s, 1H), 8.47 (d, J = 2.0 Hz, 1H), 8.42 (d, J = 2.0 Hz, 1H), 7.73 (t, J = 2.1 Hz, 1H), 7.09 (d, J = 8.8 Hz, 1H), 6.91 (d, J = 8.6 Hz, 1H), 4.25-4.32 (m, 1H), 3.90 (t, J = 6.5 Hz, 2H), 3.79-3.87 (m, 4H), 3.65 (s, 3H), 3.45-3.54 (m, 1H), 1.65-1.76 (m, 2H), 1.32 (dd, J = 8.2, 16.3 Hz, 1H), 1.03-1.12 (m, 1H), 0.99 (t, J = 7.5 Hz, 3H). LCMS m/z = 358 [MH]$^+$. |
| 168 | 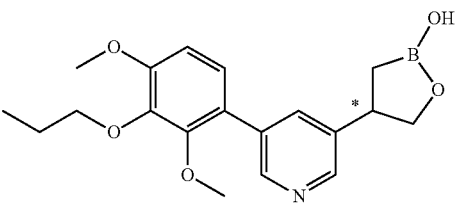 [SMILES: CCCOc1c(OC)ccc(-c2cncc(C3COB(O)C3)c2)c1OC]<br>(−) 4-(5-(2,4-dimethoxy-3-propoxphenyl)pyridin-3-yl)-1,2-oxaborolan-2-ol, enantiomer 1 | $^1$H NMR (DMSO-$d_6$, 400 MHz): δ 8.70 (s, 1H), 8.47 (d, J = 2.0 Hz, 1H), 8.42 (d, J = 2.0 Hz, 1H), 7.73 (t, J = 2.1 Hz, 1H), 7.09 (d, J = 8.8 Hz, 1H), 6.91 (d, J = 8.6 Hz, 1H), 4.25-4.32 (m, 1H), 3.90 (t, J = 6.5 Hz, 2H), 3.79-3.87 (m, 4H), 3.65 (s, 3H), 3.45-3.54 (m, 1H), 1.65-1.76 (m, 2H), 1.32 (dd, J = 8.2, 16.3 Hz, 1H), 1.03-1.12 (m, 1H), 0.99 (t, J = 7.5 Hz, 3H). LCMS m/z = 358 [MH]$^+$. [α]$^{20}_D$ −18.8 (c = 0.1, EtOH). |
| 169 | 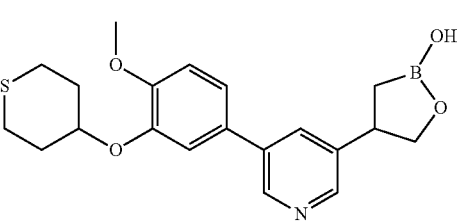 [SMILES: COc1ccc(-c2cncc(C3COB(O)C3)c2)cc1OC1CCSCC1]<br>4-(5-(4-methoxy-3-((tetrahydro-2H-thiopyran-4-yl)oxy)phenyl)pyridin-3-yl)-1,2-oxaborolan-2-ol | $^1$H NMR (DMSO-$d_6$, 400 MHz): δ 8.69 (br s, 1H), 8.42 (br s, 1H), 7.90 (br s, 1H), 7.34 (s, 1H), 7.30 (d, J = 8.3 Hz, 1H), 7.09 (d, J = 8.3 Hz, 1H), 4.44-4.54 (m, 1H), 4.27 (t, J = 7.8 Hz, 1H), 3.74-3.89 (m, 4H), 3.45-3.56 (m, 1H), 2.75-2.85 (m, 2H), 2.56-2.66 (m, 2H), 2.13-2.18 (m, 2H), 1.76-1.88 (m, 2H), 1.27-1.37 (m, 1H), 1.14 (dd, J = 10.3, 16.1 Hz, 1H). LCMS m/z = 386 [MH]$^+$. |
| 170 | 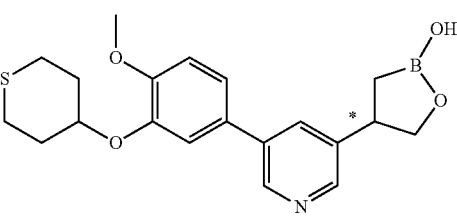 [SMILES: COc1ccc(-c2cncc(C3COB(O)C3)c2)cc1OC1CCSCC1]<br>4-(5-(4-methoxy-3-((tetrahydro-2H-thiopyran-4-yl)oxy)phenyl)pyridin-3-yl)-1,2-oxaborolan-2-ol, enantiomer 1 | $^1$H NMR (DMSO-$d_6$, 400 MHz): δ 8.69 (br s, 1H), 8.42 (br s, 1H), 7.90 (br s, 1H), 7.34 (s, 1H), 7.30 (d, J = 8.3 Hz, 1H), 7.09 (d, J = 8.3 Hz, 1H), 4.44-4.54 (m, 1H), 4.27 (t, J = 7.8 Hz, 1H), 3.74-3.89 (m, 4H), 3.45-3.56 (m, 1H), 2.75-2.85 (m, 2H), 2.56-2.66 (m, 2H), 2.13-2.18 (m, 2H), 1.76-1.88 (m, 2H), 1.27-1.37 (m, 1H), 1.14 (dd, J = 10.3, 16.1 Hz, 1H). LCMS m/z = 386 [MH]$^+$. RT [Analytical SFC Method Z] = 5.20 min. |

-continued

| Example No. | Structure and Name | Analytical Data |
|---|---|---|
| 171 | 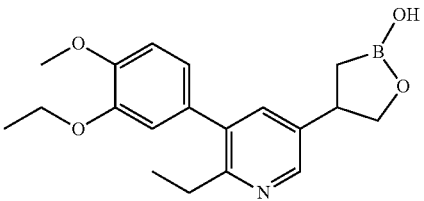 [SMILES: CCOc1cc(-c2cc(C3COB(O)C3)cnc2CC)ccc1OC]<br>4-(5-(3-ethoxy-4-methoxyphenyl)-6-ethylpyridin-3-yl)-1,2-oxaborolan-2-ol | $^1$H NMR (DMSO-$d_6$, 400 MHz): δ 8.65 (s, 1H), 8.39 (s, 1H), 7.43 (s, 1H), 7.02 (d, J = 8.0 Hz, 1H), 6.90 (s, 1H), 6.84 (d, J = 8.3 Hz, 1H), 4.24 (t, J = 8.3 Hz, 1H), 4.03 (q, J = 6.8 Hz, 2H), 3.75-3.84 (m, 4H), 3.39-3.52 (m, 1H), 2.69 (q, J = 7.4 Hz, 2H), 1.21-1.37 (m, 4H), 1.00-1.17 (m, 4H). LCMS m/z = 342 [MH]$^+$. |
| 172 | 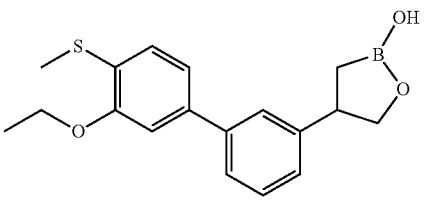<br>4-(3'-ethoxy-4'-(methylthio)-[1,1'-biphenyl]-3-yl)-1,2-oxaborolan-2-ol | $^1$H NMR (DMSO-$d_6$, 400 MHz): δ 8.66 (s, 1H), 7.54 (s, 1H), 7.49 (d, J = 7.6 Hz, 1H), 7.37 (t, J = 7.6 Hz, 1H), 7.25 (d, J = 9.8 Hz, 2H), 7.17-7.22 (m, 2H), 4.26 (t, J = 8.2 Hz, 1H), 4.19 (q, J = 7.1 Hz, 2H), 3.81 (t, J = 8.9 Hz, 1H), 3.43-3.52 (m, 1H), 2.40 (s, 3H), 1.36 (t, J = 7.0 Hz, 3H), 1.29 (dd, J = 8.2, 16.3 Hz, 1H), 1.09 (dd, J = 10.1, 16.3 Hz, 1H). LCMS m/z = 329 [MH]$^+$. |
| 173 | 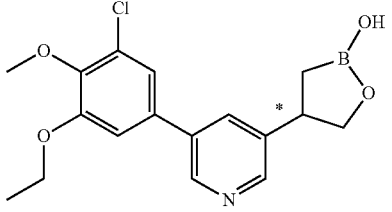 [SMILES: CCOc1cc(-c2cncc(C3COB(O)C3)c2)cc(Cl)c1OC]<br>4-(5-(3-chloro-5-ethoxy-4-methoxyphenyl)pyridin-3-yl)-1,2-oxaborolan-2-ol, enantiomer 2 | $^1$H NMR (DMSO-$d_6$, 400 MHz): δ 8.75 (d, J = 2.0 Hz, 1H), 8.70 (s, 1H), 8.48 (d, J = 2.0 Hz, 1H), 8.02 (t, J = 2.2 Hz, 1H), 7.42 (d, J = 2.0 Hz, 1H), 7.34 (d, J = 2.0 Hz, 1H), 4.18-4.30 (m, 3H), 3.83-3.91 (m, 1H), 3.81 (s, 3H), 3.44-3.57 (m, 1H), 1.39 (t, J = 6.9 Hz, 3H), 1.26-1.34 (m, 1H), 1.12-1.22 (m, 1H). LCMS m/z = 348 [MH]$^+$. RT [Analytical SFC Method E] = 5.33 min |
| 174 | 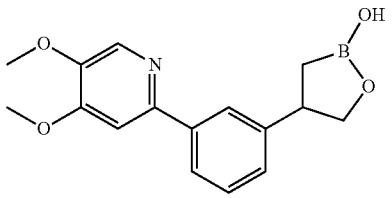 [SMILES: COc1cnc(-c2cccc(C3COB(O)C3)c2)cc1OC]<br>4-(3-(4,5-dimethoxypyridin-2-yl)phenyl)-1,2-oxaborolan-2-ol | $^1$H NMR (DMSO-$d_6$, 400 MHz): δ 8.65 (s, 1H), 8.24 (s, 1H), 7.94 (s, 1H), 7.87 (d, J = 8.0 Hz, 1H), 7.51 (s, 1H), 7.38 (t, J = 7.6 Hz, 1H), 7.29 (d, J = 7.2 Hz, 1H), 4.27 (t, J = 8.4 Hz, 1H), 3.95 (s, 3H), 3.89 (s, 3H), 3.82 (t, J = 8.4 Hz, 1H), 3.44-3.53 (m, 1H), 1.30 (q, J = 8.0 Hz, 1H), 1.08 (q, J = 10.0 Hz, 1H). LCMS m/z = 300 [MH]$^+$. |
| 175 | 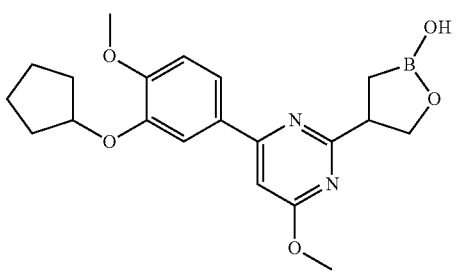 [SMILES: COc1cc(-c2ccc(OC)c(OC3CCCC3)c2)nc(C2COB(O)C2)n1]<br>4-(4-(3-(cyclopentyloxy)-4-methoxyphenyl)-6-methoxypyrimidin-2-yl)-1,2-oxaborolan-2-ol | $^1$H NMR (DMSO-$d_6$, 400 MHz): δ 8.60 (s, 1H), 7.72-7.79 (m, 2H), 7.23 (s, 1H), 7.05 (d, J = 8.5 Hz, 1H), 4.92 (br s, 1H), 4.29 (t, J = 8.0 Hz, 1H), 4.10 (dd, J = 6.0, 8.5 Hz, 1H), 3.94 (s, 3H), 3.81 (s, 3H), 3.55-3.63 (m, 14.2 Hz, 1H), 1.93 (d, J = 5.5 Hz, 2H), 1.72 (br s, 4H), 1.58 (br s, 2H), 1.22-1.36 (m, 2H). LCMS m/z = 385 [MH]$^+$. |

-continued

| Example No. | Structure and Name | Analytical Data |
|---|---|---|
| 176 | 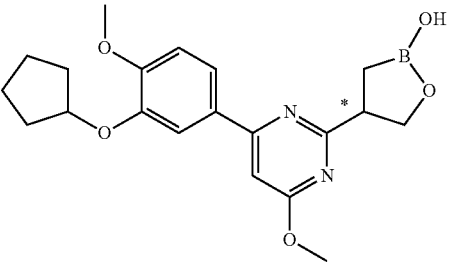 [SMILES: COc1cc(-c2ccc(OC)c(OC3CCCC3)c2)nc(C2COB(O)C2)n1]<br>4-(4-(3-(cyclopentyloxy)-4-methoxyphenyl)-6-methoxypyrimidin-2-yl)-1,2-oxaborolan-2-ol, enantiomer 2 | $^1$H NMR (DMSO-d$_6$, 400 MHz): δ 8.60 (s, 1H), 7.72-7.79 (m, 2H), 7.23 (s, 1H), 7.05 (d, J = 8.5 Hz, 1H), 4.92 (br s, 1H), 4.29 (t, J = 8.0 Hz, 1H), 4.10 (dd, J = 6.0, 8.5 Hz, 1H), 3.94 (s, 3H), 3.81 (s, 3H), 3.55-3.63 (m, 14.2 Hz, 1H), 1.93 (d, J = 5.5 Hz, 2H), 1.72 (br s, 4H), 1.58 (br s, 2H), 1.22-1.36 (m, 2H).<br>LCMS m/z = 385 [MH]$^+$. RT [Analytical SFC Method Z] = 2.79 min. |
| 177 | 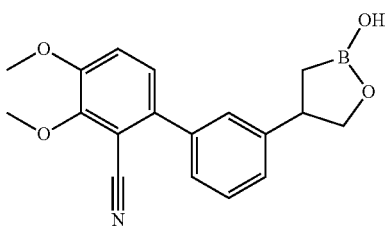 [SMILES: COc1ccc(-c2cccc(C3COB(O)C3)c2)c(C#N)c1OC]<br>3'-(2-hydroxy-1,2-oxaborolan-4-yl)-3,4-dimethoxy-[1,1'-biphenyl]-2-carbonitrile | $^1$H NMR (DMSO-d$_6$, 400 MHz): δ 7.19-7.53 (m, 7H) 4.22-4.31 (m, 1H), 3.94 (s, 3H), 3.91 (s, 3H), 3.79-3.83 (t, J = 8.8 Hz, 1H), 3.42-3.53 (m, 1H), 1.26-1.32 (m, 1H), 1.04-1.11 (m, 1H). LCMS m/z = 322 [MH]$^+$. |
| 178 | 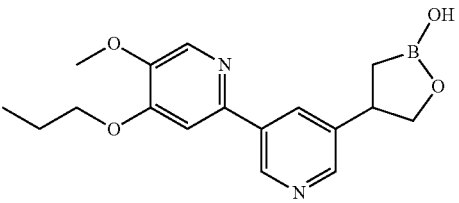 [SMILES: CCCOc1cc(-c2cncc(C3COB(O)C3)c2)ncc1OC]<br>4-(5-methoxy-4-propoxy-[2,3'-bipyridin]-5-yl)-1,2-oxaborolan-2-ol | $^1$H NMR (DMSO-d$_6$, 400 MHz): δ 8.89 (d, J = 2.0 Hz, 1H), 8.45 (d, J = 2.0 Hz, 1H), 8.24 (s, 1H), 8.20 (s, 1H), 7.47 (s, 1H), 4.18 (t, J = 6.4 Hz, 2H), 3.97 (s, 3H), 3.87 (br s, 1H), 3.39 (br s, 1H), 1.85-1.94 (m, 2H), 1.29 (d, J = 8.8 Hz, 2H), 1.10 (t, J = 7.6 Hz, 3H). LCMS m/z = 329 [MH]$^+$. |
| 179 | 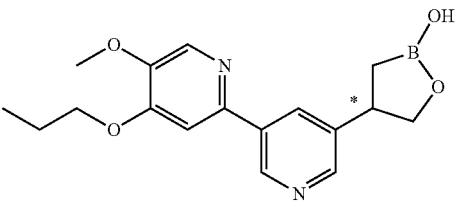 [SMILES: CCCOc1cc(-c2cncc(C3COB(O)C3)c2)ncc1OC]<br>4-(5-methoxy-4-propoxy-[2,3'-bipyridin]-5-yl)-1,2-oxaborolan-2-ol, enantiomer 1 | $^1$H NMR (DMSO-d$_6$, 400 MHz): δ 8.89 (d, J = 2.0 Hz, 1H), 8.45 (d, J = 2.0 Hz, 1H), 8.24 (s, 1H), 8.20 (s, 1H), 7.47 (s, 1H), 4.18 (t, J = 6.4 Hz, 2H), 3.97 (s, 3H), 3.87 (br s, 1H), 3.39 (br s, 1H), 1.85-1.94 (m, 2H), 1.29 (d, J = 8.8 Hz, 2H), 1.10 (t, J = 7.6 Hz, 3H). LCMS m/z = 329 [MH]$^+$. RT [Analytical SFC Method G] = 4.36 min. |
| 180 | 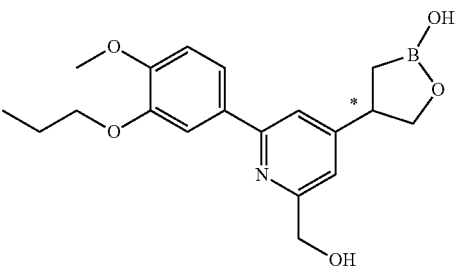 [SMILES: CCCOc1cc(-c2cc(C3COB(O)C3)cc(CO)n2)ccc1OC]<br>4-(2-(hydroxymethyl)-6-(4-methoxy-3-propoxyphenyl)pyridin-4-yl)-1,2-oxaborolan-2-ol, enantiomer 1 | $^1$H NMR (DMSO-d$_6$, 400 MHz): δ 8.73 (s, 1H), 7.61-7.67 (m, 3H), 7.26 (s, 1H), 7.03 (d, J = 8.3 Hz, 1H), 5.40 (t, J = 5.9 Hz, 1H), 4.58 (d, J = 5.4 Hz, 2H), 4.29 (t, J = 8.3 Hz, 1H), 4.00 (t, J = 6.6 Hz, 2H), 3.85 (t, J = 8.8 Hz, 1H), 3.81 (s, 3H), 3.46-3.54 (m, 1H), 1.72-1.81 (m, 2H), 1.32 (dd, J = 8.3, 16.1 Hz, 1H), 1.09 (dd, J = 9.5, 16.4 Hz, 1H), 0.98-1.03 (m, 3H). LCMS m/z = 358 [MH]$^+$. RT [Analytical SFC Method L] = 3.58 min. |

| Example No. | Structure and Name | Analytical Data |
|---|---|---|
| 181 | 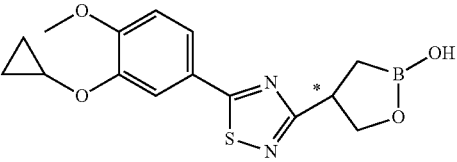 [SMILES: COc1ccc(-c2nc(C3COB(O)C3)ns2)cc1OC1CC1]<br>(−) 4-(5-(3-cyclopropoxy-4-methoxyphenyl)-1,2,4-thiadiazol-3-yl)-1,2-oxaborolan-2-ol, enantiomer 2 | $^1$H NMR (DMSO-d$_6$, 400 MHz): δ 8.69 (s, 1H), 7.78 (d, J = 2.2 Hz, 1H), 7.60 (d, J = 8.3 Hz, 1H), 7.12 (d, J = 8.3 Hz, 1H), 4.32 (dd, J = 7.6, 9.0 Hz, 1H), 4.12 (dd, J = 6.6, 9.0 Hz, 1H), 3.97-3.99 (m, 1H), 3.76-3.88 (m, 4H), 1.25-1.43 (m, 2H), 0.77-0.86 (m, 2H), 0.67-0.74 (m, 2H). LCMS m/z = 333 [MH]$^+$. [α]$^{20}{}_D$ −12.7 (c = 0.1, EtOH). |
| 182 | 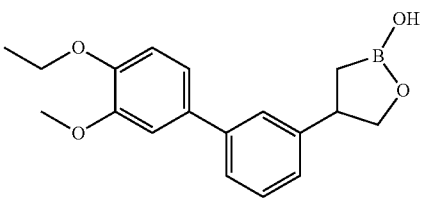 [SMILES: CCOc1ccc(-c2cccc(C3COB(O)C3)c2)cc1OC]<br>4-(4'-ethoxy-3'-methoxy-[1,1'-biphenyl]-3-yl)-1,2-oxaborolan-2-ol | $^1$H NMR (DMSO-d$_6$, 400 MHz): δ 7.50 (br s, 1H), 7.46 (d, J = 7.8 Hz, 1H), 7.35 (t, J = 7.8 Hz, 1H), 7.14-7.22 (m, 3H), 7.01 (d, J = 8.2 Hz, 1H), 4.26 (t, J = 7.8 Hz, 1H), 4.04 (q, J = 7.0 Hz, 2H), 3.79-3.84 (m, 4H), 3.42-3.51 (m, 1H), 1.26-1.36 (m, 4H), 1.05-1.12 (m, 1H). LCMS m/z = 313 [MH]$^+$. |
| 183 | 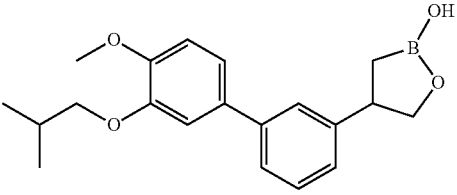<br>4-(3'-isobutoxy-4'-methoxy-[1,1'-biphenyl]-3-yl)-1,2-oxaborolan-2-ol | $^1$H NMR (DMSO-d$_6$, 400 MHz): δ 7.44-7.56 (m, 2H), 7.32-7.39 (m, 1H), 7.15-7.24 (m, 3H), 7.00-7.04 (m, 1H), 4.15 (t, J = 10.5 Hz, 1H), 4.02-4.06 (m, 1H), 3.79-3.84 (m, 5H), 3.43-3.51 (m, 1H), 1.99-2.09 (m, 1H), 1.22-1.32 (m, 1H), 1.05-1.11 (m, 1H), 0.98-1.01 (m, 6H). LCMS m/z = 359 [MH + H$_2$O]$^+$. |
| 184 | 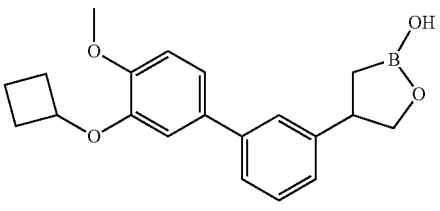 [SMILES: COc1ccc(-c2cccc(C3COB(O)C3)c2)cc1OC1CCC1]<br>4-(3'-cyclobutoxy-4'-methoxy-[1,1'-biphenyl]-3-yl)-1,2-oxaborolan-2-ol | $^1$H NMR (DMSO-d$_6$, 400 MHz): δ 7.46 (s, 1H), 7.40-7.44 (m, 1H), 7.36 (d, J = 7.6 Hz, 1H), 7.21 (d, J = 7.3 Hz, 1H), 7.16 (dd, J = 2.1, 8.4 Hz, 1H), 6.99-7.05 (m, 2H), 4.75-4.83 (m, 1H), 4.26 (t, J = 8.2 Hz, 1H), 3.78-3.84 (m, 4H), 3.41-3.54 (m, 1H), 2.39-2.47 (m, 2H), 2.02-2.14 (m, 2H), 1.74-1.84 (m, 1H), 1.59-1.71 (m, 1H), 1.29 (dd, J = 8.2, 16.3 Hz, 1H), 1.05-1.12 (m, 1H), 1.03 (d, J = 6.8 Hz, 1H). LCMS m/z = 339 [MH]$^+$. |
| 185 | 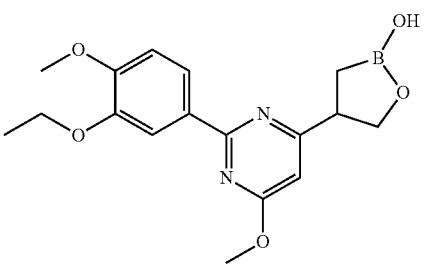 [SMILES: CCOc1cc(-c2nc(OC)cc(C3COB(O)C3)n2)ccc1OC]<br>4-(2-(3-ethoxy-4-methoxyphenyl)-6-methoxypyrimidin-4-yl)-1,2-oxaborolan-2-ol | $^1$H NMR (DMSO-d$_6$, 400 MHz): δ 8.67 (s, 1H), 7.99 (dd, J = 2.0, 8.5 Hz, 1H), 7.96 (d, J = 2.0 Hz, 1H), 7.06 (d, J = 8.5 Hz, 1H), 6.64 (s, 1H), 4.26 (dd, J = 7.3, 8.8 Hz, 1H), 4.10 (q, J = 6.9 Hz, 2H), 4.00 (s, 3H), 3.95 (dd, J = 6.0, 9.0 Hz, 1H), 3.83 (s, 3H), 3.48-3.54 (m, 1H), 1.37 (t, J = 7.0 Hz, 3H), 1.21-1.27 (m, 1H), 1.11-1.18 (m, 1H). LCMS m/z = 345 [MH]$^+$. |

| Example No. | Structure and Name | Analytical Data |
|---|---|---|
| 186 | 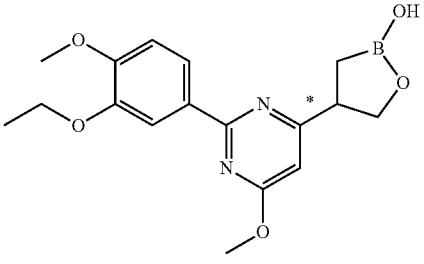 [SMILES: CCOc1cc(-c2nc(OC)cc(C3COB(O)C3)n2)ccc1OC]<br>(−) 4-(2-(3-ethoxy-4-methoxyphenyl)-6-methoxypyrimidin-4-yl)-1,2-oxaborolan-2-ol, enantiomer 2 | $^1$H NMR (DMSO-$d_6$, 400 MHz): δ 8.67 (s, 1H), 7.99 (dd, J = 2.0, 8.5 Hz, 1H), 7.96 (d, J = 2.0 Hz, 1H), 7.06 (d, J = 8.5 Hz, 1H), 6.64 (s, 1H), 4.26 (dd, J = 7.3, 8.8 Hz, 1H), 4.10 (q, J = 6.9 Hz, 2H), 4.00 (s, 3H), 3.95 (dd, J = 6.0, 9.0 Hz, 1H), 3.83 (s, 3H), 3.48-3.54 (m, 1H), 1.37 (t, J = 7.0 Hz, 3H), 1.21-1.27 (m, 1H), 1.11-1.18 (m, 1H). LCMS m/z = 345 [MH]$^+$. [α]$^{20}_D$ −37.4 (c = 0.1, EtOH). |
| 187 | 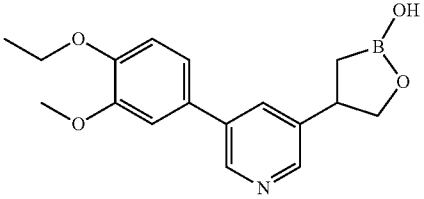 [SMILES: CCOc1ccc(-c2cncc(C3COB(O)C3)c2)cc1OC]<br>4-(5-(4-ethoxy-3-methoxyphenyl)pyridin-3-yl)-1,2-oxaborolan-2-ol | $^1$H NMR (DMSO-$d_6$, 400 MHz): δ 8.73 (s, 1H), 8.71 (d, J = 2.0 Hz, 1H), 8.42 (d, J = 2.0 Hz, 1H), 7.94 (t, J = 2.2 Hz, 1H), 7.28 (d, J = 2.0 Hz, 1H), 7.21-7.25 (m, 1H), 7.03-7.07 (m, 1H), 4.27 (t, J = 8.3 Hz, 1H), 4.05 (q, J = 7.2 Hz, 2H), 3.83-3.88 (m, 4H), 3.47-3.55 (m, 1H), 1.27-1.37 (m, 4H), 1.10-1.19 (m, 1H). LCMS m/z = 314 [MH]$^+$. |
| 188 | 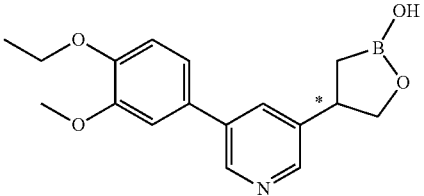 [SMILES: CCOc1ccc(-c2cncc(C3COB(O)C3)c2)cc1OC]<br>4-(5-(4-ethoxy-3-methoxyphenyl)pyridin-3-yl)-1,2-oxaborolan-2-ol, enantiomer2 | $^1$H NMR (DMSO-$d_6$, 400 MHz): δ 8.73 (s, 1H), 8.71 (d, J = 2.0 Hz, 1H), 8.42 (d, J = 2.0 Hz, 1H), 7.94 (t, J = 2.2 Hz, 1H), 7.28 (d, J = 2.0 Hz, 1H), 7.21-7.25 (m, 1H), 7.03-7.07 (m, 1H), 4.27 (t, J = 8.3 Hz, 1H), 4.05 (q, J = 7.2 Hz, 2H), 3.83-3.88 (m, 4H), 3.47-3.55 (m, 1H), 1.27-1.37 (m, 4H), 1.10-1.19 (m, 1H). LCMS m/z = 314 [MH]$^+$. RT [Analytical SFC Method AA] = 3.61 min. |
| 189 | 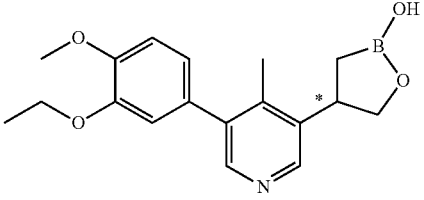 [SMILES: CCOc1cc(-c2cncc(C3COB(O)C3)c2C)ccc1OC]<br>4-(5-(3-ethoxy-4-methoxyphenyl)-4-methylpyridin-3-yl)-1,2-oxaborolan-2-ol, enantiomer 2 | $^1$H NMR (DMSO-$d_6$, 400 MHz): δ 8.71 (s, 1H), 8.43 (s, 1H), 8.21 (s, 1H), 7.04 (d, J = 8.0 Hz, 1H), 6.90 (d, J = 2.3 Hz, 1H), 6.82-6.85 (m, 1H), 4.24-4.28 (m, 1H), 4.03 (q, J = 7.0 Hz, 2H), 3.90-3.95 (m, 1H), 3.80 (s, 3H), 3.63-3.71 (m, 1H), 2.22 (s, 3H), 1.30-1.36 (m, 4H), 1.04-1.10 (m, 1H). LCMS m/z = 328 [MH]$^+$. RT [Analytical SFC Method E] = 5.71 min. |
| 190 | 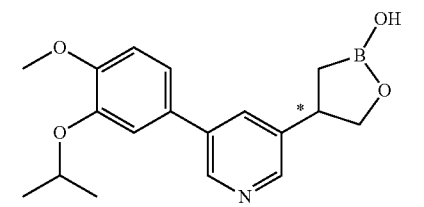 [SMILES: COc1ccc(-c2cncc(C3COB(O)C3)c2)cc1OC(C)C]<br>4-(5-(3-isopropoxy-4-methoxyphenyl)pyridin-3-yl)-1,2-oxaborolan-2-ol, enantiomer 2 | $^1$H NMR (DMSO-$d_6$, 400 MHz): δ 8.72 (s, 1H), 8.69 (d, J = 2.0 Hz, 1H), 8.42 (d, J = 2.0 Hz, 1H), 7.92 (t, J = 2.0 Hz, 1H), 7.29-7.24 (m, 2H), 7.07 (d, J = 8.0 Hz, 1H), 4.68-4.74 (m, 1H), 4.27 (t, J = 8.3 Hz, 1H), 3.86 (t, J = 9.0 Hz, 1H), 3.79 (s, 3H), 3.47-3.55 (m, 1H), 1.26-1.35 (m, 7H), 1.10-1.18 (m, 1H). LCMS m/z = 328 [MH]$^+$. RT [Analytical SFC Method BA] = 5.69 min. |

| Example No. | Structure and Name | Analytical Data |
|---|---|---|
| 191 | 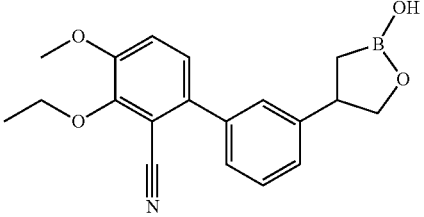 [SMILES: CCOc1c(OC)ccc(-c2cccc(C3COB(O)C3)c2)c1C#N]<br>3-ethoxy-3'-(2-hydroxy-1,2-oxaborolan-4-yl)-4-methoxy-[1,1'-biphenyl]-2-carbonitrile | $^1$H NMR (DMSO-$d_6$, 400 MHz): δ 7.31-7.46 (m, 3H), 7.33-7.36 (m, 2H), 7.27 (d, J = 8.8 Hz, 1H), 4.18-4.28 (m, 3H), 3.90 (s, 3H), 3.81 (t, J = 8.8 Hz, 1H), 3.45-3.52 (m, 1H), 1.26-1.34 (m, 4H), 1.08-1.11 (m, 1H) . LCMS m/z = 338 [MH]$^+$. |
| 192 | 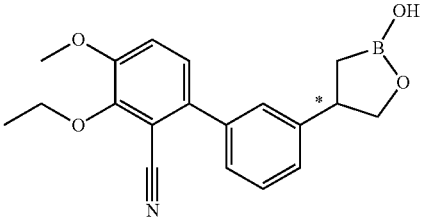 [SMILES: CCOc1c(OC)ccc(-c2cccc(C3COB(O)C3)c2)c1C#N]<br>3-ethoxy-3'-(2-hydroxy-1,2-oxaborolan-4-yl)-4-methoxy-[1,1'-biphenyl]-2-carbonitrile, enantiomer 2 | RT [Analytical SFC Method CA] = 3.14 min. |
| 193 | 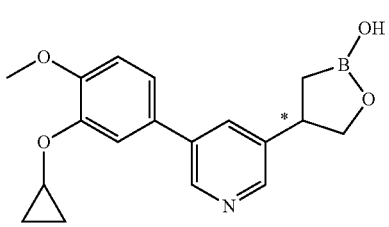 [SMILES: COc1ccc(-c2cncc(C3COB(O)C3)c2)cc1OC1CC1]<br>4-(5-(3-cyclopropoxy-4-methoxyphenyl)pyridin-3-yl)-1,2-oxaborolan-2-ol, enantiomer 1 | $^1$H NMR (DMSO-$d_6$, 400 MHz): δ 8.69-8.72 (m, 2H), 8.44 (d, J = 2.0 Hz, 1H), 7.91 (t, J = 2.0 Hz, 1H), 7.53 (d, J = 2.0 Hz, 1H), 7.28 (dd, J = 2.4, 8.3 Hz, 1H), 7.07 (d, J = 8.8 Hz, 1H), 4.25-4.31 (m, 1H), 3.97-4.01 (m, 1H), 3.86 (t, J = 8.8 Hz, 1H), 3.78 (s, 3H), 3.46-3.57 (m, 1H), 1.32 (dd, J = 8.1, 16.4 Hz, 1H), 1.14 (dd, J = 10.3, 16.1 Hz, 1H), 0.76-0.83 (m, 2H), 0.67-0.72 (m, 2H). LCMS m/z = 326 [MH]$^+$. RT [Analytical SFC Method D] = 5.38 min. |
| 194 | 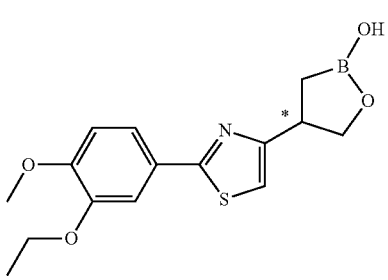 [SMILES: CCOc1cc(-c2nc(C3COB(O)C3)cs2)ccc1OC]<br>(−) 4-(2-(3-ethoxy-4-methoxyphenyl)thiazol-4-yl)-1,2-oxaborolan-2-ol, enantiomer 1 | $^1$H NMR (DMSO-$d_6$, 400 MHz): δ 8.66 (br s, 1H), 7.42-7.46 (m, 2H), 7.30 (s, 1H), 7.05 (d, J = 8.3 Hz, 1H), 4.24-4.28 (m, 1H), 4.09 (q, J = 7.0 Hz, 2H), 3.90-3.95 (m, 1H), 3.82 (s, 3H), 3.55-3.63 (m, 1H), 1.36 (t, J = 7.0 Hz, 3H), 1.25-1.31 (m, 1H), 1.11-1.18 (m, 1H). LCMS m/z = 320 [MH]$^+$. RT [Analytical SFC Method DA] = 4.47 min. [α]$^{20}_D$ −17.4 (c = 0.1, EtOH). |

| Example No. | Structure and Name | Analytical Data |
|---|---|---|
| 195 | 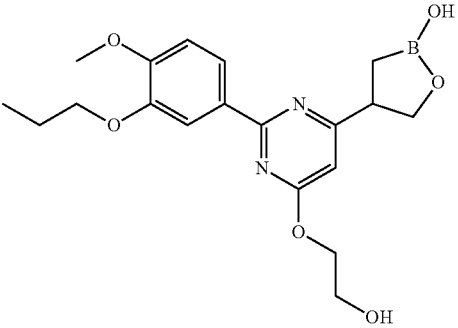 [SMILES: CCCOc1cc(-c2nc(OCCO)cc(C3COB(O)C3)n2)ccc1OC]<br>4-(6-(2-hydroxyethoxy)-2-(4-methoxy-3-propoxyphenyl)pyrimidin-4-yl)-1,2-oxaborolan-2-ol | $^1$H NMR (DMSO-d$_6$, 400 MHz): δ 8.65 (s, 1H), 7.97 (dd, J = 2.0, 8.3 Hz, 1H), 7.93 (d, J = 1.7 Hz 1H), 7.06 (d, J = 8.6 Hz 1H), 6.64 (s, 1H), 4.89 (t, J = 5.4 Hz, 1H), 4.42-4.47 (m, 2H), 4.26 (dd, J = 7.3, 9.0 Hz, 1H), 4.00 (t, J = 6.5 Hz, 2H), 3.95 (dd, J = 6.4, 9.0 Hz, 1H), 3.83 (s, 3H), 3.74-3.80 (m, 2H), 3.47-3.54 (m, 1H), 1.73-1.81 (m, 2H), 1.20-1.28 (m, 1H), 1.10-1.17 (m, 1H), 1.01 (t, J = 7.3 Hz, 3H). LCMS m/z = 406 [MH + H$_2$O]$^+$. |
| 196 | 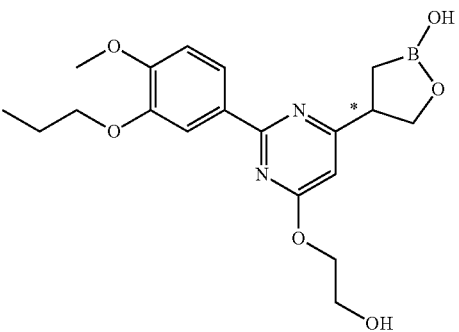 [SMILES: CCCOc1cc(-c2nc(OCCO)cc(C3COB(O)C3)n2)ccc1OC]<br>(−) 4-(6-(2-hydroxyethoxy)-2-(4-methoxy-3-propoxyphenyl)pyrimidin-4-yl)-1,2-oxaborolan-2-ol, enantiomer 1 | $^1$H NMR (DMSO-d$_6$, 400 MHz): δ 8.65 (s, 1H), 7.97 (dd, J = 2.0, 8.3 Hz, 1H), 7.93 (d, J = 1.7 Hz, 1H), 7.06 (d, J = 8.6 Hz 1H), 6.64 (s, 1H), 4.89 (t, J = 5.4 Hz, 1H), 4.42-4.47 (m, 2H), 4.26 (dd, J = 7.3, 9.0 Hz, 1H), 4.00 (t, J = 6.5 Hz, 2H), 3.95 (dd, J = 6.4, 9.0 Hz, 1H), 3.83 (s, 3H), 3.74-3.80 (m, 2H), 3.47-3.54 (m, 1H), 1.73-1.81 (m, 2H), 1.20-1.28 (m, 1H), 1.10-1.17 (m, 1H), 1.01 (t, J = 7.3 Hz, 3H). LCMS m/z = 406 [MH + H$_2$O]$^+$ −38.9 (c = 0.1, EtOH). |
| 197 | 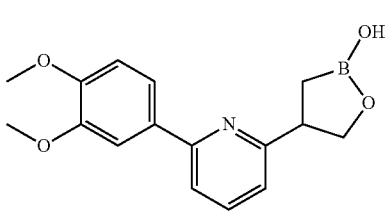 [SMILES: COc1ccc(-c2cccc(C3COB(O)C3)n2)cc1OC]<br>4-(6-(3,4-dimethoxyphenyl)pyridin-2-yl)-1,2-oxaborolan-2-ol | $^1$H NMR (DMSO-d$_6$, 400 MHz): δ 8.59 (s, 1H), 7.73-7.75 (m, 3H), 7.64 (d, J = 8.4 Hz, 1H), 7.15-7.17 (m, 1H), 7.03 (d, J = 8.4 Hz, 1H), 4.27-4.31 (m, 1H), 3.95-3.99 (m, 1H), 3.84 (s, 3H), 3.80 (s, 3H), 3.57-3.60 (m, 1H), 1.15-1.29 (m, 2H). LCMS m/z = 298 [MH]$^-$. |
| 198 | 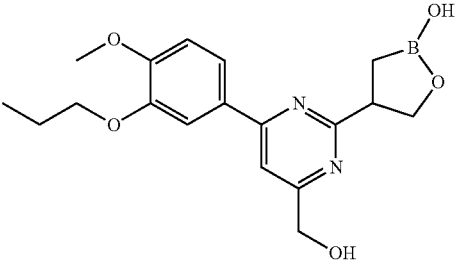 [SMILES: CCCOc1cc(-c2cc(CO)nc(C3COB(O)C3)n2)ccc1OC]<br>4-(4-(hydroxymethyl)-6-(4-methoxy-3-propoxyphenyl)pyrimidin-2-yl)-1,2-oxaborolan-2-ol | $^1$H NMR (DMSO-d$_6$, 400 MHz): δ 8.71 (br s, 1H), 7.70-7.81 (m, 3H), 7.53 (d, J = 8.0 Hz, 1H), 7.07-7.14 (m, 1H), 5.71 (br s, 1H), 4.55 (d, J = 5.5 Hz, 2H), 4.29 (t, J = 8.3 Hz, 1H), 3.95-4.11 (m, 2H), 3.81-3.88 (m, 4H), 1.71-1.83 (m, 2H), 1.27 (d, J = 8.0 Hz, 1H), 0.96-1.05 (m, 4H). LCMS m/z = 359 [MH]$^+$. |

| Example No. | Structure and Name | Analytical Data |
|---|---|---|
| 199 | 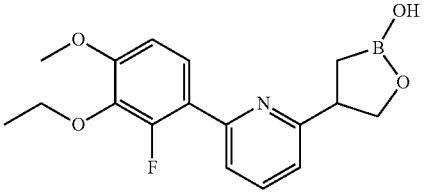 [SMILES: CCOc1c(OC)ccc(-c2cccc(C3COB(O)C3)n2)c1F]<br>4-(6-(3-ethoxy-2-fluoro-4-methoxyphenyl)pyridin-2-yl)-1,2-oxaborolan-2-ol | $^1$H NMR (DMSO-d$_6$, 400 MHz): δ 8.60 (br s, 1H), 7.75-7.82 (m, 1H), 7.67 (t, J = 8.8 Hz, 1H), 7.55 (d, J = 6.4 Hz, 1H), 7.25 (d, J = 7.6 Hz, 1H), 7.02 (d, J = 8.1 Hz, 1H), 4.25-4.32 (m, 1H), 4.06 (q, J = 7.0 Hz, 2H), 3.96-4.02 (m, 1H), 3.87 (s, 3H), 3.61 (td, J = 8.0, 15.8 Hz, 1H), 1.13-1.32 (m, 5H). LCMS m/z = 332 [MH]$^+$. |
| 200 | 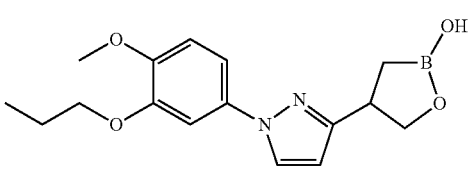 [SMILES: CCCOc1cc(-n2ccc(C3COB(O)C3)n2)ccc1OC]<br>4-(1-(4-methoxy-3-propoxyphenyl)-1H-pyrazol-3-yl)-1,2-oxaborolan-2-ol | $^1$H NMR (DMSO-d$_6$, 400 MHz): δ 8.61 (s, 1H), 8.30 (d, J = 2.0 Hz, 1H), 7.33 (d, J = 2.5 Hz, 1H), 7.25 (dd, J = 2.5, 8.5 Hz, 1H), 7.01 (d, J = 9.0 Hz, 1H), 6.37 (d, J = 2.5 Hz, 1H), 4.18-4.25 (m, 1H), 3.98 (t, J = 6.5 Hz, 2H), 3.89 (t, J = 8.5 Hz, 1H), 3.78 (s, 3H), 3.44-3.52 (m, 1H), 1.71-1.80 (m, 2H), 1.27 (dd, J = 8.5, 16.1 Hz, 1H), 1.03-1.13 (m, 1H), 0.99 (t, J = 7.3 Hz, 3H). LCMS m/z = 317 [MH]$^+$. |
| 201 | 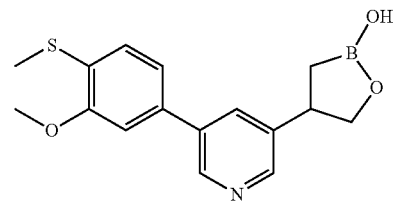<br>4-(5-(3-methoxy-4-(methylthio)phenyl)pyridin-3-yl)-1,2-oxaborolan-2-ol | $^1$H NMR (DMSO-d$_6$, 400 MHz): δ 8.60 (br s, 1H), 7.75-7.82 (m, 1H), 7.67 (t, J = 8.8 Hz, 1H), 7.55 (d, J = 6.4 Hz, 1H), 7.25 (d, J = 7.6 Hz, 1H), 7.02 (d, J = 8.1 Hz, 1H), 4.25-4.32 (m, 1H), 4.06 (q, J = 7.0 Hz, 2H), 3.96-4.02 (m, 1H), 3.87 (s, 2H), 3.57-3.65 (m, 1H), 1.13-1.33 (m, 5H). LCMS m/z = 316 [MH]$^+$. |
| 202 | 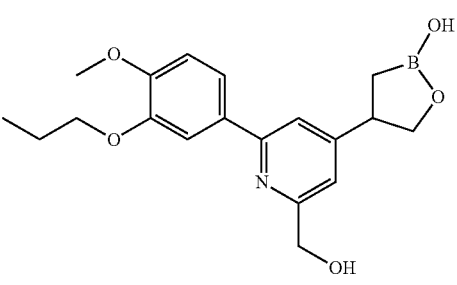 [SMILES: CCCOc1cc(-c2cc(C3COB(O)C3)cc(CO)n2)ccc1OC]<br>4-(2-(hydroxymethyl)-6-(4-methoxy-3-propoxyphenyl)pyridin-4-yl)-1,2-oxaborolan-2-ol | $^1$H NMR (DMSO-d$_6$, 400 MHz): δ 8.74 (s, 1H), 7.61-7.69 (m, 3H), 7.26 (s, 1H), 7.03 (d, J = 8.3 Hz, 1H), 5.40 (t, J = 5.6 Hz, 1H), 4.58 (d, J = 5.9 Hz, 2H), 4.29 (t, J = 8.3 Hz, 1H), 4.00 (t, J = 6.4 Hz, 2H), 3.82-3.89 (m, 1H), 3.81 (s, 3H), 3.47-3.56 (m, 1H), 1.72-1.81 (m, 2H), 1.32 (dd, J = 8.3, 16.1 Hz, 1H), 1.09 (dd, J = 9.8, 16.6 Hz, 1H), 1.01 (t, J = 7.6 Hz, 3H). LCMS m/z = 358 [MH]$^+$. |
| 203 | 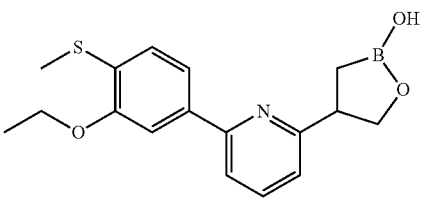 [SMILES: CCOc1cc(-c2cccc(C3COB(O)C3)n2)ccc1SC]<br>4-(6-(3-ethoxy-4-(methylthio)phenyl)pyridin-2-yl)-1,2-oxaborolan-2-ol | $^1$H NMR (DMSO-d$_6$, 400 MHz): δ 8.61 (br s, 1H), 7.44-7.83 (m, 2H), 7.67-7.73 (m, 2H), 7.18-7.24 (m, 2H), 4.26-4.32 (m, 1H), 4.19 (q, J = 7.1 Hz, 2H), 3.97 (dd, J = 6.6, 8.8 Hz, 1H), 3.57-3.64 (m, 1H), 2.42 (s, 3H), 1.38 (t, J = 7.0 Hz, 3H), 1.22-1.31 (m, 1H), 1.14-1.22 (m, 1H). LCMS m/z = 330 [MH]$^+$. |

| Example No. | Structure and Name | Analytical Data |
|---|---|---|
| 204 | 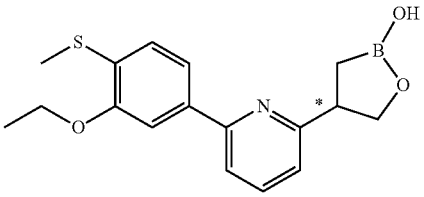 [SMILES: CCOc1cc(-c2cccc(C3COB(O)C3)n2)ccc1SC]<br>4-(6-(3-ethoxy-4-(methylthio)phenyl)pyridin-2-yl)-1,2-oxaborolan-2-ol, enantiomer 1 | RT [Analytical SFC Method Y] = 7.70 min. |
| 205 | 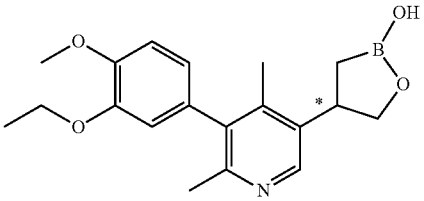 [SMILES: CCOc1cc(-c2c(C)ncc(C3COB(O)C3)c2C)ccc1OC]<br>(+) 4-(5-(3-ethoxy-4-methoxyphenyl)-4,6-dimethylpyridin-3-yl)-1,2-oxaborolan-2-ol, enantiomer 1 | $^1$H NMR (DMSO-$d_6$, 400 MHz): δ 8.70 (d, J = 2.0 Hz, 1H), 8.31 (s, 1H), 7.03 (d, J = 7.8 Hz, 1H), 6.72 (dd, J = 2.0, 3.9 Hz, 1H), 6.65 (ddd, J = 2.0, 4.2, 8.1 Hz, 1H), 4.22 (dd, J = 7.3, 8.8 Hz, 1H), 3.96-4.01 (m, 2H), 3.84-3.92 (m, 1H), 3.80 (s, 3H), 3.54-3.62 (m, 1H), 2.13 (s, 3H), 1.97 (s, 3H), 1.25-1.34 (m, 4H), 0.99-1.09 (m, 1H). LCMS m/z = 342 [MH]$^+$. [α]$^{20}_D$ +9.6 (c = 0.1, EtOH). |
| 206 | 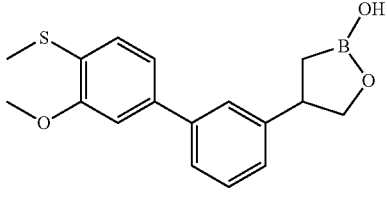 [SMILES: COc1cc(-c2cccc(C3COB(O)C3)c2)ccc1SC]<br>4-(3'-methoxy-4'-(methylthio)-[1,1'-biphenyl]-3-yl)-1,2-oxaborolan-2-ol | $^1$H NMR (DMSO-$d_6$, 400 MHz): δ 8.65 (s, 1H), 7.56 (s, 1H), 7.51 (d, J = 7.8 Hz, 1H), 7.38 (t, J = 7.6 Hz, 1H), 7.26 (d, J = 8.1 Hz, 2H), 7.20 (d, J = 8.6 Hz, 2H), 4.26 (t, J = 8.2 Hz, 1H), 3.91 (s, 3H), 3.82 (t, J = 8.9 Hz, 1H), 3.44-3.52 (m, 1H), 2.41 (s, 3H), 1.29 (dd, J = 8.2, 16.3 Hz, 1H), 1.09 (dd, J = 10.3, 16.1 Hz, 1H). LCMS m/z = 315 [MH]$^+$. |
| 207 | 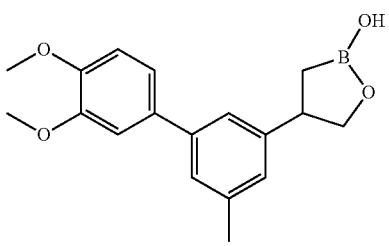 [SMILES: COc1ccc(-c2cc(C)cc(C3COB(O)C3)c2)cc1OC]<br>4-(3',4'-dimethoxy-5-methyl-[1,1'-biphenyl]-3-yl)-1,2-oxaborolan-2-ol | $^1$H NMR (DMSO-$d_6$, 400 MHz): δ 8.64 (s, 1H), 7.27-7.30 (m, 2H), 7.14-7.18 (m, 2H), 6.99-7.02 (m, 2H), 4.22-4.26 (m, 1H), 3.78-3.84 (m, 7H), 3.37-3.46 (m, 1H), 2.34 (s, 3H), 1.24-1.30 (m, 1H), 1.04-1.11 (m, 1H). LCMS m/z 313 [MH]$^+$. |
| 208 | 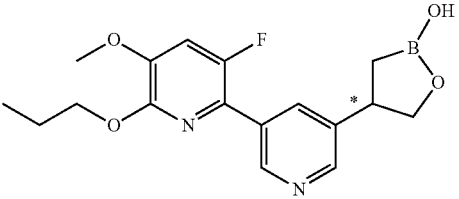 [SMILES: CCCOc1nc(-c2cncc(C3COB(O)C3)c2)c(F)cc1OC]<br>(+) 4-(3-fluoro-5-methoxy-6-propoxy-[2,3'-bipyridin]-5'-yl)-1,2-oxaborolan-2-ol, enantiomer 2 | $^1$H NMR (DMSO-$d_6$, 400 MHz): δ 8.89 (s, 1H), 8.73 (s, 1H), 8.49 (d, J = 2.0 Hz, 1H), 8.09 (s, 1H), 7.49 (d, J = 12.0 Hz, 1H), 4.28-4.33 (m, 3H), 3.87 (s, 3H), 3.82 (t, J = 8.7 Hz, 1H), 3.49-3.57 (m, 1H), 1.73-1.81 (m, 2H), 1.31-1.37 (m, 1H), 1.03-1.09 (m, 1H), 0.98 (t, J = 7.5 Hz, 3H). LCMS m/z = 347 [MH]$^+$. [α]$^{20}_D$ +20.4 (c = 0.1, EtOH). |

| Example No. | Structure and Name | Analytical Data |
|---|---|---|
| 209 | 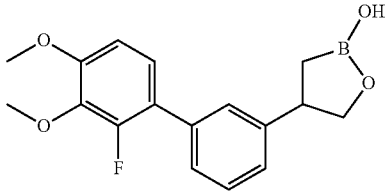 [SMILES: COc1ccc(-c2cccc(C3COB(O)C3)c2)c(F)c1OC]<br>4-(2-fluoro-3',4'-dimethoxy-[1,1'-biphenyl]-3-yl)-1,2-oxaborolan-2-ol | ¹H NMR (DMSO-d₆, 400 MHz): δ 8.66 (br s, 1H), 7.35-7.40 (m, 2H), 7.26-7.34 (m, 2H), 7.18 (t, J = 8.4 Hz, 1H), 6.95-7.00 (m, 1H), 4.22-4.28 (m, 1H), 3.86 (s, 3H), 3.77-3.84 (m, 4H), 3.41-3.52 (m, 1H), 1.29 (q, J = 8.0 Hz, 1H), 1.04 (q, 8.0 Hz, 1H). LCMS m/z = 317 [MH]⁺. |
| 210 | 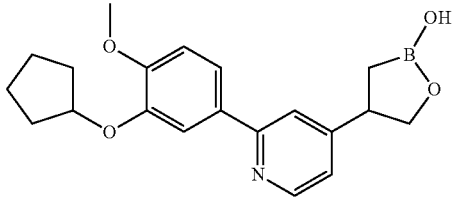 [SMILES: COc1ccc(-c2cc(C3COB(O)C3)ccn2)cc1OC1CCCC1]<br>4-(2-(3-(cyclopentyloxy)-4-methoxyphenyl)pyridin-4-yl)-1,2-oxaborolan-2-ol | ¹H NMR (DMSO-d₆, 400 MHz): δ 8.72 (s, 1H), 8.50 (d, J = 5.4 Hz, 1H), 7.77 (s, 1H), 7.66 (d, J = 2.0 Hz, 1H), 7.62 (dd, J = 2.2, 8.6 Hz, 1H), 7.18 (dd, J = 1.2, 5.1 Hz, 1H), 7.03 (d, J = 8.3 Hz, 1H), 4.87-4.94 (m, 1H), 4.24-4.31 (m, 1H), 3.84 (t, J = 9.0 Hz, 1H), 3.79 (s, 3H), 3.42-3.55 (m, 1H), 1.87-1.96 (m, 2H), 1.70-1.80 (m, 4H), 1.56-1.63 (m, 2H), 1.30 (dd, J = 8.3, 16.1 Hz, 1H), 1.10 (dd, J = 10.0, 16.4 Hz, 1H). LCMS m/z = 354 [MH]⁺. |
| 211 | 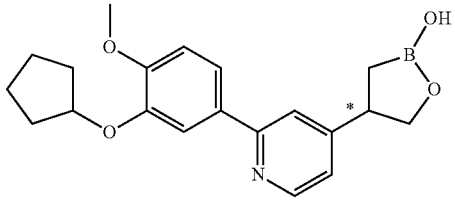 [SMILES: COc1ccc(-c2cc(C3COB(O)C3)ccn2)cc1OC1CCCC1]<br>4-(2-(3-(cyclopentyloxy)-4-methoxyphenyl)pyridin-4-yl)-1,2-oxaborolan-2-ol, enantiomer 2 | ¹H NMR (DMSO-d₆, 400 MHz): δ 8.72 (s, 1H), 8.50 (d, J = 5.4 Hz, 1H), 7.77 (s, 1H), 7.66 (d, J = 2.0 Hz, 1H), 7.62 (dd, J = 2.2, 8.6 Hz, 1H), 7.18 (dd, J = 1.2, 5.1 Hz, 1H), 7.03 (d, J = 8.3 Hz, 1H), 4.87-4.94 (m, 1H), 4.24-4.31 (m, 1H), 3.84 (t, J = 9.0 Hz, 1H), 3.79 (s, 3H), 3.42-3.55 (m, 1H), 1.87-1.96 (m, 2H), 1.70-1.80 (m, 4H), 1.56-1.63 (m, 2H), 1.30 (dd, J = 8.3, 16.1 Hz, 1H), 1.10 (dd, J = 10.0, 16.4 Hz, 1H). LCMS m/z = 354 [MH]⁺. RT [Analytical SFC Method EA] = 4.27 min. |
| 212 | 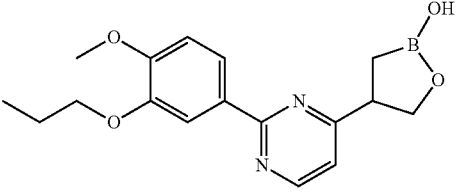 [SMILES: CCCOc1cc(-c2nccc(C3COB(O)C3)n2)ccc1OC]<br>4-(2-(4-methoxy-3-propoxyphenyl)pyrimidin-4-yl)-1,2-oxaborolan-2-ol | ¹H NMR (DMSO-d₆, 400 MHz): δ 8.71 (d, J = 5.1 Hz, 1H), 8.69 (s, 1H), 8.00 (dd, J = 1.8, 8.4 Hz, 1H), 7.96 (d, J = 1.7 Hz, 1H), 7.26 (d, J = 4.9 Hz, 1H), 7.08 (d, J = 8.3 Hz, 1H), 4.30 (dd, J = 7.5, 8.9 Hz, 1H), 3.97-4.02 (m, 3H), 3.83 (s, 3H), 3.55-3.63 (m, 1H), 1.73-1.82 (m, 2H), 1.25-1.33 (m, 1H), 1.13-1.20 (m, 1H), 1.01 (t, J = 7.5 Hz, 3H). LCMS m/z = 329 [MH]⁺. |
| 213 | 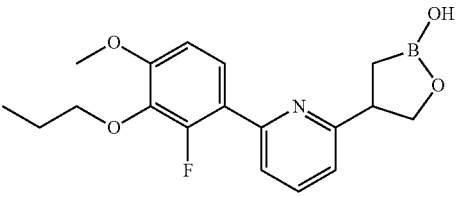<br>4-(6-(2-fluoro-4-methoxy-3-propoxyphenyl)pyridin-2-yl)-1,2-oxaborolan-2-ol | ¹H NMR (DMSO-d₆, 400 MHz): δ 8.61 (s, 1H), 7.75-7.80 (m, 1H), 7.66 (t, J = 8.8 Hz, 1H), 7.55 (dd, J = 1.8, 7.7 Hz, 1H), 7.24 (d, J = 7.6 Hz, 1H), 6.99-7.04 (m, 1H), 4.27 (dd, J = 7.8, 8.6 Hz, 1H), 3.92-4.02 (m, 3H), 3.86 (s, 3H), 3.57-3.65 (m, 1H), 1.63-1.72 (m, 2H), 1.14-1.31 (m, 2H), 0.98 (t, J = 7.3 Hz, 3H). LCMS m/z = 346 [MH]⁺. |

| Example No. | Structure and Name | Analytical Data |
|---|---|---|
| 214 | 4-(5-(3-ethoxy-5-fluoro-4-methoxyphenyl)pyridin-3-yl)-1,2-oxaborolan-2-ol, enantiomer 2 | $^1$H NMR (DMSO-$d_6$, 400 MHz): δ 8.75 (d, J = 2.0 Hz, 1H), 8.71 (s, 1H), 8.47 (d, J = 1.47 Hz, 1H), 8.00 (s, 1H), 7.27 (dd, J = 2.0, 11.7 Hz, 1H), 7.20 (s, 1H), 4.27 (t, J = 8.3 Hz, 1H), 4.21 (q, J = 6.9 Hz, 2H), 3.82-3.90 (m, 3H), 3.45-3.56 (m, 2H), 1.39 (t, J = 6.9 Hz, 3H), 1.26-1.34 (m, 1H), 1.12-1.20 (m, 1H). LCMS m/z = 349 [MH + H$_2$O]$^+$. RT [Analytical SFC Method D] = 4.59 min. |
| 215 | 4-(6-(2-fluoro-4-methoxy-3-propoxyphenyl)pyrazin-2-yl)-1,2-oxaborolan-2-ol | $^1$H NMR (DMSO-$d_6$, 400 MHz): δ 8.81 (d, J = 2.4 Hz, 1H), 8.69 (s, 1H), 8.53 (s, 1H), 7.67 (t, J = 8.8 Hz, 1H), 7.07 (d, J = 7.8 Hz, 1H), 4.31 (t, J = 8.3 Hz, 1H), 3.94-4.06 (m, 3H), 3.89 (s, 3H), 3.67-3.75 (m, 1H), 1.64-1.73 (m, 2H), 1.27-1.36 (m, 1H), 1.15-1.25 (m, 1H), 0.98 (t, J = 7.3 Hz, 3H). LCMS m/z = 347 [MH]$^+$. |
| 216 | 4-(6-(2-fluoro-4-methoxy-3-propoxyphenyl)pyrazin-2-yl)-1,2-oxaborolan-2-ol, enantiomer 1 | $^1$H NMR (DMSO-$d_6$, 400 MHz): δ 8.81 (d, J = 2.4 Hz, 1H), 8.69 (s, 1H), 8.53 (s, 1H), 7.67 (t, J = 8.8 Hz, 1H), 7.07 (d, J = 7.8 Hz, 1H), 4.31 (t, J = 8.3 Hz, 1H), 3.94-4.06 (m, 3H), 3.89 (s, 3H), 3.67-3.75 (m, 1H), 1.64-1.73 (m, 2H), 1.27-1.36 (m, 1H), 1.15-1.25 (m, 1H), 0.98 (t, J = 7.3 Hz, 3H). LCMS m/z = 347 [MH]$^+$. RT [Analytical SFC Method C] = 4.40 min. |
| 217 | 4-(5-(4-ethoxy-2-fluoro-3-methoxyphenyl)pyridin-3-yl)-1,2-oxaborolan-2-ol | $^1$H NMR (DMSO-$d_6$, 400 MHz): δ 8.72 (s, 1H), 8.54 (t, J = 2.0 Hz, 1H), 8.48 (d, J = 2.5 Hz, 1H), 7.82 (d, J = 1.5 Hz, 1H), 7.24 (t, J = 8.8 Hz, 1H), 6.98-7.02 (m, 1H), 4.25-4.31 (m, 1H), 4.14 (q, J = 6.9 Hz, 2H), 3.81-3.87 (m, 4H), 3.46-3.56 (m, 1H), 1.38 (t, J = 6.8 Hz, 3H), 1.32 (dd, J = 8.3, 16.3 Hz, 1H), 1.10 (dd, J = 10.0, 16.1 Hz, 1H). LCMS m/z = 332 [MH]$^+$. |
| 218 | 4-(6'-methoxy-2-methyl-5'-propoxy-[3,3'-bipyridin]-5-yl)-1,2-oxaborolan-2-ol | $^1$H NMR (DMSO-$d_6$, 400 MHz): δ 8.69 (s, 1H), 8.37 (d, J = 2.0 Hz, 1H), 7.69 (m, 1H), 7.54-7.56 (m, 1H), 7.27-7.33 (m, 1H), 4.23-4.27 (m, 1H), 3.98-4.01 (m, 2H), 3.91 (s, 3H), 3.78-3.83 (m, 1H), 3.43-3.49 (m, 1H), 2.41 (s, 3H), 1.72-1.77 (m, 2H), 1.26-1.30 (m, 1H), 1.07-1.11 (m, 1H), 0.96-1.00 (m, 3H). LCMS m/z = 343 [MH]$^+$. |

| Example No. | Structure and Name | Analytical Data |
|---|---|---|
| 219 | (−) 4-(6'-methoxy-2-methyl-5'-propoxy-[3,3'-bipyridin]-5-yl)-1,2-oxaborolan-2-ol, enantiomer 1 | $^1$H NMR (DMSO-$d_6$, 400 MHz): δ 8.69 (s, 1H), 8.37 (d, J = 2.0 Hz, 1H), 7.69 (m, 1H), 7.54-7.56 (m, 1H), 7.27-7.33 (m, 1H), 4.23-4.27 (m, 1H), 3.98-4.01 (m, 2H), 3.91 (s, 3H), 3.78-3.83 (m, 1H), 3.43-3.49 (m, 1H), 2.41 (s, 3H), 1.72-1.77 (m, 2H), 1.26-1.30 (m, 1H), 1.07-1.11 (m, 1H), 0.96-1.00 (m, 3H). LCMS m/z = 343 [MH]$^+$. RT [Analytical SFC Method Z] = 2.28 min. [α]$^{20}_D$ −16.2 (c = 0.1, EtOH). |
| 220 | 4-(6-(3-ethoxy-4-methoxyphenyl)-4-(trifluoromethyl)pyridin-2-yl)-1,2-oxaborolan-2-ol | $^1$H NMR (MeOD-$d_3$, 400 MHz): δ 7.85 (s, 1H), 7.76 (d, J = 2.0 Hz, 1H), 7.67 (dd, J = 2.0, 8.3 Hz, 1H), 7.39 (s, 1H), 7.06 (d, J = 8.8 Hz, 1H), 4.17 (q, J = 7.2 Hz, 3H), 4.02 (br s, 1H), 3.89 (s, 3H), 3.57 (br s, 1H), 1.45 (t, J = 7.1 Hz, 3H), 1.33-1.41 (m, 1H), 1.24-1.32 (m, 1H). LCMS m/z 382 [MH]$^+$. |
| 221 | 4-(5-(3,4-dimethoxyphenyl)pyridin-3-yl)-1,2-oxaborolan-2-ol, enantiomer 2 | $^1$H NMR (DMSO-$d_6$, 400 MHz): δ 8.72 (d, J = 2.8 Hz, 2H), 8.43 (d, J = 2.0 Hz, 1H), 7.95 (t, J = 2.0 Hz, 1H), 7.25-7.29 (m, 1H), 7.06 (d, J = 8.4 Hz, 2H), 4.28 (t, J = 4.28 Hz, 1H), 3.84-3.88 (m, 4H), 3.80 (s, 3H), 3.46-3.54 (m, 1H), 1.28-1.34 (m, 1H), 1.12-1.18 (m, 1H). LCMS m/z = 300 [MH]$^+$. RT [Analytical SFC Method FA] = 6.04 min. |
| 222 | 4-(6-ethoxy-2-(3-ethoxy-4-methoxyphenyl)pyrimidin-4-yl)-1,2-oxaborolan-2-ol | $^1$H NMR (DMSO-$d_6$, 400 MHz): δ 8.66 (s, 1H), 7.93-7.99 (m, 2H), 7.05 (d, J = 8.5 Hz, 1H), 6.59 (s, 1H), 4.47 (q, J = 6.9 Hz, 2H), 4.25 (t, J = 8.0 Hz, 1H), 4.09 (q, J = 6.9 Hz, 2H), 3.91-3.98 (m, 1H), 3.82 (s, 3H), 3.48 (br s, 1H), 1.36 (t, J = 7.0 Hz, 6H), 1.19-1.28 (m, 1H), 1.09-1.18 (m, 1H). LCMS m/z [Analytical SFC Method FA] = 359 [MH]$^+$. |

| Example No. | Structure and Name | Analytical Data |
|---|---|---|
| 223 | 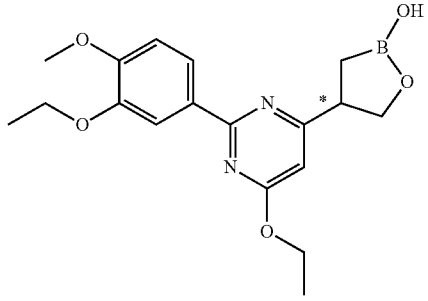 [SMILES: CCOc1cc(C2COB(O)C2)nc(-c2ccc(OC)c(OCC)c2)n1]<br>4-(6-ethoxy-2-(3-ethoxy-4-methoxyphenyl)pyrimidin-4-yl)-1,2-oxaborolan-2-ol, enantiomer 1 | $^1$H NMR (DMSO-$d_6$, 400 MHz): δ 8.66 (s, 1H), 7.93-7.99 (m, 2H), 7.05 (d, J = 8.5 Hz, 1H), 6.59 (s, 1H), 4.47 (q, J = 6.9 Hz, 2H), 4.25 (t, J = 8.0 Hz, 1H), 4.09 (q, J = 6.9 Hz, 2H), 3.91-3.98 (m, 1H), 3.82 (s, 3H), 3.48 (br s, 1H), 1.36 (t, J = 7.0 Hz, 6H), 1.19-1.28 (m, 1H), 1.09-1.18 (m, 1H). LCMS m/z = 359 [MH]$^+$. RT [Analytical SFC Method D] = 2.97 min. |
| 224 | 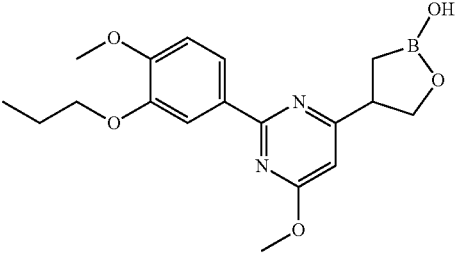 [SMILES: CCCOc1cc(-c2nc(OC)cc(C3COB(O)C3)n2)ccc1OC]<br>4-(6-methoxy-2-(4-methoxy-3-propoxyphenyl)pyrimidin-4-yl)-1,2-oxaborolan-2-ol | $^1$H NMR (DMSO-$d_6$, 400 MHz): δ 8.69 (s, 1H), 7.98 (dd, J = 2.0, 8.5 Hz, 1H), 7.94-7.97 (m, 1H), 7.06 (d, J = 8.5 Hz, 1H), 6.63 (s, 1H), 4.26 (dd, J = 7.5, 9.0 Hz, 1H), 3.97-4.03 (m, 5H), 3.94 (dd, J = 6.0, 9.0 Hz, 1H), 3.82 (s, 3H), 3.50 (d, J = 8.0 Hz, 1H), 1.72-1.81 (m, 2H), 1.20-1.27 (m, 1H), 1.10-1.17 (m, 1H), 1.00 (t, J = 7.5 Hz, 3H). LCMS m/z = 359 [MH]$^+$. |
| 225 | 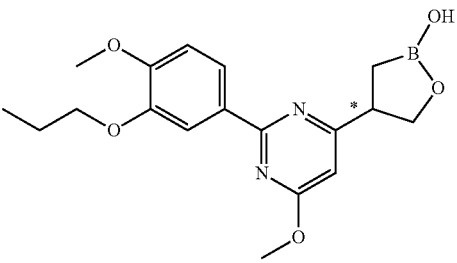 [SMILES: CCCOc1cc(-c2nc(OC)cc(C3COB(O)C3)n2)ccc1OC]<br>(−) 4-(6-methoxy-2-(4-methoxy-3-propoxyphenyl)pyrimidin-4-yl)-1,2-oxaborolan-2-ol, enantiomer 2 | $^1$H NMR (DMSO-$d_6$, 400 MHz): δ 8.69 (s, 1H), 7.98 (dd, J = 2.0, 8.5 Hz, 1H), 7.94-7.97 (m, 1H), 7.06 (d, J = 8.5 Hz, 1H), 6.63 (s, 1H), 4.26 (dd, J = 7.5, 9.0 Hz, 1H), 3.97-4.03 (m, 5H), 3.94 (dd, J = 6.0, 9.0 Hz, 1H), 3.82 (s, 3H), 3.50 (d, J = 8.0 Hz, 1H), 1.72-1.81 (m, 2H), 1.20-1.27 (m, 1H), 1.10-1.17 (m, 1H), 1.00 (t, J = 7.5 Hz, 3H). LCMS m/z = 359 [MH]$^+$. $[α]^{20}_D$ −16.9 (c = 0.1, EtOH). |
| 226 | 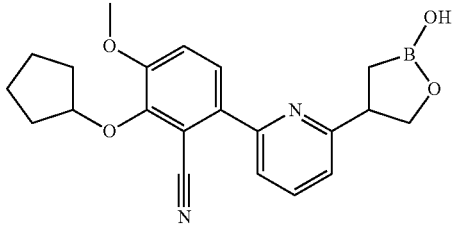 [SMILES: COc1ccc(-c2cccc(C3COB(O)C3)n2)c(C#N)c1OC1CCCC1]<br>2-(cyclopentyloxy)-6-(6-(2-hydroxy-1,2-oxaborolan-4-yl)pyridin-2-yl)-3-methoxybenzonitrile | $^1$H NMR (DMSO-$d_6$, 400 MHz): δ 8.57 (s, 1H) 7.81-7.88 (m, 1H), 7.59 (d, J = 7.8 Hz, 1H), 7.49-7.55 (m, 1H), 7.42-7.48 (m, 1H), 7.32 (d, J = 7.6 Hz, 1H), 5.11 (t, J = 5.1 Hz, 1H), 4.27 (t, J = 8.3 Hz, 1H), 4.08 (t, J = 8.7 Hz, 1H), 3.91 (s, 3H), 3.59-3.68 (m, 1H), 1.79-1.93 (m, 4H), 1.68-1.76 (m, 2H), 1.54-1.63 (m, 2H), 1.28-1.36 (m, 1H), 1.21-1.28 (m, 1H). LCMS m/z = 379 [MH]$^+$. |

| Example No. | Structure and Name | Analytical Data |
|---|---|---|
| 227 | 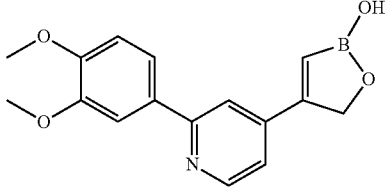 [SMILES: COc1ccc(-c2cc(C3=CB(O)OC3)ccn2)cc1OC]<br>4-(2-(3,4-dimethoxphenyl)pyridin-4-yl)-1,2-oxaborol-2(5H)-ol | $^1$H NMR (DMSO-$d_6$, 400 MHz): δ = 8.85 (s, 1H), 8.65 (d, J = 5.2 Hz, 1H), 7.97 (s, 1H), 7.73-7.74 (m, 2H), 7.43 (d, J = 4.8 Hz, 1H), 7.06 (d, J = 4.8 Hz, 1H), 6.58 (s, 1H), 5.00 (d, J = 1.6 Hz, 1H), 3.86 (m, 3H), 3.82 (s, 3H). LCMS m/z = 298 [MH]$^+$. |
| 228 | 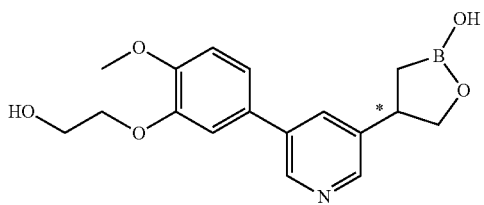 [SMILES: COc1ccc(-c2cncc(C3COB(O)C3)c2)cc1OCCO]<br>(+) 4-(5-(3-(2-hydroxyethoxy)-4-methoxyphenyl)pyridin-3-yl)-1,2-oxaborolan-2-ol, enantiomer 2 | 1H NMR (CD$_3$OD, 400 MHz): δ 8.60 (br s, 1H), 8.37 (br s, 1H), 7.93 (s, 1H), 7.22-7.30 (m, 2H), 7.10 (d, J = 8.3 Hz, 1H), 4.16 (t, J = 4.6 Hz, 2H), 4.08 (br s, 1H), 3.83-3.95 (m, 6H), 3.34-3.42 (m, 1H), 1.25-1.39 (m, 2H). LCMS m/z = 330 [MH]$^+$. [α]$^{20}_D$ +31.9 (c = 0.1, EtOH). |
| 229 | 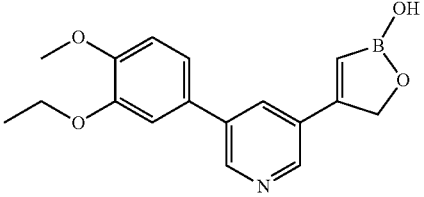 [SMILES: CCOc1cc(-c2cncc(C3=CB(O)OC3)c2)ccc1OC]<br>4-(5-(3-ethoxy-4-methoxyphenyl)pyridin-3-yl)-1,2-oxaborol-2(5H)-ol | $^1$H NMR (DMSO-$d_6$, 400 MHz): δ 8.85 (d, J = 2.0 Hz, 1H), 8.77 (s, 1H), 8.73 (d, J = 2.0 Hz, 1H), 8.13 (s, 1H), 7.31-7.33 (m, 2H), 7.07 (d, J = 8.0 Hz, 1H), 6.45 (s, 1H), 5.01 (s, 2H), 4.14 (q, J = 6.8 Hz, 2H), 3.81 (s, 3H), 1.36 (q, J = 6.8 Hz, 3H). LCMS m/z = 312 [MH]$^+$. |
| 230 | 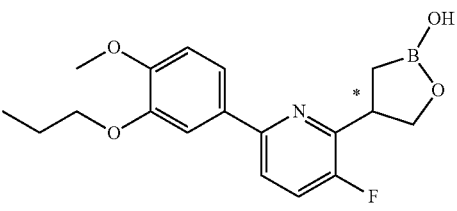 [SMILES: CCCOc1cc(-c2ccc(F)c(C3COB(O)C3)n2)ccc1OC]<br>4-(3-fluoro-6-(4-methoxy-3-propoxyphenyl)pyridin-2-yl)-1,2-oxaborolan-2-ol, enantiomer 1 | $^1$H NMR (DMSO-$d_6$, 400 MHz): δ 8.64 (br s, 1H), 7.84 (dd, J = 3.4, 8.8 Hz, 1H), 7.67 (t, J = 4.6 Hz, 2H), 7.60 (dd, J = 1.5, 8.3 Hz, 1H), 7.03 (d, J = 8.8 Hz, 1H), 4.27 (t, J = 7.8 Hz, 1H), 3.98-4.07 (m, 3H), 3.85 (d, J = 6.8 Hz, 1H), 3.81 (s, 3H), 1.72-1.80 (m, 2H), 1.22-1.27 (m, 2H), 1.00 (t, J = 7.3 Hz, 3H). LCMS m/z = 346 [MH]$^+$. RT [Analytical SFC Method G] = 3.25 min. |
| 231 | 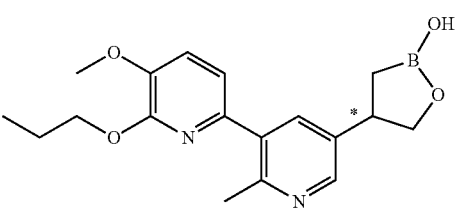 [SMILES: CCCOc1nc(-c2cc(C3COB(O)C3)cnc2C)ccc1OC]<br>(−) 4-(5-methoxy-2'-methyl-6-propoxy-[2,3'-bipyridin]-5'-yl)-1,2-oxaborolan-2-ol, enantiomer 1 | $^1$H NMR (DMSO-$d_6$, 400 MHz): δ 8.67 (s, 1H), 8.34 (s, 1H), 7.65 (s, 1H), 7.37 (d, J = 8.1 Hz, 1H), 7.13 (d, J = 8.1 Hz, 1H), 4.21-4.28 (m, 3H), 3.76-3.85 (m, 4H), 3.41-3.50 (m, 1H), 2.52 (s, 3H), 1.70-1.78 (m, 2H), 1.29 (dd, J = 8.2, 16.3 Hz, 1H), 1.06 (dd, J = 10.0, 16.1 Hz, 1H), 0.95 (t, J = 7.5 Hz, 3H). LCMS m/z = 343 [MH]$^+$. [α]$^{20}_D$ −20.1 (c = 0.1, EtOH). |

| Example No. | Structure and Name | Analytical Data |
|---|---|---|
| 232 | 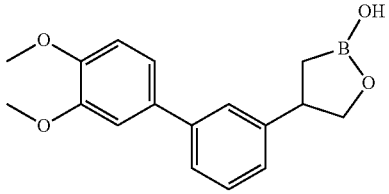
4-(3',4'-dimethoxy-[1,1'-biphenyl]-3-yl)-1,2-oxaborolan-2-ol | $^1$H NMR (DMSO-$d_6$, 400 MHz): δ 7.51 (s, 1H), 7.45 (br d, J = 7.6 Hz, 1H), 7.34-7.35 (m, 1H), 7.16-7.23 (m, 3H), 7.02 (d, J = 8.0 Hz, 1H), 4.22-4.28 (m, 1H), 3.84 (s, 3H), 3.81 (s, 1H), 3.79 (s, 3H), 3.42-3.51 (m, 1H), 1.25-1.31 (m, 1H), 1.05-1.12 (m, 1H). LCMS m/z = 299 [MH]$^+$. |
| 233 | 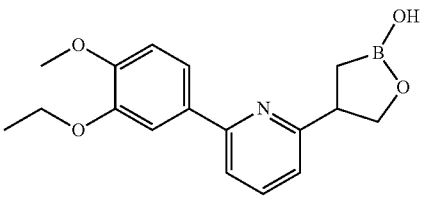 [SMILES: CCOc1cc(-c2cccc(C3COB(O)C3)n2)ccc1OC]
4-(6-(3-ethoxy-4-methoxyphenyl)pyridin-2-yl)-1,2-oxaborolan-2-ol | $^1$H NMR (DMSO-$d_6$, 400 MHz): δ 8.57 (s, 1H), 7.61-7.70 (m, 3H), 7.59 (d, J = 2.0 Hz, 1H), 7.11-7.13 (m, 1H), 7.00 (d, J = 8.4 Hz, 1H), 4.23-4.28 (m, 1H), 4.07-4.09 (m, 2H), 3.92-3.96 (m, 1H), 3.78 (s, 3H), 3.56-3.58 (m, 1H), 1.33 (t, J = 7.0 Hz, 3H), 1.16-1.24 (m, 2H). LCMS m/z = 314 [MH]$^+$. |

Single Crystal X-Ray Analysis of crystalline (R) 4-(5-(3-ethoxy-4-methoxyphenyl)pyridin-3-yl)-1,2-oxaborolan-2-ol (Example 3)

The crystal structure of Example 3 was determined by single crystal X-ray diffraction analysis. The single crystal X-ray diffraction data collection was performed on a Bruker D8 Quest diffractometer at room temperature. Data collection consisted of omega and phi scans. The structure was solved by intrinsic phasing using SHELX software suite in the Monoclinic class space group P2$_1$. The structure was subsequently refined by the full-matrix least squares method. All non-hydrogen atoms were found and refined using anisotropic displacement parameters. The hydrogen atoms located on oxygen were found from the Fourier difference map and refined with distances restrained. The remaining hydrogen atoms were placed in calculated positions and were allowed to ride on their carrier atoms. The final refinement included isotropic displacement parameters for all hydrogen atoms. Analysis of the absolute structure using likelihood methods (Hooft 2008) was performed using PLATON (Spek 2010). The Hooft parameter is reported as 0.02 with an Esd of 0.003 and the Parson's parameter is reported as 0.02 with an Esd of 0.003. The final R-index was 4.5%. A final difference Fourier revealed no missing or misplaced electron density.

FIG. 1 is the obtained X-ray structure (ORTEP drawing) of crystalline (R) 4-(5-(3-ethoxy-4-methoxyphenyl)pyridin-3-yl)-1,2-oxaborolan-2-ol (Example 3). The crystal structure data is summarized in Table 3.

TABLE 3

Crystal data and structure refinement for Example 3

| | |
|---|---|
| Empirical formula | C$_{17}$ H$_{20}$ B N O$_4$ |
| Formula weight | 313.15 |
| Temperature | 296(2) K |

TABLE 3-continued

Crystal data and structure refinement for Example 3

| | | |
|---|---|---|
| Wavelength | 1.54178 Å | |
| Crystal system | Monoclinic | |
| Space group | P2$_1$ | |
| Unit cell dimensions | a = 11.0798(5) Å | α = 90°. |
| | b = 13.1083(6) Å | β = 99.346(2)°. |
| | c = 11.2398(6) Å | γ = 90°. |
| Volume | 1610.77(13) Å$^3$ | |
| Z | 4 | |
| Density (calculated) | 1.291 Mg/m$^3$ | |
| Absorption coefficient | 0.738 mm$^{-1}$ | |
| F(000) | 664 | |
| Crystal size | 0.360 × 0.220 × 0.140 mm$^3$ | |
| Theta range for data collection | 3.986 to 70.310° | |
| Index ranges | −13 <= h <= 13, | |
| | −16 <= k <= 15, | |
| | −13 <= l <= 13, | |
| Reflections collected | 29459 | |
| Independent reflections | 6084 [R(int) = 0.0304] | |
| Completeness to theta = 67.679° | 99.9% | |
| Absorption correction | Empirical | |
| Refinement method | Full-matrix least-squares on F$^2$ | |
| Data/restraints/parameters | 6084/3/426 | |
| Goodness-of-fit on F$^2$ | 1.132 | |
| Final R indices [I > 2sigma(I)] | R1 = 0.0446, wR2 = 0.1005 | |
| R indices (all data) | R1 = 0.0452, wR2 = 0.1013 | |
| Absolute structure parameter | 0.02(3) | |
| Extinction coefficient | 0.125(4) | |
| Largest diff. peak and hole | 0.307 and −0.371 e.Å$^{-3}$ | |

Single Crystal X-Ray Analysis of crystalline (R) 4-(5-(4-methoxy-3-propoxyphenyl)pyridin-3-yl)-1,2-oxaborolan-2-ol (Example 4)

The crystal structure of Example 4 was determined by single crystal X-ray diffraction analysis. The single crystal X-ray diffraction data collection was performed on a Bruker D8 Venture diffractometer at −150° C. temperature. Data collection consisted of omega and phi scans. The structure was solved by intrinsic phasing using SHELX software suite in the Monoclinic class space group P2$_1$. The structure was subsequently refined by the full-matrix least squares method. All non-hydrogen atoms were found and refined using anisotropic displacement parameters. The hydrogen atoms located on oxygen were found from the Fourier difference map and refined with distances restrained. The remaining hydrogen atoms were placed in calculated positions and were allowed to ride on their carrier atoms. The final refinement included isotropic displacement parameters for all hydrogen atoms. Analysis of the absolute structure using likelihood methods (Hooft 2008) was performed using PLATON (Spek 2010). The Hooft parameter is reported as 0.08 with an Esd of 0.003 and the Parson's parameter is reported as 0.15 with an Esd of 0.002. The final R-index was 4.6%. A final difference Fourier revealed no missing or misplaced electron density.

Figure 2:
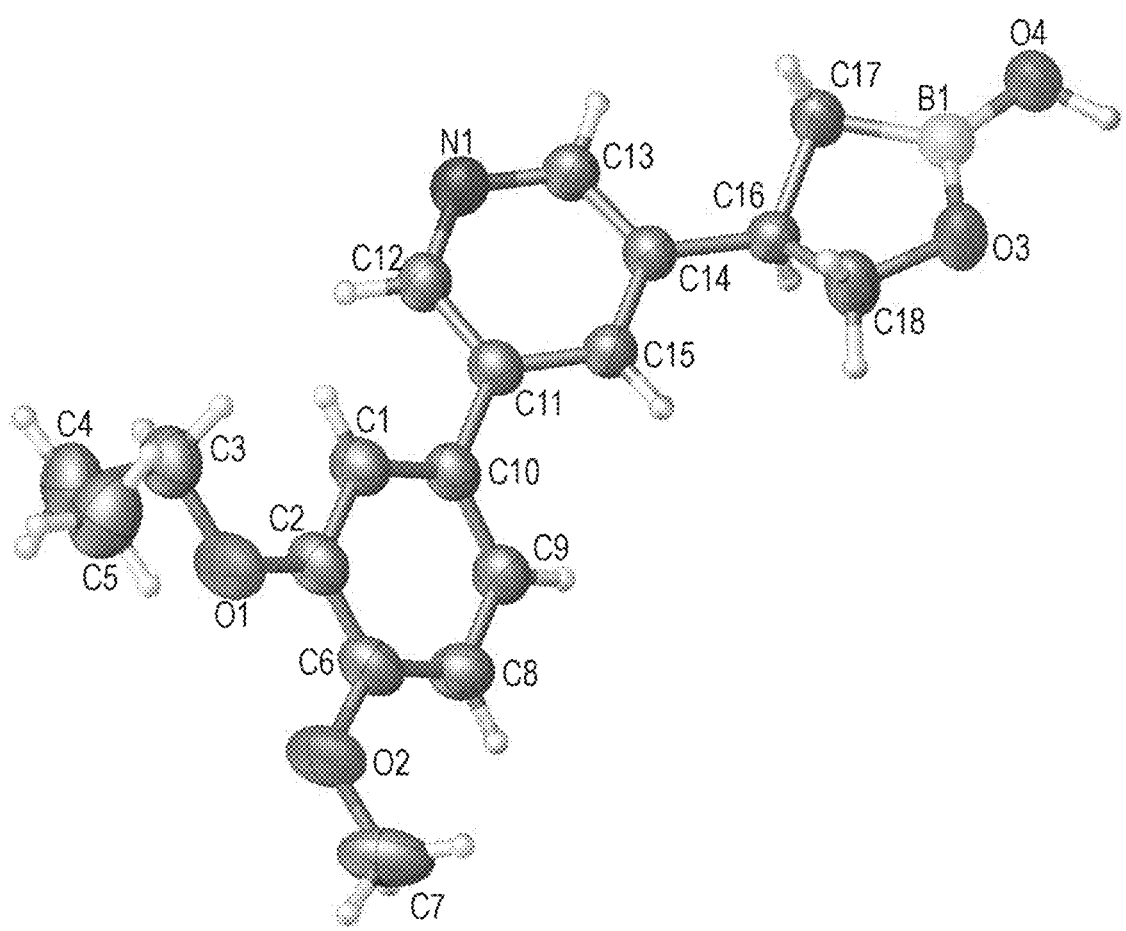
FIG. 2 is an X-ray structure (ORTEP drawing) of crystalline (R) 4-(5-(4-methoxy-3-propoxyphenyl)pyridin-3-yl)-1,2-oxaborolan-2-ol (Example 4).

FIG. 2 is the obtained X-ray structure (ORTEP drawing) of crystalline (R) 4-(5-(4-methoxy-3-propoxyphenyl)pyridin-3-yl)-1,2-oxaborolan-2-ol (Example 4). The crystal structure data is summarized in Table 4.

TABLE 4

Crystal data and structure refinement for Example 4.

| | |
|---|---|
| Empirical formula | C$_{18}$ H$_{22}$ B N O$_4$ |
| Formula weight | 327.17 |
| Temperature | 123(2) K |
| Wavelength | 1.54178 Å |
| Crystal system | Monoclinic |
| Space group | P2$_1$ |
| Unit cell dimensions | a = 10.7077(14) Å  α = 90°. |
| | b = 13.4140(17) Å  β = 100.396(5)°. |
| | c = 13.0151(16) Å  γ = 90°. |
| Volume | 1752.2(4) Å$^3$ |
| Z | 4 |
| Density (calculated) | 1.240 Mg/m$^3$ |
| Absorption coefficient | 0.699 mm$^{-1}$ |
| F(000) | 696 |
| Crystal size | 0.240 × 0.160 × 0.120 mm$^3$ |
| Theta range for data collection | 3.623 to 72.240° |
| Index ranges | −12 <= h <= 13, |
| | −16 <= k <= 16, |
| | −16 <= l <= 16 |
| Reflections collected | 63647 |
| Independent reflections | 6737 [R(int) = 0.0312] |
| Completeness to theta = 67.679° | 98.8% |
| Absorption correction | Empirical |
| Refinement method | Full-matrix least-squares on F$^2$ |
| Data/restraints/parameters | 6737/3/433 |
| Goodness-of-fit on F$^2$ | 1.044 |
| Final R indices [I > 2sigma(I)] | R1 = 0.0457, wR2 = 0.1282 |
| R indices (all data) | R1 = 0.0477, wR2 = 0.1311 |
| Absolute structure parameter | 0.08(3) |
| Extinction coefficient | n/a |
| Largest diff. peak and hole | 0.279 and −0.203 e.Å$^{-3}$ |

Bruker D8 Quest diffractometer at room temperature. Data collection consisted of omega and phi scans. The structure was solved by intrinsic phasing using SHELX software suite in the Monoclinic space group P2$_1$. The structure was subsequently refined by the full-matrix least squares method. All non-hydrogen atoms were found and refined using anisotropic displacement parameters. The hydrogen atoms located on oxygen were found from the Fourier difference map and refined with distances restrained. The remaining hydrogen atoms were placed in calculated positions and were allowed to ride on their carrier atoms. The final refinement included isotropic displacement parameters for all hydrogen atoms. Analysis of the absolute structure using likelihood methods (Hooft 2008) was performed using PLATON (Spek 2010). The Hooft parameter is reported as 0.01 with an Esd of 0.007 and the Parson's parameter is reported as 0.01 with an Esd of 0.006. The final R-index was 4.8%. A final difference Fourier revealed no missing or misplaced electron density.

Figure 3:
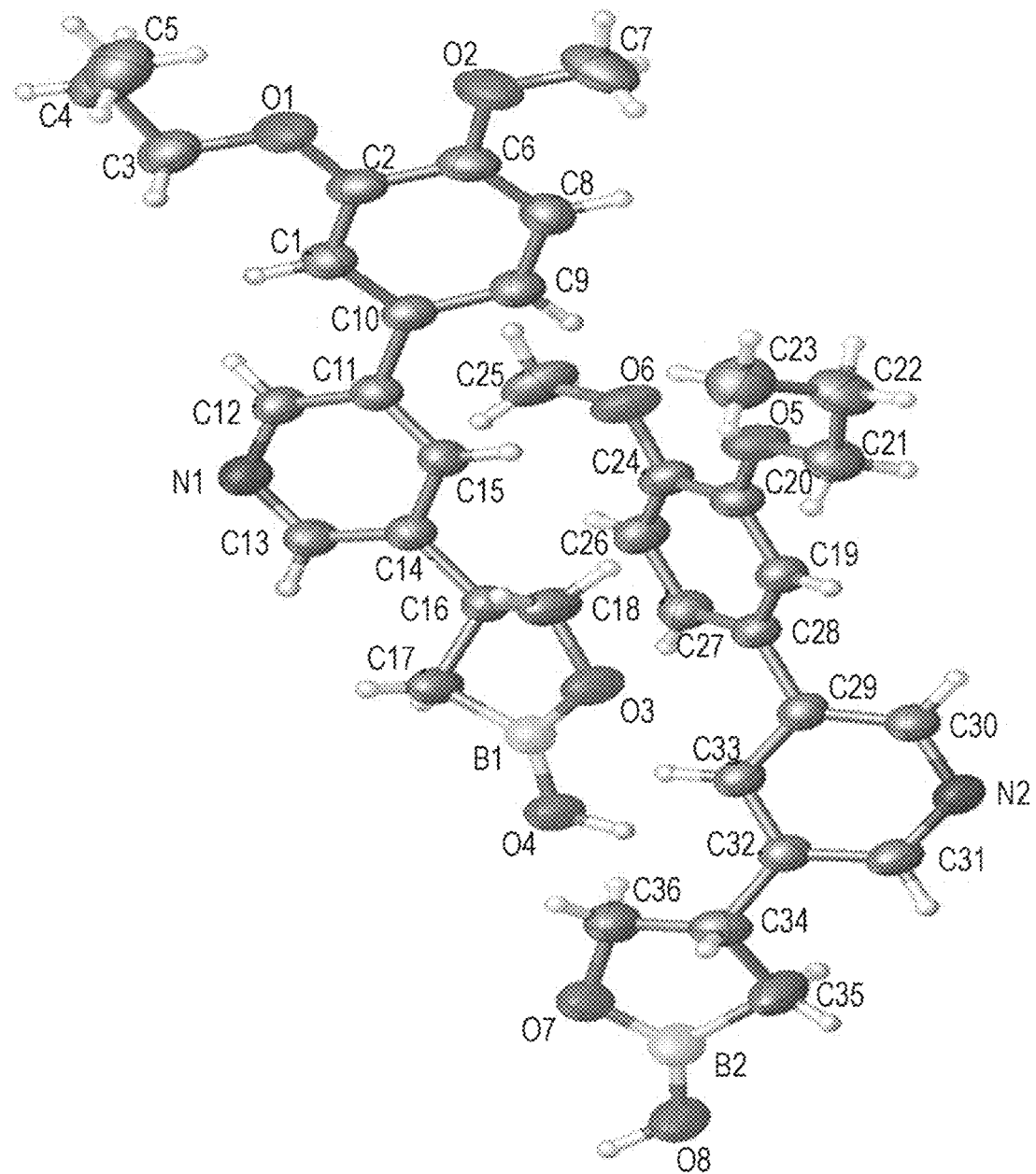
FIG. 3 is an X-ray structure (ORTEP drawing) of crystalline (S)-4-(5-(4-methoxy-3-propoxyphenyl)pyridin-3-yl)-1,2-oxaborolan-2-ol (Example 5).

FIG. 3 is the obtained X-ray structure (ORTEP drawing) of crystalline (S) 4-(5-(4-methoxy-3-propoxyphenyl)pyridin-3-yl)-1,2-oxaborolan-2-ol (Example 5). The crystal structure data is summarized in Table 5.

TABLE 5

Crystal data and structure refinement for Example 5

| | |
|---|---|
| Empirical formula | C$_{18}$ H$_{22}$ B N O$_4$ |
| Formula weight | 327.17 |
| Temperature | 296(2) K |
| Wavelength | 1.54178 Å |
| Crystal system | Monoclinic |
| Space group | P2$_1$ |
| Unit cell dimensions | a = 10.6918(4) Å  α = 90°. |
| | b = 13.4115(4) Å  β = 110.311(2)°. |
| | c = 13.0161(4) Å  γ = 90°. |
| Volume | 1750.37(10) Å$^3$ |
| Z | 4 |
| Density (calculated) | 1.242 Mg/m$^3$ |
| Absorption coefficient | 0.700 mm$^{-1}$ |
| F(000) | 696 |
| Crystal size | 0.260 × 0.220 × 0.140 mm$^3$ |
| Theta range for data collection | 3.621 to 72.234° |
| Index ranges | −12 <= h <= 13, |
| | −16 <= k <= 16, |
| | −15 <= l <= 15 |
| Reflections collected | 16854 |
| Independent reflections | 6536 [R(int) = 0.0328] |
| Completeness to theta = 67.679° | 99.3% |
| Absorption correction | Empirical |
| Refinement method | Full-matrix least-squares on F$^2$ |
| Data/restraints/parameters | 6536/3/446 |
| Goodness-of-fit on F$^2$ | 1.065 |
| Final R indices [I > 2sigma(I)] | R1 = 0.0478, wR2 = 0.1176 |
| R indices (all data) | R1 = 0.0512, wR2 = 0.1220 |
| Absolute structure parameter | 0.01(7) |
| Extinction coefficient | 0.0385(19) |
| Largest diff. peak and hole | 0.236 and −0.273 e.Å$^{-3}$ |

Single Crystal X-Ray Analysis of crystalline (S) 4-(5-(4-methoxy-3-propoxyphenyl)pyridin-3-yl)-1,2-oxaborolan-2-ol (Example 5)

The crystal structure of Example 5 was also determined by single crystal X-ray diffraction analysis. The single crystal X-ray diffraction data collection was performed on a Single Crystal X-Ray Analysis of crystalline (R) 4-(5-(3-ethoxy-4-methoxyphenyl)-6-methylpyridin-3-yl)-1,2-oxaborolan-2-ol (Example 19)

The crystal structure of Example 19 was also determined by single crystal X-ray diffraction analysis. The single crystal X-ray diffraction data collection was performed on a Bruker D8 Quest diffractometer at room temperature. Data collection consisted of omega and phi scans. The structure was solved by intrinsic phasing using SHELX software suite in the Monoclinic class space group P2$_1$. The structure was subsequently refined by the full-matrix least squares method. All non-hydrogen atoms were found and refined using anisotropic displacement parameters. The hydrogen atoms located on oxygen were found from the Fourier difference map and refined with distances restrained. The remaining hydrogen atoms were placed in calculated positions and were allowed to ride on their carrier atoms. The final refinement included isotropic displacement parameters for all hydrogen atoms. Analysis of the absolute structure using likelihood methods (Hooft 2008) was performed using PLATON (Spek 2010). The Hooft parameter is reported as 0.06 with an Esd of 0.004 and the Parson's parameter is reported as 0.06 with an Esd of 0.003. The final R-index was 4.0%. A final difference Fourier revealed no missing or misplaced electron density.

Figure 4:
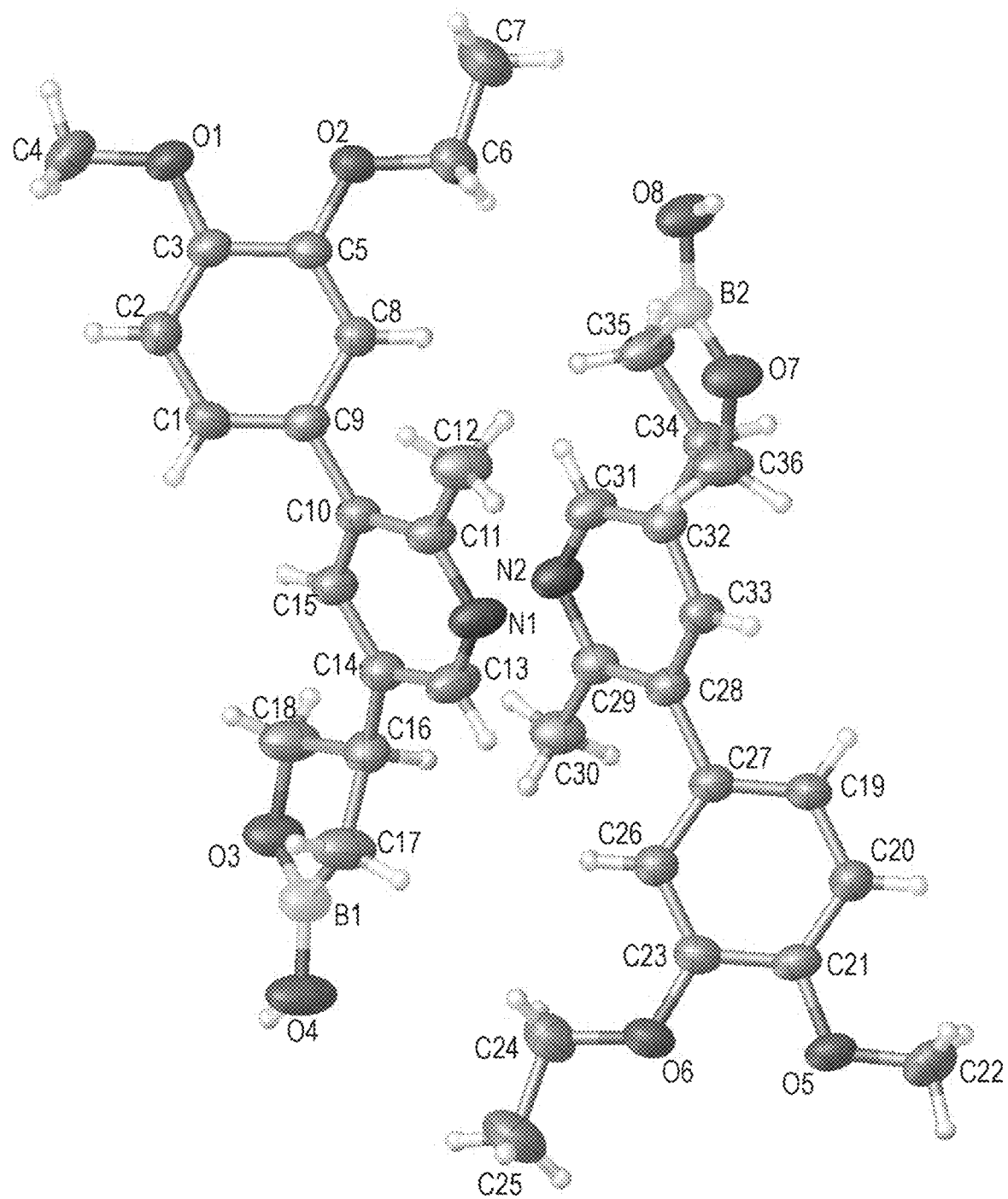
FIG. 4 is an X-ray structure (ORTEP drawing) of crystalline (R) 4-(5-(3-ethoxy-4-methoxyphenyl)-6-methylpyridin-3-yl)-1,2-oxaborolan-2-ol (Example 19).

FIG. 4 is the obtained X-ray structure (ORTEP drawing) of crystalline (R) 4-(5-(3-ethoxy-4-methoxyphenyl)-6-methylpyridin-3-yl)-1,2-oxaborolan-2-ol (Example 19). The crystal structure data is summarized in Table 6.

TABLE 6

Crystal data and structure refinement for Example 19

| | |
|---|---|
| Empirical formula | C$_{36}$ H$_{44}$ B$_2$ N$_2$ O$_8$ |
| Formula weight | 654.35 |
| Temperature | 296(2) K |
| Wavelength | 1.54178 Å |
| Crystal system | Monoclinic |
| Space group | P2$_1$ |
| Unit cell dimensions | a = 11.2655(18) Å   α = 90°. |
| | b = 12.903(2) Å   β = 111.269(5)°. |
| | c = 12.959(2) Å   γ = 90°. |
| Volume | 1755.4(5) Å$^3$ |
| Z | 2 |
| Density (calculated) | 1.238 Mg/m$^3$ |
| Absorption coefficient | 0.698 mm$^{-1}$ |
| F(000) | 696 |
| Crystal size | 0.420 × 0.360 × 0.120 mm$^3$ |
| Theta range for data collection | 3.660 to 72.747° |
| Index ranges | −13 <= h <= 13, |
| | −15 <= k <= 15, |
| | −15 <= l <= 16 |
| Reflections collected | 53020 |
| Independent reflections | 6907 [R(int) = 0.0361] |
| Completeness to theta = 67.679° | 100.0% |
| Absorption correction | Empirical |
| Refinement method | Full-matrix least-squares on F$^2$ |
| Data/restraints/parameters | 6907/3/446 |
| Goodness-of-fit on F$^2$ | 1.055 |
| Final R indices [I > 2sigma(I)] | R1 = 0.0396, wR2 = 0.1023 |
| R indices (all data) | R1 = 0.0414, wR2 = 0.1043 |
| Absolute structure parameter | 0.06(4) |
| Extinction coefficient | 0.0261(13) |
| Largest diff. peak and hole | 0.230 and −0.298 e.Å$^{-3}$ |

X-Ray Powder Diffraction

The crystal structures of Examples 3, 4, 5, 10 and 19 were analyzed using X-ray powder diffraction ("PXRD").

For Example 4, powder X-ray diffraction analysis was conducted using a Bruker AXS D8 ADVANCE diffractometer equipped with a Cu radiation source (K-α average). The system is equipped with a 2.5 axial Soller slits on the primary side. The secondary side utilizes 2.5 axial Soller slits and motorized slits. Diffracted radiation was detected by a Lynx Eye XE detector. The X-ray tube voltage and amperage were set to 40 kV and 40 mA respectively. Data was collected in the Theta-Theta goniometer at the Cu wavelength from 3.0 to 40.0 degrees 2-Theta using a step size of 0.037 degrees and a step time of 10 seconds per step. Samples were prepared by placing them in a low background holder (Bruker part number: C79298A3244B261) and rotated during collection. Data were collected using Bruker DIFFRAC Plus software. Analysis performed by EVA diffract plus software. The PXRD data file was not processed prior to peak searching. Using the peak search algorithm in the EVA software, peaks selected with a threshold value of 1 and a width of 0.3 were used to make preliminary peak assignments. To ensure validity, adjustments were manually made; the output of automated assignments was visually checked and peak positions were adjusted to the peak maximum. Peaks with relative intensity of 3% were generally chosen. The peaks which were not resolved or were consistent with noise were not selected. A typical error associated with the peak position from PXRD stated in USP up to +/−0.2° 2-Theta (USP-941).

For Examples 3, 5, 10, and 19, powder X-ray diffraction analysis was conducted using a Bruker AXS D4 Endeavor diffractometer equipped with a Cu radiation source (K-α average). The system is equipped with a 2.5 axial Soller slits on the primary side. The secondary side utilizes 2.5 axial Soller slits and motorized slits. Diffracted radiation was detected by a Lynx Eye XE detector. The X-ray tube voltage and amperage were set to 40 kV and 40 mA respectively. Data was collected in the Theta-2Theta goniometer at the Cu wavelength from 3.0 to 43.0 degrees 2-Theta using a step size of 0.020 degrees and a step time of 3 seconds per step. Samples were prepared by placing them in a low background holder and rotated during collection. Data were collected using Bruker DIFFRAC Plus software. Analysis performed by EVA diffract plus software. The PXRD data file was not processed prior to peak searching. Using the peak search algorithm in the EVA software, peaks selected with a threshold value of 1 and a width of 0.3 were used to make preliminary peak assignments. To ensure validity, adjustments were manually made; the output of automated assignments was visually checked and peak positions were adjusted to the peak maximum. Peaks with relative intensity of 3% were generally chosen. The peaks which were not resolved or were consistent with noise were not selected. A typical error associated with the peak position from PXRD stated in USP up to +/−0.2° 2-Theta (USP-941).

As will be appreciated by the skilled crystallographer, the relative intensities of the various peaks reported in the Tables and Figures below may vary due to a number of factors such as orientation effects of crystals in the X-ray beam or the purity of the material being analyzed or the degree of crystallinity of the sample. The peak positions will remain substantially as defined. The skilled crystallographer also will appreciate that measurements using a different wavelength will result in different shifts according to the Bragg equation −nλ=2d sin θ. Such further PXRD patterns of the crystalline materials of the present invention and as such are within the scope of the present information.

FIG. 5 is the obtained powder X-ray diffraction pattern for Crystalline®-4-(5-(3-ethoxy-4-methoxyphenyl)pyridin-3-yl)-1,2-oxaborolan-2-ol (Example 3) and Table 7 lists the PXRD peaks.

TABLE 7

Example 3 PXRD Data

| Angle 2-Theta (Degrees) | Rel. Intensity % |
|---|---|
| 10.5 | 87.7 |
| 12.3 | 19.2 |
| 13.5 | 10.1 |
| 15.8 | 10.6 |
| 16.0 | 15.9 |
| 16.2 | 6.0 |
| 17.3 | 2.8 |
| 18.3 | 71.9 |
| 20.4 | 3.8 |
| 21.0 | 7.9 |
| 21.1 | 7.0 |
| 21.5 | 63.0 |
| 22.9 | 27.1 |
| 23.8 | 6.4 |
| 24.4 | 67.2 |
| 24.9 | 100.0 |
| 25.4 | 23.3 |
| 25.6 | 14.4 |
| 26.5 | 10.8 |
| 27.8 | 17.4 |
| 28.4 | 6.2 |
| 29.2 | 3.3 |
| 30.2 | 10.2 |
| 32.1 | 3.2 |
| 33.5 | 5.3 |
| 33.8 | 3.0 |
| 34.5 | 4.4 |
| 37.7 | 4.7 |
| 40.5 | 6.4 |
| 41.3 | 3.5 |

FIG. 6 is the obtained powder X-ray diffraction pattern for Crystalline®-4-(5-(4-methoxy-3-propoxyphenyl)pyridin-3-yl)-1,2-oxaborolan-2-ol (Example 4) and Table 8 lists the PXRD peaks.

TABLE 8

Example 4 PXRD Data

| Angle (2-Theta) Degrees | Rel. Intensity % |
|---|---|
| 11.0 | 94.9 |
| 11.4 | 64.8 |
| 13.2 | 43.1 |
| 14.5 | 27.3 |
| 15.1 | 39.3 |
| 15.6 | 23.1 |
| 15.9 | 9.4 |
| 17.7 | 10.0 |
| 18.8 | 81.8 |
| 19.4 | 13.0 |
| 19.7 | 49.3 |
| 20.5 | 12.4 |
| 21.3 | 45.1 |
| 22.0 | 8.5 |
| 22.9 | 100.0 |
| 23.8 | 5.7 |
| 24.5 | 6.0 |
| 25.1 | 71.8 |
| 25.6 | 4.6 |
| 25.9 | 20.5 |
| 26.4 | 36.0 |
| 27.5 | 17.1 |
| 28.4 | 8.9 |
| 28.8 | 4.9 |
| 30.4 | 3.6 |

FIG. 7 is the obtained powder X-ray diffraction pattern for crystalline (S)-4-(5-(4-methoxy-3-propoxyphenyl)pyridin-3-yl)-1,2-oxaborolan-2-ol (Example 5) and Table 9 lists the PXRD peaks.

TABLE 9

Example 5 PXRD Data

| Angle (2-Theta) Degrees | Rel. Intensity % |
|---|---|
| 11.0 | 60.0 |
| 11.4 | 44.8 |
| 13.2 | 28.3 |
| 14.5 | 18.6 |
| 15.1 | 27.2 |
| 15.6 | 16.5 |
| 15.9 | 6.9 |
| 17.7 | 7.2 |
| 18.7 | 67.4 |
| 19.4 | 10.4 |
| 19.7 | 42.6 |
| 20.5 | 10.8 |
| 21.2 | 40.4 |
| 21.9 | 8.1 |
| 22.1 | 4.3 |
| 22.8 | 100.0 |
| 23.8 | 5.7 |
| 24.4 | 6.3 |
| 25.0 | 67.0 |
| 25.5 | 5.0 |
| 25.9 | 19.98 |
| 26.4 | 33.9 |
| 27.4 | 18.8 |
| 28.3 | 10.5 |
| 28.8 | 5.7 |
| 30.0 | 3.5 |
| 30.4 | 4.1 |
| 32.1 | 3.5 |
| 35.5 | 3.4 |
| 36.1 | 4.1 |
| 38.0 | 3.7 |
| 38.5 | 3.3 |
| 39.0 | 3.1 |
| 39.6 | 3.3 |
| 41.4 | 3.9 |

FIG. 8 is the obtained powder X-ray diffraction pattern for crystalline (−) 4-(5-(2-(difluoromethyl)-3-ethoxy-4-methoxyphenyl)pyridin-3-yl)-1,2-oxaborolan-2-ol (Example 10) and Table 10 lists the PXRD peaks.

TABLE 10

Example 10 PXRD Data

| Angle 2-Theta (Degrees) | Rel. Intensity % |
|---|---|
| 8.9 | 12.7 |
| 12.0 | 18.0 |
| 12.3 | 14.5 |
| 12.8 | 100.0 |
| 13.7 | 5.6 |
| 13.9 | 20.6 |
| 14.2 | 13.2 |
| 14.5 | 3.7 |
| 15.9 | 5.8 |
| 17.6 | 14.4 |
| 17.8 | 31.5 |
| 19.2 | 21.6 |
| 19.4 | 16.5 |
| 19.6 | 17.2 |
| 20.4 | 59.3 |
| 21.4 | 13.9 |
| 22.0 | 16.3 |
| 22.3 | 17.4 |
| 22.5 | 15.1 |

TABLE 10-continued

Example 10 PXRD Data

| Angle 2-Theta (Degrees) | Rel. Intensity % |
|---|---|
| 22.9 | 32.3 |
| 23.1 | 31.4 |
| 24.2 | 14.5 |
| 25.7 | 44.2 |
| 27.3 | 3.7 |
| 27.5 | 6.3 |
| 28.5 | 11.7 |
| 28.8 | 7.0 |
| 29.6 | 5.2 |
| 30.7 | 12.9 |
| 33.7 | 3.9 |
| 35.6 | 9.9 |
| 40.3 | 3.7 |
| 40.9 | 5.4 |

FIG. 9 is the obtained powder X-ray diffraction pattern for Crystalline®-4-(5-(3-ethoxy-4-methoxyphenyl)-6-methylpyridin-3-yl)-1,2-oxaborolan-2-ol (Example 19) and Table 11 lists the PXRD peaks.

TABLE 11

Example 19 PXRD Data

| Angle 2-Theta (Degrees) | Rel. Intensity % |
|---|---|
| 10.1 | 4.9 |
| 10.9 | 65.9 |
| 11.3 | 23.2 |
| 13.1 | 4.3 |
| 13.7 | 3.9 |
| 14.7 | 7.5 |
| 17.0 | 14.7 |
| 17.3 | 33.4 |
| 19.0 | 32.4 |
| 19.3 | 59.2 |
| 19.7 | 17.8 |
| 19.7 | 23.6 |
| 20.2 | 4.5 |
| 20.6 | 7.4 |
| 21.1 | 59.0 |
| 21.9 | 5.8 |
| 22.7 | 85.5 |
| 23.6 | 14.1 |
| 23.8 | 100.0 |
| 23.9 | 61.7 |
| 24.1 | 10.6 |
| 24.5 | 6.6 |
| 24.8 | 18.8 |
| 25.4 | 47.8 |
| 25.4 | 38.6 |
| 26.2 | 6.4 |
| 26.5 | 13.9 |
| 26.8 | 3.6 |
| 27.1 | 15.4 |
| 27.1 | 11.8 |
| 27.5 | 10.1 |
| 28.5 | 3.8 |
| 28.5 | 5.8 |
| 29.5 | 3.1 |
| 30.4 | 28.8 |
| 30.5 | 16.9 |
| 32.2 | 4.9 |
| 34.2 | 4.0 |
| 35.9 | 3.5 |
| 39.1 | 5.4 |
| 39.5 | 3.8 |
| 39.9 | 5.0 |
| 40.9 | 4.2 |
| 42.2 | 7.1 |

Formulation Examples

An embodiment of the present invention provides a topical pharmaceutical formulation comprising: (a) an active agent of the invention which treats an inflammatory related condition, or a pharmaceutically acceptable salt, or a hydrate or a solvate thereof, (b) from about 5% (w/w) to about 15% (w/w) solvent, and (c) an ointment base. In an embodiment, the present invention provides a topical pharmaceutical formulation comprising: (a) an active agent of the invention which treats an inflammatory related condition, or a pharmaceutically acceptable salt, or a hydrate or a solvate thereof, (b) from about 5% (w/w) to about 15% (w/w) solvent, and (c) petrolatum. In an embodiment, the present invention provides a topical pharmaceutical formulation comprising: (a) an active agent of the invention which treats an inflammatory related condition, or a pharmaceutically acceptable salt, or a hydrate or a solvate thereof, (b) from about 5% (w/w) to about 15% (w/w) solvent, (c) ointment, (d) an antioxidant, ® a stabilizer, (f) an emulsifying agent, and (g) a stiffening agent. In an embodiment, the present invention provides a topical pharmaceutical formulation comprising: (a) an active agent of the invention which treats an inflammatory related condition, or a pharmaceutically acceptable salt, or a hydrate or a solvate thereof, (b) from about 5% (w/w) to about 15% (w/w) solvent, (c) ointment, (d) an antioxidant, ® an emulsifying agent, and (f) a stiffening agent. In an embodiment, the present invention provides a topical pharmaceutical formulation comprising: (a) an active agent of the invention which treats an inflammatory related condition, or a pharmaceutically acceptable salt, or a hydrate or a solvate thereof, (b) from about 5% (w/w) to about 15% (w/w) solvent, (c) petrolatum, (d) an antioxidant, ® an emulsifying agent, and (f) a stiffening agent. In an embodiment, the present invention provides a topical pharmaceutical formulation comprising: (a) an active agent of the invention which treats an inflammatory related condition, or a pharmaceutically acceptable salt, or a hydrate or a solvate thereof, (b) from about 8% (w/w) to about 10% (w/w) propylene or hexylene glycol, (c) from about 75% (w/w) to about 80% (w/w) white petrolatum, (d) from about 8% (w/w) to about 10% of a glyceride blend, ® from about 4% to about 6% paraffin, and (f) from about 0.05% to 0.5% butylated hydroxytoluene. In an embodiment, the present invention provides a topical pharmaceutical formulation comprising: (a) an active agent of the invention which treats an inflammatory related condition, or a pharmaceutically acceptable salt, or a hydrate or a solvate thereof, (b) from about 8% (w/w) to about 10% (w/w) hexylene glycol, (c) from about 75% (w/w) to about 80% (w/w) white petrolatum, (d) from about 8% (w/w) to about 10% of a glyceride blend, ® from about 4% to about 6% paraffin, and (f) from about 0.05% to 0.5% butylated hydroxytoluene.

In an embodiment, the present invention provides a topical pharmaceutical formulation comprising an active agent wherein "active agent" is a compound of the present invention or a pharmaceutically acceptable salt, hydrate or a solvate thereof. In another embodiment, the active agent is ®-4-(5-(4-methoxy-3-propoxyphenyl)pyridin-3-yl)-1,2-oxaborolan-2-ol or a pharmaceutically acceptable salt, hydrate, or solvate thereof. In another embodiment, the active agent is (S)-4-(5-(4-methoxy-3-propoxyphenyl)pyridin-3-yl)-1,2-oxaborolan-2-ol or a pharmaceutically acceptable salt, hydrate, or solvate thereof. In another embodiment, the active agent is ®-4-(5-(3-ethoxy-4-methoxyphenyl)pyridin-3-yl)-1,2-oxaborolan-2-ol or a pharmaceutically acceptable salt, hydrate, or solvate thereof. In another embodiment, the active agent is ®-4-(5-(3-ethoxy-4-methoxyphenyl)-6-methylpyridin-3-yl)-1,2-oxaborolan-2-ol or a pharmaceutically acceptable salt, hydrate, or solvate thereof. In another embodiment, the active agent is (−)-4-(5-(2-(difluoromethyl)-3-ethoxy-4-methoxyphenyl)pyridin-3-yl)-1,2-oxaborolan-2-ol, or a pharmaceutically acceptable salt, hydrate, or solvate thereof.

In another embodiment, the present invention provides a topical pharmaceutical formulation comprising an active agent present in a concentration of about 0.0001% to about 3.0% (w/w). In another embodiment, the active agent is present in a concentration of about 0.001% to about 2.0% (w/w). In another embodiment, the active agent is present in a concentration of about 0.01% to about 1.0% (w/w). In another embodiment, the active agent is present in a concentration of about 0.05% to about 0.5% (w/w).

In another embodiment, the present invention provides an active agent, or a salt, hydrate or solvate thereof. In another embodiment, the present invention provides a combination of an active agent and a second active agent wherein the second active agent is useful for the treatment of inflammatory disorders such as atopic dermatitis, eczema, psoriasis, arthritis, asthma, fibrosis, lupus, allergy, fibromyalgia, wound healing, and inflammation resulting from surgical complications. The combination may be comprised of an admixture or co-formulation of the two active ingredients. Alternatively, the combination may be packaged in a dispenser wherein one active agent is in one chamber and another active ingredient is in a second chamber, but upon dispensing, the two active agents are simultaneously delivered together such that administration of the combination may occur in one application. Alternatively, the active agents may individually be administered with the other active agent, wherein the second active agent may be administered either orally or topically.

In another embodiment, the present invention provides an active agent described herein, or a salt, hydrate or solvate thereof, in a topical formulation which comprises a solvent. In another embodiment, the solvent is an alkyl glycol or alkyl alcohol. In another embodiment, the solvent is an alkyl glycol. In another embodiment, the solvent is propylene glycol. In another embodiment, the solvent is hexylene glycol. In another embodiment, the solvent is butylene glycol. In another embodiment, the solvent is present in a concentration of about 5.0% (w/w) to about 15.0% (w/w). In another embodiment, the solvent is present in a concentration of about 6.0% (w/w) to about 12.0% (w/w). In another embodiment, the solvent is present in a concentration of about 7.0% (w/w) to about 11.0% (w/w). In another embodiment, the solvent is present in a concentration of about 8.0% (w/w) to about 10.0% (w/w).

In another embodiment, the present invention provides an active agent described herein, or a salt, hydrate or solvate thereof, in a topical formulation which comprises an ointment base. In another embodiment, the ointment base is white petrolatum. In another embodiment, the ointment base is mineral jelly, petroleum jelly, yellow petrolatum, yellow soft paraffin, yellow petroleum jelly, white petrolatum jelly, or white soft paraffin. In another embodiment, the base is mineral oil, light mineral oil, paraffin, or lanolin alcohol. The amount of ointment base in the topical pharmaceutical formulation will be dependent on the amounts of the other components. In another embodiment, the ointment base is present in a quantum satis concentration. In another embodiment, the ointment base is present in a concentration of from about 65% (w/w) to about 85% (w/w). In another embodiment, the base is present in a concentration of from about 70% (w/w) to about 80% (w/w). In another embodiment, the base is present in a concentration of from about 75% (w/w) to about 80% (w/w).

In another embodiment, the present invention provides an active agent described herein, or a salt, hydrate or solvate thereof, in a topical formulation which further comprises an antioxidant. In another embodiment, the antioxidant is butylated hydroxytoluene, ascorbic acid, ascorbic palmitate, butylated hydroxyanisole, 2,4,5-trihydroxybutyrophenone, 4-hydroxymethyl-2,6-di-tert-butyl phenol, erythorbic acid, gum guaiac, propyl gallate, thiodipropionic acid, dilauryl thiodipropionate, tert-butylhydroquinone, or tocopherol. In another embodiment, the antioxidant is butylated hydroxytoluene. In another embodiment, the antioxidant is present in a concentration of about 0.01% (w/w) to about 1% (w/w). In another embodiment, the antioxidant is present in a concentration of about 0.01% (w/w) to about 0.5% (w/w). In another embodiment, the antioxidant is present in a concentration of about 0.05% (w/w) to about 0.5% (w/w). In another embodiment, the antioxidant is present in a concentration of about 0.075% (w/w) to about 0.2% (w/w).

In another embodiment, the topical pharmaceutical formulation further comprises an emulsifying agent. In another embodiment, the emulsifying agent is a glyceride blend. In another embodiment, the emulsifying agent is a glyceride blend, wherein the glyceride blend comprises a monoglyceride and a diglyceride. In another embodiment, the emulsifying agent is a glyceride blend, wherein the glyceride blend comprises a monoglyceride, a diglyceride, and a triglyceride. In another embodiment, the emulsifying agent is a glyceride blend, wherein the glyceride blend comprises a monoglyceride and a diglyceride, and wherein from about 40% (w/w) to about 55% (w/w) of the glyceride blend is a monoglyceride. In another embodiment, the emulsifying agent is a glyceride blend, wherein the glyceride blend comprises a monoglyceride, a diglyceride, and a triglyceride, and wherein from about 40% (w/w) to about 55% (w/w) of the glyceride blend is a monoglyceride. In another embodiment, the monoglyceride is selected from the group consisting of glyceryl monostearate, glyceryl monopalmitate, glyceryl monooleate, or combinations thereof. In another embodiment, the monoglyceride is a monoglyceryl ester of a long chain, saturated or unsaturated fatty acid. In an embodiment, the monoglyceride is an alpha-monoglyceride. In a preferred embodiment, the diglyceride is a diglyceryl ester of a long chain, saturated or unsaturated fatty acid. In another embodiment, the glyceride blend is present in a concentration of about 3.0% (w/w) to about 10.0% (w/w). In another embodiment, the glyceride blend is present in a concentration of about 5.0% (w/w) to about 10.0% (w/w). In another embodiment, the glyceride blend about 6.0% (w/w) to about 8.0% (w/w).

In another embodiment, the topical pharmaceutical formulation further comprises a stiffening agent. In another embodiment, the stiffening agent is a wax. In another embodiment, the stiffening agent is a wax and the wax is selected from the group consisting of beeswax, paraffin wax, and spermaceti wax. In another embodiment, the stiffening agent is paraffin wax. In another embodiment, the stiffening agent is present in a concentration of about 3.0% (w/w) to about 7.0% (w/w). In a preferred embodiment, the stiffening agent is present in a concentration of about 4.0% (w/w) to about 6.0% (w/w). In another embodiment, the stiffening agent is present in a concentration of about 4.5% (w/w) to about 5.5% (w/w).

In another embodiment, the topical pharmaceutical formulation further comprises a stabilizer. In another embodiment, the stabilizer is ethylenediaminetetraacetic acid, or a pharmaceutically acceptable salt thereof. In another embodiment, the stabilizer is a pharmaceutically acceptable salt of ethylenediaminetetraacetic acid, and this salt is a sodium salt or a potassium salt or a calcium salt, or a combination thereof. In another embodiment, the stabilizer is present in a concentration of about 0.000010% (w/w) to about 0.0450% (w/w).

The composition of topical formulations for compounds of the present invention include excipients that provide at least one of the following functionalities: solvent; base; dispersing agent; emulsifying agent; stiffening agent; rheology modifying agent; stabilizing agent; and antioxidant. For example, suitable topical ointment formulations for Example 4 include, but are not limited to, the formulations listed in Tables 12, 13, 15 and 16. In addition to the ointment formulations listed in Tables 12 and 13, other topical formulations suitable for the compounds of the present invention include, but are not limited to, creams, lotions, gels, solutions, suspensions, foams, and sprays.

TABLE 12

| | Quantity (% w/w) | | | | | |
|---|---|---|---|---|---|---|
| Example 4 | 0.001-1 | 0.001-1 | 0.001-1 | 0.001-1 | 0.001-1 | 0.001-1 |
| Propylene glycol | 2-9 | | | | | |
| Hexylene glycol | | 2-9 | | | | |
| Transcutol | | | 2-9 | | | |
| Diisopropyl adipate | | | | 2-20 | | |
| PEG400 | | | | | 2-9 | |
| Propylene carbonate | | | | | | 2-9 |
| White petrolatum | qs | qs | qs | qs | qs | qs |
| Mono- and diglycerides | 0-7 | 0-7 | 0-7 | 0-7 | 0-7 | 0-7 |
| Span 60 | 0-2 | 0-2 | 0-2 | 0-2 | 0-2 | 0-2 |
| Span 40 | 0-2 | 0-2 | 0-2 | 0-2 | 0-2 | 0-2 |
| Phospholipid (lecithin) | 0-10 | 0-10 | 0-10 | 0-10 | 0-10 | 0-10 |
| Butylated Hydroxytoluene | 0-0.1 | 0-0.1 | 0-0.1 | 0-0.1 | 0-0.1 | 0-0.1 |
| Butylated Hydroxyanisole | 0-0.1 | 0-0.1 | 0-0.1 | 0-0.1 | 0-0.1 | 0-0.1 |
| Paraffin Wax | 0-5 | 0-5 | 0-5 | 0-5 | 0-5 | 0-5 |
| Total (%) | 100.0 | 100.0 | 100.0 | 100.0 | 100.0 | 100.0 |

*qs or quantum satis means sufficient amount to make the total = 100%

Topical formulations prepared containing Example 4 that were tested for skin permeability and maximum flux of Example 4 are listed in Table 13.

TABLE 13

| | Quantity (% w/w) | | | |
|---|---|---|---|---|
| Example 4 | 1 | 0.1 | 0.01 | 0 |
| White petrolatum, USP | 77.9 | 78.8 | 78.89 | 78.9 |
| Mono- and diglycerides, NF | 7 | 7 | 7 | 7 |
| Butylated Hydroxytoluene (BHT), NF/PhEur | 0.1 | 0.1 | 0.1 | 0.1 |
| Paraffin Wax, NF | 5 | 5 | 5 | 5 |
| Hexylene Glycol, NF/USP | 9 | 9 | 9 | 9 |
| Total (%) | 100.0 | 100.0 | 100.0 | 100.0 |

In-vitro skin permeation study or Franz cell assay was used to demonstrate the ability of of the formulations in Table 13 to enable Example 4 permeation across stratum corneum barrier and mobility through epidermis and dermis by way of flux measurement. The formulations exhibited a concentration dependent skin flux (Table 14) and may accommodate abroad range of Example 4 concentrations, providing a range of thermodynamic driving forces for Example 4 to permeate skin. A higher driving force can be achieved via incorporation into the formulations of additional penetration enhancers such as oleyl alcohol.

TABLE 14

Cumulative Amount Permeated and Maximum Flux of Example 4

| Example 4 Formulations From Table 13 | N* | Mean, Cumulative Amount in 24 hours, (ng) | Std Error, Cumulative Amount in 24 hours (ng) | Mean, Max. Flux, (ng/cm$^2$/hr) | Std Error, Max. Flux, (ng/cm$^2$/hr) |
|---|---|---|---|---|---|
| 1% Example 4 | 15 | 3357.7 | 769.6 | 252.28 | 49.05 |
| 0.1% Example 4 | 15 | 1089.9 | 131.9 | 73.95 | 7.53 |
| 0.01% Example 4 | 15 | 233.0 | 23.5 | 20.14 | 1.75 |
| 0% Example 4 | 6 | 0 | 0 | 0 | 0 |

*Number of skin donor = 3; Replicate per donor = 5.

TABLE 15

| | Quantity (% w/w) | | | |
|---|---|---|---|---|
| Example 4 | 0.001-1 | 0.001-1 | 0.001-1 | 0.001-1 |
| Medium chain triglycerides* | 2-20 | | | |
| Crodamol GTCC | | 2-20 | | |
| Crodamol GMCC | | | 2-20 | |
| Triacetin | | | | 2-10 |
| White petrolatum | qs | qs | qs | qs |
| Mono- and diglycerides | 0-7 | 0-7 | 0-7 | 0-7 |
| Span 60 | 0-2 | 0-2 | 0-2 | 0-2 |
| Span 40 | 0-2 | 0-2 | 0-2 | 0-2 |
| Phospholipid (lecithin) | 0-10 | 0-10 | 0-10 | 0-10 |
| Butylated Hydroxytoluene | 0-0.1 | 0-0.1 | 0-0.1 | 0-0.1 |
| Butylated Hydroxyanisole | 0-0.1 | 0-0.1 | 0-0.1 | 0-0.1 |
| Paraffin Wax | 0-5 | 0-5 | 0-5 | 0-5 |
| Total (%) | 100.0 | 100.0 | 100.0 | 100.0 |

*Medium chain triglycerides contain two or three fatty acids having an aliphatic tail of 6-12 carbon atoms.

TABLE 16

Example 4 Topical Ointment Formulations

| Component | milligrams/ gram (mgs/g) | milligrams/ gram (mgs/g) | milligrams/ gram (mgs/g) |
|---|---|---|---|
| Example 4 | 0.100 | 0.300 | 0.600 |
| Hexylene Glycol | 90.000 | 90.000 | 90.000 |
| White Petrolatum | 788.900 | 788.700 | 788.400 |
| Mono- and Di-Glycerides | 70.000 | 70.000 | 70.000 |
| Paraffin Wax | 50.000 | 50.000 | 50.000 |
| Butylated Hydroxytoluene (BHT) | 1.000 | 1.000 | 1.000 |
| Total | 1000.000 | 1000.000 | 1000.000 |

PDE4 SPA Assay

Phosphodiesterase (PDE) activity is determined by measuring the effect of a test agent on the activity of the PDE4B enzyme in a scintillation proximity assay (SPA). At the time of assay, approximately 30 µL of PDE4B (aa 152-484, Uniprot ID Q07343) in 50 mM Tris pH 7.5, 1.3 mM $MgC_2$, 0.004% Brij 35 is added to a 384 well white clear bottom polystyrene plate (Corning) containing 1 µL of varying concentrations of test compound. After ~10 minutes at room temperature (RT; 21° C.), the assay is initiated by the addition of 20 µL of a mixture of $^3H$-labeled (adenosine 3′,5′-cyclic phosphate, ammonium salt, [2,8-$^3H$]; Perkin Elmer) and unlabeled cAMP. The final assay conditions are approximately 81.6 pM PDE4B in 50 mM Tris pH 7.5, 1.3 mM $MgCl_2$, 0.004% Brij 35, 1 µM $^3H$-labeled/unlabeled cAMP (1425 dpm/pmol) and the indicated final concentration of test compound (approximately 10 µM to 9.5 µM by 4-fold dilution). The final concentration of DMSO in the assay is approximately 2.0%. After 30 minutes at RT, the assay is terminated by the addition of approximately 20 µL of an aqueous solution of PDE YSI SPA beads (8 mg/mL in water; Perkin Elmer). The beads are allowed to settle for at least 2 hours and the plate is then counted on a MicroBeta2 (Perkin Elmer). The concentrations and resulting effect values for the tested compound are plotted and the concentration of compound required for 50% effect (IC50) is determined with a four-parameter logistic dose response equation (E-WorkBook, ID Business Solutions Ltd.) and shown in Table 17.

Cytokine Assays

Cytokine inhibitory activity is determined by measuring the effect of test agent on the release of the cytokines IL-4, IL-13 and IFNγ from human peripheral blood mononuclear cells (PBMCs) stimulated with the T-cell mitogen phytohemagglutinin-L (PHA-L). At the time of assay, human PBMCs (Astarte Biologics) are removed from cryopreservation, thawed quickly at 37° C., diluted in assay medium (RPMI-Gibco 1640 medium, 10% heat inactivated fetal bovine serum (HIFBS), 2 mM glutamine and 10 mM HEPES pH 7.4) and then centrifuged at 250×g for 5 minutes. The resulting cell pellet is re-suspended in assay medium to a concentration of approximately $5 \times 10^6$ cells/mL and 50 µL of this cell suspension (approximately 250,000 cells) is added to each well of a 384-well cell culture microtiter plate (Perkin Elmer). Varying concentrations of test compound are then diluted in assay medium and added to the assay plate wells in a volume of 25 µL. After ~10 minutes at room temperature (21° C.) the cells are stimulated by the addition of 25 µL of PHA-L (14 µg/mL; Millipore) and the assay plate is placed in an incubator at 37° C. in a humidified environment in 5% carbon dioxide. The final assay conditions are approximately 250,000 human PBMCs per well in assay medium containing 3.5 µg/mL PHA-L and the indicated final concentration of test compound (approximately 10 µM to 9.5 µM by 4-fold dilution). The final concentration of DMSO in the assay is approximately 0.25%. After 48 hours, the assay plate is removed from the incubator and centrifuged at 250×g for 5 minutes. A portion of the resulting cell supernatant is then used to determine the amount of IL-4, IL-13 and IFNγ in each well. Cytokine measurements are made using human IL-4, IL-13 or IFNγ HTRF assay kits (CisBio) following the manufacturer's assay protocol. The concentrations and resulting effect values for tested compounds are plotted and the concentration of compound required for 50% effect (IC50) is determined with a four-parameter logistic dose response equation (E-WorkBook, ID Business Solutions Ltd.) and shown in Table 17.

TABLE 17

| Example number | PDE4B2 $IC_{50}$ nM | IL13 $IC_{50}$ nM | IL4 $IC_{50}$ nM | IFNγ $IC_{50}$ nM |
|---|---|---|---|---|
| 1 | 3.16 | 284 | 14.34 | 2.98 |
| 2 | 0.67 | 1346 | 210.39 | 2.73 |
| 3 | 1.14 | 165 | 3.54 | 0.70 |
| 4 | 0.50 | 135 | 4.11 | 1.06 |
| 5 | 0.93 | 2394 | 36.33 | 4.04 |
| 6 | 1.05 | 283 | 17.58 | 0.72 |
| 7 | 0.97 | 289 | 7.76 | 0.71 |
| 8 | 2.42 | 25 | 0.76 | 1.20 |
| 9 | 1.26 | 265 | 3.63 | 1.87 |
| 10 | 6.92 | 438 | 2.39 | 1.62 |
| 11 | 33.49 | 10000 | 141.16 | 68.33 |
| 12 | 1.08 | 162 | 2.32 | 0.99 |
| 13 | 0.97 | 166 | 5.98 | 4.89 |
| 14 | 1.50 | 91 | 3.21 | 1.85 |
| 15 | 1.57 | 136 | 1.41 | 0.71 |
| 16 | 0.05 | 126 | 0.54 | 0.82 |
| 17 | 0.28 | 138 | 0.65 | 0.47 |
| 18 | 0.74 | 218 | 1.91 | 2.23 |
| 19 | 2.96 | 1482 | 2.56 | 1.68 |
| 20 | 26.91 | 8793 | 86.83 | 102.97 |
| 21 | 0.64 | 159 | 0.84 | 1.35 |
| 22 | 7.89 | 257 | 1.75 | 1.43 |
| 23 | 0.97 | 132 | 0.61 | 0.85 |
| 24 | 0.99 | 163 | 2.24 | 1.33 |
| 25 | 2.40 | 2315 | 67.79 | 9.17 |
| 26 | 399.28 | 10000 | 1668.34 | 3302.07 |
| 27 | 73.39 | 10000 | 3786.25 | 208.88 |
| 28 | 10.85 | 8013 | 1036.85 | 200.54 |
| 29 | 10.47 | 3470 | 9.51 | 4.82 |
| 30 | 15.54 | 10000 | 70.71 | 11.61 |
| 31 | 4.20 | 5726 | 3.92 | 2.96 |
| 32 | 12.96 | 2249 | 64.00 | 8.47 |
| 33 | 1.25 | 181 | 39.82 | 1.44 |
| 34 | 0.52 | 309 | 14.34 | 1.39 |
| 35 | 1.17 | 230 | 6.98 | 1.55 |
| 36 | 0.98 | 476 | 5.25 | 1.27 |
| 37 | | | | |
| 38 | | | | |
| 39 | 1.63 | 182 | 13.78 | 1.82 |
| 40 | 0.37 | 175 | 29.25 | 1.28 |
| 41 | 6.85 | 397 | 6.20 | 1.87 |
| 42 | 0.35 | 205 | 90.39 | 1.55 |
| 43 | 8.23 | 10000 | 232.92 | 76.01 |
| 44 | 2.50 | 167 | 7.22 | 1.34 |
| 45 | 2.29 | 450 | 12.38 | 3.88 |
| 46 | 3.46 | 317 | 11.80 | 3.77 |
| 47 | 3.01 | 143 | 4.11 | 1.54 |
| 48 | 0.12 | 252 | 0.82 | 0.98 |
| 49 | 1.59 | 166 | 4.40 | 3.21 |
| 50 | 0.79 | 234 | 1.04 | 1.52 |
| 51 | 1.27 | 337 | 3.73 | 1.64 |
| 52 | 9.25 | 2607 | 14.59 | 5.74 |
| 53 | 1.41 | 115 | 4.87 | 0.60 |
| 54 | 7.77 | 1487 | 5.58 | 4.20 |
| 55 | 2.21 | 576 | 3.94 | 2.27 |
| 56 | 2.81 | 446 | 68.04 | 3.62 |
| 57 | 10.17 | 239 | 7.54 | 2.29 |
| 58 | 0.72 | 103 | 162.84 | 1.81 |
| 59 | | | | |
| 60 | 0.34 | 308 | 2.04 | 0.53 |
| 61 | 0.53 | 499 | 0.73 | 2.12 |
| 62 | 0.28 | 2573 | 2.66 | 1.44 |
| 63 | 1.62 | 312 | 57.89 | 2.75 |
| 64 | 18.49 | 325 | 8.04 | 4.44 |
| 65 | 9.53 | 814 | 185.58 | 5.34 |
| 66 | 2.15 | 327 | 86.50 | 0.71 |
| 67 | 4.02 | 759 | 99.92 | 12.61 |
| 68 | 0.47 | 369 | 4.85 | 1.50 |
| 69 | 4.39 | 373 | 6.51 | 3.84 |
| 70 | 3.00 | 890 | 4.31 | 2.85 |
| 71 | 11.01 | 1908 | 42.00 | 18.84 |
| 72 | 0.85 | 375 | 102.82 | 6.21 |

TABLE 17-continued

| Example number | PDE4B2 IC$_{50}$ nM | IL13 IC$_{50}$ nM | IL4 IC$_{50}$ nM | IFNγ IC$_{50}$ nM |
|---|---|---|---|---|
| 73 | 2.19 | 384 | 49.87 | 1.66 |
| 74 | 3.04 | 768 | 10.91 | 2.71 |
| 75 | 4.52 | 395 | 125.12 | 5.98 |
| 76 | 10.00 | 403 | 5.75 | 2.17 |
| 77 | 2.40 | 415 | 40.81 | 2.61 |
| 78 | 0.55 | 416 | 19.09 | 1.35 |
| 79 | 1.38 | 748 | 13.33 | 0.82 |
| 80 | 1.34 | 2153 | 19.75 | 4.62 |
| 81 | 2.36 | 858 | 54.35 | 1.62 |
| 82 | 0.55 | 426 | 7.14 | 1.07 |
| 83 | 6.64 | 439 | 9.42 | 4.73 |
| 84 | 1.24 | 444 | 0.90 | 0.44 |
| 85 | 0.29 | 541 | 0.90 | 0.56 |
| 86 | 7.26 | 1334 | 104.66 | 5.00 |
| 87 | 5.03 | 444 | 19.12 | 3.02 |
| 88 | 2.64 | 609 | 63.68 | 6.14 |
| 89 | 1.21 | 449 | 26.43 | 3.50 |
| 90 | 4.33 | 2793 | 289.67 | 13.67 |
| 91 | 3.00 | 460 | 5.90 | 3.92 |
| 92 | 1.79 | 947 | 3.36 | 2.70 |
| 93 | 0.50 | 460 | 9.87 | 1.66 |
| 94 | 12.49 | 606 | 9.58 | 3.88 |
| 95 | 4.87 | 461 | 7.36 | 2.87 |
| 96 | 1.69 | 965 | 48.92 | 5.27 |
| 97 | 3.17 | 465 | 34.01 | 2.81 |
| 98 | 1.13 | 2800 | 219.37 | 2.67 |
| 99 | 1.37 | 957 | 44.33 | 9.42 |
| 100 | 1.68 | 472 | 32.73 | 4.32 |
| 101 | 2.70 | 2652 | 26.02 | 13.33 |
| 102 | 5.85 | 1236 | 2.07 | 3.01 |
| 103 | 1.43 | 487 | 0.83 | 0.76 |
| 104 | 3.58 | 750 | 29.41 | 5.46 |
| 105 | 3.20 | 490 | 14.20 | 5.46 |
| 106 | 1.83 | 2085 | 16.08 | 3.42 |
| 107 | 2.41 | 613 | 27.06 | 4.17 |
| 108 | 4.23 | 493 | 22.10 | 4.35 |
| 109 | 4.18 | 1270 | 22.69 | 6.24 |
| 110 | 0.61 | 496 | 48.41 | 5.10 |
| 111 | 0.97 | 496 | 3.01 | 2.95 |
| 112 | 1.41 | 588 | 79.88 | 8.10 |
| 113 | 1.38 | 497 | 36.10 | 3.81 |
| 114 | 3.00 | 2914 | 32.74 | 21.49 |
| 115 | 1.10 | 509 | 38.43 | 1.68 |
| 116 | 0.87 | 508 | 42.02 | 2.45 |
| 117 | 1.80 | 520 | 64.17 | 10.03 |
| 118 | 0.90 | 531 | 9.78 | 2.65 |
| 119 | 0.72 | 1188 | 5.74 | 7.34 |
| 120 | 1.11 | 2089 | 171.18 | 7.85 |
| 121 | 0.69 | 533 | 57.39 | 1.50 |
| 122 | 5.63 | 567 | 362.45 | 7.49 |
| 123 | 3.11 | 1635 | 34.10 | 3.58 |
| 124 | 2.20 | 1664 | 9.48 | 10.12 |
| 125 | 1.70 | 577 | 11.31 | 2.43 |
| 126 | 0.85 | 680 | 7.21 | 0.79 |
| 127 | 5.30 | 585 | 62.56 | 2.84 |
| 128 | 5.74 | 667 | 53.10 | 2.25 |
| 129 | 4.04 | 3337 | 34.48 | 24.60 |
| 130 | 1.60 | 587 | 120.36 | 3.21 |
| 131 | 8.10 | 591 | 11.55 | 5.70 |
| 132 | 2.63 | 604 | 12.95 | 2.42 |
| 133 | 1.91 | 628 | 1.37 | 1.92 |
| 134 | 7.46 | 1108 | 1.79 | 3.04 |
| 135 | 10.31 | 668 | 15.32 | 7.24 |
| 136 | 2.86 | 670 | 11.66 | 2.43 |
| 137 | 2.21 | 1087 | 37.16 | 2.52 |
| 138 | 2.04 | 988 | 1.08 | 0.90 |
| 139 | 0.25 | 788 | 0.78 | 0.40 |
| 140 | 2.70 | 3449 | 3.47 | 3.20 |
| 141 | 0.95 | 701 | 3.35 | 2.24 |
| 142 | 2.53 | 1035 | 4.50 | 2.04 |
| 143 | 2.71 | 1165 | 4.11 | 3.68 |
| 144 | 0.58 | 706 | 83.91 | 5.02 |
| 145 | 6.77 | 2239 | 103.33 | 52.07 |
| 146 | 1.21 | 757 | 24.35 | 23.83 |
| 147 | 0.44 | 1257 | 2.69 | 1.57 |
| 148 | 0.24 | 759 | 4.92 | 1.68 |
| 149 | 0.49 | 793 | 20.22 | 0.87 |
| 150 | 4.05 | 827 | 168.67 | 18.89 |
| 151 | 5.98 | 813 | 39.11 | 3.48 |
| 152 | 1.38 | 828 | 160.96 | 6.02 |
| 153 | 3.24 | 860 | 50.73 | 2.57 |
| 154 | 14.13 | 893 | 31.39 | 15.18 |
| 155 | 1.81 | 2602 | 292.55 | 5.64 |
| 156 | 0.82 | 901 | 127.25 | 1.56 |
| 157 | 2.96 | 906 | 189.65 | 5.62 |
| 158 | 12.04 | 929 | 59.12 | 10.23 |
| 159 | 15.08 | 931 | 467.60 | 25.05 |
| 160 | 10.09 | 2301 | 25.97 | 15.92 |
| 161 | 11.26 | 960 | 419.00 | 38.63 |
| 162 | 14.52 | 975 | 56.31 | 8.29 |
| 163 | 3.71 | 2512 | 31.09 | 14.15 |
| 164 | 5.58 | 986 | 41.11 | 7.87 |
| 165 | 2.11 | 990 | 127.75 | 3.25 |
| 166 | 0.97 | 1006 | 49.25 | 5.46 |
| 167 | 1.98 | 2786 | 1.37 | 1.13 |
| 168 | 0.88 | 1260 | 1.17 | 0.64 |
| 169 | 2.85 | 2017 | 32.95 | 5.84 |
| 170 | 3.78 | 1069 | 48.55 | 2.83 |
| 171 | 1.73 | 1351 | 2.43 | 3.22 |
| 172 | 1.76 | 1112 | 269.26 | 27.48 |
| 173 | 10.03 | 1132 | 77.06 | 30.17 |
| 174 | 8.57 | 1137 | 278.94 | 14.36 |
| 175 | 5.03 | 2307 | 14.32 | 4.35 |
| 176 | 5.51 | 1141 | 6.51 | 2.98 |
| 177 | 2.71 | 1225 | 154.73 | 8.49 |
| 178 | 2.02 | 1284 | 1.81 | 0.91 |
| 179 | 0.98 | 2730 | 0.72 | 0.74 |
| 180 | 3.01 | 1288 | 6.33 | 6.65 |
| 181 | 0.68 | 1299 | 2.23 | 3.17 |
| 182 | 5.14 | 1329 | 245.20 | 19.59 |
| 183 | 2.72 | 1367 | 102.50 | 6.40 |
| 184 | 0.80 | 1402 | 79.25 | 4.48 |
| 185 | 3.38 | 2984 | 5.75 | 1.30 |
| 186 | 4.43 | 1402 | 31.42 | 5.13 |
| 187 | 4.28 | 1420 | 41.13 | 8.84 |
| 188 | 12.46 | 1532 | 135.44 | 12.25 |
| 189 | 2.61 | 1457 | 7.72 | 1.46 |
| 190 | 1.43 | 1476 | 40.33 | 5.01 |
| 191 | 3.84 | 1502 | 175.98 | 4.42 |
| 192 | 2.15 | 1500 | 14.63 | 5.43 |
| 193 | 0.63 | 1529 | 73.11 | 2.16 |
| 194 | 3.63 | 1539 | 2.85 | 14.71 |
| 195 | 0.72 | 2190 | 0.36 | 0.33 |
| 196 | 0.34 | 1543 | 0.29 | 0.81 |
| 197 | 22.04 | 1575 | 106.85 | 12.18 |
| 198 | 14.28 | 1576 | 14.15 | 4.85 |
| 199 | 10.44 | 1586 | 90.38 | 4.55 |
| 200 | 12.88 | 1599 | 128.17 | 14.09 |
| 201 | 2.13 | 1661 | 105.21 | 9.51 |
| 202 | 4.29 | 1668 | 5.20 | 8.51 |
| 203 | 14.99 | 2185 | 176.06 | 114.15 |
| 204 | 6.07 | 1707 | 22.71 | 21.78 |
| 205 | 0.52 | 1772 | 1.06 | 1.09 |
| 206 | 2.65 | 1793 | 113.37 | 27.80 |
| 207 | 10.33 | 1802 | 389.57 | 53.50 |
| 208 | 0.22 | 1805 | 4.06 | 1.98 |
| 209 | 6.55 | 1819 | 308.43 | 21.72 |
| 210 | 1.92 | 2390 | 17.58 | 2.40 |
| 211 | 2.95 | 1839 | 27.81 | 1.83 |
| 212 | 2.27 | 1895 | 102.59 | 3.29 |
| 213 | 6.32 | 1980 | 80.86 | 3.36 |
| 214 | 4.92 | 1995 | 20.71 | 13.67 |
| 215 | 2.58 | 2052 | 62.71 | 2.18 |
| 216 | 4.05 | 2864 | 19.63 | 1.94 |
| 217 | 5.50 | 2067 | 20.53 | 10.33 |
| 218 | 1.45 | 2836 | 3.24 | 2.30 |
| 219 | 0.82 | 2130 | 4.10 | 1.67 |
| 220 | 3.29 | 2131 | 539.65 | 2.37 |
| 221 | 2.21 | 2426 | 47.35 | 9.35 |
| 222 | 1.14 | 2370 | 1.44 | 1.17 |
| 223 | 6.67 | 2689 | 30.93 | 22.52 |
| 224 | 2.17 | 2494 | 8.94 | 8.12 |
| 225 | 3.79 | 2376 | 21.22 | 4.36 |
| 226 | 8.72 | 2522 | 24.68 | 17.78 |

TABLE 17-continued

| Example number | PDE4B2 IC$_{50}$ nM | IL13 IC$_{50}$ nM | IL4 IC$_{50}$ nM | IFNγ IC$_{50}$ nM |
|---|---|---|---|---|
| 227 | 7.94 | 2541 | 285.17 | 9.16 |
| 228 | 6.32 | 2574 | 7.78 | 14.24 |
| 229 | 2.64 | 2733 | 194.76 | 2.90 |
| 230 | 17.09 | 2780 | 140.71 | 26.53 |
| 231 | 1.98 | 2954 | 1.25 | 1.72 |
| 232 | 4.65 | 583 | 197.03 | 17.92 |
| 233 | 8.74 | 508 | 103.58 | 2.94 |

PDE4B is a major PDE4 isoform in neutrophils and in monocytes, and the PDE4B2 variant is a major subtype found in these cells associated with inflammation. Interferon gamma (IFNγ), interleukin 4 (IL4), and interleukin 13 (IL13) are cytokines that are primarily produced by T cells in addition to certain innate immune cell populations. Production of these cytokines has been associated with inflammatory skin diseases, such as atopic dermatitis and with other immune and inflammatory diseases. Inhibition of release of these inflammatory cytokines would modulate the inflammatory response.

It is understood that the foregoing detailed description and accompanying Examples are merely illustrative and are not to be taken as limitations upon the scope of the invention, which is defined by the appended claims. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

Powder X-Ray Diffraction analysis for crystalline (4-methoxy-3-propoxyphenyl)boronic acid, 3-bromo-5-(4-methoxy-3-propoxyphenyl)pyridine, and 3-(3-((tert-butyldimethylsilyl)oxy)prop-1-en-2-yl)-5-(4-methoxy-3-propoxyphenyl)pyridine.

Powder X-ray diffraction analysis was conducted using a Bruker AXS D8 Endeavor diffractometer equipped with a Cu radiation source (K-α average). The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.01 degrees and a step time of 1.0 second. The antiscatter screen was set to a fixed distance of 1.5 mm. Samples were rotated at 15 rotations/min during collection. Samples were prepared by placing them in a silicon low background sample holder and rotated during collection. Data were collected using Bruker DIFFRAC Plus software and analysis was performed by EVA diffract plus software.

Data analysis was performed by EVA diffract plus software (version 4.2.1). The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of 3% were generally chosen. The peaks which were not resolved or were consistent with noise were not selected. A typical error associated with the peak position of crystalline material, from PXRD, stated in USP, is up to +/−0.2° 2-Theta (USP-941).

TABLE 18

PXRD peak list for (4-methoxy-3-propoxyphenyl)boronic acid.

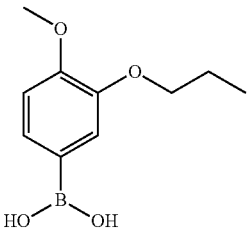

| Angle 2-Theta ° | Relative Intensity % |
|---|---|
| 8.3 | 9.2 |
| 9.6 | 19.5 |
| 9.9 | 3.0 |
| 10.6 | 8.1 |
| 12.0 | 4.9 |
| 14.8 | 100.0 |
| 15.4 | 39.1 |
| 16.6 | 7.9 |
| 17.0 | 7.5 |
| 18.3 | 3.5 |
| 18.9 | 23.7 |
| 19.3 | 24.6 |
| 20.4 | 3.9 |
| 21.1 | 6.4 |
| 21.5 | 6.5 |
| 21.7 | 7.1 |
| 22.0 | 3.9 |
| 23.1 | 35.9 |
| 23.5 | 73.6 |
| 23.8 | 32.0 |
| 24.5 | 15.7 |
| 25.0 | 16.5 |
| 25.5 | 39.7 |
| 26.2 | 10.4 |
| 27.3 | 14.4 |
| 27.9 | 22.0 |
| 28.2 | 17.0 |
| 28.5 | 4.6 |
| 29.2 | 6.8 |
| 31.0 | 12.4 |
| 31.3 | 6.4 |
| 31.7 | 6.1 |
| 32.7 | 4.1 |
| 34.4 | 4.0 |
| 34.7 | 2.7 |
| 35.8 | 5.4 |
| 38.7 | 5.6 |
| 39.3 | 7.5 |

TABLE 19

PXRD peak list for 3-bromo-5-(4-methoxy-3-propoxyphenyl)pyridine.

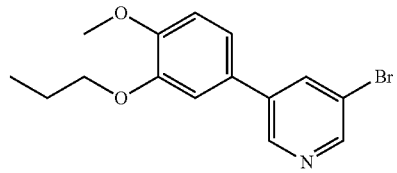 [SMILES: CCCOc1cc(-c2cncc(Br)c2)ccc1OC]

| Angle 2-Theta ° | Relative Intensity % |
|---|---|
| 5.5 | 100 |
| 11.0 | 5.1 |
| 16.4 | 4.4 |
| 21.2 | 6.6 |

TABLE 19-continued

PXRD peak list for 3-bromo-5-(4-methoxy-3-propoxyphenyl)pyridine.

| Angle 2-Theta ° | Relative Intensity % |
|---|---|
| 22.1 | 78.7 |
| 25.2 | 11.1 |
| 25.3 | 10.7 |
| 26.1 | 11.6 |
| 26.2 | 6.8 |
| 27.7 | 22 |
| 30.0 | 16.0 |
| 30.1 | 7.1 |
| 30.9 | 15.9 |
| 33.3 | 14.2 |
| 33.4 | 7.1 |
| 39.1 | 7.7 |
| 39.2 | 3.8 |

TABLE 20

PXRD peak list for 3-(3-((tert-butyldimethylsilyl)oxy)prop-1-en-2-yl)-5-(4-methoxy-3-propoxyphenyl)pyridine

| Angle 2-Theta ° | Relative Intensity % |
|---|---|
| 5.5 | 34.3 |
| 7.7 | 43.6 |
| 9.4 | 8.6 |
| 11.0 | 19.7 |
| 13.4 | 100.0 |
| 15.3 | 32.2 |
| 15.6 | 2.6 |
| 16.3 | 95.0 |
| 18.1 | 20.9 |
| 18.8 | 92.4 |
| 20.5 | 7.9 |
| 21.0 | 3.4 |
| 21.8 | 6.2 |
| 22.0 | 17.5 |
| 22.5 | 4.1 |
| 23.0 | 38.0 |
| 23.3 | 5.5 |
| 23.6 | 38.0 |
| 23.7 | 77.7 |
| 23.9 | 4.6 |
| 24.8 | 2.9 |
| 25.5 | 35.5 |
| 26.8 | 16.5 |
| 27.1 | 3.4 |
| 27.5 | 3.0 |
| 28.4 | 6.7 |
| 28.5 | 7.9 |
| 31.1 | 4.9 |
| 31.3 | 9.1 |
| 31.6 | 2.8 |
| 32.0 | 5.2 |
| 32.8 | 5.1 |
| 33.2 | 3.4 |
| 33.9 | 8.7 |
| 34.0 | 11.6 |

TABLE 20-continued

PXRD peak list for 3-(3-((tert-butyldimethylsilyl)oxy)prop-1-en-2-yl)-5-(4-methoxy-3-propoxyphenyl)pyridine

| Angle 2-Theta ° | Relative Intensity % |
|---|---|
| 34.1 | 10.3 |
| 35.2 | 4.3 |

We claim:
1. A compound of Formula (IA):

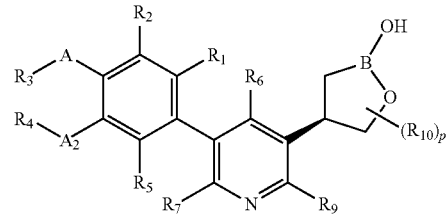

Formula (IA)

or a pharmaceutically acceptable salt thereof,
wherein:
$A_1$ is —O— or —S—;
$A_2$ is —O— or —S—;
$R_1$ is H, D, halogen, CN, $NO_2$, $(C_1\text{-}C_6)$ alkyl, $d_{1-13}\text{-}(C_1\text{-}C_6)$ alkyl, $(C_1\text{-}C_6)$ haloalkyl, $(C_1\text{-}C_6)$ alkylene-C(O)OH, $(C_1\text{-}C_6)$ alkylene-$NR_AR_B$, $(C_1\text{-}C_6)$ alkylene-OH, $(C_1\text{-}C_6)$ alkylene-O$(C_1\text{-}C_6)$ alkyl, $(C_1\text{-}C_6)$ alkylene-SH, $(C_1\text{-}C_6)$ alkylene-$(C_3\text{-}C_8)$ cycloalkyl, $(C_1\text{-}C_6)$ alkylene-(4-7 membered) heterocyclyl, $(C_1\text{-}C_6)$ alkylene-aryl, $(C_1\text{-}C_6)$ alkylene-(5-6 membered) heteroaryl, $(C_2\text{-}C_6)$ alkenyl, $(C_2\text{-}C_6)$ alkynyl, $C(O)(C_1\text{-}C_6)$ alkyl, $C(O)NR_AR_B$, C(O)OH, C(O)O$(C_1\text{-}C_6)$ alkyl, $NR_AR_B$, OH, O$(C_1\text{-}C_6)$ alkyl, $d_{1-13}$-O$(C_1\text{-}C_6)$ alkyl, O$(C_1\text{-}C_6)$ haloalkyl, O$(C_1\text{-}C_6)$ alkylene-C(O)OH, O$(C_1\text{-}C_6)$ alkylene-$NR_AR_B$, O$(C_1\text{-}C_6)$ alkylene-OH, O$(C_1\text{-}C_6)$ alkylene-O$(C_1\text{-}C_6)$ alkyl, O$(C_1\text{-}C_6)$ alkylene-aryl, O$(C_2\text{-}C_6)$ alkenyl, O$(C_2\text{-}C_6)$ alkynyl, O$(C_1\text{-}C_6)$ alkylene-$(C_3\text{-}C_8)$ cycloalkyl, O$(C_1\text{-}C_6)$ alkylene-(5-6 membered) heteroaryl, O$(C_1\text{-}C_6)$ alkylene-(4-7 membered) heterocyclyl, O$(C_3\text{-}C_8)$ cycloalkyl, O(4-7 membered) heterocyclyl, Oaryl, O(5-6 membered) heteroaryl, SH, S$(C_1\text{-}C_6)$ alkyl, S$(C_1\text{-}C_6)$ haloalkyl, S$(C_1\text{-}C_6)$ alkylene-$(C_3\text{-}C_8)$ cycloalkyl, S$(C_1\text{-}C_6)$ alkylene-(4-7 membered) heterocyclyl, S$(C_1\text{-}C_6)$ alkylene-aryl, S$(C_1\text{-}C_6)$ alkylene-(5-6 membered) heteroaryl, S$(C_2\text{-}C_6)$ alkenyl, S$(C_2\text{-}C_6)$ alkynyl, S$(C_3\text{-}C_8)$ cycloalkyl, S(4-7 membered) heterocyclyl, Saryl, S(5-6 membered) heteroaryl, $(C_3\text{-}C_8)$ cycloalkyl, (4-7 membered) heterocyclyl, aryl, or (5-6 membered) heteroaryl, wherein the (4-7 membered) heterocyclyl contains at least one heteroatom independently selected from the group consisting of N, O, and S;
$R_2$ is H, D, halogen, CN, $NO_2$, $(C_1\text{-}C_6)$ alkyl, $d_{1-13}\text{-}(C_1\text{-}C_6)$ alkyl, $(C_1\text{-}C_6)$ haloalkyl, $(C_1\text{-}C_6)$ alkylene-C(O)

OH, $(C_1-C_6)$ alkylene-$NR_AR_B$, $(C_1-C_6)$ alkylene-OH, $(C_1-C_6)$ alkylene-O$(C_1-C_6)$ alkyl, $(C_1-C_6)$ alkylene-SH, $(C_1-C_6)$ alkylene-$(C_3-C_8)$ cycloalkyl, $(C_1-C_6)$ alkylene-(4-7 membered) heterocyclyl, $(C_1-C_6)$ alkylene-aryl, $(C_1-C_6)$ alkylene-(5-6 membered) heteroaryl, $(C_2-C_6)$ alkenyl, $(C_2-C_6)$ alkynyl, C(O)$(C_1-C_6)$ alkyl, C(O)$NR_AR_B$, C(O)OH, C(O)O$(C_1-C_6)$ alkyl, $NR_AR_B$, OH, O$(C_1-C_6)$ alkyl, $d_{1-13}$-O$(C_1-C_6)$ alkyl, O$(C_1-C_6)$ haloalkyl, O$(C_1-C_6)$ alkylene-C(O)OH, O$(C_1-C_6)$ alkylene-$NR_AR_B$, O$(C_1-C_6)$ alkylene-OH, O$(C_1-C_6)$ alkylene-O$(C_1-C_6)$ alkyl, O$(C_1-C_6)$ alkylene-aryl, O$(C_2-C_6)$ alkenyl, O$(C_2-C_6)$ alkynyl, O$(C_1-C_6)$ alkylene-$(C_3-C_8)$ cycloalkyl, O$(C_1-C_6)$ alkylene-(5-6 membered) heteroaryl, O$(C_1-C_6)$ alkylene-(4-7 membered) heterocyclyl, O$(C_3-C_8)$ cycloalkyl, O(4-7 membered) heterocyclyl, Oaryl, O(5-6 membered) heteroaryl, SH, S$(C_1-C_6)$ alkyl, S$(C_1-C_6)$ haloalkyl, S$(C_1-C_6)$ alkylene-$(C_3-C_8)$ cycloalkyl, S$(C_1-C_6)$ alkylene-(4-7 membered) heterocyclyl, S$(C_1-C_6)$ alkylene-aryl, S$(C_1-C_6)$ alkylene-(5-6 membered) heteroaryl, S$(C_2-C_6)$ alkenyl, S$(C_2-C_6)$ alkynyl, S$(C_3-C_8)$ cycloalkyl, S(4-7 membered) heterocyclyl, Saryl, S(5-6 membered) heteroaryl, $(C_3-C_8)$ cycloalkyl, (4-7 membered) heterocyclyl, aryl, or (5-6 membered) heteroaryl, wherein the (4-7 membered) heterocyclyl contains at least one heteroatom independently selected from the group consisting of N, O, and S;

$R_3$ is H, D, $(C_1-C_6)$ alkyl, $d_{1-13}$-$(C_1-C_6)$ alkyl, $(C_1-C_6)$ haloalkyl, $(C_1-C_6)$ alkylene-OH, or $(C_3-C_8)$ cycloalkyl;

$R_4$ is H, D, $(C_1-C_6)$ alkyl, $d_{1-13}$-$(C_1-C_6)$ alkyl, $(C_1-C_6)$ haloalkyl, $(C_1-C_6)$ alkylene-OH, or $(C_3-C_8)$ cycloalkyl;

$R_5$ is H, D, halogen, CN, $NO_2$, $(C_1-C_6)$ alkyl, $d_{1-13}$-$(C_1-C_6)$ alkyl, $(C_1-C_6)$ haloalkyl, $(C_1-C_6)$ alkylene-C(O)OH, $(C_1-C_6)$ alkylene-$NR_AR_B$, $(C_1-C_6)$ alkylene-OH, $(C_1-C_6)$ alkylene-O$(C_1-C_6)$ alkyl, $(C_1-C_6)$ alkylene-SH, $(C_1-C_6)$ alkylene-$(C_3-C_8)$ cycloalkyl, $(C_1-C_6)$ alkylene-(4-7 membered) heterocyclyl, $(C_1-C_6)$ alkylene-aryl, $(C_1-C_6)$ alkylene-(5-6 membered) heteroaryl, $(C_2-C_6)$ alkenyl, $(C_2-C_6)$ alkynyl, C(O)$(C_1-C_6)$ alkyl, C(O)$NR_AR_B$, C(O)OH, C(O)O$(C_1-C_6)$ alkyl, $NR_AR_B$, OH, O$(C_1-C_6)$ alkyl, $d_{1-13}$-O$(C_1-C_6)$ alkyl, O$(C_1-C_6)$ haloalkyl, O$(C_1-C_6)$ alkylene-C(O)OH, O$(C_1-C_6)$ alkylene-$NR_AR_B$, O$(C_1-C_6)$ alkylene-OH, O$(C_1-C_6)$ alkylene-O$(C_1-C_6)$ alkyl, O$(C_1-C_6)$ alkylene-aryl, O$(C_2-C_6)$ alkenyl, O$(C_2-C_6)$ alkynyl, O$(C_1-C_6)$ alkylene-$(C_3-C_8)$ cycloalkyl, O$(C_1-C_6)$ alkylene-(5-6 membered) heteroaryl, O$(C_1-C_6)$ alkylene-(4-7 membered) heterocyclyl, O$(C_3-C_8)$ cycloalkyl, O(4-7 membered) heterocyclyl, Oaryl, O(5-6 membered) heteroaryl, SH, S$(C_1-C_6)$ alkyl, S$(C_1-C_6)$ haloalkyl, S$(C_1-C_6)$ alkylene-$(C_3-C_8)$ cycloalkyl, S$(C_1-C_6)$ alkylene-(4-7 membered) heterocyclyl, S$(C_1-C_6)$ alkylene-aryl, S$(C_1-C_6)$ alkylene-(5-6 membered) heteroaryl, S$(C_2-C_6)$ alkenyl, S$(C_2-C_6)$ alkynyl, S$(C_3-C_8)$ cycloalkyl, S(4-7 membered) heterocyclyl, Saryl, S(5-6 membered) heteroaryl, $(C_3-C_8)$ cycloalkyl, (4-7 membered) heterocyclyl, aryl, or (5-6 membered) heteroaryl, wherein the (4-7 membered) heterocyclyl contains at least one heteroatom independently selected from the group consisting of N, O, and S;

$R_6$ is H, D, halogen, CN, $NO_2$, $(C_1-C_6)$ alkyl, $d_{1-13}$-$(C_1-C_6)$ alkyl, $(C_1-C_6)$ haloalkyl, $(C_1-C_6)$ alkylene-C(O)OH, $(C_1-C_6)$ alkylene-C(O)O$(C_1-C_6)$ alkyl, $(C_1-C_6)$ alkylene-$NR_CR_D$, $(C_1-C_6)$ alkylene-OH, $(C_1-C_6)$ alkylene-O$(C_1-C_6)$ alkyl, C(O)$(C_1-C_6)$ alkyl, C(O)$NR_CR_D$, C(O)OH, C(O)O$(C_1-C_6)$ alkyl, $NR_CR_D$, OH, O$(C_1-C_6)$ alkyl, $d_{1-13}$-O$(C_1-C_6)$ alkyl, O$(C_1-C_6)$ haloalkyl, O$(C_1-C_6)$ alkylene-C(O)OH, O$(C_1-C_6)$ alkylene-$NR_CR_D$, O$(C_1-C_6)$ alkylene-OH, O$(C_1-C_6)$ alkylene-O$(C_1-C_6)$ alkyl, SH, or S$(C_1-C_6)$ alkyl;

$R_7$ is H, D, halogen, CN, $NO_2$, $(C_1-C_6)$ alkyl, $d_{1-13}$-$(C_1-C_6)$ alkyl, $(C_1-C_6)$ haloalkyl, $(C_1-C_6)$ alkylene-C(O)OH, $(C_1-C_6)$ alkylene-C(O)O$(C_1-C_6)$ alkyl, $(C_1-C_6)$ alkylene-$NR_CR_D$, $(C_1-C_6)$ alkylene-OH, $(C_1-C_6)$ alkylene-O$(C_1-C_6)$ alkyl, C(O)$(C_1-C_6)$ alkyl, C(O)$NR_CR_D$, C(O)OH, C(O)O$(C_1-C_6)$ alkyl, $NR_CR_D$, OH, O$(C_1-C_6)$ alkyl, $d_{1-13}$-O$(C_1-C_6)$ alkyl, O$(C_1-C_6)$ haloalkyl, O$(C_1-C_6)$ alkylene-C(O)OH, O$(C_1-C_6)$ alkylene-$NR_CR_D$, O$(C_1-C_6)$ alkylene-OH, O$(C_1-C_6)$ alkylene-O$(C_1-C_6)$ alkyl, SH, or S$(C_1-C_6)$ alkyl;

$R_9$ is H, D, halogen, CN, $NO_2$, $(C_1-C_6)$ alkyl, $d_{1-13}$-$(C_1-C_6)$ alkyl, $(C_1-C_6)$ haloalkyl, $(C_1-C_6)$ alkylene-C(O)OH, $(C_1-C_6)$ alkylene-C(O)O$(C_1-C_6)$ alkyl, $(C_1-C_6)$ alkylene-$NR_CR_D$, $(C_1-C_6)$ alkylene-OH, $(C_1-C_6)$ alkylene-O$(C_1-C_6)$ alkyl, C(O)$(C_1-C_6)$ alkyl, C(O)$NR_CR_D$, C(O)OH, C(O)O$(C_1-C_6)$ alkyl, $NR_CR_D$, OH, O$(C_1-C_6)$ alkyl, $d_{1-13}$-O$(C_1-C_6)$ alkyl, O$(C_1-C_6)$ haloalkyl, O$(C_1-C_6)$ alkylene-C(O)OH, O$(C_1-C_6)$ alkylene-$NR_CR_D$, O$(C_1-C_6)$ alkylene-OH, O$(C_1-C_6)$ alkylene-O$(C_1-C_6)$ alkyl, SH, or S$(C_1-C_6)$ alkyl;

$R_{10}$ is D, $(C_1-C_6)$ alkyl, $d_{1-13}$-$(C_1-C_6)$ alkyl, $(C_1-C_6)$ alkylene-OH, $(C_1-C_6)$ alkylene-O$(C_1-C_6)$ alkyl, $(C_1-C_6)$ alkylene-SH, or $(C_1-C_6)$ alkylene-S$(C_1-C_6)$ alkyl;

$R_A$ is H, $(C_1-C_6)$ alkyl, or C(O)$(C_1-C_6)$ alkyl;
$R_B$ is H, $(C_1-C_6)$ alkyl, or C(O)$(C_1-C_6)$ alkyl;
$R_C$ is H, $(C_1-C_6)$ alkyl, or C(O)$(C_1-C_6)$ alkyl;
$R_D$ is H, $(C_1-C_6)$ alkyl, or C(O)$(C_1-C_6)$ alkyl; and
p is 0, 1, 2, 3, 4, or 5.

2. The compound of claim 1, or a pharmaceutically acceptable salt thereof, wherein:
$A_1$ is —O—;
$A_2$ is —O—;
$R_1$ is H, halogen, CN, or $(C_1-C_6)$ haloalkyl;
$R_2$ is H, halogen, CN, or $(C_1-C_6)$ haloalkyl;
$R_3$ is $(C_1-C_6)$ alkyl, $(C_1-C_6)$ haloalkyl, $(C_1-C_6)$ alkylene-OH, or $(C_3-C_8)$ cycloalkyl;
$R_4$ is $(C_1-C_6)$ alkyl, $(C_1-C_6)$ haloalkyl, $(C_1-C_6)$ alkylene-OH, or $(C_3-C_8)$ cycloalkyl;
$R_5$ is H, halogen, CN, or $(C_1-C_6)$ haloalkyl;
$R_6$ is H, halogen, $(C_1-C_6)$ alkyl, $(C_1-C_6)$ haloalkyl, $(C_1-C_6)$ alkylene-C(O)OH, $(C_1-C_6)$ alkylene-C(O)O$(C_1-C_6)$ alkyl, $(C_1-C_6)$ alkylene-OH, $(C_1-C_6)$ alkylene-O$(C_1-C_6)$ alkyl, O$(C_1-C_6)$ alkyl, or O$(C_1-C_6)$ alkylene-OH;
$R_7$ is H, halogen, $(C_1-C_6)$ alkyl, $(C_1-C_6)$ haloalkyl, $(C_1-C_6)$ alkylene-C(O)OH, $(C_1-C_6)$ alkylene-C(O)O$(C_1-C_6)$ alkyl, $(C_1-C_6)$ alkylene-OH, $(C_1-C_6)$ alkylene-O$(C_1-C_6)$ alkyl, O$(C_1-C_6)$ alkyl, or O$(C_1-C_6)$ alkylene-OH;
$R_9$ is H, halogen, $(C_1-C_6)$ alkyl, $(C_1-C_6)$ haloalkyl, $(C_1-C_6)$ alkylene-C(O)OH, $(C_1-C_6)$ alkylene-C(O)O$(C_1-C_6)$ alkyl, $(C_1-C_6)$ alkylene-OH, $(C_1-C_6)$ alkylene-O$(C_1-C_6)$ alkyl, O$(C_1-C_6)$ alkyl, or O$(C_1-C_6)$ alkylene-OH;
$R_{10}$ is $(C_1-C_6)$ alkyl or $(C_1-C_6)$ alkylene-OH; and
p is 0 or 1.

3. The compound of claim 1, or a pharmaceutically acceptable salt thereof, wherein:
$A_1$ is —O—;
$A_2$ is —O—;
$R_1$ is H;
$R_2$ is H;
$R_3$ is $(C_1-C_3)$ alkyl, $(C_1-C_6)$ haloalkyl, $(C_1-C_6)$ alkylene-OH, or $(C_3-C_8)$ cycloalkyl;

$R_4$ is $(C_1$-$C_3)$ alkyl, $(C_1$-$C_6)$ haloalkyl, $(C_1$-$C_6)$ alkylene-OH, or $(C_3$-$C_8)$ cycloalkyl;
$R_5$ is H;
$R_6$ is H or $(C_1$-$C_3)$ alkyl;
$R_7$ is H or $(C_1$-$C_3)$ alkyl;
$R_9$ is H or $(C_1$-$C_3)$ alkyl;
$R_{10}$ is $CH_3$; and
p is 0, 1, or 2.

4. The compound of claim 1, or a pharmaceutically acceptable salt thereof, wherein:
$A_1$ is —O—;
$A_2$ is —O—;
$R_1$ is H;
$R_2$ is H;
$R_3$ is $(C_1$-$C_3)$ alkyl;
$R_4$ is $(C_1$-$C_3)$ alkyl;
$R_5$ is H;
$R_6$ is H or $(C_1$-$C_3)$ alkyl;
$R_7$ is H or $(C_1$-$C_3)$ alkyl;
$R_9$ is H or $(C_1$-$C_3)$ alkyl; and
p is 0.

* * * * *